United States Patent [19]

Tomich et al.

[11] Patent Number: 5,686,486
[45] Date of Patent: Nov. 11, 1997

[54] 4-HYDROXY-BENZOPYRAN-2-ONES AND 4-HYDROXY-CYCLOALKYL[B]PYRAN-2-ONES USEFUL TO TREAT RETROVIRAL INFECTIONS

[75] Inventors: Paul Kosta Tomich, Kalamazoo; Michael John Bohanon, Gobles; Steven Ronald Turner, Kalamazoo; Joseph Walter Strohbach, Mendon; Suvit Thaisrivongs; Richard C. Thomas, both of Kalamazoo; Karen Rene Romines, Paw Paw, all of Mich.; Chih-Ping Yang, Taipei, Taiwan; Paul Adrian Aristoff; Harvey Irving Skulnick, both of Kalamazoo, Mich.; Paul D. Johnson; Ronald B. Gammill, both of Portage, Mich.; Qingwei Zhang, Kalamazoo, Mich.; Gordon L. Bundy, Portage, Mich.; David John Anderson; Lee S. Banitt, both of Kalamazoo, Mich.

[73] Assignee: Pharmacia & Upjohn Company, Kalamazoo, Mich.

[21] Appl. No.: 492,068

[22] PCT Filed: Feb. 3, 1994

[86] PCT No.: PCT/US94/00938

§ 371 Date: Aug. 4, 1995

§ 102(e) Date: Aug. 4, 1995

[87] PCT Pub. No.: WO94/18188

PCT Pub. Date: Aug. 18, 1994

Related U.S. Application Data

[63] Continuation-in-part of Ser. No. 169,302, Dec. 17, 1993, abandoned, which is a continuation-in-part of Ser. No. 68,715, May 27, 1993, abandoned, which is a continuation-in-part of Ser. No. 14,459, Feb. 5, 1993, abandoned.

[51] Int. Cl.$^6$ .................. A61K 31/35; C07D 311/20; C07D 311/74
[52] U.S. Cl. .................. 514/456; 549/283; 514/372; 514/337; 514/233.5; 514/320; 514/255; 514/222.2; 514/211; 514/403; 514/314; 514/362; 514/363; 548/240; 548/134; 548/136; 548/361.6; 546/783.1; 546/196; 546/152; 544/151; 544/376; 544/3; 544/206; 540/544
[58] Field of Search .................. 549/283; 514/456, 514/372, 337, 233.5, 320, 255, 222.2, 211, 403, 314, 362, 363; 548/240, 361.6, 134, 136; 544/151, 376, 3, 206; 546/283.1, 196, 152; 540/544

[56] References Cited

U.S. PATENT DOCUMENTS

| | | |
|---|---|---|
| 2,723,277 | 11/1955 | Grussner . |
| 3,325,515 | 6/1967 | Schmitt . |
| 3,489,774 | 1/1970 | Kuhn et al. ............ 549/285 |
| 3,493,586 | 2/1970 | Kuhn et al. ............ 549/291 |
| 3,764,693 | 10/1973 | Boschetti et al. ............ 514/457 |
| 3,835,161 | 9/1974 | Muylder ............ 549/286 |
| 4,382,951 | 5/1983 | Grassberger et al. ............ 514/456 |
| 4,727,064 | 2/1988 | Pitha ............ 514/58 |

FOREIGN PATENT DOCUMENTS

| | | |
|---|---|---|
| 674997 | 12/1966 | Belgium . |
| 1092278 | 11/1954 | France . |
| 48-023942 | of 1973 | Japan . |
| JO 3227-923-A | 10/1991 | Japan . |
| 734142 | 3/1953 | United Kingdom . |
| WO 88/04652 | 6/1988 | WIPO . |
| WO 89/07939 | 9/1989 | WIPO . |
| WO 91/04663 | 4/1991 | WIPO . |
| WO 91/06561 | 5/1991 | WIPO . |
| WO 91/12804 | 9/1991 | WIPO . |
| WO 92/04326 | 3/1992 | WIPO . |
| WO 92/04327 | 3/1992 | WIPO . |
| WO 92/04328 | 3/1992 | WIPO . |
| WO 92/17490 | 10/1992 | WIPO . |

OTHER PUBLICATIONS

Aeigler, Mh.Chem, vol. 89, pp. 678–682, 1958.
Andrieux, Bull.Soc.Chim.Fr., vol. 5, pp. 1719–1723, 1969.
Ziegler, Monatsh.Chem., vol. 90, pp. 594–599, 1959.
Ziegler, Montash.Chem., vol. 92, pp.246–253, 1961.
Baldwin, J Org Chem, vol. 28(11), pp. 3112–3114, 1963.
Patra, Indian J Chem., vol. 25B, pp. 1167–1170, 1986.
Queval, Chimie Therapeutique, vol. 7(4), pp. 300–306, 1972.

(List continued on next page.)

*Primary Examiner*—C. Warren Ivy
*Assistant Examiner*—D. Margaret M. Mach
*Attorney, Agent, or Firm*—Martha A. Gammill

[57] ABSTRACT

The present invention relates to compounds of formula I which are 4-hydroxy-benzopyran-2-ones and 4-hydroxy-cycloalkyl[b]pyran-2-ones useful for inhibiting a retrovirus in a mammalian cell infected with said retrovirus.

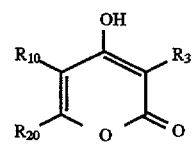

I

Wherein $R_{10}$ and $R_{20}$ taken together are:

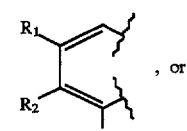

II , or

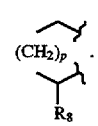

III

27 Claims, No Drawings

OTHER PUBLICATIONS

West, J Am Chem Soc, vol. 83, pp. 2676–2679, 1961.

Bourinbaiar, Acta. VIrol., vol. 37, pp. 241–250, 1993.

E. Zeigler, et al., *Synthesis of Heterocyclic Compounds, XV. 4–Hydroxy–2–Pyrono–Cyclenes*, Mh. Chem. 89:678–682 (1958), (with attached English translation).

F. Effenberger, et al., *Die Acylierung von (Trimethylsilyl)enolethern mit Malonyldichlorid—Darstellung von 4–Hydroxy–2H–Pyran–2–Onen,* Chem. Ber. 119:3394–3404 (1986). (English abstract included.).

T. Kappe and H. Wildpanner, *Nonsteroidal Antiinflammatory Agents. 4. Rearrangement of Heterocycles. II. Ketenoid Rearrangement and Oxidation of 2–Pyrones to 1,4–Naphthoquinone–5–Alkanoic Acids,* Monatsh. Chem. 119(6–7):727–737 (1988). (See AY—Chemical Abstracts 110(13):114430k below.).

Chemical Abstract 110(13):114430k, 1989.

F. S. G. Soliman and T. Kappe, *Reactions with Pyrrolidine–2,4–diones, I. New Synthesis of Pyrano[2,3–c]pyrrole and Pyrrolo[3,4–b]pyridine Systems,* Monatsh. Chem. 113(4):475–484 (1982).

Chemical Abstract 71:101655p, 1969.

Chemical Abstract 94:65472r, 1981.

P.Y. Lam, et al., *Cylic Ureas and Analogues Useful as Retroviral Protease Inhibitors,* Antimicrobial Patent Fast–Alert, Week Ending 30 Apr. 1993.

L. R. Pohl, *Synthesis and Thin–Layer Chromatographic, Ultraviolet, and Mass Spectral Properties of the Anticoagulant Phenprocoumon and Its Monohydroxylated Derivatives,* J. Med. Chem. 18(5):513–519 (1975). (Equivalent to Registry No. 55789–00–9.).

E. J. Valente, et al., *Conformations of Selected 3–Substituted 4–Hydroxycoumarins in Solution by Nuclear Magnetic Resonance. Warfarin and Phenprocoumon,* J. Med. Chem. 21(2):231–234 (1978).

L. A. Goding and B. D. West, *The Reversible Removal of Carbon 2 of 3–Substituted 4–Hydroxycoumarins,* J. Org. Chem. 33(1):437–438 (1968).

M. L. deWinter and W. Th. Nauta, *Pharmacochemistry of 2–diarylmethyl–1,3–indandiones. I. Synthesis,* Eur. J. Med. Chem.—Chim. Thur. 12(2):125–130 (1977).

J. X. DeVries, et al., *Identification of Phenprocoumon Metabolites in Human Urine by High–Performance Liquid Chromatography and Gas–Chromatography–Mass Spectrometry,* J. Chromatogr. 338(2):325–334 (1985).

J. X. DeVries and U. Völker, *Determination of the Plasma Protein Binding of the Coumarin Anticoagulants Phenprocoumon and Its Metabolites, Warfarin and Acenocoumarol, by Ultrafiltration and High–Performance Liquid Chromatography,* J. Chromatogr. 529(2):479–485 (1990).

J. X. DeVries, *Thermospray and Particle Beam Liquid Chromatographic–Mass Spectrometric Analysis of Coumarin Anticoagulants,* J. Chromatogr. 562(1–2):31–38 (1991).

L. D. Heimark, et al., *The Synthesis of Deuterium Labelled Metabolites of Warfarin and Phenprocoumon,* J. Labelled Compds. Radiopharm. 23(2):137–148 (1986).

G. Kokotos and C. Tzougraki, *Synthesis and Study of Substituted Coumarins. A Facile Preparation of D,L–o–Tyrosine,* J. Heterocyclic Chem. 23:87–92 (1986).

G. Appendino, et al., *The Chemistry of Coumarin Derivatives. Synthesis of 3–Alkyl–4–hydroxycoumarins by Reductive Fragmentation of 3,3'–Alkylidene–4,4'–dihydroxybis [coumarins],* Helv. Chim. Acta 74(7):1451–1458 (1991).

E. W. Schafer, Jr. and W. A. Bowles, Jr., *Acute Oral Toxicity and Repellency of 933 Chemicals to House and Deer Mice,* Arch. Environ. Contam. Toxicol. 14(1) 111–129 (1985).

R. I. Brinkworth, et al., *Flavones and Inhibitors of HIV–1 Proteinase,* Biochemical and Biophysical Research Communications, 188(2):631–637 (1992).

A. S. Bourinbaiar, et al., *Effect of the Oral Anticoagulant, Warfarin, on HIV–1 Replication and Spread,* AIDS 7(1):129–130 (1993).

L. Müller–Kuhrt, and A. Immelmann, *Novel Gamma–Pyrones, Gamma–Pyridones and Gamma–Thiopyrones and Their Use as Medicaments and Method for Producing Them,* Antimicrobial Patent Fast–Alert, Week Ending 4 Sep. 1992, p. AM15.

B. Chenera, et al., *Carboxylic and Heterocyclic HIV Protease Inhibitors,* Antimicrobial Patent Fast–Alert, Week Ending 8 Jan. 1993, p. AM22.

Merck Index, Eleventh Edition (1989), Entry 9950.

C.A. Selects: Antitumor Agents, Issue 19, 1992, p. 25, No. 117:90147q.

CA 51:577e (1957).

CA 51:14826f,h (1957).

CA 51:14827a,b (1957).

CA 51:16453a (1957).

CA 52:5399b (1958).

CA 52:5480g (1958).

CA 52:5480h (1958).

CA 53:12305e (1959).

CA 53:20046a (1959).

CA 53:22454a (1959).

CA 54:577e (1960).

CA 54:577f (1960).

CA 54:577g (1960).

CA 54:577h (1960).

CA 54:579e (1960).

CA 54:5699d (1960).

CA 54:5699e (1960).

CA 54:16450f (1960).

CA 55:22306e (1961).

CA 63:5589c (1965).

CA 63:14743c (1965).

CA 64:12969b (1966).

CA 71(15):69677j (1969).

CA 72(15):78882v (1970).

CA 78(7):38016h (1973).

CA 79(13):74969a (1973).

CA 83(5):37913q (1975).

CA 84(9):55338f (1976).

CA 88(19):132039w (1978).

CA 90(1):1707f (1979).

CA 93(19):181041c (1980).

CA 93(23):220546t (1980).

CA 96(19):157432x (1982).

CA 107(17):154201f (1987).

CA 107(21):193079s (1987).

CA 108(15):126707c (1988).

CA 111(13):111038y (1989).

Tr. Voronezh. Teckhnol. Inst. 19(2):27–30 (1971), Abstract No. Izh274 (Russian Language).

4-HYDROXY-BENZOPYRAN-2-ONES AND 4-HYDROXY-CYCLOALKYL[B]PYRAN-2-ONES USEFUL TO TREAT RETROVIRAL INFECTIONS

This application is the national phase of international application PCT/US94/00938, filed 3 Feb. 1994; which is a continuation-in-part of U.S. Ser. No. 08/169,302, filed 17 Dec. 1993, now abandoned; which is a continuation-in-part of U.S. Ser. No. 08/068,715, filed 27 May 1993, now abandoned; which is a continuation-in-part of U.S. Ser. No. 08/014,459, filed 5 Feb. 1993, now abandoned.

FIELD OF THE INVENTION

The present invention relates to compounds useful for inhibiting a retrovirus in a human cell infected with said retrovirus. More particularly, the present invention provides 4-hydroxy-benzopyran-2-ones and 4-hydroxy-cycloalkyl[b]pyran-2-ones and sulfonamide derivatives thereof as HIV-proteinase inhibitors.

BACKGROUND OF THE INVENTION

During the past decade, acquired immunodeficiency syndrome (AIDS) has progressed from having the status of a medical curiosity afflicting only a small number of individuals to a problem of major proportions, both medically and economically. John Saunders and Richard Storer, "New Developments in RT Inhibitors," DN&P 5(3), April 1992, pages 153–169. WHO figures reveal that more than 360,000 cases of AIDS have been reported worldwide, including nearly 175,000 cases in the U.S.A. Of these, approximately 100,000 worldwide (50,000 in the U.S.A.) were reported in the preceding 12-month period. In the U.S.A., the number of seropositive individuals is thought to be approximately two million, and estimates suggest that 5–10 million people worldwide may be seropositive. Saunders and Storer, page 153.

Since the first description of the malady in the early part of this decade, acquired immunodeficiency disease syndrome (AIDS) and its devastating consequences have been subjects of continuous and intense coverage in both the lay and scientific press. Indeed, an edition of Scientific American was entirely devoted to AIDS (Scientific American 289, #4 (1988)), and the literature on the disease and the virus is already so vast as to defy thorough citation.

On Mar. 20, 1987, the FDA approved the use of the compound, zidovudine (AZT), to treat AIDS patients with a recent initial episode of pneumocystis carinii pneumonia, AIDS patients with conditions other than pneumocystis carinii pneumonia or patients infected with the virus with an absolute CD4 lymphocyte count of less than 200/mm$^3$ in the peripheral blood. AZT is a known inhibitor of vital reverse transcriptase, an enzyme necessary for human immunodeficiency virus replication. U.S. Pat. No. 4,724,232 claims a method of treating humans having acquired immunodeficiency syndrome utilizing 3'-azido-3'-deoxy-thymidine (azidothymidine, AZT).

Following the discovery of the anti-HIV activity of AZT, much effort has been focused on a wide variety of other dideoxynucleoside analogues in the search for superior agents. In the case of the 2'.3'-dideoxy series, ddC and ddI have shown potent activity against HIV in vitro and have been evaluated in clinical trials. Saunders and Storer, page 160. The compound ddC is currently being developed by Hoffman-La Roche Co. as a potential anti-AIDS drug. Its limiting toxicity in humans is peripheral neuropathy which is reversible at low doses. Raymond R. Schinazi, Jan R. Mead and Paul M. Feorino, "Insights Into HIV Chemotherapy." AIDS Research and Human Retroviruses, Vol. 8, Number 6, 1992, pages 963–990. It has been approved by the FDA for AIDS therapy in combination with AZT. The compound ddI has also been evaluated in clinical trials. Its limiting toxicities are peripheral neuropathy and pancreatitis. It has also been shown to stimulate hepatic glycolysis leading to irreversible liver damage. Schinazi, Mead and Feorino, page 966. It has recently been approved by the FDA for the treatment of HIV-1 infections in adults and pediatric patients who are intolerant to or whose health has significantly deteriorated while on AZT treatment. Schinazi, Mead and Feorino, page 966.

Among these approved drugs, AZT is currently the only drug that has been shown to decrease the mortality and frequency of opportunistic infections associated with AIDS. Schinazi, Mead and Feorino, page 963.

Human immunodeficiency virus (HIV) has long been recognized as the causative agent in AIDS, although a minority opinion to the contrary has been expressed (e.g., P. Duesberg, Proc. Natl. Acad. Sci., USA, 86:755–764 (1989)). Sequence analysis of the complete genomes from several infective and non-infective HIV-isolates has shed considerable light on the make-up of the virus and the types of molecules that are essential for its replication and maturation to an infective species. The HIV protease is essential for the processing of the vital gag and gag-pol polypeptides into mature virion proteins. L. Ratner, et al., Nature, 313:277–284 (1985); L. H. Pearl and W. R. Taylor, Nature, 329:351 (1987). HIV exhibits the same gag/pol/env organization seen in other retroviruses. L. Ratner, et al., above; S. Wain-Hobson, et al., Cell, 40:9–17 (1985); R. Sanchez-Pescador, et al., Science, 227:484–492 (1985); and M. A. Muesing, et al., Nature, 313:450–458 (1985).

Reverse transcriptase (RT) is an enzyme unique to retroviruses that catalyzes the conversion of vital RNA into double stranded DNA. Blockage at any point during the transcription process, by AZT or any other aberrant deoxynucleoside triphosphate incapable of elongation, should have dramatic consequences relative to viral replication. Much work on the RT target is in progress based, in large measure, upon the fact that nucleosides like AZT are easily delivered to cells. However, the inefficiency of phosphorylation steps to the triphosphate, and the lack of specificity and consequent toxicity, constitute major drawbacks to use of AZT and similar nucleosides having a blocked, or missing, 3'hydroxyl group.

The T4 cell receptor for HIV, the so-called CD4 molecule, has also been targeted as an intervention point in AIDS therapy. R. A. Fisher, et al., Nature. 331:76–78 (1988); R. E. Hussey, et al., Nature, 331:78–81 (1988); and K. C. Deen et al., Nature, 331:82–84 (1988). The exterior portion of this transmembrane protein, a molecule of 371 amino acids (sCD4) has been expressed in Chinese hamster ovary (CHO) cells and Genentech (D. H. Smith, et al., Science, 238:1704–1707 (1987)) has had a product in clinical trials since the fall of 1987. CD4 has been shown to have a narrow spectrum of activity against wild-type virus and so far has failed to control HIV infection in humans. Schinazi, Mead and Feorino, page 963. The idea behind CD4 based therapy is that the molecules can neutralize HIV by interfering with viral attachment to T4, and other cells which express CD4 on their surfaces. A variant on this theme is to attach cell toxins to CD4 for specific binding and delivery to infected cells which display glycoprotein gp-120 on their surfaces. M. A. Till, et al., Science, 242:1166–1168 (1988); and V. K. Chaudhary, et al., Nature, 335:369–372 (1988).

Another therapeutic target in AIDS involves inhibition of the viral protease (or proteinase) that is essential for processing HIV-fusion polypeptide precursors. In HIV and several other retroviruses, the proteolytic maturation of the gag and gag/pol fusion polypeptides (a process indispensable for generation of infective viral particles) has been shown to be mediated by a protease that is, itself, encoded by the pol region of the viral genome. Y. Yoshinaka, et al., Proc. Natl. Acad. Sci. USA, 82:1618–1622 (1985); Y. Yoshinaka, et al., J. Virol., 55:870–873 (1985); Y. Yoshinaka, et al., J. Virol., 57:826–832 (1986); and K. von der Helm, Proc. Natl. Acad. Sci., USA, 74:911–915 (1977). Inhibition of the protease has been shown to inhibit the processing of the HIV p55 in mammalian cell and HIV replication in T lymphocytes. T. J. McQuade, et al., Science, 247:454 (1990).

The protease (or proteinase), consisting of only 99 amino acids, is among the smallest enzymes known, and its demonstrated homology to aspartyl proteases such as pepsin and renin (L. H. Pearl and W. R. Taylor, Nature, 329:351–354 (1987); and I. Katoh, et al., Nature, 329:654–656 (1987)), led to inferences regarding the three-dimensional structure and mechanism of the enzyme (L. H. Pearl and W. R. Taylor, above) that have since been borne out experimentally. Active HIV protease has been expressed in bacteria (see, e.g., P. L. Darke, et al., J. Biol. Chem., 264:2307–2312 (1989)) and chemically synthesized (J. Schneider and S. B. Kent, Cell, 54:363–368 (1988); and R. F. Nutt, et al., Proc. Natl. Acad. Sci., USA, 85:7129–7133 (1988)). Site directed mutagenesis (P. L. Darke, et al., above); and N. E. Kohl, et al., Proc. Natl. Acad. Sci., USA, 85:4686–4690 (1988)) and pepstatin inhibition (P. L. Darke, et al., J. Biol. Chem., 264:2307–2312 (1989); S. Seelmeier, et al., Proc. Natl. Acad. Sci., USA, 85:6612–6616 (1988); C.-Z. Giam and I. Borsos, J. Biol. Chem., 263:14617–14720 (1988); and J. Hansen, et al., EMBO J., 7:1785–1791 (1988)) have provided evidence for HIV protease's mechanistic function as an aspartyl protease. A study has demonstrated that the protease cleaves at the sites expected in peptides modeled after the regions actually cleaved by the enzyme in the gag and pol precursor proteins during viral maturation. P. L. Darke, et al., Biochem. Biophys. Res. Communs., 156:297–303 (1988). X-ray crystallographic analysis of the HIV-protease (M. A. Navia, et al., Nature, 337:615–620 (1989)) and a related retroviral enzyme from Rous sarcoma virus (M. Miller, et al., Nature, 337:576–579 (1989)) reveal an active site in the protease dimer that is identical to that seen in other aspartyl proteases, thus supporting the supposition (L. H. Pearl and W. R. Taylor, above) that the HIV enzyme is active as a dimer. See also Joseph A. Martin, "Recent Advances in the Design of HIV Proteinase Inhibitors," Antiviral Research, 17 (1992) 265–278.

To date, the scientific search for a fully effective and safe means of inhibiting retroviruses in a human hosting such a virus, and thereby effectively treating diseases caused by such a virus, such as acquired immunodeficiency syndrome (AIDS), continues.

Information Disclosure

Synthesis of Heterocyles, XV, 4-Hydroxy-2-pyronocyclenes. E. Ziegler, H. Junek, and E. Nolken, Monatsh., 89:678–82 (1958) (CA 53:12283–4) discloses compounds such as the following: 4-hydroxy-3-benzyl-5,6-octamethylene-2-pyrone; 4-hydroxy-3-benzyl-5,6-pentamethylene-2-pyrone; 4-hydroxy-3-benzyl-5,6-heptamethylene-2-pyrone; 4-hydroxy-3-benzyl-5,6-hexamethylene-2-pyrone; and 4-hydroxy-3-benzyl-5,6-tridecamethylene-2-pyrone.

R. Effenberberger, T. Ziegler, K.-H. Schonwalder, T. Kesmarszky, B. Bauer, Chem. Ber 119:3394–3404 (1986), discloses pyrone intermediates, such as those of formula J-1 (wherein n is 4; refer to Chart J below).

Monatsh. Chem., 119(6–7): 727–37 (1988) (CA 110(13):114430k) discloses the compounds 8H-acenaphtho[1,2-b]pyran-8-one, 10-hydroxy-9-(phenylmethyl)-; and indeno[2,1-b]pyran-3(5H)-one, 1-hydroxy-2-(phenylmethyl)-.

CA 54:14239b discloses the compound 3-benzyl-4-hydroxy-2-oxoindeno-[1,2-b]pyran.

Monatsh. Chem., 113(4): 475–84 (1982) discloses compounds such as 6,7-dihydro-4-hydroxy-6-(3-methylphenyl)-7-phenyl-3-(phenylmethyl)-pyrano-[2,3-c]pyrrole-2,5-dione; and 6,7-dihydro-4-hydroxy-6,7-diphenyl-3-(phenylmethyl)-pyrano[2,3-c]pyrrole-2,5-dione.

Monatsh. Chem. 90:594–9 (1959) (CA 54:14238g,h) discloses compounds such as 5H-benzocycloheptene-8-acrylic acid, α-benzyl-6,7-dihydro-β-9-dihydroxy-δ-lactone; and 3-benzyl-5,6,7,8-tetrahydro-4-hydroxy-8-isopropyl-5-methyl-coumarin.

Bull. Soc. Chim. Fr. 5:1719–23 (1069) (Fr) (CA 71(21): 101655p) discloses the compound 3-benzyl-5,6,7,8-tetrahydro-4-hydroxy-coumarin.

WO 8804652 (equivalent AU 8810440 (Jap.)) discloses the compound 3-(4-chloro-2-nitrobenzoyl)-5,6,7,8-tetrahydro-4-hydroxy-2H-1-benzopyran-2-one.

Monatsh. 92:246–53 (1961) (Gr) (CA 55:27296d) discloses the compound 3-(3,5-dimethylsalicyl)-5,6,7,8-tetrahydro-4-hydroxy-coumarin.

CA 94(9): 65472r discloses 5,6,7,8-hexahydro-3-phenyl-2-H-cycloocta[b]pyran-2-one; and 6,7,8,9-tetrahydro-4-hydroxy-3-phenyl-cyclohepta[b]pyran-2(5H)-one.

J. Org. Chem. 28(11): 3112–14 (1963) (CA 59:15185e) discloses the compound hexanedioic acid, 2-[hydroxy(2-hydroxy-1-cyclopenten-1-yl)methylene]-, δ-lactone.

Antimicrobial Patent Fast-Alert, Week Ending 30 Apr. 1993. discloses cyclic ureas and analogues useful as retroviral protease inhibitors.

Many 4-hydroxy-coumarin type compounds are known. For example, these references—CA 54:577e,g,h (1960); U.S. Pat. No. 2,872,457 (CA 53:12305e (1959)); CA 51:14826f,h (1957); U.S. Pat. No. 2,723,276 (CA 52:5480g,h (1958)); CA 51:14827a,b (1957); CA 51:16453a (1957); CA 54:5699d (1960); CA 54:16450f (1960); CA 53:22454a (1959); and CA 53:20046a—disclose compounds such as the following: 4-hydroxy-3-(1-phenylbutyl)-coumarin (Example 10 below); 4-hydroxy-3-(1-phenylpentyl)-coumarin (Example 11 below); 3-(cyclohexylphenylmethyl)-4-hydroxycoumarin; 4-hydroxy-3-(2-methyl-1-phenylpropyl)-coumarin (Example 9 below); 4-hydroxy-3-(2-phenylpropyl) coumarin (Example 5 below); 4-hydroxy-3-(1,3-diphenylpropyl)-coumarin (Example 16 below); 4-hydroxy-3-(1-(4-methylphenyl)-butyl)-coumarin (Example 18 below); 4-hydroxy-3-(1-(1-naphthyl)-propyl)-coumarin (Example 20 below); 4-hydroxy-7-methyl-3-(1-phenylpropyl)-coumarin (Example 90 below); 7-chloro4-hydroxy-3-(1-phenylpropyl)-coumarin (Example 92 below); 4-hydroxy-3-[1-(4-methoxyphenyl)propyl]-coumarin (Example 94 below); 3-(.alpha.-ethyl-p-fluorobenzyl)-4-hydroxy-coumarin (Example 36 below); 3-(α-ethyl-p-methoxybenzyl)-4-hydroxy-coumarin; and 3-(1-phenyl-propenyl)-4-hydroxy-coumarin.

To the best of our knowledge, from our review, these references do not disclose the use of these compounds as HIV protease inhibitors. They are disclosed as being useful as: rodenticides, lowering the prothrombin level of the blood, blood anticoagulants, and pesticides.

Additional 4-hydroxy-coumarin compounds with similar uses have been disclosed in the following references:

Indian J. Chem., Sect. B, 25B: 1167–70 (1986) (CA 107(17):154201f) and CA 93(23):220546t discloses the compound 4-Hydroxy-3-(1-phenyl-2-propenyl)-coumarin (Example 74 below).

CA 96(19):157432x; CA 90(1):1707f; CA 84(9):55338f; CA 79(13):74969a; and CA 71(15):69677j disclose the compound 4-hydroxy-3-[1-(1,2,3,4-tetrahydro)naphthyl]-coumarin (Example 34 below); CA 54:579e discloses the compound 4-hydroxy-3-[1-indanyl]-coumarin (Example 35 below); CA 63:14743c discloses the compound 4-hydroxy-3-(1-naphthylmethyl)-coumarin; CA 63:5589c discloses the compound 3-(1'-(2-methoxy,3-methyl,5-chlorophenyl)propyl)-4-hydroxy-coumarin; CA 64:12969b discloses the compound 3-(α-acetonyl-α-acetylbenzyl)-4-hydroxy-coumarin.

CA 79(13):74969a; Chim. Ther. 7(4): 300–6 (1972) (Fr) (CA 78(7):38016h); CA 52:5399b; CA 54:5699e; CA 54:57e; and CA 72(15):78882v disclose 4-hydroxycoumarin compounds substituted at the 6- or 7-position by, e.g., methyl, methoxy and chloro.

J. M. Mulder, U.S. Pat. No. 3,835,161, 10 Sep. 1974, discloses the compound 3-[1-[4-(2-bromoethyl)phenyl]ethyl]-4-hydroxy-2H-1-benzopyran-2-one.

Merck Index, Eleventh Edition, (1989), Entry 9950, discusses Warfarin, its chemical name—3-α-phenyl-β-acetylethyl-4-hydroxycoumarin—and its uses as a rodenticide and an anticoagulant. J. Med. Chem., 1978, Vol. 21, No. 2: 231–234, discloses the antivitamin K activity of warfarin and discusses the anticoagulant activity of several 3-substituted 4-hydroxycoumarins such as 4-Hydroxy-3-(1-phenylbutyl)-coumarin; and 4-hydroxy-3-(α-methylbenzyl)-coumarin (Example 6 below). J. Am. Chem. Soc. 83:2676–9 (1961) (CA 55:22306e (1961)) discusses the resolution and absolute configuration of warfarin and discloses the preparation of compounds such as 4-hydroxy-3-(1-phenylbutyl)-coumarin.

Journal of Labelled Compounds and Radiopharmaceuticals Vol. XXIII, No. 2:137–148 (1986), discloses several deuterium labelled metabolites of warfarin and phenprocoumon, such as the deuterium labelled analog of the compound 4-hydroxy-7-methoxy-3-(1-phenylpropyl)-coumarin (Example 88).

J48023942 discloses compounds, such as 4-hydroxy-3-(α-methylbenzyl)-coumarin (Example 6 below); 4-hydroxy-3-(3-methyl-1-phenylbutyl)-coumarin (Example 14 below); and 2H-1-benzopyran-2-one, 4-hydroxy-7-methoxy-3-(1-phenylpropyl)- (also cited in preceding reference) and their use as rodenticides.

Tr. Voronezh. Teckhnol. Inst. 19(2): 27–30 (1971), Abstract No. 1zh274 (Russian language), discloses the compound 4-hydroxy-3-phenethylcoumarin (Example 1 below). This reference and Helv. Chim. Acta 74(7): 1451–8 (1991) disclose the compound of 4-hydroxy-3-(3-phenylpropyl) coumarin (Example 2 below).

J. Org. Chem. 33(1): 437–8 (1968); and Eur. J. Med. Chem. - Chim Ther. 12(2): 125–30 (1977) disclose compounds such as 4-hydroxy-3-diphenylmethylcoumarin (Example 7 below).

U.S. Pat. No. 3,764,693 discloses the compound 4-hydroxy-3-(3-hydroxy-1-phenylbutyl)-coumarin (Example 8 below) and its anticoagulating and rodenticidal activity.

J. Med. Chem. 18(5): 513–19 (1975) (CA 83(5):37913q); J. Chromatogr. 338(2): 325–34 (1985); J. Chromatogr. 562 (1–2): 31–8 (1991); J. Labelled Compds. Radiopharm. 23(2): 137–48 (1986) (cited previously); and J. Chromatogr. 529(2): 479–85 (1990) disclose compounds such as 4-hydroxy-3-[1-[3-(phenylmethoxy)phenyl]propyl]-2H-1-benzopyran-2-one; 4-hydroxy-8-(phenylmethoxy)-3-(1-phenylpropyl)-2H-1-benzopyran-2-one; 4-hydroxy-3-[1-(4-hydroxyphenyl)propyl]-coumarin (Example 85 below); 4-hydroxy-6-methoxy-3-(1-phenylpropyl)-coumarin (Example 89 below); 4,7-dihydroxy-3-(1-phenylpropyl)-coumarin (Example 93 below); 4,6-dihydroxy-3-(1-phenylpropyl)-coumarin (Example 95 below); 4-hydroxy-3-[1-(3-hydroxyphenyl)propyl]-coumarin (Example 103 below); and p-chlorophenprocoumon.

The following references disclose the possible anti-HIV use of compounds, such as warfarin, and 4-hydroxy-coumarin, which are very different from the compounds of the present invention.

JO 3227-923-A (Sawai Seiyaku KK) discloses the use of coumarins as therapeutic agents for HIV-infected patients; however, unsubstituted 4-hydroxy coumarin is the only compound specifically disclosed for this use.

J. Indian Chem. Soc., 69:397–398 (July 1992), discloses that coumarin-4-acetic acids were screened for their anti-cancer and anti-AIDS activities and were found to be inactive.

AIDS 1993, Vol. 7, No. 1, pages 129–130, discusses the effect of warfarin on HIV-1 replication and spread.

CA Selects:AID & Related Immunodeficiencies, Issue 24, 1993, Abstract 119:195147j discloses the inhibitory effect of a single dose of coumarin derivatives, warfarin, 4-hydroxy-coumarin, umbelliferone, on HIV-1 replication and cell-mediated or cell-free viral transmission.

At the First National Conference on Human Retroviruses and Related Infections, 12–16 Dec. 1993, Washington, D. C., it was disclosed that coumarins, such as warfarin, and pyrones, such as 3-(thiophenyl)-6-phenyl-4-hydroxy-pyrone, displayed HIV protease inhibition in an assay.

Acta. Virol. 37:241–250 (1993) discloses the anti-HIV activity of coumarin derivatives, warfarin, 4-hydroxy-coumarin and umbelliferone.

WO 91/04663 (Univ. of Calif. at Oakland), published 18 Apr. 1991, discloses 6-amino-1,2-benzopyrones which are useful for treating viral diseases.

WO 91/12804 (Kabi Pharmaceutical), published 5 Sep. 1991, discloses the use of N-phenyl-N-methyl-1,2-dihydro-4-hydroxy-1-methyl-2-oxo-quinoline-3-carboxamide, also known as Linomide®, for the treatment of retrovirus infections.

International Publication No. WO 89/07939, published 8 Sep. 1989, discloses specific coumarin compounds which are reverse transcriptase inhibitors.

U.S. Pat. Nos. 3,489,774 and 3,493,586 disclose 3-(beta-aryl-beta-(arylthio) (or aryl seleno) propionyl-coumarin and pyrone products useful as parasiticides.

Biochemical and Biophysical Research Communications, Vol. 188, No. 2, 1992, pages 631–637, discloses chromones bearing hydroxyl substituents and a phenolic group at the 2-position (flavones) as having anti-HIV-1 proteinase activity.

Antimicrobial Patent Fast-Alert, Week Ending 4 Sep. 1992, disclose gamma-pyrones, gamma-pyridones and gamma-thio-pyrones as antiviral agents.

International Publication Nos. WO 92/04326, 92/04327 and 92/04328, all published 19 Mar. 1992, disclose antiviral heterocyclic derivatives, such as quinolinones and benzopyranones, as replication inhibitors for treating herpes simples 1 and 2, cytomegalovius and Epstein-Barr virus.

C. A. Selects: Antitumor Agents, Issue 19, 1992, page 25, No. 117: 90147q (PCT International Application WO 92 06,687) discloses the preparation of 5-iodo-6-amino-1,2-benzopyrones and analogs as cytostatic and antiviral agents.

The following published PCT applications disclose peptides useful as retroviral protease inhibitors: International Publication No. WO 91/06561, published 16 May 1991; and International Publication No. WO 92/17490, published 15 Oct. 1992.

WO 93/07868, published 29 Apr. 1993, discloses new nitroso-benzopyrone, -benzamide and -isoquinolinone derivatives as adenosine di-phospho:ribose transferase inhibitors for treating viral infections and cancer.

WO 93/07128, published 15 Apr. 1993, relates to substituted cyclic carbonyls and derivatives thereof useful as retroviral protease inhibitors.

The Journal of Antibiotics, 46(7):1126 (July 1993), discloses germicidin, which is 6-(2-butyl)-3-ethyl-4-hydroxy-2-pyrone, to be an autoregulative germination inhibitor of *Streptomyces viridochromogenes* NRRL B-1551.

Derwent Abstract 92-166863/20 discloses new optionally substituted 5-iodo-6-amino-1,2-benzopyrone derivatives which are adenosine di:phospho-ribose inhibitors for the treatment and prevention of viruses and tumors associated with AIDS.

SUMMARY OF THE INVENTION

The present invention provides:
A compound of the formula I
wherein $R_{10}$ and $R_{20}$ taken together are
  a) the moiety of formula II, or
  b) the moiety of formula III,
wherein $R_0$ is —H;
wherein $R_1$ is
  a) —H,
  b) —$OC_nH_{2n+1}$,
  c) —F,
  d) —$NH_2$—, or
  e) —O—$C_nH_{2n}$—Het;
wherein $R_2$ is
  a) —H,
  b) —$OC_nH_{2n+1}$,
  c) —$CF_3$,
  d) —O—$C_nH_{2n}$—CH=$CH_2$, or
  e) —O—$C_nH_{2n}$—Het;
or wherein $R_1$ and $R_2$ taken together are phenyl;
or wherein $R_0$ and $R_2$ taken together are phenyl;
wherein $R_3$ is
  a) the moiety of formula IVA,
  b) diphenylethyl—,
  c) diphenylethenyl—,
  d) —CH—($C_3$–$C_6$ cycloalkyl)$_2$,
  e) -5,6,7,8,9-tetrahydro-5H-benzocycloheptenyl,
  f) -1,2,3,4-tetrahydro-naphthalenyl substituted by one (1) or two (2) —$OC_nH_{2n+1}$ or —$CH_3$,
  g) —CH($C_nH_{2n+1}$)—C(O)—O—$C_nH_{2n+1}$,
  h) —CH($CH_2$—phenyl)$_2$,
  i) —$C_rH_{2r}$—CH($R_4$)—$C_rH_{2r}$—Het—$R_5$,
  j) —$C_rH_{2r}$—CH($R_4$)—$C_rH_{2r}$—Het,
  k) diphenylmethyl—,
  l) diphenylpropyl—, or
  m) phenylcyclobutyl—;
wherein $R_4$ is
  a) —$C_mH_{2m+1}$,
  b) —$CH_2$—C(O)—O—$C_nH_{2n+1}$,
  c) —$C_3$–$C_6$ cycloalkyl,
  d) —$C_nH_{2n}$—$C_3$–$C_6$ cycloalkyl, or
  e) $C_2$–$C_6$ alkenyl;
wherein each $R_5$ is independently
  a) —H,
  b) —$NH_2$,
  c) —C(O)—$C_nH_{2n+1}$,
  d) (o-) or (m-) —O—$C_nH_{2n}$—CH=$CH_2$,
  e) —$C_1$–$C_5$ alkoxy substituted on each carbon atom by zero (0) or one (1) hydroxy,
  f) —O—C(O)—$C_nH_{2n+1}$,
  g) —Br,
  h) —CN,
  i) —$C_mH_{2m}$—$X_1$—$C_rH_{2r+1}$,
  j) —$X_1$—$C_nH_{2n}$—halo,
  k) —$X_1$—$C_nH_{2n}$—$NH_2$,
  l) —$X_1$—$C_nH_{2n}$—NH—C(O)—O—$C_nH_{2n+1}$,
  m) —$X_1$—$C_nH_{2n}$—CH(NH—C(O)—O—$C_nH_{2n+1}$)C(O)—O—$C_nH_{2n+1}$,
  n) —$X_1$—$C_mH_{2m}$—CH(NH—C(O)—O—$C_nH_{2n+1}$)$C_nH_{2n}$—Het,
  o) —$X_1$—$C_nH_{2n}$—CH($NH_2$)COOH,
  p) —$X_1$—$C_nH_{2n}$—C(O)—O—$C_nH_{2n+1}$,
  q) —$X_1$—$C_nH_{2n}$—$C_3$–$C_6$ cycloalkyl,
  r) —$C_mH_{2m}$—$X_1$—$C_mH_{2m}$—aryl,
  s) —$X_1$—$C_mH_{2m}$—O—aryl,
  t) —$C_mH_{2m}$—$X_1$—$C_mH_{2m}$—O—$C_nH_{2n+1}$,
  u) —$C_mH_{2m}$—$X_1$—$C_mH_{2m}$—Het,
  v) —$X_1$—$C_nH_{2n}$—C(O)—Het,
  w) —$X_1$—$C_nH_{2n}$—C(O)—NH—$C_nH_{2n}$—Het,
  x) —$X_1$—$C_nH_{2n}$—S—Het,
  y) —$C_mH_{2m}$—$X_1$—O—$C_nH_{2n}$—aryl,
  z) —$C_mH_{2m}$—$X_1$—O—$C_nH_{2n}$—Het,
  a1) —$X_1$—H,
  b1) —$X_1$—CH=$CH_2$,
  c1) —$X_1$—CH=CH—aryl,
  d1) —$X_1$—N($R_{40}$)$_2$,
  e1) —$X_1$—$C_nH_{2n}$—phthalimido,
  f1) —$X_1$—(penta-fluoro)—phenyl,
  g1) —$X_1C_nH_{2n}$—bicyclo[2.2.1]heptane,
  h(1) —$C_u$—$H_{2u}$—$R_{30}$,
  i1) —N=C—(NH—CH($C_nH_{2n+1}$)$_2$)$_2$,
  j1) —NH—P(O)($R_9$)—aryl,
  k1) —NH—P(O)(O—$R_{11}$)—aryl,
  l1) —NH—C(S)—NH—$R_{42}$, or
  m1) —NH—C(S)—$CH_2$—$R_{42}$;
wherein $X_1$ is
  a) —NH—C(O)—,
  b) —C(O)—NH—,
  c) —NH—$SO_2$—
  d) —$SO_2$—NH—,
  e) —NH—$SO_2$—NH—,
  f) —C(O)—O—,
  g) —O—C(O)—,
  h) —N($C_nH_{2n}$—aryl)—C(O)—,
  i) —NH—C(O)—NH—,
  j) —N($C_nH_{2n}$—aryl)—$SO_2$—, or
  k) —N($C_mH_{2m}$—$C_nH_{2n+1}$)—$SO_2$—;
wherein m is zero (0) to five (5) inclusive;
wherein n is one (1) to five (5) inclusive;
wherein p is one (1) to eight (8) inclusive;
wherein q is zero (0) to five (5) inclusive;

wherein r is one (1) to eight (8) inclusive;
wherein s is one (1) to six (6) inclusive;
wherein t is one (1) to twelve (12) inclusive;
wherein u is two (2) to six (6) inclusive;
wherein v is zero (0) to two (2) inclusive;
wherein w is one (1) or two (2);
wherein aryl is
   a) phenyl substituted by zero (0) to three (3) $R_6$,
   b) naphthyl substituted by zero (0) to three (3) $R_6$, or
   c) biphenyl substituted by zero (0) to three (3) $R_6$;
wherein Het is a 5-, 6- or 7-membered saturated or unsaturated ring containing from one (1) to three (3) heteroatoms selected from the group consisting of nitrogen, oxygen and sulfur; and including any bicyclic group in which any of the above heterocyclic rings is fused to a benzene ring or another heterocycle; and the ring may be connected through a carbon or secondary nitrogen in the ring or an exocyclic nitrogen; and if chemically feasible, the nitrogen and sulfur atoms may be in the oxidized forms; and if chemically feasible, the nitrogen atom may be in the protected form; and substituted by zero (0) to three (3) $R_7$;
wherein $R_6$ and $R_7$ are independently
   a) —$C_1$-$C_5$ alkyl, substituted by zero (0) to three (3) halo or substituted on each carbon atom by zero (0) or one (1) hydroxy,
   b) —OH,
   c) —$C_1$-$C_5$ alkyl—OH,
   d) —O—$C_1$-$C_5$ alkyl substituted by zero (0) to three (3) halo or substituted on each carbon atom by zero (0) or one (1) hydroxy,
   e) —O—$C_2$-$C_7$ alkenyl substituted by zero (0) or one (1) hydroxy,
   f) halo,
   g) —$NH_2$,
   h) —$NH_2$—$C_1$-$C_5$ alkyl,
   i) mono-or di-$C_1$-$C_5$ alkylamino,
   j) —NH—OH,
   k) —$N(C_nH_{2n}-OH)_2$,
   l) —$C(O)-NH_2$,
   m) —$C(O)$—$C_1$-$C_5$ alkyl,
   n) —CHO,
   o) —COOH,
   p) —$COX_2$,
   q) nitro,
   r) —CN,
   s) —$SO_3H$,
   t) —$SO_2NH_2$,
   u) —$SO_2$—$R_{42}$,
   v) —$NR_{40}$—$SO_2$—$R_{42}$,
   w) —$SO_2$—$NR_{40}R_{41}$,
   x) —$O[C_nH_{2n}O]_qC_nH_{2n+1}$,
   y) —$C(O)$—O—$C_nH_{2n+1}$,
   z) —$NR_{40}$—$C(O)$—$C_nH_{2n+1}$,
   a1) —$C_nH_{2n}$—$NR_{40}$—$C(O)$—$R_{41}$,
   b1) —N=N-phenyl substituted by zero (0) or one (1) —$N(C_nH_{2n+1})_2$,
   c1) isoxazolyl,
   d1) pyridinyl,
   e1) —$X_3$—$C_uH_{2u}$—$R_{30}$,
   f1) morpholino,
   g1) piperidino,
   h1) piperazino,
   i1) —$NR_{40}R_{41}$,
   j1) —$OR_{40}$,
   k1) the moiety of formula X,
   l1) —$C_nH_{2n}$—O—$C_nH_{2n}$—$OC_nH_{2n+1}$,
   m1) —N—methyl-piperazino,
   n1) —$SO_2$—morpholino,
   o1) —$SO_2$—piperazino,
   p1) —$SO_2$—N—methyl-piperazino,
   q1) —$SO_2$—piperidino, or
   r1) —$NR_{40}$—$C(O)$—$C_nH_{2n}$—O—$R_{41}$;
wherein $X_2$ is —$NR_{40}R_{41}$;
wherein $X_3$ is
   a) —O—,
   b) —$CH_2$—O—,
   c) —$SO_2NR_{40}$—,
   d) —$NR_{40}SO_2$—,
   e) —$C(O)$—,
   f) —$C(O)NR_{40}$—,
   g) —$NR_{40}C(O)$, or
   h) —$NR_{40}$—;
wherein $R_8$ is
   a) —H,
   b) —$C_nH_{2n}$-phenyl substituted by zero (0) to three (3) $R_6$,
   c) —$C_nH_{2n}$—Het,
   d) —$C_nH_{2n}$—$C_3$-$C_6$ cycloalkyl,
   e) —$C_rH_{2r+1}$,
   f) —$C_nH_{2n}$—CH=$CH_2$,
   g) —$C_sH_{2s+1}$ substituted by one (1) or two (2) hydroxy,
   h) —$CH_2$—epoxide,
   i) —$C_nH_{2n}$—oxiranyl,
   j) —$(C_nH_{2n}-O)_n$—$C_nH_{2n+1}$,
   k) —$C(O)$—$C_sH_{2s+1}$, or
   l) —CH(OH)—$C_3$-$C_6$ cycloalkyl;
wherein $R_9$ is
   a) —$C_1$-$C_4$ alkyl, or
   b) aryl;
wherein $R_{11}$ is
   a) —H,
   b) —$C_1$-$C_4$ alkyl,
   c) aryl, or
   d) pharmaceutically acceptable salts;
wherein $R_{12}$ is
   a) $C_1$-$C_4$ alkyl,
   b) $C_1$-$C_3$ alkoxy,
   c) dimethylamino,
   d) diethylamino,
   e) $CF_3$,
   f) CN,
   g) halo,
   h) —$NH_2$,
   i) —OH,
   j) —$SO_2$—$NH_2$, or
   k) —$C(O)$—$NH_2$;
wherein $R_{30}$ is
   a) morpholino,
   b) piperidino,
   c) piperazino,
   d) —$NR_{40}R_{41}$,
   e) —$OR_{40}$,
   f) the moiety of formula X,
   g) —N—methyl-piperazino, or
   h) halo;
wherein $R_{40}$ and $R_{41}$ are independently
   a) —H,
   b) —$C_1$-$C_4$ alkyl,
   c) phenyl substituted by zero (0) to three (3) $R_{12}$, or
   d) —$C_nH_{2n}$-phenyl substituted by zero (0) to three (3) $R_{12}$;

wherein $R_{42}$ is
  a) $C_1$-$C_4$ alkyl,
  b) phenyl substituted by zero (0) to three (3) $R_{12}$, or
  c) —$C_nH_{2n}$-phenyl substituted by zero (0) to three (3) $R_{12}$;

provided that:
1) when $R_{10}$ and $R_{20}$ taken together are the moiety of formula II, and $R_1$ and $R_2$ are independently —H, —F, or —$OC_nH_{2n+1}$, and $R_3$ is the moiety of formula IVA, and $R_4$ is —$C_mH_{2m+1}$ or cyclohexyl, then $R_5$ is other than —H, —Br or —$OC_nH_{2n+1}$;
2) when $R_5$ is $C_mH_{2m}$—$X_1$—O—$C_nH_{2n}$—aryl, —$C_mH_{2m}$—$X_1$—O—$C_nH_{2n}$—Het, or $X_1$—$N(R_{40})_2$, $X_1$ is not —C(O)—NH—, —NHSO$_2$—, —SO$_2$—NH—, —NH—SO$_2$—NH—, —C(O)—O—, —NH—C(O)—NH—, —N($C_nH_{2n}$—aryl)—SO$_2$—;
3) when $R_4$ in the moiety of formula IVA is —H, $R_5$ is a substituent containing $X_1$ wherein $X_1$ is —NHSO$_2$—;
4) when $R_5$ is —$X_1$—$C_mH_{2m}$—O—aryl or —$C_mH_{2m}$—$X_1$—$C_mH_{2m}$—O—$C_nH_{2n+1}$ and m is zero (0), then $X_1$ is not —C(O)—NH—, —NH—SO$_2$—, —SO$_2$—NH—, —NH—SO$_2$—NH—, —C(O)—O—, —NH—C(O)—NH—, —N—($C_nH_{2n}$—aryl)—SO$_2$—, or —N($C_mH_{2m}$—$C_nH_{2n+1}$)—SO$_2$—;
5) $R_4$ in the moiety of formula IVA is $C_2$-$C_6$ alkenyl only when $R_{10}$ and $R_{20}$ taken together are the moiety of formula III;
6) $R_3$ is diphenylethyl-, diphenylmethyl-, diphenylpropyl-, diphenylethenyl- or phenylcyclobutyl-, only when $R_{10}$ and $R_{20}$ taken together are the moiety of formula III; and
7) when $R_{10}$ and $R_{20}$ taken together are the moiety of formula II, and $R_1$ and $R_2$ are independently —H, —F, —$OC_nH_{2n+1}$ or —NH$_2$, $R_3$ is other than —CH($C_nH_{2n+1}$)—C(O)—O—$C_nH_{2n+1}$;

and pharmaceutically acceptable salts thereof.

Especially, the present invention provides compounds wherein $R_{10}$ and $R_{20}$ taken together are the moiety of formula III, and $R_3$ is the moiety of formula IV.

Especially provided are the following compounds of the present invention:

The compound of the formula I
wherein $R_{10}$ and $R_{20}$ taken together are a moiety of the formula II;
wherein $R_0$ is —H;
wherein $R_1$ is
  a) —H, or
  b) —$OC_nH_{2n+1}$;
wherein $R_2$ is
  a) —H, or
  b) —$OC_nH_{2n+1}$;
wherein $R_3$ is
  a) a moiety of the formula V, or
  b) -5,6,7,8,9-tetrahydro-5H-benzocycloheptenyl;
wherein $R_4$ is
  a) —cyclopropyl, or
  b) $C_mH_{2m+1}$;
wherein $R_5$ is
  a) —H,
  b) —$X_1$—$C_nH_{2n}$—NH$_2$,
  c) —$X_1$—$C_nH_{2n}$—NH—C(O)—O—$C_nH_{2n+1}$,
  d) —$X_1$—$C_nH_{2n}$—CH(NH$_2$)COOH,
  e) —$X_1$—$C_nH_{2n}$—aryl, or
  f) —$X_1$—$C_mH_{2m}$—Het;
wherein $X_1$ is —NH—C(O)—;

wherein m is two (2) to four (4), inclusive;
wherein n is one (1) to four (4), inclusive; and The compound of the formula I
wherein $R_{10}$ and $R_{20}$ taken together are a moiety of the formula III;
wherein $R_3$ is
  a) a moiety of the formula V, or
  b) —CH—(cyclopropyl)$_2$;
wherein $R_4$ is
  a) —$C_nH_{2n+1}$, or
  b) —cyclopropyl;
wherein $R_5$ is —H;
wherein $R_8$ is
  a) —H,
  b) —$C_nH_{2n}$—CH=CH$_2$,
  c) —$C_nH_{2n+1}$,
  d) —$C_n$—$H_{2n}$—cyclopropyl,
  e) —CH(OH)—$C_nH_{2n+1}$, or
  f) —$C_nH_{2n}$—tetrahydrofuranyl;
wherein n is one (1) to five (5) inclusive;
wherein p is three (3) to five (5) inclusive.

The present invention also provides for:

A method of inhibiting a retrovirus in a mammalian cell infected with said retrovirus which comprises treating said cell with an effective amount of a compound selected from the group consisting of:

4-Hydroxy-3-(α-methylbenzyl)-coumarin,
4-Hydroxy-3-phenethylcoumarin,
4-Hydroxy-3-(3-phenylpropyl)coumarin,
4-Hydroxy-3-diphenylmethylcoumarin,
4-Hydroxy-3-(3-hydroxy-1-phenylbutyl)-coumarin,
4-Hydroxy-3-(2-methyl-1-phenylpropyl)-coumarin,
4-Hydroxy-3-(1-phenylbutyl)-coumarin,
4-Hydroxy-3-(1-phenylpentyl)-coumarin,
4-Hydroxy-3-(3-methyl-1-phenylbutyl)-coumarin,
4-Hydroxy-3-(2-phenylpropyl)coumarin.
4-Hydroxy-3-(1,3-diphenylpropyl)-coumarin.
4-Hydroxy-3-(1-(4-methylphenyl)-butyl)-coumarin,
Coumarin, 4-hydroxy-3-[1-(4-hydroxyphenyl)propyl]-,
4-Hydroxy-3-(1-(1-naphthyl)-propyl)-coumarin,
Coumarin, 4- hydroxy -7-methoxy-3-(1-phenylpropyl)-,
Coumarin, 4-hydroxy-6-methoxy-3-(1-phenylpropyl)-,
Coumarin, 4,7-dihydroxy-3-(1-phenylpropyl)-,
Coumarin, 4,6-dihydroxy-3-(1-phenylpropyl)-,
Coumarin, 4-hydroxy-7-methyl-3-(1-phenylpropyl)-,
Coumarin, 7-chloro-4-hydroxy-3-(1-phenylpropyl)-,
Coumarin, 4-hydroxy-3-[1-(4-methoxyphenyl)propyl]-,
Coumarin, 4-hydroxy-3-[1-(3-hydroxyphenyl)propyl]-,
4-Hydroxy-3-(1-phenyl-2-propenyl)-coumarin,
Coumarin, 3-(,alpha.-ethyl-p-fluorobenzyl)-4-hydroxy-,
4-Hydroxy-3-[1-(1,2,3,4-tetrahydro)naphthyl]-coumarin,
4-Hydroxy-3-[1-indanyl]-coumarin,
4-Hydroxy-3-(1-phenylpropyl)-coumarin,
3-(1-(4-Bromophenyl)-2-methylpropyl)-4-hydroxycoumarin,
Butanoic acid, 2-(4-hydroxy-2-oxo-2H-1-benzopyran-3-yl)-, ethyl ester,
3-(1,2-Diphenylethyl)-4-hydroxycoumarin,
4-Hydroxy-3-(2,2-diphenylethyl)-coumarin,
3-(1,2-Diphenylethenyl)-4-hydroxycoumarin, Coumarin, 6-fluoro-4-hydroxy-3-(1-phenylpropyl)-, Coumarin, 3-[1-(4-bromophenyl)propyl]-4-hydroxy-, 3-(1'-(3-Bromophenyl)propyl)-4-hydroxycoumarin, Coumarin, 3-(.alpha.-ethylbenzyl)-4-hydroxy-7-(1-methylethoxy)-, and Coumarin, 7-ethoxy-3-(.alpha.-ethylbenzyl)-4-hydroxy-.

In addition, the present invention provides the following compounds:

The compound of the formula VII wherein $R_4$ is
 a) $C_mH_{2m+1}$, or
 b) cyclopropyl;

wherein $R_5$ is
 a) $-X_1-C_mH_{2m}-aryl$,
 b) $-X_1-C_mH_{2m}-Het$,
 c) $-X_1-CH=CH-aryl$,
 d) $-X_1-C_nH_{2n}-NH-C(O)-O-C_nH_{2n+1}$,
 e) $-X_1-C_tH_{2t+1}$,
 f) $-X_1-C_mH_{2m}-CH(NH-C(O)-O-C_nH_{2n+1})C_nH_{2n}-Het$, or
 g) $-X_1-C_nH_{2n}-halo$;

wherein $X_1$ is
 a) $-NHSO_2-$, or
 b) $-NHC(O)-$;

wherein m is zero (0) to four (4) inclusive;

wherein n is one (1) to four (4) inclusive;

wherein p is three (3) or four (4);

wherein t is three (3) or four (4);

wherein aryl is
 a) phenyl substituted by zero (0) to two (2) $R_6$, or
 b) naphthyl;

wherein Het is a 5- or 6-membered saturated or unsaturated ring containing from one (1) to three (3) heteroatoms selected from the group consisting of nitrogen, oxygen and sulfur; and including any bicyclic group in which any of the above heterocyclic rings is fused to a benzene ring or another heterocycle; and substituted by zero (0) to two (2) $R_7$;

and pharmaceutically acceptable salts thereof.

In particular, the present invention provides such compounds:

wherein aryl is phenyl;

wherein Het is
 a) imidazolyl,
 b) quinolinyl,
 c) benzothiadiazolyl,
 d) benzofurazanyl,
 e) thiophenyl,
 f) pyridinyl, or
 g) thiazolyl;

wherein $R_6$ is
 a) methyl,
 b) ethyl,
 c) $-Cl$,
 d) $-F$,
 e) $-Br$,
 f) $-I$,
 g) $-NO_2$,
 h) $-OCH_3$,
 i) $-CF_3$,
 j) $-CN$,
 k) $-COOH$,
 l) $-N=N-phenyl$,
 m) $-NH-OH$,
 n) $-N(CH_3)_2$,
 o) $-NH_2$,
 p) $-OCF_3$,
 q) $-CH_2-Br$,
 r) $-C(O)NH_2$,
 s) $-C(O)OCH_3$,
 t) $-OH$,
 u) the moiety of formula X,
 v) $-CH_2OH$,
 w) $-NH-(CH_2)_2-OH$,
 x) $-N((CH_2)_2-OH)_2$,
 y) $-NHSO_2-(CH_2)_3-Cl$,
 z) $-O[C_2H_4-O]_3-CH_3$,
 a1) $-NH-C(O)-CH_2-OH$,
 b1) $-SO_2-morpholino$,
 c1) $-SO_2-NH-CH_2-phenyl$, or
 d1) $-SO_2-NH-C_3H_7$;

wherein $R_7$ is
 a) methyl,
 b) $-SO_2-phenyl$,
 c) $-Cl$,
 d) $-Br$,
 e) isoxazolyl, or
 f) pyridinyl;

wherein $R_8$ is $-H$;

wherein u is three (3).

More particularly, the present invention provides the following compounds:

The compound of the formula VIII wherein $R_4$ is
 a) $C_mH_{2m+1}$, or
 b) cyclopropyl;

wherein $R_5$ is
 a) $-X_1-aryl$,
 b) $-X_1-Het$, or
 c) $-X_1-CH(NH-C(O)-O-C_nH_{2n+1})-CH_2-Het$;

wherein $X_1$ is
 a) $-NHSO_2-$, or
 b) $-NHC(O)-$;

wherein m is two (2) to four (4) inclusive;

wherein n is four (4);

wherein aryl is phenyl substituted by one (1) or two (2) $R_6$;

wherein Het is a 5- or 6-membered saturated or unsaturated ring containing from one (1) to three (3) heteroatoms selected from the group consisting of nitrogen, oxygen and sulfur; and including any bicyclic group in which any of the above heterocyclic rings is fused to a benzene ring or another heterocycle; and substituted by zero (0) or one (1) $R_7$;

and pharmaceutically acceptable salts thereof.

Most particularly, the present invention provides the following compounds:

The compound of the formula IX wherein $R_5$ is
 a) $-NHSO_2-aryl$, or
 b) $-NHSO_2-Het$;

wherein aryl is phenyl substituted by one (1) $R_6$;

wherein Het is a 5- or 6-membered saturated or unsaturated ring containing from one (1) to three (3) heteroatoms selected from the group consisting of nitrogen, oxygen and sulfur; and including any bicyclic group in which any of the above heterocyclic rings is fused to a benzene ring; and substituted by zero (0) or one (1) $R_7$;

and pharmaceutically acceptable salts thereof.

In particular the present invention provides such compounds:

wherein Het is
a) quinolinyl,
b) benzothiadiazolyl,
c) imidazolyl, or
d) thiazolyl;

wherein $R_6$ is
a) —CN,
b) —Cl,
c) —F,
d) —NHOH,
e) —C(O)NH$_2$,
f) —C(O)OCH$_3$,
g) the moiety of formula X,
h) —NHSO$_2$—(CH$_2$)$_3$—Cl,
i) —CH$_2$—OH, or
j) —N((CH$_2$)$_2$—OH)$_2$;

wherein $R_7$ is methyl;

wherein u is three (3);

and pharmaceutically acceptable salts thereof.

Also the present invention provides:

A method of inhibiting a retrovirus in a mammalian cell infected with said retrovirus which comprises treating said cell with an effective amount of a compound of the formula I wherein $R_{10}$ and $R_{20}$ taken together are
a) the moiety of formula II, or
b) the moiety of formula III, wherein $R_0$ is —H;

wherein $R_1$ is
a) —H,
b) —OC$_n$H$_{2n+1}$,
c) —F,
d) —NH$_2$—, or
e) —O—C$_n$H$_{2n}$—Het;

wherein $R_2$ is
a) —H,
b) —OC$_n$H$_{2n+1}$,
c) —CF$_3$,
d) —O—C$_n$H$_{2n}$—CH=CH$_2$, or
e) —O—C$_n$H$_{2n}$—Het;

or wherein $R_1$ and $R_2$ taken together are phenyl;

or wherein $R_0$ and $R_2$ taken together are phenyl;

wherein $R_3$ is
a) the moiety of formula IVA,
b) diphenylethyl-,
c) diphenylethenyl-,
d) —CH—(C$_3$-C$_6$ cycloalkyl)$_2$,
e) -5,6,7,8,9-tetrahydro-5H-benzocycloheptenyl,
f) -1,2,3,4-tetrahydro-naphthalenyl substituted by one (1) or two (2) —OC$_n$H$_{2n+1}$ or —CH$_3$,
g) —CH(C$_n$H$_{2n+1}$)—C(O)—O—C$_n$H$_{2n+1}$,
h) —CH(CH$_2$-phenyl)$_2$,
i) —C$_v$H$_{2v}$—CH(R$_4$)—C$_v$H$_{2v}$—Het—R$_5$,
j) —C$_v$H$_{2v}$—CH(R$_4$)—C$_v$H$_{2v}$—Het,
k) diphenylmethyl-,
l) diphenylpropyl-, or
m) phenylcyclobutyl-;

wherein $R_4$ is
a) —C$_m$H$_{2m+1}$,
b) —CH$_2$—C(O)—O—C$_n$H$_{2n+1}$,
c) —C$_3$-C$_6$ cycloalkyl,
d) —C$_n$H$_{2n}$—C$_3$-C$_6$ cycloalkyl, or
e) C$_2$-C$_6$ alkenyl;

wherein each $R_5$ is independently
a) —H,
b) —NH$_2$,
c) —C(O)—C$_n$H$_{2n+1}$,
d) (o-) or (m-) —O—C$_n$H$_{2n}$—CH=CH$_2$,
e) —C$_1$-C$_5$ alkoxy substituted on each carbon atom by zero (0) or one (1) hydroxy,
f) —O—C(O)—C$_n$H$_{2n+1}$,
g) —Br,
h) —CN,
i) —C$_m$H$_{2m}$—X$_1$—C$_r$H$_{2r+1}$,
j) —X$_1$—C$_n$H$_{2n}$—halo,
k) —X$_1$—C$_n$H$_{2n}$—NH$_2$,
l) —X$_1$—C$_n$H$_{2n}$—NH—C(O)—O—C$_n$H$_{2n+1}$,
m) —X$_1$—C$_n$H$_{2n}$—CH(NH—C(O)—O—C$_n$H$_{2n+1}$)C(O)—O—C$_n$H$_{2n+1}$,
n) —X$_1$—C$_m$H$_{2m}$—CH(NH—C(O)—O—C$_n$H$_{2n+1}$)C$_n$H$_{2n}$—Het,
o) —X$_1$—C$_n$H$_{2n}$—CH(NH$_2$)COOH,
p) —X$_1$—C$_n$H$_{2n}$—C(O)—O—C$_{2n}$H$_{2n+1}$,
q) —X$_1$—C$_n$H$_{2n}$—C$_3$-C$_6$ cycloalkyl,
r) —C$_m$H$_{2m}$—X$_1$—C$_m$H$_{2m}$—aryl,
s) —X$_1$—C$_m$H$_{2m}$—O—aryl,
t) —C$_m$H$_{2m}$—X$_1$—C$_m$H$_{2m}$—O—C$_n$H$_{2n+1}$,
u) —C$_m$H$_{2m}$—X$_1$—C$_m$H$_{2m}$—Het,
v) —X$_1$—C$_n$H$_{2n}$—C(O)—Het,
w) —X$_1$—C$_n$H$_{2n}$—C(O)—NH—C$_n$H$_{2n}$—Het,
x) —X$_1$—C$_n$H$_{2n}$—S—Het,
y) —C$_m$H$_{2m}$—X$_1$—O—C$_n$H$_{2n}$—aryl,
z) —C$_m$H$_{2m}$—X$_1$—O—C$_n$H$_{2n}$—Het,
a1) —X$_1$—H,
b1) —X$_1$—CH=CH$_2$,
c1) —X$_1$—CH=CH—aryl,
d1) —X$_1$—N(R$_{40}$)$_2$,
e1) —X$_1$—C$_n$H$_{2n}$—phthalimido,
f1) —X$_1$—(penta-fluoro)—phenyl,
g1) —X$_1$—C$_n$H$_{2n}$—bicyclo[2.2.1]heptane,
h1) —C$_u$—H$_{2u}$—R$_{30}$,
i1) —N=C—(NH—CH(C$_n$H$_{2n+1}$)$_2$)$_2$,
j1) —NH—P(O)(R$_9$)—aryl,
k1) —NH—P(O)(O—R$_{11}$)—aryl,
l1) —NH—C(S)—NH—R$_{42}$, or
m1) —NH—C(S)—CH$_2$—R$_{42}$;

wherein $X_1$ is
a) —NH—C(O)—,
b) —C(O)—NH—,
c) —NH—SO$_2$—,
d) —SO$_2$—NH—,
e) —NH—SO$_2$—NH—,
f) —C(O)—O—,
g) —O—C(O)—,
h) —N(C$_n$H$_{2n}$—aryl)—C(O)—,
i) —NH—C(O)—NH—,
j) —N(C$_n$H$_{2n}$—aryl)—SO$_2$—, or
k) —N(C$_m$H$_{2m}$—C$_n$H$_{2n+1}$)—SO$_2$—;

wherein m is zero (0) to five (5) inclusive;

wherein n is one (1) to five (5) inclusive;

wherein p is one (1) to eight (8) inclusive;

wherein q is zero (0) to five (5) inclusive;

wherein r is one (1) to eight (8) inclusive;

wherein s is one (1) to six (6) inclusive;

wherein t is one (1) to twelve (12) inclusive;

wherein u is two (2) to six (6) inclusive;

wherein v is zero (0) to two (2) inclusive;

wherein w is one (1) or two (2);
wherein aryl is
- a) phenyl substituted by zero (0) to three (3) $R_6$,
- b) naphthyl substituted by zero (0) to three (3) $R_6$, or
- c) biphenyl substituted by zero (0) to three (3) $R_6$;

wherein Het is a 5-, 6- or 7-membered saturated or unsaturated ring containing from one (1) to three (3) heteroatoms selected from the group consisting of nitrogen, oxygen and sulfur; and including any bicyclic group in which any of the above heterocyclic rings is fused to a benzene ring or mother heterocycle; and the ring may be connected through a carbon or secondary nitrogen in the ring or an exocyclic nitrogen; and if chemically feasible, the nitrogen and sulfur atoms may be in the oxidized forms; and if chemically feasible, the nitrogen atom may be in the protected form; and substituted by zero (0) to three (3) $R_7$;

wherein $R_6$ and $R_7$ are independently
- a) —$C_1$-$C_5$ alkyl, substituted by zero (0) to three (3) halo or substituted on each carbon atom by zero (0) or one (1) hydroxy,
- b) —OH,
- c) —$C_1$-$C_5$ alkyl—OH,
- d) —O—$C_1$-$C_5$ alkyl substituted by zero (0) to three (3) halo or substituted on each carbon atom by zero (0) or one (1) hydroxy,
- e) —O—$C_2$-$C_7$ alkenyl substituted by zero (0) or one (1) hydroxy,
- f) halo,
- g) —$NH_2$,
- h) —$NH_2$—$C_1$-$C_5$ alkyl,
- i) mono-or di-$C_1$-$C_5$ alkylamino,
- j) —NH—OH,
- k) —$N(C_nH_{2n}$—$OH)_2$,
- l) —C(O)—$NH_2$,
- m) —C(O)—$C_1$-$C_5$ alkyl,
- n) —CHO,
- o) —COOH,
- p) —$COX_2$,
- q) nitro,
- r) —CN,
- s) —$SO_3H$,
- t) —$SO_2NH_2$,
- u) —$SO_2$—$R_{42}$,
- v) —$NR_{40}$—$SO_2$—$R_{42}$,
- w) —$SO_2$—$NR_{40}R_{41}$,
- x) —$O[C_nH_{2n}O]_qC_nH_{2n+1}$,
- y) —C(O)—O—$C_nH_{2n+1}$,
- z) —$NR_{40}$—C(O)—$C_nH_{2n+1}$,
- a1) —$C_nH_{2n}$—$NR_{40}$—C(O)—$R_{41}$,
- b1) —N=N-phenyl substituted by zero (0) or one (1) —$N(C_nH_{2n+1})_2$,
- c1) isoxazolyl,
- d1) pyridinyl,
- e1) —$X_3$—$C_uH_{2u}$—$R_{30}$,
- f1) morpholino,
- g1) piperidino,
- h1) piperazino,
- i1) —$NR_{40}R_{41}$,
- j1) —$OR_{40}$,
- k1) the moiety of formula X,
- l1) —$C_nH_{2n}$—O—$C_nH_{2n}$—$OC_nH_{2n+1}$,
- m1) —N-methyl-piperazino,
- n1) —$SO_2$—morpholino,
- o1) —$SO_2$—piperazino,
- p1) —$SO_2$—N—methyl-piperazino,
- q1) —$SO_2$—piperidino, or
- r1) —$NR_{40}$—C(O)—$C_nH_{2n}$—O—$R_{41}$;

wherein $X_2$ is —$NR_{40}R_{41}$;
wherein $X_3$ is
- a) —O—,
- b) —$CH_2$—O—,
- c) —$SO_2NR_{40}$—,
- d) —$NR_{40}SO_2$—,
- e) —C(O)—,
- f) —C(O)$NR_{40}$—,
- g) —$NR_{40}$C(O), or
- h) —$NR_{40}$—;

wherein $R_8$ is
- a) —H,
- b) —$C_nH_{2n}$—phenyl substituted by zero (0) to three (3) $R_6$,
- c) —$C_nH_{2n}$—Het
- d) —$C_nH_{2n}$—$C_3$-$C_6$ cycloalkyl,
- e) —$C_r$—$H_{2r+1}$,
- f) —$C_n$—$H_{2n}$—CH=$CH_2$,
- g) —$C_sH_{2s+1}$ substituted by one (1) or two (2) hydroxy,
- h) —$CH_2$—epoxide,
- i) —$C_nH_{2n}$—oxiranyl,
- j) —($C_nH_{2n}$—O)$_n$—$C_nH_{2n+1}$,
- k) —C(O)—$C_sH_{2s+1}$, or
- l) —CH(OH)—$C_3$-$C_6$ cycloalkyl;

wherein $R_9$ is
- a) —$C_1$-$C_4$ alkyl, or
- b) aryl;

wherein $R_{11}$ is
- a) —H,
- b) —$C_1$-$C_4$ alkyl,
- c) aryl, or
- d) pharmaceutically acceptable salts;

wherein $R_{12}$ is
- a) $C_1$-$C_4$ alkyl,
- b) $C_1$-$C_3$ alkoxy,
- c) dimethylamino,
- d) diethylamino,
- e) $CF_3$,
- f) CN,
- g) halo,
- h) —$NH_2$,
- i) —OH,
- j) —$SO_2$—$NH_2$, or
- k) —C(O)—$NH_2$;

wherein $R_{30}$ is
- a) morpholino,
- b) piperidino,
- c) piperazino,
- d) —$NR_{40}R_{41}$,
- e) —$OR_{40}$,
- f) the moiety of formula X,
- g) —N—methyl-piperazino, or
- h) halo;

wherein $R_{40}$ and $R_{41}$ are independently
- a) —H,
- b) —$C_1$-$C_4$ alkyl,
- c) phenyl substituted by zero (0) to three (3) $R_{12}$, or
- d) —$C_nH_{2n}$—phenyl substituted by zero (0) to three (3) $R_{12}$;

wherein $R_{42}$ is
- a) $C_1$-$C_4$ alkyl,
- b) phenyl substituted by zero (0) to three (3) $R_{12}$, or
- c) —$C_nH_{2n}$—phenyl substituted by zero (0) to three (3) $R_{12}$;

provided that:

1) when $R_{10}$ and $R_{20}$ taken together are the moiety of formula II, and $R_1$ and $R_2$ are independently —H, —F, or —OC$_n$H$_{2n+1}$, and $R_3$ is the moiety of formula IVA, and $R_4$ is —C$_m$H$_{2m+1}$ or cyclohexyl, then $R_5$ is other than —H, —Br or —OC$_n$H$_{2n+1}$;

2) when $R_5$ is —C$_m$H$_{2m}$—X$_1$—O—C$_n$H$_{2n}$—aryl, —C$_m$H$_{2m}$—X$_1$—O—C$_n$H$_{2n}$—Het, or X$_1$—N(R$_{40}$)$_2$, X$_1$ is not —C(O)—NH—, —NHSO$_2$—, —SO$_2$—NH—, —NH—SO$_2$—NH—, —C(O)—O—, —NH—C(O)—NH—, —N(C$_n$H$_{2n}$—aryl)—SO$_2$—;

3) when $R_4$ in the moiety of formula IVA is —H, $R_5$ is a substituent containing X$_1$ wherein X$_1$ is —NHSO$_2$—;

4) when $R_5$ is —X$_1$—C$_m$H$_{2m}$—O—aryl or —C$_m$H$_{2m}$—X$_1$—C$_m$H$_{2m}$—O—C$_n$H$_{2n+1}$ and m is zero (0), then X$_1$ is not —C(O)—NH—, —NH—SO$_2$—, —SO$_2$—NH—, —NH—SO$_2$—NH—, —C(O)—O—, —NH—C(O)—NH—, —N—(C$_n$H$_{2n}$—aryl)—SO$_2$—, or —N(C$_m$H$_{2m}$—C$_n$H$_{2n+1}$)—SO$_2$—;

5) $R_4$ in the moiety of formula IVA is $C_2$–$C_6$ alkenyl only when $R_{10}$ and $R_{20}$ taken together are the moiety of formula III;

6) $R_3$ is diphenylethyl-, diphenylmethyl-, diphenylpropyl-, diphenylethenyl- or phenylcyclobutyl-, only when $R_{10}$ and $R_{20}$ taken together are the moiety of formula III; and 7) when $R_{10}$ and $R_{20}$ taken together are the moiety of formula II, and $R_1$ and $R_2$ are independently —H, —F, —OC$_n$H$_{2n+1}$ or —NH$_2$, $R_3$ is other than —CH(C$_n$H$_{2n+1}$)—C(O)—O—C$_n$H$_{2n+1}$;

and pharmaceutically acceptable salts thereof.

Finally, the present invention provides:

A process for making a compound of the formula XI wherein $R_6$ is as defined above which comprises:

a) reacting a compound of the formula XII with a compound of the formula XIII in a hydrocarbon solvent in the presence of a trialkylamine at an elevated temperature to yield a compound of the formula XIV;

b) hydrogenating the compound of formula XIV with a catalyst in an organic solvent to obtain a compound of the formula XV c) reacting the compound of formula XV with a benzenesulfonyl chloride of the formula XVI wherein $R_6$ is as defined above to yield the compound of formula XI.

This process is especially preferred for making compounds wherein $R_6$ is —F or —CN.

Especially preferred compounds of the present invention are those of formula I wherein $R_{10}$ and $R_{20}$ taken together are the moiety of formula III, wherein $R_3$ is the moiety of formula IV and wherein $R_5$ is a moiety containing X$_1$ wherein X$_1$ is —NHSO$_2$—.

The compounds of the present invention are named according to the IUPAC or CAS nomenclature system.

The carbon atoms content of various hydrocarbon-containing moieties is indicated by a prefix designating the minimum and maximum number of carbon atoms in the moiety, i.e., the prefix C$_i$–C$_j$ indicates a moiety of the integer "i" to the integer "j" carbon atoms, inclusive. Thus, for example, C$_1$–C$_3$ alkyl refers to alkyl of one to three carbon atoms, inclusive, or methyl, ethyl, propyl, and isopropyl, straight and branched forms thereof.

Also, the carbon atom content of various hydrocarbon-containing moieties of the present invention is indicated by a subscripted integer representing the number of carbon and hydrogen atoms in the moiety, e.g., "C$_n$H$_{2n}$" indicates a moiety of the integer "n" carbon atoms, inclusive, and the integer "2n" hydrogen atoms, inclusive. Thus, for example, "C$_n$H$_{2n}$" wherein n is one to three carbon atoms, inclusive, and two to six hydrogen atoms, inclusive, or methyl, ethyl, propyl and isopropyl, and all isomeric, straight and branched forms thereof.

Examples of alkyl of one to nine carbon atoms, inclusive, are methyl, ethyl, propyl, butyl, pentyl, hexyl, heptyl, octyl, and nonyl, and all isomeric forms thereof and straight and branched forms thereof.

Examples of alkenyl of one to five carbon atoms, inclusive, are ethenyl, propenyl, butenyl, pentenyl, all isomeric forms thereof, and straight and branched forms thereof.

By "halo" is meant the typical halogen atoms, such as fluorine, chlorine, bromine, and iodine.

The compounds of formula I of the present invention inhibit retroviral proteinases and thus inhibit the replication of the virus. They are useful for treating patients infected with human immunodeficiency virus (HIV) which results in acquired immunodeficiency syndrome (AIDS) and related diseases.

More particularly, the compounds of the present invention are useful as novel human retroviral protease inhibitors. Therefore, the compounds inhibit retroviral proteases and thus inhibit the replication of the virus. They are useful for treating human patients infected with a human retrovirus, such as human immunodeficiency virus (strains of HIV-1 or HIV-2) or human T-cell leukemia viruses (HTLV-I or HTLV-II) which results in acquired immunodeficiency syndrome (AIDS) and/or related diseases.

The capsid and replicative enzymes (i.e. protease, reverse transcriptase, integrase) of retroviruses are translated from the viral gag and pol genes as polyproteins that are further processed by the viral protease (PR) to the mature proteins found in the viral capsid and necessary for viral functions and replication. If the PR is absent or nonfunctional, the virus cannot replicate. The retroviral PR, such as HIV-I PR, has been found to be an aspartic protease with active site characteristics similar to those exhibited by the more complex aspartic protease, renin.

The term human retrovirus (HRV) includes human immunodeficiency virus type I, human immunodeficiency virus type II, or strains thereof, as well as human T cell leukemia virus 1 and 2 (HTLV-1 and HTLV-2) or strains apparent to one skilled in the art, which belong to the same or related viral families and which create similar physiological effects in humans as various human retroviruses.

Patients to be treated would be those individuals: 1) infected with one or more strains of a human retrovirus as determined by the presence of either measurable viral antibody or antigen in the serum and 2) in the case of HIV, having either an asymptomatic HIV infection or a symptomatic AIDS defining infection such as i) disseminated histoplasmosis, ii) isopsoriasis, iii) bronchial and pulmonary candidiasis including pneumocystic pneumonia iv) non-Hodgkin's lymphoma or v) Kaposi's sarcoma and being less than sixty years old; or having an absolute CD4+ lymphocyte count of less than 500/mm$^3$ in the peripheral blood. Treatment would consist of maintaining an inhibitory level of the compound used according to this invention in the patient at all times and would continue until the occurrence of a second symptomatic AIDS defining infection indicates alternate therapy is needed.

More specifically, an example of one such human retrovirus is the human immunodeficiency virus (HIV, also known as HTLV-III or LAV) which has been recognized as the causative agent in human acquired immunodeficiency syndrome (AIDS), P. Duesberg, Proc. Natl. Acad. Sci. USA, 86:755 (1989). HIV contains a retro viral encoded protease, HIV-I protease that cleaves the fusion polypeptides into the functional proteins of the mature viral particle, E. P. Lillehoj, et al., J. Virology, 62:3053 (1988); C. Debuck, et al., Proc. Natl. Acad. Sci., 84:8903 (1987). This enzyme, HIV-I protease, has been classified as an aspartyl protease and has a demonstrated homology to other aspartyl proteases such as renin, L. H. Pearl, et al., Nature 329:351 (1987); I. Katoh, et al., Nature 329:654 (1987). Inhibition of HIV-I protease blocks the replication of HIV and thus is useful in the treatment of human AIDS, E. D. Clerq, J. Med. Chem. 29:1561 (1986). Inhibitors of HIV-I protease are useful in the treatment of HIV-infected individuals who are asymptomatic or symptomatic of AIDS.

Pepstatin A, a general inhibitor of aspartyl proteases, has been disclosed as an inhibitor of HIV-I protease, S. Seelmeier, et al., Proc. Natl. Acad. Sci. USA, 85:6612 (1986). Other substrate derived inhibitors containing reduced bond isosteres or statine at the scissle position have also been disclosed, M. L. Moore, et al., Biochem. Biophys, Res. Commun. 159:420 (1989); S. Billich, et al., J. Biol. Chem. 263:17905 (1988); Sandoz, D. E. 3812-576-A.

Thus, the compounds of the present invention are useful for treating diseases caused by retroviruses, such as human acquired immunodeficiency disease syndrome (AIDS).

The compounds are also useful for treating non-human animals infected with a retrovirus, such as cats infected with feline leukemia virus. Other viruses that infect cats include, for example, feline infectious peritonitis virus, calicivirus, rabies virus, feline immunodeficiency virus, feline parvovirus (panleukopenia virus), and feline chlamydia. Exact dosages, forms and modes of administration of the compounds of the present invention to non-human animals would be apparent to one of ordinary skill in the art, such as a veterinarian.

The compounds of formula I of the present invention are prepared as described in the Charts, Preparations and Examples below, or are prepared by methods analogous thereto, which are readily known and available to one of ordinary skill in the art of organic synthesis.

CHART A

According to literature procedures (R. B. Silversman, *J. Am. Chem Soc.* 103:3910–3915, 1981; M. A. Stahmann, I. Wolff, K. P. Link, *J. Am. Chem Soc.* 65:2285–2287, 1943), diisopropyl carbodiimide mediated esterification and catalyzed by dimethylaminopyridine of commerically available ethyl salicylate of formula A-1 by appropriate carboxylic acids, specifically 4-phenylbutyric acid and 5-phenylvaleric acid, provides substrates of formula A-2 and A-4, respectively. Treatment with sodium hydride in refluxing benzene effects ring closure to the substituted 4-hydroxycoumarins of formula A-3 and A-5.

CHART B

According to literature procedures (G. Appendino, G. Cravotto, S. Tagliapietra, S. Ferraro, G. M. Nano, G. Palmisano, *HCA* 74:1451–1458, 1991), treatment of commercially available 4-hydroxycoumarin of formula B-1 with aldehydes of formula B-2, wherein R is naphthalene-2-yl, diphenylmethyl, or α-methylbenzyl, prepared as described in Chart C below, in ethanol with ethylenediamine diacetate (EDDA) catalyst, provides dimeric structures of formula B-3, wherein R is naphthalene-2-yl, diphenylmethyl, or α-methylbenzyl. The yield of this reaction is highly variable, probably due to differential solubility of the products which are generally isolated by filtration from the reaction mixture. Reductive cleavage of the dimers B-3 is accomplished with sodium cyanoborohydride in refluxing methanol to give compounds of formula B4a, B-4b, and B4c. Again, yields and reaction times are highly variable. The reactions are monitored by TLC, with further aliquots of sodium cyanoborohydride added over time as deemed necessary.

CHART C

The preparation of aldehydes of formula C-3 and C-6 necessary for the route of Chart B is illustrated in Chart C. 2-Nathaldehyde is commercially available. Commercially available Carboxylic acids of formula C-1 and C-4 can be derivatized as their methyl(N-methoxy) aides using bis(2-oxo-3-oxazolidinyl)phosphinic chloride as the coupling reagent. Reduction of these with lithium aluminum hydride in ether (J.-A. Fehrentz, B. Castro, *Synthesis* 676–678, 1983) smoothly provides aldehydes of formula C-3 and C-6.

CHART D

Chart D describes the direct alkylation of 4-hydroxycoumarin with various benzylic bromides at elevated temperatures according to literature procedures (C. H. Schroeder, E. D. Titus, K. P. Link, *J. Am. Chem. Soc.* 79:3291, 1957; L. R. Pohl, R. Haddock, W. A. Garland, W. F. Trager, *J. Med. Chem.* 18:513, 1975.). Treatment of commercially available 4-hydroxycoumarin of formula D-1 with (1-bromoethyl)-benzene of formula D-2 (wherein R is α-methyl benzyl) at 155° C. for 2 hours affords 4-hydroxy-3-(α-methylbenzyl)-coumarin of formula D-3 (wherein R is α-methylbenzyl). Additional compounds that may be prepared by this method are 4-Hydroxy-3-(2-methyl-1-phenylpropyl)-coumarin and 4-Hydroxy-3-(1,3-diphenylpropyl)-coumarin of formula D-3 (wherein R is 2-methyl-1-phenylpropyl or 1,3-diphenylpropyl, respectively). Direct alkylation appears to be limited in scope to groups that can withstand the rather harsh reaction conditions.

Chart D also describes the use of benzylic alcohols for the attachment of substituents to the 3-position of 4-hydroxycoumarin according to literature procedures (L. R. Pohl, R. Haddock, W. A. Garland, W. F. Trager, *J. Med. Chem.* 18:513, 1975; A. C. Jain, A. Kumar, P. C. Ray, *Indian J. Chem.* 25B:623, 1986). The reaction is Lewis acid catalyzed and typically employing boron trifluoride etherate. 3-(-Cyclopropylphenylmethyl)-4-hydroxycoumarin of formula D-3 (wherein R is cyclopropylphenylmethyl) is prepared in 50% yield by the reaction of α-cyclopropylbenzyl alcohol of formula D-4 (wherein R is cyclopropylphenylmethyl) with 4-hydroxycoumarin of formula D-5 in dioxane in the presence of a large excess of boron trifluoride etherate at room temperature overnight. The major by-product appears to be derived from elimination of starting benzylic alcohol under the reaction conditions. Most of the compounds of the present invention may be prepared by this method.

CHART E

3-Acetylbenzonitrile of formula E-1 is reacted with the anion of dimethyl tert-butoxycarbonyl methylphosphonate, using sodium hydride/benzene, to give the unsaturated ester of formula E-2 as a mixture of E and Z isomers. This diastereomeric mixture is hydrogenated using palladium on carbon as a catalyst in ethyl acetate to give the saturated compound of formula E-3. The nitrile function is then hydrolyzed with potassium hydroxide, using water-ethanol, to the corresponding acid as in compound of formula E-4. The free acidic functions are protected, using isobutylene and acid catalyst in methylene chloride, as the tert-butyl ester protecting groups as in compound of formula E-5. The ester enolate of compound of formula E-5, which is formed by treatment with lithium diisopropylamide, is reacted with methyl salicylate to give the Claisen condensation product of formula E-6. Treatment with trifluoroacetic acid effects hydrolysis of the tert-butyl ester protecting groups and also leads to the ring closure product of formula E-7.

The acid of formula E-7 can be condensed with a variety of amines, for example glycine tert-butyl ester, using diethylcyanophosphonate as a condensing agent, to give the corresponding amide final products (for example, 4-hydroxy-3-(1-(3-((((1,1-dimethylethoxycarbonyl)methyl)amino)carbonyl)phenyl)ethyl)-coumarin).

CHART F m-Nitropropiophenone is reacted with the anion of dimethyl tert-butoxycarbonyl methylphosphonate, using sodium hydride/benzene, to give the unsaturated ester of formula F-2 as a mixture of E and Z isomers. This diastereomeric mixture is hydrogenated using platinum on carbon as a catalyst (50 psi hydrogen gas, methanol) to give the corresponding saturated amino compound of formula F-3. The free amino function is protected by treatment with chlorotriphenylmethane and diisopropylethylamine to give the tritylated compound of formula F-4. The ester enolate of compound of formula F-4, which is formed by treatment with lithium diisopropylamide, is reacted with methyl salicylate to give the Claisen condensation product of formula F-5. Treatment with trifluoroacetic acid effects hydrolysis of the tert-butyl ester and the trityl protecting group, and also leads to the ring closure product of formula F-6.

The amine of formula F-6 can be condensed with a variety of carboxylic acids, for example Boc-β-alanine, using diethyl cyanophosphonate as a condensing agent, to give the corresponding amide final products (for example, 4-hydroxy-3-(1-(3-((3-((1,1-dimethylethoxycarbonyl)amino)-1-oxopropyl)amino)phenyl)propyl)-coumarin. Subsequent treatment with trifluoro acetic acid gives the corresponding free amine material (for example, 3-(1-(3-((3-amino-1-oxopropyl)amino)phenyl)propyl)-4-hydroxycoumarin, trifluoroacetate).

CHART G

Addition of ethylmagnesium bromide to 3-hydroxy benzaldehyde gives the compound of formula G-2, which can be alkylated with allyl bromide to give the compound of formula G-3. Reaction between 4-hydroxycoumarin and the compound of formula G-3 using boron trifluoride etherate as an acidic catalyst gives the compound of formula G-4 (for example, 3-(1'-(3-Allyloxyphenyl)propyl)-4-hydroxycoumarin.

The compound of formula G-4 can be di-hydroxylated using osmium tetroxide to give the compound of formula G-5 (3-(1'-(3-((2,3-dihydroxy)propyloxy)phenyl)propyl)-4-hydroxycoumarin).

CHART H

Treatment of 1-(4-hydroxyphenyl)propanol of formula H-1 with acetic anhydride in pyridine gives the compound of formula H-2, which upon reaction with the cesium salt of 4-hydroxycoumarin gives the compound of formula H-3 (3-(1'-(4-Acetoxyphenyl)propyl)-4-hydroxycoumarin).

CHART I

Reaction of 4-hydroxycoumarin with 3-phenyl-2-propyn-1-ol of formula I-1 in the presence of diethylazodicarboxylate and triphenylphosphine gives the compound of formula of I-2, which is partially reduced with hydrogen gas and Lindlar's catalyst to give the compound of formula I-3. Heating of the compound of formula I-3 in o-xylene at 145° C. gives the compound of formula I-4 (4-Hydroxy-3-(1-phenyl-2-propenyl)-coumarin).

CHART J

Preparation of the compounds of the present invention of formula J-3 (wherein $R_1$ is ethyl, $R_2$ is phenyl; $R_1$ is cyclopropyl, $R_2$ is phenyl; $R_1$ is cyclopropyl, $R_2$ is cyclopropyl; $R_1$ is cyclopropyl, $R_2$ is m-(NHCO$_2$benzyl)phenyl; $R_1$ is benzyl, $R_2$ is benzyl; wherein n is 4) has proceeded by alkylation of known pyrone intermediates of formula J-1 (wherein n is 4) with secondary alcohols of formula J-2 (wherein $R_1$ and $R_2$ are the same as for formula J-3) in the presence of p-toluenesulfonic acid, as outlined in Chart J. Pyrones of formula J-1 (wherein n is 4) are prepared by acylation of trimethylsilyl enol ethers with malonyl dichloride as described in R. Effenberger, T. Ziegler, K.-H. Schonwalder, T. Kesmarszky, B. Bauer, Chem. Ber. 119:3394–3404 (1986). The alcohols of formula J-2 (wherein $R_1$ is ethyl, $R_2$ is phenyl; $R_1$ is cyclopropyl, $R_2$ is phenyl; $R_1$ and $R_2$ are each cyclopropyl) are commercially available. The alcohols of formula J-2 (wherein $R_1$ is cyclopropyl, $R_2$ is m-(NHCO$_2$benzyl)phenyl; $R_1$ and $R_2$ are each benzyl) are prepared as described in the Preparations below. In most cases, an excess of the alcohol is used to drive the alkylation, and water is removed either by refluxing the reaction mixture through a column of molecular sieves or by adding sieves directly to the reaction mixture. In a couple of cases, 3-(dicyclopropylmethyl)-5,6,7,8,9,10-hexahydro-4-hydroxy-2H-cycloocta[b]pyran-2-one and [3-[cyclopropyl(5,6,7,8,9,10-hexahydro-4-hydroxy-2-oxo-2H-cycloocta[b]pyran-3-yl)methyl]phenyl]-carbamic acid, phenylmethyl ester, reaction conditions are altered slightly. For 3-(dicyclopropylmethyl)-5,6,7,8,9,10-hexahydro-4-hydroxy-2H-cycloocta[b]pyran-2-one (n is 4, $R_1$ and $R_2$ are cyclopropyl), a shorter reaction time is used because of the instability of the product under reaction conditions. In the case of [3-[cyclopropyl(5,6,7,8,9,10-hexahydro-4-hydroxy-2-oxo-2H-cycloocta[b]pyran-3-yl)methyl]phenyl]-carbamic acid, phenylmethyl ester, (n is 4, $R_1$ is cyclopropyl, $R_2$ is m-(NHCO$_2$benzyl)phenyl), a slight excess of pyrone is used since the alcohol is not commercially available.

CHART K

As shown in Chart K, the benzyloxycarbonyl protective group on [3-[cyclopropyl(5,6,7,8,9,10-hexahydro-4-hydroxy-2-oxo-2H-cycloocta[b]pyran-3-yl)methyl]phenyl]-carbamic acid, phenylmethyl ester, of formula K-1 is readily removed via catalytic hydrogenation in a solvent such as methanol. The product of this reaction, the free amine of formula K-2, is used in a coupling reaction with N-t-BOC-β-alanine/diisopropylcarbodiimide in methylene chloride. The only product under these conditions, is N-(3-(cyclopropyl-(4-hydroxy-2-oxo-5,6,7,8,9,10-hexahydro-2H-cyclooctal[b]pyran-3-yl)-methyl)-phenyl)-N',N''-diisopropylguanidine of formula K-3, the adduct of the compound of formula K-2 and the DIC coupling reagent.

CHART L

Analogs made from the 3-(cyclopropylphenylmethyl)-5,6,7,8,9,10-hexahydro-4-hydroxy-2H-cycloocta[b]pyran-2-one template have a variety of substituents at the 6-alpha position of the pyrone. Substitution at this position can be achieved in moderate to good yields by trapping the dianion of 3-(cyclopropylphenylmethyl)-5,6,7,8,9,10-hexahydro-4-hydroxy-2H-cycloocta[b]pyran-2-one of formula L-1 (wherein n is 4, $R_1$ is cyclopropyl) (formed with 2.4 eq of LDA) with an alkylating agent, a strategy which also works well for the analogs with 6- and 7-membered rings, 3-(cyclopropylphenylmethyl)-6,7,8,9-tetrahydro-4-hydroxycyclohepta[b]pyran-2(5H)-one of formula L-1 (wherein n is 3, $R_1$ is cyclopropyl) and 5,6,7,8-tetrahydro-4-hydroxy-3-(1-phenylpropyl)-2H-1-benzopyran-2-one of formula L-1 (wherein n is 2, $R_1$ is ethyl).

An aldehyde may be used to trap the dianion intermediate of the compound of formula L-1 (wherein $R_1$ is cyclopropyl, n is 4) and form the analog with a hydroxyl group alpha to the cyclooctyl ring, 3-(cyclopropyl-phenyl-methyl)-4-hydroxy-10-(1-hydroxy-propyl)-5,6,7,8,9,10-hexahydro-cycloocta[b]pyran-2-one of formula L-2 (wherein $R_1$ is cyclopropyl, $R_2$ is —CH(OH)CH$_2$CH$_3$, n is 4). When 1,4-diiodobutane is used as an alkylating agent for the compound of formula L-1 (wherein $R_1$ is cyclopropyl, n is 3), 9-but-3-enyl-3-(cyclopropyl-phenyl-methyl)-4-hydroxy-6,7,8,9-tetrahydro-5H-cyclohepta[b]pyran-2-one of formula L-2 (wherein $R_1$ is cyclopropyl, $R_2$ is —(CH$_2$)$_2$—CH=CH$_2$, n is 3) which has 3-butene at the 6-alpha position, may be isolated. In this case, three equivalents of LDA are used, and it appears that monoalkylation is followed by elimination.

Following analogous procedures, 8-cyclopropylmethyl-4-hydroxy-3-(1-phenyl-propyl)-5,6,7,8-tetrahydro-chromen-2-one of formula L-2 (wherein $R_1$ is ethyl, $R_2$ is —CH$_2$-cyclopropyl, n is 2) may be obtained from the compound of formula L-1 (wherein $R_1$ is ethyl, n is 2); and 10-cyclopropylmethyl-3-(cyclopropyl-phenyl-methyl)-4-hydroxy-5,6,7,8,9,10-hexahydrocycloocta[b]pyran-2-one of formula L-2 (wherein $R_1$ is cyclopropyl, $R_2$ is —CH$_2$-cyclopropyl, n is 4) may be obtained from the compound of formula L-1 (wherein $R_1$ is cyclopropyl, n is 4).

CHART M

The preferred procedure for the preparation of the compound of formula M-7 (which is also the compound of formula K-2 in Chart K) is described in Chart M.

Nitration of cyclopropylphenyl ketone of formula M-1 with fuming nitric acid at –40° C. produces a ca. 2:1 mixture of isomers. The desired meta-nitro compound of formula M-2 is easily separated from the crude mixture by recrystallization from methanol. Catalytic hydrogenation of cyclopropyl-(3-nitrophenyl)methanone of formula M-2 with 10% platinum on carbon in methanol at 0° C. provides the aniline of formula M-3. The product is isolated by filtration and concentration. The amino group is then protected using benzyl chloroformate and diisopropylethylamine in methylene chloride to give the ketone of formula M-4. The ketone is then reduced with sodium borohydride in 5:1 THF and ethanol to give the alcohol of formula M-5.

The compound of formula M-5 is then used to alkylate the known cyclooctylpyranone of formula J-1 wherein n is four, which is prepared in Chart J, R. Effenberger, T. Ziegler, K.-H. Schönzoalder, T. Kesmarsky, B. Bauer, Chem. Ber. 119:3394–3404 (1986), to give the compound of formula M-6 which is also the compound of formula K-1 of Chart K.

The preferred conditions for this alkylation reaction are p-toluene-sulfonic acid in refluxing methylene chloride with a Soxhlet extractor containing molecular sieves. Finally, the compound of formula M-7, which is also the compound of formula K-2 of Chart K, is obtained by cleaving the benzyl protective group in a transfer hydrogenation. Best results for this reactions are achieved with 10% Pd/C in neat cyclohexene.

CHART N

The starting compound of formula N-1, which is also the compound of formula M-7 in Chart M, is converted to the final compound of formula N-2 wherein $R_1$ is, e.g., 2-N-t-BOC-ethylamine by coupling with N-t-BOC-β-alanine. The use of bis(2-oxo-3-oxazolidinyl)phosphinic chloride as a coupling reagent with triethylamine in methylene chloride at room temperature gives compounds of the formula N-2 in good yields. A number of analogs of the formula N-2 can be made using other commercially available N-t-BOC amino acids, and compounds of the formula N-2 wherein $R_1$ is an aryl group can be made using commercially available aryl carboxylic acids. Also, the compound of formula N-2 wherein $R_1$ is naphthalene is prepared from the amine of formula N-1, and 1-naphthoic acid using bis(2-oxo-3-oxazolidinyl)phosphinic chloride as the coupling reagent.

CHART O

The tosyl protective group of the compound of formula O-1, prepared in Chart N above, is removed with hydroxybenztriazole in THF to obtain the compound of the formula O-2.

CHART P

A pair of m-amide compounds of the formula P-2 wherein $R_1$ is 2-N-t-BOC-ethylamine or 2-ethylindole are prepared from the seven-membered cycloalkylpyranone of formula P-1 prepared as the compound of formula CC-4 in Chart CC and the appropriate carboxylic acid using bis(2-oxo-3-oxazolidinyl)phosphinic chloride and triethylamine in methylene chloride. Compounds of the formula P-2 are formed in good yields at room temperature.

CHART Q

The compound of formula Q-2, having two substituents on the m-amine, is prepared from the compound of formula Q-1, prepared as the compound of formula BB-2 wherein $R_{62}$ is benzyl in Chart BB. The reaction is carried out by coupling the benzyl amine of formula Q-2 with N-t-BOC-glycine using bis(2-oxo-3-oxazolidinyl)phosphinic chloride and triethylamine in methylene chloride at room temperature.

CHART R

The compound of formula R-3 is prepared from the compounds of formula R-1, a known cyclooctylpyranone (prepared as described in Chart J, see formula J-1, wherein n is 4), and formula R-2, which is prepared in Preparation 53 below from propiophenone in the same fashion as the compound of formula M-5 (see Chart M). This alkylation reaction takes place in refluxing toluene with p-toluenesulfonic acid and gives the compound of formula R-3 in moderate yield. Cleavage of the benzyloxy protecting group is achieved with 10% Pd/C in 1:1 cyclohexene-ethanol to give the compound of the formula R-4, an analog of the compound of formula M-7 in Chart M. This amine compound is then reacted with aryl sulfonyl chlorides to obtain the compounds of formula R-5 wherein $R_1$ is, e.g., a cyano or chloro group. Also the compound of formula R-4 is coupled with N-t-BOC-β-alanine using bis(2-oxo-3-oxazolidinyl)phosphinic chloride and triethylamine in methylene chloride to give the compound of formula R-6. Finally, this amide compound is converted to the hydrochloride salt of the formula R-7 with ethereal HCl.

CHART S

The compound of formula S-1, which is also the compound of formula M-7 in Chart M, is reacted with phenyl or ethyl isocyanate in acetonitrile to obtain the compound of formula S-2, wherein $R_1$ is phenyl or ethyl.

CHART T

The m-carbamate compounds of the formula T-2 wherein $R_1$ is phenyl or ethyl are prepared from the compound of formula T-1, which is also the compound of formula M-7 in Chart M, using phenyl or ethyl chloroformate in pyridine.

CHART U

The compound of formula U-1, a known cyclooctylpyranone (see formula J-1 wherein n is 4) is alkylated with the compound of formula U-2 wherein $R_1$ is an alkyl group such as isopropyl, propyl, isobutyl or butyl prepared by sodium brohydride reduction of the corresponding commercially available ketone as described in Preparation 54. The alkylation reaction, which takes place in refluxing toluene with p-toluenesulfonic acid gives compounds of the formula U-3 wherein $R_1$ is, e.g., isopropyl or propyl.

CHART V

The compound of the formula V-1, which is also the compound of formula M-7 in Chart M, is reacted with, e.g., phenyl or ethyl thioisocyanate in acetonitrile to obtain the compound of formula V-2, wherein $R_1$ is, e.g., phenyl or ethyl.

CHART W

The compound of the formula W-1, which is also the compound of the formula N-2 where $R_1$ is benzyl in Chart N, is converted to the sulfur analog of the formula W-2 using Lawesson's reagent in refluxing toluene.

CHART X

The compound of formula X-3 is prepared from the compounds of formula X-1, a known cyclooctylpyranone (see formula J-1 wherein n is 4), and formula X-2, which is prepared in Preparation 62 below from isobutyrophenone in the same fashion as the compound of formula M-5 (see Chart M). The alkylation reaction is carried out in refluxing toluene with p-toluenesulfonic acid. The benzyloxy protecting group is then cleaved to give the amine of the formula X-4 using 10% Pd/C in 1:1 cyclohexene-ethanol. This amine compound is then reacted with aryl sulfonyl chlorides to obtain the compounds of formula X-5 wherein $R_1$ is. e.g., 4-chlorobenzene, 4-cyanobenzene, or N-methyl-imidazole.

CHART Y

The commercially available amine of the formula Y-1 is protected using benzyl chloroformate and sodium bicarbonate in THF/water solution to give the compound of the formula Y-2. The aldehyde of formula Y-2 is then reacted with a Grignard reagent to give the secondary alcohol of formula Y-3, wherein $R_1$ can be a number of alkyl groups, including propyl, cyclopropyl, isopropyl, butyl, isobutyl, and allyl. The alcohol of formula Y-3 is then used to alkylate the known cyclooctylpyranone of formula Y-4, which is the same as formula J-1 wherein n is 4, in refluxing toluene and p-toluenesulfonic acid to obtain the compound of the formula Y-5. The benzyloxy protecting group is then cleaved using 10% Pd/C in cyclohexene to give the amine of formula Y-6, which is reacted with aryl sulfonyl chlorides to give the compounds of the formula Y-7, wherein $R_1$ is an alkyl group, and $R_2$ is, e.g., 4-chlorobenzenyl or 4-cyanobenzenyl.

CHART Z

Treatment of the amine of formula Z-1 with sulfonyl chlorides and a base such as pyridine in dichloromethane gives the sulfonamides of formula Z-2 wherein $R_{60}$ is, for example, 4-nitrophenyl. These sulfonamides are further modified by standard literature procedures as is apparent to those of ordinary skill in the art to give sulfonamides of formula Z-3 wherein $R_{61}$ is, for example, 4-aminophenyl and other functional groups that are not readily available from readily available sulfonyl chlorides. For example, the nitro group of N-[3-[cyclopropyl(5,6,7,8,9,10-hexahydro-4-hydroxy-2-oxo-2H-cycloocta[b]pyran-3-yl)methyl]phenyl]-4-nitro-benzenesulfonamide is reduced by catalytic hydrogenation in ethyl acetate with palladium on carbon to give the amine in 4-amino-N-[3-[cyclopropyl(5,6,7,8,9,10-hexahydro-4-hydroxy-2-oxo-2H-cycloocta[b]pyran-3-yl) methyl]phenyl]-benzenesulfonamide. Also, the carboxylic acid of 3-[[[3-[cyclopropyl(5,6,7,8,9,10-hexahydro-4-hydroxy-2-oxo-2H-cycloocta[b]pyran-3-yl)methyl]phenyl]amino]sulfonyl]-benzoic acid is esterified with methanol and catalytic sulfuric acid to give the methyl ester in 3-[[[3-[cyclopropyl(5,6,7,8,9,10-hexahydro-4-hydroxy-2-oxo-2H-cycloocta[b]pyran-3-yl)methyl]phenyl]amino] sulfonyl]-benzoic acid, methyl ester. Sulfonamides of formula Z-3 are also obtained from compounds of formula Z-2 by further elaboration of reactive functional groups. For example, the amine of 3-amino-N-[3-[cyclopropyl(5,6,7,8, 9,10-hexahydro-4-hydroxy-2-oxo-2H-cycloocta[b]pyran-3-yl)methyl]phenyl]-benzenesulfonamide is reacted with benzoyl chloride and a base such as pyridine to give the benzamide in N-[3-[[[3-[cyclopropyl(5,6,7,8,9,10-hexahydro-4-hydroxy-2-oxo-2H-cycloocta[b]pyran-3-yl) methyl]phenyl]amino]sulfonyl]henyl]-benzamide. Using commonly available sulfonyl chlorides, additional compounds of the present invention of formula I, wherein $R_{10}$ and $R_{20}$ is the moiety of formula III, are prepared wherein $R_5$ is substituent i) through gl) and $X_1$ is —NH—$SO_2$—.

CHART AA

Chart AA illustrates the chromatographic separation of the enantiomers of the compound of formula AA-1 by chiral HPLC. The protecting group of the separated enantiomers (formula AA-2 and AA-5) is removed by catalytic hydrogenation to give the enantiomerically pure amines of formula AA-3 and AA-6. AA-3 and AA-6 are then individually reacted with sulfonyl chlorides and a base such as pyridine to give sulfonamides AA-4 and AA-7, wherein $R_{60}$ is for example 4-fluorophenyl. Using commonly available sulfonyl chlorides, additional compounds of the present invention of formula I, wherein $R_{10}$ and $R_{20}$ is the moiety of formula III, are prepared wherein $R_5$ is i) through gl) and $X_1$ is —NH—$SO_2$—.

CHART BB

The preparation of amines of formula BB-2 is illustrated in Chart BB. Condensation of an amine BB-1 with aldehydes, such as benzaldehyde or phenethylaldehyde, followed by reduction of the resulting imine with sodium borohydride gives N-alkyl amines of formula BB-2 wherein $R_{62}$ is, for example, benzyl. Chart BB also describes the sulfonation of the N-alkyl amines of formula BB-2 by reaction with commonly available sulfonyl chlorides catalyzed by a base such as pyridine to give sulfonamides of formula BB-3 wherein $R_{61}$ is, for example, alkyl, aryl, or substituted aryl and $R_{62}$ is, for example, benzyl or alkyl.

CHART CC

A preparation of the amines of formula CC-5 is illustrated in Chart CC. Treatment of the compound of formula CC-2 with the compound of formula CC-1 in toluene at room temperature with p-toluene sulfonic acid added gives the Cbz protected cycloheptapyrane of formula CC-3, which, after deprotection by standard literature procedures gives the amine of formula CC-4. Treatment of the amine with a sulfonyl chloride and a base, such as pyridine, in dichloromethane gives the sulfonamides of formula CC-5 wherein $R_{60}$ is, e.g., 4-cyanophenyl.

CHART DD

Chart DD illustrates the hydrolysis of the cyano group in the compound of formula DD-1. Hydrolysis of this compound in DMSO with potassium carbonate and aqueous hydrogen peroxide gives the amide of formula DD-2.

CHART EE

Treatment of the compound of formula EE-1 with an amine, such as morpholine, in refluxing acetonitrile, with sodium iodide added, gives both the cyclized product, of formula EE-2 and the morpholinepropylsulfonamide of formula EE-3 and its hydrogen iodide salt of formula EE-4.

CHART FF

Commercially available cyclopropyl thien-2-yl carbinol of formula FF-1 is reacted with the pyrone of formula FF-2 in methylene chloride in the presence of catalytic trifluoroacetic acid (TFA) to afford the compound 3-(alpha-cyclopropyl thien-2-ylmethyl)-4-hydroxy-5,6,7,8,9,10-hexahydrocycloocta[b]pyran-2-one of formula FF-3.

CHART GG

Commercially available thiophene 2-carboxaldehyde of formula GG-1 is treated with ethyl magnesium bromide in ether below room temperature to yield carbinol of formula GG-2. Treatment of a mixture of formula GG-2 and the pyrone of formula GG-3 in methylene chloride with catalytic TFA then affords the compound of formula GG-4, 3-(alpha-ethylthien-2-ylmethyl)4-hydroxy-5,6,7,8,9,10-hexahydrocycloocta[b]pyran-2-one.

CHART HH

Commercially available 5-methyl 2-carboxaldethiopene of formula HH-1 is treated with ethyl magnesium bromide in ether below room temperature to yield carbinol of formula HH-2. Treatment of a mixture of the carbinol of formula HH-2 and the pyrone of formula HH-3 in methylene chloride with catalytic TFA then affords 3-(alpha-ethyl-(5-methylthien-2-ylmethyl)-4-hydroxy-5,6, 7,8,9,10-hexahydrocycloocta[b]pyran-2-one, the compound of formula HH-4.

CHART II

Commercially available benzothiophene of formula II-1 is treated with n-butyl lithium in THF below more temperature. Cyclopropane carboxaldehyde is added to the above solution to yield carbinol of formula II-2. Treatment of a mixture of formula II-2 and the pyrone of formula II-3 in methylene chloride with catalytic TFA then affords 3-(alpha-ethyl benzothien-2-ylmethyl)-4-hydroxy-5,6,7,8,9,10-hexahydrocycloocta[b]pyran-2-one, the compound of formula II-4.

CHART JJ

Commercially available furfur-2-yl alcohol of formula JJ-1 is treated with two equivalents of n-butyl lithium in THF below room temperature. Cyclopropane carboxaldehyde is added and the reaction quenched with dilute acid. This affords the diol of formula JJ-2. Treatment of a mixture of the diol of formula JJ-2 and the pyrone of formula JJ-3 with catalytic TFA in methylene chloride at room temperature affords the compound, 3-(alpha-cyclopropyl (5-hydroxymethylfurfur-2-yl)-4-hydroxy-5,6,7,8,9,10-hexahydrocycloocta[b]pyran-2-one, of formula JJ-4.

CHART KK

Commercially available 2-thiophene methanol of formula KK-1 is treated with two equivalents of n-butyl lithium in THF below room temperature. Cyclopropane carboxaldehyde is added and the reaction quenched with dilute acid. This affords the diol of formula KK-2. Treatment of a mixture of the diol of formula KK-2 and the pyrone of formula KK-3 with catalytic TFA in methylene chloride at room temperature affords the compound, 3-(alpha-cyclopropyl (5-hydroxymethylthien-2-ylmethyl)-4-hydroxy-5,6,7,8,9,10 -hexahydrocycloocta[b]pyran-2-one, of formula KK-4.

CHART LL

Commercially available 2-thiophene ethanol of formula LL-1 is treated with two equivalents of n-butyl lithium in THF below room temperature. Cyclopropane carboxaldehyde is added and the reaction quenched with dilute acid. This affords the diol of formula LL-2. Treatment of a mixture of the diol of formula LL-2 and the pyrone of formula LL-3 with catalytic TFA in methylene chloride at room temperature affords the compound, 3-(alpha-cyclopropyl (5-(2-hydroxyethyl)thien-2-ylmethyl)-4-hydroxy-5,6,7,8,9,10-hexahydrocycloocta[b]pyran-2-one, of formula LL-4.

CHART MM

The compound of formula MM-2 is prepared from commercially available furfuryl alcohol of formula MM-1 as described in Bull. Chem. Soc. Jpn., 65(9), 1992 and Zh. Org. Khim., 25(4), 843–6 (Russ), 1989. The compound of formula MM-2 is treated with n-butyl lithium followed by the addition of cyclopropane carboxaldehyde to yield the compound of formula MM-3. A mixture of the compound of formula MM-3 and the pyrone of formula MM-4 is treated with catalytic TFA in methylene chloride to yield the compound, 3-(α-cyclopropyl (5-(2-hydroxymethyl (methoxymethylether)furfur-2-yl)-4-hydroxy-5,6,7,8,9,10-hexahydrocycloocta[b]pyran-2-one, of formula MM-5.

CHART NN

The compound of formula NN-2 is prepared from commercially available thiophene 2-methanol of formula NN-1 as described in Bull. Chem. Soc. Jpn., 65(9), 1992 and Zh. Org. Khim., 25(4), 843–6 (Russ), 1989. The compound of formula NN-2 is treated with n-butyl lithium followed by the addition of cyclopropyl carboxaldehyde to yield the compound of formula NN-3. A mixture of the compound of formula NN-3 and the pyrone of formula NN-4 is treated with catalytic TFA in methylene chloride to yield the compound, 3-(α-cyclopropyl (5-(2-hydroxymethyl (methoxymethylether)thien-2-ylmethyl)-4-hydroxy-5,6,7,8, 9,10-hexahydrocycloocta[b]pyran-2-one, of formula NN-5.

CHART OO

Carbobenzyloxy chloride is added to a saturated solution of NaHCO₃ containing furfurylamine of formula OO-1 with vigorous stirring. After extraction with ether the product of formula OO-2 is isolated by removal of solvent in vacuo. A mixture of the compound of formula OO-2 and cyclopropylcarbonyl chloride in methylene chloride is treated with excess aluminum chloride. This yields the compound of formula OO-3. The compound of formula OO-3 is treated with NaBH4 in an ethanol/THF mixture followed by an acid work up to yield the compound of formula OO-4. Treatment of a mixture of the compound of formula OO-4 and the pyrone of formula OO-5 with TFA in methylene chloride affords the title compound 3 -(alpha-cyclopropyl (5-(N-carbobenzoxyphenyl)aminomethyl)furfur-2-yl)-4-hydroxy-5,6,7,8,9,10-hexahydrocycloocta[b]pyran-2-one of formula OO-6.

CHART PP

Carbobenzyloxy chloride is added to a saturated solution of NaHCO3 containing 2-thienylamine of formula PP-1 with vigorous stirring. After extraction with ether the product of formula PP-2 is isolated by removal of solvent in vacuo. A mixture of the compound of formula PP-2 and cyclopropylcarbonyl chloride in methylene chloride is treated with excess aluminum chloride. This yields the compound of formula PP-3. The compound of formula PP-3 is treated with NaBH4 in an ethanol/THF mixture followed by an acid work up to yield the ether of formula PP-4. Treatment of a mixture of the compound of formula PP-4 and the pyrone of formula PP-5 with TFA in methylene chloride affords the compound, 3-(alpha-cyclopropyl (5-(N-carbobenzoxyphenyl)aminomethyl)thien-2-ylmethyl)-4-hydroxy-5,6,7,8,9,10-hexahydrocycloocta[b]pyran-2-one, of formula PP-6.

CHART QQ

Commercially available furfurylamine of formula QQ-1 is treated with two equivalents of n-butyl lithium in THF below room temperature. To that solution is added cyclopropane carboxaldehyde which affords the amino alcohol of formula QQ-2. Treatment of a mixture of the alcohol of formula QQ-2 and 4-fluorobenzenesulfonylchloride in methylene chloride with triethylamine affords the sulfonamide of formula QQ-3. Treatment of a mixture of the compound of formula QQ-3 and the pyrone of formula XX-4 with catalytic TFA in methylene chloride affords the compound 4-fluoro-N-[5-[cyclopropyl(5,6,7,8,9,10-hexahydro-4-hydroxy-oxo-2H-cycloocta[b]pyran-3-yl)methyl]furfur-2-yl]benzenesulfonamide of formula QQ-5.

CHART RR

Treatment of a mixture of the compound of formula RR-1 and 4-cyanobenzenesulfonylchloride in methylene chloride with triethylamine affords the sulfonamide of formula RR-2. Treatment of a mixture of the compound of formula RR-2 and the pyrone of formula RR-3 with catalytic TFA in methylene chloride affords the compound, 4-cyano-N-[5-[cyclopropyl(5,6,7,8,9,10-hexahydro-4-hydroxy-oxo-2H-cycloocta[b]pyran-3-yl)methyl]furfur-2-yl] benzenesulfonamide, of formula RR-4.

CHART SS

Commercially available 2-thienylamine of formula SS-1 is treated with two equivalents of n-butyl lithium in THF below room temperature. To that solution is added cyclopropane carboxaldehyde which affords the amino alcohol of formula SS-2. Treatment of a mixture of the compound of formula SS-2 and 4-fluorobenzenesulfonylchloride in methylene chloride with triethylamine affords the sulfonamide of formula SS-3. Treatment of a mixture of the compound of formula SS-3 and the pyrone of formula SS-4 with catalytic TFA in methylene chloride affords the compound, 4-fluoro-N-[5-[cyclopropyl(5,6,7,8,9,10-hexahydro-4-hydroxy-oxo-2-2H-cycloocta[b]pyran-3-yl)methyl]thien-2-yl] benzenesulfonamide, of formula SS-5.

CHART TT

Treatment of a mixture of the compound of formula TT-1 and 4-cyanobenzenesulfonylchloride in methylene chloride with triethylamine affords the sulfonamide of formula TT-2. Treatment of a mixture of the compound of formula TT-2 and the pyrone of formula TT-3 with catalytic TFA in methylene chloride affords the compound, N-[3-[cyclopropyl(5,6,7,8,9,10-hexhydro-4-hydroxy-2-oxo-2H-cycloocta[b]pyran-3-yl)methyl]thien-2-ylmethyl]4-cyanobenzenesulfonamide, of formula TT4.

CHART UU

Treatment of commercially available 2-thienylmethanol of formula UU-1 with two equivalents of n-butyl lithium followed by the addition of methyl iodide, then addition of another equivalent of n-butyl lithium followed by cyclopropane carboxaldehyde affords the diol of formula UU-2. Treatment of a mixture of the compound of formula UU-2 and the pyrone of formula UU-3 with a catalytic amount of TFA in methylene chloride affords the compound, 3-(α-cyclopropyl (5-methyl-4-hydroxymethylthien-2-ylmethyl)-4-hydroxy-5,6,7,8,9,10-hexahydrocycloocta[b]pyran-2-one, of the formula UU-4.

CHART VV

2-Carboethoxycycloocatanone is prepared as described in Organic Synthesis, Vol 47, p 20. Treatment of 2-carboethoxycycloocatanone with sodium hydroxide affords the β-ketoacid of formula VV-1. Treatment of the compound of formula VV-1 with a catalytic amount of sulfuric acid in acetic anhydride and acetone yields the intermediate of formula VV-2. Treatment of 3[R]-phenylvaleric acid of formula VV-3 with oxalyl chloride in methylene chloride affords the acid chloride of formula VV-4. Addition of a mixture of the compound of formula VV-2 and triethylamine to a refluxing solution (1,3,5-trimethylbenzene) of formula VV-4 affords the compound, [S]3-(ethylbenzyl)-5,6,7,8,9,10-hexahydro-4-hydroxy-2H-cycloocta[b]pyran-2-one, of formula VV-5.

CHART WW

Treatment of 3[S]-phenylvaleric acid of formula WW-3 with oxalyl chloride in methylene chloride affords the acid chloride of formula WW-4. Addition of a mixture of the formula WW-2 and triethylamine to a refluxing solution (1,3,5-trimethylbenzene) of the compound of formula WW-3 affords the compound, [R]3-(ethylbenzyl)-5,6,7,8,9, 10-hexahydro-4-hydroxy-2H-cycloocta[b]pyran-2-one, of formula WW-5.

CHART XX

The unsaturated amide of formula XX-1 (Chemistry Letters (1981, 913–16) is treated with ethyl magnesium bromide in diethyl ether at −40° C. to yield the compound of formula XX-2. Acid hydrolysis of the compound of formula XX-2 affords the intermediate of formula XX-3. In a manner similar to the above, treatment of the compound of formula XX-4 with phenyl magnesium bromide in diethyl ether affords the compound of formula XX-5 which upon treatment with acid affords the intermediate of formula XX-6. Compounds of the formula XX-3 and XX-6 wherein phenyl is substituted with, e.g., halogen, trifluoromethyl, —NHBOC, —NHCBz, —NHSO$_2$Ph, or N-(1,1,4,4-tetramethyl-1,4-bisdisilethylene) (e.g., see the compound of formula ZZ-5 in Chart ZZ, or wherein phenyl is replaced with optionally substituted heterocycles, e.g., furan and thiophene, are prepared following the above procedure.

CHART YY

The unsaturated amide of the formula YY-1 (Hruby, et. al., J. Org. Chem. (1993) 58, 766) is treated with phenyl magnesium bromide in the presence of a copper catalyst in tetrahydrofuran to yield the compound of formula YY-2. Hydrolysis of the compound of formula YY-2 yields the compound of the formula YY-3 (same as the compound of formula XX-6 in Chart XX). In a similar fashion, the compound of formula YY-4 is converted to the compound of formula YY-5 and finally to the compound of formula YY-6 (same as the compound of formula XX-3 in Chart XX). Compounds of the formula YY-3 and YY-6 wherein phenyl is substituted with, e.g., halogen, trifluoromethyl, —NHBOC or —NHCBz, or wherein phenyl is replaced with optionally substituted heterocycles, e.g., furan and thiophene, are prepared following the above procedure. Also beginning with compounds of the formula YY-7 and YY-8, compounds of the formula YY-3 and YY-6 wherein the ethyl group is replaced with a cyclopropyl, are prepared by the procedure of this chart.

CHART ZZ

The commerically available 3-nitrocinnamic acid of formula ZZ-1 is treated with oxalyl chloride in either methylene chloride or toluene to yield an acid chloride intermediate which is reacted with the lithium salt of commerically available (S)-(+)-4-phenyl-2-oxazolidinone (formed via treatment of the oxazolidinone at low temperature in THF with n-butyl lithium) to afford the compound of formula ZZ-2a. In a similar fashion, the compound of formula ZZ-2b is produced in the same manner using the lithium salt of commerically available (R)-(−)-4-phenyl-2-oxazolidinone (formed via treatment of the oxazolidinone at low temperature in THF with n-butyl lithium) to afford the compound of formula ZZ-2b. Treatment of the compound of formula ZZ-2a with a mixture of vinyl magesium bromide and CuBr (vinyl cuprate) then affords the adduct of formula ZZ-3. Cyclopropanation of the compound of formula ZZ-3 using a Zn/Cu couple and diiodomethane then affords the cyclopropyl adduct of formula ZZ-4. Hydrolysis of the compound of formula ZZ-4 with LiOH/H$_2$O$_2$ then affords the acid of formula ZZ-5. Alternately, the compound of formula ZZ-3 is first hydrolyzed to the corresponding acid and then that olefinic acid is cyclopropanated to yield the compound of formula ZZ-5. Treatment of the compound of formula ZZ-5 with oxalyl chloride in either methylene chloride or toluene affords an acid chloride which is placed in a reaction vessel containing either toluene or mesitylene and to that solution, at 145°–165° C. is added a mixture of the compound of formula ZZ-6 and triethylamine. This then yields the product of formula ZZ-7. Reduction of the nitro group using Pt/H$_2$ yields the compound of formula ZZ-8 which is then treated with 4-fluorobenzenesulfonyl chloride to yield the compound of formula ZZ-9. The compounds of formulas ZZ-14 and ZZ-19 are prepared using this same strategy.

CHART AAA

The alcohol of formula AAA-1 is treated with commerically avialable Meldrum's acid of formula AAA-2 in the presence of triphenylphosphorane and diethylazodicarboxylate to yield, after basic hydrolysis the acid of formula AAA-3. The [R] isomer of formula AAA-4a and the [S] isomer of formula AAA-4b are obtained from fraction crystallization of the racemic acid of formula AAA-3 with either the [R] or [S] isomer of α-methylbenzyl amine, ephedrine, brucine, strychnine, quinine, cinchonidine, quinidine or cinchonine. Following the protocol described in Chart ZZ, the compounds of formulas AAA-6 a and b, which are also the compounds of formula ZZ-18 and ZZ-8, respectively, of Chart ZZ, are prepared.

CHART BBB

Conversion of commercially available sulfonyl chloride BBB-1 to sulfonamide BBB-2 is accomplished by treatment with the appropriate aromatic amine ArNH$_2$ (commercially available or easily synthesized by known procedures). Halogen-metal exchange with butyllithium, followed by condensation with commercially available cyclopropanecarboxaldehyde yields intermediate BBB-3. Alkylation of pyrone intermediate BBB-4 with the benzylic alcohol BBB-3 can be accomplished under a variety of acidic conditions several of which have been described in previous charts. This yields the final products BBB-5.

CHART CCC

The phosphinamides CCC-4 are synthesized from aromatic amine intermediate CCC-1 by reaction with phosphinic chlorides CCC-2. The latter are either commercially available or readily prepared via procedures such as those described in Tetrahedron 49:11055 (1993). The phosphonamidate esters CCC-6 are prepared by treating aromatic amine intermediate CCC-1 with excess of the appropriate phosphonic dichloride. (The dichlorides are commercially available or easily synthesized by using procedures in Organic Phosphorous Compounds, G. M. Kosolapoff and L. Maier, eds., Vol. 4, p. 155–253 (1972). The resulting intermediate CCC-5 is converted to the phosphonamidate ester CCC-6 with the appropriate alcohol R'OH. Alternative general routes to the phosphonamidate esters of type CCC-6 are reported in Biorganic and Medicinal Chemistry, Vol. 2, 1047 (1992).

CHART DDD

Aromatic amine intermediates (DDD-1) are converted to sulfonylureas DDD-3 by treatment with the appropriate sulfonyl chloride DDD-2, either commercially available or easily prepared as described in J. Org. Chem. 41:4028 (1976) or J. Med. Chem. 15:538 (1972).

CHART EEE

The preferred procedure for the preparation of the sulfonamides of formula EEE-6 is described in Chart EEE. The amino group of the cyclopropyl aryl ketone EEE-1 is protected using benzyl chloroformate to give the ketone EEE-2. Reduction of the ketone EEE-2 is accomplished with sodium borohydride to give carbinol EEE-3. The carbinol EEE-3 is used to alkylate the known cyclooctylpyrone of formula J-1 wherein n is 4 to provide the compound of formula EEE-4. Removal of the amino protecting group of EEE-4 is accomplished by transfer hydrogenolysis with 10% Pd/C and cyclohexene to provide the free amine EEE-5. Sulfonation of the free amine EEE-5 with various sulfonyl chlorides gives the sulfonamides EEE-6 wherein R is, e.g., 4-cyanophenyl, 4-chlorophenyl, 4-fluorophenyl, 3-nitrophenyl, or N-methylimidazol-4-yl.

As is apparent to those of ordinary skill in the art, the compounds of the present invention can occur in several diastereomeric forms, depending on the configuration around the asymmetric carbon atoms. All such diastereomeric forms are included within the scope of the present invention. Also, the compounds of the present invention can exist in several tautomeric forms of the 4-hydroxy-pyrone ring, including the particular enol forms depicted by formulas I and XVII, and the particular keto form depicted by formula VI, and mixtures thereof. All such tautomeric forms are included within the scope of the present invention.

The compounds of the present invention may be in either free form or in protected form at one or more of the remaining (not previously protected) carboxyl, amino, hydroxy, or other reactive groups. The protecting groups may be any of those known in the art. Examples of nitrogen and oxygen protecting groups are set forth in T. W. Greene, Protecting Groups in Organic Synthesis, Wiley, New York, (1981); J. F. W. McOmie, ed. Protective Groups in Organic Chemistry, Plenum Press (1973); and J. Fuhrhop and G. Benzlin, Organic Synthesis, Verlag Chemie (1983). Included among the nitrogen protective groups are t-butoxycarbonyl (BOC), benzyloxycarbonyl, acetyl, allyl, phthalyl, benzyl, benzoyl, trityl and the like.

The present invention provides for compounds of formula I or pharmacologically acceptable salts and/or hydrates thereof. Pharmacologically acceptable salts refers to those salts which would be readily apparent to a manufacturing pharmaceutical chemist to be equivalent to the parent compound in properties such as formulation, stability, patient acceptance and bioavailability. Examples of such salts include the hydrohalide salts, such as the hydrochloride and hydroiodide salts, the sodium salt, the potassium salt, and the calcium salt.

The compounds of the present invention are useful for treating patients infected with human immunodeficiency virus (HIV) which results in acquired immunodeficiency syndrome (AIDS) and related diseases. For this indication, these compounds may be administered by oral, intranasal, transdermal, subcutaneous and parenteral (including intramuscular and intravenous) routes in doses of 0.1 mg to 100 mg/kg of body weight per day.

Those skilled in the art would know how to formulate the compounds of this invention into appropriate pharmaceutical dosage forms. Examples of the dosage forms include oral formulations, such as tablets or capsules, or parenteral formulations, such as sterile solutions.

When the compounds in this invention are administered orally, an effective amount is from about 0.1 mg to 100 mg per kg of body weight per day. Either solid or fluid dosage forms can be prepared for oral administration. Solid compositions are prepared by mixing the compounds of this invention with conventional ingredients such as talc, magnesium stearate, dicalcium phosphate, magnesium aluminum silicate, calcium sulfate, starch, lactose, acacia, methyl cellulose, or functionally similar pharmaceutical diluents and carriers. Capsules are prepared by mixing the compounds of this invention with an inert pharmaceutical diluent and placing the mixture into an appropriately sized hard gelatin capsule. Soft gelatin capsules are prepared by machine encapsulation of a slurry of the compounds of this invention with an acceptable inert oil such as vegetable oil or light liquid petrolatum. Syrups are prepared by dissolving the compounds of this invention in an aqueous vehicle and adding sugar, aromatic flavoring agents and preservatives. Elixirs are prepared using a hydroalcoholic vehicle such as ethanol, suitable sweeteners such as sugar or saccharin and an aromatic flavoring agent. Suspensions are prepared with an aqueous vehicle and a suspending agent such as acacia, tragacanth, or methyl cellulose.

When the compounds of this invention are administered parenterally, they can be given by injection or by intravenous infusion. An effective amount is from about 0.1 mg to 100 mg per kg of body weight per day. Parenteral solutions are prepared by dissolving the compounds of this invention in aqueous vehicle and filter sterilizing the solution before placing in a suitable sealable vial or ampule. Parenteral suspensions are prepared in substantially the same way except a sterile suspension vehicle is used and the compounds of this invention are sterilized with ethylene oxide or suitable gas before it is suspended in the vehicle. The exact route of administration, dose, or frequency of administration would be readily determined by those skilled in the art and is dependant on the age, weight, general physical condition, or other clinical symptoms specific to the patient to be treated. Patients to be treated would be those individuals: 1) infected with one or more than one strain of a human immunodeficiency virus as determined by the presence of either measurable viral antibody or antigen in the serum and 2) having either an asymptomatic HIV infection or a symptomatic AIDS defining infection such as i) disseminated histoplasmosis, ii) isoporiasis, iii) bronchial and pulmonary candidiasis including pneumocystis pneumonia, iv) non-Hodgkin's lymphoma, or v) Kaposi's sarcoma and being less than sixty years old; or having an absolute CD4+ lymphocyte count of less than 500/mm$^3$ in the peripheral blood. Treatment would consist of maintaining an inhibitory level of the compounds of this invention in the patient at all times and would continue until the occurrence of a second symptomatic AIDS defining infection indicates alternate therapy is needed.

The utility of representative compounds of the present invention has been demonstrated in the biological tests described below:

The HIV protease screening assay is based on fluorescently labeled substrate which can be resolved from nonlabeled cleavage product using special beads coated with streptavidin. The substrate is biotinylated at the amino terminal arginine and fluorescently labeled with fluorescein isothiocynate (FITC) at the carboxyl terminal lysine. This assay has been employed to detect novel, nonpeptidic inhibitors of HIV-1 protease. Substrate (20 µl of 0.2 µM), sample (10 µl of desired concentration), and enzyme (10 µl of 0.1 µM) are added to a 96 well pandex plate. The assay is run in 0.1M sodium acetate buffer at pH 5.5 in the presence of 1.0M sodium chloride and 0.05% NP-40 with incubated in the dark for one hour at room temperature. Strepavidin coated polystyrene beads {40 μl of 0.1% (w/v)} are added and the plate is incubated in the dark for an additional half hour. The labeled cleavage product is separated from the unreacted substrate via filtration and is read on the Idexx screen machine. The data are analyzed by appropriate computer algorithms to ascertain percent inhibition values.

Determination of $K_i$ values utilizes the same materials and equipment employed for percent inhibition studies. Two-fold serial dilutions are made for a given inhibitor from 2, 3 or 4 starting concentrations with a total of 24, 36 or 48 individual inhibitor concentrations. These dilutions are performed utilizing the BioMek robotics system. The assay consists of 10 μL of 40 nM HIV-1 protease, 10 μL of the various inhibitor concentrations, and 20 μL of 200 μM substrate (40 μL total). The reaction is allowed to proceed for 90 min at room temperature, terminated with 40 μL of avidin beads and processed (supra vide). An inhibitor with a known $K_i$ is run in parallel to verify the validity of the assay. The data is processed utilizing a computer program employing a nonlinear least square analysis of the data to generate the $K_i$ values.

The % inhibition values and, in some instances, $IC_{50}$ values or $K_i$ values, of representative compounds of the present invention are listed in Tables II and IV below.

The compounds of the present invention have been further evaluated in a CV-1 cellular assay described below, where it was demonstrated that the retrovirus-inhibiting effect was due to the inhibition of HIV-1 protease:

Inhibition of p55 Processing in vVk-1 infected CV-1 Cells. CV-1 cells are seeded at 2× $10^5$ cells per well in 24-well Costar dishes and infected 4 to 6 hours later with vVK-1 at 5 plaque-forming units (PFU) per cell. Each compound is dissolved in Dulbecco's Modified Eagles medium (DMEM) containing 2.5% fetal bovine serum and is added to duplicate wells at the indicated final concentration 2 hours after virus addition. After 24 hours, the culture medium is removed and the monolayer washed with 1 mL of phosphate buffered saline (PBS), and the cells lysed by the addition of 0.1 mL of loading buffer (62.5 mM Tris (hydroxymethyl) aminomethane (Tris), pH 6.8, 2.3% sodium dodecyl sulfate (SDS), 5% β-mercaptoethanol, and 10% glycerol). The cell lysates are collected individually, placed in boiling water for 3 minutes, and then 0.025 mL of each sample is subjected to electrophoresis on 12% SDS-polyacrylamide gels. The proteins are electroblotted onto nitrocellulose and analyzed by protein immunoblotting. The primary antibodies are sheep antibody to p24 (International Enzyme, Inc., Fallbrook, Calif.) and the secondary antibody is alkaline-phosphatase-conjugated rabbit antibody to sheep immunoglobulin G (Kirkegaard & Perry Laboratories, Gaithersburg, Md.). The levels of immunoreactive proteins are quantified by densitometry (Bio-Rad, Model 260) with the accompanying 1-D Analyst Software. Inhibition refers to the mean percent decrease in p24 levels determined from the duplicate drug-treated samples compared to the nondrug-treated controls. In general, the percent inhibition did not vary more than 10% in the duplicates. The inhibition of p24 levels by treatment of cultures with 1 μM of peptide 1-Noa-His-Cha PSI [CHOHCHOH] Val-Ile-Amp (also known as N-[1-(cyclohexylmethyl)-2,3-dihydroxy-5-methyl-4-[[[2-methyl-1-[[(2-pyridinylmethyl)amino]carbonyl]butyl]-amino]carbonyl]hexyl]-α-[[(1-naphthalenyloxy)acetyl]amino]-, [1S-[1R*(R*),2S*,3S*,4S*(1R*,2R*)]]-1H-imidazole-4-propanamide) (which was disclosed in International Publication Number WO 87/05302, published 11 Sep. 1987) was also determined in each experiment.

The % inhibition values of representative compounds of the present invention are listed in Table III below.

Several compounds of the present invention, such as N-[3-[cyclopropyl(5,6,7,8,9,10-hexahydro-4-hydroxy-2-oxo-2H-cycloocta[b]pyran-3-yl)methyl]phenyl]-4-fluorobenzenesulfonamide and 4-cyano-N-[3-[cyclopropyl (5,6,7,8,9,10-hexahydro-4-hydroxy-2-oxo-2H-cycloocta[b] pyran-3-yl)methyl]phenyl]-benzenesulfonamide were tested in known human cell lines, such as human T-cell lines, e.g., MT4 and H9, which were infected with HIV-1$_{IIIB}$, and certain of these compounds were further tested in peripheral blood mononuclear cells (PBMC), which were infected with HIV-1$_{JRCSF}$ (a clinical isolate). The compounds were found to inhibit retroviral replication.

The following compounds of the present invention are preferred:

N-[3-[Cyclopropyl(5,6,7,8,9,10-hexahydro-4-hydroxy-2-oxo-2 H-cycloocta[b]pyran-3-yl)methyl]phenyl]-benzenesulfonamide N-[3-[Cyclopropyl(5,6,7,8,9,10-hexahydro-4-hydroxy-2-oxo-2H-cycloocta[b]pyran-3-yl)methyl]phenyl]-2-phenyl-ethenesulfonamide Carbamic acid, [3-[[3-[cyclopropyl(5,6,7,8,9,10-hexahydro-4-hydroxy-2-oxo-2H-cycloocta[b]pyran-3-yl)methyl]phenyl]amino]-3-oxopropyl]-, 1,1-dimethylethyl ester N-[3-[Cyclopropyl(5,6,7,8,9,10-hexahydro-4-hydroxy-2-oxo-2H-cycloocta[b]pyran-3-yl)methyl]phenyl]-1-propanesulfonamide N-[3-[Cyclopropyl(5,6,7,8,9,10-hexahydro-4-hydroxy-2-oxo-2H-cycloocta[b]pyran-3-yl)methyl]phenyl]-4-methyl-benzenesulfonamide N-[3-[Cyclopropyl(5,6,7,8,9,10-hexahydro-4-hydroxy-2-oxo-2H-cycloocta[b]pyran-3-yl)methyl]phenyl]-1-butanesulfonamide 4-Chloro-N-[3-[cyclopropyl(5,6,7,8,9,10-hexahydro-4-hydroxy-oxo-2H -cycloocta[b]pyran-3-yl)methyl]phenyl]-benzenesulfonamide N-[3-[Cyclopropyl(5,6,7,8,9,10-hexahydro-4-hydroxy-2-oxo-2H-cycloocta[b]pyran-3-yl)methyl]phenyl]-2-naphthalenesulfonamide 3,4-Dichloro-N-[3-[cyclopropyl(5,6,7,8,9,10-hexahydro-4-hydroxy-2-oxo-2H-cycloocta[b]pyran-3-yl)methyl]phenyl]-benzenesulfonamide N-[3-[Cyclopropyl(5,6,7,8,9,10-hexahydro-4-hydroxy-2-oxo-2H-cycloocta[b]pyran-3-yl)methyl]phenyl]-(R)-benzenesulfonamide (−)-N-[3-[Cyclopropyl(5,6,7,8,9,10-hexahydro-4-hydroxy-2-oxo-2H-cycloocta[b]pyran-3-yl)methyl]phenyl]-2-phenyl-[(E)]-ethenesulfonamide (+)-N-[3-[Cyclopropyl(5,6,7,8,9,10-hexahydro-4-hydroxy-2-oxo-2H-cycloocta[b]pyran-3-yl)methyl]phenyl]-2-phenyl-[(E)]-ethenesulfonamide Carbamic acid, [2-[[3-[cyclopropyl(5,6,7,8,9,10-hexahydro-4-hydroxy-2-oxo-2H-cycloocta[b]pyran-3-yl)methyl]phenyl]amino]-2-oxyethyl]-, 1,1-dimethylethyl ester Carbamic acid, [2-[[3-[cyclopropyl(5,6,7,8,9,10-hexahydro-4-hydroxy-2-oxo-2H-cycloocta[b]pyran-3-yl)methyl]phenyl]amino]-1-(S)-(1H-imidazol-4-ylmethyl)-2-oxoethyl]-, 1,1-dimethylethyl ester N-[3-[Cyclopropyl(5,6,7,8,9,10-hexahydro-4-hydroxy-2-oxo-2H-cycloocta[b]pyran-3-yl)methyl]phenyl]-4-fluoro-benzenesulfonamide 4-Bromo-N-[3-[cyclopropyl(5,6,7,8,9,10-hexahydro-4-hydroxy-2-oxo-2H-cycloocta[b]pyran-3-yl)methyl]phenyl]-benzenesulfonamide N-[3-[Cyclopropyl(5,6,7,8,9,10-hexahydro-4-hydroxy-2-oxo-2H-cycloocta[b]pyran-3-yl)methyl]phenyl]-4-nitro-benzenesulfonamide N-[3-[Cyclopropyl(5,6,7,8,9,10-hexahydro-4-hydroxy-2-oxo-2H-cycloocta[b]pyran-3-yl)methyl]phenyl]-3-nitro-benzenesulfonamide N-[3-[Cyclopropyl(5,6,7,8,9,10-hexahydro-4-hydroxy-2-oxo-2H-cycloocta[b]pyran-3-yl)methyl]phenyl]-4-methoxy-benzenesulfonamide N-[3-[Cyclopropyl(5,6,7,8,9,10-hexahydro-4-hydroxy-2-oxo-2H-cycloocta[b]pyran-3-yl)methyl]phenyl]-3-(trifluoromethyl)-benzenesulfonamide N-[3-[Cyclopropyl(5,6,7,8,9,10-hexahydro-4-hydroxy-2-oxo-2H-cycloocta[b]pyran-3-yl)methyl]phenyl]-2,4-difluoro-benzenesulfonamide 3-Chloro-N-[3-[cyclopropyl(5,6,7,8,9,10-hexahydro4-hydroxy-2-oxo-2H-cycloocta[b]pyran-3-yl)methyl]phenyl]-1-propanesulfonamide 4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide Sodium Salt of 4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide N-[3-[Cyclopropyl(5,6,7,8,9,10-hexahydro-4-hydroxy-2-oxo-2H-cycloocta[b]pyran-3-yl)methyl]phenyl]-8-quinolinesulfonamide Carbamic acid, [2-[[3-(R or S)-[cyclopropyl(5,6,7,8,9,10)-hexahydro-4-hydroxy-2-oxo-2H-cycloocta[b]pyran-3-yl)methyl]phenyl]amino]-2-oxoethyl]-, 1,1-dimethyl ethyl ester N-[3-[Cyclopropyl(5,6,7,8,9,10-hexahydro-4-hydroxy-2-oxo-2H-cycloocta[b]pyran-3-yl)methyl]phenyl]-2,1,3-benzothiadiazole-4-sulfonamide 3-Chloro-N-[3-[cyclopropyl(5,6,7,8,9,10-hexahydro-4-hydroxy-2-oxo-2H-cycloocta[b]pyran-3-yl)methyl]phenyl]-benzenesulfonamide N-[3-[Cyclopropyl(5,6,7,8,9,10-hexahydro-4-hydroxy-2-oxo-2H-cycloocta[b]pyran-3-yl)methyl]phenyl]-4-benzofurazansulfonamide 3-Bromo-N-[3-[cyclopropyl(5,6,7,8,9,10-hexahydro-4-hydroxy2-oxo-2H-cycloocta[b]pyran-3-yl)methyl]phenyl]-benzenesulfonamide 3-[[[3-[Cyclopropyl(5,6,7,8,9,10-hexahydro-4-hydroxy-2-oxo-2H-cycloocta[b]pyran-3-yl)methyl]phenyl]amino]sulfonyl]-benzoic acid (+)-4-Chloro-N-[3-[cyclopropyl(5,6,7,8,9,10-hexahydro-4-hydroxy-2-oxo-2H-cycloocta[b]pyran-3-yl)methyl]phenyl]-benzenesulfonamide (−)-4-Chloro-N-[3-[cyclopropyl(5,6,7,8,9,10-hexahydro-4-hydroxy-2-oxo-2H-cycloocta[b]pyran-3-yl)methyl]phenyl]-benzenesulfonamide (+)4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide (−)-4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide N-[3-[Cyclopropyl(5,6,7,8,9,10-hexahydro-4-hydroxy-2-oxo-2H-cycloocta-3-yl)methyl]phenyl]-1-methyl-(S)-1H-imidazole-4-sulfonamide N-[3-[Cyclopropyl(5,6,7,8,9,10-hexahydro-4-hydroxy-2-oxo-2H-cycloocta[b]pyran-3-yl)methyl]phenyl]-4-(phenylsulfonyl)-2-thiophenesulfonamide N-[3-[Cyclopropyl(5,6,7,8,9,10-hexahydro-4-hydroxy-2-oxo-2H-cycloocta[b]pyran-3-yl)methyl]phenyl]-5-(phenylsulfonyl)-2-thiophenesulfonamide N-[3-[Cyclopropyl(5,6,7,8,9,10-hexahydro-4-hydroxy-2-oxo-2H-cycloocta[b]pyran-3-yl)methyl]phenyl]-4-iodo-benzenesulfonamide 5-Chloro-N-[3-[cyclopropyl(5,6,7,8,9,10-hexahydro-4-hydroxy-2-oxo-2H-cycloocta[b]pyran-3-yl)methyl]phenyl]-2-thiophenesulfonamide 4,5-Dichloro-N-[3-[cyclopropyl(5,6,7,8,9,10-hexahydro-4-hydroxy-2-oxo-2H-cycloocta[b]pyran-3-yl)methyl]phenyl]-2-thiophenesulfonamide 4,5-Dibromo-N-[3-[cyclopropyl(5,6,7,8,9,10-hexahydro-4-hydroxy-2-oxo-2H-cycloocta[b]pyran-3-yl)methyl]phenyl]-2-thiophenesulfonamide Benzenesulfonamide, 4-chloro-N-[3-[1-(5,6,7,8,9,10-hexahydro-4-hydroxy-2-oxo-2H-cycloocta[b]pyran-3-yl)propyl]phenyl]-

Benzenesulfonamide, 4-cyano-N-[3-[1-(5,6,7,8,9,10-hexahydro-4-hydroxy-2-oxo-2H-cycloocta[b]pyran-3-yl)propyl]phenyl]-

N-[3-[Cyclopropyl(5,6,7,8,9,10-hexahydro-4-hydroxy-2-oxo-2H-cycloocta[b]pyran-3-yl)methyl]phenyl]-4-ethyl-benzenesulfonamide N-[3-[Cyclopropyl(5,6,7,8,9,10-hexahydro-4-hydroxy-2-oxo-2H-cycloocta[b]pyran-3-yl)methyl]phenyl]-4-(phenylazo)-benzenesulfonamide (+)-N-[3-[Cyclopropyl(5,6,7,8,9,10-hexahydro-4-hydroxy-2-oxo-2H-cycloocta[b]pyran-3-yl)methyl]phenyl]-4-fluoro-benzenesulfonamide (−)-N-[3-[Cyclopropyl(5,6,7,8,9,10-hexahydro-4-hydroxy-2-oxo-2H-cycloocta[b]pyran-3-yl)methyl]phenyl]-4-fluoro-benzenesulfonamide Carbamic acid, [2-[[3-(R or S)-[cyclopropyl(5,6,7,8,9,10-hexahydro-4-hydroxy-2-oxo-2H-cycloocta[b]pyran-3-yl)methyl]phenyl]amino]-1-(S)-(1H-imidazol-4-ylmethyl)-2-oxoethyl]-, 1,1 dimethyl ethyl ester Carbamic acid, [2-[[3-(R or S)-[Cyclopropyl(5,6,7,8,9,10-hexahydro-4-hydroxy-2-oxo-2H-cycloocta[b]pyran-3-yl)methyl]phenyl]amino]-1-(S)-(1H-imidazol-4-ylmethyl)-2-oxoethyl]-, 1,1 dimethyl ethyl ester N-[3-[Cyclopropyl(5,6,7,8,9,10-hexahydro-4-hydroxy-2-oxo-2H-cycloocta[b]pyran-3-yl)methyl]phenyl]-benzeneethanesulfonamide N-[3-[Cyclopropyl(5,6,7,8,9,10-hexahydro-4-hydroxy-2-oxo-2H-cycloocta[b]pyran-3-yl)methyl]phenyl]-5-(3-isoxazolyl)-2-thiophenesulfonamide N-[3-[Cyclopropyl(5,6,7,8,9,10-hexahydro-4-hydroxy-2-oxo-2H-cycloocta[b]pyran-3-yl)methyl]phenyl]-3-pyridinesulfonamide (+)-N-[3-[Cyclopropyl(5,6,7,8,9,10-hexahydro-4-hydroxy-2-oxo-2H-cycloocta[b]pyran-3-yl)methyl]phenyl]-8-quinolinesulfonamide (−)-N-[3-[Cyclopropyl(5,6,7,8,9,10-hexahydro-4-hydroxy-2-oxo-2H-cycloocta[b]pyran-3-yl)methyl]phenyl]-8-quinolinesulfonamide N-[3-[Cyclopropyl(5,6,7,8,9,10-hexahydro-4-hydroxy-2-oxo-2H-cycloocta[b]pyran-3-yl)methyl]phenyl]-5-(2-pyridinyl)-2-thiophenesulfonamide N-[3-[cyclopropyl(5,6,7,8,9,10-hexahydro-4-hydroxy-2-oxo-2H-cycloocta[b]pyran-3-yl)methyl]phenyl]-4-(hydroxyamino)-benzenesulfonamide N-[3-[Cyclopropyl(5,6,7,8,9,10-hexahydro-4-hydroxy2-oxo-2H-cycloocta[b]pyran-3-yl)methyl]phenyl]-4-(dimethylamino)-benzenesulfonamide 3-Amino-N-[3-[cyclopropyl(5,6,7,8,9,10-hexahydro4-hydroxy-2-oxo-2H-cycloocta[b]pyran-3-yl)methyl]phenyl]-benzenesulfonamide N-[3-[Cyclopropyl(5,6,7,8,9,10-hexahydro-4-hydroxy-2-oxo-2-cycloocta[b]pyran-3-yl)methyl]phenyl]-4-(trifluoromethoxy)-benzenesulfonamide 4-(Bromomethyl)-N-[3-[cyclopropyl(5,6,7,8,9,10-hexahydro-4-hydroxy-2-oxo-2H-cycloocta[b]pyran-3-yl)methyl]phenyl]-benzenesulfonamide 4-[[[3-[Cyclopropyl(5,6,7,8,9,10-hexahydro-4-hydroxy-2-oxo-2H-cycloocta[b]pyran-3-yl)methyl]phenyl]amino]sulfonyl]-benzamide (−)-N-[3-[Cyclopropyl(5,6,7,8,9,10-hexahydro-4-hydroxy-2-oxo-2H-cycloocta-3-yl)methyl]phenyl]-1-methyl-1H-imidazole-4-sulfonamide N-[3-cyclopropyl(5,6,7,8,9,10-hexahydro-4-hydroxy-2-oxo-2H-cycloocta[b]pyran-3-yl)methyl]phenyl]-5-(phenylsulfonyl)-, (S)-2-thiophenesulfonamide N -[3-[Cyclopropyl(5,6,7,8,9,10-hexahydro-4-hydroxy-2-oxo-2H-cycloocta[b]pyran-3-yl)methyl]phenyl]-5-methyl-3-pyridinesulfonamide N-[3-[Cyclopropyl(5,6,7,8,9,10-hexahydro-4-hydroxy-2-oxo-2H-cycloocta[b]pyran-3-yl)methyl]phenyl]-3-(hydroxyamino)-benzenesulfonamide 3-[[[3-[Cyclopropyl(5,6,7,8,9,10-hexahydro-4-hydroxy-2-oxo-2H-cycloocta[b]pyran-3-yl)methyl]phenyl]amino]sulfonyl]-benzoic acid, methyl ester N-[3-[Cyclopropyl(5,6,7,8,9,10-hexahydro-4-hydroxy-2-oxo-2H-cycloocta[b]pyran-3-yl)methyl]phenyl]-3-hydroxy-benzenesulfonamide Benzenesulfonamide, 4-cyano-N-[3-[1-(5,6,7,8,9,10-hexahydro-4-hydroxy-2-oxo-2H-cycloocta[b]pyran-3-yl)butyl]phenyl]-

Benzenesulfonamide, 4-chloro-N-[3-[1-(5,6,7,8,9,10-hexahydro-4-hydroxy-2-oxo-2H-cycloocta[b]pyran-3-yl)butyl]phenyl]-

N-[3-[Cyclopropyl[3-(2-isothiazolidinyl)phenyl]methyl-(5,6,7,8,9,10-hexahydro-4-hydroxy-S,S'-dioxide)methyl]phenyl]-3[(phenylsulfonyl)amino]-4-2H-cycloocta[b]pyran-2-one 3-Chloro-N-[3-[cyclopropyl(5,6,7,8,9,10-hexahydro-4-hydroxy-2-oxo-2H-cycloocta[b]pyran-3-yl)methyl]phenyl]-3-[(phenylsulfonyl)amino]-1-propanesulfonamide N-[3-[Cyclopropyl(5,6,7,8,9,10-hexahydro-4-hydroxy-2-oxo-2H-cycloocta[b]pyran-3-yl)methyl]phenyl]-3-[methanol]-benzenesulfonamide N-[3-[Cyclopropyl(5,6,7,8,9,10-hexahydro-4-hydroxy-2-oxo-2H-cycloocta[b]pyran-3-yl)methyl]phenyl]-3-[(2-ethanol)amino]-benzenesulfonamide N-[3-[Cyclopropyl(5,6,7,8,9,10-hexahydro4-hydroxy-2-oxo-2H-cycloocta[b]pyran-3-yl)methyl]phenyl]-3-[(bis-(2-ethanol))amino]-benzenesulfonamide N-[3-[1-(5,6,7,8,9,10-Hexahydro-4-hydroxy-2-oxo-2H-cycloocta[b]pyran-3-yl)-2-methylpropyl]phenyl]-1-methyl-1H-imidazole4-sulfonamide 3-(Hydroxyacetylamino)-N-[3-[cyclopropyl(5,6,7,8,9,10-hexahydro-4-hydroxy-2-oxo-2H-cycloocta[b]pyran-3-yl)methyl]phenyl]-benzenesulfonamide N-[3-[Cyclopropyl(5,6,7,8,9,10-hexahydro4-hydroxy-2-oxo-2H-cycloocta[b]pyran-3-yl)methyl]phenyl]-(3-N-morpholinebenzenesulfonyl)benzenesulfonamide N-[3-[Cyclopropyl(5,6,7,8,9,10-hexahydro-4-hydroxy-2-oxo-2H-cycloocta[b]pyran-3-yl)methyl]phenyl]-(3-N-ethylbenzenesulfonyl)benzenesulfonamide 8-Quinolinesulfonamide, N-[3-[1-(5,6,7,8,9,10-hexahydro4-hydroxy-2-oxo-2H-cycloocta[b]pyran-3-yl)-2-methylpropyl]phenyl]-, Benzenesulfonamide, N-[3-[cyclopropyl(5,6,7,8,9,10-hexahydro-4-hydroxy-2-oxo-2H-cycloocta[b]pyran-3-yl)methyl]phenyl]-4-[2-[2-(2-methoxyethoxy)ethoxy]ethoxy]-, Benzenesulfonamide, 4-cyano-N-[3-[1-(5,6,7,8,9,10-hexahydro-4-hydroxy-2-oxo-2H-cycloocta[b]pyran-3-yl)pentyl]phenyl]-, Benzenesulfonamide, N-[3-[1-(5,6,7,8,9,10-hexahydro-4-hydroxy-2-oxo-2H-cycloocta[b]pyran-3-yl)butyl]phenyl]-4-fluoro-, Benzenesulfonamide, N-[3-[1-(5,6,7,8,9,10-hexahydro-4-hydroxy-2-oxo-2H-cycloocta[b]pyran-3-yl)-3-methylbutyl]phenyl]-4-fluoro-, Benzenesulfonamide, 4-cyano-N-[3-[1-(5,6,7,8,9,10-hexahydro-4-hydroxy-2-oxo-2H-cycloocta[b]pyran-3-yl)-3-methylbutyl]phenyl]-, (R or S)-Benzenesulfonamide, 4-cyano-N-[3-[1-(5,6,7,8,9,10-hexahydro-4-hydroxy-2-oxo-2H-cycloocta[b]pyran-3-yl)butyl]phenyl]-, (R or S)-Benzenesulfonamide, 4-cyano-N-[3-[1-(5,6,7,8,9,10-hexahydro-4-hydroxy-2-oxo-2H-cycloocta[b]pyran-3-yl)butyl]phenyl]-, 1H-Imidazole-4-sulfonamide, N-[3-[1-(5,6,7,8,9,10-hexahydro-4-hydroxy-2-oxo-2H-cycloocta[b]pyran-3-yl)butyl]phenyl]-1-methyl-, 8-Quinolinesulfonamide, N-[3-[1-(5,6,7,8,9,10-hexahydro-4-hydroxy-2-oxo-2H-cycloocta[b]pyran-3-yl)butyl]phenyl]-.

3-Pyridinesulfonamide, N-[3-[1-(5,6,7,8,9,10-hexahydro-4-hydroxy-2-oxo-2H-cycloocta[b]pyran-3-yl)butyl]phenyl]-, 1H-Imidazole-4-sulfonamide, N-[3-[1-(5,6,7,8,9,10-hexahydro-4-hydroxy-2-oxo-2H-cycloocta[b]pyran-3-yl)-3-methylbutyl]phenyl]-1-methyl-, 8-Quinolinesulfonamide, N-[3-[1-(5,6,7,8,9,10-hexahydro-4-hydroxy-2-oxo-2H-cycloocta[b]pyran-3-yl)-3-methylbutyl]phenyl]-, The following compounds of the present invention are more preferred:

N-[3-[Cyclopropyl(5,6,7,8,9,10-hexahydro4-hydroxy-2-oxo-2H-cycloocta[b]pyran-3-yl)methyl]phenyl]-4-fluoro-benzenesulfonamide 4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide Sodium Salt of 4-Cyano-N-[3-[cyclopropyl(5,6,7,8,9,10-hexahydro4-hydroxy-2-oxo-2H-cycloocta[b]pyran-3-yl)methyl]phenyl]-benzenesulfonamide N-[3-[Cyclopropyl(5,6,7,8,9,10-hexahydro-4-hydroxy-2-oxo-2H-cycloocta[b]pyran-3-yl)methyl]phenyl]-8-quinolinesulfonamide N-[3-[Cyclopropyl(5,6,7,8,9,10-hexahydro-4-hydroxy-2-oxo-2H-cycloocta[b]pyran-3-yl)methyl]phenyl]-2,1,3-benzothiadiazole-4-sulfonamide (+)-4-Chloro-N-[3-[cyclopropyl(5,6,7,8,9,10-hexahydro-4-hydroxy-2-oxo-2H-cycloocta[b]pyran-3-yl)methyl]phenyl]-benzenesulfonamide (−)-4-Chloro-N-[3-[cyclopropyl(5,6,7,8,9,10-hexahydro-4-hydroxy-2-oxo-2H-cycloocta[b]pyran-3-yl)methyl]phenyl]-benzenesulfonamide (+)-4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide (−)-4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide N-[3-[Cyclopropyl(5,6,7,8,9,10-hexahydro-4-hydroxy-2-oxo-2H-cycloocta-3-yl)methyl]phenyl]-1-methyl-(S)-1H-imidazole-4-sulfonamide (+)-N-[3-[Cyclopropyl(5,6,7,8,9,10-hexahydro-4-hydroxy-2-oxo-2H-cycloocta[b]pyran-3-yl)methyl]phenyl]-4-fluoro-benzenesulfonamide (−)-N-[3-[Cyclopropyl(5,6,7,8,9,10-hexahydro-4-hydroxy-2-oxo-2H-cycloocta[b]pyran-3-yl)methyl]phenyl]-4-fluoro-benzenesulfonamide Carbamic acid, [2-[[3-(R or S)-[Cyclopropyl(5,6,7,8,9,10-hexahydro-4-hydroxy-2-oxo-2H-cycloocta[b]pyran-3-yl)methyl]phenyl]amino]-1-(S)-(1H-imidazol-4-ylmethyl)-2-oxoethyl]-, 1,1 dimethyl ethyl ester (+)-N-[3-[Cyclopropyl(5,6,7,8,9,10-hexahydro-4-hydroxy-2-oxo-2H-cycloocta[b]pyran-3-yl)methyl]phenyl]-8-quinolinesulfonamide (−)-N-[3-[Cyclopropyl(5,6,7,8,9,10-hexahydro-4-hydroxy-2-oxo-2H-cycloocta[b]pyran-3-yl)methyl]phenyl]-8-quinolinesulfonamide N-[3-[cyclopropyl(5,6,7,8,9,10-hexahydro4-hydroxy-2-oxo-2H-cycloocta[b]pyran-3-yl)methyl]phenyl]-4-(hydroxyamino)-benzenesulfonamide 4-[[[3-[Cyclopropyl(5,6,7,8,9,10-hexahydro-4-hydroxy-2-oxo-2H-cycloocta[b]pyran-3-yl)methyl]phenyl]amino]sulfonyl]-benzamide (−)-N-[3-[Cyclopropyl(5,6,7,8,9,10-hexahydro-4-hydroxy-2-oxo-2H-cycloocta-3-yl)methyl]phenyl]-1-methyl-1H-imidazole-4-sulfonamide 3-[[[3-[Cyclopropyl(5,6,7,8,9,10-hexahydro-4-hydroxy-2-oxo-2H-cycloocta[b]pyran-3-yl)methyl]phenyl]amino]sulfonyl]-benzoic acid, methyl ester Benzenesulfonamide, 4-cyano-N-[3-[1-(5,6,7,8,9,10-hexahydro-4-hydroxy-2-oxo-2H-cycloocta[b]pyran-3-yl)butyl]phenyl]-

N-[3-[Cyclopropyl[3-(2-isothiazolidinyl)phenyl]methyl-(5,6,7,8,9,10-hexahydro-4-hydroxy-S,S'-dioxide)methyl]phenyl]-3-[(phenylsulfonyl)amino]-4-2H-cycloocta[b]pyran-2-one 3-Chloro-N-[3-[cyclopropyl(5,6,7,8,9,10-hexahydro-4-hydroxyl-2-oxo-2H-cycloocta[b]pyran-3-yl)methyl]phenyl]-3-[(phenylsulfonyl)amino]-1-propanesulfonamide N-[3-[Cyclopropyl(5,6,7,8,9,10-hexahydro-4-hydroxy-2-oxo-2H-cycloocta[b]pyran-3-yl)methyl]phenyl]-3-[methanol]-benzenesulfonamide N-[3-[Cyclopropyl(5,6,7,8,9,10-hexahydro4-hydroxy-2-oxo-2H-cycloocta[b]pyran-3-yl)methyl]phenyl]-3-[(bis-(2-ethanol))amino]-benzenesulfonamide N-[3-[1-(5,6,7,8,9,10-Hexahydro-4-hydroxy-2-oxo-2H-cycloocta[b]pyran-3-yl)-2-methylpropyl]phenyl]-1-methyl-1H -imidazole-4-sulfonamide Benzenesulfonamide, 4-cyano-N-[3-[1-(5,6,7,8,9,10-hexahydro-4-hydroxy-2-oxo-2H-cycloocta[b]pyran-3-yl)-3-methylbutyl]phenyl]-, 1H-Imidazole-4-sulfonamide, N-[3-[1-(5,6,7,8,9,10-hexahydro-4-hydroxy-2-oxo-2H-cycloocta[b]pyran-3-yl)butyl]phenyl]-1-methyl-, 8-Quinolinesulfonamide, N-[3-[1-(5,6,7,8,9,10-hexahydro-4-hydroxy-2-oxo-2H-cycloocta[b]pyran-3-yl)butyl]phenyl]-, 1H-Imidazole-4-sulfonamide, N-[3-[1-(5,6,7,8,9,10-hexahydro-4-hydroxy-2-oxo-2H-cycloocta[b]pyran-3-yl)-3-methylbutyl]phenyl]-1-methyl-, The following compounds of the present invention are most preferred:

(3R), (3S) and N-[3-[Cyclopropyl(5,6,7,8,9,10-hexahydro-4-hydroxy-2-oxo-2H-cycloocta[b]pyran-3-yl)methyl]phenyl]-4-fluoro-benzenesulfonamide and its sodium salt 4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide Sodium Salt of 4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide (+)4-Cyano-N-[3-[cyclopropyl(5,6,7,8,9,10-hexahydro4-hydroxy-2-oxo-2H-cycloocta[b]pyran-3-yl)methyl]phenyl]-benzenesulfonamide (−)-4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide (+)-N-[3-[Cyclopropyl(5,6,7,8,9,10-hexahydro4-hydroxy-2-oxo-2H-cycloocta[b]pyran-3-yl)methyl]phenyl]-8-quinolinesulfonamide (−)-N-[3-[Cyclopropyl(5,6,7,8,9,10-hexahydro4-hydroxy-2-oxo-2H-cycloocta[b]pyran-3-yl)methyl]phenyl]-8-quinolinesulfonamide (−)-N-[3-[Cyclopropyl(5,6,7,8,9,10-hexahydro4-hydroxy-2-oxo-2H-cycloocta-3-yl)methyl]phenyl]-1-methyl-1H-imidazole-4-sulfonamide N-[3-[1-(5,6,7,8,9,10-Hexahydro-4-hydroxy-2-oxo-2H-cycloocta[b]pyran-3-yl )-2-methylpropyl]phenyl]-1-methyl-1H-imidazole-4-sulfonamide N-[3-[Cyclopropyl[3-(2-isothiazolidinyl)phenyl]methyl-(5,6,7,8,9,10-hexahydro-4-hydroxy-S,S'-dioxide)methyl]phenyl]-3-[(phenylsulfonyl)amino]-4-2H-cycloocta[b]pyran-2-one 1H-Imidazole-4-sulfonamide, N-[3-[1-(5,6,7,8,9,10-hexahydro-4-hydroxy-2-oxo-2H-cycloocta[b]pyran-3-yl)butyl]phenyl]-1-methyl-, 1H-Imidazole-4-sulfonamide, N-[3-[1-(5,6,7,8,9,10-hexahydro-4-hydroxy-2-oxo-2H-cycloocta[b]pyran-3-yl)-3-methylbutyl]phenyl]-1-methyl-,

DESCRIPTION OF THE PREFERRED EMBODIMENTS

In the Preparations and Examples below and throughout this document:

°C. is degrees Centigrade.
M is molar (concentration).
N is normal (concentration).
mL is milliliter.
mg is milligram.
mmHg is millimeter of mercury.
$^1$H-NMR is proton nuclear magnetic resonance spectrum.
$^{13}$C-NMR is carbon nuclear magnetic resonance spectrum.
δ is chemical shift (parts per million) relative to TMS.
$CDCl_3$ is deuterio-chloroform.
$CD_3OD$ is deuterio-methanol.
DMSO is deuterio dimethylsulfoxide.
FAB MS is fast-atom-bombardment mass spectroscopy.
EI MS is electron impact mass spectroscopy.
HRMS high-resolution mass spectroscopy.
Anal. is analytical data.
Pd/C is palladium on charcoal.
THF is tetrahydrofuran.
HOBT is 1-hydroxybenzotriazole hydrate.
$R_f$ is chromatographic movement relative to solvent front.

cm$^{-1}$ is reciprocal centimeters.
TFA is trifluoroacetic acid.
MP is melting point.
TMS is tetramethyl silane.

The following Preparations and Examples illustrate the present invention:

PREPARATIONS 1

Ethyl 2-(4-Phenylbutanoyl)salicylate (Formula A-2) Refer to Chart A

To a stirred solution of 1.00 g of 4-phenylbutyric acid and 60 mg of N,N-dimethylaminopyridine in 20 ml of dichloromethane is added 0.75 ml of ethyl salicylate, followed by 0.95 ml of diisopropyl carbodiimide. After 18 hours, the mixture is concentrated under reduced pressure, and the residue triturated with ether. The organic phase is washed with aq. sodium bicarbonate and brine, dried (magnesium sulfate), and concentrated under reduced pressure. Flash chromatography on silica with 10% ethyl acetate in hexane affords 1.61 g of the title product as a colorless oil.

Physical characteristics are as follows:

$^1$H NMR δ 1.32; 2.10; 2.65; 2.76; 4.28; 7.06; 7.25; 7.5; 8.01.

EXAMPLE 1

4-Hydroxy-3-phenethylcoumarin (Formula A-3) Refer to Chart A

To a suspension of 24 mg of 60% sodium hydride/mineral oil in 1.0 ml of benzene in a flame dried flask, at 0° C. under argon, is added a solution of 94 mg of ester of Preparation 1 in 2.0 ml benzene. The mixture is heated at 80° C. overnight, then cooled and quenched with methanol. The mixture is partitioned between ether and 1N sodium hydroxide with two additional ether washes of the aqueous phase. Acidification of the aqueous phase gives a white precipitate, which is extracted with 4 portions of dichloromethane-methanol. The organic is concentrated under reduced pressure, and the residue flash chromatographed on silica with 50–70% ethyl acetate in hexane to provide 16 mg of the title product as a white solid.

Physical characteristics are as follows:

$^1$H NMR δ 2.87; 3.33; 7.25; 7.51; 7.86. $^{13}$C NMR δ 25.54; 33.62; 104.54; 115.99; 116.25; 122.75; 123.54; 125.48; 127.85; 128.10; 131.08; 141.41; 151.94; 160.85; 164.84. EI HRMS [m]=266.0936.

PREPARATION 2

Ethyl 2-(5-Phenylvaleryl)salicylate (Formula A-4) Refer to Chart A

To a stirred solution of 1.07 g of 5-phenylvaleric acid and 60 mg of N,N-dimethylaminopyridine in 20 ml of dichloromethane is added 0.75 ml of ethyl salicylate, followed by 0.95 ml of diisopropyl carbodiimide. After 18 hours, the mixture is concentrated under reduced pressure, and the residue triturated with ether. The organic phase is washed with aq. sodium bicarbonate and brine, dried (magnesium sulfate), and concentrated under reduced pressure. Flash chromatography on silica with 10% ethyl acetate in hexane affords 1.60 g of the title product as a colorless oil.

Physical characteristics are as follows:

$^1$H NMR δ 1.31; 1.75; 2.65; 4.25; 7.04; 7.2; 7.49; 7.99. IR 2937, 1765, 1723, 1294, 1272, 1261, 1204, 1133, 1121, 1082 cm$^{-1}$. Anal. Found: C, 73.37; H, 6.72.

EXAMPLE 2

4-Hydroxy-3-(3-phenylpropyl)coumarin (Formula A-5) Refer to Chart A

To a suspension of 80 mg of 60% sodium hydride/mineral oil in 3.0 ml of benzene in a flame dried flask, under argon, is added a solution of 326 mg of ester of Preparation 2 in 6.0 ml benzene. The mixture is refluxed overnight, then cooled and quenched with methanol. The mixture is partitioned between ether and 1N sodium hydroxide with two additional ether washes of the aqueous phase. Acidification of the aqueous gives a precipitate, which is extracted with 4 portions of dichloromethane-methanol. The organic is concentrated under reduced pressure, and the residue flash chromatographed on silica with 50–70% ethyl acetate in hexane to provide 108 mg of the title product as a white solid.

Physical characteristics are as follows:

$^1$H NMR δ 1.87; 2.63; 2.72; 7.2; 7.49; 7.87. $^{13}$C NMR δ 23.35, 29.46, 35.41, 104.94, 116.09, 116.16, 122.81, 123.51, 125.45, 128.02, 128.21, 131.06, 142.11, 151.97, 160.13, 164.55. EI HRMS [m]=280.1102.

PREPARATION 3

Ethylaminediamine diacetate (EDDA)

To a cold (0° C.), stirred solution of 0.67 ml of ethylenediamine in 5 ml of ether is added dropwise a solution of 1.3 ml of acetic acid in 5 ml of ether. The mixture, thick with precipitate, is stirred for 5 minutes at room temperature, then filtered on a coarse frit. The solid is washed well with ether and dried to constant weight under vacuum to afford 1.68 g of the salt title product as a white solid.

Physical characteristics are as follows:

M.p. 115°–116.5° C. (cf lit. value of 114° C. from Fieser & Fieser vol. 13, p. 172).

PREPARATION 4

2-Naphthyl dimer (Formula B-3: wherein R is naphthalene-2-yl) Refer to Chart B

A mixture of 778 mg of 4-hydroxycoumarin of formula B-1, 312 mg of 2-naphthaldehyde of formula B-2, wherein R is naphthalene-2-yl, and 18 mg of EDDA in 8 ml of absolute ethanol is stirred overnight. The precipitated solid is isolated by filtration on a medium frit, washed once with cold ethanol, and dried under vacuum to provide 722 mg of the title product as a pale yellow solid.

PREPARATION 5

Diphenylmethyl dimer (Formula B-3: wherein R is diphenylmethyl) Refer to Chart B.

A mixture of 1.56 g of 4-hydroxycoumarin of formula B-1, 0.71 ml of diphenylacetaldehyde of formula B-2, wherein R is diphenylmethyl, and 36 mg of EDDA in 16 ml of absolute ethanol is stirred at room temperature for seven days. The precipitated solid is isolated by filtration on a medium flit, washed twice with cold ethanol, and dried under vacuum to provide 945 mg of the title product as a white solid.

Physical characteristics are as follows:

FAB HRMS [m+H]=503.1511.

PREPARATION 6

Phenyl methyl dimer (Formula B-3: wherein R is α-methylbenzyl) Refer to Chart B.

A mixture of 778 mg of 4-hydroxycoumarin of formula B-1, 0.27 ml of 2-phenylpropanal of formula B-2, wherein R is α-methylbenzyl, and 18 mg of EDDA in 8 ml of absolute ethanol is stirred at room temperature for one week. The precipitated solid is isolated by filtration on a medium frit, washed once with cold ethanol, and dried under vacuum to provide 268 mg of the title product as a white solid.

Physical characteristics are as follows:
$R_f$=0.43 (EtOAc).
FAB MS [m+H]=441.

EXAMPLE 3

4-Hydroxy-3-(2-naphthylmethyl)coumarin (Formula B-4a) Refer to Chart B.

A mixture of 440 mg of the title product of Preparation 4 and 120 mg of sodium cyanoborohydride in 15 ml of methanol is refluxed under nitrogen for two days, after which TLC indicates some remaining starting material. Additional sodium cyanoborohydride (100 mg) is added, and refluxing continued for mother day. Methanol is then removed under a stream of nitrogen, aqueous ammonium chloride is added, and the mixture filtered. The solid is washed well with water and dried under vacuum to provide 267 mg of the title product as a white solid.

Physical characteristics are as follows:
$^1$H NMR (d-6 DMSO) δ3.82; 7.0–7.9.
$^{13}$C: δ 31.09, 97.66, 116.35, 122.52, 124.08, 125.33, 125.42, 126.33, 126.41, 127.71, 128.04. 128.17, 129.16, 130.27, 132.22, 133.99, 142.85. 154.44, 165.63, 172.52.
FAB MS [m+H]=303.1015.

EXAMPLE 4

4-Hydroxy-3-(2,2-diphenylethyl)-coumarin (Formula B-4b) Refer to Chart B.

A mixture of 640 mg of the title product of Preparation 5 and 240 mg of sodium cyanoborohydride in 19 ml of methanol is heated to reflux under argon. Refluxing is continued for several days, with periodic additions of ca 250 mg portions of sodium cyanoborohydride. The mixture is then partitioned between ethyl acetate and aqueous ammonium chloride, and the organic phase dried (magnesium sulfate) and concentrated under reduced pressure to give a solid of extraordinarily poor solubility. This is dissolved as best possible in chloroform-methanol and adsorbed onto silica for flash chromatography using 20% ethyl acetate in dichloromethane. Concentration of product fractions provides 335 mg of the title product as a white solid.

Physical characteristics are as follows:
M.p. 233°–234.5° C.
$^1$H NMR (d6-DMSO) δ 3.29; 4.48; 7.1–7.3; 7.42; 7.67.
EI MS [m]=342.

EXAMPLE 5

4-Hydroxy-3-(2-phenylpropyl)coumarin (Formula B-4c) Refer to Chart B.

A mixture of 157 mg of the title product of Preparation 6 and 45 mg of sodium-cyanoborohydride in 5 ml of methanol is refluxed under argon for two days, with one additional portion of 60 mg of reducing agent added midway. Methanol is removed, and the mixture partitioned between ethyl acetate and aq. ammonium chloride. The organic phase is washed with brine, dried (magnesium sulfate) and concentrated under reduced pressure. Flash chromatography on silica with 1:1 ethyl acetate in hexane provides 87.5 mg of the title product as a white crystalline solid.

Physical characteristics are as follows:
$R_f$=0.35 (1:1 ethyl acetate-hexane).
M.p. 158°–159° C.
$^1$H NMR δ 1.41; 2.78; 3.02; 3.16; 7.2; 7.50; 7.75.
FAB HRMS [m+H]=281.1170.

PREPARATION 7

3,3-Diphenylpropanoic acid methyl(N-methoxy) amide (Formula C-2)

Refer to Chart C.

To a cold (0° C.) suspension of 1.13 g of diphenylpropionic acid and 537 mg of N,O-dimethylhydroxylamine hydrochloride in 10 ml of dichloromethane is added 2.8 ml of diisopropylethylamine (most solid dissolved), followed by 1.27 g of bis(2-oxo-3-oxazolidinyl)phosphinic chloride. The solution is stirred for 1 hour at 0° C., then allowed to warm to room temperature and stirred overnight. The solution is then washed with excess dilute hydrochloric acid, with two additional methylene chloride extractions of the aqueous phase, and the combined organic phase dried (magnesium sulfate) and concentrated under reduced pressure. Flash chromatography of the residue on silica with 40–50% ethyl acetate in hexane affords 1.31 g of the title product as a colorless oil.

Physical characteristics are as follows:
$R_f$=0.35 (1:1 ethyl acetate-hexane).
$^1$H NMR δ 3.09; 3.18; 3.55; 4.69; 7.2–7.3.
IR 3027, 2937, 1661, 1495, 1450, 1417, 1385, 994, 752, 739, 701 cm$^{-1}$.
EI MS [m]=269.
Anal. Found: C, 75.10; H, 7.17; N, 5.12.

PREPARATION 8

3,3-Diphenylpropanal (Formula C-3) Refer to Chart C.

To a cold (0° C.), stirred solution of 1.26 g of the title product of Preparation 7 in 19 ml of dry tetrahydrofuran is added 213 mg of lithium aluminum hydride in one portion. After 45 minutes at 0° C., the dark gray slurry is pipetted into a stirred slurry of ice and 25 ml of 1M potassium hydrogen sulfate. The mixture is filtered to remove a small amount of insoluble inorganic material, and the organic phase extracted with one additional portion of ether. The combined organic phase is dried (magnesium sulfate) and concentrated under reduced pressure to provide 980 mg of the title product as a colorless oil. The material thus obtained is used without further purification.

Physical characteristics are as follows:
$R_f$=0.34 (20% ethyl acetate in hexane).
$^1$H NMR δ 3.17; 4.64; 7.1–7.4; 9.74.

PREPARATION 9

2-Phenylbutanoic acid methyl(N-methoxy)amide (Formula C-5) Refer to Chart C.

To a cold (0° C.) suspension of 1.64 g of 2-phenylbutanoic acid and 976 mg of N,O-dimethylhydroxylamine hydrochloride in 20 ml of dichloromethane is added 5.6 ml of diisopropylethylamine (most solid dissolved), followed by 2.55 g of bis(2-oxo-3-oxazolidinyl)phosphinic chloride. The solution is stirred for 0.5 hour at 0° C., then allowed to warm to room temperature and stirred overnight. Solvent is then removed under a flow of nitrogen gas, and the residue partitioned between ethyl acetate and water containing 12 ml of 1N hydrochloric acid. The organic phase is washed with dil. aq. sodium bicarbonate and brine, dried (magnesium sulfate), and concentrated under reduced pressure. Flash chromatography of the residue on silica with 35% ethyl acetate in hexane provides 2.06 g of the title product as a colorless liquid.

Physical characteristics are as follows:
$R_f$=0.30 (30% ethyl acetate in hexane).
$^1$H NMR δ 0.87; 1.7; 2.1; 3.15; 3.47; 3.89; 7.3.
IR 2967, 1662, 1461, 1454, 1382, 997, 700 cm$^{-1}$.
EI MS [m]=207.

PREPARATION 10

2-Phenylbutanal (Formula C-6) Refer to Chart C.

To a cold (0° C.). stirred solution of 1.45 g of the title product of Preparation 9 in 28 ml of dry tetrahydrofuran, under argon, is added 350 mg of lithium aluminum hydride in several portions. After 45 minutes at 0° C., the dark gray slurry is pipetted into a stirred slurry of ice and 35 ml of 1M potassium hydrogen sulfate. The mixture is filtered to remove a small amount of insoluble inorganic material, and the organic phase extracted with one additional portion of ether. The combined organic phase is washed with brine, dried (magnesium sulfate), and concentrated under reduced pressure to provide 1.06 g of the title product as a colorless oil. The material thus obtained is used without further purification.

Physical characteristics are as follows:
$R_f$=0.46 (20% ethyl acetate in hexane).
$^1$H NMR δ 0.90; 1.8; 2.1; 3.4; 7.3.

EXAMPLE 6

4-Hydroxy-3-(α-methylbenzyl)-coumarin (Formula D-3: wherein R is α-methylbenzyl) Refer to Chart D.

A suspension of 500 mg of 4-hydroxycoumarin of formula D-1 in 2.8 mL of (1-bromoethyl)-benzene of formula D-2 (wherein R is α-methylbenzyl) at room temperature is heated to 155° C. over 0.5 hours. After 0.5 hours at 155° C. the 4-hydroxycoumarin dissolves and a deep orange solution results. After a total of 2 hours at 155° C. the solution is cooled to room temperature (reaction mixture solidified). The material is partioned between 10 mL of diethyl ether and 25 mL of 1N sodium hydroxide. The aqueous phase is washed with diethyl ether, acidified to pH=1 with 6N hydrochloric acid; the resulting precipitant is repeatedly extracted with dichloromethane/methanol. The combined organic extractions are dried (magnesium sulfate) and concentrated under reduced pressure. The residue is flash column chromatographed using 50% to 70% ethyl acetate in hexanes to afford 430 mg of the title product as a white solid.

Physical characteristics are as follows:
$^1$H NMR δ 7.84, 7.45, 7.3–7.2, 4.65, 1.71;
IR (mull) 3237, 2925, 1671, 1627, 1396, 752 cm$^{-1}$;
EI-MS M+=266.0946 found.

EXAMPLE 7

4-Hydroxy-3-diphenylmethylcoumarin

To a mixture of 324 mg of 4-hydroxycoumarin and 368 mg of commercially available diphenylcarbinol in 30 mL of dioxane is added 0.37 mL of boron trifluoride etherate. After 100 hours at room temperature the reaction solution is diluted with 40 mL of diethyl ether and washed with water. The organic phase is dried (magnesium sulfate) and concentrated under reduced pressure. The residue is flash column chromatographed with 20% to 80% ethyl acetate in hexanes to give 587 mg of the title product.

Physical characteristics are as follows:
$^1$H NMR δ 7.73, 7.55, 7.42–7.23, 6.25, 5.99;
FAB-MS [m+H]=329 found.

EXAMPLE 8

4-Hydroxy-3-(3-hydroxy-1-phenylbutyl)-coumarin

To a milky white suspension of 924 mg of commercially available warfarin in diethyl ether at 0° C. under an argon atmosphere is slowly added 125 mg of lithium aluminum hydride in portions. After 3 hours at 0° C. the reaction is warmed to room temperature. After 1 hour the mixture is re-cooled to 0° C. and slowly treated with 5 mL of water followed by 10 mL of 1N sodium hydroxide. After the bubbling ceases the layers are separated and the aqueous phase is washed with diethyl ether, acidified with 6 N hydrochloric acid, and repeatedly extracted with dichloromethane (methanol-chloroform co-solvents). The combined organic layers are dried (magnesium sulfate) and concentrated under reduced pressure. The residue is flash column chromatographed using 2% to 20% methanol in dichloromethane to afford 590 mg of a diastereomeric mixture of the title product as a white solid.

Physical characteristics are as follows:
$^1$H NMR δ 7.91, 7.48–7.15, 4.59, 3.76, 2.59, 2.06, 1.25;
IR (mull) 3294, 2924, 1677, 1611, 1495, 756 cm$^{-1}$;
EI-MS M+=310 found.

PREPARATION 11

1-Bromo-2-methyl-1-phenylpropane (Formula D-2: wherein R is 2-methyl-1-phenylpropyl) Refer to Chart D.

To a flame-dried flask under an argon atmosphere equipped with a reflux condenser is added 3.0 g of commercially available 2-methyl-1-phenylpropan-1-ol. The alcohol is slowly treated with 0.60 mL of phosphorus tribromide in a dropwise fashion. Upon addition the exothermic mixture turns cloudy and becomes biphasic. After 0.25 hours, the reaction is partioned between diethyl ether-hexane and water. The organic phase is washed with dilute aqueous sodium bicarbonate, brine, dried (magnesium sulfate), and concentrated under reduced pressure employing a cold bath to yield 4.44 g of crude title product as a clear, colorless oil. The crude bromide is used directly in the next reaction without further purification.

Physical characteristics are as follows:
$^1$H NMR δ 7.25, 3.19, 1.74.

EXAMPLE 9

4-Hydroxy-3-(2-methyl-1-phenylpropyl)-coumarin (Formula D-3: wherein R is 2-methyl-1-phenylpropyl) Refer to Chart D.

To a pressure tube containing 250 mg of 4-hydroxycoumarin is added 2.14 g of crude 1-bromo-2-methyl-1-phenylpropane of Preparation 1 I. The resulting suspension is tightly sealed and heated to 110° C. After 2 hours the mixture is heated to 150° C. overnight. The resulting red solution is cooled to room temperature and partioner between diethyl ether and 1N sodium hydroxide; the aqueous phase is washed with diethyl ether, acidified to pH=1 with 6N hydrochloric acid, and repeatedly extracted with dichloromethane (methanol-chloroform co-solvents). The combined dichloromethane extracts are dried (magnesium sulfate) and concentrated under reduced pressure. The residue is flash column chromatographed using 30% to 50% ethyl acetate in hexane to afford 148 mg of the title product as a tan solid.

Physical characteristics are as follows:

$^1$H NMR δ 7.84, 7.59, 7.42, 7.31–7.13, 3.99, 3.14, 0.97, 0.90;

IR (mull) 3254, 2925, 1655, 1616, 754 cm$^{-1}$;

EI-MS M+=294.1249 found.

PREPARATION 12

1-Phenyl-1-butanol

To a stirring solution of 890 mg of commercially available butyrophenone in 30 mL of diethyl ether under an argon atmosphere at 0° C. is slowly added 250 mg of lithium aluminum hydride in portions. After 2 hours the grey suspension is slowly treated with 0.25 mL of water followed by 1.10 mL of 1N sodium hydroxide. After 0.5 hours the resulting whim precipitant is filtered through a pad of magnesium sulfate with diethyl ether washings. The filtrate is concentrated under reduced pressure to afford 0.90 g of the title product as a clear, colorless oil. This product may be used directly in the next reaction without further purification.

Physical characteristics are as follows:

$^1$H NMR δ 7.27, 4.61 and 4.59, 2.27, 1.77–1.57, 1.41–1.22, 0.90.

EXAMPLE 10

4-Hydroxy-3-(1-phenylbutyl)-coumarin

To a mixture of 792 mg of 4-hydroxycoumarin and 809 mg of 1-phenyl-1-butanol of Preparation 12 in 25 mL of dioxane under an argon atmosphere is added 2.6 mL of boron trifluoride etherate. The resulting yellow solution is left to stir at room temperature overnight. The volatiles are removed under reduced pressure and the residue is partioned between diethyl ether and 1N sodium hydroxide. The basic aqueous phase is washed with diethyl ether, acidified to pH=1 with 6N hydrochloric acid. The resulting precipitant is repeatedly extracted with dichloromethane (methanol-chloroform co-solvents). The combined dichloromethane extracts are washed once with dilute sodium bicarbonate to remove most of the unreacted 4-hydroxycoumarin, then brine, dried (magnesium sulfate), and finally concentrated under reduced pressure. The residue is adsorbed onto silica and flash column chromatographed with 40% to 50% ethyl acetate in hexane to yield 183 mg of the title product as white crystals.

Physical characteristics are as follows:

$^1$H NMR δ 7.84, 7.47, 7.33–7.17, 4.51 and 4.48, 2.40–2.27, 2.21–2.09, 1.37, 0.95;

IR (mull) 3192, 2926, 1674, 1669, 1604, 1202 cm$^{-1}$;

EI-MS M+=294.1259 found.

PREPARATION 13

1-Phenyl-1-pentanol

To a stirring suspension of 1.20 g of lithium aluminum hydride in 100 mL of diethyl ether under an argon atmosphere at 0° C. is slowly added a solution of 4.40 mL of commercially available valerophenone in 5.0 mL of diethyl ether over 10 minutes. After 0.5 hours the grey suspension is warmed to room temperature. After 1 hour the reaction mixture is re-cooled to 0° C. and slowly treated with 1.25 mL of water followed by 5.50 mL of 1N sodium hydroxide. After 1 hour the resulting white precipitant is filtered through a pad of magnesium sulfate with diethyl ether washings. The filtrate is concentrated under reduced pressure to afford 4.5 g of 1-phenyl-1-pentanol as a clear, colorless oil. This product may be used directly in the next reaction without further purification.

Physical characteristics are as follows:

$^1$H NMR δ 7.31, 4.65, 1.95, 1.82–1.68, 1.40–1.18, 0.87.

EXAMPLE 11

4-Hydroxy-3-(1-phenylpentyl)-coumarin

To a flame-dried flask containing a mixture of 811 mg of 4-hydroxycoumarin and 985 mg of 1-phenyl-1-pentanol in 30 mL of dioxane under an argon atmosphere is added 3.0 mL of boron trifluoride etherate. The resulting yellow solution is left to stir at room temperature overnight. The volatiles are removed and the residue is partioned between diethyl ether and 1N sodium hydroxide. The basic aqueous phase is washed with diethyl ether, acidified to pH=1 with 6N hydrochloric acid. The resulting precipitant is repeatedly extracted with dichloromethane (methanol-chloroform co-solvents). The combined dichloromethane extracts are washed once with dilute sodium bicarbonate to remove most of the unreacted 4-hydroxycoumarin, then brine, dried (magnesium sulfate), and finally concentrated under reduced pressure. The residue is adsorbed onto silica and flash column chromatographed with 40% to 50% ethyl acetate in hexane to yield 193 mg of the title product as white crystals.

Physical characteristics are as follows:

$^1$H NMR δ 7.87, 7.48, 7.29–7.17, 4.65, 2.43–2.31, 2.23–2.14, 1.43–1.24, 0.87;

IR (mull) 3223, 2925, 1676, 1669, 1605, 1196 cm$^{-1}$;

EI-MS M+=308.1423 found;

Elem. Anal. found C, 77.52, H, 6.66.

PREPARATION 14

1-(4-Bromophenyl)-2-methylpropan-1-ol

To a flame-dried flask under an argon atmosphere is added 1.85 g of commercially available 4-bromobenzaldehyde and charged with 30 mL of tetrahydrofuran. The solution is cooled to 0° C. and slowly treated with 7.0 mL of isopropylmagnesium bromide. After stirring overnight at room temperature the reaction mixture is concentrated under reduced pressure. The residue is partioned between diethyl ether and saturated ammonium chloride; the aqueous layer is then extracted with diethyl ether. The combined organic phases are dried (magnesium sulfate), and the volatiles are removed. The residue is flash column chromatographed using 30% to 60% diethyl ether in hexane to afford 1.25 g of the title product as a viscous, tan oil.

Physical characteristics are as follows:

$^1$H NMR δ 7.42, 7.13, 4.28, 2.27, 1.86, 0.94, 0.76.

EXAMPLE 12

3-(1-(4-Bromophenyl)-2-methylpropyl)-4-hydroxycoumarin

To a flame-dried flask containing a near-solution of 324 mg of 4-hydroxycoumarin and 573 mg of 1-(4-bromophenyl)-2-methylpropan-1-ol of Preparation 14 in 10 mL of dioxane under an argon atmosphere is added 1.2 mL of boron trifluoride etherate. The resulting yellow solution is left to stir at room temperature overnight. The volatiles are removed and the residue is partioned between diethyl ether and 1N sodium hydroxide. The basic aqueous phase is washed with diethyl ether and acidified to pH=1 with 6N hydrochloric acid. The resulting precipitant is repeatedly extracted with dichloromethane (methanol-chloroform co-solvents). The combined dichloromethane extracts are washed once with dilute sodium bicarbonate to remove most of the unreacted 4-hydroxycoumarin, then brine, dried (magnesium sulfate), and finally concentrated under reduced pressure. The residue is adsorbed onto silica and flash column chromatographed with 50% to 60% ethyl acetate in hexanes to yield 28 mg of the title product as a tan solid.

Physical characteristics are as follows:

$^1$H NMR δ 7.86, 7.50–7.44, 7.35, 7.25, 3.94, 3.10, 0.95, 0.88;

EI-MS M+=374 and 372 found.

PREPARATION 15

1,2-Diphenylethanol

To a stirring suspension of 1.20 g of lithium aluminum hydride in 100 mL of diethyl ether under an argon atmosphere at 0° C. Is slowly added a solution of 5.50 g of commercially available deoxybenzoin in 25.0 mL of diethyl ether. After 0.5 hours the grey suspension is warmed to room temperature. After 1 hour the reaction mixture is re-cooled to 0° C. and slowly treated with 1.25 mL of water followed by 5.50 mL of 1N sodium hydroxide. After 0.5 hour the resulting white precipitant is filtered through a pad of magnesium sulfate with diethyl ether washings. The filtrate is concentrated under reduced pressure to afford 5.50 g of the title product as off-white crystals. This product may be used directly in the next reaction without further purification.

Physical characteristics are as follows:

$^1$H NMR δ 7.38–7.12, 4.80 and 4.78, 2.95, 2.17.

EXAMPLE 13

3-(1,2-Diphenylethyl)-4-hydroxycoumarin

To a flame-dried flask containing a near-solution of 810 mg of 4-hydroxycoumarin and 1.20 mg of 1,2-diphenylethanol of Preparation 15 in 30 mL of dioxane under an argon atmosphere is added 3.0 mL of boron trifluoride etherate. The resulting yellow solution is left to stir at room temperature overnight; the reaction is then heated to reflux for 48 hours. The volatiles are removed and the residue is partioned between diethyl ether and 1N sodium hydroxide. The basic aqueous phase is washed with diethyl ether and acidified to pH=1 with 6 N hydrochloric acid. The resulting precipitant is repeatedly extracted with dichloromethane (methanol-chloroform co-solvents). The combined dichloromethane extracts are washed once with dilute sodium bicarbonate to remove most of the unreacted 4-hydroxycoumarin, then brine, dried (magnesium sulfate), and finally concentrated under reduced pressure. The residue is adsorbed onto silica and flash column chromatographed with 40% to 50% ethyl acetate in hexanes to yield 167 mg of the title product as a white solid.

Physical characteristics are as follows:

$^1$H NMR δ 7.77, 7.55, 7.36, 7.29–7.06, 4.88 and 4.85, 3.80 and 3.74, 3.48 and 3.42;

IR (mull) 3172, 2924, 1668, 1607, 1170, 699 cm$^{-1}$;

PREPARATION 16

3-Methyl-1-phenylbutan-1-ol

To a time-dried flask under an argon atmosphere is added 0.50 mL of commercially available isovaleraldehyde and charged with 15 mL of diethyl ether. The solution is cooled to 0° C. and is treated with 2.0 mL (3.0 M in diethyl ether) of phenylmagnesium bromide. The reaction mixture is left to warm to room temperature overnight and then partioned between diethyl ether and saturated ammonium chloride. The aqueous phases are extracted with diethyl ether and the combined organic layers are dried (magnesium sulfate) and finally concentrated under reduced pressure. The residue is flash column chromatographed using 20% diethyl ether in hexanes to yield 800 mg of the title product as a clear, colorless oil.

Physical characteristics are as follows:

$^1$H NMR δ 7.30–7.10, 4.60, 2.84, 1.69–1.55, 1.47–1.40, 1.28, 0.90, 0.87.

EXAMPLE 14

4-Hydroxy-3-(3-methyl-1-phenylbutyl)-coumarin

To a time-dried flask containing a near-solution of 650 mg of 4-hydroxycoumarin and 800 mg of 3-methyl-1-phenylbutan-1-ol of Preparation 16 in 25 mL of dioxane under an argon atmosphere is added 2.5 mL of boron trifluoride etherate. The resulting yellow solution is left to stir at room temperature. After 3 days the volatiles are removed and the residue is partioned between diethyl ether and 1N sodium hydroxide. The basic aqueous phase is washed with diethyl ether and acidified to pH=1 with 6N hydrochloric acid. The resulting precipitant is repeatedly extracted with dichloromethane (methanol-chloroform Co-solvents). The combined dichloromethane extracts are washed once with dilute sodium bicarbonate to remove most of the unreacted 4-hydroxycoumarin, then brine, dried (magnesium sulfate), and finally concentrated under reduced pressure. The residue is adsorbed onto silica and flash column chromatographed with 30% to 40% ethyl acetate in hexane to yield 248 mg of the title product as a white solid.

Physical characteristics are as follows:

$^1$H NMR δ 7.85, 7.52–7.43, 7.31–7.17, 4.62. 2.41–2.31, 2.20–1.90, 1.60–1.51, 0.96;

IR (mull) 3221, 2925, 1670, 1624, 1397, 750 cm$^{-1}$;

EI-MS M+=308 found.

Elem. Anal. found C, 77.82, H, 6.52.

EXAMPLE 15

3-(Cyclopropylphenylmethyl)-4-hydroxycoumarin (Formula D-3: where R is cyclopropylphenylmethyl) Refer to Chart D.

To a flame-dried flask containing a mixture of 650 mg of 4-hydroxycoumarin of formula D-5 and 741 mg of α-cyclopropylbenzyl alcohol of formula D-4, wherein R is cyclopropylphenylmethyl, in 20 mL of dioxane under an argon atmosphere is added 2.5 mL of boron trifluoride etherate. The resulting yellow solution is left to stir at room temperature. After 3 days the volatiles are removed under reduced pressure and the residue is partioned between diethyl ether and 1N sodium hydroxide. The basic aqueous phase is washed with diethyl ether and acidified to pH=1 with 6N hydrochloric acid. The resulting precipitant is repeatedly extracted with dichloromethane (methanol-chloroform co-solvents). The combined dichloromethane extracts are washed once with dilute sodium bicarbonate to remove most of the unreacted 4-hydroxycoumarin, then brine, dried (magnesium sulfate), and finally concentrated under reduced pressure. The residue is adsorbed onto silica and flash column chromatographed with 40% to 60% ethyl acetate in hexane to yield 580 mg of the title product as a whim solid. Physical characteristics are as follows:

$^1$H NMR δ 7.87, 7.52, 7.32–7.20, 3.75, 1.90–1.81, 0.81–0.74, 0.57–0.52, 0.41–0.31;

IR (mull) 2925, 1671, 1662, 1604, 1560, 761 cm$^{-1}$;

EI-MS M+=292 found.

PREPARATION 17

1,3-Diphenylpropan-2-ol

To a stirring suspension of 1.10 g of lithium aluminum hydride in 50 mL of diethyl ether under an argon atmosphere at 0° C. is slowly added a solution of 5.30 g of commercially available 1,3-diphenylacetone in 10.0 mL of diethyl ether with a 10 mL rinse. After 0.25 hours the grey suspension is warmed to room temperature. After 1.5 hours the reaction mixture is re-cooled to 0° C. and slowly treated with 1.2 mL of water followed by 5.0 mL of 1N sodium hydroxide. After 1 hour the resulting white precipitant is filtered through a pad of magnesium sulfate with diethyl ether washings. The filtrate is concentrated under reduced pressure to afford 5.2 g, of the title product as a viscous, clear, colorless oil. This product may be used directly in the next reaction without further purification. Physical characteristics are as follows:

$^1$H NMR δ 7.35–7.20, 4.05, 2.8, 1.64.

PREPARATION 18

2-Bromo-1,3-diphenylpropane (Formula D-2: where R is dibenzylmethyl) Refer to Chart D.

To a flame-dried flask under an argon atmosphere equipped with a reflux condenser is added 2.12 g of 1,3-diphenyl-propan-2-ol of Preparation 17. The alcohol is slowly treated with 0.32 mL of phosphorus tribromide in a dropwise fashion. Upon addition the exothermic mixture turns cloudy and becomes biphasic. After 1 hour the reaction is partioned between diethyl ether-hexane and water. The organic phase is washed with dilute aqueous sodium bicarbonate, brine, dried (magnesium sulfate), and concentrated under reduced pressure employing a cold bath to yield 2.08 g of crude title product as a viscous tan oil. The crude bromide may be used directly in the next preparation without further purification.

EXAMPLE 16

4-Hydroxy-3-(1,3-diphenylpropyl)-coumarin (Formula D-3: wherein R is 1,3-diphenylpropyl) Refer to Chart D.

To a flask containing 485 mg of 4-hydroxycoumarin of formula D-1 is added 2.08 g crude 2-bromo-1,3-diphenylpropane of Preparation 18. The resulting suspension is equipped with a reflux condenser and heated to 130° C. overnight. The reaction mixture is cooled to room temperature and partioned between diethyl ether and 1N sodium hydroxide; the aqueous phase is washed with diethyl ether, acidified to pH=1 with 6N hydrochloric acid, and repeatedly extracted with dichloromethane (methanol-chloroform co-solvents). The combined dichloromethane extracts are washed with dilute aqueous sodium bicarbonate, brine, dried (magnesium sulfate) and concentrated under reduced pressure. The residue is adsorbed onto silica gel and then flash column chromatographed using 40 % to 60% ethyl acetate in hexane to afford 32 mg of the title product as a tan solid.

Physical characteristics are as follows:

$^1$H NMR δ 7.72, 7.49, 7.39–7.14, 6.73, 4.65, 2.86–2.66, 2.51;

EI-MS M+=356.1410 found.

PREPARATION 19

2-Cyclohexyl-1-phenylethanol

To a flame-dried flask is added 5.4 g of pyridinium chlorochromate and charged with 20 mL of dichloromethane. The resulting orange suspension is treated with 0.70 mL of commercially available 2-cyclohexylethanol. After 3 hours the brown mixture is filtered through a pad of Celite with dichloromethane washings. The filtrate is washed with dilute hydrochloric acid, dilute aqueous sodium bicarbonate, brine, dried (magnesium sulfate) and finally filtered though a pad of Celite.

The pale tan filtrate is cooled to 0° C. under an argon atmosphere and slowly treated with 5.0 mL (3.0M in diethyl ether) of phenylmagnesium bromide. The reaction mixture is left to warm to room temperature overnight. The material is then washed with dilute aqueous ammonium chloride, saturated ammonium chloride, brine, dried (magnesium sulfate), and concentrated under reduced pressure. The residue is flash column chromatographed using 15% to 25% diethyl ether in hexane to give 1.01 g of the title product as a viscous, clear, tan oil.

Physical characteristics are as follows:

$^1$H NMR δ 7.40–7.21, 4.78, 1.81–0.86.

EXAMPLE 17

3-(2-Cyclohexyl-1-phenylethyl)-4-hydroxycoumarin

To a time-dried flask containing a mixture of 650 mg of 4-hydroxycoumarin and 1.01 g of 2-cyclohexyl-1-phenylethanol of Preparation 19 in 20 mL of dioxane under an argon atmosphere is added 2.5 mL of boron trifluoride etherate. The resulting yellow solution is left to stir at room temperature overnight. The volatiles are removed and the residue is partioned between diethyl ether and 1N sodium hydroxide. The basic aqueous phase is washed with diethyl ether and acidified to pH=1 with 6N hydrochloric acid. The resulting precipitant is repeatedly extracted with dichloromethane (methanol-chloroform co-solvents). The combined dichloromethane extracts are washed once with dilute sodium bicarbonate to remove most of the unreacted 4-hydroxycoumarin, then brine, dried (magnesium sulfate), and finally concentrated under reduced pressure. The residue is adsorbed onto silica and flash column chromatographed with 30% to 60% ethyl acetate in hexanes to yield 110 mg of the title product as a tan solid.

Physical characteristics are as follows:

$^1$H NMR δ 7.71, 7.53–7.20, 6.67, 4.75, 2.13–0.93;

IR (mull) 3217, 2924, 1673, 1623, 757 cm$^{-1}$;

EI-MS M+=348.1724 found.

PREPARATION 20

1-(4-Methylphenyl)-butan-1-ol

To a flame-dried flask under an argon atmosphere is added 0.59 mL of commercially available p-tolualdehyde and charged with 15 mL of tetrahydrofuran. The solution is cooled to 0° C. and is treated with 3.0 mL (2.0M in diethyl ether) of propylmagnesium bromide. The reaction mixture is left to warm to room temperature overnight and then quenched by the addition of aqueous ammonium chloride. After dilution with diethyl ether the phases are separated; the organic layer is washed with saturated ammonium chloride, brine, dried (magnesium sulfate) and finally concentrated under reduced pressure. The residue is flash column chromatographed using 20% to 30% diethyl ether in hexane to yield 980 mg of the title product as a clear, colorless oil.

Physical characteristics are as follows:

$^1$H NMR δ 7.22, 4.62, 2.33, 1.86–1.26, 0.92.

EXAMPLE 18

4-Hydroxy-3-(1-(4-methylphenyl)-butyl)-coumarin

To a flame-dried flask containing a mixture of 650 mg of 4-hydroxycoumarin and 980 mg of 1-(4-methylphenyl)-butan-1-ol of Preparation 20 in 20 mL of dioxane under an argon atmosphere is added 2.5 mL of boron trifluoride etherate. The resulting yellow solution is left to stir at room temperature overnight. The volatiles are removed and the residue is partioned between diethyl ether and 1N sodium hydroxide. The basic aqueous phase is washed with diethyl ether and acidified to pH=1 with 6N hydrochloric acid. The resulting precipitant is repeatedly extracted with dichloromethane (methanol-chloroform co-solvents). The combined dichloromethane extracts are washed once with dilute sodium bicarbonate to remove most of the unreacted 4-hydroxycoumarin, then brine, dried (magnesium sulfate), and finally concentrated under reduced pressure. The residue is adsorbed onto silica and flash column chromatographed with 40% to 50% ethyl acetate in hexane to yield 660 mg of the title product as a white solid.

Physical characteristics are as follows:

$^1$H NMR δ 7.84, 7.8, 7.47, 7.39, 7.22, 7.13, 4.60, 2.30, 2.15, 1.42, 0.96;

IR (mull) 2955, 2925, 2857, 1666, 1607 cm$^{-1}$;

EI-MS M+=308.1400 found.

PREPARATION 21

1-(4-Ethylphenyl)-butan-1-ol

To a flame-dried flask under an argon atmosphere is added 0.69 mL of commercially available 4-ethylbenzaldehyde and charged with 15 mL of diethyl ether. The solution is cooled to 0° C. and is treated with 3.0 mL (2.0M in diethyl ether) of propylmagnesium bromide. The reaction mixture is left to warm to room temperature overnight and then quenched by the addition of aqueous ammonium chloride. After dilution with diethyl ether the phases are separated; the organic layer is washed with saturated ammonium chloride, dried (magnesium sulfate) and finally concentrated under reduced pressure. The residue is flash column chromatographed using 25% to 30% diethyl ether in hexane to yield 1.08 g of the title product as a clear, colorless oil.

Physical characteristics are as follows:

$^1$H NMR δ 7.28–7.15, 4.62 and 4.60, 2.63, 1.90, 1.79–1.61, 1.5–1.2, 1.22, 0.90.

EXAMPLE 19

3-(1-(4-Ethylphenyl)-butyl)-4-hydroxycoumarin

To a flame-dried flask containing a mixture of 325 mg of 4-hydroxycoumarin and 500 mg of 1-(4-ethylphenyl)-butan-1-ol of Preparation 21 in 10 mL of dioxane under an argon atmosphere is added 1.25 mL of boron trifluoride etherate. The resulting yellow solution is left to stir at room temperature overnight. The volatiles are removed and the residue is partioned between diethyl ether and 1N sodium hydroxide. The basic aqueous phase is washed with diethyl ether and acidified to pH=1 with 6N hydrochloric acid. The resulting precipitant is repeatedly extracted with dichloromethane (methanol-chloroform co-solvents). The combined dichloromethane extracts are washed once with dilute sodium bicarbonate to remove most of the unreacted 4-hydroxycoumarin, then brine, dried (magnesium sulfate), and finally concentrated under reduced pressure. The residue is flash column chromatographed with 40% ethyl acetate in hexane to yield 360 mg of the title product as a white solid.

Physical characteristics are as follows:

$^1$H NMR δ 7.85, 7.49–7.33, 7.26–7.20, 7.12, 4.49 and 4.46, 2.59, 2.36–2.26, 2.19–2.08, 1.42–1.36, 1.20, 0.96;

IR (mull) 2956, 2927, 2871, 1663, 1605, 1454, 1378 cm$^{-1}$;

EI-MS M+=322.1561 found.

PREPARATION 22

1-(1-Naphthyl)-propan-1-ol

To a flame-dried flask containing 8.0 mL of dry tetrahydrofuran under an argon atmosphere cooled to −78° C. Is added 4.0 mL (3.0 M) of a solution of ethylmagnesium bromide in tetrahydrofuran. The stirrable mixture is treated with a solution of 1.36 g of commercially available 1-naphthaldehyde in 4.0 mL of tetrahydrofuran with a 2 mL rinse. The reaction is stirred at −78° C. for 5 minutes then warmed to room temperature. After 1 hour the mixture is re-cooled to 0° C., carefully quenched with saturated ammonium chloride, and diluted with diethyl ether. The layers are separated; organic phase washed with brine, dried (magnesium sulfate), and concentrated under reduced pressure. The residue is flash column chromatographed using 25% ethyl acetate in hexane to give 1.76 g of the title product as a pale pink oil.

Physical characteristics are as follows:

$^1$H NMR δ 8.08, 7.85, 7.75, 7.60, 7.52–7.23, 5.36 and 5.34, 2.14, 2.02–1.62, 0.94.

EXAMPLE 20

4-Hydroxy-3-(1-(1-naphthyl)-propyl)-coumarin

To a cloudy solution of 324 mg of 4-hydroxycoumarin and 373 mg of 1-(1-naphthyl)-propan-1-ol of Preparation 22 in 7 mL of dioxane under an argon atmosphere is added 0.85 mL of boron trifluoride etherate. After stirring overnight the resulting yellow solution is concentrated under reduced pressure. The residue is partioned between water and ethyl acetate; the organic phase is washed with brine, dried (magnesium sulfate), and concentrated. The residue is adsorbed onto silica gel and then flashed column chromatographed using 40% to 50% ethyl acetate in hexane to yield 337 mg of the title product as a pale yellow solid. An analytical sample may be prepared by crystallization from ethyl acetate-hexanes.

Physical characteristics are as follows:

(M.p. 200°–202 ° C.):

$^1$H NMR δ 8.10, 7.88–7.81, 7.59–7.41, 7.27, 7.13, 6.74, 5.13, 2.42–2.21, 1.18;

IR (mull) 3234, 2954, 2924, 2855, 1678, 1622, 1610 cm$^{-1}$;

FAB-MS [m+H]=331 found.

EXAMPLE 21

3-(1,2-Diphenylethenyl)4-hydroxycoumarin

To a flame-dried flask containing a mixture of 650 mg of 4-hydroxycoumarin and 1.0 g of commercially available trans-stilbene oxide in 20 mL of dioxane under an argon atmosphere is added 2.5 mL of boron trifluoride etherate. The resulting yellow solution is left to stir at room temperature overnight. The volatiles are removed and the residue is partioned between diethyl ether and 1N sodium hydroxide. The basic aqueous phase is washed with diethyl ether and acidified to pH=1 with 6N hydrochloric acid. The resulting precipitant is repeatedly extracted with dichloromethane (methanol-chloroform co-solvents). The combined dichloromethane extracts are washed once with dilute sodium bicarbonate to remove most of the unreacted 4-hydroxycoumarin, then brine, dried (magnesium sulfate), and finally concentrated under reduced pressure. The residue is flash column chromatographed with 50% to 66% ethyl acetate in hexane to yield 880 mg of the title product as a white solid.

Physical characteristics are as follows:

$^1$H NMR δ 7.48, 7.14, 7.06–6.82, 6.31;

$^{13}$C NMR δ 161, 160, 152, 147, 142, 140, 131, 129, 128 (2), 127, 123 (2), 117, 116 (2), 103;

IR (mull) 2954, 2925, 2855, 1670, 1611, 755, 701 cm$^{-1}$;

EI-MS M+=340 found.

PREPARATION 23

3-(3-Cyano-phenyl)-but-2-enoic acid tert-butyl ester (Formula E-2) Refer to Chart E.

To a flame-dried, 3-neck, round-bottom flask equipped with a reflux condenser under an argon atmosphere is added 880 mg (60% dispersion in mineral oil) of sodium hydride and 10 mL of dry benzene. The suspension is cooled to 0°

C. and treated dropwise with 4.2 mL of dimethyl tert-butoxycarbonyl-methylphosphonate. The addition is at a rate to control the evolution of gas and exotherm. After 10 minutes the solution is warmed to room temperature. After 1 hour the solution is re-cooled to 0° C. and treated with 2.90 g of commercially available 3-acetylbenzonitrile of formula E-1 as a solid. The walls of the reaction flask are rinsed with 5 mL of dry benzene. As the reaction is warmed to room temperature, the mixture becomes cloudy with the formation of a precipitant. After 1 hour at room temperature the reaction is heated in an 80° C. oil bath overnight. The resulting gummy residue is cooled to room temperature and partioner between diethyl ether and dilute aqueous potassium hydrogen sulfate. The aqueous layer is extracted twice with additional portions of diethyl ether. The combined diethyl ether extractions are dried over magnesium sulfate, filtered and finally concentrated under reduced pressure. The residue is purified by flash column chromatographed on silica gel eluting with 10% to 15% ethyl acetate in hexane to afford 4.30 g of diastereomeric (@3:1 major:minor isomeric ratio) title product as a pale tan oil.

Physical characteristics are as follows:
$^1$H NMR (CDCl$_3$) δ 7.74–7.43, 6.06, 5.90, 2.53, 2.13, 1.52, 1.27.

PREPARATION 24

3-(3-Cyano-phenyl)-butyric acid tert-butyl ester (Formula E-3) Refer to Chart E.

To a Parr bottle containing 500 mg of 5% palladium on carbon is added 4.30 g of 3-(3-cyano-phenyl)-but-2-enoic acid tert-butyl esters of Preparation 23 as a solution in 15 mL of ethyl acetate. The reaction mixture is shaken at 45 psi of hydrogen gas overnight. The resulting black slurry is filtered through Celite with ethyl acetate washings of the filter cake. The combined filtrates are concentrated under reduced pressure to afford 4.30 g of the title product as a clear, colorless oil.

Physical characteristics are as follows:
$^1$H NMR (CDCl$_3$) δ 7.54–7.37, 3.28, 2.51, 1.34, 1.30.

PREPARATION 25

3-(2-Carboxy-1-methyl-ethyl)-benzoic acid (Formula E-4) Refer to Chart E.

To a stirring solution of 1.09 g of 3-(3-cyano-phenyl)-butyric acid tert-butyl ester of Preparation 24 in 1.0 ml of ethanol is added 5.0 mL of a 30% potassium hydroxide aqueous solution. The resulting mixture is heated at 70° C. for 3 days. The reaction is cooled to room temperature and washed twice with diethyl ether. The aqueous layer is acidified to pH=2 with 1N aqueous hydrochloric acid. The resulting precipitant is extracted with chloroform containing methanol until none of the desired material is visible in the aqueous layer by thin layer chromatography. The combined chloroform extractions are dried over magnesium sulfate, filtered and finally concentrated under reduced pressure to afford 0.67 g of the title product as a pale tan solid.

Physical characteristics are as follows:
$^1$H NMR (CDCl$_3$-CD$_3$OD) δ 7.92, 7.46, 7.38, 4.88, 3.34, 2.62, 1.34;
EI-MS: [M+]=208.0755 found.
Elemental analysis, found C, 63.42; H, 5.78.

PREPARATION 26

3-(2-tert-Butoxycarbonyl-1-methyl-ethyl)-benzoic acid tert-butyl ester (Formula E-5) Refer to Chart E.

To a flask containing a suspension of 2.71 g of 3-(2-carboxy-1-methyl-ethyl)-benzoic acid of Preparation 25 in 40 mL of dichloromethane is added isobutylene gas via a Claisen head adapter. The gas is condensed on a dry ice-acetone cold finger trap to a liquid which is dripped into the reaction vessel until the reaction volume has approximately doubled. The introduction of isobutylene is ceased and the resulting tan solution is allowed to stir at room temperature overnight. The reaction mixture is slowly added to excess saturated sodium bicarbonate and partioned against diethyl ether. The aqueous layer is extracted with three additional portions of diethyl ether. The combined diethyl ether layers are washed with brine, dried over magnesium sulfate, filtered and finally concentrated under reduced pressure. The resulting residue is purified by flash column chromatographed on silica gel eluting with 5% to 10% ethyl acetate in hexane to afford 2.38 g of the title product as a clear, light tan oil.

Physical characteristics are as follows:
$^1$H NMR (CDCl$_3$) δ 7.83, 7.36, 3.28, 2.51, 1.60, 1.35, 1.28;
EI-MS: [M$^+$–15]=305 found.

PREPARATION 27

3-[2-tert-Butoxycarbonyl-3-(2-hydroxy-phenyl)- 1-methyl-3-oxo-propyl]-benzoic acid tert-butyl ester (Formula E-6) Refer to Chart E.

To a flame-dried flask under argon is added 1.40 mL of diisopropylamine and 10 mL of dry tetrahydrofuran. The solution is cooled to –78° C. and treated with 6.20 mL (1.6M in hexane) of n-butyllithium. The solution is warmed to 0° C. for 30 minutes, then re-cooled to –78° C. The tan lithium diisopropylamine solution is treated with 1.98 g of 3-(2-tert-butoxycarbonyl-1-methyloethyl)-benzoic acid tert-butyl ester of Preparation 26 as a solution in 6.0 mL of dry tetrahydrofuran (1.0 mL rime) via cannula. The resulting bright yellow enolate solution is stirred for 45 minutes and then treated with 0.40 mL of methyl salicylate as a solution in 2.0 mL of tetrahydrofuran (1.0 mL rinse) via cannula. The resulting reddish reaction mixture is left to slowly warm to room temperature overnight. The reaction mixture is then concentrated under reduced pressure and partioner between ethyl acetate and cold, dilute aqueous hydrochloric acid. The aqueous phase is extracted with two additional portions of ethyl acetate. The combined ethyl acetate extractions are washed with brine, dried over magnesium sulfate, filtered and finally concentrated under reduced pressure. The resulting residue is purified by flash column chromatography on silica gel eluting with 10% to 25% ethyl acetate in hexane to afford 0.895 g of diastereomeric (@3:1 major:minor isomeric ratio) title product as a pale oil.

Physical characteristics are as follows:
$^1$H NMR (CDCl$_3$) δ 12.19, 11.88, 8.0–6.9, 4.62, 4.56, 3.86, 1.61, 1.56, 1.43, 1.40, 1.27, 1.07.

PREPARATION 28

3-[1-(4-Hydroxy-2-oxo-2H-chromen-3-yl)-ethyl]-benzoic acid (Formula E-7) Refer to Chart E.

To a flask containing 187 mg of 3-[2-tert-butoxycarbonyl-3-(2-hydroxy-phenyl)- 1-methyl-3-oxo-propyl]-benzoic acid tert-butyl ester of Preparation 27 is added 2.0 mL of trifluoroacetic acid. The resulting tan solution is left to stir at room temperature. After 14 hours the reaction becomes milk-like with a large mount of white precipitant. The reaction mixture is concentrated under reduced pressure and triturated with toluene (3×) to remove the residual trifluoroacteic acid to afford 124 mg of the title product as a tan solid.

Physical characteristics are as follows:
$^1$H NMR (d$_7$-DMF) δ 8.05, 7.85, 7.64, 7.30, 4.75, 1.76;
EI-MS: [M$^+$]=310.0841 found.

EXAMPLE 22

4-Hydroxy-3-[1-[3-[[[(1,1-dimethylethoxycarbonyl) methyl]amino]carbonyl]phenyl]ethyl]-coumarin To a stirring solution of 46 mg of the title product of Preparation 28, 30 mg of the hydrochloride salt of glycine tert-butyl ester and 60 μL of diisopropylethylamine in 0.5 mL of dichloromethane is added 30 μL of diethyl cyanophosphonate. The mixture is left to stir at room temperature overnight. The reaction is diluted with additional dichloromethane and washed sequentially with dilute aqueous hydrochloric acid, water and finally brine. The dichloromethane layer is dried over magnesium sulfate, filtered and finally concentrated under reduced pressure. The residue is purified by flash column chromatography on silica gel eluting with 5% to 8% methanol in dichloromethane to afford 48 mg of the title product as a white solid.

Physical characteristics are as follows:
$^1$H NMR (CDCl$_3$) δ 7.83, 7.46, 7.20, 4.60, 4.13, 1.64, 1.47;
FAB-MS: [M+H]=424.1733 found.

PREPARATION 29

(E and Z)-3-(3-nitrophenyl)-pent-2-enoic acid tert-butyl ester (Formula F-2) Refer to Chart F.

Sodium hydride (1.0 g of 60% oil dispersion) is suspended under argon in 25 ml of benzene in a dry three-necked flask fitted with addition funnel, argon inlet, and electronic thermometer probe. The flask is immersed in an ice bath, and to the magnetically stirred suspension is added 4.8 ml of tert-butyl-P,P-dimethylphosphonoacetate (neat) via the addition funnel. The rate of addition is regulated to maintain the reaction temperature between 10–15° C. Following the addition, the ice bath is removed and the mixture stirred at room temperature for 60 minutes. After this time, 4.48 g of commercially available finely powdered m-nitropropiophenone of formula F-1 is quickly added as a solid through an available neck of the reaction vessel. The reaction mixture immediately turns dark and evolves heat, and magnetic stirring soon becomes impossible. The dark gum that soon forms is broken up with a spatula (with minimal exposure to atmospheric moisture) and the reaction stirred as best possible overnight.

The following day, the mixture is partitioned between ether and aqueous sodium hydrogen sulfate. The organic phase is washed with brine and dried (magnesium sulfate). The solvent is removed under reduced pressure and the residue flash chromatographed on silica gel 60 (230–400 mesh) with 10% ethyl acetate in hexane to afford 6.16 g of the title products as a yellow oil. The E/Z isomers are separable by column chromatography, although this is not necessary since both are convened to the same product in the next chemical step.

For isomer A physical characteristics are as follows:
$^1$H NMR δ 1.08, 1.53, 3.10, 6.00, 7.57, 7.76, 8.21, 8.29.
R$_f$ 0.38 (15% ethyl acetate in hexane).

For isomer B physical characteristics are as follows:
$^1$H NMR δ 1.07, 1.24, 2.46, 5.89, 7.5, 8.03, 8.17.
R$_f$ 0.32 (15% ethyl acetate in hexane).

For the E/Z mixture of the title products as obtained from the reaction:

Physical characteristics are as follows:
EI MS 277.
IR 2977, 1712, 1531, 1349, 1150 cm$^{-1}$.
Anal. Found: C, 64.95; H, 6.93; N, 5.04.

PREPARATION 30

3-(3-Aminophenyl)pentanoic acid tert-butyl ester (Formula F-3) Refer to Chart F.

To a solution of 4.64 g of the starting olefin of Preparation 29 in 40 ml of methanol is added 260 mg of 5% platinum on carbon. The mixture is placed in a Parr apparatus and shaken under 50 psi hydrogen gas overnight. The following day, GC analysis shows the reduction incomplete. Platinum oxide (200 mg) is added, and shaking resumed under 50 psi hydrogen gas. After a few more hours, GC indicates complete reduction. The mixture is filtered through a pad of Celite with ethyl acetate rinses, and the filtrate concentrated under reduced pressure to provide 4.15 g of the title product as a tan oil.

Physical characteristics are as follows:
$^1$H NMR δ 0.79, 1.34, 1.6, 2.5, 2.85, 3.6, 6.5, 7.1.
EI MS 249.

PREPARATION 31

3-(3-Triphenylmethylaminophenyl)pentanoic acid tert-butyl ester (Formula F-4) Refer to Chart F.

To a stirred solution of 4.15 g of the starting amine Preparation 30 and 3.5 ml of diisopropylethylamine in 40 ml of dichloromethane is added 5.10 g of chlorotriphenylmethane in several portions over the course of about 10 minutes. A slight exotherm is noted. The resulting solution is stirred at room temperature overnight. The following day, solvent is removed under reduced pressure, and the residue partitioned between ethyl acetate and cold water. The aqueous phase is extracted with one additional portion of ethyl acetate, and the combined organic phase washed with brine and dried (magnesium sulfate). After removal of solvent under reduced pressure, the residue is flash chromatographed on silica gel 60 (230–400 mesh), using 10% ethyl acetate in hexane as eluant, to provide 8.75 g of the title product as a white solid.

Physical characteristics are as follows:
$^1$H NMR δ 0.57, 1.3, 1.36, 2.24, 2.55, 5.01, 6.14, 6.25, 6.40, 6.86, 7.2–7.4.
EI MS 491.
IR 3418, 2958, 2925, 2856, 1729, 1602, 1485, 1446, 1153, 1145, 702, 698 cm$^{-1}$.
TLC R$_f$ 0.32 (10% ethyl acetate in hexane.)
Anal. Found: C, 83.01; H, 7.70; N, 2.87.

PREPARATION 32

3-(3-Triphenylmethylaminophenyl)-2-(2-hydroxybenzoyl) pentanoic acid tert-butyl ester (Formula F-5) Refer to Chart F.

Into a flame-dried 250 round-bottom flask, under argon, is introduced 25 ml of dry tetrahydrofuran and 3.7 ml of dry diisopropylumine. The solution is cooled to −78°, and 16.1 ml of a 1.6M solution of butyllithium in hexane is added via syringe over the course of a few minutes. The solution is warmed to 0°, kept at this temperature for ten minutes, then re-cooled to −78°.

Into this stirred solution of lithium diisopropylamide is cannulated a solution of 8.2 g of the trityl tert-butyl ester of Preparation 31 in 25 ml of dry tetrahydrofuran, with one 4 ml rinse of the source flask. Enolization is allowed to proceed for 50 minutes at −78°, giving a red-orange solution, then 1.1 ml of methyl salicylate is added dropwise via syringe. After five minutes, the solution is allowed to warm to ambient temperature. The reaction color changes to very deep red, and then lightened substantially overnight.

The following day, the reaction mixture is partitioned between ethyl acetate and ice water containing 100 ml of pH 7 phosphate buffer and 50 ml of 1M aqueous potassium hydrogen sulfate. The pH of the aqueous phase is near neutral at this point, and one additional ethyl acetate extraction is sufficient to remove all UV active material. The combined organic phase is dried (magnesium sulfate). TLC at this point (10% ethyl acetate in hexane) shows two spots: A (more mobile, $R_f$ 0.36, corresponding to the expected recovered starting material of Preparation 31), and B (less mobile, $R_f$ 0.24, corresponding to the title product).

Removal of solvents under reduced pressure provides a crude mixture of the desired product and starting material as an orange-red foam. Hash chromatography of this mixture on silica gel 60 (230400 mesh) using 60–70% dichloromethane in hexane as eluant gives clean separation of product from starting material. Obtained is 944 mg of desired title product as a tan, broken up foam, and 869 mg of starting material of Preparation 31. The starting material can be recycled.

For the product (mixture of diastereomers) physical characteristics are as follows:

$^1$H NMR δ 0.41, 1.13, 3.19, 4.28, 6.25, 4.48, 6.8–7.0, 7.2–7.4, 7.5, 7.84.

FAB MS [m+H]=612.

Anal. Found: C, 78.91; H, 6.72; N, 2.21.

PREPARATION 33

3-[1-(3-Aminophenyl)propyl]4-hydroxycoumarin (Formula F-6) Refer to Chart F.

To 918 mg of the title product of Preparation 32 is added 6 ml of trifluoroacetic acid (TFA). A bright yellow-orange color immediately forms, and the solid dissolves. The solution is stirred at room temperature for 24 hours. TFA is removed under reduced pressure, and the residue partitioned between dichloromethane and cold pH 7 phosphate buffer, and sufficient aqueous sodium hydroxide is added to render the aqueous phase neutral. The biphasic mixture, containing a small amount of undissolved solid, is placed in a continuous extractor and extracted overnight with a brisk flow of dichloromethane. When the aqueous phase no longer shows ninhydrin activity, the organic extract is removed and dried (sodium sulfate). Removal of the solvent under reduced pressure is followed by flash column chromatography on silica gel 60 (230–400 mesh). The flash column is prepared and eluted initially with 30% ethyl acetate in dichloromethane. Elution is continued with 50–100% ethyl acetate, followed by 5% methanol in ethyl acetate. Product fractions are combined and concentrated to provide 369 mg of the title product as a tan solid.

Physical characteristics are as follows:

$^1$H NMR δ 1.02, 2.12, 4.41, 4.6, 6.60, 6.75, 6.88, 7.1–7.3, 7.48, 7.71.

EI MS: 295.1213, 266.

TLC $R_f$ 0.24 (30% ethyl acetate in dichloromethane).

EXAMPLE 23

4-Hydroxy-3-[1-[3-[[3-[(1,1-dimethylethoxycarbonyl)amino]-1-oxopropyl]amino]phenyl]propyl]-coumarin To a cold (0°) stirred solution of 22.2 mg of amine of Preparation 33 and 18.5 mg of Boc-β-alanine in 0.5 ml of dichloromethane is added 17 µL of diisopropylethylamine, followed by 14 µL of diethylcyanophosphorate. The solution is stirred and allowed to warm slowly overnight. Flash chromatography of the reaction mixture on silica gel, eluting with 80% ethyl acetate in dichloromethane then 24–8–12% methanol in this solvent, provides 26.6. mg of the title product as a glassy solid.

Physical characteristics are as follows:

$^1$H NMR δ 0.79, 1.28, 2.0–2.5, 3.25, 4.30, 6.8–7.3, 7.8.

EXAMPLE 24

3-[1-[3-[(3-Amino-1-oxopropyl)amino]phenyl]propyl]-4-hydroxy-coumarin, trifluoroacetate (salt)

A solution of 10.2 mg of the title product of Example 23 in 0.5 ml of trifluoroacetic acid is allowed to stand for 20 minutes at room temperature, then is diluted with dichloromethane and concentrated under reduced pressure. The residue is dissolved in 0.5 ml of water and this solution lyophilized to afford 11.1 mg of the title product as a fluffy white solid.

Physical characteristics are as follows:

FAB HRMS [m+H]=367.1644.

EXAMPLE 25

4-Hydroxy-3-[1-[3-[(1-oxo-3-phenylpropyl)amino]phenyl]propyl]-coumarin

To a cold (0° C.), stirred solution of 22.2 mg of the amine of Preparation 33 and 15 mg of hydrocinnamic acid in 0.5 ml of dichloromethane is added 17 µL of diisopropylethylamine, followed by 14 µL of diethylcyanophosphorate. The solution is stirred and allowed to warm slowly overnight. Flash chromatography of the reaction mixture on silica gel, eluting with 20% ethyl acetate in dichloromethane then 2–5% methanol in this solvent, provides 23.8 mg of the title product as a glassy solid.

Physical characteristics are as follows:

$^1$H NMR δ 0.95, 2.1–2.4, 2.6, 3.0, 4.32, 7.1–7.3, 7.45, 7.55, 7.84.

EI MS 427.

EXAMPLE 26–66

Utilizing procedures analogous to those described above, the following additional compounds of the present invention, having the mass spectral data indicated in Table I below, are prepared.

26) Coumarin, 3-[1-[3-[[[(2-benzimidazo131)methyl]amino]carbonyl]phenyl]ethyl]-4-hydroxy- 27) Coumarin, 4-hydroxy-3-[1-[3-[[[(2-pyridinyl)methyl]amino]carbonyl]phenyl]ethyl]-

28) Coumarin, 4-hydroxy-3-[1-[3-[[(phenylmethyl)amino]carbonyl]phenyl]ethyl]-

29) Benzamide, N-(2,3-dihydro-2-hydroxy-1H-inden-1-yl)-3-[1-(4-hydroxy-2-oxo-2H-1-benzopyran-3-yl)ethyl]-

30) Benzamide, 3-[1-(4-hydroxy-2-oxo-2H-1-benzopyran-3-yl)ethyl]-N-[2-methyl-1-[[(2-pyridinylmethyl)amino]carbonyl]butyl]-

31) Coumarin, 3-[1-[3-[(butylamino)carbonyl]phenyl]ethyl]-4-hydroxy-

32) Coumarin, 4-hydroxy-3-[1-[3-[[[[(4-morpholino)carbonyl]methyl]amino]carbonyl]phenyl]ethyl]-

33) Coumarin, 3-[1-[3-[[[[[(2-benzimidazolyl)methyl]amino]carbonyl]methyl]amino]carbonyl]phenyl]ethyl]4-hydroxy- 34) 4-hydroxy-3-[1-(1,2,3,4-tetrahydro)naphthyl]-coumarin 35) 4-hydroxy-3-[1-indanyl]-coumarin 36) Coumarin, 3-(.alpha.-ethyl-p-fluorobenzyl)4-hydroxy- 37) Coumarin, 7-methoxy-3-(.alpha.-propylbenzyl)4-hydroxy- 38) 3-cyclopropylphenylmethyl-4-hydroxy-7-methoxy coumarin 39) 3-(α,α-dimethylbenzyl)4-hydroxy coumarin 40) Coumarin, 3-[1-(3-aminophenyl)propyl]4-hydroxy-, monohydrochloride- 41) Coumarin, 4-hydroxy-3-[1-[3-[[(1-naphthoxymethyl)carbonyl]amino]phenyl]propyl]-

42) Carbamic acid, [1-[[[3-[1-(4-hydroxy-2-oxo-2H-1-benzopyran-3-yl)propyl]phenyl]amino]carbonyl]-2-methylpropyl]-, 1,1-dimethylethyl ester 43) Coumarin, 4-hydroxy-3-[1-[3-[[[[(1,1-dimethylethoxycarbonyl)amino]methyl]carbonyl]amino]phenyl]propyl]-

44) Coumarin, 4-hydroxy-3-[1-[3-[(1-oxopentyl)amino]phenyl]propyl]-

45) Coumarin, 4-hydroxy-3-[1-[3-[[(2-pyridinyl)carbonyl]amino]phenyl]propyl]-

46) Coumarin, 3-[1-[3-[[(aminomethyl)carbonyl]amino]phenyl]propyl]4-hydroxy-, trifluoroacetate (salt)

47) Coumarin, 4-hydroxy-3-[1-[3-[[1-oxo-3-methyl-3-[(1,1-dimethylethoxycarbonyl) amino]butyl]amino]phenyl]propyl]-

48) Coumarin, 3-[1-[3-[(3-amino-3-methyl-1-oxobutyl)amino]phenyl]propyl]-4-hydroxy-, trifluoroacetate (salt)

49) Coumarin, 4-hydroxy-3-[1-[3-[(1-oxo-3-phenylpentyl)amino]phenyl]propyl]-

50) Coumarin, 4-hydroxy-3-[1-[3-[[4-[(1,1-dimethylethoxycarbonyl)amino]-1-oxobutyl]amino]phenyl]propyl]-

51) L-Glutamine, N2-[(1,1-dimethylethoxy)carbonyl]-N-[3-[1-(4-hydroxy-2-oxo-2H-1-benzopyran-3-yl)propyl]phenyl]-, 1,1-dimethylethyl ester 52) L-Glutamine, N-[3-[1-(4-hydroxy-2-oxo-2H-1-benzopyran-3-yl)propyl]phenyl]-, mono(trifluoroacetate) (salt)

53) Coumarin, 4-hydroxy-3-[1-[3-[(i-oxo-4-phenylbutyl)amino]phenyl]propyl]-

54) Coumarin, 4-hydroxy-3-[1-[3-[(1-oxo-5-phenylpentyl)amino]phenyl]propyl]-

55) Coumarin, 4-hydroxy-3-[1-[3-[[(phenylmethyl)carbonyl]amino]phenyl]propyl]-

56) Coumarin, 3-[1-[3-[(3-cyclohexyl-1-oxopropyl)amino]phenyl]propyl]-4-hydroxy- 57) Coumarin, 4-hydroxy-7-methoxy-3-[1-[3-[(1-oxo-3-phenylpropyl)amino]phenyl]propyl]-

58) Coumarin, 4-hydroxy-3-[1-[3-[[3-[(1,1-dimethylethoxycarbonyl)amino]-1-oxopropyl]amino]phenyl]propyl]-7-methoxy- 59) 1-Pyrrolidinecarboxylic acid, 2-[[[3-[1-(4-hydroxy-2-oxo-2H-1-benzopyran-3-yl) propyl]phenyl]amino]carbonyl]-, 1,1-dimethylethyl ester 60) Carbamic acid, [2-[[3-[1-(4-hydroxy-2-oxo-2H-1-benzopyran-3-yl)propyl]phenyl]amino]-1-methyl-2-oxoethyl]-, 1,1-dimethylethyl ester 61) Propanamide, 2-amino-N-[3-[1-(4-hydroxy-2-oxo-2H-1-benzopyran-3-yl)propyl]phenyl]-, mono(trifluoroacetate) (salt)

62) Coumarin, 4-hydroxy-3-[1-[3-[[3-(4-hydroxyphenyl)-1-oxopropyl]amino]phenyl]propyl]-

63) Coumarin, 4-hydroxy-3-[1-[3-[[3-($^{1}$H-indol-1-yl)-1-oxopropyl]amino]phenyl]propyl]-

64) Coumarin, 4-hydroxy-3-[1-[3-[[3-(1-naphthyl)-1-oxopropyl]amino]phenyl]propyl]-

65) Coumarin, 3-[1-[3-[[3-[(2-benzothiazolyl)thio]-1-oxopropyl]amino]phenyl]propyl]4-hydroxy- 66) 4-hydroxy-3-[α-tert-butyloxycarbonylmethyl]benzylcoumarin

PREPARATION 34

1-(3-Hydroxyphenyl)propanol (Formula G-2) Refer to Chart G.

To a solution of ethylmagnesium bromide (3.0M in ether, 5.6mL) in dry tetrahydrofuran (5.6mL) at 0° C. under nitrogen in a flame-dried flask is added a solution of 3-hydroxybenzaldehyde of formula G-1 (1.00 g) in dry tetrahydrofuran (5 mL) over 30 min. The mixture is stirred at 0° C. for 30 min and then carefully quenched with saturated aqueous ammonium chloride (15 mL). The layers are separated, the aqueous phase is extracted with diethyl ether (25 mL), and the combined organic phase is washed with saline (10 mL), dried over sodium sulfate and concentrated under reduced pressure to give a pale yellow semisolid which is chromatographed on silica gel (230–400 mesh, 120 g), eluting with a gradient of ethyl acetate/hexane (8/92–30/70). Pooling of fractions having an $R_f$=0.18 by TLC (ethyl acetate/hexane, 25/75) and removal of solvent under reduced pressure gives the title compound.

Physical characteristics are as follows:

NMR (CDCl$_3$) 7.12, 6.77, 6.65, 4.43, 1.79–1.62, 0.87 δ.

PREPARATION 35

1-(3-Allyloxyphenyl)propanol (Formula G-3) Refer to Chart G.

To a solution of 1-(3-hydroxyphenyl)propanol of Preparation 34 and anhydrous potassium carbonate (708 mg) in dry dimethylformamide (9.8 mL) under nitrogen in a flame-dried flask is added allyl bromide (0.44 mL). The resulting mixture is stirred at RT for 7 hrs, diluted with ethyl acetate (65 mL), washed with water (30 mL) and saline (30 mL), dried over anhydrous magnesium sulfate, and concentrated under reduced pressure to give an oil which is then chromatographed on silica gel (230–400 mesh, 100g), eluting with a gradient of ethyl acetate/hexane (5/95–15/85). Pooling of fractions having an $R_f$=0.46 by TLC (ethyl acetate/hexane, 25/75) and removal of solvent under reduced pressure gives the title compound.

Physical characteristics are as follows:

CHN: Found: C, 74.60; H, 8.35.

EXAMPLE 67

3-(1'-(3-Allyloxyphenyl)propyl)-4-hydroxycoumarin (Formula G4) Refer to Chart G.

To a time-dried flask containing a near-solution of 4-hydroxycoumarin (494 mg) and 1-(3-allyloxyphenyl)propanol of Preparation 35 in anhydrous dioxane (17mL) under nitrogen is added boron trifluoride etherate (1.92 mL). The resulting solution is stirred at RT for 24 hrs, concentrated to remove solvent, diluted with aqueous sodium hydroxide (5%, 10 mL) and extracted with methylene chloride (2×50mL). The combined organic phase is washed with saline (20 mL), dried over sodium sulfate, and concentrated under reduced pressure to give an oil which is then chromatographed on silica gel (230–400 mesh, 45 g), eluting with ethyl acetate/hexane (25/75). Pooling of fractions with an $R_f$=0.22 by TLC (ethyl acetate/hexane. 50/50) and removal of solvent gives the title compound.

Physical characteristics are as follows:
MS(EI) M⁺=336.1371.

EXAMPLE 68

3-(1'-(3-((2,3-Dihydroxy)propyloxy)phenyl)propyl)-4-hydroxycoumarin (Formula G-5) Refer to Chart G.

To a mixture of 3-(1'-(3-allyloxyphenyl)propyl)-4-hydroxycoumarin of Example 67 and 4-methylmorpholine N-oxide (49 mg) in acetone/water (2.5 mL, 1: 1) under nitrogen is added osmium tetroxide (2.5 wt % in t-butanol, 35 µL). The resulting mixture is stirred at RT for 46 hrs, during which 4-methylmorpholine N-oxide (35 mg) is added in one portion, and then concentrated, diluted with 3M hydrochloric acid (1.5 mL) and saturated aqueous sodium bisulfite (0.2 mL), saturated with sodium chloride, and extracted with ethyl acetate (4×10mL). The combined organic phase is dried over anhydrous magnesium sulfate and concentrated under reduced pressure to give an oily film which is then chromatographed on two 2000µ preparative silica gel plates, eluting with methanol/chloroform (10/90). Extraction of the band with $R_f$=0.17–0.29 and removal of solvent under reduced pressure gives a film which is again chromatographed on a 2000µ preparative silica gel plate, eluting with methanol/chloroform (10/90 and 15/85). Extraction of the appropriate band gives the title compound.

Physical characteristics are as follows:
MS(EI) M⁺=370.1419.

PREPARATION 36

1-(2-Allyloxyphenyl)propanol

To a solution of 2-hydroxypropiophenone (2.00 g) and anhydrous potassium carbonate (5.52 g) in dry dimethylformamide (20 mL) under nitrogen is added allyl bromide (1.38 mL). The resulting mixture is stirred at RT for 8 hrs, concentrated to remove solvent, diluted with methylene chloride (30 mL) and water (15 mL), and the layers are separated. The aqueous phase is extracted with methylene chloride (30 mL) and the combined organic phase is washed with saline (10 mL), dried over sodium sulfate, and concentrated under reduced pressure to give the allyl ether intermediate ($R_f$=0.42 by TLC, ethyl acetate/hexane, 10/90). To a solution of this allyl intermediate (2.54 g) in absolute ethanol (25 mL) at 0° C. under nitrogen is added sodium borohydride (252 mg). The resulting solution is warmed to RT, stirred for 16 hrs, cooled to 0° C., quenched with saturated aqueous ammonium chloride (15 mL), concentrated to remove ethanol, re-diluted with water (30 mL) and extracted with methylene chloride (2×40 mL). The combined organic phase is washed with saline (15 mL), dried over sodium sulfate, and concentrated under reduced pressure to give the title compound.

Physical characteristics are as follows:
NMR (CDCl₃) 7.30, 7.21, 6.95, 6.86, 6.05, 5.41, 5.29, 4.82, 4.57, 2.59, 1.84, 0.95 δ.

EXAMPLE 69

3-(1'-(2-Allyloxyphenyl)propyl)-4-hydroxycoumarin

To a flame-dried flask containing a near-solution of 4-hydroxycoumarin (337mg) and 1-(2-allyloxyphenyl) propanol of Preparation 36 (500 mg) in anhydrous dioxane (10 mL) under nitrogen is added boron trifluoride etherate (1.31 mL). The resulting solution is stirred at RT for 25 hrs. concentrated to remove solvent, diluted with aqueous sodium hydroxide (5%, 20 mL) and extracted with methylene chloride (2×25 mL). The organic phase is discarded and the aqueous phase is adjusted to pH 1 using 6M hydrochloric acid and extracted with methylene chloride (2×25 mL). The organic phase is washed with saline (10 mL), dried over sodium sulfate, and concentrated under reduced pressure to give a viscous residue which is then chromatographed on silica gel (230400 mesh, 45g), eluting with a gradient of ethyl acetate/hexane (5/95–10/90). Pooling of fractions having an $R_f$=0.44 by TLC (ethyl acetate/hexane, 25/75) and removal of solvent gives the title compound.

Physical characteristics are as follows:
Mp 118°–120° C.

PREPARATION 37

1-(2-Methoxyphenyl)propanol

To a time-dried flask containing a solution of o-anisaldehyde (2.00 g) in dry tetrahydrofuran (9.8 mL) at 0° C. under nitrogen is added a solution of ethylmagnesium bromide (3M in diethyl ether, 5.4 mL) in dry tetrahydrofuran (5.4 mL) over 25 min. The resulting mixture is stirred at 0° C. for 1 hr, quenched with saturated aqueous ammonium chloride (15 mL), and the layers are separated. The aqueous phase is extracted with diethyl ether (2×30 mL) and the combined organic phase is washed with saline (15 mL), dried over anhydrous magnesium sulfate, and concentrated under reduced pressure to give an oil which is then chromatographed on silica gel (230–400 mesh, 250 g), eluting with a gradient of ethyl acetate/hexane (5/95–10/90). Pooling of fractions having an $R_f$=0.44 by TLC (ethyl acetate/hexane, 25/75) and removal of solvent gives the title compound.

Physical characteristics are as follows:
MS(EI) M⁺=166.0998.

EXAMPLE 70

3-(1'-(2-Methoxyphenyl)propyl)-4-hydroxycoumarin

Following the general procedure of Example 67, and making non-critical variations but substituting 1-(2-methoxyphenyl)propanol of Preparation 37 for 1-(3-allyloxyphenyl)propanol and purifying the crude product by recrystallization from diethyl ether/chloroform, the title compound is obtained.

Physical characteristics are as follows:
Mp 214°–217° C.

PREPARATION 38

1-(3-Bromophenyl)propanol

Following the general procedure of Preparation 37, and making non-critical variations but substituting 3-bromobenzaldehyde for o-anisaldehyde, the title compound is obtained.

Physical characteristics are as follows:
CHN: Found: C, 50.20; H, 5.31.

PREPARATION 39

1-Bromo-1-(3-bromophenyl)propane

To a flame-dried flask containing a solution of 1-(3-bromophenyl)propanol of Preparation 38 (3.50 g) and triethylamine (4.54 mL) in dry methylene chloride (18 mL) at 0° C. under nitrogen is added methanesulfonyl chloride (1.39 mL) over 1 min. The resulting mixture is stirred at 0° C. for 2 hrs, diluted with water (8 mL), and the layers are separated. The aqueous phase is extracted with methylene chloride (25 mL) and the combined organic phase is washed with saline (5 mL), dried over sodium sulfate, and concentrated under reduced pressure to give an oily intermediate. A mixture containing the intermediate and lithium bromide (1.42g) in acetone (50 mL) under nitrogen is refluxed for 4 hrs, cooled to RT, concentrated to remove acetone, re-diluted with methylene chloride (40 mL) and water (20 mL), and the layers are separated. The aqueous phase is extracted with methylene chloride (40 mL) and the combined organic phase is washed with saline (15 mL), dried over sodium sulfate, and concentrated to give a crude oil which is then chromatographed on silica gel (70–230 mesh, 250 g), eluting with ethyl acetate/hexane (5/95). Pooling of fractions with an $R_f$=0.63 by TLC (ethyl acetate/hexane, 25/75) and removal of solvent under reduced pressure gives the title compound.

Physical characteristics are as follows:
MS(EI) M$^+$=275.9143.

EXAMPLE 71

3-(1'-(3-Bromophenyl)propyl)-4-hydroxycoumarin

A mixture of 4-hydroxycoumarin (898 mg) and 1-bromo-1-(3-bromophenyl)propane of Preparation 39 (3.08 g) under nitrogen is sealed in a screw-cap vial and placed in an oil bath at 100° C. The mixture is heated to 175° C. over approximately 45 rain, and the resulting melt is stirred at this temperature for 45 rain, cooled to RT, diluted with methylene chloride (45 mL), washed with water (10 mL) and saline (10 mL), dried over sodium sulfate, and concentrated under reduced pressure to give a residue which is then chromatographed on silica gel (230–400 mesh, 350 g), eluting with a gradient of ethyl acetate/hexane (15/85–60/40). Pooling of fractions with an $R_f$=0.20 by TLC (ethyl acetate/hexane, 50/50) and removal of solvent gives the title compound.

Physical characteristics are as follows:
Mp 168°–172° C.

PREPARATION 40

1-(4-Acetoxyphenyl)propyl acetate (Formula H-2) Refer to Chart H.

To a solution of 1-(4-hydroxyphenyl)propanol (400 mg) in acetic anhydride (2 mL) at 0° C. under nitrogen is added pyridine (0.45 mL). The solution is stirred at 0° C. for 30 rain and at RT for 2.5 hrs and then added to 1M hydrochloric acid (10 mL). The mixture is extracted with methylene chloride (2×20 mL) and the combined organic phase is washed with saline (10 mL), dried over sodium sulfate, and concentrated under reduced pressure to give the title compound.

Physical characteristics are as follows:
CHN: Found: C, 65.95; H, 6.75.

EXAMPLE 72

3-(1'-(4-Acetoxyphenyl)propyl)4-hydroxycoumarin (Formula H-3) Refer to Chart H.

A mixture of 4-hydroxycoumarin (125 mg) and cesium carbonate (552 mg) in dry acetonitrile (2.5 mL) under nitrogen is refluxed for 5 min and then treated with a solution of 1-(4-acetoxyphenyl)propyl acetate of Preparation 40 (400 mg) in dry acetonitrile (1 mL) in six portions over 30 min. The resulting mixture is stirred at reflux for 3 hrs and at RT for 2.6 days and then added to 0.1M hydrochloric acid (10 mL). The mixture is extracted with ethyl acetate (3×15 mL) and the combined organic phase is dried over anhydrous magnesium sulfate and concentrated to give a semi-solid residue which is then chromatographed on silica gel (230–400 mesh, 45 g), eluting with a gradient of ethyl acetate/hexane (20/80–50/50). Pooling of fractions with an $R_f$=0.09 by TLC (ethyl acetate/hexane, 50/50) and removal of solvent under reduced pressure gives the title compound.

Physical characteristics are as follows:
MS(EI) M$^+$=338.1144.

PREPARATION 41

1-(2-Hydroxyphenyl)propanol

A mixture of platinum oxide (302 mg) in methanol (30 mL) is stirred under a hydrogen atmosphere (balloon) for 1 hr and then treated with 2-hydroxypropiophenone (2.00 g). The mixture is stirred under hydrogen for 4 hrs, the catalyst is removed by filtration, and the filtrate is concentrated under reduced pressure to give an oily residue which is chromatographed on silica gel (230–400 mesh, 200 ), eluting with a gradient of ethyl acetate/hexane (5/95–20/80). Pooling of fractions with an $R_f$=0.41 by TLC (ethyl acetate/hexane, 25/75) and removal of solvent under reduced pressure gives the title compound.

Physical characteristics are as follows:
NMR (CDCl$_3$) 8.04, 7.16, 6.92, 6.83, 4.73, 2.78, 1.86, 0.95 δ.

PREPARATION 42

1-(2-Acetoxyphenyl)propyl acetate

Following the general procedure of Preparation 40, and making non-critical variations but substituting 1-(2-hydroxyphenyl)propanol of Preparation 41 for 1-(4-hydroxyphenyl)propanol, the title compound is obtained.

Physical characteristics are as follows:
MS(EI) M$^+$=236.1051.

EXAMPLE 73

3-(1'-(2-Acetoxyphenyl)propyl)-4-hydroxycoumarin

Following the general procedure of Example 72, and making non-critical variations but substituting 1-(2-acetoxyphenyl)propyl acetate for 1-(4-acetoxyphenyl) propyl acetate, the title compound is obtained.

Physical characteristics are as follows:
CHN: Found: C, 70.69; H, 5.19.

PREPARATION 43

4-(3-Phenyl-2-propynyloxy)-coumarin (Formula I-2) Refer to Chart I.

To a flame dried flask equipped with a nitrogen inlet is introduced tetra-hydrofuran (10 mL), 4-hydroxycoumarin (293 mg), 3-phenyl-2-propyn-1-ol (332 µL). and triphenylphosphine (711 mg) under a nitrogen flush. The flask is stirred magnetically and cooled to 0° C. Diethylazodicarboxylate (427 µL) in tetrahydrofuran (5 mL) is added dropwise to the reaction flask. The reaction mixture is stirred for 15 hrs while slowly being warmed to room temperture. The solvent is removed under reduced pressure to yield a brown residue. The residue is partitioned between methylene chloride (50 mL) and water (50 mL). The organic phase is separated and washed with water (3×25 mL) and saline (25 mL), dried over sodium sulfate, and concentrated under reduced pressure to give a bright yellow residue which is chromatographed on silica gel (230–400 mesh, 75 ), eluting with hexane/ethyl acetate (90/10). The appropriate fractions ($R_f$=0.35, TLC, hexane/ethyl acetate, 75/25) are combined and concentrated to give the title compound.

Physical characteristics are as follows:
Mp 142°–146° C.

PREPARATION 44

4-(Z-3-phenyl-2-propenyloxy)-coumarin (Formula I-3) Refer to Chart I.

Lindlar's catalyst (8 mg) is added to a solution of 4-(3-phenyl-2-propynyloxy)-coumarin of Preparation 43 (200 mg), freshly distilled quinoline (14 L), in ethyl acetate (20 mL). The mixture is agitated under a hydrogen atmosphere (50 psi) for 4 hrs. The mixture is filtered through a pad of celite and the filtrate is concentrated under reduced pressure to give a pale yellow oil that is chromatographed on silica gel (230–400 mesh, 75 ), eluting with hexane/ethyl acetate (95/5). The appropriate fractions are combined ($R_f$=0.46, TLC, hexane/ethyl acetate, 75/25) and concentrated to give the title compound.

Physical characteristics are as follows:
Mp 130°–132° C.

EXAMPLE 74

4-Hydroxy-3-(1-phenyl-2-propenyl)-coumarin (Formula I-4) Refer to Chart I.

To a flame dried flask equipped with a reflux condenser is added 4-(Z-3-phenyl-2-propenyloxy)-coumarin of Preparation 44 (83 mg) in dry o-xylene. The flask is immersed in an oil bath that is preheated to 145° C. The solution is refluxed for 36 min. and then the flask is removed from the bath. The solvent is removed under reduced pressure to yield a yellow solid residue which is chromatographed on silica gel (70–230 mesh, 100 ), eluting with hexane/ethyl acetate (50/50). The appropriate fractions are combined ($R_f$=0.16, TLC, hexane/ethyl acetate, 50/50) and concentrated to give the title compound.

Physical characteristics are as follows:
Mp 127°–133° C.

EXAMPLE 75

4-Hydroxy-3-(5,6,7,8,9-tetrahydro-5H-benzocycloheptenyl)-coumarin

To a flame dried flask equipped with a nitrogen inlet and 6,7,8,9-tetrahydro-5H-benzocyclohepten-5-ol (500 mg), 4-hydroxycoumarin (399 mg) in anhydrous dioxane (20 mL) is added boron trifluoride etherate (1.51 mL) under a nitrogen atmosphere. The mixture is stirred for 4 hrs., concentrated under reduced pressure, diluted with sodium hydroxide (10%, 10 mL), and extracted with methylene chloride (3×50 mL). The organic extracts are combined, washed with saline (10 mL), dried over sodium sulfate, concentrated under reduced pressure and chromatographed on silica gel (70–230 mesh, 75 g), eluting with chloroform/methanol (95/5). The appropriate fractions are combined and concentrated under reduced pressure to give the title compound.

Physical characteristics are as follows:
Mp 183°–185° C.

EXAMPLE 76

4-Hydroxy-3-(1-(6-methoxy)-1,2,3,4-tetrahydronaphthyl)-coumarin

Following the general procedure of Example 75, and making non-critical variations but substituting 1,2,3,4-tetrahydro-6-methoxy-1-naphthol (692 mg) for 6,7,8,9-tetrahydro-5H-benzocyclohepten-5-ol, the title compound is obtained.

Physical characteristics are as follows:
Mp 90°–95° C.

EXAMPLE 77

4-Hydroxy-3-(1 -(7-methoxy)-1,2,3,4-tetrahydronaphthyl)-coumarin

Following the general procedure of Example 75, and making non-critical variations but substituting 1,2,3,4-tetrahydro-7-methoxy- 1 -naphthol (692 mg) for 6,7,8,9-tetrahydro-5H-benzocyclohepten-5-ol, the title compound is obtained.

Physical characteristics are as follows:
Mp 95°–100° C.

EXAMPLE 78–106

Utilizing procedures analogous to those described above, the following additional compounds of the present invention (some of which have the mass spectral data indicated in Table I below) are prepared:

78) Coumarin, 7-(allyloxy)-3-(.alpha.-ethylbenzyl)-4-hydroxy-

79) Coumarin, 3-[.alpha.-ethyl-[[[2-(indol-3-yl)ethyl]carbonyl]amino]benzyl]-4-hydroxy- 80) Coumarin, 3-[bis(cyclopropyl)methyl]-4-hydroxy-7-methoxy- 81) Coumarin, 3-(.alpha.-ethylbenzyl)-4-hydroxy-7-(1-methylethoxy)-

82) Coumarin, 7-ethoxy-3-(.alpha.-ethylbenzyl)-4-hydroxy-

83) Butanoic acid, 2-(4-hydroxy-2-oxo-2H-1-benzopyran-3-yl)-, ethyl ester

84) Coumarin, 4-hydroxy-3-(2-phenylbutyl)-

85) Coumarin, 4-hydroxy-3-[1 -(4-hydroxyphenyl)propyl]-

86) Coumarin, 7-trifluoromethyl-4-hydroxy-3-(1-phenylpropyl)-

87) Coumarin, 6-fluoro-4-hydroxy-3-(1-phenylpropyl)-

88) Coumarin, 4-hydroxy-7-methoxy-3-(1-phenylpropyl)-

89) Coumarin, 4-hydroxy-6-methoxy-3-(1-phenylpropyl)-

90) Coumarin, 4-hydroxy-7-methyl-3-(1-phenylpropyl)-

91) Coumarin, 3-[1-(4-bromophenyl)propyl]-4-hydroxy-; Mp:188.5°–191° C.

92) Coumarin, 7-chloro-4-hydroxy-3-(1-phenylpropyl)-

93) Coumarin, 4,7-dihydroxy-3-(1-phenylpropyl)-

94) Coumarin, 4-hydroxy-3-[1-(4-methoxyphenyl)propyl]-; Mp:149°–151° C.

95) Coumarin, 4,6-dihydroxy-3-(1-phenylpropyl)-

96) Coumarin, 6-amino-4-hydroxy-3-(1-phenylpropyl)-

97) Coumarin, 4-hydroxy-3-[1-(3-methylphenyl)butyl]-

98) Coumarin, 3-[1-(3-cyanophenyl)propyl]-4-hydroxy- 99) 2H-Naphtho[1,2-b]pyran-2-one, 4-hydroxy-3-(1-phenylpropyl)-

100) Coumarin, 4-hydroxy-3-[1-[4-(2,3-dihydroxy)propoxyphenyl]propyl]-

101) Coumarin, 3-[1-(3-Cyanophenyl)ethyl]-4-hydroxy-

102) Coumarin, 4-hydroxy-3-[1-(3-methoxyphenyl)propyl]-; Mp: 141°–143.5° C.

103) Coumarin, 4-hydroxy-3-[1-(3-hydroxyphenyl)propyl]-

104) 3-(dicyclopropyl)methyl-4-hydroxycoumarin 105) 4-hydroxy-3-(1-phenylpropyl)-coumarin 106) Coumarin, 4-hydroxy-3-[1-(4-propionylphenyl)propyl]-

EXAMPLE 107

3-(Cyclopropylphenylmethyl)-5,6,7,8,9,10-hexahydro-4-hydroxy-2h-cycloocta[b]pyran-2-one (Formula J-3 wherein $R_1$ is cyclopropyl, $R_2$ is phenyl, n is 4) (Also Formula L-1 wherein n is 4, $R_1$ is cyclopropyl) Refer to Charts K and L.

A 50-mL, three-necked, round-bottomed flask with a 10-mL pressure-equalizing addition funnel filled with activated 3 Å molecular sieves and fitted with a reflux condensor and nitrogen inlet is charged with cyclooctene-1-acrylic acid, β, 2-dihydroxy-5-lactone (0.753 g), p-toluenesulfonic acid (0.184 g), and 10 mL of toluene. α-Cyclopropylbenzyl alcohol (0.55 mL) is added, and the reaction mixture is warmed to ca. 140° C. Additional α-cyclopropylbenzyl alcohol (0.37 mL) is added after 2.5 h and after 5 h. After a total of 7 h, the reaction mixture is diluted with 100 mL of 1N sodium hydroxide and washed with two 50-mL portions of ether. The pH of the aqueous layer is adjusted from 14 to 1 with concentrated hydrochloric acid. A white precipitate forms, which is extracted with four 50-mL portions of methylene chloride. The organic (methylene chloride) layers are then combined, dried over magnesium sulfate, filtered and concentrated to give 1.128 g of white solid. Column chromatography on 50 g silicia gel (elution with 20% ethyl acetate-hexane) yields 0.859 g of the title product as a white solid.

Physical characteristics are as follows:
Mp 173.8°–175.6° C.
$^1$H NMR (CDCl$_3$) δ 7.51, 7.38, 7.28, 6.26, 3.99, 2.62, 2.44, 1.80–1.72, 1.60–1.32, 0.78–0.70, 0.64–0.56, 0.32–0.26 ppm.
$^{13}$C NMR (CDCl$_3$) δ 3.71, 4.81, 13.06, 22.03, 25.75, 26.17, 28.77, 29.13, 30.63, 43.63, 106.19, 110.66, 127.31, 127.84, 129.09, 140.93, 161.21, 163.97, 165.68 ppm.
IR (Nujol) 3155, 3080, 2954, 2921, 2852, 1665, 1559, 1407, 1190, 1182, 1172, 706 cm$^{-1}$.
Elemental analysis, found: C, 77.90; H, 7.68.
MS (EI) m/e 324, 296, 295, 283, 233, 207, 131, 91.

EXAMPLES 108–117

Utilizing procedures analogous to those described above, the following additional compounds of the present invention are prepared:

108) 5,6,7,8,9,10-Hexahydro-4-hydroxy-3-(1-phenylpropyl)-2H-cycloocta[b]pyran-2-one (Formula J-3 wherein $R_1$ is ethyl, $R_2$ is phenyl, n is 4) Refer to Chart J.

Physical characteristics are as follows:
Isolated 0.404 g of the title product as a white solid.
Mp 188.9°–190.6° C.
$^1$H NMR (CDCl$_3$) δ 7.44–7.35, 7.30–7.24, 5.76, 4.37, 2.63–2.59, 2.42–2.37, 2.21–1.98, 1.77–1.71, 1.53–1.38, 1.02 ppm.
$^{13}$C NMR (CDCl$_3$) δ 165.5, 163.8, 161.2, 141.5, 129.3, 127.5, 127.2, 110.5, 106.2, 41.2, 30.6, 29.1, 28.8, 26.1, 25.7, 23.9, 22.0, 12.2 ppm.
IR (Nujol) 3174, 2954, 2924, 2868, 2853, 1664, 1640, 1566, 1462, 1447, 1410, 1188, 1172, 1114, 1101, 1057, 611 cm$^{-1}$.
Elemental analysis, Found: C, 76.58; H, 7.66.
MS (EI) m/z 312, 297, 283, 255, 221, 153, 91.
For high resolution, Found: 312.1721.

109) 5,6,7,8-Tetrahydro-4-hydroxy-3-(1-phenylpropyl)-2H-1-benzopyran-2-one (Formula L-1 wherein n is 2, $R_1$ is ethyl) Refer to Chart L.

Physical characteristics are as follows:
Isolated 0.549 g of the title product as a white solid.
Mp 177.5°–179.8° C.
$^1$H NMR (CDCl$_3$) δ 7.45–7.35, 7.30–7.25, 5.76, 4.35, 2.48, 2.24–2.20, 2.18–1.99, 1.81–1.70, 1.69–1.63, 1.03 ppm.
$^{13}$C NMR (CDCl$_3$) δ 165.03, 163.9, 158.4, 141.8. 129.2, 127.5, 127.1, 108.4, 106.0, 41.2, 27.1, 23.9, 21.5, 21.4, 20.2, 12.3 ppm.
IR (Nujol) 3156, 3085, 3058, 3025, 2954, 2926, 2870, 2856, 1668, 1634, 1559, 1460, 1451, 1430, 1404, 1377, 1216, 1182, 1153, 1117, 1107, 1090, 756, 699 cm$^{-1}$.
Elemental analysis, Found: C, 75.79; H, 7.05.
MS (EI) m/z 284, 269, 255, 227, 131, 125, 91.

110) 6,7,8,9-Tetrahydro-4-hydroxy-3-(1-phenylpropyl)-cyclohepta[b]pyran-2(5H)-one Physical characteristics are as follows:
Isolated 0.172 g of the title product as a white solid.
Mp 72°–75° C. (decomposition).
$^1$H NMR (CDCl$_3$) δ 7.44–7.36, 7.31–7.26, 5.84, 4.38, 2.71–2.67, 2.42–2.38, 2.23–1.96, 1.77–1.73, 1.70–1.62, 1.56–1.49, 1.3 ppm.
$^{13}$C NMR (CDCl$_3$) δ 165.0, 163.8, 141.5, 129.4, 127.5, 127.3, 113.1, 105.6, 41.2, 33.8, 31.3, 26.1, 24.4, 23.8, 22.1, 12.2 ppm.
IR (Nujol) 3126, 3085, 3058, 3025, 2954, 2922, 2869, 2855, 1657, 1627, 1602, 1548, 1494, 1453, 1434, 1406, 1377, 1266, 1225, 1194, 1154, 759, 699 cm$^{-1}$.
Elemental analysis, Found: C, 76.22; H, 7.67.
MS (EI) m/z 298, 269, 242, 139, 119.

111) 6,7-Dihydro-4-hydroxy-3-(1-phenylpropyl)-cyclopenta[b]pyran-2(5H)-one

Physical characteristics are as follows:
Isolated 0.285 g of the title product as a pale yellow solid.
Mp 183.4°–185.6° C.
$^1$H NMR (CDCl$_3$) δ 7.43, 7.34, 7.24, 6.29, 4.30, 2.76, 2.62–2.57, 2.22–2.00, 1.00 ppm.
$^{13}$C NMR (CDCl$_3$) δ 166.7, 163.6, 163.2, 142.2, 129.0, 127.6, 126.9, 111.3, 104.9, 41.7, 31.1, 25.4, 23.9, 19.8, 12.4 ppm.
IR (Nujol) 3079, 3056, 3022, 2956, 2925, 2871, 2855, 1672, 1662, 1627, 1561, 1461, 1448, 1436, 1425, 1377, 1245, 700 cm$^{-1}$.
Elemental analysis, Found: C, 75.37; H, 6.65.
MS (EI) m/z 270, 241, 213, 153, 111, 91.

112) 3-(Cyclopropylphenylmethyl)-6,7,8,9-tetrahydro-4-hydroxy-cyclohepta[b]pyran-2(5H)-one (Formula L-1 wherein n is 3, $R_1$ is cyclopropyl) Refer to Chart L.

Physical characteristics are as follows:
Isolated 0.896 g (69%) of the title product as a white solid.
Mp 85°–88° C. (decomposition).
$^1$H NMR (CDCl$_3$) δ 7.52, 7.37, 7.28, 6.24, 3.97, 2.70, 2.47–2.43, 1.82–1.75, 1.71–1.64, 1.59–1.52, 1.37–1.29, 0.78–0.71, 0.65–0.57, 0.32–0.26 ppm.
$^{13}$C NMR (CDCl$_3$) δ 165.3, 163.9, 163.8, 140.9, 129.1, 127.9, 127.4, 113.2, 105.7, 43.7, 33.8, 31.3, 26.1, 24.4, 22.1, 13.0, 4.9, 3.8 ppm.
IR (Nujol) 3138, 3076, 3060, 3025, 2997, 2952, 2923, 2868, 2855, 1658, 1628, 1549, 1495, 1455, 1433, 1406, 1377, 1275, 1228, 1196, 1154, 1138, 1071, 1067, 704 cm$^{-1}$.
Elemental analysis, Found: C, 77.03; H, 7.18.
MS (EI) m/z 310, 282, 281, 269, 219, 131, 91.

113) 3-(Cyclopropylphenylmethyl)-6,7-dihydro-4-hydroxy-cyclopenta[b]pyran-2(5H)-one Physical characteristics are as follows:

Isolated 0.695 g of the title product as a white solid.

Mp 183.3°–184.8° C.

$^1$H NMR (CDCl$_3$) δ 7.50, 7.35, 7.26, 6.51, 3.84, 2.77, 2.60, 2.05, 1.51–1.40, 0.78–0.70, 0.69–0.49, 0.31–0.23 ppm.

$^{13}$C NMR (CDCl$_3$) δ 166.9, 163.6, 163.3, 141.6, 128.9, 127.8, 127.0, 111.5, 105.1, 44.3, 31.1, 25.5, 19.8, 13.0, 5.1, 3.8 ppm.

IR (Nujol) 3001, 2955, 2924, 2867, 2856, 1661, 1612, 1566, 1544, 1439, 1424, 1375, 1261, 1223 cm$^{-1}$.

Elemental analysis, Found: C, 76.21; H, 6.33.

MS (EI) m/z 282, 253, 241, 165, 131, 111, 91.

114) 3-(Cyclopropylphenylmethyl)-5,6,7,8,9,10,11,12,13,14-decahydro-4-hydroxy-2H-cyclododeca[b]pyran-2-one Physical characteristics are as follows:

Isolated 0.245 g of the title product as a white solid.

Mp 97.8°–99.0° C.

$^1$H NMR (CDCl$_3$) δ 7.51, 7.37, 7.29, 6.20, 3.97, 2.55–2.49, 2.32, 1.88–1.83, 1.57–1.50, 1.40–1.33, 1.31–1.23, 0.77–0.70, 0.65–0.58, 0.32–0.26 ppm.

$^{13}$C NMR (CDCl$_3$) δ 165.3, 164.7, 160.7, 140.9, 129.1, 127.9, 127.4, 111.7, 106.4, 43.6, 27.5, 26.8, 25.0, 24.9, 24.8, 23.7, 22.5, 22.1, 21.9, 14.0, 13.0, 4.9, 3.9 ppm.

IR (Nujol) 2942, 2923, 2855, 1658, 1632, 1546, 1468, 1208 cm$^{-1}$.

Elemental analysis, Found: C, 78.93; H, 8.48.

MS (EI) m/z 380, 352, 339, 289, 131.

115) 3-(Cyclopropylphenylmethyl)-5,6,7,8-tetraphydro-4-hydroxy-2H- 1-benzopyran-2-one Mp 180.0°–181.2° C.

$^1$H NMR (CDCl$_3$) δ 7.52, 7.35, 7.26, 6.14, 3.92, 2.49, 2.30–2.26, 1.82–1.74, 1.72–1.65, 1.40–1.31, 0.79–0.70, 0.63–0.56, 0.32–0.24 ppm.

$^{13}$C NMR (CDCl$_3$) δ 165.3, 163.9, 158.4, 141.2, 129.1, 127.8, 127.3, 108.6, 106.1, 43.7, 27.1, 21.6, 21.4, 20.2, 13.0, 5.0. 3.8 ppm.

IR (Nujol) 3025, 2996, 2952, 2924. 2867, 2855, 1668, 1634, 1564, 1460, 1450, 1407, 1377, 1219, 1181, 705 cm$^{-1}$.

Elemental analysis, Found: C, 76.99; H, 6.96.

MS (EI) m/z 298, 268, 179, 131.

116) 3-(Cyclopropylphenylmethyl)-5,6,7,8,9,10,11,12-octahydro-4-hydroxy-2H-cyclodeca[b]pyran-2-one Physical characteristics are as follows:

Isolated 0.315 g of the title product as a white solid.

Mp 87.6°–90.4° C.

$^1$H NMR (CDCl$_3$) δ 7.51, 7.38, 7.28, 6.20, 4.02, 2.74–2.68, 2.50, 1.88–1.84, 1.67–1.57, 1.45–1.40, 1.38–1.31, 1.29–1.21, 0.77–0.71, 0.67–0.56, 0.33–0.27 ppm.

$^{13}$C NMR (CDCl$_3$) δ 165.5, 164.6, 160.3, 140.8, 129.1, 127.8, 127.4, 111.1, 106.2, 43.4, 28.8, 26.9, 25.7, 25.4, 25.3, 22.7, 33.5, 21.1, 20.7, 13.0, 4.8, 3.6 ppm.

IR (Nujol) 3076, 3024, 2998, 2929, 2856, 2857, 1660, 1632, 1547, 1455, 1449, 1396, 1230, 1206, 1193, 1171, 1130, 696 cm$^{-1}$.

Elemental analysis, Found: C, 78.41; H, 8.12.

MS (EI) m/z 352, 324, 311, 261, 248, 234, 131.

For high resolution, Found: 310.1578.

For high resolution, Found: 352.2038.

117) 3-(Cyclopropylphenylmethyl)-6,7,8,9,10,11-hexahydro-4-hydroxy-cyclonona[b]pyran-2(5H)-one Physical characteristics are as follows:

Isolated 0.194 g of the title product as a white solid.

Mp 81.7°–84.0° C.

$^1$H NMR (CDCl$_3$) δ 7.51, 7.37, 7.29, 6.22, 4.01, 2.65–2.61, 2.46–2.43, 1.79–1.78, 1.58–1.31, 0.79–0.70, 0.66–0.57, 0.33–0.25 ppm.

$^{13}$C NMR (CDCl$_3$) δ 165.6, 164.2, 161.1, 140.8, 129.1, 127.9, 127.4, 111.6, 106.3, 43.5, 30.2, 25.9, 25.7, 25.0, 24.9, 24.0, 22.9, 13.1, 4.8, 3.7 ppm.

IR (Nujol) 3133, 3075, 3060, 3024, 2996, 2950, 2923, 2867. 2856, 1659. 1632, 1550, 1466,, 1451, 1400, 1207, 1181, 1157, 1138, 700 cm$^{-1}$.

Elemental analysis, Found: C, 77.47; H, 7.59.

MS (EI) m/z 338, 310, 247, 221, 131, 91.

For high resolution, Found: 338.1872.

EXAMPLE 118

3-(Dicyclopropylmethyl)-5,6,7,8,9,10-hexahydro-4-hydroxy-2H-cyclootca[b]pyran-2-one (Formula J-3 wherein R$_1$ is cyclopropyl, R$_2$ is cyclopropyl, n is 4) Refer to Chart J.

A 50-mL, three-necked, round-bottomed flask with a 10-mL pressure-equalizing addition funnel filled with activated 3 Å molecular sieves and fitted with a reflux condenser and nitrogen inlet is charged with cyclooctene-1-acrylic acid, B, 2-dihydroxy-β-lactone (0.483 g), p-toluenesulfonic acid (0.118 g), and 2 mL of toluene. A solution of dicyclopropyl carbinol (0.418 g) in 8 mL of toluene is added, and the reaction mixture is warmed to ca. 140° C. After 1 h, more carbinol (0.280 g) is added. After a total of 2 h, the reaction mixture is diluted with 100 mL of 1N sodium hydroxide and washed with two 50-mL portions of ether. The pH of the aqueous layer is adjusted from 14 to 1 with concentrated hydrochloric acid. A white precipitate forms, which is extracted with three 50-mL portions of methylene chloride. The organic (methylene chloride) layers are then combined, dried over magnesium sulfate, filtered and concentrated to give 0.483 g of white solid. Column chromatography on 50 g silicia gel (elution with 20–30% ethyl acetate-hexane) yields 0.341 g of the title product as a white solid.

Physical characteristics are as follows:

Mp 196.9°–197.5° C.

$^1$H NMR (CDCl$_3$) δ 7.44, 2.68, 2.64–2.60, 2.56–2.52, 1.79–1.71, 1.69–1.61, 1.55–1.41, 1.04–0.93, 0.60–0.51, 0.48–0.42 ppm.

$^{13}$C NMR (CDCl$_3$) δ 165.7, 164.3, 160.8, 110.4, 105.4, 39.7, 30.6, 29.2, 28.8, 26.2, 26.0, 22.1, 12.4, 3.6, 2.4 ppm.

IR (Nujol) 3078, 3008, 2996, 2954, 2926, 2856, 1658, 1610, 1547, 1413, 1235, 1215, 1205, 1176, 1160, 1102, 1179 cm$^{-1}$.

MS (EI) m/z 288, 260, 259, 247, 232, 95.

For high resolution, Found: 288.1731.

EXAMPLE 119

Carbamic acid, [3-[cyclopropyl(5,6,7,8,9,10-hexahydro-4-hydroxy-2-oxo-2H-cycloocta[b]pyran-3-yl)methyl]phenyl]-, phenylmethyl ester (Formula M-6) Refer to Chart M.

A 12-L, three-necked, round-bottomed flask with a Soxhlet extractor containing 3 Å molecular sieves (180 g) and nitrogen inlet is charged with cyclooctene-1-acrylic acid, β, 2-dihydroxy-δ-lactone (59.6 g), p-toluenesulfonic acid (14.9 g), and methylene chloride (7.2 L). Cyclopropyl-(3-aminocarbobenzoxyphenyl)methanol (90.0 g) prepared as described in Preparations 49–52 is added, and the reaction mixture is warmed to reflux for 1 h. The reaction mixture is then cooled to 20° C. and washed with 1:1 saturated sodium chloride/saturated sodium bicarbonate (3 L), water (3 L), and saturated sodium chloride (3 L), backwashing each aqueous phase with methylene chloride (2×1.5 L). The organic layers are then combined, dried over magnesium sulfate, filtered and concentrated to ca. 1.5 L. The reaction mixture is cooled to −20° C. for 72 h, filtered, and dried under reduced pressure to give 103.5 g. The crude product is then slurried with 12.5 mL/g of hexane, filtered, and dried to give 102.4 g of the title compound. An additional 10.9 g of the title compound is obtained by concentrating the another liquors from the crystallization and recrystallizing the residue from ethyl acetate.

Physical characteristics for the title compound are in Example 119A below.

EXAMPLE 119A

Carbamic acid, [3-[cyclopropyl(5,6,7,8,9,10-hexahydro4-hydroxy-2-oxo-2H-cycloocta[b]pyran-3-yl)methyl]phenyl]-, phenylmethyl ester, (Formula J-3 wherein $R_1$ is cyclopropyl, $R_2$ is m-($NHCO_2$-benzyl)phenyl, n is 4) (Also Formula K-1) Refer to Charts J and K.

A 50-mL, three-necked, round-bottomed flask with a reflux condensor and nitrogen inlet is charged with cyclooctene-1-acrylic acid, 13, 2-dihydroxy-β-lactone (0.219 g), p-toluenesulfonic acid (0.053 g), and 3 Å molecular sieves. A solution of cyclopropyl-(3-aminocarbobenzoxyphenyl)methanol (0.300 g) prepared as described in Preparations 45–47 in 5 mL of toluene is added, and the reaction mixture is warmed to 110 ° C. for 7 h. The reaction mixture is then diluted with 50 mL of 1N sodium hydroxide and washed with two 25-mL portions of ether. The pH of the aqueous layer is adjusted from 14 to 1 with concentrated hydrochloric acid. A white precipitate forms, which is extracted with three 50-mL portions of methylene chloride. The organic (methylene chloride) layers are then combined, dried over magnesium sulfate, filtered and concentrated to give 0.275 g of beige solid. Column chromatography on 20 g silicia gel (elution with 35–100% ether-hexane, then 5% methanol-methylene chloride) yields 0.46 g of the title product as a white solid and 0.176 g of a mixture of the title product and the starting pyrone.

Physical characteristics are as follows:

Mp 113°–115° C. (decomposition).

$^1$H NMR ($CDCl_3$) δ 7.48, 7.38–7.26, 7.17, 6.70, 6.29, 5.20, 3.95, 2.64–2.60, 2.47–2.43, 1.76–1.72, 1.61–1.42, 0.88, 0.73–0.72, 0.63–0.55, 0.29–0.26 ppm.

$^{13}$C NMR ($CDCl_3$) δ 165.6, 164.0, 161.3, 142.2, 138.5, 129.9. 128.5, 128.3, 128.2, 122.9, 118.0, 117.9, 117.6, 110.7, 106.0, 67.0, 43.7, 30.7, 29.1, 28.8, 26.2, 25.8, 22.1, 13.0, 4.9, 3.8 ppm.

IR (Nujol) 3304, 2995, 2953, 2923, 2855, 1734, 1698, 1665, 1666, 1633, 1610, 1595, 1553, 1491, 1463, 1455, 1445, 1406, 1377, 1313, 1222, 1175, 1085, 1068, 740, 696 $cm^{-1}$.

MS (EI) m/z 473, 445, 382, 338, 91.

For high resolution, Found: 473.2202.

EXAMPLE 120

N-(3-(cyclopropyl-(4-hydroxy-2-oxo-5,6,7,8,9,10-hexahydro-2H-cycloocta[b]pyran-3-yl)-methyl)-phenyl)-N',N''-diisopropyl-guanidine (Formula K-3) Refer to Chart K.

A Parr hydrogenation tube is charged with palladum on carbon (0.024 g), the title product of Example 119A (Formula K-1) (0.133 g) and 2 mL of methanol. The tube is shaken at room temperature under 48 psi of hydrogen for 20 h. The reaction mixture is then diluted with methanol, filtered through Celite and concentrated to give 0.120 g of the compound of formula K-2 as a white solid, which is used without further purification (MS (EI) m/z 339, 311, 310, 213, 187, 159). A 10-mL, two-necked pear flask with a nitrogen inlet is charged with N-t-BOC-β-alanine (0.064 g), the compound of formula K-2 (0.120 g), and 1 mL of methylene chloride. 1,3-Diisopropylcarbodiimide (0.044 mL) is added dropwise and the reaction mixture is stirred at room temperature for 4 d. The reaction mixture is concentrated to give 0.300 g of rose oil. Column chromatography on 25 g of silica gel yields 0.080 g of the title product as a pale rose solid.

Physical characteristics are as follows:

Mp 172°–175° C. (decomposition).

$^1$H NMR ($CDCl_3$) δ 7.40, 7.23, 7.19, 6.97, 6.74, 3.92–3.85, 3.72, 3.48, 1.76–1.68, 1.42–1.26, 1.21–1.18, 0.91–0.86, 0.62–0.70, 0.42–0.51, 0.37–0.36 ppm.

$^{13}$C NMR ($CDCl_3$) δ 165.7, 160.4, 153.7, 150.5, 146.4, 134.8. 129.6, 129.2. 126.6, 123.7, 121.6, 112.3, 105.7, 45.7, 30.8, 29.3, 28.9, 28.3, 26.2, 25.9, 22.4. 13.9, 12.7. 6.2, 3.9 ppm.

IR (Nujol) 3073, 3058, 2952, 2921, 2868, 2854, 1658, 1637, 1619, 1588, 1589, 1488, 1461, 1445, 1425, 1389, 1368, 1353, 1334, 1171, 1128 $cm^{-1}$.

MS (EI) 465, 379, 339, 310, 277, 233, 213, 187, 146, 130, 119, 85, 69, 58, 44 m/z.

EXAMPLE 121

10-Cyclopropylmethyl-3-(cyclopropyl-phenyl-methyl)-4-hydroxy-5,6,7,8,9,10-hexahydro-cycloocta[b]pyran-2-one (Formula L-2 wherein $R_1$ is cyclopropyl, $R_2$ is —$CH_2$-cyclopropyl, n is 4) Refer to Chart L.

A 50-mL, 3-necked, round-bottomed flask with a nitrogen inlet and a 10-mL pressure-equalizing addition funnel is charged with diisopropylamine (0.25 mL) and 2 mL of tetrahydrofuran, and the addition funnel is charged with a solution of the title product of Example 107 (0.229 g) in 4 mL of tetrahydrofuran. The flask is placed in an ice bath and n-butyllithium (1.10 mL) is added dropwise over 2 min. After stirring at 0° C. for 20 min. the reaction is cooled to −40° C. in a dry ice/acetone bath and the solution of the title product of Example 107 is added dropwise over 5 min. The addition funnel is timed with an additional 1 mL of tetrahydrofuran, and the bright orange reaction mixture is stirred for 20 rain at −50° to −30° C. Bromomethyl cyclopropane (0.083 mL) is added dropwise over 1 min, and the reaction mixture is stirred an additional 2.5 h as it warmed to 10° C. The pale yellow solution is quenched with 10 mL of 10% hydrochloric acid, and a small amount of sodium chloride is added. The reaction mixture is then extracted with two 30-mL portions of methylene chloride, dried over magnesium sulfate, filtered, and concentrated to give 0.271 g of off-white solid. Column chromatography on 25 g of silica gel yields 0.132 g of the title product as a white solid.

Physical characteristics are as follows:

Mp 86°–90° C.

$^1$H NMR ($CDCl_3$) δ 7.51, 7.38, 7.30, 6.23, 4.01, 3.07–3.03, 2.78–2.73, 2.24–2.20, 2.02–1.94, 1.79–1.56, 1.39–1.24, 1.21–1.14, 0.86–0.64, 0.63–0.58, 0.43–0.39, 0.32–0.27, 0.09–0.07 ppm.

$^{13}$C NMR ($CDCl_3$) δ 165.5, 163.7, 162.4, 162.3, 141.0, 129.1. 127.9, 127.8, 127.3, 112.0, 105.9, 105.7, 43.6, 43.5, 39.5, 39.4, 36.2, 35.5, 30.4, 30.3, 27.2, 25.7, 25.6, 23.0, 13.1, 13.0, 9.6, 9.5, 4.9, 4.6, 4.4, 3.7, 3.6 ppm.

IR (Nujol) 3024, 2996, 2953, 2922, 2868, 2855, 1657, 1631, 1545, 1460, 1455, 1402, 1209, 1197, 1179, 1131 cm$^{-1}$.

Elemental analysis, Found: C, 79.34; H, 8.29.

MS (EI) m/z 378, 350, 349, 337, 287, 131, 91, 55.

EXAMPLES 122–133

Utilizing procedures analogous to those described above, the following additional compounds of the present invention are prepared:

122) 10-Benzyl-4-hydroxy-3-(1-phenyl-propyl-5,6,7,8,9,10-hexahydro-cycloocta[b]pyran-2-one Isolated 0.041 g of the title product as a white solid.

Physical characteristics are as follows:

Mp 76°–80° C. (decomposition).

$^1$H NMR (CDCl$_3$) δ 7.40–7.30, 7.28–7.17, 5.77–5.75, 4.40–4.35, 3.30–3.19, 2.88–2.81, 2.78–2.59, 2.21–1.94, 1.70–1.60, 1.33–1.23, 1.05–0.90 ppm.

$^{13}$C NMR (CDCl$_3$) δ 140.1, 129.4, 129.4, 128.9, 128.3, 128.2, 128.0, 127.5, 127.4, 127.3, 126.0, 41.0, 40.9, 37.3, 37.2, 35.2, 30.2, 27.0, 25.6, 23.9, 22.9, 12.1 ppm.

IR (Nujol) 2953, 2924, 2870, 2855, 1659, 1630, 1543, 1454, 1403, 1207, 1196, 698 cm$^{-1}$.

Elemental analysis, Found: C, 80.51; H, 7.53.

MS (EI) m/z 402, 373, 120, 91.

123) 10-Benzyl-3-dicyclopropylmethyl-4-hydroxy-5,6,7,8,9,10-hexahydro-cycloocta[b]pyran-2-one Isolated 0.085 g of the title product as a white solid.

Physical characteristics are as follows:

Mp 94°–97° C.

$^1$H NMR (CDCl$_3$) δ 7.49, 7.29–7.14, 3.29–3.21, 2.89–2.75, 2.22–2.13, 1.84–1.81, 1.77–1.55, 1.43–1.31, 1.00–0.86, 0.53–0.43 ppm.

$^{13}$C NMR (CDCl$_3$) δ 194.4, 164.0, 160.9, 140.2, 128.9, 128.3, 125.9, 111.9, 105.0, 40.9, 39.2, 37.3, 35.2, 30.2, 27.1, 25.6, 23.0, 12.4, 12.2, 3.6, 3.4, 2.5, 2.2 ppm.

IR (Nujol) 3000, 2953, 2922, 2855, 1657, 1631, 1543, 1455, 1231, 1212, 1197, 1175 cm$^{-1}$.

Elemental analysis, Found: C, 79.21; H, 7.98.

MS (EI) m/z 378, 349, 337, 287, 91.

For high resolution, Found: 378.2191.

124) 8-Cyclopropylmethyl-4-hydroxy-3-(1-phenyl-propyl)-5,6,7,8-tetrahydro-chromen-2-one (Formula L-2 wherein R$_1$ is ethyl, R$_2$ is —CH$_2$-cyclopropyl, n is 2) Refer to Chart L.

Isolated 0.108 g of the title product as a white solid.

Physical characteristics are as follows:

Mp 68°–73° C.

$^1$H NMR (CDCl$_3$) δ 7.43, 7.37, 7.28, 5.82, 4.37–4.31, 2.65–2.64, 2.23–2.21, 2.19–2.12, 2.09–1.99, 1.97–1.89, 1.80–1.45, 1.02, 0.77–0.71, 0.53–0.43, 0.10–0.09 ppm.

$^{13}$C NMR (CDCl$_3$) δ 163.7, 161.0, 141.8, 129.2, 128.5, 127.6, 127.1, 108.4, 106.0, 41.2, 37.4, 37.1, 26.8, 23.9, 20.7, 19.1, 12.3, 8.7, 8.6, 5.3, 3.9 ppm.

IR (Nujol) 2953, 2926, 2855, 1661, 1632, 1551, 1458, 1454, 1403, 1215, cm$^{-1}$.

MS (EI) m/z 338, 323, 209, 178, 131, 91.

For high resolution, Found: 338.1881.

125) 9-Cyclopropylmethyl-3-(cyclopropyl-phenyl-methyl)-4-hydroxy-6,7,8,9-tetrahydro-5-H-cyclohepta[b]pyran-2-one Isolated 0.087 g of the title product as a white solid.

Physical characteristics are as follows:

Mp 77°–83° C.

$^1$H NMR (CDCl$_3$) δ 7.52, 7.38, 7.29, 6.21–6.20, 3.97, 2.94–2.90, 2.60–2.50, 2.44–2.33, 1.83–1.69, 1.64–1.60, 1.37–1.26, 0.80–0.71, 0.65–0.53, 0.52–0.38, 0.32–0.24, 0.13–0.07 ppm.

$^{13}$C NMR (CDCl$_3$) δ 165.7, 165.3, 164.0, 140.9, 129.2, 127.9, 127.4, 112.4, 105.6, 44.5, 43.7, 35.4, 28.7, 28.6, 26.6, 26.5, 26.3, 20.7, 13.0, 9.2, 4.9, 4.1, 3.8, 3.7 ppm.

IR (Nujol) 2951, 2923, 2855, 1654, 1628, 1541, 1205 cm$^{-1}$.

Elemental analysis, Found: C, 79.04; H, 7.60.

MS (EI) m/z 364, 336, 335, 323, 273, 193, 131, 91, 55.

126) 4-Hydroxy-10-methyl-3-(1-phenyl-propyl)-5,6,7,8,9,10-hexahydro-cycloocta[b]pyran-2-one Isolated 0.057 g of the title product as a white solid.

Physical characteristics are as follows:

Mp 182°–186° C.

$^1$H NMR (CDCl$_3$) δ 7.44–7.35, 7.30–7.25, 5.89–5.82, 4.43–4.33, 3.07–3.00, 2.71–2.61, 2.24–2.12, 2.09–1.98, 1.73–1.51, 1.39–1.15, 1.29, 1.02 ppm.

$^{13}$C NMR (CDCl$_3$) δ 165.4, 163.8, 162.9, 162.8, 141.7, 141.6, 129.4, 127.6, 127.3, 111.0, 110.9, 106.0, 105.9, 41.3, 41.1, 37.9, 33.5, 33.4, 30.2, 30.1, 26.9, 26.0, 24.0, 23.9, 22.8, 22.7, 16.9, 12.3. 12.2 ppm.

IR (Nujol) 2954, 2924, 2870, 2855, 1669, 1632, 1546, 1535, 1453, 1206, 1178, cm$^{-1}$.

Elemental analysis, Found: C, 77.10; H, 8.19.

For high resolution, Found: 326.1873.

127) 3-(Cyclopropyl-phenyl-methyl)-10-ethyl-4-hydroxy-5,6,7,8,9,10-hexahydro-cycloocta[b]pyran-2-one Isolated 0.103 g of the title product as a white solid.

Physical characteristics are as follows:

Mp 94°–98° C.

$^1$H NMR (CDCl$_3$) δ 7.52, 7.38, 7.28, 6.22, 4.01, 2.84–2.70, 2.23–2.14, 2.01–1.97, 1.80–1.51, 1.39–1.31, 0.98–0.86, 0.76–0.71, 0.64–0.57, 0.32–0.27 ppm.

$^{13}$C NMR (CDCl$_3$) δ 165.7, 163.8, 162.3, 141.1, 129.2, 128.0, 127.9, 127.5, 112.5, 112.4, 106.0, 105.8, 43.8, 43.6, 41.0, 40.9, 35.7, 30.5, 30.4, 27.3, 25.8, 24.4, 23.1, 13.2, 13.1, 12.8, 5.0, 4.7, 3.8 ppm.

IR (Nujol) 2952, 2924, 2855, 1658, 1632, 1545, 1209, 1196, 1180 cm$^{-1}$.

Elemental analysis, Found: C, 78.19; H, 8.11.

MS (EI) m/z 352, 324, 323, 311, 261, 131, 91.

128) 3-(Cyclopropyl-phenyl-methyl)-4-hydroxy-10-propyl-5,6,7,8,9,10-hexahydro-cycloocta[b]pyran-2-one Isolated 0.093 g of the title product as a white solid.

Physical characteristics are as follows:

Mp 78°–84° C.

$^1$H NMR (CDCl$_3$) δ 7.51, 7.38, 7.29, 6.23, 4.02, 2.97–2.91, 2.76–2.69, 2.18–2.14, 2.02–1.94, 1.78–1.56, 1.36–1.26, 1.22, 1.07, 0.95–0.86, 0.77–0.71, 0.65–0.57, 0.31–0.25 ppm.

$^{13}$C NMR (CDCl$_3$) δ 165.7, 163.8, 162.4, 141.1, 129.2, 128.0, 127.9, 127.4, 112.3, 112.2, 106.0, 105.8, 43.8, 43.6, 38.6, 38.5, 35.9, 33.4, 30.5, 30.4, 27.3, 25.8, 25.7, 23.1, 21.2, 14.1, 13.2, 13.1, 5.1, 4.7, 3.8 ppm.

IR (Nujol) 2955, 2926, 2868, 2855, 1658, 1632, 1546, 1454, 1209, 1196, cm$^{-1}$.

MS (EI) m/z 366, 338, 325, 275, 131, 91.

For high resolution, Found: 366.2191.

129) 10-Butyl-3-(cyclopropyl-phenyl-methyl)4-hydroxy-5,6,7,8,9,10-hexahydro-cycloocta[b]pyran-2-one Isolated 0.178 g of the title product as a white solid.
Physical characteristics are as follows:
Mp 78°–82° C.

$^1$H NMR (CDCl$_3$) δ 7.52, 7.38, 7.29, 6.22, 4.01, 2.92–2.89, 2.76–2.69, 2.18–2.17, 1.98–1.96, 1.78–1.59, 1.56–1.46, 1.40–1.26, 1.23–1.09, 0.93–0.86, 0.76–0.72, 0.64–0.57, 0.32–0.27 ppm.

$^{13}$C NMR (CDCl$_3$) δ 165.6, 163.6, 162.4, 141.0, 129.1, 127.9, 127.8, 127.3, 112.1, 105.9, 43.7, 43.5, 38.8, 38.7, 35.7, 30.9, 30.4, 30.3, 30.2, 27.2, 25.6, 23.0, 22.6, 14.0, 13.1, 13.0, 4.9, 4.6, 3.7 ppm.

IR (Nujol) 2953, 2922, 2868, 2856, 1657, 1632, 1545, 1402, 1209, 1195 cm$^{-1}$.

Elemental analysis, Found: C, 78.78; H, 8.68.

MS (EI) m/z 380, 352, 339, 289, 131, 91.

For high resolution, Found: 380.2343.

130) 3-(Cyclopropyl-phenyl-methyl)-4-hydroxy-10-(tetrahydro-pyran-2-ylmethyl)-5,6,7,8,9,10-hexahydro-cycloocta[b]pyran-2-one Isolated 0.41 g of the title product as a white solid.
Physical characteristics are as follows:
Mp 88°–93° C.

$^1$H NMR (CDCl$_3$) δ 7.50, 7.3, 7.28, 6.19, 4.04–3.94, 3.42–3.34, 3.21–3.12, 2.70–2.68, 2.26–2.20, 1.80–1.69, 1.61–1.43, 1.34–1.20, 0.90–0.83, 0.74–0.73, 0.62–0.56, 0.39–0.25 ppm.

$^{13}$C NMR (CDCl$_3$) δ 165.7, 165.6, 163.9, 162.6, 162.5, 141.1. 129.3, 129.2, 128.1, 128.0, 127.4, 111.7, 111.6, 106.0, 105.9, 74.9, 68.5, 43.8, 43.7, 37.7, 34.9, 34.0, 2.3. 30.4, 27.3, 27.2, 26.2, 25.7, 23.6, 23.0, 13.3, 13.1, 5.1, 4.8, 3.8 ppm.

IR (Nujol) 2930, 2854, 1658, 1631, 1546, 1461, 1452, 1403, 1208, 1202, 1181, 1092 cm$^{-1}$.

Elemental analysis, Found: C, 76.52; H, 8.27.

MS (EI) m/z 422, 394, 337, 331, 131, 91.

For high resolution, Found: 422.2465.

131) 3-(Cyclopropyl-phenyl-methyl)-4-hydroxy-10-isobutyl-5,6,7,8,9,10-hexahydro-cycloocta[b]pyran-2-one Isolated 0.073 g of the title product as a white solid.
Physical characteristics are as follows:
Mp 86°–92° C.

$^1$H NMR (CDCl$_3$) δ 7.51, 7.37, 7.29, 6.20, 4.01, 3.03–2.98, 2.74–2.67, 2.21–2.18, 1.99–1.92, 1.79–1.65, 1.61–1.57, 1.34–1.22, 1.19–0.96, 0.92–0.87, 0.75–0.73, 0.63–0.58, 0.29–0.28 ppm.

$^{13}$C NMR (CDCl$_3$) δ 165.5, 163.6, 162.3. 162.2, 141.0, 129.2, 129.1, 128.1, 128.0, 127.4, 112.0, 105.9, 105.7, 43.7, 43.5, 40.2, 40.1, 36.3, 36.0, 35.9, 30.5, 30.4. 27.3, 26.1, 26.0. 25.6, 23.2, 23.1, 22.4, 22.3. 13.1, 5.0. 4.6. 3.7 ppm.

IR (Nujol) 2956, 2922, 2866, 2854, 1658, 1633, 1545, 1465, 1454, 1402, 1209, 1196, 1178 cm$^{-1}$.

Elemental analysis, Found: C, 78.78; H, 8.67.

MS (EI) m/z 380, 352, 339, 289, 131.

For high resolution, Found: 380.2342.

132) 3-(Cyclopropyl-phenylmethyl)-4-hydroxy- 10-(3-methyl-butyl)-5,6,7,8,9,10-hexahydro-cycloocta[b]pyran-2-one Isolated 0.235 g of the title product as a white solid.

Physical characteristics are as follows:
Mp 83°–88° C.

$^1$H NMR (CDCl$_3$) δ 7.50, 7.37, 7.27, 6.21, 4.00, 2.86–2.80, 2.75–2.72, 2.21–2.15, 1.99–1.89, 1.77–1.47, 1.37–1.26, 1.21–1.11, 0.91–0.86, 0.77–0.72, 0.64–0.60, 0.29–0.28 ppm.

$^{13}$C NMR (CDCl$_3$) δ 165.7, 165.6, 163.8, 162.5, 162.4, 141.1, 129.3, 129.2, 128.0, 127.9, 127.5, 127.4, 112.2, 106.0, 105.8, 43.8, 43.7, 39.4, 39.3, 37.4, 35.9, 35.8, 30.5, 30.4, 29.2, 29.1, 28.2, 28.1, 27.4, 25.8, 23.2, 22.7, 22.6, 13.3, 13.2, 5.1, 4.,7, 3.8 ppm.

IR (Nujol) 2954, 2923, 2868, 2854, 1658, 1632, 1546, 1456, 1209, 1195 cm$^{-1}$.

Elememal analysis, Found: C, 79.04; H, 8.75.

MS (EI) m/z 394, 366, 353, 303, 223, 172, 131, 91.

For high resolution, Found: 394.2510.

133) 3-(Cyclopropyl-phenyl-methyl)-4-hydroxy-10-(tetrahydro-furan-3-ylmethyl)-5,6,7,8,9,10-hexahydro-cycloocta[b]pyran-2-one Isolated 0.087 g of the title product as a white solid.
Physical characteristics are as follows:
Mp 80°–84° C.

$^1$H NMR (CDCl$_3$) δ 7.53–7.49, 7.41–7.36, 7.31, 6.29, 4.06–3.97, 3.92–3.83, 3.79–3.70, 3.40–3.30, 2.99–2.89, 2.79–2.73, 2.22–1.98, 1.80–1.50, 1.40–1.22, 1.21–1.08, 0.77–0.71, 0.64–0.56, 0.32–0.26 ppm.

$^{13}$C NMR (CDCl$_3$) δ 165.5, 163.7, 161.3, 140.9, 129.3, 128.1, 127.9, 127.5, 112.7, 112.6, 106.3, 73.4, 73.0, 67.9, 43.8, 43.6, 37.9, 37.8, 36.0, 34.5, 34.4, 32.8, 32.3, 30.5, 30.4, 27.4, 25.6, 23.3, 13.2, 13.1, 5.1, 4.7, 3.9, 3.8 ppm.

IR (Nujol)2953, 2923, 2868, 2855, 1701, 1661, 1635, 1550, 1452. 1209, 1198 cm$^{-1}$.

MS (EI) m/z 408, 380, 337, 317, 131, 91.

For high resolution, Found: 408.2293.

EXAMPLE 134

3-(Cyclopropyl-phenyl-methyl)-4-hydroxy-10-(1-hydroxy-propyl)-5,6,7,8,9,10-hexahydro-cycloocta[b]pyran-2-one (Formula L-2 wherein R$_1$ is cyclopropyl, R$_2$ is —CH(OH)CH$_2$CH$_3$, n is 4) Refer to Chart L.

A 50-mL, 3-necked, round-bottomed flask with a nitrogen inlet and a 10-mL pressure-equalizing addition funnel is charged with diisopropylamine (0.27 mL) and 2 mL of tetrahydrofuran, and the addition funnel is charged with a solution of the title product of Example 107 (0.249 g) in 4 mL of tetrahydrofuran. The flask is placed in an ice bath and n-butyllithium (1.15 mL) is added dropwise over 2 min. After stirring at 0° C. for 20 min, the reaction is cooled to −40° C. in a dry ice/acetone bath and the solution of the title product of Example 107 is added dropwise over 5 min. The addition funnel is rinsed with an additional 1 mL of tetrahydrofuran, and the bright orange reaction mixture is stirred for 20 min at −50° to −30° C. Propionaldehyde (0.17 mL) is added dropwise over 1 rain, and the reaction mixture is stirred an additional 1 h as it warmed to 5° C. The pale yellow solution is quenched with 10 mL of 10% hydrochloric acid, and a small amount of sodium chloride is added. The reaction mixture is then extracted with two 30-mL portions of methylene chloride, dried over magnesium sulfate, filtered, and concentrated to give 0.376 g of clear solid. Column chromatography on 25 g of silica gel yields 0.047 g of the title product as a white solid.

Physical characteristics are as follows:
Mp 115°–118° C.

$^1$H NMR (CDCl$_3$) δ 7.53–7.49, 7.41–7.36, 7.31, 6.29, 4.06–3.97, 3.92–3.83, 3.79–3.70, 3.40–3.30, 2.99–2.89, 2.79–2.73, 2.22–1.98, 1.80–1.50, 1.40–1.22, 1.21–1.08, 0.77, 0.71, 0.64–0.56, 0.32–0.26 ppm.

$^{13}$C NMR (CDCl$_3$) δ 165.1, 163.6, 161.2, 140.7, 129.2, 127.9, 127.8, 127.4, 112.5, 106.2, 106.0, 72.7, 44.4, 44.3, 43.8, 43.6, 30.6, 30.2, 30.1, 28.6, 27.5, 27.1, 25.3, 23.3, 23.1, 13.1, 13.0, 9.9, 5.0, 4.6, 3.8 ppm.

MS (EI) m/z 382, 354, 324, 131, 91.

For high resolution, Found: 382.2137.

EXAMPLE 135

9-But-3-enyl-3-(cyclopropyl-phenyl-methyl)4-hydroxy-6,7,8,9-tetrahydro-5H-cyclohepta[b]pyran-2-one (Formula L-2 wherein R$_1$ is cyclopropyl, R$_2$ is —(CH$_2$)$_2$—CH=CH$_2$, n is 3) Refer to Chart L.

A 50-mL, 3-necked, round-bottomed flask with a nitrogen inlet and a 10-mL pressure-equalizing addition funnel is charged with diisopropylamine (0.36 mL) and 2 mL of tetrahydrofuran, and the addition funnel is charged with a solution of the title product of Example 112 (0.242 g) in 4 mL of tetrahydrofuran. The flask is cooled to –78° C. and n-butyllithium (1.6 mL) is added dropwise over 2 min. After stirring at –78° C. for 5 min, the reaction mixture is stirred at 0° C. for 20 min, and then cooled to –40° C. The solution of the title product of Example 112 is added dropwise over 7 min, and the gold solution is stirred for 20 min at –40° to –20° C. Diiodobutane (0.10 mL) is added dropwise over I min. and the reaction mixture is stirred an additional 2 h as it warms to 0° C. The pale yellow solution is quenched with 10 mL of 10% hydrochloric acid, and a small amount of sodium chloride is added. The reaction mixture is then extracted with two 30-mL portions of methylene chloride, dried over magnesium sulfate, filtered, and concentrated to give a gold solid. Column chromatography on 25 g of silica gel yields 0.037 g of the title product as a white solid.

Physical characteristics are as follows:

Mp 59°–65° C.

$^1$H NMR (CDCl$_3$) δ 7.52, 7.38, 7.30, 6.22, 5.86–5.75, 5.00, 3.97, 2.83–2.78, 2.56–2.38, 2.20–1.94, 1.88–1.48, 1.47–1.26, 0.77–0.71, 0.65–0.57, 0.32–0.26 ppm.

$^{13}$C NMR (CDCl$_3$) δ 165.5, 165.2, 163.9, 140.9, 137.9, 129.2, 127.9, 127.4, 115.0, 112.5, 105.8, 105.7, 43.7, 43.1, 31.6, 29.5, 28.4, 28.3, 26.5, 26.3, 26.2, 20.7, 20.6, 13.0, 4.9, 3.9, 3.8 ppm.

MS (EI) m/z 364, 336, 335, 323, 273, 193, 191, 91, 55.

For high resolution, Found: 364.2049.

EXAMPLE 136

3-(1-Benzyl-2-phenyl-ethyl)-4-hydroxy-5,6,7,8,9,10-hexahydro-cycloocta[b]pyran-2-one (Formula J-3 wherein R$_1$ is benzyl, R$_2$ is benzyl, n is 4) Refer to Chart J.

Utilizing a procedure analogous to that described above for Example 107 and the compound of Preparation 48, the title compound may be prepared. Isolated 0.042 g the title product as a white solid.

Mp 194°–196° C.

$^1$H NMR (CDCl$_3$) δ 7.45, 7.36, 7.26, 7.18, 6.08, 4.45, 2.77–2.58, 2.47–2.40, 1.74, 1.54–1.42 ppm.

MS (EI) 388, 297, 284, 195, 194, 91 m/z.

For high resolution, Found: 388.2038.

PREPARATION 45

Cyclopropyl-(3-nitrophenyl)methanone

A 250-mL three-necked flask equipped with a thermometer and an addition funnel is charged with fuming nitric acid (90%, 130 mL) and cooled to –10° C. Cyclopropyl phenyl ketone (21 mL) is added dropwise via the addition funnel over 15 min. During the addition of the ketone, the reaction temperature is maintained between –7° and –13° C. After stirring an additional 10 min at –10° C., the reaction mixture is poured onto 1 L of crashed ice, extracted with 700 mL of toluene, washed with two portions of 5% sodium hydroxide solution and one portion of brine, dried over magnesium sulfate and concentrated to give 28.14 g of yellow oil. Recrystallization from 50 mL of methanol gives 14.62 g of the title product as white crystals.

Physical characteristics are as follows:

$^1$H NMR (CDCl$_3$) δ 8.86, 8.43, 8.34, 7.70, 2.72, 1.33, 1.17 ppm.

IR (Nujol) 2954, 2925, 1664, 1614, 1529, 1442, 1386, 1352, 1225, 1082, 1047, 852, 720, 689 cm$^{-1}$.

Elemental analysis, Found: C, 62.89; H, 4.73; N, 7.32.

MS (EI) 191, 150, 104, 69 m/z.

PREPARATION 46

Cyclopropyl-(3-aminophenyl)methanone

A Parr hydrogenation tube is charged with palladium on carbon (0.030 g). cyclopropyl-(3-nitrophenyl)methanone of Preparation 45 (0.250 g) and 10 mL of methanol. The tube is shaken at room temperature under 40 psi of hydrogen overnight. The reaction mixture is then filtered through Celite and concentrated to give 0.207 g of the title product which is used without further purification.

Physical characteristics are as follows:

$^1$H NMR (CDCl$_3$) δ 7.40, 7.27, 7.22, 6.87, 3.87, 2.62, 1.20, 1.02 ppm.

PREPARATION 47

Cyclopropyl-(3-aminocarbobenzoxyphenyl)methanol (Formula J-2 wherein R$_1$ is cyclopropyl, R$_2$ is m-(NHCO$_2$benzyl)phenyl) Refer to Chart J.

A solution of cyclopropyl-(3-aminophenyl)methanone of Preparation 46 (0.427 g) and diisopropylethylamine (0.55 mL) in 10 mL of methylene chloride is cooled to 0° C. and benzyl chloroformate (0.42 mL) is added dropwise. The reaction mixture is stirred for 15 min at 0° C. and then allowed to warm to room temperature over 2 h. The reaction mixture is then washed with dilute hydrochloric acid, and the aqueous layer is extracted with 2 additional portions of methylene chloride. The combined organic layers are dried over magnesium sulfate and concentrated to 0.861 g of Cyclopropyl-(3-aminocarbobenzoxyphenyl)methanone as a tan solid, which is used without further purification.

Cyclopropyl-(3-aminocarbobenzoxyphenyl)methanone (0.861 g) is dissolved in 10 mL of tetrahydrofuran and 10 mL of methanol and sodium borohydride (0.601 g) is added. The reaction mixture is stirred at room temperature overnight, then partitioned between methylene chloride and cold dilute hydrochloric acid. The aqueous layer is extracted with two additional portions of methylene chloride, and the combined organic layers are dried then over magnesium sulfate. Column chromatography on silica gel (elution with 40% ethyl acetate-hexane) gives 0.688 g of the title product as a pale yellow solid.

Physical characteristics are as follows:

Mp 91°–92° C.

$^1$H NMR (CDCl$_3$) δ 7.41, 7.39–7.31, 7.26, 7.08, 7.05, 5.16, 3.91, 2.48, 1.16–1.12, 0.59–0.31 ppm.

IR (Nujol) 3414, 3262, 2955, 2924, 2870, 2855, 1694, 1599, 1559, 1449, 1287, 1262, 1250, 1235, 1054, 1035, 789, 769, 748, 697 cm$^{-1}$.

PREPARATION 48

1,3-Diphenyl-2-propanol (Formula J-2 wherein $R_1$ is benzyl, $R_2$ is benzyl) Refer to Chart J.

A 500-mL, three-necked round-bottomed flask equipped with a nitrogen inlet and a 60-mL pressure-equalizing addition funnel is charged with lithium aluminum hydride (2.27 g) and 100 mL of ether and is cooled to 0° C. The addition funnel is charged with a solution of 1,3-diphenyl acetone (10.23 g) in 20 mL of ether which is added dropwise to the reaction mixture over 30 min. After stirring 18.5 h at room temperature, the reaction mixture is cooled to 0° C. and quenched by adding 3 mL of water and 10 mL of 1N sodium hydroxide dropwise. The reaction mixture is stirred at room temperature for an additional 30 rain, filtered through magnesium sulfate and concentrated to yield 10.57 g of title product as a colorless oil, which is used without further purification.

Physical characteristics are as follows:

$^1$H NMR (CDCl$_3$) δ 7.34–7.30, 7.25–7.22, 4.07, 2.91–2.73 ppm.

EXAMPLE 137

Ethenesulfonic acid (3-(1-(4-hydroxy-2-oxo-2H-chromen-3-yl)-propyl)-phenyl)-amide; or [2-[[[3-[1-(4-hydroxy-2-oxo-2H-1-benzopyran-3-yl)propyl]phenyl]amino]sulfonyl]ethenyl]-

To 14.7 mg of 3-[1-(3-aminophenyl)propyl]4 hydroxycoumarin is added 1 ml of methylene chloride and 8.1 microliters of pyridine. 5.71 microliters of chloroethylsulfonyl chloride is added at room temperature and protection from moisture. The reaction mixture is allowed to stir at room temperature for 3 hours. 5 ml of methylene chloride is added and the solution is washed twice with 5 ml of water. The organic solution is dried over anhydrous sodium sulfate, filtered and dried to give crude title product. Chromatography over 15 g of silica gel using 5% methanol in chloroform and collecting material with $R_f$=0.3 gives 6.3 mg of the title product.

Physical characteristics are as follows:

HRMS measured: 386.1059.

EXAMPLE 138

Ethanesulfonic acid (3-(1-(4-hydroxy-2-oxo-2H-chromen-3-yl)-propyl)-phenyl)-amide; or [2-[[[3-[1-(4-hydroxy-2-oxo-2H-1-benzopyran-3-yl)propyl]phenyl]amino]sulfonyl]ethyl]-

14.75 mg of 3-[1-(3-aminophenyl)propyl]-4 hydroxycoumarin is dissolved in 1 ml of methylene chloride with 8.1 microliters of pyridine added. To this solution, at room temperature with protection from moisture, is added 5.14 microliters of ethylsulfuryl chloride. The reaction is allowed to stir, at room temperature, for 18 hours. 5 ml of methylene chloride is added to the reaction mixture, the resulting mixture is washed twice with 1 ml of water, and the methylene chloride solution is separated, dried over anhydrous sodium sulfate and evaporated to dryness to yield 28 mg of crude title product. Chromatography over 15 g of silica gel using 5% methanol in chloroform as solvent gives 6.8 mg of pure title product.

Physical characteristics are as follows:

Rf=0.4; 5% Methanol/Chloroform.

EXAMPLE 139

2-(1,3-Dioxo-1,3-dihydro-isoindol-2-yl)-ethanesulfonic acid(3-(1-(4-hydroxy-2-oxo-2H-chromen-3-yl)-propyl)-phenyl)amide; or [2-[[[3-[1-(4-hydroxy-2-oxo-2H-1-benzopyran-3-yl)propyl]phenyl]amino]sulfonyl]ethyl]-phthalimido]-

Substituting 15.7 mg of N-phthalimido-2-aminoethylsulfonyl chloride for chloroethylsulfonyl chloride in Example 137 gives 10.1 mg of the title product.

Physical characteristics are as follows:

Rf=0.5 in 5% methanol in chloroform.

HRMS measured: 533.1384.

EXAMPLE 140

2-(N-t-butyloxycarbonyl-amino)-ethanesulfonic acid (3-(1-(4-hydroxy-2-oxo-2H-chromen-3-yl)-propyl)-phenyl)-amide; or Carbamic acid, [2-[[[3-[1-(4-hydroxy-2-oxo-2H-1-benzopyran-3-yl)propyl]phenyl]amino]sulfonyl]ethyl]-, 1,1-dimethylethyl ester.

To 31 mg of the title product of Example 139 is added 6 ml of 95% ethanol. Added, at room temperature, 3.2 ml of a 100 microliter/100 ml solution of hydrazine hydrate in 95% ethanol (3.2 microliters of hydrazine hydrate). After stirring for 48 hours, an additional 3 ml of the hydrazine hydrate solution is added and the reaction is allowed to continue to stir for an additional 96 hours at room temperature. The reaction mixture is evaporated to dryness under vacuum, and triturated twice with 5 ml of ethyl acetate. The resulting residue is chromatographed over 15 g of silica gel using 25% methanol in chloroform as eluent to give 11 mg of the unprotected amino sulfonamide.

Physical characteristics are as follows:

Rf=0.3 in 25% methanol in chloroform.

MS measured: 403.1319.

To 8 mg of the amino compound is added 2 ml of a 1:1 dioxane:water solution and, when solution is complete, 20 mg of BOC-ON+2 drops of triethylamine is added. After stirring for 15 minutes, the reaction mixture is evaporated to dryness, the residue is dissolved in ethyl acetate and chromatographed over 10 g of silica gel using 35% ethyl acetate in hexane as eluent. After all the unreacted BOC-ON is collected, the eluent is switched to 25% methanol in chloroform. Material with an RF=0.75 (25% methanol in chloroform) is collected, evaporated to dryness, dissolved in chloroform with a trace of methanol, filtered and evaporated to dryness to give 10 mg of pure title product.

Physical characteristics are as follows:

MS measured: 503.1858.

EXAMPLES 141–160

Utilizing procedures analogous to those described above, the following additional commpounds of the present invention are prepared:

141) 4-Hydroxy-7-(2-morpholin-4-yl-ethoxy)-3-(1-phenyl-propyl)-chromen-2-one

Physical characteristics are as follows:

HRMS: 409.1889.

142) 4-Hydroxy-3-(1-phenyl-cyclopropyl)-chromen-2-one

Physical characteristics are as follows:

HRMS: 278.0942.

143) N-(2-Hydroxy-indan-1-yl)-3-(1-(4-hydroxy-2-oxo-2H-chromen-3-yl)-propyl)-benzamide Physical characteristics are as follows:

HRMS: 455.1741.

144) 3-(1-Benzyl-propyl)4-hydroxy-chromen-2-one

Physical characteristics are as follows:

---

Elemental analysis, Found: C. 72.57; H. 6.51;N. 4.61.

MS (EI) m/z 297, 269, 253, 225, 91.

MW Found: 294;

Found: C, 77.40; H, 6.29.

145) 3-(1-Benzyl-3-phenyl-propyl)4-hydroxy-chromen-2-one

Physical characteristics are as follows:

HRMS: 370.1569.

146) 3-(1-Benzyl-2-phenyl-ethyl)4-hydroxy-chromen-2-one

Physical characteristics are as follows:

HRMS: 356.1412.

147) 3-(1 -Benzyl-butyl)-4-hydroxy-chromen-2-one

Physical characteristics are as follows:

MW Found: 308;

Found: C, 78.00; H, 6.51.

148) N-(1H-Benzoimidazol-2-ylmethyl)-3-(1-(4-hydroxy-2-oxo-2H-chromen-3-yl)-propyl)-benzamide Physical characteristics are as follows:

HRSM: 454.1758.

149) 3-(1-(4-Hydroxy-2-oxo-2H-chromen-3-yl)-propyl)-N-(2-methyl-1-(pyridin-2-ylmethylcarbomoyl)-butyl)-benzamide Physical characteristics are as follows:

HRMS: 528.2506.

150) Acetic acid 4-(1-(4-Hydroxy-2-oxo-2H-chromen-3-yl)-1-methyl-ethyl)-phenylester Physical characteristics are as follows:

HRMS: 339.1232.

151) 4-Hydroxy-7-(2-(2-methoxy-ethoxy)-ethoxy)-3-(1-phenyl-propyl)-chromen-2-one Physical characteristics are as follows:

HRMS: 398.1729.

152) 3-(2,2-Dimethyl-1-phenyl-propyl)-4-hydroxy-chromen-2-one

Physical characteristics am as follows:

HRMS: 308.1417.

153) 4-Hydroxy-6',8'-Dimethyl-3',4'-dihydro-2'H-[3',4'] bicromenyl-2-one 154) 4-Hydroxy-7-(2-(2-methoxy-ethoxy)-ethoxy) -ethoxy)-3-(1 -phenyl-propyl)-chromen-2-one Physical characteristics are as follows:

HRMS: 442.1991.

155) 3-(1-Ethyl-3-phenyl-propyl)4-hydroxy-chromen-2-one

Physical characteristics are as follows:

MW Found: 308;

Found: C, 77.86; H, 6.74.

156) 3-(1-Ethyl4-phenyl-butyl)-4-hydroxy-chromen-2-one

Physical characteristics are as follows:

MW Found: 322.

157) 2-((4-Hydroxy-2-oxo-2H-chromen-3-yl)-phenyl-methyl)-malonic acid dimethyl ester Physical characteristics are as follows:

Found: C, 64.8; H, 4.87;N, 0.00.

158) 4-Hydroxy-3',4'-dihydro-2'H-[3,4]bichromenyl-2-one 159) 3-(1-Benzyl- 1,2,3,4-tetrahydro-quinolin4-yl)-4-hydroxy-chromin-2-one Physical characteristics are as follows:

HRMS: 383.1510.

160) 4-Hydroxy-3-(3-hydroxy-1-phenyl-propyl)-chromen-2-one

Physical characteristics are as follows:

HRMS: 296.1041.

EXAMPLE 161

3-(Cyclopropylphenylmethyl)-5,6,7,8,9,10-hexahydro-4-hydroxy-10-(2-hydroxy-1-methylethyl)-2H-cyclooct[b] pyran-2-one (Formula L-2 wherein n is 4, $R_1$ is cyclopropyl, $R_2$ is —CH(CH$_3$)(CH$_2$OH)) Refer to Chart L.

Following the general procedure of Example 121, and making non-critical variations, but substituting propylene oxide for bromomethyl cyclopropane, 0.017 g of the title compound is obtained as a white solid.

Physical characteristics are as follows:

HRMS: 382.2139

MS (EI) m/z 382, 354, 337, 291, 166, 131, 91.

For high resolution, Found: 382.2144.

EXAMPLE 162

3-(Cyclopropylphenylmethyl)-5,6,7,8,9,10-hexahydro-4-hydroxy-10-(2-hydroxypropyl)-2H-cycloocta[b]pyran-2-one (Formula L-2 wherein n is 4, $R_1$ is cyclopropyl, $R_2$ is —CH$_2$—CH(CH$_3$)(OH)) Refer to Chart L.

Utilizing the procedure described above, 0.010 g of the title compound is obtained as a white solid.

Physical characteristics are as follows:

HRMS: 382.2137

MS (EI) m/z 382, 354, 337, 291, 166, 131, 91, 45.

For high resolution, Found: 382.2144.

EXAMPLE 163

3-(Cyclopropylphenylmethyl)-5,6,7,8,9,10-hexahydro-4-hydroxy-10-(oxiranylmethyl)-2H-cycloocta[b]pyran-2-one Following the general procedure of Example 121, and making non-critical variations, but substituting epichlorohydrin for bromomethyl cyclopropane, 0.031 g of the title compound is obtained as a white solid.

Physical characteristics are as follows:

Low resolution mass spec: 380, 352, 337, 322, 289, 171, 131, 91.

MP 67–71° C. (decomposition).

MS (EI) m/z 380, 352, 337, 322, 289, 171, 131, 91.

PREPARATION 49

Cyclopropyl-(3-nitrophenyl)methanone (Formula M-2) Refer to Chart M.

Charge a jacketed 1 L three neck round bottom flask equipped with stirrer and addition funnel under nitrogen with 580 mL fuming nitric acid and cool to −40° C. Slowly, over 1.5 hours, add cyclopropyl phenyl ketone of formula M-1 (100 g) keeping the temperature below −35° C. Stir 3 hours, monitoring reaction by TLC. Pour reaction mixture into 3 kg ice/water. Extract with 3×500 mL ethyl acetate. Wash combined organic phase with 2×1.5 L saturated aqueous sodium bicarbonate, dry over magnesium sulfate, filter and concentrate to 138 g. Dissolve residue in 270 mL methanol, cool to −20° C. for 18 hours, filter and wash cake with cold methanol. Dry product under reduced pressure for 72 hours, obtaining 63.86 g. GC analysis (15 m. DB-1, $T_o$=100° C, 10° C./min., RT - 6.0 min.) indicates material to be >98% pure.

Physical characteristics for the title compound are in Preparation 45 above.

PREPARATION 50

Cyclopropyl-(3-aminophenyl)methanone (Formula M-3) Refer to Chart M.

Charge platinum on carbon (8.7 g) to Paar bottle. Charge a flask with cyclopropyl(3-nitrophenyl)methanone of Preparation 49 (86.7 g) and methanol (1.56 L) and warm to dissolve, then cool with ice bath to 9° C. Hydrogenate for 50 minutes, keeping temperature below 35° C. and monitoring reaction by TLC. Filter reaction mixture through solka floc, and concentrate under reduced pressure to 70 g.

Physical characteristics are as follows:

$^1$H NMR (CDCl$_3$) δ 7.99, 7.47–7.19, 6.84, 3.84, 2.60, 1.23–1.15, 1.03–0.96 ppm.

$^{13}$C NMR (CDCl$_3$) δ 200.9, 146.8, 139.1, 129.4, 119.3, 118.4, 113.9, 17.2, 11.6 ppm.

PREPARATION 51

Cyclopropyl-(3-aminocarbobenzoxyphenyl)methanone (Formula M-4) Refer to Chart M.

Charge a 3 L round bottom flask equipped with mechanical stirrer and addition funnel under nitrogen with cyclopropyl-(3-aminophenyl)methanone of Preparation 50 (70.0 g), diisopropylethylamine (DIPEA, 90.2 mL) and methylene chloride (CH$_2$Cl$_2$) (1.3 L). Cool reaction mixture to 0° C. Dilute the benzylchloroformate (67.5 mL) with methylene chloride (186 mL) and add to the substrate solution over one hour keeping temperature at 0°–5° C. A heavy precipitate will form. Allow to warm with stirring for 1.5 hours monitoring reaction by TLC. Pour reaction mixture into 600 mL 1N HCl/600 g ice/4.2 L methylene chloride and stir to dissolve. Separate phases and dry organic phase over magnesium sulfate, filter and concentrate to a dryness. Slurry solids in 3 mL/g hexane, filter, and vacuum dry for 125 g.

Physical characteristics are as follows:

$^1$H NMR (CDCl$_3$) δ 8.01, 7.76–7.69, 7.43–7.33, 7.18, 5.21, 2.64, 1.25–1.20, 1.03–0.97 ppm.

$^{13}$C NMR (CDCl$_3$) δ 200.6, 153.4, 138.7, 138.5, 135.9, 129.3, 128.6, 128.4, 123.1, 122.8, 118.1, 67.2, 17.3, 12.0 ppm.

PREPARATION 52

Cyclopropyl-(3-aminocarbobenzoxyphenyl)methanol (Formula M-5) Refer to Chart M.

Charge a 2 L three neck round bottom flask equipped with overhead stirrer under nitrogen with cyclopropyl-(3-aminocarbobenzoxyphenyl)methanone of Preparation 51 (25 g), tetrahydrofuran (THF) (450 mL) and ethanol (90 mL). Cool reaction mixture to 0°–5° C. and add the sodium borohydride pellets (12.4 g) in three equal portions over 30 minutes. Allow to warm to 23° C. and stir for 20 hours, monitoring reaction by TLC. Recool reaction mixture to 0°–5° C. and slowly quench by adding 90 mL 1N hydrochloric acid, keeping the temperature below 10° C. Pour with stirring into methylene chloride (600 mL) and 1N hydrochloric acid (400 mL). Separate the phases and wash the organic phase with saturated sodium chloride solution (1 L). Dry over magnesium sulfate, filter, and concentrate to 23.7 g.

Physical characteristics are as follows:

$^1$H NMR (CDCl$_3$) δ 7.41–7.35, 7.33, 7.17, 7.10, 5.17, 3.93, 2.36, 1.16–1.12, 0.60–0.32 ppm.

$^{13}$C NMR (CDCl$_3$) δ 153.5, 145.0, 137.9, 136.1, 1290, 128.6, 128.3, 121.2, 117.9, 116.5, 67.9, 67.0, 19.1, 3.6, 2.8 ppm.

EXAMPLE 164

3-[(3-Aminophenyl)cyclopropylmethyl]-5,6,7,8,9,10-hexahydro-4-hydroxy-2H-cycloocta[b]pyran-2-one (Formula M-7) Refer to Chart M.

In a 100-mL, three-necked, round-bottomed flask with a reflux condensor and nitrogen inlet, 10% palladium on carbon (1.0 g) is added to a mixture of the title product of formula M-6, prepared in Example 119 (1.95 g) in cyclohexene (50 mL) and the mixture is refluxed for 4h. The mixture is then filtered through Celite, washed with methylene chloride (CH$_2$Cl$_2$), and concentrated to give 1.25 g of the title compound as a white solid.

Physical characteristics are as follows:

M.P. 75°–79° C.

IR (Nujol) 2995, 2951, 2921, 2868, 1660, 1619, 1605, 1590, 1551, 1491, 1460, 1447, 1428, 1404, 1247, 1226, 1202, 1191, 1172, 1126 cm$^{-1}$.

MS (EI) m/z 339, 310, 213, 187, 159.

$^1$H NMR (CDCl$_3$) δ 7.16, 6.96, 6.84, 6.63, 5.67, 3.87, 2.61, 2.48–2.37, 1.98, 1.75, 1.63–1.26, 0.74–0.65, 0.61–0.53, 0.28–0.22 ppm.

$^{13}$C NMR (CDCl$_3$) δ 164.2, 161.1, 142.8, 130.2, I17.7, 117.6, 114.7, 114.6, 114.5, 110.9, 106.2, 43.5, 30.6, 29.1, 28.8, 26.2, 25.8, 22.0, 12.8, 4.7, 3.7 ppm.

For high resolution, Found: 339.1845.

EXAMPLES 165–169

Utilizing procedures analogous to those described above, the following additional compounds of the present invention are prepared:

EXAMPLE 165

Carbamic acid, [3-[[3-[cyclopropyl(4-hydroxy-2-oxo-2H-1-benzopyran-3-yl)methyl]phenyl]amino]-3-oxopropyl]-, 1,1-dimethylethyl ester Physical characteristics are as follows:

$^1$H NMR δ 0.04, 0.18, 0.38, 1.23, 2.32, 3.22, 6.7–7.3, 7.82, 7.96.

EXAMPLE 166

Carbamic acid, [3-[cyclopropyl(4-hydroxy-7-methoxy-2-oxo-2H- 1-benzopyran-3-yl)methyl]phenyl]-, phenylmethyl ester Physical characteristics are as follows:

M+471.1672.

EXAMPLE 167

Carbamic acid, [3-[[3-[cyclopropyl(4-hydroxy-7-methoxy-2-oxo-2H-1-benzopyran-3-yl)methyl]phenyl]amino]-3-oxopropyl]-, 1,1-dimethylethyl ester Physical characteristics are as follows:

$^1$H NMR δ 0.05, 0.23, 0.40, 1.29, 2.35, 3.37, 3.62, 6.39, 6.85, 7.06, 7.25, 7.7.

EXAMPLE 168

Coumarin, 4-hydroxy-3-(α-(3-((3-(1H-indol-1-yl)-1-oxopropyl)amino)phenyl)cyclopropylmethyl)

Physical characteristics are as follows:

$^1$H NMR δ 0.30, 0.46, 0.7, 1.9, 2.73, 3.6, 4.45, 6.39, 7.0–7.6, 7.9.

EXAMPLE 169

Coumarin, 4-hydroxy-3-(1-phenylpropyl)-7-propoxy
Physical characteristics are as follows:
M+338.1524.

EXAMPLES 170–195

Utilizing procedures described in Example 121 above (Refer to Chart L), the following additional compounds of the present invention are prepared:

EXAMPLE 170

3-(Cyclopropylphenylmethyl)-5,6,7,8,9,10-hexahydro-4-hydroxy-10-[(tetrahydro-2-furanyl)methyl]-2H-cycloocta[b]pyran-2-one
Isolated 0.039 g of the title compound as a white solid. This compound is isolated from the same reaction mixture as the compound of Example 171 and is the more polar stereoisomer.
Physical characteristics are as follows:
MS (EI) m/z 408, 380, 337, 191, 131, 91, 71.
For high resolution, Found: 408.2300.

EXAMPLE 171

3-(Cyclopropylphenylmethyl)-5,6,7,8,9,10-hexahydro-4-hydroxy-10-[(tetrahydro-2-furanyl)methyl]-2H-cycloocta[b]pyran-2-one
Isolated 0.017 g of the title compound as a white solid. This compound is isolated from the same reaction mixture as the compound of Example 170 and is the less polar stereoisomer.
Physical characteristics are as follows:
MS (EI) m/z 408, 380, 337, 191, 131, 91, 71.
For high resolution, Found: 408.2300.

EXAMPLE 172

3-(Cyclopropylphenylmethyl)-5,6,7,8,9,10-hexahydro-4-hydroxy-10-[2-(2-methoxyethoxy)ethyl]-2H-cycloocta[b]pyran-2-one
Isolated 0.032 g of the title compound as a white solid.
Physical characteristics are as follows:
MP 129°–133 ° C.
$^1$H NMR (CDCl$_3$) δ 7.51, 7.39, 7.30, 6.26, 6.24, 4.04, 3.98, 3.61–3.39, 3.38, 3.36, 3.29–3.21, 2.76–2.67, 2.30–2.17, 1.86–1.73, 1.66–1.60, 1.19–1.07, 0.79–0.72, 0.66–0.56, 0.32–0.26 ppm.
$^{13}$C NMR (CDCl$_3$) δ 165.5, 163.7, 161.6, 161.5, 140.9, 129.1, 128.1, 127.9, 127.8, 127.4, 112.6, 112.5, 106.0, 105.8, 71.9, 69.8, 69.1, 58.9, 43.7, 43.5, 35.5, 35.1, 35.0, 31.0, 30.4, 30.3, 27.1, 25.6, 22.9, 13.1, 13.0, 5.0, 4.6, 3.7 ppm.
IR (Nujol) 2996, 2952, 2923, 2868, 2854, 2856, 1653, 1613, 1537, 1453, 1404, 1198, 1177, 1155, 1136, 1116, 1085 cm$^{-1}$.
MS (EI) m/z 426, 398, 350, 337, 335, 322, 179, 131, 91, 59, 45.
For high resolution, Found: 426.2406.

EXAMPLE 173

3-(Cyclopropylphenylmethyl)-5,6,7,8,9,10-hexahydro-4-hydroxy-10-(hydroxymethyl)-2H-cycloocta[b]pyran-2-one
Isolated 0.076 g of the title compound as a white solid.
Physical characteristics are as follows:
MP 110°–113 ° C. (decomposition).
$^1$H NMR (CDCl$_3$) δ 7.50, 7.38, 7.29, 4.78–4.10, 3.99, 3.93, 3.77–3.72, 3.22–3.17, 2.78–2.70, 2.28–2.17, 1.77–1.65, 1.62–1.48, 1.43–1.26, 0.77–0.71, 0.63–0.55, 0.32–0.27 ppm.
$^{13}$C NMR (CDCl$_3$) δ 165.4, 163.9, 160.4, 140.9, 140.8, 113.0, 112.9, 106.5, 106.3, 63.1, 43.9, 43.7, 42.2, 42.1, 31.6, 31.5, 29.9, 29.8, 26.8, 25.5, 22.6, 13.1, 13.0, 5.0, 4.7, 3.9, 3.8 ppm.
IR (Nujol) 3266, 3077, 3061, 3025, 2998, 2953, 2924, 2855, 1667, 1636, 1553, 1453, 1404, 1378, 1210, 1199, 1184, 1137, 1045, 697 cm$^{-1}$.
MS (EI) m/z 354, 326, 313, 295, 263, 131, 91.
For high resolution, Found: 354.1831.

EXAMPLE 174

3-(Cyclopropylphenylmethyl)-5,6,7,8,9,10-hexahydro-4-hydroxy-10-(1-oxopropyl)-2H-cycloocta[b]pyran-2-one
Isolated 0.013 g of the title compound as a white solid.
Physical characteristics are as follows:
MP 71°–76° C. (decomposition).
MS (EI) m/z 380, 352, 324, 296, 295, 289, 131, 91, 57.
For high resolution, Found: 380.1987.

EXAMPLE 175

3-(Cyclopropyl phenylmethyl )-5,6,7,8,9,10-hexahydro-4-hydroxy-10-(1-hydroxy-1-methylethyl)-2H-cycloocta[b]pyran-2-one
Isolated 0.067 g of the title compound as a white solid.
Physical characteristics are as follows:
MP 223°–225 ° C.
IR (Nujol) 3216, 3082, 3053, 3022, 2952, 2925, 2854, 1663, 1655, 1630, 1559, 1461, 1456, 1374, 1267, 1250, 1220, 1165, 1134, 695 cm$^{-1}$.
Elemental analysis, Found: C, 74.92; H, 8.05.
MS (EI) m/z 382, 367, 324, 296, 295, 131, 91, 59.
For high resolution, Found: 382.2144.

EXAMPLE 176

10-(Cyclopropylhydroxymethyl)-3-(cyclopropylphenylmethyl)-5, 6,7,8,9, 10-hexahydro-4-hydroxy-2H-cycloocta[b]pyran-2-one
Isolated 0.059 g of the title compound as a white solid.
Physical characteristics are as follows:
MP 107°–115° C. (decomposition).
$^{13}$C NMR (CDCl$_3$) δ 165.5, 165.1, 161.3, 160.7, 141.0, 140.9. 129.3, 128.1, 128.0, 127.6, 127.5, 113.4, 112.5, 106.1, 76.1, 75.6, 46.4, 46.3, 45.6, 44.0, 43.8, 43.7, 31.6, 30.9, 30.8, 30.4, 30.3, 27.6, 27.5, 27.2, 25.5, 23.5, 23.2, 22.7, 17.1, 16.9, 16.8, 14.1, 13.3, 13.2, 5.1, 4.9, 4.8, 4.4, 4.0, 3.9, 3.8, 3.6, 3.5, 2.4, 1.8 ppm.
IR (Nujol) 3252, 3078, 3065, 3024, 3000, 2953, 2925, 2856, 1666, 1637, 1555, 1454, 1402, 1378, 1265, 1242, 1210, 1197, 1137, 1034, 1018, 697 cm$^{-1}$.
MS (EI) m/z 394, 324, 296, 295, 131.
For high resolution, Found: 394.2144.

EXAMPLE 177

3-(Cyclopropylphenylmethyl)-5,6,7,8,9,10-hexahydro4-hydroxy-10-(methoxymethyl)-2H-cycloocta[b]pyran-2-one
Isolated 0.085 g of the title compound as a white solid.
Physical characteristics are as follows:
MP 70°–78° C. (decomposition).
$^1$H NMR (CDCl$_3$) δ 7.50, 7.37, 7.30, 6.25, 4.02, 3.95, 3.92–3.88, 3.52–3.47, 3.39, 3.38, 3.34–3.23, 2.76–2.69, 2.22–2.18, 1.75–1.72, 1.64–1.46, 1.42–1.31, 0.77–0.71, 0.63–0.56, 0.31–0.27 ppm.
$^{13}$C NMR (CDCl$_3$) δ 163.7, 160.0, 140.9, 140.8, 129.1, 128.0, 127.9, 127.8, 127.4, 112.5, 106.4, 72.8, 59.0, 43.8, 43.6, 39.9, 39.8, 32.0, 31.9, 30.1, 30.0, 26.9, 25.3, 22.8, 13.1, 13.0, 5.0, 4.6, 3.9, 3.7 ppm.

IR (Nujol) 3076, 2922, 2855, 1661, 1548, 1460, 1431, 1405, 1209, 1134, 708, 696 cm$^{-1}$.

MS (EI) m/z 368, 340, 327, 295, 271, 131, 91, 45.

For high resolution, Found: 368.1982.

EXAMPLE 178

3-(Cyclopropylphenylmethyl)-5,6,7,8,9,10-hexahydro-4-hydroxy-10-(2-methoxyethyl)-2H-cycloocta[b]pyran-2-one Isolated 0.039 g of the title compound as a white solid.
Physical characteristics are as follows:
MP 78°–80° C.

$^1$H NMR (CDCl$_3$) δ 7.50, 7.38, 7.29, 6.23, 4.03, 3.98, 3.47–3.44, 3.32–3.31, 3.21–3.16, 2.96–2.90, 2.72–2.60, 2.46–2.42, 2.26–2.18, 1.78–1.53, 1.37–1.30, 1.23–1.08, 0.79–0.72, 0.66–0.54, 0.32–0.27 ppm.

IR (Nujol) 3074, 2924, 2855, 1659, 1547, 1495, 1455, 1403, 1377, 1209, 1135, 1123, 1086, 707, 696 cm$^{-1}$.

MS (EI) m/z 382, 337, 43.

For high resolution, Found: 382.2136.

EXAMPLE 179

3-(Cyclopropylphenylmethyl)-5,6,7,8,9,10-hexahydro-4-hydroxy-10-[(tetrahydro-2H-pyran-3-yl)methyl]-2H-cycloocta[b]pyran-2-one Isolated 0.047 g of the title compound as a white solid.
Physical characteristics are as follows:
MP 89°–95° C.

$^1$H NMR (CDCl$_3$) δ 7.54–7.49, 7.41–7.35, 7.31–7.27, 6.27–6.21, 4.05–3.96, 3.88–3.84, 3.38–3.30, 3.13–2.94, 2.79–2.69, 2.16–2.08, 1.95–1.51, 1.43–1.14, 0.78–0.69, 0.65–0.58, 0.33–0.25 ppm.

$^{13}$C NMR (CDCl$_3$) δ 165.4, 163.6, 163.5, 161.4, 161.3, 140.9, 140.8, 140.7, 129.2, 129.1, 128.1, 128.0, 127.9, 127.8, 127.4, 112.4, 112.2, 106.2, 73.3, 73.1, 68.4, 68.3, 43.7, 43.5, 36.1, 36.0, 35.6, 35.5, 34.3, 34.1, 34.0, 33.8, 33.7, 30.4, 30.3, 30.2, 30.0, 37.2, 25.7, 25.5, 23.2, 13.1, 13.0, 5.0, 4.6, 3.8, 3.7 ppm.

IR (Nujol) 3173, 3025, 2924, 2853, 1660, 1550, 1495, 1452, 1402, 1383, 1209, 1134, 1094, 1031, 1017, 967, 707, 696 cm$^{-1}$.

MS (EI) m/z 422, 394, 337, 331, 131, 97, 91.

For high resolution, Found: 422.2456.

EXAMPLE 180

3-(Cyclopropylphenylmethyl)-6,7,8,9-tetrahydro-4-hydroxy-9-[2-(2-methoxyethoxy)ethyl]-cyclohepta[b]pyran-2(5H)-one Isolated 0.025 g of the title compound as a white solid.
Physical characteristics are as follows:

$^1$H NMR (CDCl$_3$) δ 7.51, 7.32, 7.30, 6.24, 3.98, 3.58–3.55, 3.39, 3.02–2.94, 2.50–2.44, 2.29–2.19, 1.88–1.48, 1.37–1.25, 0.78–0.71, 0.68–0.58, 0.32–0.25 ppm.

EXAMPLE 181

3-(Cyclopropylphenylmethyl)-6,7,8,9-tetrahydro-4-hydroxy-9-[2-[2-(2-methoxyethoxy) ethoxy]ethyl]-cyclohepta[b]pyran-2(5H)-one Isolated 0.048 g of the title compound as a colorless gum.
Physical characteristics are as follows:

$^1$H NMR (CDCl$_3$) δ 7.52, 7.38, 7.31, 6.25, 3.96, 3.68–3.53, 3.38, 3.01–2.95, 2.51–2.45, 2.28–2.17, 1.88–1.50, 1.42–1.26, 0.79–0.71, 0.68–0.57, 0.32–0.25 ppm.

EXAMPLE 182

3-(Cyclopropylphenylmethyl)-6,7,8,9-tetrahydro-4-hydroxy-9-(phenylmethyl)-cyclohepta[b]pyran-2(5H)-one Isolated 0.047 g of the title compound as a white solid:
Physical characteristics are as follows:
MP 178°–182° C.

$^1$H NMR (CDCl$_3$) δ 7.52, 7.42–7.19, 6.24. 3.97, 3.25–3.19, 3.12–3.10, 2.83, 2.51–2.48, 1.89–1.86, 1.73–1.43, 1.35–1.30, 0.88–0.78, 0.76–0.74, 0.66–0.59, 0.30–0.28 ppm.

$^{13}$C NMR (CDCl$_3$) δ 165.1, 164.5, 163.8, 140.9, 139.4, 129.2, 129.0. 128.6, 128.5, 128.3, 128.0, 127.9, 127.4, 126.2, 112.8, 105.9, 105.8, 45.5, 43.8, 43.7, 36.3, 29.6, 27.6, 27.4, 27.1, 26.8, 26.0, 20.8, 20.7, 13.0, 5.0, 4.9, 3.8 ppm.

IR (Nujol) 3072, 2924, 2855, 1665, 1641, 1542, 1508, 1496, 1451, 1425, 1203, 1187, 1166, 1134, 750, 702 cm$^{-1}$.

MS (EI) m/z 400, 372, 309, 131, 91.

For high resolution, Found: 400.2037.

EXAMPLE 183

3-(Cyclopropylphenylmethyl)-6,7,8,9-tetrahydro4-hydroxy-9-(2-methylpropyl)-cyclohepta[b]pyran-2(5H)-one Isolated 0.141 g of the title compound as a white solid.
Physical characteristics are as follows:
MP 164°–167° C.

$^1$H NMR (CDCl$_3$) δ 7.52, 7.38, 7.30, 6.19, 2.98, 2.90–2.78, 2.60–2.50, 2.47–2.38, 1.84–1.46, 1.38–1.26, 0.97, 0.90, 0.80–0.71, 0.65–0.58, 0.32–0.26 ppm.

$^{13}$C NMR (CDCl$_3$) δ 166.3, 165.3, 164.1, 141.1, 129.3, 128.0, 127.5, 112.4, 105.8, 43.9, 41.5, 39.3, 28.8, 28.7, 26.7, 26.5, 26.4, 25.5, 23.2, 23.2. 22.1, 20.9, 20.8, 13.1, 5.0, 4.0 ppm.

IR (Nujol) 2955, 2854, 1654, 1541, 1495, 1404, 1378, 1205, 1140, 961, 705 cm$^{-1}$.

MS (EI) m/z 366, 338, 325, 310, 275, 249, 195, 172, 131, 91.

For high resolution, Found: 366.2191.

EXAMPLE 184

3-(Cyclopropylphenylmethyl)-6,7,8,9-tetrahydro4-hydroxy-9-(3-methylbutyl)-cyclohepta[b]pyran-2(5H)-one Isolated 0.056 g of the title compound as a white solid.
Physical characteristics are as follows:
MP 67°–77° C.

$^1$H NMR (CDCl$_3$) δ 7.52, 7.38, 7.30, 6.24, 6.21, 3.98, 2.79–2.73, 2.52–2.43, 1.86–1.50, 1.34–1.18, 0.90, 0.77–0.74, 0.65–0.60, 0.31–0.27 ppm.

$^{13}$C NMR (CDCl$_3$) δ 166.1, 165.3, 164.1, 141.1, 129.3, 128.0, 127.5, 112.3, 105.7, 44.2, 43.9, 36.9, 36.8, 28.6, 28.4, 28.2, 28.1, 26.6, 26.4, 26.3, 22.8, 22.5, 20.8, 13.1, 5.1, 5.0, 4.0 ppm.

IR (Nujol)3060, 2925, 2855, 1655, 1542, 1495, 1462, 1405, 1383, 1231, 1204, 1171, 1140, 1017, 705 cm$^{-1}$.

MS (EI) m/z 380, 352, 289, 131.

For high resolution, Found: 280.2340.

EXAMPLE 185

3-(Cyclopropylphenylmethyl)-9-ethyl-6,7,8,9-tetrahydro-4-hydroxy-cyclohepta[b]pyran-2(5H)-one Isolated 0.089 g of the title compound as a white solid.
Physical characteristics are as follows:
MP 63°–71° C.

$^1$H NMR (CDCl$_3$) δ 7.52, 7.38, 7.31, 6.24–6.21, 3.96, 2.79–2.67, 2.57–2.35, 1.97–1.44, 1.38–1.23, 0.97, 0.80–0.71, 0.65–0.58, 0.32–0.26 ppm.

$^{13}$C NMR (CDCl$_3$) δ 165.9, 165.4, 164.1, 141.1, 129.3, 128.0, 127.5, 112.4, 105.7, 45.6, 43.9, 28.4, 28.3, 26.7, 26.5, 26.4, 23.6, 20.8, 13.1, 12.3, 5.1, 4.0 ppm.

IR (Nujol) 3060, 2924, 2856, 1654, 1540, 1495, 1460, 1404, 1378, 1226, 1205, 1170, 1130, 705 cm$^{-1}$.

MS (EI) m/z 338, 310, 309, 297, 247, 221, 131, 91.

For high resolution, Found: 338.1884.

EXAMPLE 186

3-(Cyclopropylphenylmethyl)-9-[2-(1,3-dioxolan-2-yl)ethyl]-6,7,8,9-tetrahydro-4-hydroxy-cyclohepta[b]pyran-2(5H)-one Isolated 0.042 g of the title compound as a whim solid.
Physical characteristics are as follows:
MP 68°–76 ° C.

$^1$H NMR (CDCl$_3$) δ 7.52, 7.38, 7.30, 6.23–6.19, 4.89, 4.00–3.91, 3.87–3.75, 2.82–2.78, 2.58–2.39, 2.06–1.97, 1.82–1.51, 1.35–1.22, 0.77–0.71, 0.64–0.61, 0.31–0.24 ppm.

$^{13}$C NMR (CDCl$_3$) δ 165.3, 165.2, 164.0, 141.1, 129.3, 128.0, 127.5, 112.6, 105.9, 104.3, 64.9, 43.9, 43.7, 31.9, 28.8, 28.7, 26.6, 26.4, 26.3, 24.8, 20.8, 13.1, 5.1, 4.0 ppm.

IR (Nujol) 3060, 2922, 2855, 1656, 1544, 1495, 1454, 1405, 1378, 1206, 1139, 1033, 962, 945, 776, 705 cm$^{-1}$.

MS (EI) m/z 410, 382, 322, 294, 131, 99, 91, 73.

For high resolution, Found: 410.2089.

EXAMPLE 187

3-(Cyclopropylphenylmethyl)-6,7,8,9-tetrahydro-4-hydroxy-9-[(tetrahydro-2H-pyran-3-yl)methyl]-cyclohepta[b]pyran-2(5H)-one Isolated 0.080 g of the title compound as a white solid.
Physical characteristics are as follows:
MP 82°–90° C.

$^1$H NMR (CDCl$_3$) δ 7.52, 7.38, 7.30, 6.24–6.20, 3.97, 3.90–3.86, 3.42–3.34, 3.15–3.04, 2.89–2.70, 2.56–2.36, 1.96–1.41, 1.39–1.13, 0.80–0.71, 0.65–0.59, 0.32–0.26 ppm.

$^{13}$C NMR (CDCl$_3$) δ 165.3, 165.1, 164.0, 141.0, 129.3, 128.0, 127.6, 112.7, 106.0, 73.6, 73.2, 68.6, 68.5, 43.9, 40.6, 40.5, 33.6, 33.3, 33.2, 30.4, 29.3, 29.2, 28.0, 27.9, 27.1, 26.9, 26.8, 26.3, 25.8, 25.6, 20.9, 14.1, 13.1, 5.1, 4.0 ppm.

IR (Nujol) 3060, 2924, 2854, 1658, 1546, 1495, 1453, 1404, 1378, 1204, 1139. 1094. 1032, 1017, 705 cm$^{-1}$.

MS (EI) m/z 408, 380, 323, 131, 97, 85.

For high resolution, calculated: 408.2300. Found: 408.2304.

EXAMPLE 188

3-(Cyclopropylphenylmethyl)-6,7,8,9-tetrahydro-4-hydroxy-9-propyl-cyclohepta[b]pyran-2(5H)-one Isolated 0.089 g of the title compound as a white solid.
Physical characteristics are as follows:
MP 60°–65 ° C.

$^1$H NMR (CDCl$_3$) δ 7.52, 7.37, 7.30, 6.22, 6.19, 3.97, 2.81–2.72, 2.57–2.50, 2.46–2.36, 1.89–1.39, 1.35–1.29, 0.96–0.92, 0.78–0.71, 0.63–0.58, 0.31–0.26 ppm.

$^{13}$C NMR (CDCl$_3$) δ 166.0, 165.9, 165.3, 164.0, 141.0, 129.2, 127.9, 127.4, 112.3, 105.6, 43.8, 43.6, 32.5, 29.6, 28.6, 28.5, 26.5, 26.3, 20.8, 20.7, 14.0, 13.0, 4.9, 3.9 ppm.

IR (Nujol) 3025, 2927, 2856, 1654, 1542, 1495, 1456, 1403, 1378, 1204, 1131, 1017, 705 cm$^{-1}$.

MS (EI) m/z 352, 324, 131, 91.

For high resolution, Found: 352.2042.

EXAMPLE 189

3-(Cyclopropylphenylmethyl)-6,7,8,9-tetrahydro4-hydroxy-9-[(tetrahydro-2-furanyl)methyl]-cyclohepta[b]pyran-2(5H)-one Isolated 0.068 g of the title compound as a white solid.
Physical characteristics are as follows:
MP 74°–88° C. (decomposition).

$^1$H NMR (CDCl$_3$) δ 7.52–7.50, 7.39–7.35, 7.30–7.28, 6.21, 3.98–3.88, 3.87–3.81, 3.74–3.69, 3.03–3.01, 2.54–2.43, 2.20–2.00, 1.94–1.82, 1.75–1.43, 1.33–1.32, 0.78–0.71, 0.64–0.58, 0.31–0.28 ppm.

IR (Nujol) 3060, 2921, 2856, 1656, 1543, 1495, 1458, 1404, 1378, 1206, 1139, 1074, 1051, 1017, 706 cm$^{-1}$.

Elememal analysis, Found: C, 75.73; H, 7.86.

MS (EI) m/z 394, 366, 323, 131, 91.

For high resolution, Found: 394.2144.

EXAMPLE 190

3-(Cyclopropylphenylmethyl)-6,7,8,9-tetrahydro4-hydroxy-9-[(tetrahydro-2H-pyran-2-yl)methyl]-cyclohepta[b]pyran-2(5H)-one Isolated 0.082 g of the title compound as a white solid.
Physical characteristics are as follows:
MP 76°–86° C. (decomposition).

$^1$H NMR (CDCl$_3$) δ 7.52, 7.39, 7.30, 6.27–6.18, 3.99–3.93, 3.42–3.24, 3.18–3.03, 2.50–2.46, 2.12–1.96, 1.81–1.71, 1.66–1.47, 1.33–1.29, 0.79–0.70, 0.63–0.58, 0.32–0.24 ppm.

$^{13}$C NMR (CDCl$_3$) δ 165.9, 165.3, 164.1, 141.1, 141.0, 129.3, 129.2, 128.2, 128.0, 127.5, 112.5, 105.7, 75.3, 75.2, 68.5, 68.4, 43.9, 43.8, 39.9, 39.8, 39.7, 38.4, 38.3, 37.0, 32.4, 32.3, 30.9, 30.6, 29.0, 28.9, 28.0, 27.6, 27.4, 26.3, 26.1, 23.6, 23.5, 21.1, 21.0, 20.9, 13.2, 13.1, 5.0, 43.0. 4.0, 3.9 ppm.

IR (Nujol) 3060, 2997, 2949, 2923, 2854, 1656, 1629, 1544, 1461, 1454, 1404, 1378, 1233, 1202, 1176, 1139, 1089, 1050, 705 cm$^{-1}$.

MS (EI) m/z 408, 380, 323, 131.

For high resolution, Found: 408.2292.

EXAMPLE 191

3-(Cyclopropylphenylmethyl)-6,7,8,9-tetrahydro-4-hydroxy-9-[(tetrahydro-3-furanyl)methyl]-cyclohepta[b]pyran-2(5H)-one Isolated 0.082 g of the title compound as a white solid.
Physical characteristics are as follows:
MP 80°–84° C. (decomposition).

$^1$H NMR (CDCl$_3$) δ 7.53, 7.41–7.36, 7.30, 3.96, 3.92–3.83, 3.79–3.72, 3.38, 3.32, 2.82–2.77, 2.55–2.46, 2.44–2.38, 2.29–2.23, 2.06–1.98, 1.81–1.46, 1.36–1.26, 0.78–0.71, 0.65–0.58, 0.31–0.26 ppm.

$^{13}$C NMR (CDCl$_3$) δ 165.1, 164.0, 140.9, 129.3, 128.0, 127.6, 112.8, 106.0, 73.4, 73.2, 67.9, 43.9, 42.9, 37.4, 37.3, 34.2, 33.9, 32.8, 32.7, 32.2, 29.5, 29.4, 29.0, 28.9, 26.9, 26.7, 26.5, 26.3, 20.8, 13.1, 5.0, 4.0 ppm.

IR (Nujol) 3075, 3060, 2923, 2856, 1700, 1657, 1545, 1495, 1454, 1403, 1378, 1265, 1205, 1102, 1020, 705 cm$^{-1}$.

MS (EI) m/z 394, 366, 223, 131, 91.

For high resolution, Found: 394.2131.

EXAMPLE 192

3-(Cyclopropylphenylmethyl)-6,7,8,9-tetrahydro-4-hydroxy-9-(2-hydroxypropyl)-cyclohepta[b]pyran-2(5H)-one Isolated 0.151 g of the title compound as a white solid.
Physical characteristics are as follows:
MP 81°–84° C. (decomposition).

$^1$H NMR (CDCl$_3$) δ 7.52–7.50, 7.40–7.35, 7.31–7.28, 3.95, 3.89, 3.16–3.03, 2.51–2.45, 2.09–1.99, 1.83–1.54, 1.29–1.23, 0.77–0.72, 0.62–0.58, 0.32–0.25 ppm.

IR (Nujol) 3281, 2995, 2922, 2854, 1663, 1548, 1495, 1456, 1405, 1377, 1208, 1130, 1017, 705 cm$^{-1}$.

MS (EI) m/z 368, 350, 340, 323, 233, 179, 152, 131, 91.
For high resolution, Found: 368.1996.

EXAMPLE 193

3-(Cyclopropylphenylmethyl)-6,7,8,9-tetrahydro-4-hydroxy-9-(methoxyethyl)-cyclohepta[b]pyran-2(5H)-one Isolated 0.075 g of the title compound as a white solid.
Physical characteristics are as follows:
MP 69°–71° C.
$^1$H NMR (CDCl$_3$) δ 7.54–7.49, 7.41–7.35, 7.32–7.29, 6.25, 3.95, 3.82–3.76, 3.59, 3.40, 3.10–3.07, 2.63–2.55, 2.40–2.32, 1.93–1.84, 1.73–1.53, 1.47–1.42, 1.37–1.30, 0.77–0.71, 0.66–0.57, 0.31–0.26 ppm.
$^{13}$C NMR (CDCl$_3$) δ 165.0, 163.7, 162.9, 140.8, 129.1, 128.0, 127.4, 113.4, 106.0, 71.7, 58.8, 43.8, 43.7, 28.3, 28.1, 26.8, 25.9, 25.8, 21.0, 20.9, 13.0, 4.9, 4.0, 3.9 ppm.
IR (Nujol) 3060, 2924, 2855, 1657, 1544, 1495, 1455, 1406, 1378, 1205, 1138, 1125, 706 cm$^{-1}$.
Elemental analysis, Found: C, 74.72; H, 7.68.
MS (EI) m/z 354, 326, 313, 281, 263, 131, 91, 45.
For high resolution, Found: 354.1832.

EXAMPLE 194

3-(Cyclopropylphenylmethyl)-6,7,8,9-tetrahydro4-hydroxy-9-(2-methoxyethyl)-cyclohepta[b]pyran-2(5H)-one Isolated 0.098 g of the title compound as a white solid.
Physical characteristics are as follows:
MP 58°–60° C.
$^1$H NMR (CDCl$_3$) δ 7.51, 7.38, 7.29, 6.26, 3.96, 3.46, 3.33, 2.99–2.96, 2.50–2.45, 2.23–2.17, 1.87–1.50, 1.34–1.32, 0.77–0.72, 0.64–0.57, 0.31–0.26 ppm.
$^{13}$C NMR (CDCl$_3$) δ 165.1, 140.9, 129.2, 128.0, 127.9, 127.4, 112.7, 105.7, 70.7, 70.6, 58.6, 43.8, 40.4, 30.7, 29.5, 29.4, 27.3, 27.1, 26.1, 20.9, 20.8, 13.0, 4.9, 3.9 ppm.
IR (Nujol) 3076, 3060, 2922, 2856, 1656, 1543, 1495, 1456, 1404, 1378, 1204, 1138, 1119, 1017, 706 cm$^{-1}$.
Elemental analysis, Found: C, 74.77; H, 7.94.
MS (EI) m/z 368, 340, 323, 131, 91, 43.
For high resolution, Found: 368.1993.

EXAMPLE 195

9-(Cyclopropylhydroxymethyl)-3-(cyclopropylphenylmethyl)-6,7,8,9-tetrahydro-4-hydroxy-cyclohepta[b]pyran-2(5H)-one Isolated 0.168 g of the title compound as a white solid.
Physical characteristics are as follows:
MP 88°–90° C.
$^1$H NMR (CDCl$_3$) δ 7.52–7.48, 7.38, 7.30, 6.30, 4.00–3.93, 3.44–3.31, 3.03–2.98, 2.61–2.54, 2.49–2.36, 1.97–1.47, 1.35–1.30, 1.15–1.01, 0.98–0.83, 0.76–0.71, 0.63–0.56, 0.43–0.32, 0.31–0.26 ppm.
IR (Nujol) 3281, 3077, 2925, 2855, 1662, 1548, 1455, 1404, 1378, 1205, 1139, 1032, 1018, 702 cm$^{-1}$.
MS (EI) m/z 380, 310, 131.
For high resolution, Found: 380.1980.

EXAMPLE 196

Carbamic acid, [3-[[3-[cyclopropyl(5,6,7,8,9,10-hexahydro-4-hydroxy-2-oxo-2H-cycloocta[b]pyran-3-yl)methyl]phenyl]amino]-3-oxopropyl]-, 1,1-dimethylethyl ester (Formula N-2 wherein R$_1$ is 2-N-t-BOC-ethylmine) Refer to Chart N.

A 25-mL, two-necked, round-bottomed flask with a nitrogen inlet is charged with the compound of formula N-1, prepared in Example 164 (0.050 g), N-t-BOC-β-alanine (0.028 g), triethylamine (0.030 g), and methylene chloride (1.0 mL). Bis(2-oxo-3-oxazolidinyl)phosphinic chloride (0.0375 g) is added at 0° C., and the solution is stirred at room temperature for 1 h. Water (0.8 mL) and 4N hydrochloric acid (3 drops-until acidic) are added and the mixture is extracted with methylene chloride (30 mL). The organic layer is concentrated to give 0.077 g of solid. Column chromatography on 15 g silica gel yields 0.055 g of the title compound as an off-white solid.

Physical characteristics are as follows:
MP 197°–198.5° C. (decomposition).
$^1$H NMR (CDCl$_3$) δ 8.01, 7.60, 7.55, 7.31, 7.20, 3.90, 3.46, 2.63–2.52, 2.47, 1.73, 1.64–1.56, 1.43, 0.77–0.73, 0.63–0.51, 0.29–0.25 ppm.
$^{13}$C NMR (CDCl$_3$, DMSO) δ 169.0, 163.8, 163.3, 159.4, 154.9, 143.5, 137.4, 127.0, 122.0, 118.1, 116.4, 109.5, 105.4, 77.6, 44.0, 39.0, 35.8, 29.9, 28.3, 27.8, 27.4, 25.2, 24.6, 21.3, 11.6, 5.6, 2.9 ppm.
IR (Nujol) 3445, 3259, 3100, 3086, 2954, 2922, 2868, 2856, 1714, 1679, 1656, 1641, 1614, 1592, 1561, 1452, 1437, 1398, 1377, 1366, 1342, 1254, 1218, 1198, 1182, 1172, 1142, 1054 cm$^{-1}$.
Elemental analysis, Found: C, 67.72; H, 7.54; N, 5.33.
MS (EI) m/z 510, 437, 410, 381, 339, 310, 57.
For high resolution, Found: 510.2731.

EXAMPLES 197–212

Utilizing procedures described in Example 196 above (refer to Chart N), the following additional compounds of the present invention are prepared:

EXAMPLE 197

1H-Indole-1-propanamide, N-[3-[cyclopropyl(5,6,7,8,9,10-hexahydro-4-hydroxy-2-oxo-2H-cycloocta[b]pyran-3-yl)methyl]phenyl]-

Isolated 0.042 g of the title compound as a white solid.
Physical characteristics are as follows:
MP 199°–204° C.
$^1$H NMR (DMSO) δ 10.38, 9.87, 7.52, 7.45, 7.31, 7.17–7.11, 7.00, 6.39, 4.48, 3.10–3.06, 2.80, 2.55–2.80, 1.81, 1.63, 1.55, 1.43–1.38, 0.68, 0.42–0.38, 0.22–0.18, 0.11–0.07 ppm.
$^{13}$C NMR (DMSO) δ 168.7, 163.9, 163.5, 160.3, 144.5, 138.6, 135.6, 128.6, 128.2, 127.9, 127.5, 121.1, 120.5, 119.0, 118.4, 116.7, 110.1, 109.9, 106.0, 100.7, 45.7, 44.6, 37.1, 30.3, 29.2, 28.7, 25.9, 25.4, 21.9, 12.4, 6.6, 3.8 ppm.
IR (Nujol) 3261, 3104, 2953, 2922, 2868, 2855, 2868, 2855, 1682, 1660, 1640, 1616, 1594, 1562, 1464, 1458, 1441, 1402, 1377, 1368, 1261, 1216, 1203, 1184, 744 cm$^{-1}$.
MS (EI) m/z 510, 482, 130.
For high resolution, Found: 510.2516.

EXAMPLE 198

Carbamic acid, [2-[[3-[cyclopropyl(5,6,7,8,9,10-hexahydro-4-hydroxy-2-oxo-2H-cycloocta[b]pyran-3-yl)methyl]phenyl]amino]-1-(S)-methyl-2-oxy ethyl]-, 1,1-dimethylethyl ester Isolated 0.288 g of the title compound as an off-white solid.

Physical characteristics are as follows:
MP 134°–139° C. (decomposition).
$^1$H NMR (CDCl$_3$) δ 8.55, 7.60, 7.49, 7.30–7.17, 5.04, 4.30, 3.88, 2.61, 2.46, 1.73, 1.66–1.47, 1.45, 1.42, 0.72, 0.61–0.50, 0.28–0.23 ppm.
$^{13}$C NMR (CDCl$_3$) δ 170.8, 165.6, 164.1, 161.3, 142.2, 129.7, 129.6, 123.8, 123.7, 119.0, 118.7, 110.7, 106.0, 50.7, 43.8, 30.7, 29.1, 28.8, 28.2, 26.2, 25.8, 25.7, 22.1, 17.2, 12.9, 5.0, 3.8 ppm.

IR (Nujol) 3299, 2953, 2925, 2855, 1669, 1660, 1612, 1593, 1557, 1489, 1455, 1446, 1405, 1393, 1376, 1367, 1249, 1202, 1170, 1070 cm$^{-1}$.

MS (EI) m/z 511, 510, 455, 411, 340.

For high resolution, Found: 511.2831.

EXAMPLE 199

Carbamic acid, [2-[[3-[cyclopropyl(5,6,7,8,9,10-hexahydro-4-hydroxy-2-oxo-2H-cycloocta[b]pyran-3-yl)methyl]phenyl]amino]-1-[[1-(S)-[(4-methylphenyl)sulfonyl]-1H-imidazol-5-yl]methyl]-2-oxoethyl]-, 1,1-dimethylethyl ester Isolated 0.349 g of the title compound as a white foamy solid.

Physical characteristics are as follows:

MP 120°–124° C. (decomposition).

$^1$H NMR (CDCl$_3$) δ 9.85, 8.59, 7.88, 7.51, 7.39, 7.28–7.15, 6.55, 5.92, 4.79, 3.90, 3.43–3.29, 3.02–2.89, 2.59, 2.49–2.40, 2.45, 1.74, 1.61–136, 1.32, 0.74, 0.58–0.51, 0.27 ppm.

$^{13}$C NMR (CDCl$_3$) 15 165.6, 161.4, 161.3, 146.3, 142.3, 138.1, 136.0, 130.5, 130.4, 130.1, 129.6, 127.2, 126.9, 123.8, 119.1, 118.7, 115.0, 114.9, 110.7, 105.9, 43.8, 30.7, 30.5, 29.9, 29.1, 28.9, 28.1, 26.2, 25.7, 22.1, 21.6, 14.1, 13.0, 5.0, 3.8 ppm.

IR (Nujol) 3297, 2953, 2923, 2868, 2854, 1672, 1612, 1595, 1558, 1488, 1467, 1456, 1446, 1401, 1378, 1368, 1342, 1308, 1278, 1249, 1221, 1191, 1174, 1127, 1093, 1082, 1049, 1018, 703, 675, 609 cm$^{-1}$.

MS (EI) m/z 731, 631, 577, 477, 264, 110.

For high resolution, Found: 731.3137.

EXAMPLE 200

Carbamic acid, [2-[[3-[cyclopropyl(5,6,7,8,9,10-hexahydro-4-hydroxy-2-oxo-2H-cycloocta[b]pyran-3-yl)methyl]phenyl]amino]-2-oxyethyl]-, 1,1-dimethylethyl ester Isolated 0.115 g of the title compound as an off-white solid.

Physical characteristics are as follows:

MP 114°–124° C. (decomposition).

$^1$H NMR (CDCl$_3$) δ 8.30, 7.55, 7.49, 7.31–7.21, 5.30, 3.90–3.86, 2.60, 2.46, 1.74, 1.57–1.48, 1.47, 0.75, 0.60–0.51, 0.28 ppm.

$^{13}$C NMR (CDCl$_3$) δ 167.8, 165.7, 164.1, 161.3, 156.2, 142.4, 137.9, 129.6, 123.8, 119.3, 118.7, 110.7, 106.0, 45.4, 43.9, 30.7, 30.2, 29.1, 28.8, 28.2, 26.2, 25.7, 22.1, 12.9, 5.0, 3.8 ppm.

IR (Nujol) 3299, 2953, 2924, 2855, 1670, 1661, 1612, 1594, 1557, 1516, 1489, 1455, 1445, 1405, 1394, 1367, 1279, 1267, 1250, 1231, 1203, 1171 cm$^{-1}$.

MS (EI) m/z 497, 496, 441, 423, 397, 340, 247, 146, 57.

For high resolution, Found: 497.2635.

EXAMPLE 201

Carbamic acid, [4-[[3-[cyclopropyl(5,6,7,8,9,10-hexahydro,-hydroxy-2-oxo-2H-cycloocta[b]pyran-3-yl)methyl]phenyl]amino]-4-oxybutyl]-, 1,1-dimethylethyl ester Isolated 0.192 g of the title product as an off-white solid.

Physical characteristics are as follows:

MP 188°–191° C. (decomposition).

$^1$H NMR (CDCl$_3$) δ 8.87, 7.76, 7.62, 7.30, 7.17, 6.41, 4.79, 3.93, 3.24, 2.61, 2.45–2.36, 1.91–1.82, 1.75–1.71, 1.66–1.47, 1.45, 0.75, 0.62–0.55, 0.30–0.25 ppm.

$^{13}$C NMR (CDCl$_3$) δ 171.2, 165.7, 164.0, 161.2, 157.1, 142.1, 139.0, 129.7, 123.5, 118.8, 118.6, 110.7, 106.0, 79.8, 43.7, 39.2, 34.4, 30.7, 29.1, 28.8, 28.2, 27.1, 26.2, 25.7, 22.0, 13.0, 4.9, 3.8 ppm.

IR (Nujol) 3357, 3002, 2996, 2954, 2922, 2855, 1771, 1663, 1653, 1621, 1594, 1562, 1545, 1454, 1443, 1402, 1390, 1386, 1363, 1332, 1219, 1211, 1198, 1183, 1169, 1159, 1123 cm$^{-1}$.

MS (EI) m/z 525, 524, 425, 340, 247, 86, 57.

For high resolution, Found: 525.2999.

EXAMPLE 202

1-(S)-Pyrrolidinecarboxylic acid, 2-[[[3-[cyclopropyl(5,6,7,8,9,10-hexahydro- 4-hydroxy-2-oxo-2H-cycloocta[b]pyran-3-yl)methyl]phenyl]amino]carbonyl]-, 1,1-dimethylethyl ester Isolated 0.317 g of the title compound as an off-white solid.

Physical characteristics are as follows:

MP 132°–136° C. (decomposition).

$^1$H NMR (CDCl$_3$) δ 7.68–7.49, 7.29, 7.18, 6.38, 4.45, 3.92, 3.45–3.38, 2.78, 2.64–2.42, 1.92, 1.75–1.71, 1.66–1.55, 1.48, 0.73, 0.63–0.54, 0.29–0.24 ppm.

$^{13}$C NMR (CDCl$_3$) δ 164.0, 161.2, 129.8, 123.7, 123.6, 123.5, 118.8, 118.7, 118.6, 118.5, 110.7, 106.1, 105.9, 80.9, 47.1, 43.7, 43.6, 30.6, 29.1, 28.8, 28.3, 26.2, 25.7, 24.4, 22.0, 13.0, 12.9, 4.9, 3.8 ppm.

IR (Nujol) 3286, 2953, 2924, 2868, 2854, 1701, 1667, 1668, 1611, 1593, 1557, 1488, 1479, 1455, 1445, 1437, 1404, 1378, 1368, 1247, 1234, 1201, 1163, 1126 cm$^{-1}$.

MS (EI) m/z 536, 463, 436, 339, 170, 114, 70.

For high resolution, Found: 536.2876.

EXAMPLE 203

Carbamic acid, [2-[[3-[cyclopropyl(5,6,7,8,9,10-hexahydro-4-hydroxy-2-oxo-2H-cycloocta[b]pyran-3-yl)methyl]phenyl]amino]- 1-(R)-methyl-2-oxyethyl]-, 1,1-dimethylethyl ester Isolated 0.058 g of the title compound as a white solid.

Physical characteristics are as follows:

MP 122°–127° C. (decomposition).

$^1$H NMR (CDCl$_3$) δ 8.50, 7.60, 7.49, 7.30–7.17, 5.02, 4.31, 3.88, 2.61, 2.46, 1.73, 1.66–1.47, 1.45, 1.42, 0.72, 0.62–0.53, 0.28–0.25 ppm.

$^{13}$C NMR (CDCl$_3$) δ 170.8, 165.6, 164.1, 161.3, 142.2, 129.7, 129.6, 123.8, 123.7, 119.0, 118.7, 110.7, 106.0, 50.7, 43.8, 30.7, 29.1, 28.8, 28.2, 26.2, 25.8, 25.7, 22.1, 17.2, 12.9, 5.0, 3.8 ppm.

IR (Nujol) 3297, 2954, 2924, 2855, 1671, 1611, 1593, 1557, 1488, 1455, 1446, 1404, 1393, 1375, 1367, 1249, 1202, 1170, 1070 cm$^{-1}$.

MS (EI) m/z 510, 437, 410, 366, 339, 311, 172, 146, 57.

For high resolution, Found: 510.2743.

EXAMPLE 204

Carbamic acid, [2-[[3-[cyclopropyl(5,6,7,8,9,10-hexahydro-4-hydroxy-2-oxo-2H-cycloocta[b]pyran-3-yl)methyl]phenyl]amino ]- 1 -(R)-(1H-imidazol-4-ylmethyl)-2-oxoethyl]-, 1,1-dimethylethyl ester Isolated 0.196 g of the title compound as a white solid.

Physical characteristics am as follows:

MP 175°–179° C. (decomposition).

$^1$H NMR (DMSO) δ 9.90, 7.59, 7.53–7.48, 7.13, 7.05–6.98, 6.81, 4.31, 3.36, 2.94–2.77, 1.85, 1.63, 1.53, 1.36, 1.27, 0.66, 0.40–0.36, 0.18, 0.10 ppm.

$^{13}$C NMR (DMSO) δ 170.4, 159.7, 155.3, 145.3, 138.5, 134.7, 127.8, 122.7, 118.7, 118.6, 116.9, 116.8, 116.7, 116.6, 111.1, 105.1, 78.2, 55.1, 44.6, 30.3, 29.7, 29.3, 28.7, 28.2, 26.0, 25.5, 22.0, 12.7, 6.6, 3.9 ppm.

IR (Nujol) 3260, 3141, 3073, 2925, 2868, 2854, 1679, 1658, 1610, 1592, 1553, 1488, 1457, 1444, 1393, 1368, 1343, 1336, 1322, 1295, 1276, 1251, 1169 cm$^{-1}$.

MS (EI) m/z 577, 576, 477, 110, 57.
For high resolution, Found: 577.3058.

EXAMPLE 205

1-Piperidinepropanamide, N-[3-[cyclopropyl(5,6,7,8,9,10-hexahydro4-hydroxy-2-oxo-2H-cycloocta[b]pyran-3-yl)methyl]phenyl]-

Isolated 0.117 g of the title compound as a white solid.
Physical characteristics are as follows:
MP 157°–162° C. (decomposition).

$^1$H NMR (DMSO) δ 10.12, 7.51, 7.42, 7.11, 7.05, 3.35, 2.81, 2.62–2.53, 1.87, 1.61–1.37, 0.61, 0.38–0.32, 0.14, 0.09 ppm.

$^{13}$C NMR (DMSO) δ 169.1, 164.5, 160.5, 159.3, 151.0, 138.3, 127.5, 122.5, 118.3, 116.1, 112.0, 104.7, 53.5, 53.0, 44.5, 33.0, 30.0, 31.5, 29.1, 28.5, 25.8, 25.4, 24.5, 23.0, 22.0, 14.2, 12.6, 6.3, 3.8 ppm.

IR (Nujol) 2992, 2949, 2923, 2854, 1658, 1610, 1591, 1557, 1488, 1458, 1443, 1428, 1403, 1377, 1366, 1353, 1341, 1337, 1318, 1295, 1279, 1269, 1254, 1225, 1210, 1126 cm$^{-1}$.

MS (EI) m/z 478, 461, 449, 393, 283, 246, 98, 84.
For high resolution, Found: 478.2820.

EXAMPLE 206

Benzamide, 4-chloro-N-[3-[cyclopropyl(5,6,7,8,9,10-hexahydro-4-hydroxy-2-oxo-2H-cycloocta[b]pyran-3-yl)methyl]phenyl]-

Isolated 0.157 g of the title compound as a white solid.
Physical characteristics are as follows:
MP 234.5°–237.5° C. (decomposition).

$^1$H NMR (DMSO) δ 10.38, 10.22, 7.96, 7.73, 7.62, 7.59, 7.21, 7.12, 3.39, 2.55, 1.89–1.82, 1.63, 1.55, 1.45, 1.38, 0.74–0.69, 0.44–0.38, 0.26–0.21, 0.14–0.09 ppm.

$^{13}$C NMR (DMSO) δ 164.2, 163.8, 162.5, 160.1, 144.3, 138.4, 136.1, 133.7, 129.5, 128.3, 127.7, 122.9, 119.6, 117.8, 110.0, 105.8, 44.5, 30.2, 29.0. 28.5, 25.8, 25.2, 21.7, 12.4, 6.4, 3.6 ppm.

IR (Nujol) 3283, 2954, 2924, 2855, 1674, 1640, 1615, 1596, 1587, 1557, 1443, 1435, 1404, 1210, 1196 cm$^{-1}$.

MS (EI) m/z 477, 448, 338, 139, 111.
For high resolution, Found: 477.1712.

EXAMPLE 207

N-[3-[Cyclopropyl(5,6,7,8,9,10-hexahydro-4-hydroxy-2-oxo-2H-cycloocta[b]pyran-3-yl)methyl]phenyl]-benzacetamide Isolated 0.144 g of the title product as a white solid.
Physical characteristics are as follows:
MP 211°–212° C.

$^1$H NMR (CDCl$_3$, CD$_3$OD) δ 7.53, 7.37, 7.30, 7.20, 3.67, 3.43, 2.61, 2.53, 1.75, 1.62, 1.45, 0.71, 0.51, 0.28 ppm.

$^{13}$C NMR (DMSO) δ 169.0, 163.9, 163.4, 160.3, 144.5, 138.8, 136.2, 129.2, 128.3, 128.0, 126.5, 122.5, 118.4, 116.6, 110.2, 106.0, 44.6, 43.4, 30.3, 29.2, 28.7, 26.0, 25.4, 21.9, 12.5, 6.6, 3.8 ppm.

IR (Mineral oil) 3255, 3104, 2954, 2923, 2869, 2854, 1676, 1654, 1618, 1594, 1560, 1455, 1440, 1404, 1216 cm$^{-1}$.

MS (EI) m/z 458, 457, 340, 264, 247, 91.
For high resolution (FAB M+1), Found: 458.2308.

EXAMPLE 208

N-[3-[Cyclopropyl(5,6,7,8,9,10-hexahydro-4-hydroxy-2-oxo-2H-cycloocta[b]pyran-3-yl)methylphenyl]-3-phenyl-2-propenamide Isolated 0.093 g of the title product as a white solid.
Physical characteristics are as follows:
MP 253°–254° C.

$^1$H NMR (CDCl$_3$, CD$_3$OD) δ 7.64, 7.57, 7.49, 7.31, 7.21, 6.60, 3.49, 2.55, 2.46, 1.68, 1.56, 1.40, 0.68, 0.48, 0.25 ppm.

$^{13}$C NMR (DMSO) δ 164.1, 163.4, 160.2, 144.7, 139.9, 138.9, 134.9, 129.8, 129.1. 128.1, 127.7, 122.7, 122.6, 118.5, 116.8, 110.2, 105.9, 44.6, 30.4, 29.2, 28.7, 26.0, 25.5, 21.9, 12.6, 6.6, 3.8, 0.2 ppm.

IR (Mineral oil) 3080, 2952, 2924, 2855, 1680, 1661, 1644, 1629, 1611, 1591, 1560, 1460, 1450, 1441, 1434, 1401, 1368, 1216, 1199 cm$^{-1}$.

MS (EI) m/z 469, 439, 338, 276, 263, 131, 103.
For high resolution, Found: 469.2255.

EXAMPLE 209

N-[3-[Cyclopropyl(5,6,7,8,9,10-hexahydro-4-hydroxy-2-oxo-2H-cycloocta[b]pyran-3-yl)methyl]phenyl]-butanamide Isolated 0.148 g of the title product as a white solid.
Physical characteristics are as follows:
MP 222°–224° C.

$^1$H NMR (CDCl$_3$, CD$_3$OD) δ 7.52, 7.41, 7.22, 3.56, 2.62, 2.52, 2.33, 1.78–1.44, 1.00, 0.73, 0.54, 0.35, 0.27 ppm.

$^{13}$C NMR (DMSO) δ 171.3, 164.7, 163.9, 160.1, 143.7, 138.0, 127.8, 122.5, 118.7. 117.4, 110.1, 106.0, 44.4, 30.4, 28.8, 28.3, 25.8, 25.2, 21.8, 18.5, 13.3, 12.2.5.8, 3.3 ppm.

IR (Mineral oil) 3280, 3252, 3226, 3197, 3152, 3102, 3081, 3042, 3023, 2952, 2922, 2868, 2854, 1677, 1654, 1616, 1595, 1561, 1480, 1458, 1448, 1405, 1377. 1367. 1359, 1218, 1203, 785 cm$^{-1}$.

MS (EI) m/z 409, 380, 362, 339, 310, 216, 203, 146.
For high resolution, Found: 409.2244.

EXAMPLE 210

Benzamide, N-[3-[cyclopropyl(5,6,7,8,9,10-hexahydro4-hydroxy-2-oxo-2H-cycloocta[b]pyran-3-yl)methyl]phenyl]-4-fluoro- Isolated 0.172 g of the title product as a white solid.
Physical characteristics are as follows:
MP 239°–240° C.

$^1$H NMR (CDCl$_3$, CD$_3$OD) δ 7.96, 7.63, 7.55, 7.29, 7.24, 7.19, 7.17, 3.49. 2.63, 2.56, 1.75, 1.64, 1.48, 0.75, 0.53, 0.30 ppm.

$^{13}$C NMR (DMSO) δ 165.7, 164.4, 164.1, 163.4, 160.2, 144.5, 138.6, 131.6, 130.5, 130.4, 127.8, 123.0, 119.8, 118.0, 115.4, 115.2, 110.2, 106.0, 44.7, 30.4, 29.2, 28.8, 26.0, 25.4, 21.9, 12.6, 6.6, 3.8 ppm.

IR (Mineral oil) 3080, 3001, 2954, 2924, 2855, 1675, 1640, 1616, 1603, 1589, 1554, 1508, 1480, 1453, 1445, 1436, 1402, 1378, 1370, 1327, 1263, 1228, 1210, 1193. 1183, 1171, 1162, 1137, 852, 691 cm$^{-1}$.

MS (EI) m/z 461, 433, 432, 268, 233, 220, 207, 123, 95.
For high resolution, Found: 461.2007.

EXAMPLE 211

Benzamide, N-[3-[cyclopropyl(5,6,7,8,9,10-hexahydro-4-hydroxy-2-oxo-2H-cycloocta[b]pyran-3-yl)methyl]phenyl]

Isolated 0.136 g of the title product.
Physical characteristics are as follows:
MP 217° C.

$^{13}$C NMR (DMSO) δ 165.5, 164.2, 163.4, 160.2, 144.5, 138.8, 135.2, 131.5, 128.4, 127.7, 122.9, 119.8, 117.9, 110.3, 106.0, 44.7, 30.4, 29.2, 28.7, 26.0, 25.5, 21.9, 12.6, 6.7, 3–8 ppm.

IR (Mineral oil) 3220, 2997, 2954, 2923, 2854, 1679, 1640, 1614, 1595, 1578, 1551, 1447, 1432, 1404, 1378, 1368, 1219, 1202, 1140, 692 cm$^{-1}$.

MS (EI) m/z 443, 338, 250, 105, 77.

For high resolution, Found: 443.2094.

EXAMPLE 212

1-Naphthalenecarboxamide, N-[3-[cyclopropyl(5,6,7,8,9, 10-hexahydro4-hydroxy-2-oxo-2H-cyclooct[b]pyran-3-yl)methyl ]phenyl]-

Isolated 0.092 g of the title compound as an off-white solid.

Physical characteristics are as follows:

MP 222°–223° C.

$^{13}$C NMR (DMSO) δ 167.3, 164.0, 163.4, 160.3, 144.6, 139.0, 135.1, 133.3, 130.1, 129.8, 128.4, 128.0, 127.0, 126.4, 125.5, 125.3, 125.1, 122.9, 119.2, 117.3, 110.2, 106.1, 44.7, 30.4, 29.3, 28.8, 26.0, 25.5, 22.0, 12.6, 6.7, 3.4 ppm.

IR (Nujol) 3269, 3081, 2954, 2925, 2856, 1675, 1637, 1613, 1586, 1554, 1462, 1446, 1439, 1404, 1371, 1220, 1211, 1202, 781 cm$^{-1}$.

MS (EI) m/z 493, 465, 464, 155, 127.

For high resolution, Found: 493.2255.

EXAMPLE 213

Carbamic acid, [2-[[3-[cyclopropyl(5,6,7,8,9,10-hexahydro-4-hydroxy-2-oxo-2H-cycloocta[b]pyran-3 -yl)methyl]phenyl]amino]- 1 -(S)- (1H-imidazol-4-ylmethyl)-2-oxoethyl]-, 1,1-dimethylethyl ester (Formula O-2) Refer to Chart O.

In a 25-mL, two-necked, round-bottomed flask with a nitrogen inlet, the title product of Example 199 (0.204 g) is dissolved in 5 mL of tetrahydrofuran (THF). Hydroxybenztriazole (0.207 g) is added, and the solution is stirred at room temperature for 16 h. The reaction mixture is concentrated under reduced pressure. Column chromatography on 30 g of silica gives 0.255 of the title compound and HOBT. The mixture is partitioned between chloroform and sat'd. sodium bicarbonate, and the organic layer is concentrated to give 0.221 g of the title compound as a white crystalline solid.

Physical characteristics are as follows:

MP 160°–165° C. (decomposition).

$^{1}$H NMR (DMSO) δ 9.88, 7.58, 7.53–7.48, 7.14, 7.05–6.98, 6.81, 4.31, 3.35, 2.94–2.77, 1.85, 1.63, 1.53, 1.42–1.23, 1.36, 0.67, 0.41–0.37, 0.20, 0.10 ppm.

$^{13}$C NMR (DMSO) δ 170.5, 159.7, 155.3, 145.0, 138.5, 134.7, 127.8, 122.6, 118.7, 118.6, 116.9, 116.8, 116.7, 116.6, 110.8, 105.4, 78.2, 55.1, 44.7, 30.3, 29.7, 29.3, 28.7, 28.2, 26.0, 25.5, 22.0, 12.6, 6.6, 3.9 ppm.

IR (Nujol) 3292, 2996, 2952, 2923, 2868, 2855, 1705, 1661, 1660, 1610, 1592, 1553, 1488, 1459, 1442, 1427, 1393, 1375, 1368, 1342, 1336, 1294, 1280, 1269, 1253, 1231, 1170 cm$^{-1}$.

MS (EI) m/z 653,577, 576, 477, 340, 110, 57.

For high resolution, Found: 577.3042.

EXAMPLES 214 and 215

Utilizing procedures described in Example 196 above and the compound of formula P-1, prepared in Preparation 58 below (refer to Chart P), the following additional compounds of the present invention are prepared:

EXAMPLE 214

Carbamic acid. [3-[[3-[cyclopropyl(2,5,6,7,8,9-hexahydro-4-hydroxy-2-oxocyclohepta[b]pyran-3-yl)methyl] phenyl]amino]-3-oxopropyl]-, 1,1-dimethylethyl ester (Formula P-2 wherein R$_1$ is 7-N-t-BOC-ethylamine) Refer to Chart P.

Isolated 0.033 g of the title compound as a white foamy solid.

Physical characteristics are as follows:

MP 116°–122° C. (decomposition).

$^{1}$H NMR (DMSO) δ 9.83, 7.52, 7.47, 7.13, 7.05, 6.84, 3.22–3.16, 2.59–2.50, 2.44, 1.84, 1.73, 1.59–1.50, 1.37, 1.25, 0.88–0.80, 0.69–0.63, 0.42–0.38, 0.20–0.08 ppm.

$^{13}$C NMR (DMSO) δ 169.3, 163.0, 162.8, 155,6, 144.6, 138.7, 131.6, 127.8, 122.5, 118.4, 116.6, 113.1, 105.6, 77.7, 44.8, 36.8, 36.6, 33.2, 30.9, 28.3, 26.1, 24.2, 22.5, 12.4, 6.4, 4.0 ppm.

IR (Nujol) 3303, 2953, 2919, 2867, 2855, 1666, 1611, 1593, 1552, 1513, 1489, 1456, 1406, 1392, 1376, 1367, 1275, 1251, 1192, 1169, 1138, 1070 cm$^{-1}$.

MS (EI) m/z 519, 497, 496, 397, 326, 146, 57.

For high resolution, Found: 497.2635.

EXAMPLE 215

1H-Indole-1-propanamide, N-[3-[cyclopropyl(2,5,6,7,8,9-hexahydro-4-hydroxy-2-oxocyclohepta[b]pyran-3-yl) methyl]phenyl]- (Formula P-2 wherein R$_1$ is indole) Refer to Chart P.

Isolated 0.018 g of the title compound as a beige solid.

Physical characteristics are as follows:

MP 173°–176° C.

$^{1}$H NMR (CDCl$_3$) δ 7.64, 7.49, 7.39, 7.32–7.09, 6.95, 6.48, 6.28. 4.59, 3.87, 2.83, 2.70, 2.46, 1.78, 1.67, 1.33–1.23, 0.72, 0.65–0.52, 0.23 ppm.

MS (EI) m/z 496, 367, 325, 324, 172, 144, 130.

For high resolution, Found: 496.2369.

EXAMPLE 216

Carbamic acid, [2-[[3-[cyclopropyl(5,6,7,8,9,10-hexahydro4-hydroxy-2-oxo-2H-cycloocta[b]pyran-3-yl) methyl]phenyl](phenylmethyl)amino]-2-oxyethyl]-, 1,1-dimethylethyl ester (Formula Q-2) Refer to Chart Q.

Utilizing procedures described in Example 196 above and the compound of formula Q-1, prepared in Example 242 below, the title compound is prepared.

Isolated 0.021 g of the title compound as a white solid.

Physical characteristics are as follows:

MP 92°–96° C.

$^{1}$H NMR (CDCl$_3$) δ 8.48, 7.33, 7.27, 7.18, 6.87. 5.68. 5.18, 4.71, 4.28–4.14, 3.62, 3.12, 2.59, 2.46, 1.76, 1.65, 1.66–1.48, 1.41, 0.87, 0.55–0.38, 0.00 ppm.

MS (EI) m/z 586, 486, 429, 338, 234, 92, 57.

For high resolution, Found: 586.3044.

PREPARATION 53

Ethyl-(3-aminocarbobenzoxyophenyl)methanol (Formula R-2) Refer: to Chart R.

Following the general procedures of Preparations 49–52, and making non-critical variations, but substituting propiophenone for cyclopropyl phenyl ketone, the title compound is obtained.

Physical characteristics are as follows:

MP 90°–91° C.

$^{1}$H NMR (CDCl$_3$) δ 7.39–7.31, 7.28, 7.27–7.21, 7.02, 6.94, 5.18, 4.52, 2.31, 1.79–1.65, 0.88 ppm.

IR (Nujol) 3423, 3252, 3088, 2959, 2925, 2873, 2856, 1694, 1601, 1565, 1449, 1281, 1258, 1233, 1170, 1059, 1044, 1024, 755, 697 cm$^{-1}$.

Elemental analysis, found: C, 71.58; H, 6.70; N, 4.80.
MS (EI) m/z 241, 212, 91.

EXAMPLE 217

Carbamic Acid, [3-[1-(5,6,7,8,9,10-hexahydro-4-hydroxy-2-oxo-2H-cycloocta[b]pyran-3-yl)propyl]phenyl]-, phenyl methyl ester, (Formula R-3) Refer to Chart R.

Utilizing procedures described in Example 107 above and the compound of formula R-2, prepared in Preparation 53 above, the title compound is prepared.

Isolated 0.772 g of the title compound as a pale yellow foam.

Physical characteristics are as follows:

MP 78°–83° C. (decomposition).

$^1$H NMR (CDCl$_3$) δ 7.38–7.20, 7.12, 6.71, 5.90, 5.20, 4.31, 2.60. 2.43–2.33, 2.15, 2.05, 1.73), 1.70–1.25, 0.98 ppm.

$^{13}$C NMR (CDCl$_3$) δ 165.4, 163.8, 161.3, 142.9, 138.6, 135.8, 130.0, 129.5, 129.4, 128.7, 128.5, 128.3, 128.2, 122.5, 117.6, 117.4, 110.4, 105.9, 67.0, 41.2, 30.6, 29.0, 28.8, 26.1, 25.7, 23.9, 22.0, 12.2 ppm.

IR (Nujol) 3297, 2954, 2924, 2868, 2854, 1734, 1697, 1667; 1668, 1635, 1611, 1596, 1551, 1493, 1461, 1455, 1447, 1426, 1405, 1377, 1338, 1311, 1279, 1221, 1174, 1106, 1085, 1061, 740, 697 cm$^{-1}$.

MS (EI) m/z 461, 417, 370, 194, 91.

For high resolution, Found: 461.2210.

EXAMPLE 218

2H-Cycloocta[b]pyran-2-one, 3-[1-(3-aminophenyl)propyl]-5,6,7,8,9,10-hexahydro-4-hydroxy- (Formula R-4) Refer to Chart R.

In a 100-mL, three-necked, round-bottomed flask with a reflux condenser and nitrogen inlet, 10% palladium on carbon (0.5 g) is added to a mixture of the title compound of Example 217 (0.85 g) in 15 mL of cyclohexene and 15 mL of absolute ethanol, and the mixture is refluxed for 1 h. The mixture is filtered through Celite, washed with ethanol (EtOH), and concentrated to give 0.57 g of the title compound as a white solid.

Physical characteristics are as follows:

MP 70°–77° C. (decomposition).

$^1$H NMR (CDCl$_3$) δ 7.20–7.15, 6.82, 6.71, 6.60, 4.27, 2.60, 2.45–2.33, 2.15–2.05, 2.02–1.90, 1.74, 1.67–1.22, 1.00 ppm.

$^{13}$C NMR (DMSO) δ 164.8, 163.0, 160.5, 145.7, 139.4, 128.9, 119.9, 118.1, 117.6, 110.1, 104.1, 40.9, 30.3, 29.2, 28.7, 25.9, 25.4, 23.3, 21.8, 12.6 ppm.

MS (EI) m/z 327, 312, 298, 284, 270, 134.

For high resolution, Found: 327.1843.

EXAMPLE 219

Carbamic acid, [3-[[3-[1-(5,6,7,8,9,10-hexahydro4-hydroxy-2-oxo-2H-cycloocta[b]pyran-3-yl)propyl]phenyl]amino]-3-oxopropyl]-, 1,1-dimethylethyl ester (Formula R-6) Refer to Chart R.

Utilizing procedures described in Example 196 and the title product of Example 218, the title compound is prepared.

Isolated 0.35 g of the title compound as an off-white solid.

Physical characteristics are as follows:

MP 106°–111° C. (decomposition).

$^1$H NMR (CDCl$_3$) a 8.12, 7.54, 7.30–7.14, 4.28, 3.45, 2.58, 2.45, 2.16–2.05, 1.72, 1.58–1.43, 0.97 ppm.

$^{13}$C NMR (CDCl$_3$) δ 169.9, 165.4, 161.3, 156.4, 143.0, 138.4, 129.7, 129.3, 123.4, 118.9, 118.6, 110.5, 105.8, 41.3, 37.4, 36.4, 30.7, 29.0, 28.8, 28.3, 26.1, 25.7, 23.9, 22.9, 22.0, 12.7 ppm.

IR (Nujol) 3306, 2954, 2925, 2870, 2855, 1673, 1611, 1593, 1555, 1509, 1490, 1461, 1455, 1445, 1404, 1376, 1367, 1280, 1249, 1234, 1197, 1171 cm$^{-1}$.

MS (EI) m/z 498, 425, 398, 381, 369, 327, 298, 57.

For high resolution, Found: 498.2728.

EXAMPLE 220

Propanamide, 3-amino-N-[3-[1-(5,6,7,8,9,10-hexahydro4-hydroxy-2-oxo-2H-cycloocta[b]pyran-3-yl)propyl]phenyl]-, monohydrochloride (Formula R-7) Refer to Chart R.

Methanol is added to a mixture of the title product of Example 219 (0.208 g) and ethereal HCl (5 mL), and the solution is stirred at room temperature for 2 h. The solvent is removed in vacuo to give 0.0184 g of the title compound as an off-white foam.

Physical characteristics are as follows:

MP 125°–130° C. (decomposition).

$^1$H NMR (DMSO) δ 10.49, 10.11, 7.93, 7.47, 7.34–6.98, 4.23–4.12, 3.07–2.99, 2.70, 2.61–2.51, 2.17, 2.00, 1.61, 1.53, 1.43, 1.35, 0.81 ppm.

$^{13}$C NMR (DMSO) δ 168.0, 164.5, 162.9, 160.2, 144.5, 138.3, 127.8, 122.8, 118.6, 116.6, 109.9, 104.3, 51.6, 34.8, 33.0, 30.1, 29.0, 28.5, 25.8, 25.2, 23.1, 21.7, 12.4 ppm.

IR (Nujol) 3235, 3181, 3132, 3050, 2923, 2867, 2855, 2735, 1666, 1631, 1611, 1595, 1552, 1489, 1462, 1445, 1406, 1377, 1260, 1243, 1223, 1200, 1172, 1107 cm$^{-1}$.

EXAMPLE 221

Benzenesulfonamide, 4-chloro-N-[3-[1-(5,6,7,8,9,10-hexahydro-4-hydroxy-2-oxo-2H-cycloocta[b]pyran-3-yl)propyl]phenyl]- (Formula R-5 wherein R$_1$ is Cl) Refer to Chart R.

A 10-mL, one-necked, pear flask with a nitrogen inlet is charged with the compound of formula R-4 of Example 218 (0.050 g), 4-chlorobenzenesulfonyl chloride (0.032 g), and 3 mL of methylene chloride (CH$_2$Cl$_2$). Pyridine (24 mL) is added, and the reaction mixture is stirred at room temperature for 16.5 h. Column chromatography of crude reaction mixture on 25 g of silica gel yields 0.057 g of the title compound as a white solid.

Physical characteristics are as follows:

MP 108°–111° C.

$^1$H NMR (DMSO) δ 10.48, 10.23, 7.70, 7.57, 7.12–7.06, 6.99, 6.81, 4.07–4.01, 2.57–2.54, 2.18–2.05, 1.97–1.88, 1.63–1.54, 1.43–1.36, 0.75 ppm.

$^{13}$C NMR (DMSO) δ 164.7, 162.9, 160.5, 145.3, 138.4, 137.7, 137.0, 129.3, 128.7, 128.5, 123.8, 119.7, 117.9, 110.0, 104.2, 41.0, 30.6, 29.2, 28.8, 25.9, 25.4, 23.2, 21.8, 12.5 ppm.

IR (Nujol) 3256, 2954, 2924, 2869, 2854, 1661, 1634, 1559, 1478, 1462, 1407, 1335, 1188, 1167, 1158, 1085, 760 cm$^{-1}$.

MS (EI) m/z 501, 486, 472, 444, 326, 307, 284, 153.

For high resolution, Found: 501.1377.

EXAMPLE 222

Benzenesulfonamide, 4-cyano-N-[3-[1-(5,6,7,8,9,10-hexahydro-4-hydroxy-2-oxo-2H-cycloocta[b]pyran-3-yl)propyl]phenyl]- (Formula R-5 wherein R$_1$ is CN) Refer to Chart R.

Utilizing procedures described in Example 221 above, the title compound is prepared.

Isolated 0.050 g of the title compound as a white solid.

Physical characteristics are as follows:

MP 108°–111° C.

$^1$H NMR (DMSO) δ 10.46, 10.39, 7.98, 7.84, 7.13–7.08, 7.01, 6.83, 4.05–4.00, 2.56–2.54, 2.11–2.07, 1.99–1.86, 1.63–1.53, 1.43–1.28, 0.74 ppm.

$^{13}$C NMR (DMSO) δ 164.7, 162.9, 160.5, 145.4, 143.6, 136.5, 133.4, 128.6, 127.5, 124.2, 120.1, 118.3, 117.7, 115.3, 110.0, 104.1, 40.9, 30.4, 29.2, 28.8, 25.9, 25.5, 23.2, 22.2, 21.8, 12.5 ppm.

IR (Nujol) 2954, 2924, 2869, 2855, 1667, 1558, 1464, 1405, 1198, 1182, 1167, 1091 cm$^{-1}$.

MS (EI) m/z 492, 477, 463, 435, 326, 166, 153, 102.

For high resolution, Found: 492.1719.

EXAMPLE 223

N-[3-[Cyclopropyl(5,6,7,8,9,10-hexahydro-4-hydroxy-2-oxo-2H-cycloocta[b]pyran-3-yl)methyl]phenyl]-N'-ethyl-urea (Formula S-2 wherein R$_1$ is ethyl) Refer to Chart S.

In a flame-dried 10-mL two-necked flask under nitrogen, ethyl isocyanate (0.021 g) is added dropwise to the compound of formula S-1, prepared in Example 164 above, (0.100 g) in 1 mL CH$_3$CN. The reaction mixture is stirred at room temperature for 24 hrs, and then solid is collected by filtration to yield 0.075 g of the title compound.

Physical characteristics are as follows:

MP 215° C. (decompose).

$^1$H NMR (CDCl$_3$, CD$_3$OD) δ 7.40, 7.18, 7.10, 3.48, 3.23, 2.62, 2.53, 1.74, 1.63, 1.47, 1.15, 0.72, 0.52, 0.29) ppm.

$^{13}$C NMR (DMSO) δ 163.9, 163.4, 160.2, 155.2, 144.3, 140.1, 128.0, 120.3, 116.9, 115.2, 110.1, 106.1, 44.7, 34.0, 30.3, 29.2, 28.7, 26.0, 25.4, 21.9, 15.6, 12.6, 6.6, 3.8 ppm.

IR (Nujol) 2954, 2924, 2868, 2853, 1682, 1660, 1631, 1595, 1562, 1535, 1461, 1453, 1448, 1408, 1252, 1220, 1202, 692 cm$^{-1}$.

MS (EI) m/z 365, 337, 336, 324, 233, 207, 172.

For high resolution (FAB), Found: 411.2293.

EXAMPLE 224

N-[3-[Cyclopropyl(5,6,7,8,9,10-hexahydro-4-hydroxy-2-oxo-2H-cycloocta[b]pyran-3-yl)methyl]phenyl]-N'-phenyl-urea (Formula S-2 wherein R$_1$ is phenyl) Refer to Chart S.

Utilizing procedures described in Example 223 above, the title compound is prepared.

Isolated 0.197 g of the title compound as a white solid.

Physical characteristics are as follows:

MP 214°–215° C.

$^1$H NMR (CDCl$_3$, CD$_3$OD) δ 7.43, 7.31–7.13, 7.03, 3.47, 2.62, 2.55, 1.75, 1.64, 1.48, 0.73, 0.52, 0.29 ppm.

$^{13}$C NMR (DMSO) δ 163.9, 163.3, 160.2, 152.5, 144.6, 139.8, 139.3, 128.8, 128.1, 121.8, 121.2, 118.1, 117.4, 115.6, 110.1, 106.0, 44.7, 30.3, 29.2, 28.7, 26.0, 25.5, 22.0, 12.6, 6.6, 3.8 ppm.

IR (Mineral oil) 3360, 2953, 2924, 2855, 1660, 1630, 1596, 1562, 1548, 1446, 1409, 1237, 1220, 1199, 694 cm$^{-1}$.

MS (EI) m/z 459, 458, 366, 340, 265, 247, 94.

EXAMPLE 225

[3-[Cyclopropyl(5,6,7,8,9,10-hexahydro-4-hydroxy-2-oxo-2H-cycloocta[b]pyran-3-yl)methyl]phenyl]-, phenyl ester carbamic acid (Formula T-2 wherein R$_1$ is phenyl) Refer to Chart T.

In a flame-dried 10-mL two-necked flask under nitrogen at 0° C., phenyl chloroformate (0.092 g) is added dropwise to the compound of formula T-1, prepared in Example 164 above, (0.200 g) in 2.3 mL pyridine. The reaction mixture is stirred at 0° C. for 3.5 hrs, warmed to room temperature and concentrated. The residue is taken up in 5 mL toluene and concentrated 3 times. Column chromatography on 25 g of silica gel yields 0.161 g of the title compound as a white solid.

Physical characteristics are as follows:

MP 208°–209° C. (decomposition).

$^1$H NMR (CDCl$_3$) δ 7.58, 7.43–7.30, 7.28, 6.54, 3.93, 2.60, 2.44, 1.73, 1.58–1.41, 0.78–0.69, 0.64–0.52, 0.31–0.24 ppm.

$^{13}$C NMR (CDCl$_3$) δ 165.6, 164.1, 161.3, 151.5, 150.4, 142.4, 138.0, 129.8, 129.3, 125.6, 123.3, 121.5, 118.1, 117.5, 110.7, 105.9, 43.8, 30.6, 29.1, 28.7, 26.1, 25.7, 22.1, 13.0, 5.0, 3.8 ppm.

IR (Mineral oil) 3325, 2951, 2925, 2868, 2854, 1742, 1668, 1654, 1614, 1596, 1559, 1538, 1492, 1464, 1456, 1439, 1293, 1248, 1228, 1202, 1166, 691 cm$^{-1}$.

MS (EI) m/z 459, 365, 337, 233, 220, 207, 94.

For high resolution, Found: 459.2051.

EXAMPLE 226

[3-[Cyclopropyl(5,6,7,8,9,10-hexahydro4-hydroxy-2-oxo-2H-cycloocta[b]pyran-3-yl)methyl]phenyl]-, ethyl ester carbamic acid (Formula T-2 wherein R$_1$ is ethyl) Refer to Chart T.

Utilizing procedures described in Example 225 above, the title compound is prepared.

Isolated 0.186 g of the title compound as a white sample.

Physical characteristics are as follows:

MP 162° C.

$^1$H NMR (CDCl$_3$) δ 7.48, 7.38, 7.28, 7.15, 6.71, 6.50, 4.21,–3.91, 2.61, 2.44, 1.73, 1.57–1.35, 1.30, 0.74, 0.58, 0.27 ppm.

$^{13}$C NMR (CDCl$_3$) δ 165.6, 164.1, 161.2, 153.4, 142.3, 138.6, 129.7, 122.7, 117.9, 117.4, 110.7, 106.0, 61.1, 43.8, 30.6, 29.1, 28.8, 26.1, 25.7, 22.0, 14.4, 13.0, 4.9, 3.8 ppm.

IR (Mineral oil) 3293, 3258, 3219, 3207, 3146, 3099, 3081, 2995, 2954, 2923, 2855, 1679, 1647, 1614, 1598, 1558, 1482, 1464, 1447, 1440, 1405, 1378, 1368, 1359, 1303, 1251, 1214, 1199, 1187, 1172, 1071 cm$^{-1}$.

MS (EI) m/z 411, 383, 370, 336, 259, 233, 207, 205, 172, 144.

For high resolution, Found: 411.2056.

EXAMPLE 227

2H-Cycloocta[b]pyran-2-one,5,6,7,8,9,10-hexahydro-4-hydroxy-3-(2-methyl-1-phenylpropyl)- (Formula U-3 wherein R$_1$ is isopropyl) Refer to Chart U.

Utilizing procedures described in Example 107 above and the title compound of Preparation 54 below, the title compound is prepared.

Isolated 0.493 g of the title compound as a white solid.

Physical characteristics are as follows:

MP 214°–216° C.

$^1$H NMR (CDCl$_3$) δ 7.46, 7.32, 7.23, 6.02, 3.94, 2.86–2.79, 2.58, 2.47–2.40, 1.73–1.71, 1.59–1.54, 1.48–1.46, 1.41–1.39, 0.98, 0.97 ppm.

$^{13}$C NMR (CDCl$_3$) δ 165.3, 163.5, 161.3, 142.2, 129.0, 128.2, 126.8, 110.0, 106.4, 48.5, 30.8, 29.2, 28.9, 28.3, 26.3, 25.8, 22.2, 22.1, 21.0 ppm.

IR (Nujol)2955, 2925, 2867, 2855, 1658, 1632, 1621, 1541, 1454, 1409, 1211, 1185, 1169 cm$^{-1}$.

PREPARATION 54

2-Methyl-1-phenyl-1-propanol (Formula U-2 wherein R$_1$ is isopropyl) Refer to Chart U.

A 500-mL, three-necked, round-bottomed flask with a nitrogen inlet is charged with isobutyrophenone (7.5 mL)

and 90 mL of ethanol. Sodium borohydride (7.6 g) is added in three portions, and the resulting mixture is stirred for 5 days at 25° C. The reaction mixture is then cooled in an ice bath, and 100 mL of 10% hydrochloric acid (HCl) is added dropwise over 1 hour. After stirring for an additional hour, the reaction mixture is exacted with three 100-mL portions of methylene chloride ($CH_2Cl_2$). The organic layers are combined, dried over magnesium sulfate ($MgSO_4$), filtered and concentrated to give 6.768 g of colorless oil. Column chromatography on 100 g silicia gel yields 6.601 g of the title compound as a colorless liquid.

$^1$H NMR ($CDCl_3$) δ 7.35–7.24, 4.32, 1.98, 1.97–1.91, 0.98, 0.78 ppm.

$^{13}$C NMR ($CDCl_3$) δ 143.51, 128.0, 127.2, 126.4, 79.9, 35.1, 18.8, 18.1 ppm.

IR (neat) 3404, 2960, 2931, 2908, 2894, 2872, 1469, 1453, 1034, 1022, 760, 750, 740, 701 $cm^{-1}$.

MS (EI) m/z 150, 107, 79, 77.

EXAMPLE 228

(+)-(R)-3-(Cyclopropylphenylmethyl)-5,6,7,8,9,10-hexahydro-4-hydroxy-2H-cyclo [b]pyran-2-one The title compound of Example 107 is separated by HPLC, as described in Example 247, using a 2.0×25 cm Chiralcel OD as the stationary phase and 4% ethanol and 0.1% acetic acid in hexane as the mobile phase (16 mL/min).

Physical characteristics are as follows:
The retention time of the title compound was 24.1 min.
Elemental analysis, Found: C, 77.34; H, 7.80.

EXAMPLE 229

(−)-(S)-3-(Cyclopropylphenylmethyl)-5,6,7,8,9,10-hexahydro-4-hydroxy-2H-cyclo[b]pyran-2-one The title compound of Example 107 is separated as described in Example 228 above.

Physical characteristics are as follows:
The retention time of the title compound was 33.6 min.
Elemental analysis, Found: C, 77.74; H, 7.62.

EXAMPLE 230

(R or S)-3-(Cyclopropylphenylmethyl)-6,7,8,9-tetrahydro-4-hydroxy-cyclohepta[b]pyran-2(5H)-one The title compound of Example 112 is separated by HPLC, as described in Example 247, using a 2.0×25 cm Chiralcel OD as the stationary phase and 4.5% ethanol and 0.2% acetic acid in hexane as the mobile phase (16 mL/min).

Physical characteristics are as follows:
The retention time of the title compound was 20.5 min.

EXAMPLE 231

(R or S)-3-(Cyclopropylphenylmethyl)-6,7,8,9-tetrahydro-4-hydroxy-cyclohepta[b]pyran-2(5H)-one The title compound of Example 112 is separated as described in Example 230 above.

Physical characteristics are as follows:
The retention time of the title compound was 27.4 min.

EXAMPLE 232

3-(R)-(Cyclopropylphenylmethyl)-4-hydroxy-10-(R and S)-propyl-5,6,7,8,9,10-hexahydro-cycloocta[b]pyran-2-one Following the general procedure of Example 121, and making non-critical variations, but substituting the title compound of Example 228 (0.268 g) for 3-(cyclopropylphenylmethyl)-5,6,7,8,9,10-hexahydro-4-hydroxy-2H-cycloocta[b]pyran-2-one, 0.085 g of the title compound is obtained as a white solid.

Physical characteristics are as follows:
$^1$H NMR ($CDCl_3$) δ 7.51, 7.37, 7.29, 6.18, 6.16, 4.05, 3.99, 2.93–2.90, 2.76–2.65, 2.18–2.10, 2.01–1.94, 1.78–1.61, 1.54–1.41, 1.37–1.27, 1.22–1.13, 0.97–0.83, 0.77–0.73, 0.63–0.58, 0.29–0.26 ppm.

MS (EI) m/z 366, 338, 325, 275, 131, 91.
For high resolution, found: 366.2200.

EXAMPLE 233

3-(R)-(Cyclopropylphenylmethyl)4-hydroxy-10-(R or S)-propyl-5,6,7,8,9,10-hexahydro-cycloocta[b]pyran-2-one The title compound of Example 232 is separated by HPLC, as described in Example 247, using a 2.0×25 cm Chiralcel OD as the stationary phase and 1.5% ethanol and 0.2% acetic acid in hexane as the mobile phase (16 mL/min).

Physical characteristics are as follows:
The retention time of the title compound was 16.4 min.

EXAMPLE 234

3-(R)-(Cyclopropylphenylmethyl)4-hydroxy-10-(R or S)-propyl-5,6,7,8,9,10-hexahydro-cycloocta[b]pyran-2-one The title compound of Example 232 is separated as described in Example 233 above.

Physical characteristics are as follows:
The retention time of the title compound was 18.4 min.

EXAMPLE 235

3-(S)-(Cyclopropylphenylmethyl)-4-hydroxy-10-(R and S)-propyl-5,6,7,8,9,10-hexahydro-cycloocta[b]pyran-2-one Following the general procedure of Example 121, and making non-critical variations but substituting the title compound of Example 229 (0.230 g) for 3-(cyclopropylphenylmethyl)-5,6,7,8,9,10-hexahydro4-hydroxy-2H-cycloocta[b]pyran-2-one, 0.081 g of the title compound is obtained as a white solid.

Physical characteristics are as follows:
$^1$H NMR ($CDCl_3$) δ 7.53–7.50, 7.37, 7.29, 6.18, 6.16, 4.05, 3.99, 2.96–2.93, 2.79–2.73, 2.18–2.10, 2.01–1.94, 1.78–1.61, 1.43–1.22, 1.19–1.28, 0.97–0.86, 0.78–0.69, 0.63–0.58, 0.52–0.50, 0.29–0.15 ppm.

MS (EI) m/z 366, 338, 325, 275, 131, 91.
For high resolution, found: 366.2200.

EXAMPLE 236

3-(S)-(Cyclopropylphenylmethyl)-4-hydroxy- 10-(R or S)-propyl-5,6,7,8,9,10-hexahydro-cycloocta[b]pyran-2-one The title compound of Example 235 is separated by HPLC, as described in Example 247, using a 2.0×25 cm Chiralcel OD as the stationary phase and 4.5% ethanol and 0.2% acetic acid in hexane as the mobile phase (16 mL/min).

Physical characteristics are as follows:
The retention time of the title compound was 14.7 min.

EXAMPLE 237

3-(S)-(Cyclopropylphenylmethyl)-4-hydroxy-10-(R or S)-propyl-5,6,7,8,9,10-hexahydro-cycloocta[b]pyran-2-one The title compound of Example 235 is separated as described above in Example 236.

Physical characteristics are as follows:
The retention time of the title compound was 20.9 min.

EXAMPLE 238

Carbamic acid, [2-[[3-(R or S)-[cyclopropyl(5,6,7,8,9,10-hexahydro-4-hydroxy-2-oxo-2H-cycloocta[b]pyran-3-yl) methyl]phenyl]amino]-2-oxoethyl]-, 1,1-dimethyl ethyl ester, The title compound of Example 200 is separated by HPLC, as described in Example 247, using a 1.0×25 cm Whelk-O I as the stationary phase and 15% ethanol and 0.1% acetic acid in hexane as the mobile phase (5 mL/min).
Physical characteristics are as follows:
The retention time of the title compound was 15.0 min.

EXAMPLE 239

Carbamic acid, [2-[[3-(R or S)-[cyclopropyl(5,6,7,8,9,10)-hexahydro-4-hydroxy-2-oxo-2H-cycloocta[b]pyran-3-yl) methyl]phenyl]amino]-2-oxoethyl]-, 1,1-dimethyl ethyl ester The title compound of Example 200 is separated as described above in Example 238.
Physical characteristics are as follows:
The retention time of the title compound was 19.6 min.

EXAMPLE 240

Carbamic acid, [2-[[3-(R or S)-[cyclopropyl(5,6,7,8,9,10-hexahydro-4-hydroxy-2-oxo-2H-cycloocta[b]pyran-3-yl) methyl]phenyl]amino]-1-(S)-(1H-imidazol-4-ylmethyl)-2-oxoethyl]-, 1,1 dimethyl ethyl ester The title compound of Example 213 is separated by HPLC, as described in Example 247, using a 2.0×25 cm Chiralpak AD as the stationary phase and 8% ethanol and 0.1% acetic acid in hexane as the mobile phase (12 mL/min).
Physical characteristics are as follows:
The retention time of the title compound was 125 min.

EXAMPLE 241

Carbamic acid, [2-[[3-(R or S)-[Cyclopropyl(5,6,7,8,9,10-hexahydro-4-hydroxy-2-oxo-2H-cycloocta[b]pyran-3-yl) methyl]phenyl]amino]-1-(S)-(1H-imidazol-4-ylmethyl)-2-oxoethyl]-, 1,1 dimethyl ethyl ester The title compound of Example 213 is separated as described above in Example 240.
Physical characteristics are as follows:
The retention time of the title compound was 152 min.

EXAMPLE 242

3-[Cyclopropyl-[3-[(phenylmethyl)amino]phenyl]methyl]-5,6,7,8,9,10-hexahydro-4-hydroxy-2H-cycloocta[b] pyran-2-one (Formula BB-2 wherein $R_{62}$ is benzyl) Refer to Chart BB.

A solution of the title product of Example 164 of formula II-1 (100 mg) and benzaldehyde in ethanol (6 mL) is refluxed for 30 min, cooled, and concentrated in vacuo. The resulting oil is dissolved in methanol (6 mL) and treated with sodium cyanoborohydride (15 mg) and stirred at room temperature for 18 h. The reaction is quenched with water, diluted with ethyl acetate, and the organic layer washed with water and brine, dried (anhydrous sodium sulfate), filtered, and concentrated in vacuo. The crude product is chromatographed on silica gel to give 93 mg of the title compound as a white amorphous solid.
Physical characteristics are as follows:
$^1$H NMR (CDCl$_3$) δ 7.1–7.4, 6.88, 6.75, 6.6, 6.37, 4.3, 3.9, 2.6, 2.4, 1.7, 1.2–1.8, 0.6, 0.2 ppm.

$^{13}$C NMR (CDCl$_3$) δ 166, 164.2, 160.9, 142.4, 138.8, 130.1, 128.5, 127.3, 127.1, 116.2, 112.0, 111.9, 110.8, 106.2, 48.0, 43.6, 30.54, 29.1, 28.7, 26.1, 25.7, 21.9, 12.8, 4.6, 3.7 ppm.
MS(EI):429, 338, 303, 277, 236, 222, 209, 144, 132, 91.
HERMS: 429.2309.
TLC(silica gel GF): $R_f$=0.24 40% ethyl acetate in hexane.

EXAMPLE 243

3-[Cyclopropyl-[3-[(2-phenylethyl)amino]phenyl]methyl]-5,6,7,8,9, 10-hexahydro-4-hydroxy-2H-cycloocta[b] pyran-2-one (Formula BB-2 wherein $R_{62}$ is phenylethyl) Refer to Chart BB.

Utilizing procedures analogous to those described above in Example 242, the title compound is prepared from the title compound of Example 164 and phenylacetaldehyde.
Physical characteristics are as follows:
white amorphous solid
$^1$H NMR (CDCl$_3$) δ 57.1–7.4, 6.9, 6.7, 6.5, 6.4, 3.9, 3.4, 2.9, 2.6, 2.4, 1.2–1.7, 0.6, 0.25 ppm.
MS(EI):443, 352, 200, 158, 143, 130, 117, 105, 91, 55.
HRMS: 443.2460.
TLC(silica gel GF): $R_f$=0.24 40% ethyl acetate in hexane.

EXAMPLE 244

N-[3-[Cyclopropyl(5,6,7,8,9, 10-hexahydro-4-hydroxy-2-oxo-2H-cycloocta[b]pyran-3-yl)methyl]phenyl]-N-(phenylmethyl)-benzenesulfonamide (Formula BB-3 wherein $R_{61}$ is phenyl and $R_{62}$ is benzyl) Refer to Chart BB.

A solution of the title product of Example 242 (30 mg), benzenesulfonyl chloride (9 µL), and pyridine (20 µL) in dichloromethane (2 mL) is stirred at room temperature for 18 h. The solution is then diluted with ethyl acetate, washed with water and brine, dried (anhydrous sodium sulfate), filtered, concentrated in vacuo, and chromatographed on silica gel to give 32 mg of the title compound as a white amorphous solid.
Physical characteristics are as follows:
$^1$H NMR (CDCl$_3$) δ 7.6, 7.5, 7.2–7.3, 7.0, 6.9, 6.2, 4.7, 3.8, 2.6, 2.4, 1.7, 1.1–1.8, 1.1, 0.5, 0.4, 0.04 ppm.
$^{13}$C NMR (CDCl$_3$) δ 166, 164, 160, 142, 139, 138, 135, 132, 129. 128.8, 128.5, 128.3, 127.9, 127.5, 111, 106, 55, 43, 30.5, 29.0. 28.7, 26.1, 25.7, 21.9, 12.8, 4.6, 3.7 ppm.
MS(EI):569, 541, 428, 302, 276, 234, 207, 91, 44.
HRMS: 569.2227.
TLC(silica gel GF): $R_f$=0.38 40% ethyl acetate in hexane.

EXAMPLE 245

N-[3-[Cyclopropyl(5,6,7,8,9, 10-hexahydro-4-hydroxy-2-oxo-2H-cycloocta[b]pyran-3-yl)methyl]phenyl]-N-(phenylmethyl)-methanesulfonamide (Formula BB-3 wherein $R_{61}$ is methyl and $R_{62}$ is benzyl) Refer to CHART BB.

Utilizing procedures analogous to those described above and beginning with the title compound of Example 243 and methanesulfonyl chloride the title compound is prepared.
Physical characteristics are as follows:
white amorphous solid
MS(EI): 507, 479, 428, 302, 276, 233, 220, 207, 91.
HRMS: 507.2070
TLC(silica gel GF): $R_f$=0.10 40% ethyl acetate in hexane.

EXAMPLE 246

N-[3-[cyclopropyl(5,6,7,8,9,10-hexahydro-4-hydroxy-2-oxo-2H-cycloocta[b]pyran-3-yl)methyl]phenyl]-N-(2- phenylethyl)-benzenesulfonamide (Formula BB-3 wherein $R_{61}$ is phenylethyl and $R_{62}$ is phenyl) Refer to Chart BB.

Utilizing procedures analogous to those described above beginning with the title compound of Example 243 and benzenesulfonyl chloride the title compound is prepared.

Physical characteristics are as follows:
white amorphous solid,
MS(EI):583, 492, 442, 351, 322, 158, 143, 91, 77.
HRMS: 583.2398.
TLC(silica gel GF): $R_f$=0.22 40% ethyl acetate in hexane.

EXAMPLE 247

(−)-3[(3-aminophenyl)cyclopropylmethyl]-5,6,7,8,9,10-hexahydro-4-hydroxy-2H-cycloocta[b]pyran-2-one (Formula AA-2); and (+)-3[(3'-aminophenyl)cyclopropylmethyl]-5,6,7,8,9,10-hexahydro-4-hydroxy-2H -cycloocta[b]pyran-2-one (Formula AA-5) Refer to Chart AA.

A stock solution of the title compound of Example 119 (9 mg/mL) in 35% isopropanol in hexane is chromatographed on a 1.0×25 cm (R,R) Whelk-O 1 (Regis Technologies, Inc., Morton Grove, Ill. 60053) column at 5 mL per injection using an automated chromatographic system. The eluant is monitored at 310 nm and appropriate fractions from multiple injections combined and concentrated in vacuo to give snowy white solids. Fractions from multiple injections are analyzed on a 0.46×25 cm (R,R) Whelk-O 1 column with the same solvent at 1.0 mL/min. The first peak from the 1.0 cm column is ($R_t$ 15.1 min, k=3.03 on the 0.46 cm column, [α]=+49° (c=3.6 g/mL methanol), >95% pure) and the latter peak is ($R_t$ 26.5 min, k=5.64, α=1.86 on the 0.46 cm column, [α]=49° (c=3.1 g/mL methanol), >95% pure).

EXAMPLE 248

(−)-3-[Cyclopropyl-[3-amino]phenyl]methyl]-5,6,7,8,9,10-hexahydro-4-hydroxy-2H-cycloocta[b]pyran-2-one (Formula AA-3) Refer to Chart AA.

A mixture of the first title compound ([α]=49°) of Example 247 (650 mg) and 10% palladium on carbon (350 mg) in cyclohexene (25 mL) is heated at 100° C. for 4 hr. cooled, diluted with ethyl acetate (50 mL), filtered through celite, washing the filter cake with ethyl acetate. The combined filtrates are concentrated in vacuo and chromatographed on silica gel to give 366 mg of the title compound as a white amorporous solid.

Physical characteristics are as follows:
$^1$H NMR (CDCl$_3$) δ 7.2, 7.0, 6.8, 6.6, 3.8, 2.6, 2.4, 1.8, 1.2–1.6, 0.7, 0.6, 0.3 ppm.
TLC (silica gel GF): $R_f$=0.16 40% ethyl acetate in hexane. [α]=−65° (c=0.0016 g/mL methanol), >95% pure.

EXAMPLE 249

(+)-3-[Cyclopropyl-[3-amino]-5,6,7,8,9,10-hexahydro-4-hydroxy-2H-cycloocta[b]pyran-2-one (Formula AA-6) Refer to Chart AA.

A mixture of the second title compound ([α]=+49°) of Example 247 (800 mg) and 10% palladium on carbon (400 mg) in cyclohexene (25 mL) is heated at 100° C. for 4 hr, cooled, diluted with ethyl acetate (50 mL), filtered through celite, washing the filter cake with ethyl acetate. The combined filtrates are concentrated in vacuo and chromatographed on silica gel to give 460 mg of the title compound as a white amorphorous solid.

Physical characteristics are as follows:
$^1$H NMR (CDCl$_3$)δ7.2, 7.0, 6.8, 6.6, 3.8, 2.6, 2.4, 1.8, 1.2–1.6, 0.7, 0.6, 0.3 ppm.

TLC (silica gel GF): $R_f$=0.16 40% ethyl acetate in hexane. [α]=+67° (c=0.0016 g/mL methanol), >95% pure.

EXAMPLE 250

(−)-4-Chloro-N-[3-[cyclopropyl(5,6,7,8,9,10-hexahydro-4-hydroxy-2-oxo-2H-cycloocta[b]pyran-3-yl)methyl]phenyl]-benzenesulfonamide (Formula AA-4 wherein $R_{60}$ is 4-chlorophenyl) Refer to Chart AA.

A solution of the title compound of Example 248 (50 mg), pyridine (25 µL), and 4-chlorobenzenesulfonyl chloride (33 mg) in dichloromethane 3 mL) is stirred at room temperature for 18 h. The crude reaction mixture is chromatographed on silica gel to give 53 mg of the title compound as a white amorphorous solid. A portion of the product was crystallized from dichloromethane and hexane.

Physical characteristics are as follows:
$^1$H NMR (CDCl$_3$)δ7.6, 7.4, 7.2, 7.1, 7.0, 6.5, 3.8, 2.6, 2.5, 1.3–1.8, 0.7, 0.6, 0.4, 0.15 ppm.
$^{13}$C NMR (CDCl$_3$) 166, 164.4, 161.6, 143.1, 139.4, 138, 136.8, 129.8, 129.2, 128.7, 125.1, 121.1, 120.3, 110.8, 105.9, 44.0, 30.8, 29.2, 28.9, 26.2, 25.8, 22.2, 12.9, 4.6, 3.7 ppm.
TLC (silica gel GF): $R_f$=0.18 40% ethyl acetate in hexane.

EXAMPLE 251

(+)-4-Chloro-N-[3-[cyclopropyl(5,6,7,8,9,10-hexahydro-4-hydroxy-2-oxo-2H-cycloocta[b]pyran-3-yl)methyl]phenyl]-benzenesulfonamide
(Formula AA-7 wherein $R_{60}$ is 4-chlorophenyl) Refer to Chart AA.

A solution of the title compound of Example 249 (50 mg), pyridine (25 µL), and 4-chlorobenzenesulfonyl chloride (33 mg) in dichloromethane 3 mL) is stirred at room temperature for 18 h. The crude reaction mixture is chromatographed on silica gel to give 63 mg of the title compound as a white amorphorous solid.

Physical characteristics are as follows:
$^1$H NMR (CDCl$_3$)δ7.6, 7.4, 7.2, 7.1, 7.0, 6.5, 3.8, 2.6, 2.5, 1.3–1.8, 0.7, 0.6, 0.4. 0.15 ppm.
TLC (silica gel GF): $R_f$=0.18 40% ethyl acetate in hexane. [α]=+28° (c=0.0019 g/mL methanol), >95% pure.

EXAMPLE 252

(−)-N-[3-[Cyclopropyl(5,6,7,8,9,10-hexahydro4-hydroxy-2-oxo-2H-cycloocta[b]pyran-3-yl)methyl]phenyl]-4-fluoro-benzenesulfonamide (Formula AA-4 wherein $R_{60}$ is 4-fluorophenyl) Refer to Chart AA.

A solution of the title product of Example 248 (50 mg), pyridine (25 µL), and 4-fluorobenzenesulfonyl chloride (34 mg) in dichloromethane (3 mL) is stirred at room temperature for 18 h. The crude reaction mixture is chromatographed on silica gel to give 55 mg of the title compound as a white amorphorous solid.

Physical characteristics are as follows:
MP 204°–206° C.
$^1$H NMR (CDCl$_3$)δ57.7, 6.9–7.3, 3.8, 2.6, 2.4, 1.7, 1.3, 1.6, 0.7, 0.6, 0.4, 0.1.
TLC (silica gel GF): $R_f$=0.19 40% ethyl acetate in hexane. [α]=−66° (c=0.0019 g/mL methanol), >95% pure.

EXAMPLE 253

(+)-N-[3-[Cyclopropyl(5,6,7,8,9,10-hexahydro-4-hydroxy-2-oxo-2H-cycloocta[b]pyran-3-yl)methyl]phenyl]4-fluoro-benzenesulfonamide (Formula AA-7 wherein $R_{60}$ is 4-fluorophenyl) Refer to Chart AA.

A solution of the title product of Example 249 (50 mg), pyridine (25 µL), and 4-fluorobenzenesulfonyl chloride (35 mg) in dichloromethane (3 mL) is stirred at room temperature for 18 h. The crude reaction mixture is chromatographed on silica gel to give 50 mg of the title compound as a white amorphorous solid.

Physical characteristics are as follows:

$^1$H NMR (CDCl$_3$)δ7.7, 6.9–7.3, 3.8, 2.6, 2.4, 1.7, 1.3–1.6, 0.7, 0.6. 0.4, 0.1.

TLC (silica gel GF): R$_f$=0.19 40% ethyl acetate in hexane.

[α]=+68° (c=0.0020 g/mL methanol), >95% pure.

EXAMPLE 254

(–)-N-[3-[Cyclopropyl(5,6,7,8,9,10-hexahydro-4-hydroxy-2-oxo-2H-cycloocta[b]pyran-3-yl)methyl]phenyl]-1-methyl-1H-imidazole-4-sulfonamide (Formula AA-4 wherein R$_{60}$ is 1-methyl-1H-imidazole) Refer to Chart AA.

A solution of the title product of Example 248 (50 mg). pyridine (30 µL). and 1-methylimidazole-3-sulfonyl chloride (30 mg) in dichloromethane 3 mL) is stirred at room temperature for 18 h. The crude reaction mixture is chromatographed on silica gel to give 62 mg of the title compound as a white amorphorous solid.

Physical characteristics are as follows:

$^1$H NMR (CDCl$_3$)δ7.7, 6.9–7.3, 3.8, 2.6, 2.4, 1.7, 1.3–1.6, 0.7, 0.6, 0.4, 0.1.

TLC (silica gel GF): R$_f$=0.11 50% ethyl acetate in hexane.

EXAMPLE 255

(–)-4-Cyano-N-[3-[cyclopropyl(5,6,7,8,9, 10-hexahydro-4-hydroxy-2-oxo-2H-cycloocta[b]pyran-3-yl)methyl] phenyl]-benzenesulfonamide (Formula AA-4 wherein R$_{60}$ is 4-cyanophenyl) Refer to Chart AA.

A solution of the title product of Example 248 (66 mg), pyridine (32 µL), and 4-cyanobenzenesulfonyl chloride (45 mg) in dichloromethane 4 mL) is stirred at room temperature for 18 h. The crude reaction mixture is chromatographed on silica gel using 50% ethyl acetate in hexane to give 75 mg of the title compound as a white amorphous solid.

Physical characteristics are as follows:

White amorphous solid.

MS(EI):504, 475, 338, 310, 233, 207, 195, 186, 153, 144, 130, 117, 102, 91, 55.

HRMS:504.1715.

TLC(silica gel GF): R$_f$=0.4 (5% methanol in chloroform).

$^1$H NMR (CDCl$_3$)δ7.85–7.82, 7.75–7.69, 7.35, 7.19–7.11, 6.95–6.93, 3.47–3.43, 2.64–2.59, 2.55–2.51, 1.73–1.62, 1.46–1.26, 0.63–0.61, 0.51–0.48, 0.26–0.23, 0.15–0.11 ppm.

[α]=–87° (c=0.24 methanol).

EXAMPLE 256

(–)-N-[3-[Cyclopropyl(5,6,7,8,9,10-hexahydro-4-hydroxy-2-oxo-2H-cycloocta[b]pyran-3-yl)methyl]phenyl]-8-quinolinesulfonamide (Formula AA-4 wherein R$_{60}$ is 8-quinolinyl) Refer to Chart AA.

A solution of the title product of Example 248 (66 mg), pyridine (32 µL), and 8-quinolinesulfonyl chloride (50 mg) in dichloromethane 4 mL) is stirred at room temperature for 72 h. The crude reaction mixture is chromatographed on silica gel, fist with 50% ethyl acetate in hexane, followed by 100% ethyl acetate to give 74 mg of the title compound as a white amorphous solid.

Physical characteristics are as follows:

White amorphous solid.

MS(EI):530, 513, 501, 489, 338, 310, 298, 233, 186, 158, 144, 129, 106, 77, 55, 41.

HRMS:530.1889.

TLC(silica gel GF): R$_f$=0.7 in ethylacetate.

$^1$H NMR (CDCl$_3$)δ8.31–8.25, 8.02–7.99, 7.62–7.52, 7.10–6.95, 3.71–3.68, 2.61–2.57, 2.42–2.38, 1.73, 1.54–1.43, 1.25–1.12, 0.97–0.85, 0.47–0.44, 0.32–0.29, 0.09–0.11.

[α]=–18° (c=0.16 methanol).

EXAMPLES 257–258

Utilizing procedures analogous to those described above in Example 256 and using the appropriate sulfonyl chloride, the following additional compounds of the present invention are prepared:

EXAMPLE 257

(–)-N-[3-[Cyclopropyl(5,6,7,8,9,10-hexahydro4-hydroxy-2-oxo-2H cycloocta[b]pyran-3-yl)methyl]phenyl]-2-phenyl-[(E)]-ethenesulfonamide (Formula AA-4 wherein R$_{60}$ is 2-phenyl-[E]-ethenyl) Refer to Chart AA.

Physical characteristics are as follows:

White amorphous solid.

MS(EI):505, 477, 441, 338, 310, 248, 233, 207, 195, 186, 144, 132, 117. 103.

HRMS:505.1924.

TLC(silica gel GF): R$_f$=0.4 (5% methanol in chloroform).

EXAMPLE 258

(–)-N-[3-[Cyclopropyl(5,6,7,8,9,10-hexahydro4-hydroxy-2-oxo-2H-cycloocta[b]pyran-3-yl)methyl] phenyl]-benzenesulfonamide (Formula AA4 wherein R$_{60}$ is phenyl) Refer to Chart AA.

Physical characteristics are as follows:

White amorphous solid.

$^1$H NMR (CDCl$_3$)δ5 7.76–7.73, 7.52–7.41, 7.17, 6.99, 3.83, 3.80, 2.61, 2.46, 1.74, 1.58, 1.42, 0.6–0.5, 0.42, 0.2 ppm.

TLC(silica gel GF): R$_f$=0.4 (50% ethylacetate in hexane).

EXAMPLE 259

(+)4-Cyano-N-[3-[cyclopropyl(5,6,7,8,9,10-hexahydro4-hydroxy-2-oxo-2H-cycloocta[b]pyran-3-yl)methyl] phenyl]-benzenesulfonamide (Formula AA-7 wherein R$_{60}$ is 4-cyanophenyl) Refer to Chart AA.

A solution of the title product of Example 249 (66 mg), pyridine (32 µL), and 4-cyanobenzenesulfonyl chloride (45 mg) in dichloromethane 4 mL) is stirred at room temperature for 18 h. The crude reaction mixture is chromatographed on silica gel, with 50% ethyl acetate in hexane, to give 72 mg of the title compound as a white amorphous solid.

Physical characteristics are as follows:

White amorphous solid.

HRMS:504.170.

MS(EI):504, 476, 338, 310, 233, 220, 207, 195, 186, 153, 144, 130, 117. 102, 55.

TLC(silica gel GF): R$_f$=0.4 (5% methanol in chloroform).

$^1$H NMR (CDCl$_3$)δ7.85–7.82, 7.75–7.69, 7.35, 7.19–7.11, 6.95–6.93, 3.47–3.43, 2.64–2.59, 2.55–2.51, 1.73–1.62, 1.46–1.26, 0.63–0.61, 0.51–0.48, 0.26–0.23, 0.15–0.11 ppm.

EXAMPLES 260–261

Utilizing procedures analogous to those described above in Example 259 and using the appropriate sulfonyl chloride, the following additional compounds of the present invention are prepared:

EXAMPLE 260

(+)-N-[3-[Cyclopropyl(5,6,7,8,9, 10-hexahydro-4-hydroxy-2-oxo-2H-cycloocta[b]pyran-3-yl)methyl]phenyl]-8-quinolinesulfonamide (Formula AA-7 wherein R60 is 8-quinolinyl) Refer to Chart AA.
Physical characteristics are as follows:
White amorphous solid.
TLC(silica gel GF): $R_f=0.7$ (100% ethyl acetate).
$^1$H NMR (CDCl$_3$)δ8.31–8.25, 8.02–7.99, 7.62–7.52, 7.10–6.95, 3.71–3.68, 2.61–2.57, 2.42–2.38, 1.73, 1.54–1.43, 1.25–1.12, 0.97–0.85, 0.47–0.44, 0.32–0.29, −0.09 to −0.11.

EXAMPLE 261

(+)-N-[3-[Cyclopropyl(5,6,7,8,9,10-hexahydro-4-hydroxy-2-oxo-2H-cycloocta[b]pyran-3-yl)methyl]phenyl]-2-phenyl-[(E)]-ethenesulfonamide (Formula AA-7 wherein R$_{60}$ is 2-phenyl-[E]-ethenyl) Refer to Chart AA.
Physical characteristics are as follows:
White amorphous solid.
HRMS:505.1914.
MS(EI):505, 477, 441, 338, 310, 233, 220, 207, 195, 186, 144, 130, 117, 103, 77.
TLC(silica gel GF): $R_f=0.4$ (5% methanol in chloroform).

EXAMPLE 262

4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide, Refer to Chart Z.
A solution of the title product of Example 164 (660 mg), pyridine (320 μL), and 4-cyanobenzenesulfonyl chloride (440 mg) in dichloromethane (40 mL) is stirred at room temperature for 18 hr. The crude reaction mixture was evaporated to a volume of 5 ml and chromatographed on silica gel using 50% ethyl acetate in hexane as eluent to give the title compound (641 mg) as a white amorphous solid. This amorphous solid is alternatively crystallized from acetone:hexane to give 499 mg.
Physical characteristics are as follows:
White solid mp: 183°–183.5° C.
Elemental analysis: found, C, 66.76; H, 5.68; N, 5.38; 6.30.
MS(EI):504, 476, 463, 338, 309, 233, 220, 207, 195, 186, 153, 144, 130, 117, 102.
HRMS:504.1710.
TLC(silica gel GF): $R_f=0.4$ in 50% ethyl acetate in hexane.

EXAMPLE 263

N-[3-[Cyclopropyl(5,6,7,8,9, 10-hexahydro4-hydroxy-2-oxo-2H-cycloocta[b]pyran-3-yl)methyl]phenyl]-8-quinolinesulfonamide Refer to Chart Z.
A solution of the title product of Example 164 (32 mg), pyridine (16 μL), and 8-quinolinesulfonyl chloride (25 mg) in dichloromethane (2 mL) is stirred at room temperature for 18 hr. The reaction mixture is chromatographed on silica gel using 50% ethyl acetate in hexane followed by 100% ethyl acetate as eluent to give the title compound (32 mg) as a white amorphous solid.
Physical characteristics are as follows:
White amorphous solid.
MS(EI):530, 513, 501, 338, 310, 298, 233, 212, 186, 176, 158, 144, 129, 91, 55.
HRMS:530.1882.
TLC(silica gel GF): $R_f=0.7$ in ethyl acetate.

EXAMPLE 264

4-Chloro-N-[3-[cyclopropyl(5,6,7,8,9,10-hexahydro4-hydroxy-oxo-2H-cycloocta[b]pyran-3-yl)methyl]phenyl]-benzenesulfonamide (Formula Z-3 wherein R$_{61}$ is 4-chlorophenyl) Refer to Chart Z.
A solution of the title product of Example 164 (40 mg), pyridine (20 μL), and 4-chlorobenzenesulfonyl chloride (25 mg) in dichloromethane (2 mL) is stirred at room temperature for 18 hr. The crude reaction mixture is chromatographed on silica gel to give the title compound (50 mg) as a white amorphous solid.
Physical characteristics are as follows:
$^1$H NMR (CDCl$_3$)δ7.6, 7.4, 7.2, 7.1, 7.0, 6.5, 3.8, 2.6, 2.5, 1.3–1.8, 0.7, 0.6, 0.4, 0.15ppm.
$^{13}$C NMR (CDCl$_3$)δ166, 164.4, 161.6, 143.1, 139.4, 138, 136.8, 129.8, 129.2, 128.7, 125.1, 121.1, 120.3, 110.8, 105.9, 44.0, 30.8, 29.2, 28.9, 26.2, 25.8, 22.2, 12.9, 4.6, 3.7 ppm.
MS(EI):513, 485, 338, 309, 233, 207, 195, 186, 144, 130, 117.
HRMS:513.1371.
TLC(silica gel GF): $R_f=0.55$ in 50% ethyl acetate in cyclohexane.

EXAMPLES 265–313

Utilizing procedures analogous to those described above in Example 264 and using the appropriate sulfonyl chloride (refer to Chart Z), the following additional compounds of the present invention are prepared.

EXAMPLE 265

N-[3-[Cyclopropyl(5,6,7,8,9,10-hexahydro-4hydroxy-2-oxo-2H-cycloocta[b]pyran-3-yl)methyl]phenyl]-4-(1,1-dimethylethyl)-benzenesulfonamide
Physical characteristics are as follows:
white amorphous solid,
MS(EI):535, 507, 338, 310, 233, 207, 185, 144. 117, 91, 55.
HRMS:535.2389
TLC(silica gel GF): $R_f=0.32$ (40% ethyl acetate in hexane)

EXAMPLE 266

N-[3-[Cyclopropyl(5,6,7,8,9,10-hexahydro-4-hydroxy-2-oxo-2H-cycloocta[b]pyran-3-yl)methyl]phenyl]-2-naphthalenesulfonamide
Physical characteristics are as follows:
white amorphous solid,
MS(EI):529, 501, 338, 309, 233, 207, 185, 144, 127.
HRMS:529.1929
TLC(silica gel GF): $R_f=0.13$ 40% ethyl acetate in hexane

EXAMPLE 267

N-[3-[Cyclopropyl(5,6,7,8,9,10-hexahydro-4-hydroxy-2-oxo-2H-cycloocta[b]pyran-3-yl)methyl]phenyl]-4-(trifluoromethyl)-benzenesulfonamide
Physical characteristics are as follows:
white amorphous solid,
MS(EI):547, 519, 508, 338, 233, 220, 207, 186, 144.
HRMS:547.1637
TLC(silica gel GF): $R_f=0.30$ 40% ethyl acetate in hexane.

EXAMPLE 268

N-[3-[Cyclopropyl(5,6,7,8,9,10-hexahydro-4-hydroxy-2-oxo-2H-cycloocta[b]pyran-3-yl)methyl]phenyl]-4-fluoro-benzenesulfonamide
Physical characteristics are as follows:
white amorphous solid, MS(EI):497, 469, 456, 338, 309, 233, 207, 186, 144, 95.
HRMS:497.1666
TLC (silica gel GF): $R_f$=0.20 40% ethyl acetate in hexane.

EXAMPLE 269

3,4-Dichloro-N-[3-[cyclopropyl(5,6,7,8,9,10-hexahydro-4-hydroxy-2-oxo-2H-cycloocta[b]pyran-3-yl)methyl]phenyl]-benzenesulfonamide
Physical characteristics are as follows:
white amorphous solid,
MS(EI):529, 501, 338, 233, 207, 185, 144, 127, 117, 55.
HRMS:529.1930.
TLC (silica gel GF): $R_f$=0.25 40% ethyl acetate in hexane.

EXAMPLE 270

N-[3-[Cyclopropyl(5,6,7,8,9,10-hexahydro4-hydroxy-2-oxo-2H-cycloocta[b]pyran-3-yl)methyl]phenyl]-1-naphthalenesulfonamide
Physical characteristics are as follows:
white amorphous solid,
MS(EI):547, 519, 338, 309, 233, 207, 186, 144, 130, 117, 55.
HRMS:547.0979
TLC (silica gel GF): $R_f$=0.32 40% ethyl acetate in hexane.

EXAMPLE 271

2,5-Dichloro-N-[3-[cyclopropyl(5,6,7,8,9,10-hexahydro-4-hydroxy-2-oxo- 2H-cycloocta[b]pyran-3-yl)methyl]phenyl]-benzenesulfonamide
Physical characteristics are as follows:
white amorphous solid
MS(EI):547, 519, 338, 309, 233, 207, 195, 186, 144, 130, 117, 91, 55.
HRMS:547.0987
TLC(silica gel GF): $R_f$=0.28 40% ethyl acetate in hexane.

EXAMPLE 272

4-Bromo-N-[3-[cyclopropyl(5,6,7,8,9,10-hexahydro-4-hydroxy-2-oxo-2H-cycloocta[b]pyran-3-yl)methyl]phenyl]-benzenesulfonamide
Physical characteristics are as follows:
white amorphous solid
MS(EI):557, 531, 338, 309, 233, 207, 195, 186, 144.
HRMS:557.0863
TLC(silica gel GF): $R_f$=0.23 40% ethyl acetate in hexane.

EXAMPLE 273

N-[3-[Cyclopropyl(5,6,7,8,9,10-hexahydro-4-hydroxy-4-oxo-2H-cycloocta[b]pyran-3-yl)methyl]phenyl]4-nitro-benzenesulfonamide
Physical characteristics are as follows:
pale yellow amorphous solid
MS(EI):524, 507, 495, 338, 309, 233, 220, 207, 185, 153, 144, 50.
HRMS:524.1612
TLC(silica gel GF): $R_f$=0.18 40% ethyl acetate in hexane.

EXAMPLE 274

N-[3-[Cyclopropyl(5,6,7,8,9,10-hexahydro-4-hydroxy-2-oxo-2H-cycloocta[b]pyran-3-yl)methyl]phenyl]-3-nitro-benzenesulfonamide
Physical characteristics are as follows:
white amorphous solid
MS(EI):524, 507, 496, 338, 233, 220, 207, 144, 50.
HRMS:524.1622
TLC(silica gel GF): $R_f$=0.17 40% ethyl acetate in hexane.

EXAMPLE 275

N-[3-[Cyclopropyl(5,6,7,8,9, 10-hexahydro-4-hydroxy-2-oxo-2H-cycloocta[b]pyran-3-yl)methyl]phenyl]-4-methoxy-benzenesulfonamide
Physical characteristics are as follows:
white amorphous solid
MS(EI):509, 481, 338, 309, 233, 207, 171, 144, 132, 107, 77.
HRMS:509.1869.
TLC(silica gel GF): $R_f$=0.10 40% ethyl acetate in hexane.

EXAMPLE 276

4-[[[3-[Cyclopropyl(5,6,7,8,9,10-hexahydro-4-hydroxy-2-oxo-2H-cycloocta[b]pyran-3-yl)methyl]phenyl]amino]sulfonyl]-benzoic acid
Physical characteristics are as follows:
white amorphous solid
MS(EI):523, 495, 476, 338, 233, 207, 194, 166, 144, 55.
HRMS:523.1661.
TLC(silica gel GF): $R_f$=0.13 40% ethyl acetate in hexane with 1% acetic acid.

EXAMPLE 277

N-[3-[Cyclopropyl(5,6,7,8,9,10-hexahydro-4-hydroxy-2-oxo-2H-cycloocta[b]pyran-3-yl)methyl]phenyl]-2,4,6-trimethyl-benzenesulfonamide Physical characteristics are as follows:
white amorphous solid
MS(EI):521, 493, 338, 310, 233, 207, 186, 144, 132, 119.
HRMS:521.2245.
TLC(silica gel GF): $R_f$=0.25 40% ethyl acetate in hexane.

EXAMPLE 278

N-[3-[Cyclopropyl(5,6,7,8,9,10-hexahydro-4-hydroxy-2-oxo-2H-cycloocta[b]pyran-3-yl)methyl]phenyl]-2,3,4,5,6-pentafluoro-benzenesulfonamide Physical characteristics are as follows:
white amorphous solid
MS(EI):569, 541, 528, 338, 233, 207, 186, 153, 144, 117.
HRMS:569.1294.
TLC(silica gel GF): $R_f$=0.33 40% ethyl acetate in hexane.

EXAMPLE 279

N-[3-[Cyclopropyl(5,6,7,8,9,10-hexahydro-4-hydroxy-2-oxo-2H-cycloocta[b]pyran-3-yl)methyl]phenyl]-2,4-difluoro-benzenesulfonamide Physical characteristics are as follows:
white amorphous solid
MS(EI):515, 487, 338, 309, 233, 207, 177, 144, 113, 55.
HRMS:515.1574.
TLC(silica gel GF): $R_f$=0.38 40% ethyl acetate in hexane.

EXAMPLE 280

N-[3-[Cyclopropyl(5,6,7,8,9,10-hexahydro-4-hydroxy-2-oxo-2H-cycloocta[b]pyran-3-yl)methyl]phenyl]-3-(trifluoromethyl)-benzenesulfonamide Physical characteristics are as follows:
white amorphous solid MS(EI):547, 519, 338, 309, 233, 207, 144, 130, 117, 55.
HRMS:547.1641
TLC(silica gel GF): $R_f$=0.35 40% ethyl acetate in hexane.

EXAMPLE 281

N-[3-[Cyclopropyl(5,6,7,8,9,10-hexahydro-4-hydroxy-2-oxo-2H-cycloocta[b]pyran-3-yl)methyl]phenyl]-2-fluoro-benzenesulfonamide Physical characteristics are as follows:
White amorphous solid
MS(EI):497, 469, 338, 309, 233, 207, 186, 144.
HRMS:497.1671.
TLC(silica gel GF): $R_f$=0.28 40% ethyl acetate in hexane.

EXAMPLE 282

4-Butoxy-N-[3-[cyclopropyl(5,6,7,8,9,10-hexahydro-4-hydroxy-2-oxo-2H-cycloocta[b]pyran-3-yl)methyl]phenyl]-benzenesulfonamide Physical characteristics are as follows:
white amorphous solid
MS(EI):551, 523, 508, 428, 338, 233, 207, 144, 91.
HRMS:551.2347.
TLC(silica gel GF): $R_f$=0.43 40% ethyl acetate in hexane.

EXAMPLE 283

N-[3-[Cyclopropyl(5,6,7,8,9,10-hexahydro4-hydroxy-2-oxo-2H-cycloocta[b]pyran-3-yl)methyl]phenyl]-5-(dimethylamino)-1-naphthalenesulfonamide Physical characteristics are as follows:
white amorphous solid
MS(EI):572, 338, 207, 186, 170, 154, 144, 91.
HRMS:572.2349.
TLC(silica gel GF): $R_f$=0.35 40% ethyl acetate in hexane.

EXAMPLE 284

3,5-Dichloro-N-[3-[cyclopropyl(5,6,7,8,9,10-hexahydro-4-hydroxy-2-oxo-2H-cycloocta[b]pyran-3-yl)methyl]]phenyl]-2-hydroxylbenzenesulfonamide Physical characteristics are as follows:
white amorphous solid
MS(EI):563, 507, 428, 338, 310, 233, 207, 144, 91.
HRMS:563.0940.
TLC(silica gel GF): $R_f$=0.27 40% ethyl acetate in hexane.

EXAMPLE 285

2,3-Dichloro-N-[3-[cyclopropyl(5,6,7,8,9,10-hexahydro4-hydroxy-2-oxo-2H-cycloocta[b]pyran-3-yl)methyl]phenyl]-benzenesulfonamide Physical characteristics are as follows:
white amorphous solid
MS(EI):547, 519, 397, 338, 233, 207, 144, 91, 55.
HRMS:547.0989.
TLC(silica gel GF): $R_f$=0.15 40% ethyl acetate in hexane.

EXAMPLE 286

N-[3-[Cyclopropyl(5,6,7,8,9,10-hexahydro4-hydroxy-2-oxo-2H-cycloocta[b]pyran-3-yl)methyl]phenyl]-2-(trifluoromethyl)-benzenesulfonamide Physical characteristics are as follows:
white amorphous solid
MS(EI):547, 519, 338, 233, 207, 186, 144, 91, 55.
HRMS:547.1654.
TLC(silica gel GF): $R_f$=0.12 40% ethyl acetate in hexane.

EXAMPLE 287

2-Chloro-N-[3-[cyclopropyl(5,6,7,8,9,10-hexahydro4-hydroxy-2-oxo-2H-cycloocta[b]pyran-3-yl)methyl]phenyl]-6-methyl-benzenesulfonamide Physical characteristics are as follows:
white amorphous solid
MS(EI):527, 499, 338, 233, 207, 186, 144, 125, 91, 49.
HRMS:527.1544.
TLC(silica gel GF): $R_f$=0.15 40% ethyl acetate in hexane.

EXAMPLE 288

3,5-Dichloro-N-[3-[cyclopropyl(5,6,7,8,9,10-hexahydro-4-hydroxy-2-oxo-2H-cycloocta[b]pyran-3-yl)methyl]phenyl]-benzenesulfonamide Physical characteristics are as follows:
white amorphous solid
MS(EI):547, 519, 338, 233, 207, 144, 130, 117, 55.
HRMS:547.0973.
TLC(silica gel GF): $R_f$=0.23 40% ethyl acetate in hexane.

EXAMPLE 289

3-Chloro-N-[3-[cyclopropyl(5,6,7,8,9,10-hexahydro-4-hydroxy-2-oxo-2H-cycloocta b]pyran-3-yl)methyl]phenyl]-benzenesulfonamide Physical characteristics are as follows:
white amorphous solid
MS(EI):513, 485, 338, 233, 207, 186, 144, 130, 111, 55.
HRMS:513.1377.
TLC(silica gel GF): $R_f$=0.17 40% ethyl acetate in hexane.

EXAMPLE 290

N-[3-[Cyclopropyl(5,6,7,8,9,10-hexahydro-4-hydroxy-2-oxo-2H-cycloocta[b]pyran-3-yl)methyl]phenyl]-4-benzofurazansulfonamide Physical characteristics are as follows:
white amorphous solid
MS(EI):521, 493, 338, 233, 220, 207, 145, 84, 55.
HRMS:521.1608.
TLC(silica gel GF): $R_f$=0.12 40% ethyl acetate in hexane.

EXAMPLE 291

3-Bromo-N-[3-[cyclopropyl(5,6,7,8,9,10-hexahydro-4-hydroxy-2-oxo-2H-cycloocta[b]pyran-3-yl)methyl]phenyl]-benzenesulfonamide Physical characteristics are as follows:
white amorphous solid
MS(EI):557, 529, 338, 399, 233, 207, 186, 157, 144, 130, 117, 91, 55.
HRMS:557.0885.
TLC(silica gel GF): $R_f$=0.15 40% ethyl acetate in hexane.

EXAMPLE 292

3-[[[3-[Cyclopropyl(5,6,7,8,9,10-hexahydro4-hydroxy-2-oxo-2H-cycloocta[b]pyran-3-yl)methyl]phenyl]amino]sulfonyl]-benzoic acid Physical characteristics are as follows:
white amorphous solid

MS(EI):523, 495, 476, 338, 233, 207, 194, 166, 144, 121, 55.

HRMS:523.1671.

TLC(silica gel GF): R$_f$=0.15 40% ethyl acetate in hexane with 1% acetic acid.

EXAMPLE 293

2-Chloro-N-[3-[cyclopropyl(5,6,7,8,9,10-hexahydro-4-hydroxy-2-oxo-2H-cycloocta[b]pyran-3-yl)methyl]phenyl]-benzenesulfonamide Physical characteristics are as follows:
white amorphous solid
MS(EI):513, 485, 338, 233, 207, 186, 144, 130, 111, 91, 55.

HRMS:513.1371.

TLC(silica gel GF): R$_f$=0.18 40% ethyl acetate in hexane.

EXAMPLE 294

5-Chloro-N-[3-[cyclopropyl(5,6,7,8,9,10-hexahydro-4-hydroxy-2-oxo-2H-cycloocta[b]pyran-3-yl)methyl]phenyl]-1,3-dimethyl-1H-pyrazole-4-sulfonamide Physical characteristics are as follows:
white amorphous solid.
MS(EI):531, 503, 338, 233, 207, 193, 144, 130, 117, 55.
HRMS:531.1608.

TLC(silica gel GF): R$_f$=0.10 40% ethyl acetate in hexane.

EXAMPLE 295

2,6-Dichloro-N-[3-[cyclopropyl(5,6,7,8,9,10-hexahydro-4-hydroxy-2'-oxo-2H-cycloocta[b]pyran-3-yl)methyl]phenyl]-benzenesulfonamide Physical characteristics are as follows:
white amorphous solid
MS(EI):547, 519, 338, 310, 233,207, 144, 84, 55.
HRMS:547.0997.

TLC(silica gel GF): R$_f$=0.20 40% ethyl acetate in hexane.

EXAMPLE 296

N-[[5-[[[3-[Cyclopropyl(5,6,7,8,9,10-hexahydro-4-hydroxy-2-oxo-2H-cycloocta[b]pyran-3-yl)methyl]phenyl]amino]sulfonyl]-2-thienyl]methyl]-benzamide Physical characteristics are as follows:
white amorphous solid
MS(FAB):619, 434, 338, 118, 105.
HRMS:619.1926.

TLC(silica gel GF): R$_f$=0.65 50% ethyl acetate in dichloromethane.

EXAMPLE 297

N-[3-[Cyclopropyl(5,6,7,8,9,10-hexahydro-4-hydroxy-2-oxo-2H-cycloocta-3-yl)methyl]phenyl]-1-methyl-(S)-1H-imidazole-4-sulfonamide Physical characteristics are as follows:
white amorphous solid
MS(EI):483, 454, 338, 251, 212, 186, 144, 132.

HRMS:483.1818.

TLC(silica gel GF): R$_f$=0.11 50% ethyl acetate in hexane.

EXAMPLE 298

N-[3-[Cyclopropyl(5,6,7,8,9,10-hexahydro-4-hydroxy-2-oxo-2H-cycloocta[b]pyran-3-yl)methyl]phenyl]4-(phenylsulfonyl)-2-thiophenesulfonamide Physical characteristics are as follows:
white amorphous solid
MS(FAB):626, 391, 338, 207, 149, 118, 57.
HRMS:626.1359.

TLC(silica gel GF): R$_f$=0.10 40% ethyl acetate in hexane.

EXAMPLE 299

N-[3-[Cyclopropyl(5,6,7,8,9,10-hexahydro-4-hydroxy-2-oxo-2H-cycloocta[b]pyran-3-yl)methyl]phenyl]-5 -(phenylsulfonyl)-2-thiophenesulfonamide Physical characteristics are as follows:
white amorphous solid
MS(FAB):626, 338, 207, 195, 144, 118, 55.
HRMS:626.1347.

TLC(silica gel GF): R$_f$=0.12 40% ethyl acetate in hexane.

EXAMPLE 300

N-[3-[Cyclopropyl(5,6,7,8,9,10-hexahydro-4-hydroxy-2-oxo-2H-cycloocta[b]pyran-3-yl)methyl]phenyl]-4-iodo-benzenesulfonamide Physical characteristics are as follows:
white amorphous solid
MS(EI):605, 338, 207, 194. 144, 118, 91, 55.
HRMS:605.0763.

TLC(silica gel GF): R$_f$=0.21 40% ethyl acetate in hexane.

EXAMPLE 301

5-Chloro-N-[3-[cyclopropyl(5,6,7,8,9,10-hexahydro-4-hydroxy-2-oxo-2H-cycloocta[b]pyran-3-yl)methyl]phenyl]-2-thiophenesulfonamide Physical characteristics are as follows:
white amorphous solid
MS(EI):519, 338, 310, 270, 207, 144, 118, 91, 64, 55.
HRMS:519.0958.

TLC(silica gel GF): R$_f$=0.23 40% ethyl acetate in hexane.

EXAMPLE 302

4,5-Dichloro-N-[3-[cyclopropyl(5,6,7,8,9,10-hexahydro-4-hydroxy-2-oxo-2H-cycloocta[b]pyran-3-yl)methyl]phenyl]-2-thiophenesulfonamide Physical characteristics are as follows:
white amorphous solid
MS(FAB):554, 338, 217, 207, 144, 118, 55, 40.
HRMS:554.0627.

TLC(silica gel GF): R$_f$=0.26 40% ethyl acetate in hexane.

EXAMPLE 303

4,5-Dibromo-N-[3-[cyclopropyl(5,6,7,8,9,10-hexahydro-4-hydroxy-2-oxo-2H-cycloocta[b]pyran-3-yl)methyl]phenyl]-2-thiophenesulfonamide Physical characteristics are as follows:
white amorphous solid MS(FAB):644, 642, 338, 247, 217, 207, 195, 144, 55.
HRMS:641.9627.
TLC(silica gel GF): $R_f$=0.23 40% ethyl acetate in hexane.

EXAMPLE 304

2,5-Dichloro-N-[3-[cyclopropyl(5,6,7,8,9,10-hexahydro-4-hydroxy-2-oxo-2H-cycloocta[b]pyran-3-yl)methyl]phenyl]-3-thiophenesulfonamide Physical characteristics are as follows:
white amorphous solid
MS(FAB):554, 338, 207, 144, 69, 55.
HRMS:554.0621.
TLC(silica gel GF): $R_f$=0.21 40% ethyl acetate in hexane.

EXAMPLE 305

2,4-Dichloro-N-[3-[cyclopropyl(5,6,7,8,9,10-hexahydro-4-hydroxy-2'-oxo-2H-cycloocta[b]pyran-3-yl)methyl]phenyl]-benzenesulfonamide Physical characteristics are as follows:
white amorphous solid
MS(EI):547, 520, 338, 233, 207, 144, 130, 117, 91.
HRMS:547.0983.
TLC(silica gel GF): $R_f$=0.28 40% ethyl acetate in hexane.

EXAMPLE 306

2,4,6-Trichloro-N-[3-[cyclopropyl(5,6,7,8,9,10-hexahydro-4-hydroxy-2-oxo-2H-cycloocta[b]pyran-3-yl)methyl]phenyl]-benzenesulfonamide Physical characteristics are as follows:
white amorphous solid
MS(EI):581, 555, 338, 310, 270, 233, 207, 180, 144.
HRMS:581.0597.
TLC(silica gel GF): $R_f$=0.28 40% ethyl acetate in hexane.

EXAMPLE 307

N-[4-[[[3-[Cyclopropyl(5,6,7,8,9,10-hexahydro-4-hydroxy-2-oxo-2H-cycloocta[b]pyran-3-yl)methyl]phenyl]amino]sulfonyl]phenyl]-acetamide Physical characteristics are as follows:
white amorphous solid
MS(EI):536, 507, 465, 338, 233, 207, 186, 156, 144, 50.
HRMS:536.1993.
TLC(silica gel GF): $R_f$=0.25 4% methanol in dichloromethane.

EXAMPLE 308

N-[3-[Cyclopropyl(5,6,7,8,9,10-hexahydro-4-hydroxy-2-oxo-2H-cycloocta[b]pyran-3-yl)methyl]phenyl]4-(phenylazo)-benzenesulfonamide Physical characteristics are as follows:
orange amorphous solid
MS(EI):583, 338, 233, 186, 144, 105, 77.
HRMS:583.2133.
TLC(silica gel GF): $R_f$=0.62 4% methanol in dichloromethane.

EXAMPLE 309

N-[3-[Cyclopropyl(5,6,7,8,9,10-hexahydro-4-hydroxy-2-oxo-2H-cycloocta[b]pyran-3-yl)methyl]phenyl]-4-[[4-(dimethylamino)phenyl]azo]-benzenesulfonamide u-103389

Physical characteristics are as follows:
red amorphous solid
MS(FAB):627, 224, 148, 135, 120.
HRMS:627.2660.
TLC(silica gel GF): $R_f$=0.60 4% methanol in dichloromethane.

EXAMPLE 310

N-[3-[Cyclopropyl(5,6,7,8,9,10-hexahydro4-hydroxy-2-oxo-2H-cycloocta[b]pyran-3-yl)methyl]phenyl]-5-(2-pyridinyl)-2-thiophenesulfonamide Physical characteristics are as follows:
white amorphous solid
MS(EI):562, 533, 367, 338, 304, 194, 176, 161, 144, 116, 55.
HRMS:562.1595.
TLC(silica gel GF): $R_f$=0.37 20% ethyl acetate in dichloromethane.

EXAMPLE 311

3-Chloro-N-[3-[cyclopropyl(5,6,7,8,9,10-hexahydro-4-hydroxy-2-oxo-2H-cycloocta[b]pyran-3-yl)methyl]phenyl]-2-methyl-benzenesulfonamide Physical characteristics are as follows:
white amorphous solid
MS(EI):527, 499, 338, 310, 274, 233, 207, 144, 125, 91, 79.
HRMS:527.1527.
TLC(silica gel GF): $R_f$=0.21 40%ethyl acetate in hexane.

EXAMPLE 312

N-[3-[Cyclopropyl(5,6,7,8,9,10-hexahydro-4-hydroxy-2-oxo-2-cycloocta[b]pyran-3-yl)methyl]phenyl]-4-(trifluoromethoxy)-benzenesulfonamide Physical characteristics are as follows:
white amorphous solid
MS(EI):563, 535, 338, 309, 233, 207, 144.
HRMS:563.1596.
TLC(silica gel GF): $R_f$=0.33 40% ethyl acetate in hexane.

EXAMPLE 313

3-Chloro-N-[3-[cyclopropyl(5,6,7,8,9,10-hexahydro-4-hydroxy-2-oxo-2H-cycloocta[b]pyran-3-yl)methyl]phenyl]-3-[(phenylsulfonyl)amino]-1-propanesulfonamide (Formula Z-3 wherein $R_{61}$ is 3-(1-propane sulfonamide)phenyl) Refer to Chart Z A solution of the title product of Example 353 (100 mg), chloropropylsulfonylchloride (40 mg), and pyrdine (50 µl) in dichloromethane (4 mL) is stirred at room temperature for 18 h. The crude reaction mixture is chromatographed on silica gel to give the title compound (75 mg).

Physical characteristics are as follows:
MS(EI):.. 634, 534, 505, 494, 338, 309, 233, 207, 144.
HRMS:.. 635.1655.
TLC(silica gel GF): $R_f$=0.60 50% ethyl acetate in dichloromethane.

PREPARATION 55

3-Pyridine sulfonyl chloride

To 1.2 g of 3-pyridine sulfonic acid (Aldrich Chemical Co.) is added 1.70 g of $PCl_5$ and 5.4 ml of $POCl_3$. The reaction mixture is heated to reflux temperature and allowed to stir at reflux for 5 hours. The reaction mixture is cooled to room temperature and evaporated to dryness under vacuum. The solid residue is distributed between methylene chloride and saturated aqueous sodium bicarbonate solution and the organic phase is washed twice with aqueous bicarbonate solution followed by drying over anhydrous sodium sulfate. The organic solution is evaporated to dryness to give 900 mg of the title compound which is used directly in the preparation of sulfonamides.

Physical characteristics are as follows:
Colorless oil.
$^1$H NMR (CDCl$_3$) δ: 8.99–8.92, 8.35–8.31, 7.64–7.59 ppm.

PREPARATION 56

5-Methyl-3-pyridine sulfonyl chloride

Utilizing procedures analogous to those described above in Preparation 55 but substituting 5-methyl-3-pyridine sulfonic acid (Sigma-Aldrich), the title product is prepared.

Physical characteristics are as follows:
White crystalline solid.
$^1$H NMR (CDCl$_3$) δ7.85–7.83, 7.56–7.47 ppm.

EXAMPLE 314

N-[3-[Cyclopropyl(5,6,7,8,9,10-hexahydro-4-hydroxy-2-oxo-2H-cylcloocta[b]pyran-3-yl)methyl]phenyl]-3-pyridinesulfonamide Utilizing procedures described above in Example 264 and using the title sulfonyl chloride of Preparation 55 above, the title compound is prepared.

Physical characteristics are as follows:
White amorphous solid.
HRMS:480.1725.
MS(EI):480, 451, 338, 274, 248, 233, 207, 144, 130, 117, 106, 79, 67, 55, 41.
TLC(silica gel GF): R$_f$=0.8 (ethyl acetate).

EXAMPLE 315

N-[3-[Cyclopropyl(5,6,7,8,9,10-hexahydro4-hydroxy-2-oxo-2H-cycloocta[b]pyran-3-yl)methyl]phenyl]-5-methyl-3-pyridinesulfonamide Utilizing procedures described above in Example 264 and using the title sulfonyl chloride of Preparation 56, the title compound is prepared.

Physical characteristics are as follows:
White amorphous solid.
HRMS:494.1878.
MS(EI):494, 465, 453, 338, 301, 288, 262, 233, 207, 186, 144, 130, 92.
TLC(silica gel GF): R$_f$=0.8 (ethyl acetate).

EXAMPLES 316–347

Utilizing procedures analogous to those described above in Example 264 and using the appropriate sulfonyl chloride, which is commercially available, the following additional compounds of the present invention are prepared:

EXAMPLE 316

N-[3-[Cycloproopyl(5,6,7,8,9,10-hexahydro4-hydroxy-2-oxo-2H-cycloocta[b]pyran-3-yl)methyl]phenyl]-ethenesulfonamide Physical characteristics are as follows:
White amorphous solid.
HRMS:429.1617.
TLC(silica gel GF): R$_f$=0.4 (5% methanol in chloroform).

EXAMPLE 317

N-[3-[Cyclopropyl(5,6,7,8,9,10-hexahydro-4-hydroxy-2-oxo-2H-cycloocta[b]pyran-3-yl)methyl]phenyl]-methanesulfonamide Physical characteristics are as follows:
White amorphous solid.
HRMS:417.1619.
TLC(silica gel GF): R$_f$=0.4 (5% methanol in chloroform).

EXAMPLE 318

N-[3-[Cyclopropyl(5,6,7,8,9,10-hexahydro-4-hydroxy-2-oxo-2H-cycloocta[b]pyran-3-yl)methyl]phenyl]-ethanesulfonamide Physical characteristics are as follows:
White amorphous solid.
HRMS:431.1760.
TLC(silica gel GF): R$_f$=0.3 (5% methanol in chloroform).

EXAMPLE 319

N-[3-[Cyclopropyl(5,6,7,8,9,10-hexahydro-4-hydroxy-2-oxo-2H-cycloocta[b]pyran-3-yl)methyl]phenyl]-benzenesulfonamide Physical characteristics are as follows:
White amorphous solid.
HRMS :479.1750.
TLC(silica gel GF): R$_f$=0.4 (5% methanol in chloroform).

EXAMPLE 320

N-[3-[Cyclopropyl(5,6,7,8,9,10-hexahydro-4-hydroxy-2-oxo-2H-cycloocta[b]pyran-3-yl)methyl]phenyl]-2-phenyl-ethenesulfonamide Physical characteristics are as follows:
White amorphous solid.
HRMS :505.1933.
TLC(silica gel GF): R$_f$=0.4 (5% methanol in chloroform).

EXAMPLE 321

N-[3-[Cyclopropyl(5,6,7,8,9,10-hexahydro-4-hydroxy-2-oxo-2H-cycloocta[b]pyran-3-yl)methyl]phenyl]-benzenemethanesulfonamide Physical characteristics are as follows:
White amorphous solid.
HRMS :493.1922.
TLC(silica gel GF): R$_f$=0.3 (5% methanol in chloroform).

EXAMPLE 322

N-[5-[[[3-[Cyclopropyl(5,6,7,8,9,10-hexahydro-4-hydroxy-2-oxo-2H-cycloocta[b]pyran-3-yl)methyl]phenyl]amino]sulfonyl]-4-methyl-2-thiazolyl]-acetamide Physical characteristics are as follows:
White amorphous solid.

HRMS:557.1652.

TLC(silica gel GF): R$_f$=0.15 (5% methanol in chloroform).

EXAMPLE 323

N-[3-[Cyclopropyl(5,6,7,8,9,10-hexahydro-4-hydroxy-2-oxo-2H-cycloocta[b]pyran-3-yl)methyl]phenyl]-2-thiophenesulfonamide Physical characteristics are as follows:
White amorphous solid.
HRMS:485.1323.

TLC(silica gel GF): R$_f$=0.2 (5% methanol in chloroform).

EXAMPLE 324

N-[3-[Cyclopropyl(5,6,7,8,9,10-hexahydro-4-hydroxy-2-oxo-2H-cycloocta[b]pyran-3-yl)methyl]phenyl]-1-propanesulfonamide Physical characteristics are as follows:
White amorphous solid.
HRMS:445.1928.

TLC(silica gel GF): R$_f$=0.3 (5% methanol in chloroform).

EXAMPLE 325

N-[3-[Cyclopropyl(5,6,7,8,9,10-hexahydro-4-hydroxy-2-oxo-2H-cycloocta[b]pyran-3-yl)methyl]phenyl]4-methyl-benzenesulfonamide Physical characteristics are as follows:
White amorphous solid.
HRMS:493.1932.

TLC(silica gel GF): R$_f$=0.4 (5% methanol in chloroform).

EXAMPLE 326

N-[3-[Cyclopropyl(5,6,7,8,9,10-hexahydro-4-hydroxy-2-oxo-2H-cycloocta[b]pyran-3-yl)methyl]phenyl]-1-butanesulfonamide Physical characteristics are as follows:
White amorphous solid.
HRMS:459.2087.

TLC(silica gel GF): R$_f$=0.4 (5% methanol in chloroform).

EXAMPLE 327

N-[3-[Cyclopropyl(5,6,7,8,9,10-hexahydro-4-hydroxy-2-oxo-2H-cycloocta[b]pyran-3-yl)methyl]phenyl]-1,3-dihydro-1,3-dioxo-2H-isoindole-2-ethanesulfonamide Physical characteristics are as follows:
White amorphous solid.
HRMS:576.1923.

TLC(silica gel GF): R$_f$=0.4 (5% methanol in chloroform).

EXAMPLE 328

N-[3-[Cyclopropyl(5,6,7,8,9,10-hexahydro-4-hydroxy-2-oxo-2H-cycloocta[b]pyran-3-yl)methyl]phenyl]-2-propanesulfonamide Physical characteristics are as follows:
White amorphous solid.
HRMS:445.1928.

TLC(silica gel GF): R$_f$=0.3 (5% methanol in chloroform).

EXAMPLE 329

N-[3-[Cyclopropyl(5,6,7,8,9,10-hexahydro-4-hydroxy-2-oxo-2H-cycloocta[b]pyran-3-yl)methyl]phenyl]-2,6-dimethyl-benzenesulfonamide Physical characteristics are as follows:
White amorphous solid.
HRMS:507.2082.

TLC(silica gel GF): R$_f$=0.5 (50% ethyl acetate in hexane).

EXAMPLE 330

N-[3-[Cyclopropyl(5,6,7,8,9,10-hexahydro-4-hydroxy-2-oxo-2H-cycloocta[b]pyran-3-yl)methyl]phenyl]-2-methyl-benzenesulfonamide Physical characteristics are as follows:
White amorphous solid.
HRMS:493.1929.

TLC(silica gel GF): R$_f$=0.5 (50% ethyl acetate in hexane).

EXAMPLE 331

3-Chloro-N-[3-[cyclopropyl(5,6,7,8,9,10-hexahydro-4-hydroxy-2-oxo-2H-cycloocta[b]pyran-3-yl)methyl]phenyl]-1-propanesulfonamide Physical characteristics are as follows:
White amorphous solid.
HRMS :479.1544.

TLC(silica gel GF): R$_f$=0.5 (50% ethyl acetate in hexane).

EXAMPLE 332

N-[3-[Cyclopropyl(5,6,7,8,9,10-hexahydro-4-hydroxy-2-oxo-2H-cycloocta[b]pyran-3-yl)methyl]phenyl]-3,5-bis(trifluoromethyl)-benzenesulfonamide Physical characteristics are as follows:
White amorphous solid.
HRMS:616.1631.

TLC(silica gel GF): R$_f$=0.5 (50% ethyl acetate in hexane +0:5% acetic acid).

EXAMPLE 333

N-[3-[Cyclopropyl(5,6,7,8,9,10-hexahydro-4-hydroxy-2-oxo-2H-cycloocta[b]pyran-3-yl)methyl]phenyl]-7,7-dimethyl-2-oxo-bicyclo[2.2.1]heptane-1-methanesulfonamide Physical characteristics are as follows:
White amorphous solid.
HRMS:553.2507.

TLC(silica gel GF): R$_f$=0.5 (50% ethyl acetate in hexane).

EXAMPLE 334

N-[3-[Cyclopropyl(5,6,7,8,9,10-hexahydro-4-hydroxy-2-oxo-2H-cycloocta[b]pyran-3-yl)methyl]phenyl]-2,6-dimethoxy-benzenesulfonamide Physical characteristics are as follows:
White amorphous solid.

EXAMPLE 335

N-[3-[Cyclopropyl(5,6,7,8,9,10-hexahydro-4-hydroxy-2-oxo-2H-cycloocta[b]pyran-3-yl)methyl]phenyl]-3,4-dimethoxy-benzenesulfonamide Physical characteristics are as follows:
White amorphous solid.
HRMS:539.1981.
TLC(silica gel GF): $R_f$=0.5 (50% ethyl acetate in hexane).

EXAMPLE 336

N-[3-[Cyclopropyl(5,6,7,8,9,10-hexahydro-4-hydroxy-2-oxo-2H-cycloocta[b]pyran-3-yl)methyl]phenyl]-3-methyl-benzenesulfonamide Physical characteristics are as follows:
White amorphous solid.
HRMS:493.1931.
TLC(silica gel GF): $R_f$=0.5 (50% ethyl acetate in hexane).

EXAMPLE 337

2-Bromo-N-[3-[cyclopropyl(5,6,7,8,9,10-hexahydro-4-hydroxy-2-oxo-2H-cycloocta[b]pyran-3-yl)methyl]phenyl]-6-methoxy-benzenesulfonamide Physical characteristics are as follows:
White amorphous solid.
HRMS:588.1060.
TLC(silica gel GF): $R_f$=0.4 (50% ethyl acetate in hexane).

EXAMPLE 338

N-[3-[Cyclopropyl(5,6,7,8,9,10-hexahydro-4-hydroxy-2-oxo-2H-cycloocta[b]pyran-3-yl)methyl]phenyl]-3,5-dimethyl-4-isoxazolesulfonamide Physical characteristics are as follows:
White amorphous solid.
FIRMS:498.1822
TLC(silica gel GF): $R_f$=0.4 (50% ethyl acetate in hexane).

EXAMPLE 339

2-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide Physical characteristics are as follows:
White amorphous solid.
HRMS:504.1713.
TLC(silica gel GF): $R_f$=0.4 (50% ethyl acetate in hexane).

EXAMPLE 340

N-[3-[Cyclopropyl(5,6,7,8,9,10-hexahydro-4-hydroxy-2-oxo-2H-cycloocta[b]pyran-3-yl)methyl]phenyl]-2,1,3-benzothiadiazole-4-sulfonamide Physical characteristics are as follows:
White amorphous solid.
HRMS:537.1391
HRMS:539.1983.
TLC(silica gel GF): $R_f$=0.5 (50% ethyl acetate in hexane).

TLC(silica gel GF): $R_f$=0.4 (50% ethyl acetate in hexane).

EXAMPLE 341

N-[3-[Cyclopropyl(5,6,7,8,9,10-hexahydro-4-hydroxy-2-oxo-2H-cycloocta[b]pyran-3-yl)methyl]phenyl]-4-ethyl-benzenesulfonamide Physical characteristics are as follows:
White amorphous solid.
HRMS:507.2083.
TLC(silica gel GF): $R_f$=0.4 (50% ethyl acetate in hexane).

EXAMPLE 342

N-[3-[Cyclopropyl(5,6,7,8,9,10-hexahydro-4-hydroxy-2-oxo-2H-cycloocta[b]pyran-3-yl)methyl]phenyl]4-propyl-benzenesulfonamide Physical characteristics are as follows:
White amorphous solid.
HRMS:521.2241.
TLC(silica gel GF): $R_f$=0.4 (50% ethyl acetate in hexane).

EXAMPLE 343

N-[3-[Cyclopropyl(5,6,7,8,9,10-hexahydro-4-hydroxy-2-oxo-2H-cycloocta[b]pyran-3-yl)methyl]phenyl]-1-octanesulfonamide Physical characteristics are as follows:
White amorphous solid.
HRMS:516.2767.
TLC(silica gel GF): $R_f$=0.4 (50% ethyl acetate in hexane).

EXAMPLE 344

N-[3-[Cyclopropyl(5,6,7,8,9,10-hexahydro-4-hydroxy-2-oxo-2H-cycloocta[b]pyran-3-yl)methyl]phenyl]-1-dodecanesulfonamide Physical characteristics are as follows:
White amorphous solid.
HRMS:571.3327.
TLC(silica gel GF): $R_f$=0.4 (50% ethyl acetate in hexane).

EXAMPLE 345

N-[3-[Cyclopropyl(5,6,7,8,9,10-hexahydro-4-hydroxy-2-oxo-2H-cycloocta[b]pyran-3-yl)methyl]phenyl]-4-(1-methylethyl)-benzenesulfonamide Physical characteristics are as follows:
White amorphous solid.
HRMS:521.2228.
TLC(silica gel GF): $R_f$=0.4 (50% ethyl acetate in hexane).

EXAMPLE 346

N-[3-[Cyclopropyl(5,6,7,8,9,10-hexahydro-4-hydroxy-2-oxo-2H-cycloocta[b]pyran-3-yl)methyl]phenyl]-benzeneethanesulfonamide Physical characteristics are as follows:
White amorphous solid.
HRMS:507.2086.
TLC(silica gel GF): $R_f$=0.4 (50% ethyl acetate in hexane).

EXAMPLE 347

N-[3-[Cyclopropyl(5,6,7,8,9,10-hexahyro-4-hydroxy-2-oxo-2H-cycloocta[b]pyran-3-yl)methyl]phenyl]-5-(3-isoxazolyl)-2-thiophenesulfonamide Physical characteristics are as follows:
White amorphous solid.
HRMS:552.1390.

TLC(silica gel GF): $R_f$=0.4 (50% ethyl acetate in hexane).

EXAMPLE 348

4-Amino-N-[3-[cyclopropyl(5,6,7,8,9,10-hexahydro-4-hydroxy-2-oxo-2H-cycloocta[b]pyran-3-yl)methyl]phenyl]-benzenesulfonamide and N-[3-[cyclopropyl(5,6,7,8,9,10-hexahydro-4-hydroxy-2-oxo-2H-cycloocta[b]pyran-3-yl)methyl]phenyl]4-(hydroxyamino)-benzenesulfonamide (Formula Z-3 wherein $R_{61}$ is 4-aminophenyl or 4-hydroxyaminophenyl) Refer to Chart Z A mixture of the title compound of Example 273 (465 mg) and 10% palladium on carbon (50 mg) in ethyl acetate (30 mL) is hydrogenated with shaking at 20 psi for 2 h then filtered through celite and the filter cake washed with ethyl acetate. The filtrates are concentrated in vacuo and chromatographed on silica gel to give 140 mg of the first title compound and 260 mg of the second title compound as white amorpous solids.

Physical characteristics of the first title compound are as follows:
MS(EI):494, 338, 310, 212, 186, 156, 144, 132, 108, 92.
HRMS:494.1876.

TLC(silica gel GF): $R_f$=0.26 3% methanol in dichloromethane.

Physical characteristics of the second title compound are as follows:
MS(FAB):511, 495, 338, 247, 207, 195.

TLC(silica gel GF): $R_f$=0.16 3% methanol in dichloromethane.

EXAMPLE 349

N-[3-[Cyclopropyl(5,6,7,8,9,10-hexahydro-4-hydroxy-2-oxo-2H-cycloocta[b]pyran-3-yl)methyl]phenyl]4-[(phenylsulfonyl)amino]-benzenesulfonamide (Formula Z-3 wherein $R_{61}$ is 4 [(phenylsulfonyl)amino]phenyl) Refer to Chart Z A solution of the first title compound from Example 348 (28 mg), benzenesulfonyl chloride (10 μL), and pyridine (14 μL) in dichloromethane (2 mL) is stirred at room temperature for 18 h. The crude product is chromatographed en silica gel to give 18 mg of the title compound as a white amorphorous solid.

Physical characteristics are as follows:
MS(EI):634, 477, 442, 339, 310, 265, 233, 194, 144, 124, 77.
FIRMS:634.1822.

TLC(silica gel GF): $R_f$=0.21 40% ethyl acette in hexane.

EXAMPLE 350

N-[3-[Cyclopropyl(5,6,7,8,9,10-hexahydro-4-hydroxy-2-oxo-2H-cycloocta[b]pyran-3-yl)methyl]phenyl]-3-[(phenylsulfonyl)amino]-benzenesulfonamide (Formula Z-3 wherein $R_{61}$ is 3-[(phenylsulfonyl)amino]phenyl) Refer to Chart Z Utilizing procedures identical to those above in Example 349, beginning with the first title compound of Example 353 the title compound is obtained.

Physical characteristics are as follows:
white amorphous solid
MS(EI):634, 605, 493, 338, 233, 207, 144, 77.
HRMS:634.1811.

TLC(silica gel GF): $R_f$=0.11 40% ethyl acetate in hexane.

EXAMPLE 351

N-[3-[[[3-[Cyclopropyl(5,6,7,8,9,10-hexahydro4-hydroxy-2-oxo-2H-cycloocta[b]pyran-3-yl)methyl]phenyl]amino]sulfonyl]phenyl]-benzamide (Formula Z-3 wherein R61 is 3-(benzamide)phenyl) Refer to Chart Z Utilizing procedures similar to those above in Example 349 and beginning with the first title compound of Example 353 and benzoyl chloride, the title compound is obtained as a white amorporous solid.

Physical characteristics are as follows
MS(EI):598, 493, 338, 212, 186, 144, 132, 105.
HRMS:598.2133.

TLC(silica gel GF): $R_f$=0.11 40% ethyl acetate in hexane.

EXAMPLE 352

N-[3-[Cyclopropyl(5,6,7,8,9,10-hexahydro-4-hydroxy-2-oxo-2H-cycloocta[b]pyran-3-yl)methyl]phenyl]-4-(dimethylamino)-benzenesulfonamide (Formula Z-3 wherein $R_{61}$ is 4-dimethylaminophenyl) Refer to Chart Z A solution of the first title compound of Example #348 (50 mg) in methanol (3 mL) is treated with paraformaldehyde (24 mg) and refluxed for 45 min, cooled to room temperature. and then treated with sodium cyanoborohydride (20 mg) and stirred 18 h at room temperature. The mixture is quenched with water, diluted with ethyl acetate and the organic layer washed with water, brine, and dried (anhydrous sodium sulfate), filtered, concentrated and then chromatographed on silica gel to give 35 mg of the title compound.

Physical characteristics are as follows:
white amorphous solid
MS(EI):522, 338, 184, 136, 120.
HRMS:522.2190.

TLC(silica gel GF): $R_f$=0.41 50% methanol in dichloromethane.

EXAMPLE 353

3-Amino-N-[3-[cyclopropyl(5,6,7,8,9,10-hexahydro-4-hydroxy-2-oxo-2H-cycloocta[b]pyran-3-yl)methyl]phenyl]-benzenesulfonamide and N-[3-[Cyclopropyl(5,6,7,8,9, 10-hexahydro-4-hydroxy-2-oxo-2H-cycloocta[b]pyran-3-yl)methyl]phenyl]-3-(hydroxyamino)-benzenesulfonamide (Formula Z-3 wherein $R_{61}$ is 3-aminophenyl or 4-hydroxyaminophenyl) Refer to Chart Z A mixture of the title compound from Example 274 (600 mg) and 10% palladium on carbon (100 mg) in ethyl acetate (30 mL) is hydrogenated with shaking at 20 psi for 2 h then filtered through celite and the filter cake washed with ethyl acetate. The combined filtrates are concentrated in vacuo and chromatographed on silica gel to give 380 mg of the first title product and 260 mg of the second title product as white amorporous solids.

Physical characteristics of the first title product are as follows:

white amorphous solid

MS(EI):494, 466, 338, 309, 233, 207, 186, 144, 92.

HRMS:494.1885.

TLC(silica gel GF): $R_f$=0.28 5% methanol in dichloromethane.

Physical characteristics of the second title product are as follows:

white amorphous solid

MS(EI):510, 495, 371, 340, 247, 207, 144, 118.

HRMS:511.1905.

TLC(silica gel GF): $R_f$=0.23 5% methanol in dichloromethane.

EXAMPLE 354

3-[[[3-[Cyclopropyl(5,6,7,8,9,10-hexahydro-4-hydroxy-2-oxo-2H-cycloocta[b]pyran-3-yl)methyl] phenyl]amino]sulfonyl]-benzoic acid, methyl ester (Formula Z-3 wherein R61 is 4-methylbenzoate) Refer to Chart Z A solution of the title compound from Example 292 (300 mg) and concentrated sulfuric acid (300 µL) in methanol (10 mL) is stirred for 2 days at room temperature, diluted with ethyl acetate, washed with water, brine, dried (anhydrous sodium sulfate), filtered, concentrated, and chromatographed on silica gel to give 225 mg of the title compound.

Physical characteristics are as follows:

white amorphous solid

MS(EI):537, 509, 476, 338, 233, 207, 185, 144.

HRMS:537.1821.

TLC(silica gel GF): $R_1$=0.38 40% ethyl acetate in hexane.

EXAMPLE 355

N-[3-[Cyclopropyl(5,6,7,8,9,10-hexahydro4-hydroxy-2-oxo-2H-cycloocta[b]pyran-3-yl)methyl] phenyl]-3-[(2-ethanol)amino]-benzenesulfonamide and N-[3-[Cyclopropyl(5,6,7,8,9,10-hexahydro-4-hydroxy-2-oxo-2H-cycloocta[b]pyran-3-yl)methyl] phenyl]-3-[(bis-(2-ethanol))amino]-benzenesulfonamide (Formula Z-3 wherein $R_{61}$ is 3-[(2-ethanol)amino]phenyl or 3-[(bis-(2-ethanol) amino]phenyl) Refer to Chart Z A solution of the first title compound of Example 353 (50 mg) and p-toluenesulfonic acid (5 mg) in methanol (2 mL) is cooled to −70° C. in a flask equipped with a dry-ice condenser. Ethylene oxide (5 mL) is condensed into the solution and the reaction is allowed to stir at ambient temperature for 18 h and then concentrated in vacuo. The crude product is chromatographed on silica gel to give 30 mg of the first title product as a white amorphorous solid and 10 mg of the second title product as a white amorporous solid.

Physical characteristics of the first title product are as follows:

MS(EI):538, 520, 507, 491, 368, 338, 233, 186, 144, 105.

HRMS:538.2126.

TLC(silica gel GF): $R_f$=0.30 50% ethyl acetate in dichloromethane.

Physical characteristics of the second title product are as follows:

MS(EI):582, 564, 551, 521, 505, 357, 338, 214, 144, 105.

HRMS:582.2446.

TLC(silica gel GF): $R_f$=0.11 50% ethyl acetate in dichloromethane.

EXAMPLE 356

N-[3-[Cyclopropyl(5,6,7,8,9,10-hexahydro-4-hydroxy-2-oxo-2H-cycloocta[b]pyran-3-yl)methyl] phenyl]-3-[methanol]-benzenesulfonamide (Formula Z-3 wherein $R_{61}$ is 3-methanol-phenyl) Refer to Chart Z A solution of the title product of Example 354 (50 mg) in dry tetrahydrofuran at 0° C. is treated with lithium aluminum hydride (5 mg). The mixture is stirred at 0° C. for 30 min, quenched with water, diluted with ethyl acetate and washed with 1N hydrochloric acid, water, and brine, dried (anhydrous sodium sulfate), filtered, concentrated in vacuo, and chromatographed on silica gel to give 45 mg of the title compound as a white amorphorous solid.

Physical characteristics are as follows:

MS(EI): 509, 491, 481, 463, 338, 233, 220, 207, 186, 144.

HRMS: 509.1883.

TLC(silica gel GF): $R_f$=0.27 40% ethyl acetate in hexane.

EXAMPLE 357

N-[3-[Cyclopropyl[3-(2-isothiazolidinyl)phenyl] methyl-(5,6,7,8,9,10-hexahydro4-hydroxy-S,S'-dioxide)methyl ]phenyl ]-3-[(phenylsulfonyl)amino] 4-2H-cycloocta[b]pyran2-one (Formula Z-3 wherein $R_{61}$ is 3-(2-isothiazolidinyl)phenyl) Refer to Chart Z A solution of the title product of Example 363 (25 mg), sodium iodide (7 mg), and morpholine (17 µL) in acetonitrile (2 mL) is heated at reflux for 24 h, cooled, diluted with ethyl acetate, washed with water, brine, dried (anhydrous sodium sulfate), filtered, concentrated in vacuo and chromatographed on silica gel to give 15 mg of the title product.

Physical characteristics the title product are as follows:

white amorphous solid

MS(EI):598, 569, 534, 505, 338, 309, 233, 207, 186, 144.

TLC(silica gel GF): $R_f$=0.40 50% ethyl acetate in dichloromethane.

EXAMPLES 358–362A

Following procedures described above, additional compounds of the present invention are also prepared: Refer to Chart Z.

EXAMPLE 358

N-[3-[Cyclopropyl(5,6,7,8,9,10-hexahydro-4-hydroxy-2-oxo-2H-cycloocta[b]pyran-3-yl)methyl]phenyl]-3-(2-methoxyethyoxymethoxy) benzenesulfonamide

EXAMPLE 359

N-[3-[Cyclopropyl(5,6,7,8,9,10-hexahydro-4-hydroxy-2-oxo-2H-cycloocta[b]pyran-3-yl)methyl]phenyl]-3-hydroxy-benzenesulfonamide

EXAMPLE 360

N-[3 -[Cyclopropyl (5,6,7,8,9,10-hexahydro-4-hydroxy-2-oxo-2H-cycloocta[b]pyran-3-yl)methyl]phenyl]-3-(4-morpholineethoxy)-benzenesulfonamide

EXAMPLE 361

N-[3-[Cyclopropyl(5,6,7,8,9,10-hexahydro-4-hydroxy-2-oxo-2H-cycloocta[b]pyran-3-yl)methyl]phenyl]-3-(N,N-diethylaminoethoxy) benzenesulfonamide

EXAMPLE 362

N-[3-[Cyclopropyl(5,6,7,8,9,10-hexahydro-4-hydroxy-2-oxo-2H-cycloocta[b]pyran-3-yl)methyl]phenyl]4-hydroxy-benzenesulfonamide

EXAMPLE 362

A N-[3-[Cyclopropyl(5,6,7,8,9,10-hexahydro-4-hydroxy-2-oxo-2H-cycloocta-3-yl)methyl]phenyl]-thiazole-4-sulfonamide (Formula Z-3 wherein R61 is -5-thiazolyl)

PREPARATION 57

Carbamic acid, [3-[cyclopropyl(5,6,7,8,9,10-hexahydro-4-hydroxy-2-oxo-2H-cyclohepta[b]pyran-3-yl)methyl]phenyl]-, phenylmethyl ester, Refer to Chart CC To 175 mg of p toluenesulfonic acid is added toluene (50 ml) and then heated to reflux, under nitrogen atmosphere, and 10 ml of toluene is distilled from the reaction solution. The mixture is cooled to 20° C. and 750 mg of 2H-cycloocta [b]pyran-2-one along with 1.065 g of the title product of Preparation 52 is added. The reaction is allowed to stir at 20° C. for 72 hours. The reaction mixture is poured into 100 ml of ethyl acetate, and the ethyl acetate solution is washed with saturated aqueous sodium bicarbonate followed by saturated aqueous sodium chloride and dried over anhydrous sodium sulfate. The organic solution is evaporated to dryness to give 1.48 g of crude title compound. Chromatography over silica gel using 50% ethyl acetate in hexane with 0.5% acetic acid added gives 1.13 g of pure title product as an amorphous solid.

Physical characteristics are as follows:
White amorphous solid.
HRMS:459.2041.
MS(EI):459, 431, 415, 368, 350, 340, 324, 280, 230, 219, 186, 158, 144, 91, 55.
TLC(silica gel GF): $R_f$=0.75 (5% methanol in chloroform).
$R_f$=0.80 (50% ethyl acetate in hexane with 0.5% acetic acid)

PREPARATION 58

3-[(3-aminophenyl)cyclopropylmethyl]-5,6,7,8,9,10-hexahydro-4-hydroxy-2H-Cyclohepta[b]pyran-2-one, Refer to Chart CC To 970 mg of the title product of Preparation 57 is added 100ml of methanol and 240 mg of 10% Pd/C. The reaction mixture is reduced under 48 lb of hydrogen for 18 hours. The reaction mixture is filtered, washed well with ethyl acetate and evaporated to dryness to give 652 mg of crude title compound. The crude product is dissolved in 5 ml of methylene chloride, filtered through celite and evaporated to dryness to give 560 mg of the title product as an amorphous solid.

Physical characteristics are as follows:
White amorphous solid.
HRMS:325.1675.
MS(EI):325, 308, 296, 282, 240, 213, 187, 172, 159, 146, 130, 117, 106, 91, 55.
TLC(silica gel GF): $R_f$=0.4 (5% methanol in chloroform).
$R_f$=0.3 (33% acetone in cyclohexane).

EXAMPLES 363–365

Utilizing procedures analogous to those described above with the appropriate sulfonyl chloride and substituting the title product of Preparation 58 for the title product of Preparation 57, the following additional compounds of the present invention are prepared: Refer to Chart CC.

EXAMPLE 363

N-[3-[Cyclopropyl(2,5,6,7,8,9-hexahydro-4-hydroxy-2-oxocyclohepta[b]pyran-3-yl)methyl]phenyl]-ethenesulfonamide Physical characteristics are as follows:
White amorphous solid.
HRMS:325.1675.
MS(EI):325, 308, 296, 282, 240, 213, 187, 172, 159, 146, 130, 117, 106, 91, 55.
TLC(silica gel GF): $R_f$=0.3 (33% acetone in cyclohexane).

EXAMPLE 364

N-[3-[Cyclopropyl(2,5,6,7,8,9-hexahydro-4-hydroxy-2-oxocyclohepta[b]pyran-3-yl)methyl]phenyl]-methanesulfonamide Physical characteristics are as follows:
White amorphous solid.
HRMS:403.1463.
MS(EI):403, 375, 362, 324, 295, 265, 233, 219, 193, 158, 144, 130, 117, 91, 79.
TLC(silica gel GF): $R_f$=0.3 (33% acetone in cyclohexane).

EXAMPLE 365

N-[3-[Cyclopropyl(2,5,6,7,8,9-hexahydro-4-hydroxy-2-oxocyclohepta[b]pyran-3-yl)methyl]phenyl]-ethanesulfonamide Physical characteristics are as follows:
White amorphous solid.

HRMS:417.1607.

MS(EI):417, 389, 376, 324, 306, 295, 279, 219, 193, 158, 144, 130, 117, 91, 55.

TLC(silica gel GF): $R_f$=0.3 (33% acetone in cyclohexane).

EXAMPLE 365

A 4-[[[3-[Cyclopropyl(5,6,7,8,9,10-hexahydro-4-hydroxy-2-oxo-2H-cycloocta[b]pyran-3-yl)methyl] phenyl]amino]sulfonyl]-benzamide (Formula DD-2) Refer to Chart DD To 50 mg of the title product of Example 262 is added 0.3 ml of DMSO. The mixture is cooled to 0° C. and 30mg of potasium carbonate is added and the mixture is allowed to stir for 30 minutes. To this stirring mixture is added 120 microliters of 30% hydrogen peroxide. The mixture is allowed to warm to room temperature and stir at room temperature for 15 minutes. 5 ml of water is added and the resulting aqueous solution is washed three times with 10 ml of ethyl acetate. The resulting aqueous solution is acidified by the addition of. 1N HCl and the resulting acidic aqueous solution is extracted twice with 15 ml of ethyl acetate. The ethyl acetate solution is dried over anhydrous sodium sulfate, filtered and evaporated to dryness to give the title product as an amorphous solid.

Physical characteristics are as follows:

White amorphous solid.

HRMS:522.1853.

MS(EI):522, 507, 338, 310, 233, 207, 195, 186, 144, 131, 119, 105, 69, 55

TLC(silica gel GF): $R_f$=0.3 (50% ethyl acetate in hexane with 0.5% acetic acid added).

EXAMPLE 365B

2H-Cycloocta[b]pyran-2-one, 3-[cyclopropyl[3-(2-isothiazolidinyl)phenyl]methyl]-5,6,7,8,9,10-hexahydro-4-hydroxy-,S,S-dioxide (Formula EE-2);

N-[3-[Cyclopropyl(5,6,7,8,9,10-hexahydro-4-hydroxy-2-oxo-2H-cycloocta[b]pyran-3-yl)methyl] phenyl]-4-morpholinepropanesulfonamide (Formula EE-3); and P N-[3-[Cyclopropyl(5,6,7,8,9,10-hexahydro-4-hydroxy-2-oxo-2H-cycloocta[b]pyran-3-yl)methyl] phenyl]-4-morpholinepropanesulfonamide hydrogen iodide salt (Formula EE-4) Refer to Chart EE To 96 mg of the title product of Example 331 is added 2 ml of acetonitrile, 34 mg of sodium iodide and 26 microliters of morpholine. The reaction mixture is heated at 100° C. for 24 hours. The reaction mixture is cooled to room temperature and evaporated to dryness under vacuum to give a crude foam. The crude material is dissolved in a minimum amount of methelyene chloride and chromatographed over silica gel, first with 50% ethyl acetate in hexane followed by 5% methanol in chloroform to give the three title products.

Physical characteristics of the first title product are as follows:

White amorphous solid.

HRMS:443.1766.

MS(EI):443, 415, 402, 379, 350, 322, 291, 250, 233, 220, 207, 184, 172, 158, 129.

TLC(silica gel GF): $R_f$=0.15 (50% ethyl acetate in hexane).

Physical characteristics of the second title product am as follows:

White amorphous solid.

HRMS:530.2447

MS(EI):530, 513, 499, 487, 338, 307, 192, 158, 148, 128, 100, 70, 56, 40.

TLC(silica gel GF): $R_f$=0.3 (15% methanol in chloroform).

Physical characteristics of the third title product are as follows:

Light yellow solid.

HRMS:530.2447.

MS(EI):530, 499, 487, 338, 192, 100, 70.

TLC(silica gel GF): $R_f$=0.33 (15% methanol in chloroform).

EXAMPLE 365C

3-Iodo-N-[3-[cyclopropyl(5,6,7,8,9,10-hexahydro-4-hydroxy-2-oxo-2H-cycloocta[b]pyran-3-yl)methyl] phenyl]-1 -propanesulfonamide To 96 mg (2 mmol) of the title compound of Example 331 is added 34 mg of NaI and 2 ml of methylene chloride. The reaction mixture is heated at reflux for 18 hours. The solution is cooled to room temperature and evaporated to dryness under vacuum. The residue is distributed between water and methylene chloride, the organic solution is washed twice with water, dried over anhydrous sodium sulfate, filtered and evaporated to dryness to give the title compound as an amorphous solid.

Physical characteristics are as follows:

MS(EI): 543, 443, 415, 338, 207, 144

HRMS: 572.0969

TLC(silica gel GF): $R_f$=0.5 in 50% ethyl acetate in hexane.

EXAMPLE 366

Thiourea, N-[3-[cyclopropyl(5,6,7,8,9,10-hexahydro-4-hydroxy-2-oxo-2H-cycloocta[b]pyran-3-yl)methyl]phenyl]-N'-phenyl- (Formula V-2 wherein $R_1$ is phenyl) Refer to Chart V In a flame-dried 10-mL two-necked flask under nitrogen, phenylisothiocyanate (0.039 g) is added dropwise to the title compound of Example 164 (0.100 g,) in 1 mL $CH_3CN$, and the reaction mixture is stirred at room temperature for 24 hrs. Column chromatography of crude reaction mixture on 25 g of silica gel yields 0.118 g of the title compound as a solid.

Physical characteristics are as follows:

MP 120°–123 ° C.

IR (Nujol) 3188, 3074, 3060, 3028, 2994, 2953, 2922, 2855, 1664, 1630, 1599, 1591, 1545, 1498, 1492, 1464, 1446, 1406, 1376, 1357, 1314, 1295, 1252, 1231, 1201, 1172, 1126, 695 $cm^{-1}$.

MS (FAB) m/z 949, 551, 497, 475, 382, 340, 338, 281, 247, 94.

For high resolution, Found: 475.2064.

EXAMPLE 367

Thiourea, N-[3-[cyclopropyl(5,6,7,8,9,10-hexahydro-4-hydroxy-2-oxo-2H-cycloocta[b]pyran-3-yl)methyl]phenyl]-N'-ethyl- (Formula V-2 wherein $R_1$ is ethyl) Refer to Chart V.

Prepared as described above in Example 366. Isolated 0.200 g of the title compound as a solid.

Physical characteristics are as follows:

MP 105°–107 °C.

$^{13}$C NMR (DMSO) δ180.0, 165.1, 163.9, 161.7, 144.0, 136.2, 130.0, 126.4, 124.4, 122.7, 110.3, 105.7, 44.4, 40.3, 30.8, 29.1, 28.8, 26.1, 25.7, 22.2, 14.1, 12.8, 5.6, 4.1 ppm.

IR (Nujol) 3217, 3074, 3063, 2995, 2954, 2923, 2868, 1664, 1665, 1631. 1606, 1588, 1542, 1487, 1461, 1453, 1405, 1376, 1336, 1309, 1279, 1248,. 1226, 1202, 1172, 1126 cm$^{-1}$.

MS (EI) m/z 426, 381, 353, 352, 340, 233, 220, 207.

EXAMPLE 368

Benzeneethanethioamide, N-[3-[cyclopropyl(5,6,7,8,9,10-hexahydro-4-hydroxy-2-oxo-2H-cycloocta[b]pyran-3-yl)methyl]phenyl]- (Formula W-2) Refer to Chart W In a flame-dried flask under nitrogen, 1.9 mL toluene is added to a mixture of the title product of Example 207 (0.200 g) and Lawesson's reagent (0.177 g). The reaction mixture is brought to reflux for 1.5 hrs, and then cooled in an ice bath to induce precipitation. Solid is collected by filtration and dried under vacuum at 60 °C. to afford 0.111 g of the title compound.

MP 163° C.

$^{13}$C NMR (DMSO) δ201.3, 165.6, 164.2, 161.3, 141.9, 138.8, 134.8, 129.5, 129.3, 129.3, 128.0, 126.5, 123.3, 122.0, 110.8, 105.7, 54.8, 43.7, 30.7, 29.1, 28.8, 26.1, 25.8, 22.1, 13.0, 4.9, 3.8 ppm.

IR (Nujol) 3304, 2953, 2925, 2870, 2854, 1660, 1646, 1593, 1559, 1552, 1533, 1482, 1466, 1456, 1437, 1393, 1381, 1237, 1199, 1123, 737, 700 cm$^{-1}$.

MS (EI) m/z 473, 440, 281, 280, 227, 226, 134, 128, 91, 55.

PREPARATION 59

1-Phenyl-1-butanol (Formula U-2 wherein R$_1$ is propyl) See Chart U

Following the general procedure of Preparation 54, and making non-critical variations, but substituting butyrophenone for isobutyrophenone, 1.52 g of the title compound is obtained as a colorless oil.

Physical characteristics are as follows:

$^1$H NMR (CDCl$_3$) δ7.30, 4.68, 1.81–1.62, 1.45–1.23, 0.93 ppm.

EXAMPLE 369

5,6,7,8,9,10-Hexahydro-4-hydroxy-3-(1-phenylbutyl)-2H-cycloocta[b]pyran-2-one (Formula U-3 wherein R$_1$ is propyl) Refer to Chart U Following the general procedure of Example 107, and making non-critical variations, but substituting the title product of Preparation 59 for cyclopropyl phenyl ketone, 0.698 g of the title compound is obtained as a white solid.

Physical characteristics are as follows:

MP 173°–175 °C.

IR (Nujol) 3158, 2954, 2924, 2855, 1663, 1638, 1563, 1463, 1408, 1376, 1189, 1175, 1110, 699 cm$^{-1}$.

$^1$H NMR (CDCl$_3$) δ7.44–7.34, 7.29–7.25, 5.84, 4.45, 2.60, 2.40, 2.12–1.96, 1.73, 1.60–1.33, 0.98 ppm.

$^{13}$C NMR (CDCl$_3$) δ165.4, 163.7, 161.1, 141.7, 129.3, 129.2, 127.4, 127.2, 110.5, 106.5, 39.4, 33.2, 30.6, 29.1, 28.8, 26.1, 25.7, 22.0, 20.8, 14.1 ppm.

PREPARATION 60

Carbamic acid, [3-(1-hydroxy-2-methylpropyl)phenyl]-, phenylmethyl ester (Formula X-2) Refer to Chart X Following the general procedure of Preparations 49–52, and making non-critical variations, but substituting isobutyrophenone for cyclopropyl phenyl ketone, 0.698 g of the title compound is obtained as a white solid.

Physical characteristics are as follows:

MP 99°–102° C.

$^1$H NMR (CDCl$_3$) δ7.42–7.24, 7.02, 6.68, 5.20, 4.35, 1.94, 1.75, 0.97, 0.80 ppm.

$^{13}$C NMR (CDCl$_3$) δ153.2, 144.8, 137.6, 135.9, 128.8, 128.5, 128.3, 128.2, 121.6, 117.6, 116.7, 79.6, 66.9, 35.1, 18.9, 17.9 ppm.

IR (Nujol) 3432, 3277, 2963, 2954, 2924, 2866, 2856, 1700, 1602, 1561, 1467, 1447, 1284, 1256, 1240, 1068, 1028, 798, 739, 697 cm$^{-1}$.

Elemental analysis, found: C, 71.89; H, 7.20; N, 4.83.

MS (EI) m/z 299, 256, 212, 91.

For high resolution, Found: 299.1524.

EXAMPLE 370

[3-[1-(5,6,7,8,9,10-Hexahydro-4-hydroxy-2-oxo-2H-cycloocta[b]pyran-3-yl)-2-methylpropyl]phenyl]-carbamic acid, phenylmethyl ester (Formula X-3) Refer to Chart X Following the general procedure of Example 107, and making non-critical variations, but substituting the title compound of Preparation 60 for α-cyclopropylbenzyl alcohol, 0.196 g of the title compound is obtained as a white solid.

Physical characteristics are as follows:

MP 96°–101 °C.

$^1$H NMR (CDCl$_3$) δ7.44–7.15, 6.70, 6.10, 5.19, 3.87, 2.82, 2.57, 2.43, 1.71, 1.61–1.36, 0.95 ppm.

$^{13}$C NMR (CDCl$_3$) δ165.0, 163.4, 161.2, 153.2, 143.4, 138.2, 135.9, 129.5, 128.5, 128.2, 128.1, 123.3, 118.2, 117.0, 109.8, 106.0, 66.9, 48.5, 30.7, 29.0, 28.8, 28.1, 26.1, 25.6, 22.1, 21.9, 20.9 ppm.

IR (Nujol) 3300, 2955, 2923, 2866, 2854, 1735, 1698, 1665, 1632, 1609, 1596, 1549, 1494, 1465, 1455, 1446, 1427, 1405, 1383, 1377, 1368, 1335, 1320, 1315, 1219, 1174, 1086, 1067, 740, 732, 696 cm$^{-1}$.

Elemental analysis, found: C, 73.30; H, 6.87; N, 2.78.

MS (EI) m/z 475, 432, 414, 388, 384, 324, 281, 195, 194, 193, 91.

EXAMPLE 371

3-[1-(3-Aminophenyl)-2-methylpropyl]-5,6,7,8,9,10-hexahydro-4-hydroxy-2H-cycloocta[b]pyran-2-one (Formula X-4) Refer to Chart X Following the general procedure of Example 164, and making non-critical variations, but substituting the title product of Example 370 for the title product of Example 119, 1.07 g of the title compound is obtained as a grey solid.

Physical characteristics are as follows:

MP 105°–110° C. (decomposition).

$^1$H NMR (CDCl$_3$) δ7.13, 6.84. 6.78, 6.57, 3.92, 2.73–2.65, 2.58, 2.50–2.35, 1.72. 1.59– 1.34, 0.99, 0.95 ppm.

¹³C NMR (CDCl₃) δ165.5, 163.8, 161.0, 143.3, 129.9, 116.9, 116.8, 115.3, 114.0, 110.4, 106.3, 47.9, 30.6, 29.1, 28.8, 28.0, 26.1, 25.7, 22.1, 22.0, 20.7 ppm.

IR (Nujol)2956, 2924, 2855, 1661, 1619, 1605, 1591, 1548, 1491, 1462, 1404, 1381, 1367, 1280, 1265, 1245, 1225, 1197, 1172, 1127, 1114, 1106, 1069, 729 cm⁻¹.

Elemental analysis, found: C, 73.44; H, 8.05; N, 3.72.

MS (EI) m/z 341, 298, 280, 172, 147.

For high resolution, Found: 341.1995.

EXAMPLE 372

4-Cyano-N-[3-[1-(6,7,8,9,10-hexahydro-4-hydroxy-2-oxo-2H-cycloocta[b]pyran-3-yl)-2-methylpropyl]phenyl]-benzenesulfonamide (Formula X-5 wherein aryl is 4-cyanobenzene) Refer to Chart X Following the general procedure of Example 221, and making non-critical variations, but substituting the title product of Example 371 for the title product of Example 164 and 4-cyanobenzenesulfonyl chloride for 4-chlorobenzenesulfonyl chloride, 0.152 g of the title compound is obtained as a white solid.

Physical characteristics are as follows:

MP 158°–163 ° C. (decomposition).

IR (Nujol) 3127, 3088, 3074, 2956, 2924, 2866, 2857, 1703, 1673, 1633, 1550, 1466, 1454, 1422, 1402, 1378, 1348, 1284, 1241, 1221, 1199, 1185, 1168, 1157, 1091, 734, 644, 634, 624 cm⁻¹.

¹H NMR (CDCl₃) δ7.82, 7.68, 7.23–7.16, 7.03, 3.68, 2.82–2.74, 2.60, 2.48, 1.84, 1.73–1.42, 0.90, 0.75 ppm.

¹³C NMR (CDCl₃) δ164.5, 163.0, 161.7, 144.4, 142.9, 135.7, 132.6, 129.5, 127.9, 126.3, 122.2, 120.5, 117.1, 116.4, 109.2, 105.6, 49.0, 30.9, 29.0, 28.8, 28.1, 26.0, 25.5, 22.2, 21.7, 21.0 ppm.

Elemental analysis, Found: C, 66.01; H, 6.01; N, 5.28; S, 6.37.

MS (EI) m/z 506, 491, 463, 312, 270, 269, 195, 153, 145, 43.

For high resolution, Found: 506.1875.

EXAMPLE 373

4-Chloro-N-[3-[1-(6,7,8,9,10-hexahydro-4-hydroxy-2-oxo-2H-cycloocta[b]pyran-3-yl)-2-methylpropyl]phenyl]-benzenesulfonamide (Formula X-5 wherein aryl is 4-chlorobenzene) Refer to Chart X Following the general procedure of Example 221, and making non-critical variations, but substituting the title product of Example 371 for the title compound of Example 218, 0.150 g of the title compound is obtained as a white solid.

Physical characteristics are as follows:

MP 92°–95° C. (decomposition).

IR (Nujol) 3374, 3132, 3096, 2991, 2955, 2923, 2867, 1703, 1695, 1670, 1634, 1605, 1591, 1553, 1474, 1468, 1457, 1450, 1409, 1398, 1378, 1355, 1340, 1322, 1298, 1266, 1229, 1214, 1196, 1172, 1164, 1121, 1095, 1083, 1067, 1015, 989, 829, 774, 754, 730, 608 cm⁻¹.

¹H NMR (CDCl₃) δ7.65, 7.34, 7.25–7.15, 6.98, 3.71, 2.78, 2.58, 2.47, 1.71, 1.59–1.40, 0.90, 0.77 ppm.

¹³C NMR (CDCl₃) δ164.7, 163.1, 161.5, 144.3, 139.4, 137.2, 136.2, 129.5, 129.1, 128.6, 126.0, 121.8, 120.2, 109.4, 105.7, 48.9, 30.8, 29.0, 28.8, 28.1, 26.0, 25.5, 22.1, 21.7, 21.0 ppm.

Elemental analysis, Found: C, 62.48; H, 5.87; N, 2.57; Cl, 6.83; S, 6.21.

MS (EI) m/z 515, 500, 472, 321, 195, 153, 145.

EXAMPLE 374

N-[3-[1-(5,6,7,8,9,10-Hexahydro-4-hydroxy-2-oxo-2H-cycloocta[b]pyran-3-yl)-2-methylpropyl]phenyl]-1-methyl-1H-imidazole4-sulfonamide (Formula X-5 wherein aryl is 1-methylimidazole) Refer to Chart X Following the general procedure of Example 221, and making non-critical variations, but substituting the title product of Example 371 for the title product of Example 218 and 1-methylimidazole-4-sulfonyl chloride for 4-chlorobenzenesulfonyl chloride, 0.125 g of the title compound is obtained as a white solid.

Physical characteristics are as follows:

MP 143°–147° C. (decomposition).

¹H NMR (CD₃OD) δ7.65, 7.57, 7.29, 7.18, 7.08, 6.92, 3.66, 3.00–2.88, 2.65–2.56, 1.77–1.58, 1.54–1.37, 0.85, 0.74 ppm.

IR (Nujol) 3448, 3116, 2957, 2952, 2924, 2857, 1696, 1596, 1558, 1534, 1466, 1451, 1421, 1398, 1383, 1328, 1303, 1230, 1160, 1150, 1116, 988, 772, 639, 635, 625 cm⁻¹.

MS (EI) m/z 485,470, 442, 145.

PREPARATION 61

(3-Benzaldehyde)-carbamic acid, phenylmethyl ester (Formula Y-2) Refer to Chart Y A flask with a nitrogen inlet is charged with sodium bicarbonate (10.4 g) in 200 mL THF and 200 mL of water, and m-aminobenzaldehyde (10.0 g) and benzyl chloroformate (13.6 mL) are added sequentially. The mixture is stirred at room temperature for 40 min. Ether is then added, and the organic layer is separated, washed with saturated NaHCO₃, dried over Na₂SO₄, filtered and concentrated to give a brown oil. Column chromatography on 300 g of silica gel yields 16.3 g of the title compound as a pale yellow oil. An analytical sample is crystallized from ethyl acetate-hexane.

Physical characteristics are as follows:

MP 100°–104° C.

IR (Nujol) 3269, 2954, 2925, 2868, 2855, 1729, 1682, 1597, 1560, 1465, 1455, 1445, 1326, 1294, 1237, 1229, 1170, 1155, 1048, 695 cm⁻¹.

MS (EI) m/z 255, 211, 91.

For high resolution, found 255.0900.

¹H NMR (CDCl₃) δ9.98, 7.91, 7.69, 7.59, 7.47, 7.43–7.35, 6.83, 5.23 ppm.

¹³C NMR (CDCl₃) δ191.8, 153.0, 138.6, 137.1, 135.6, 129.7, 128.6, 128.4, 128.3, 124.6, 124.2, 119.1, 67.2 ppm.

Elemental analysis Found: C, 70.74; H, 5.14; N, 5.33.

PREPARATION 62

[3-(1-Hydroxybutyl)phenyl]-carbamic acid, phenylmethyl ester (Formula Y-3 wherein R₁ is propyl) Refer to Chart Y A 50-mL, three-necked, round-bottomed flask with a nitrogen inlet is charged with the title product of Preparation 61 (0.51 g) and 15 mL of THF. Propyl magnesium chloride (2.2 mL) is added, and the resulting mixture is stirred at more temperature for 18 h. Saturated NH$_4$Cl is then added, and the mixture is partitioned between ether and water. The organic layer is washed with 4N NaOH. The base wash is then acidified with 4N HCl, and extracted with ethyl acetate. The ethyl acetate layer is evaporated to give 1.2 g of oil. Column chromatography on 50 g of silica gel gives a pale yellow oil, which is crystallized from ethyl acetate-hexane to give 0.35 g of the title compound as a white crystalline solid.

Physical characteristics are as follows:

MP 103°–106° C.

IR (Nujol) 3396, 3249, 3208, 3101, 3082, 3068, 2950, 2927, 2870, 2863, 2857, 1695, 1602, 1568, 1465, 1448, 1306, 1279, 1256, 1244, 1174, 1068, 1037, 772, 736, 694 cm$^{-1}$.

$^1$H NMR (CDCl$_3$) δ7.42–7.26, 7.05, 6.68, 5.20, 4.65, 1.79–1.62, 1.44–1.29, 0.92 ppm.

$^{13}$C NMR (CDCl$_3$) δ153.2, 146.1, 137.8, 135.9, 129.0, 128.5, 128.3, 128.2, 120.9, 117.6, 116.1, 74.1, 66.9, 41.1, 18.9, 13.8 ppm.

Elemental analysis, Found: C, 72.07; H, 6.99; N, 4.68.

MS (EI) m/z 299, 255, 213, 166, 91.

For high resolution, Found: 299.1536.

EXAMPLE 375

[3-[1-(5,6,7,8,9,10-Hexahydro-4-hydroxy-2-oxo-2H-cycloocta[b]pyran-3-yl)butyl]phenyl]-carbamic acid, phenylmethyl ester (Formula Y-5 wherein R$_1$ is propyl) Refer to Chart Y Following the general procedure of Example 107, and making non-critical variations, but substituting the title product of Preparation 62 for α-cyclopropylbenzyl alcohol, 0.813 g of the title compound is obtained as a beige solid.

Physical characteristics are as follows:

MP 64°–67° C.

$^1$H NMR (CDCl$_3$) δ7.40–7.26, 7.12, 6.71, 5.92, 5.20. 4.39. 2.59, 2.41, 2.09–1.94. 1.70, 1.61–1.26, 0.96 ppm.

$^{13}$C NMR (CDCl$_3$) δ165.1, 163.8, 161.2, 153.2, 143.2, 138.6, 135.9, 130.0, 128.5, 128.3, 128.2, 122.4, 117.6, 117.4, 110.4, 106.2, 67.0, 39.5, 33.1, 30.6, 29.1, 28.8, 26.1, 25.7, 22.0, 20.8, 14.1 ppm.

IR (Nujol) 3302, 2954, 2926, 2868, 2855, 1734, 1700, 1665, 1633, 1610, 1596, 1552, 1493, 1465, 1455, 1447, 1405, 1377, 1221, 1173, 1085, 1068, 697 cm$^{-1}$.

MS (EI) m/z 475, 446, 432, 384, 281, 194, 91.

For high resolution, Found: 475.2368.

EXAMPLE 376

3-[1-(3-Aminophenyl)butyl]-5,6,7,8,9,10-hexahydro4-hydroxy-2H-cycloocta[b]pyran-2-one (Formula Y-6 wherein R$_1$ is propyl) Refer to Chart Y Following the general procedure of Example 164 (M-7), and making non-critical variations, but substituting the title product of Example 375 for the title product of Example 119, 0.51 g of the title compound is obtained as a beige solid.

Physical characteristics are as follows:

$^1$H NMR (CDCl$_3$) δ7.17, 6.83, 6.71, 6.59, 4.37, 3.73, 2.59, 2.38, 2.10–1.98, 1.95–1.84, 1.75, 1.60–1.33, 0.97 ppm.

MP 86°–91° C. (decomposition).

IR (Nujol)2953, 2925, 2867, 2855, 1663, 1617, 1606, 1551, 1492, 1463, 1404, 1377, 1265, 1240, 1222, 1197, 1171, 1127, 1108 cm$^{-1}$.

Elemental analysis, Found: C, 73.88; H, 8.09; N, 3.95.

MS (EI) m/z 341, 312, 298, 189, 172, 147, 106.

EXAMPLE 377

Benzenesulfonamide, 4-chloro-N-[3-[1-(5,6,7,8,9,10-hexahydro-4-hydroxy-2-oxo-2H-cycloocta[b]pyran-3-yl)butyl]phenyl]- (Formula Y-7 wherein R$_1$ is propyl and aryl is 4-chlorobenzene) Refer to Chart Y Following the general procedure of Example 221, and making non-critical variations, but substituting the title product of Example 376 for the title product of Example 218, 0.107 g of the title compound is obtained as a white solid.

Physical characteristics are as follows:

MP 97°–101° C. (decomposition).

$^1$H NMR (CDCl$_3$) δ7.67, 7.39, 7.23–7.11, 7.00, 6.77, 5.75, 4.29, 2.60, 2.45, 2.05–1.92. 1.73, 1.59–1.26, 0.93 ppm.

$^{13}$C NMR (CDCl$_3$) δ165.0, 163.5, 161.5, 144.0, 139.5, 137.2, 136.6, 130.0, 129.2, 128.6, 124.9, 120.9, 120.3, 110.0, 105.9, 39.5, 33.1, 30.8, 29.1, 28.8, 26.1, 25.6, 22.1, 20.9, 14.0 ppm.

IR (Nujol) 3258, 2952, 2928, 2867, 2855, 1666, 1635, 1607, 1587, 1558, 1476, 1465, 1458, 1404, 1377, 1339, 1225, 1199, 1166, 1108, 1094, 1086, 755, 706, 619 cm$^{-1}$.

Elemental analysis, Found: C, 62.98; H. 5.89; N, 2.45; Cl, 6.67; S. 6.00.

MS (EI) m/z 515, 486, 472, 340, 321.

For high resolution, Found: 515.1533.

EXAMPLE 378

Benzenesulfonamide, 4-cyano-N-[3-[1-(5,6,7,8,9,10-hexahydro-4-hydroxy-2-oxo-2H-cycloocta[b]pyran-3-yl)butyl]phenyl]- (Formula Y-7 wherein R$_1$ is propyl and aryl is cyanobenzene) Refer to Chart Y Following the general procedure of Example 221, and making non-critical variations, but substituting the title product of Example 376 for the title product of Example 218 and 4-cyanobenzenesulfonyl chloride for 4-chlorobenzenesulfonyl chloride, 0.101 g of the title compound is obtained as a white solid.

Physical characteristics are as follows:

MP 130°–135° C.

$^1$H NMR (CDCl$_3$) δ7.83, 7.70, 7.22, 7.12, 7.00, 4.25, 2.62, 2.46. 2.00, 1.80–1.36, 1.26, 0.93 ppm.

IR (Nujol) 3269, 3090, 2955, 2924, 2870, 2857, 2235, 1669, 1652, 1632, 1594, 1557, 1537, 1481, 1462, 1405, 1377, 1346, 1328, 1236, 1229, 1216, 1183, 1173, 1158, 1111, 1092, 636 cm$^{-1}$.

Elemental analysis, Found: C, 66.00; H, 5.99; N, 5.28; S, 6.38.

MS (EI) m/z 506, 477, 463, 340, 312, 195.

For high resolution, Found: 506.1901.

EXAMPLE 379

3-(α-Cyclopropyl thien-2-ylmethyl)-4-hydroxy-5,6,7,8,9,10-hexahydrocycloocta[b]pyran-2-one (Formula FF-3) Refer to Chart FF To a methylene chloride solution of 2H-cycloocta[b]pyran-2-one of formula FF-2 (1.94 g) and α-cyclopropyl thien-2-yl carbinol (1.54 g) is added five drops of trifluoroacetic acid (TFA) at room temperature. The reaction is stirred for 15 hours. MgSO$_4$ is added and the reaction filtered and evaporated to yield a yellow oil. That oil is dissolved in 25% EtOAc/hexane and placed in the freezer to yield upon filtration 2.5 g of impure title product. Chromatography over silica gel (2% Methanol/methylene chloride) affords 830 mg of pure title product.

Physical characteristics are as follows:

IR (mull)2953, 2923, 1657, 1631, 1552, 1531, 1464, 1223, 1198, 1187 cm-1; Mass spectrum: m/e (relative intensity) 330 (99), 313 (13), 302 (13), 301 (15), 207 (27), 204 (15), 137 (25), 97 (18);

H-NMR (CDCl$_3$) 7.3 (d, 1H), 7.2 (m, 1H), 7.0 (m, 1H), 4.1 (d, 1H), 2.6 (m, 2H), 2.4 (m, 2H), 1.7 (m, 1H), 1.5 (m, 4H), 0.7 (m, 1H), 0.6 (m, 2H), 0.4.(m, 1H).

PREPARATION 63

Ethyl thien-2-yl carbinol (Formula GG-2) Refer to Chart GG

A 1.0M solution of ethylmagnesium bromide in THF (100 mL) is cooled to −78° C. and 2-thiophene carboxaldehyde (9.35 mL) is added. The reaction is allowed to warm to 23° C. for 1 h, then recooled to −78° C. and quenched with saturated ammonium chloride. After allowing to warm to 23° C., the reaction is extracted with ether (800 mL) and the ethereal layer is washed with water (2×150 mL) and brine. The organic phase is dried over MgSO$_4$, filtered and concentrated in vacuo. The product is purified by chromatography over silica gel(2 kg), eluting with 30% ether in pentane to give 13.4 g of the title product as a colorless oil.

Physical characteristics are as follows:

$^1$H NMR, 300 MHz (CDCl$_3$) δ: 7.24 (m, 1 H), 6.96 (m, 1 H), 4.84 (m, 1 H), 3.37 (m, 2 H), 2.21 (d, J=3.6 Hz, 1 H), 1.83 (br s, 1 H), 0.96 (t, J=7.5 Hz, 3 H).

EXAMPLE 380

3-(α-Ethyl thien-2-ylmethyl)4-hydroxy-5,6,7,8,9,10-hexahydrocycloocta[b]pyran-2-one (Formula GG-4) Refer to Chart GG 2H-Cycloocta[b]pyran-2-one of formula GG-3 (388 mg) is dissolved in methylene chloride (2.0 mL) and ethyl thien-2-ylcarbinol of Preparation 63 (450 mg) is added along with trifluoroacetic acid (5 drops) at 23° C. The reaction is stirred for 4 h, then chromatographed over silica gel (300 g), eluting with 1:1 ether:pentane to give the title product (220 mg) as a white solid.

Physical characteristics are as follows:

MP=163°–5° C.;

IR (mull): 3171, 2954, 2923, 2869, 2854, 1662, 1638, 1564, 1448, 1461, 1411, 1189, 1171, 1057, 694.4 cm$^{-1}$;

UV (EtOH) λ max (E): 210 (22,100), 220 sh (15,400), 234 sh (9,700), 296 (9,200); 1 H NMR (CDCl$_3$) 300 MHz, δ10.6 (br 1 H), 7.23 (d, J=5.1 Hz, 1 H), 6.88 (m, 2 H), 4.36 (dd, J=6.1, 9.3 Hz, 1 H), 3.34 (m, 4 H), 2.21 (m, 1 H), 2.02 (m, 1 H), 1.63 (m, 2 H), 1.54 (m, 2 H), 1.41 (m, 2 H), 1.35 (m, 2 H), 0.80 (t, J=7.3 Hz, 3 H);

MS (EI) m/e (relative intensity): 318 (36), 290 (19), 289 (100), 261 (13), 153 (10), 137 (22), 125 (28), 97 (24), 55 (16), 40 (21);

Analysis Found: C, 67.72, H, 7.03, S, 10.37.

PREPARATION 64

Ethyl (5-methylthien-2-yl) carbinol (Formula HH-2) Refer to Chart HH

5-Methyl-2-thiophenecarboxaldehyde (10.0 g) is dissolved in THF and cooled to −78° C. To that solution is added ethyl magnesium bromide (1M in hexane; 80 cc) dropwise over several minutes. The cooling bath is removed and the reaction allowed to equilibrate to room temperature. The reaction is quenched by adding a saturated solution of NH$_4$Cl. The reaction is extracted with ether, dried and evaporated to yield the title product as an almost colorless oil.

Physical characteristics are as follows:

IR (mull) 3374, 2964, 2921, 2875, 1462, 1454, 1408, 798 cm$^{-1}$;

H-NMR (CDCl$_3$) 6.73 (d, 1H), 6.59 (m, 1H), 4.72 (t, 1H), 2.45 (s, 3H), 2.05 (s, 1H), 1.80 (m, 2H), 0.94 (t, 3H).

Mass spectrum: ions at m/e (relative intensity) 156 (3), 141 (6), 140 (40), 139 (99), 127 (21), 123 (6), 99 (12), 97 (7), 65 (6).

EXAMPLE 381

3-(α-Ethyl (5-methylthien-2-ylmethyl)-4-hydroxy-5,6,7,8,9,10-hexahydrocycloocta[b]pyran-2-one (Formula HH4) Refer to Chart HH To a methylene chloride solution of 2H-cycloocta[b]pyran-2-one of formula HH-3 (196 mg) and ethyl (5-methylthien-2-yl) carbinol of Preparation 64 (156 mg) is added several drops of TFA. The progress of the reaction is monitored by thin layer chromatography (TLC, silica gel; eluting with 25% EtOAc/hexane). After several hours the reaction is evaporated and the product collected on a filter with the aid of a mixture of ethyl acetate and hexane to yield 225.5 mg of the title product.

Physical characteristics are as follows:

IR (mull) 2950, 2924, 2869, 1660, 1635, 1564, 1413, 1192, 1170, 1157 cm-1.

H-NMR (CDCl$_3$) 6.86 (d, 1H), 6.62 (d, 1H), 4.47 (t, 1H), 2.62 (m, 2H), 2.44 (m, 5H), 2.14 (m, 1H), 1.98 (m, 1H), 1.75 (m, 1H), 1.45 (m, 4H), 1.04 (t, 3H).

Mass spectrum: ions at m/e (relative intensity) 332 (27), 304 (20), 303 (99), 275 (8), 153 (7), 151 (22), 139 (44), 111 (9), 55 (9).

PREPARATION 65

Cyclopropyl benzo[b]thien-2-yl carbinol (Formula II-2) Refer to Chart II

Benzo[b]thiophene of formula II-1 (2.68 g) is added to THF (70 mL) and cooled to −78° C. n-Butyl lithium (1M in hexane, 20 mmol) is then added and the resulting solution stirred for 1.5 hours. The cooling bath is removed for 30 minutes and then cooled back to −78° C. Cyclopropylcarboxaldehyde (1.4 g) is then added in a single portion and the reaction quenched by adding a saturated NH$_4$Cl solution. The reaction is extracted with ether, dried and solvent removed in vacuo to yield the title product as a clear oil that solidified on standing.

Physical characteristics are as follows:

IR (mull) 3296, 3201, 2954, 2925, 2869, 2854, 1459, 1438, 1270, 1258 cm-1.

H-NMR (CDCl$_3$) 7.79 (m, 1H), 7.70 (m, 1H), 7.30 (m, 3H), 4.26 (d, 1H), 2.39 (s, 1H), 1.35 (m, 1H), 0.65 (m, 1H), 0.55 (m, 1H), 0.49 (m, 1H).

Mass spectrum: ions at m/e (relative intensity) 204 (75), 176 (63), 163 (29), 160 (27), 147 (54), 135 (99).

EXAMPLE 382

3-(α-Ethyl benzo[b]thien-2-ylmethyl)-4-hydroxy-5,6,7,8,9,10-hexahydrocycloocta[b]pyran-2-one (Formula II-4) Refer to Chart II To a methylene chloride solution of 2H-cycloocta[b] pyran-2-one of formula II-3 (196 mg) and cyclopropyl benzothien-2-yl carbinol of Preparation 65 (204 mg) is added several drops of TFA. The reaction is stirred for 30 minutes at room temperature without reaction. Several addition drops of TFA is added and the reaction stirred an additional 30 minutes. The solvent is removed in vacuo and the resulting solid dissolved in hot 40% EtOAc/hexane and placed in the freezer over night. The solid is collected on a filter to yield 257.5 mg of the title product.

Physical characteristics are as follows:

IR (mull )2952, 2925, 2853, 1670, 1656, 1627, 1550, 1528, 1458, 1436, cm-1.

H-NMR (CDCl$_3$) 7.74 (m, 2H), 7.33 (m, 2H), 6.4 (s, 1H), 4.12 (d, 1H), 2.64 (m, 2H), 2.45 (m, 2H), 1.77 (m, 1H), 1.47 (m, 4H), 0.82 (m, 1H), 0.68 (m, 2H), 0.46 (m, 1H). Mass spectrum: ions at m/e (relative intensity) 380 (99), 254 (45), 233 (36), 228 (53), 220 (75), 207 (98), 187 (63), 172 (37), 160 (75), 55 (36).

PREPARATION 66

Cyclopropyl (5-hydroxymethylfuran-2-yl) carbinol (Formula JJ-2) Refer to Chart JJ Furfuryl alcohol of formula JJ-1 (7.0 g) is added to Tiff (100 mL) and cooled to −78° C. n-Butyl lithium (1.6M, 98.6 cc) is added dropwise and after complete addition, the reaction is stirred at −78° C. for 2 hours. The cooling bath is removed for 30 minutes and then cooled back to −78° C. Cyclopropanecarboxaldehyde (5.0 g) is then added dropwise (in THF). Stirring is continued for 30 minutes and then the reaction quenched with a saturated NH$_4$Cl solution. The reaction is extracted with ether, dried and evaporated to yield a dark oil. Chromatography of 0.80 g of crude title product over silica gel affords 0.64 g of the title product.

Physical characteristics are as follows:

H-NMR (CDCl$_3$) 6.21 (m, 2H), 4.53 (s, 2H), 3.94 (d, 1H), 3.0 (broad, 2H), 1.75 (m, 1H), 0.50 (m, 4H).

EXAMPLE 383

3-(α-Cyclopropyl (5-hydroxymethylfurfur-2-yl)-4-hydroxy-5,6,7,8,9,10-hexahydrocycloocta[b]pyran-2-one (Formula JJ4) Refer to Chart JJ Cyclopropyl (5-hydroxymethylfuran-2-yl) carbinol of Preparation 66 (336 mg) and 2H-cycloocta[b]pyran-2-one of formula JJ-3 (427 mg) are dispersed in methylene chloride (25 mL) at 23° C. and trifluoroacetic acid (4 drops) is added. The reaction is stirred for 2.5 h, then poured into EtOAc (400 mL) and washed with water (2×50 mL) and brine. Drying over MgSO$_4$, filtration and concentration in vacuo affords a yellow foam. The product is isolated via column chromatography (150 g silica gel), eluting with 30% EtOAc in CH$_2$Cl$_2$, giving the title product (275 mg) as a white foam.

Physical characteristics are as follows:

IR (mull): 2923, 2952, 2854, 1668, 1665, 1557, 1203, 1463, 1456, 1408, 1247, 1237, 1446, 1016, 1636 cm-1;

UV (EtOH) λmax (E): 215 (23, 900), 234 sh (10,800), 292 (8.560);

$^1$H NMR 300 MHz, CDCl$_3$, δ:7.26 (s, 1 H). 6.36 (d, J =3.1 Hz, 1 H), 6.26 (d, J =3.1 Hz, 1 H), 4.57 (s, 2 H), 3.98 (d, J =8.1 Hz, 1 H). 2.62 (br t, J =6.1 Hz, 2 H), 2.49 (br t. J =5.8 Hz. 2 H), 1.75 (m, 3 H). 1.60 (m, 2 H), 1.47 (m. 4 H), 1.26 (m. 1 H). 0.57 (m, 3 H). 0.29 (m, 1 H);

MS (EI) m/e (relative intensity): 326 (81), 297 (27), 174 (100), 133 (28), 105 (27), 91 (37), 79 (29), 55 (51), 42 (28), 40 (38);

Analysis Found: C, 70.08, H, 6.97.

PREPARATION 67

Cyclopropyl (5-hydroxymethylthien-2-yl, carbinol (Formula KK-2) Refer to Chart KK 2-Thiophenemethanol of formula KK-1 (5.2 mL) in THF (50 mL) is cooled to −78° C. and n-butyllithium (Aldrich, 1.6M in hexane, 73.4 mL) is added and the reaction is allowed to warm to 0° C. for 15 min. The reaction is cooled back to −78° C. and cyclopropane carboxaldehyde (4.2 mL) is added and the reaction is allowed to warm to 0° C. for 30 minutes. The reaction is quenched with ammonium chloride (30 mL) and extracted with ether (400 mL), then washed with water (120 mL) and brine. The organic phase is dried over MgSO$_4$, filtered and concentrated in vacuo. The residue is purified by column chromatography over silica gel (1 kg), eluting with 70% ether in pentane (30%) to give the title product (5.35 g) as a pale yellow oil that slowly crystallizes.

Physical characteristics are as follows:

IR (neat film): 3403, 3004, 2873, 1374, 1289, 1271, 1214, 1160, 1133, 1096, 1026, 965.4, 939.3, 919.1, 810.1 cm-1;

UV (EtOH) λmax (E): 216 sh (2790), 240 (9870);

$^1$H NMR 300 MHz, (CDCl$_3$) δ: 6.89 (m, 2 H), 4.81 (s, 2 H), 4.20 (d, J =8.3, 1 H), 2.22 (br s, 1 H), 1.28 (m, 1 H), 0.64 (m, 2 H), 0.52 (m, 1 H), 0.40 (m, 1 H); MS (EI) m/e (relative intensity): 157 (30), 149 (37), 139 (37), 137 (32), 97 (81), 69 (91), 45 (100), 43 (36), 41 (53);

Analysis Found: C, 59.56, H, 6.63, S, 15.80.

EXAMPLE 384

3-(α-Cyclopropyl (5-hydroxymethylthien-2-ylmethyl)-4-hydroxy-5,6,7,8,9,10-hexahydrocycloocta[b]pyran-2-one (Formula KK-4) Refer to Chart KK 2H-Cycloocta[b]pyran-2-one of formula KK-3 (200 mg) and cyclopropyl (5-hydroxymethylthien-2-yl)carbinol of Preparation 67 (200 mg) are dissolved in methylene chloride (3.0 mL). Trifluoroacetic acid (4 drops) is added and the reaction is stirred at 23° C. for 90 min. The crude reaction mixture is chromatographed over silica gel (150 g), eluting with EtOAc to give the title product (100 mg) as a white foam.

Physical characteristics are as follows:

IR (mull): 2994, 2953, 2923, 2868, 2854, 1664, 1632, 1556, 1463, 1458, 1408, 1377, 1246, 1233, 1202 cm-b 1;

UV (EtOH) λmax (E): 210 (18.600), 219 sh (15,800), 239 (9,330). 294 (7,840);

$^1$H NMR (CDCl$_3$), 300 MHz, δ: 6.98 (dd, J =1.4, 3.4 Hz, 1 H). 6.85 (d. J =3.4 Hz. 1 H). 4.74 (s. 2 H), 3.64 (d, J =9.2 Hz. 1 H), 2.62 (m. 2 H). 2.48 (m. 2 H). 1.75 (m. 2 H) 1.59 (m, 2 H), 1.46 (m, 5 H), 0.73 (m. 1 H), 0.55 (m, 2 H), 0.35 (m, 1 H);

MS (EI) m/e (relative intensity): 342 (100), 247 (50), 207 (66), 190 (57), 167 (41), 137 (71), 135 (39), 97 (47), 55 (61), 40 (53);

Analysis Found: C, 66.51, H, 7.28.

PREPARATION 68

Cyclopropyl (5-(2-hydroyxethyl)thien-2-yl) carbinol (Formula LL-2) Refer to Chart LL 2-Thiopheneethanol of formula LL-1 (4,51 g) is added to THF (75 mL) and cooled to −78° C. n-Butyl lithium (1.6M, 46.8 cc) is added dropwise and complete addition the reaction is stirred an additional hour. The cooling bath is then removed for 20 minutes and then the reaction temperature returned to −78° C. Cyclopropylcarboxaldehyde (2.46 g) is then added dropwise and the reaction is then warmed to room temperature and quenched by adding a saturated NH$_4$Cl solution. The reaction is extracted, dried and solvent removed in vacuo to the title product as a pale yellow oil.

Physical characteristics are as follows:

H-NMR (CDCl$_3$) 6.85 (d, 1H), 6.70 (d, 1H), 4.12 (d, 1H), 3.83 (m, 2H), 3.00 (m, 2H), 1.75 (m, 1H), 0.65 (m, 2H), 0.55 (m, 1H), 0.45 (m, 1H).

EXAMPLE 385

3-(α-Cyclopropyl (5-(2-hydroxyethyl)thien-2-ylmethyl)-4-hydroxy-5,6,7,8,9,10-hexahydrocycloocta[b]pyran-2-one (Formula LL-4) Refer to Chart LL To a methylene chloride solution of 2H-cycloocta[b]pyran-2-one of formula LL-3 (196 mg) and cyclopropyl (5-(2-hydroyxethyl)thien-2-yl) carbinol of Preparation 68 (198 mg) is added several drops of TFA. The reaction is stirred for 1.5 hours and the solvent removed in vacuo. The resulting oil is dissolved in 40% EtOAc/hexane and placed in the freezer over night. The solid is collected on a filter to yield 136.3 mg of the title product.

Physical characteristics are as follows:

IR (mull) 2951, 2922, 2868, 2854, 1670, 1637, 1556, 1448, 1273, 1022 cm-1.

H-NMR (CDCl$_3$) 7.02 (m, 1H), 6.76 (d, 1H), 6.43 (s, 1H), 3.97 (d, 1H), 3.85 (t, 2H), 3.03 (t, 2H), 2.61 (m, 2H), 2.46 (m, 2H), 1.76 (m, 2H), 1.46 (m, 4H); 0.75 (m, 1H), 0.6 (m, 2H), 0.45 (m, 1H).

Mass spectrum: ions at m/e (relative intensity) 374 (71), 344 (43), 329 (40), 315 (13), 303 (11), 248 (80), 233 (41), 220 (58), 181 (66), 163 (65).

PREPARATION 69

Methoxymethylfurfuryl alcohol. For the conversion of MM-1 to MM-2 see: Bull. Chem. Soc. Jpn., 65 (9), 1992 and Zh. Org. Khim., 25(4), 843–6 (Russ), 1989.

PREPARATION 70

Cyclopropyl (5-hydroxymethyl(methoxymethyl) furfur-2-yl) carbinol (Formula MM-3) Refer to Chart MM Methoxymethylfurfuryl alcohol (1.42 g) of Preparation 69 is dissolved in THF (20 mL) and cooled to −78° C. The reaction is degassed under a nitrogen atmosphere and treated with nButyllithium (Aldrich, 1.6M in hexane, 6.6 mL). The reaction is stirred for 30 min. Cyclopropane carboxaldehyde (0.75 mL) is added and the reaction is allowed to warm to 23° C. over 20 minutes. The reaction is quenched with saturated ammonium chloride solution (3.0 mL) and stirred 15 minutes, then extracted with ethyl acetate (400 mL) and washed with water (2×50 mL) and brine. The organic layer is dried over MgSO$_4$, filtered and concentrated in vacuo. The product is purified by column chromatography (300 g silica gel), eluting with 30% ethyl acetate in hexane, giving the title product (1.0 g) as a colorless oil.

Physical characteristics are as follows:

IR (neat film): 3419, 2937, 2887, 1212, 1199, 1148, 1100, 1041, 1017, 995.3, 973.1, 946.1, 929.7, 919.1, 799.5 cm-1; UV (EtOH) λmax (E): 223 (11,200);

$^1$H NMR (CDCl$_3$) δ:6.29 (d, J =3.1 Hz, 1 H), 6.26 (d, J =3.2 Hz, 1 H), 4.67 (s, 2 H), 4.51 (s, 2 H), 3.39 (s, 3 H), 2.40 (br s, 1 H), 1.33 (m, 1 H), 0.61 (m, 2 H), 0.46 (m, 1 H), 0.36 (m 1H);

MS (EI) m/e (relative intensity):109 (17), 105 (19), 85 (100), 82 (17), 81 (45), 79 (19), 69 (61), 57 (64), 55 (21), 53 (18);

Analysis Found: C, 61.65, H, 7.71.

EXAMPLE 386

3-(α-Cyclopropyl (5-(2-hydroxymethyl (methoxymethylether)furfur-2-yl)-4-hydroxy-5,6,7,8,9, 10-hexahydrocycloocta[b]pyran-2-one (Formula MM-5) Refer to Chart MM Cyclopropyl (5-hydroxymethyl(methoxymethyl)) carbinol of Prepartion 70 (1.5 g) is dissolved in methylene chloride (15 mL) and 2H-cycloocta[b]pyran-2-one of formula MM-4 (1.36 g) is added. Trifluoroacetic acid (5 drops) is added to the reaction mixture at 23° C. and the reaction is stirred overnight. The crude reaction mixture is chromatographed over silica gel (300 g) and eluted with 2.5% methanol in methylene chloride to yield the title product (1.94 g) as a pale yellow glass.

Physical characteristics are as follows:

IR (neat film): 2927, 2855, 1721, 1696, 1666, 1639, 1563, 1257,1203, 1148, 1126, 1102, 1072, 1040, 1019 cm-1;

UV (EtOH) λmax (E): 213 (24100), 234 sh (10,600), 292 (8,110); 1H NMR (CDCl$_3$), δ: 7.37 (s, 1 H), 6.35 (d, J =3.3 Hz, 1 H), 6.31 (d, J =3.2 Hz, 1 H), 4.63 (s, 2 H), 4.49 (s, 2 H), 3.97 (d, J =8.7 Hz, 1 H), 3.37 (s, 3 H), 2.62 (m, 2 H), 2.49 (m. 2 H), 1.74 (m, 2 H), 1.60 (n, 2 H), 1.37 (m, 4 H), 1.26 (m, 1 H), 0.58 (m. 3 H), 0.26 (m. 1 H):

MS (EI) m/e (relative intensity): 327 (28), 326 (69). 298 (12). 175 (15). 174 (100). 149 (41), 57 (12), 55 (15), 45 (12), 43 (14);

Analysis Found: C, 68.20, H, 7.43.

PREPARATION 71

Methoxymethylthiophenemethan-2-ol (Formula NN-2) Refer to Chart NN

2-Thiophenemethanol of formula NN-1 (50 g) is dissolved in methylene chloride (400 mL) and Hunig's Base (84 mL) is added. The reaction is cooled to 0° C. and chloromethyl methyl ether (36.6 mL) is added dropwise. The reaction is allowed to warm to 23° C. and stirred for 2 hours. No reaction is observed. The reaction mixture is refluxed for 2 more hours with almost no reaction observed by TLC. A second equivalent of chorormethyl methyl ether (37 mL) is added and the starting alcohol is rapidly converted to the desired ether. The reaction is washed with water (2×500 mL) and dried over MgSO$_4$. Filtration and concentration in vacuuo gives a colorless oil which is purified by column chromatography over silica gel (2 Kg), eluting with 30% ether/pentane to give the title product as a colorless oil (51.78 g).

Physical characteristics are as follows:

$^1$H NMR 300 MHz, CDCl$_3$ δ:7.30 (m, 1 H), 7.02 (m, 1 H), 6.97 (m, 1 H), 4.72 (s, 2 H), 4.69 (s, 2 H), 3.41 (s, 3 H).

PREPARATION 72

Cyclopropyl (5-hydroxymethyl(methoxymethyl) thien-2-yl) carbinol (Formula NN-3) Refer to Chart NN Methoxymethylthiophenemethan-2-ol of Preparation 71 (31.5 g) is dissolved in THF (150 mL) and cooled to −78°

C. The solution is degassed under nitrogen and nButyl-lithium (Aldrich, 1.6M in hexane, 133 mL) is added. The reaction is stirred at −78° C. for 1 h., then the cyclopropane carboxyaldehyde (20.9 mL) is added. The color changed from very dark to a pale yellow, and the reaction is allowed to warm to 0° C. The reaction is quenched with saturated ammonium chloride solution (40 mL) and extracted with ether (1.5L). The ether extract is washed with water (2×400 mL) and brine. The ethereal solution is dried over $MgSO_4$, filtered and concentrated in vacuo. The product is purified with column chromatography (2 kg silica gel), eluting with 1:1 ether:pentane, giving 42.4 g of the title product as a colorless oil.

Physical characteristics are as follows:

IR (neat film): 3422, 3004, 2944, 2885, 1375, 1212, 1147, 1099, 1042, 1031, 970.2, 939.3, 920.0, 826.5, 810.1 cm-1;

UV (EtOH) λ, max (E): 216 sh (2940), 240 (10,300);

$^1$H NMR 300 MHz, ($CDCl_3$) δ: 6.89 (m, 2 H), 4.70 (s, 2 H), 4.69 (s, 2 H), 4.19 (d,J =8.2 Hz, 1 H), 3.41 (s, 3 H), 2.20 (br s, 1 H), 1.26 (m, 1 H), 0.64 (m, 2 H), 0.49 (m, 1 H), 0.43 (m, 1 H);

MS (EI) m/e (relative intensity): 228 (33), 167 (32), 139 (63), 138 (51), 125 (26), 111 (30), 91 (23), 69 (100), 53 (23);

Analysis Found: C. 57.54, H, 7.13.

EXAMPLE 387

3-(α-Cyclopropyl (5-(2-hydroxymethyl (methoxymethylether)thien-2-ylmethyl)-4-hydroxy-5,6,7,8,9, 10-hexahydrocycloocta[b]pyran-2-one (Formula NN-5) Refer to Chart NN 2H-Cycloocta[b]pyran-2-one (3.0 g) and cyclopropyl (5-hydroxymethyl(methoxy-methyl)thien-2-yl) carbinol of Preparation 72 (3.65 g) are dissolved in methylene chloride (5.0 mL) and trifluoroacetic acid (13 drops) is added. The reaction is stirred at 23° C. for 2 hours. All material goes into solution and the reaction mixture is a pale yellow color. The crude reaction is applied to a silica gel (400 g) column and eluted with ethyl acetate, giving the title product (6.05 g) as a pale yellow foam.

Physical characteristics are as follows:

IR (neat film): 2927, 2855, 1698, 1662, 1632, 1557, 1407, 1247, 1220, 1202, 1171, 1147, 1102, 1071, 1044 cm$^{-1}$;

UV (EtOH) λmax (E): 208 sh (20,700), 209 (20,800), 220 sh (14,600), 241 (10, 400), 294 (9, 110);

$^1$H NMR ($CDCl_3$) 300 MHz, δ: 7.01 (d, J=4.4 Hz, 1 H), 6.90 (d, J =3.5 Hz, 1 H), 6.44 (s, 1 H), 4.68 (s, 4H), 3.99 (d, J=8.7 Hz, 1 H), 3.40 (s, 3 H), 2.63 (m. 2 H), 2.47 (t, J =6.2 Hz, 2 H), 1.75 (m, 2H), 1.60–1.36 (m, 7 H), 0.75 (m, 1 H), 0.59 (m, 2 H), 0.39 (m, 1 H);

MS (EI) m/e (relative intensity): 343 (19), 342 (54), 314 (14), 190 (44), 135 (13), 97 (23), 69 (13), 55 (18), 41 (19);

Analysis Found: C, 64.89, H, 7.01, S, 7.75.

PREPARATION 73

N-Carbobenzoxyfurfur-2-ylamine (Formula OO-2) Refer to Chart OO

Furfurylamine of formula OO-1 (21.97 g) is added to a saturated $NaHCO_3$ solution. Carbobenzyloxy chloride (38.5 g) is added portionwise over 5–10 minutes. After complete addition the reaction is stirred for 30 minutes and then diluted with ether. The ether is separated, dried, and solvent removed in vacuo. The resulting oil is chromatographed over silica gel (eluting with 25–50% EtOAc/hexane) to yield 30 g of pure title product as a colorless oil. An addition 18 g of title product is isolated which has a slight yellow color.

Physical characteristics are as follows:

IR (mull) 3331, 1706, 1708, 1525, 1455, 1248, 1220, 698 cm$^{-1}$.

H-NMR ($CDCl_3$) 7.34 (s, 6H), 6.30 (s, 1H). 6.22 (s, 1H), 5.11 (s, 2H), 4.36 (s, 2H).

Mass spectrum: ions at m/e (relative intensity) 231 (0.3), 140 (99), 96 (81), 91 (87), 81 (18), 69 (22), 65 (17), 53 (12), 41 (12), 38 (13).

PREPARATION 74

Cyclopropyl-(5-(N-carbobenzoxyfurfurylamine)) ketone (Formula OO-3) Refer to Chart OO N-Carbobenzoxyfurfur-2-ylamine of Preparation 73 (4.54 g) and cyclopropane carbonyl chloride (3.05 g) is added to methylene chloride with stirring. To that mixture is added $AlCl_3$ (total of 5.28 g) portionwise. After complete addition, the reaction is stirred for an additional 30 minutes and then poured over ice. The reaction is extracted with methylene chloride and the combined organic extracts are washed with 2N HCl to disperse the emulsion. The extracts are dried and evaporated to yield a dark oil. Chromatography over silica gel (elufing with 25–50% EtOAc/hexane) affords 3.2 g of the title product.

Physical characteristics are as follows:

IR (mull) 3259, 2953, 2940, 2925, 1707, 1679, 1655, 1550, 1524, 1270 cm$^{-1}$.

H-NMR ($CDCl_3$) 7.93 (t, 1H, NH), 7.45 (d, 1H), 7.35 (m, 5H), 6.57 (d, 1H), 5.04 (s, 2H), 4.28 (d, 2H), 2.68 (m, 1H), 0.95 (m, 4H).

Mass spectrum: ions at m/e (relative intensity) 299 (1), 258 (0.7), 246 (0.2), 230 (3), 208 (15), 191 (2), 164 (61), 150 (18), 91 (99).

Anal. Found: C, 68.16; H, 5.70; N, 4.62.

PREPARATION 75

Cyclopropyl-(5-(N-carbobenzoxyfurfurylamine)) methanol ethylether (Formula OO-4) Refer to Chart OO Cyclopropyl-(5-(N-carbobenzoxyphenyl furfurylamine)) ketone of Preparation 74 (500 mg) is added to a 1/1 mixture of THF and ethanol (5 mL). To that solution is added $NaBH_4$ (55 mg). The reaction is stirred over night and then quenched by adding 1N HCl. The reaction is extracted with ether, dried and solvent removed to yield 500 mg of the title product as a colorless oil.

Physical characteristics are as follows:

H-NMR ($CDCl_3$) 7.3 (m, 5H), 6.18 (m, 2H), 5.10 (s, 2H), 4.32 (d. 2H), 3.56 (d, 1H), 3.45 (q, 2H), 1.25 (m), 1.17 (t, 3H), 0.64 (m, 1H), 0.45 (m, 2H), 0.23 (m, 1H).

Mass spectrum: ions at m/e (relative intensity) 329 (0.7), 283 (9), 238 (11), 222 (3), 210 (5), 194 (4), 179 (7), 166 (8), 148 (45), 132 (21), 107 (45), 91 (99).

EXAMPLE 388

3-(α-Cyclopropyl (5-(N-carbobenzoxy) aminomethyl)furfur-2-yl)-4-hydroxy-5,6,7,8,9,10-hexahydrocycloocta[b]pyran-2-one (Formula OO-6) Refer to Chart OO To a mixture of 2H-cycloocta[b]pyran-2-one of formula OO-5 (196 mg) and the title ether of Preparation 75 (300 mg) in methylene chloride is added several drops of TFA. The reaction is stirred for 15 minutes, the solvent removed in vacuo and the resulting oil chromatographed over silica gel (40% EtOAc/hexane) to yield 347 mg of the title product.

Physical characteristics are as follows:

H-NMR (CDCl$_3$) 7.29 (s, 5H), 6.27 (d, 1H), 6.13 (d, 1H), 5.25 (t. 1H, NH), 5.06 (s, 2H), 4.26 (d, 2H), 3.84 (d, 1H), 2.56 (t, 2H), 2.45 (t, 2H), 1.69 (m, 2H), 1.55 (m. 2H), 1.35 (m, 4H), 0.54 (m, 3H), 0.22 (m, 1H).

PREPARATION 76

N-Carbobenzoxythien-2-ylamine (Formula PP-2) Refer to Chart PP

Thienylamine of formula PP-1 (22.6 g) is added to a saturated NaHCO$_3$ solution. Carbobenzyloxy chlroide (34.0 g) is then added portionwise over 5–10 minutes. After complete addition the reaction is stirred for 30 minutes and then diluted with ether. The ether is separated, dried, and solvent removed in vacuo. The resulting oil is chromatographed over silica gel (eluting with 1/1 EtOAc/hexane) to yield 40.2 g of pure title product as a colorless oil which solidifies on standing.

Physical characteristics are as follows:

IR (mull) 3349, 2927, 2955, 2927, 1684, 1539, 1526, 1456, 1269, 701 cm$^{-1}$.

H-NMR (CDCl$_3$) 7.3 (s, 5H), 7.19 (d, 1H), 6.92 (m, 2H), 5.10 (s, 2H), 4.50 (d, 2H).

Mass spectrum: ions at m/e (relative intensity) 247 (0.2), 156 (99), 112 (22), 108 (10), 107 (9), 97 (20), 85 (19), 79 (11), 85 (19), 65 (8), 44 (8).

PREPARATION 77

Cyclopropyl-(5-(N-carbobenzoxythien-2-ylamine)) ketone (Formula PP-3) Refer to Chart PP N-Carbobenzoxythien-2-ylamine of Preparation 76 (4.94 g) and cyclopropropane carbonyl chloride (3.12 g) is added to methylene chloride with stirring. To that mixture is added AlCl$_3$ (total of 3.12 g) portionwise. After complete addition, the reaction is stirred for an additional 30 minutes and then poured over ice. The reaction is extracted with methylene chloride and the combined organic extracts are washed with 2N HCl to disperse the emulsion. The extracts are dried and evaporated to yield an oil which slowly crystallizes on standing. Recrystallization from EtOAc/hexane affords 1.47 g of the tide product as a slightly grey solid.

Physical characteristics are as follows:

H-NMR (CDCl$_3$)

PREPARATION 78

Cyclopropyl-(5-(N-carbobenzoxythien-2-ylamine)) methanol ethylether (Formula PP-4) Refer to Chart PP Cyclopropyl-(5-(N-carbobenzoxythien-2-ylamine)) ketone of Preparation 77 (500 mg) is added to a 1/1 mixture of THF and ethanol (5 mL). To that solution is added NaBH$_4$ (51 mg). The reaction is stirred over night and then quenched by adding 1N HCl. The reaction is extracted with ether, dried and solvent removed to yield 500 mg of the rifle product as a colorless oil.

Physical characteristics are as follows:

H-NMR (CDCL$_3$) 7.20 (s, 5H), 6.66 (s, 2H), 5.40 (t, 1H), 4.98 (2H), 4.34 (d, 2H), 3.70 (d, 1H), 3.34 (m, 2H), 1.07 (t, 3H), 0.52 (m, 1H), 0.8 (m, 2H), 0.16 (m, 1H).

EXAMPLE 389

3-(α-Cyclopropyl (5-(N-carbobenzoxy) aminomethyl)thien-2-ylmethyl)-4-hydroxy-5,6,7,8,9, 10-hexahydrocycloocta[b]pyran-2-one (Formula PP-6) Refer to Chart PP To a mixture of 2H-cycloocta[b]pyran-2-one of formula PP-5 (150 mg) and cyclopropyl-( 5-(N-carbobenzoxy thien-2-ylamine))-methanol ethylether of Prepartion 78 (500 mg) in methylene chloride (5 mL) is added several drops of TFA. The reaction is stirred for 15 minutes, the solvent removed in vacuo and the resulting oil chromatographed over silica gel (40% EtOAc/hexane) to yield 163.1 mg of the title product.

Physical characteristics are as follows:

H-NMR (CDCl$_3$) 7.31 (s, 5H), 6.92 (d, 1H), 6.78 (d, 1H), 5.31 (t, 1H), 5.09 (s, 2H), 4.43 (d, 2H), 3.86 (d, 1H), 2.60 (t, 2H), 2.48 (t, 2H), 1.74 (m, 2H), 1.3 (m, 6H), 0.70 (m, 1H), 0.53 (m, 2H), 0.37 (m, 1H).

Mass spectrum: ions at m/e (relative intensity) 493 (5), 402 (16), 358 (10), 342 (38), 329 (38), 314 (7), 299 (7), 276 (5), 250 (47), 207 (13), 190 (14), 177 (19), 164 (18), 135 (13), 91 (99).

PREPARATION 79

5-(1-cyclopropane-1-hydroxy)-2-furfurylamine (Formula QQ-2) Refer to Chart QQ

To a flask containing a solution of 5.0 g of furfuryl amine of formula QQ-1 in 150 mL of THF under a nitrogen atmosphere at −78° C. is slowly added 67.6 mL of a 1.6M n-butyllithium-hexane solution. The dark brown solution is allowed to stir at −78° C. for 1 hour and is then treated with 4.25 mL of cyclopropanecarboxaldehyde. Stirring at 0° C. is continued for 2.5 hours. The reaction mixture is treated with saturated ammonium chloride and the volatiles are removed under reduced pressure. The residue is partitioned between ethyl acetate and water. The organic phase is washed with brine, dried (magnesium sulfate) and concentrated under reduced pressure. The residue is adsorbed onto silica gel and flash chromatographed with 20% methanol in methylene chloride to yield 240 mg of the title product as a tan oil.

Physical characteristics are as follows:

$^1$H NMR (CDCl$_3$) δ6.23 (d, J =3.1 Hz, 1H), 6.09 (d, J =3.1 Hz, 1H), 4.01 (d, J =8.4 Hz, 1H), 3.81 (s, 2H), 1.82 (br s, 1H), 1.35 (m, 1H), 0.65–0.60 (m, 2H), 0.45 (m, 1H), 0.36 (m, 1H).

PREPARATION 80

N-(5-(α-hydroxycyclopropylmethyl)-furfur-2-ylmethyl) 4-fluorobenzenesulfonamide (Formula QQ-3) Refer to Chart QQ To a flask containing a solution of 0.120 g of 5-(1-cyclopropane-1-hydroxy)-2-furfurylamine of Preparation 79 in 4 mL of methylene chloride under a nitrogen atmosphere at 0° C. is added 0.12 mL of triethylamine. The solution is stirred at 0° C. for 20 min. and then treated with a solution of 0.14 g of 4-fluorobenzenesulfonyl chloride (in 1 mL of methylene chloride) by syringe. The reaction mixture is stirred overnight at room temperature and poured into 100 mL of ethyl acetate. The organics are washed with water, brine, dried (magnesium sulfate). and concentrated under reduced pressure. The residue is adsorbed onto silica gel and flash chromatographed with 5% methanol in methylene chloride to yield 199 mg of the title product as a tan oil.

Physical characteristics are as follows:

$^1$H NMR (CDCl$_3$) δ7.80–7.75 (m, 2H), 7.09–7.04 (m, 2H), 6.05–5.89 (m, 2H). 4.10 (d, J =5.9 Hz, 2H) 3.79 (d, J =8.5 Hz, 1H), 2.94 (br s, 1H), 1.20–1.12 (m. 1H), 0.57–0.49 (m, 2H), 0.45–0.34 (m, 1H), 0.22–0.18 (m, 1H);

EI-MS: 137 (9999), 148 (9839), 95 (7979), 122 (5619), 69 (4939), 96 (4779), 40 (4089), 121 (3829), 136 (3809), 109 (3739).

EXAMPLE 390

N-[3-[Cyclopropyl(5,6,7,8,9,10-hexhydro-4-hydroxy-2-oxo-2H-cycloocta[b]pyran-3-yl)methyl]furfur-2-ylmethyl]4-fluorobenzenesulfonamide (Formula QQ-5) Refer to Chart QQ To a stirring solution of 0.197 g of the title carbinol of Preparation 80 in 2 mL of methylene chloride under nitrogen is added 0.129 g of cyclooctanone pyrone of formula QQ-4 followed by 3 drops of trifluoroacetic acid. The resulting yellow suspension is left to stir at room temperature for 2 hours. The reaction mixture is poured into ethyl acetate and washed with water, brine, dried (magnesium sulfate), filtered and concentrated under reduced pressure. The residue is adsorbed onto silica gel and flash chromatographed with 30% hexane in ethyl acetate to yield 201 mg of the title product as a white foam.

Physical characteristics are as follows:

IR (mull) 2925, 2953, 2855, 1154, 1666, 1166, 1561 cm$^{-1}$;

UV (95% ethanol) 217. 31600, 295. 8390;

$^1$H NMR (CDCl$_3$) δ7.87 (m, 2H), 7.16 (m, 2H), 6.95 (s, 1H), 6.25 (d, J =3.3 Hz, 1H), 6.05 (d, J =3.0 Hz, 1H), 5.01 (t, J =6.0 Hz, 1H), 4.15 (d, J =9.9 Hz, 2H), 3.85 (d, J =8.4 Hz, 1H), 2.78–2.43 (m, 4H), 1.75–1.37 (m, 8H), 1.28 (m, 1H), 0.65–0.44 (m, 3H), 0.23 (m. 1H);

EI-MS: 326 (9999), 174 (5999), 95 (2689), 327 (2419), 161 (2299), 55 (2069), 133 (1909), 271 (1829), 298 (1789), 207 (1659);

Elem. Anal. Found: C, 60.92, H, 5.66, N, 2.66, S, 6.28, F, 4.10.

PREPARATION 81

N-(5-(α-hydroxycyclopropylmethyl)-furfur-2-ylmethyl) 4-cyanobenzenesulfonamide] (Formula RR-2) Refer to Chart RR To a flask containing a solution of 0.120 g of 5-(1-cyclopropane-1-hydroxy)-2-furfurylamine of formula RR-1 in 4 mL of methylene chloride under a nitrogen atmosphere at 0° C. is added 0.12 mL of triethylamine. The solution is stirred at 0° C. for 20 min. and then treated with a solution of 0.15 g of 4-cyanobenzenesulfonyl chloride (in 1 mL of methylene chloride) by syringe. The reaction mixture is stirred overnight at room temperature and poured into 100 mL of ethyl acetate. The organics are washed with water, brine, dried (magnesium sulfate), and concentrated under reduced pressure. The residue is adsorbed onto silica gel and flash chromatographed with 5% methanol in methylene chloride to yield 119 mg of the title product as a tan oil.

Physical characteristics are as follows:

$^1$H NMR (CDCl$_3$) δ7.87 (m, 2H), 7.71 (m, 2H), 6.05 (m, 1H). 5.95 (m. 1H), 4.19–4.15 (m, 2H), 3.78 (d, J =8.5 Hz, 1H), 2.87 (br s, 1H), 1.22–1.10 (m, 1H), 0.63–0.48 (m, 2H), 0.41–0.33 (m, 1H), 0.24–0.17 (m, 1H);

EI-MS: 137 (9999), 122 (6039), 148 (4939), 109 (3999), 121 (3959), 40 (3619), 69 (3599), 102 (3499), 136 (2859), 26 (2459).

EXAMPLE 391

N-[3-[Cyclopropyl(5,6,7,8,9,10-hexhydro-4-hydroxy-2-oxo-2H-cycloocta[b]pyran-3-yl)methyl]furfur-2-ylmethyl]4-cyanobenzenesulfonamide (Formula RR-4) Refer to Chart RR To a stirring solution of 0.117 g of carbinol of Prepartion 81 in 2 mL of methylene chloride under a nitrogen atmosphere is added 0.075 g of cyclooctanone pyrone of formula RR-3 followed by 3 drops of trifluoroacetic acid. The resulting yellow suspension is left to stir at room temperature for 2 hours. The reaction mixture is poured into ethyl acetate and washed with water, brine, dried (magnesium sulfate) and concentrated under reduced pressure. The residue is adsorbed onto silica gel and flash chromatographed with 30% hexane in ethyl acetate to yield 144 mg of the title product as a yellow foam.

Physical characteristics are as follows:

IR (mull) 2953, 2922, 2868, 2854, 1667, 1561, 1162 cm$^{-1}$

UV (95% ethanol) 220. 30700, (SH) 235. 21500, (SH) 279. 7840, 286. 8870, (SH) 293. 8310;

$^1$H NMR (CDCl$_3$) δ7.96 (d, J=8.5 Hz, 2H), 7.76 (d, J=8.5 Hz, 2H), 6.25 (d, J=3.3 Hz, 1H), 6.07 (d, J=3.0 Hz, 1H), 5.15 (m, 1H), 4.22 (m, 2H), 3.85 (m, 1H), 2.65 (m, 2H), 2.45 (m, 2H), 1.60 (m, 8H), 1.25 (m, 1H), 0.60 (m, 3H), 0.20 (m, 1H);

Elem. Anal. Found: C, 62.26, H. 5.48, N, 5.38, S, 6.08.

PREPARATION 82

Cyclopropyl (5-aminomethylthien-2-yl) carbinol (Formula SS-2) Refer to Chart SS

Thienylamine of formula SS-1 (0.95 mL) is dissolved in dry THF under a nitrogen atmosphere and cooled to −78° C. n-Butyllithium (Aldrich, 1.6M in hexane, 13.4 mL) is added and the reaction turned a deep purple color. The reaction is allowed to warm to 0° C. for 10 min, then recooled to −78° C. for the addition of the aldehyde (0.82 mL). A thick slurry forms and stirring becomes difficult. The reaction is allowed to warm to 0° C., then quenched with ammonium chloride solution (10 mL). The reaction is extracted with EtOAc (200 mL) and washed with water (2×40 mL) and brine. The organic phase is dried over MgSO$_4$, filtered and concentrated in vacuo. Chromatography over silica gel (300 g) eluting with 5% MeOH in CH$_2$Cl$_2$ gives the title product (356 mg) as a colorless oil.

Physical characteristics are as follows:

$^1$H NMR 300 MHz, CDCl$_3$ δ:6.78 (d, J =3.5 Hz, 1 H), 6.69 (d, J =3.6 Hz, 1 H), 4.05 (d, J =8.2 Hz, 1 H), 3.87 (s, 2 H), 1.18 (m, 1 H), 0.55 (m, 2 H), 0.43 (m, 1 H), 0.28 (m, 1 H).

PREPARATION 83

N-(5-((α-Hydroxy)cyclopropylmethyl)thien-2-ylmethyl)4-cyanobenzenesulfonamide (Formula SS-3) Refer to Chart SS Cyclopropyl (5-aminomethylthien-2-yl) carbinol of Preparation 82 (183 mg) in methylene chloride (5.0 mL) is cooled to 0° C. and triethylamine (170 uL) is added. 4-Cyanobenzenesulfonyl chloride (200 mg) is dissolved in methylene chloride (3.5 mL) and this solution is slowly added to the amine solution. The reaction is stirred for 20 min at 0° C., then poured into EtOAc (200 mL) and washed with water (2×40 mL) and brine. The organic phase is dried over MgSO$_4$, filtered and concentrated in vacuo to a yellow oil which is purified by chromatography over silica gel (300 g), elution with 5% MeOH in CH$_2$Cl$_2$ gives the title product as a colorless oil (284 mg, 82%) which is crystallized from EtOAc/hexane as a white powder.

Physical characteristics are as follows:

IR (mull): 2924, 1162, 2953, 1334, 2854, 1329, 3260, 3308, 2869, 1456, 1435, 1090, 1442, 1069 cm$^{-1}$;

UV (EtOH) λ, max (E): 239 (23,100), 276 (2080), 285 (1620);

$^1$H NMR 300 MHz, CDCl$_3$, δ: 7.92 (d, J =6.7 Hz, 2 H), 7.64 (d, J =6.6 Hz, 2 H), 6.77 (dd, J =0.7, 3.5 Hz, 1 H), 6.70 (d, J =3.6 Hz, 1 H), 5.20 (br m, 1 H), 4.37 (d, J =5.6 Hz, 2 H), 2.21 (br 1 H), 1.72 (m, 1 H), 0.66 (m, 2 H), 0.48 (m, 1 H), 0.37 (m, 1 H); MS (EI) m/e (relative intensity): 320 (30), 153 (100), 152 (31), 140 (26), 138 (33), 137 (52), 125 (24), 112 (46), 97 (25), 69 (65);

Analysis Found: C, 54.86, H, 4.62, N, 7.90, S, 18.20.

EXAMPLE 392

N-[3-[Cyclopropyl(5,6,7,8,9,10-hexhydro-4-hydroxy-2-oxo-2H-cycloocta[b]pyran-3-yl)methyl]thien-2-ylmethyl]4-cyanobenzenesulfonamide (Formula SS-5) Refer to Chart SS N-(5-((cc-Hydroxy)cyclopropylmethyl)thien-2-ylmethyl) 4-cyanobenzenesulfonamide of Preparation 83 (100 mg) and 2H-cycloocta[b]pyran-2-one of formula SS-4 (72 mg) are dissolved in methylene chloride (25 g) and trifluoroacetic acid (22 ga needle, 3 drops) is added. Most of the materials go into solution immediately and on addition of 2 more drops of trifluoroacetic acid the reaction becomes completely homogeneous. The reaction is stirred for 10 min then poured into EtOAc (200 mL) and washed with water (2×40-mL) and brine. The organic layer is dried over MgSO$_4$, filtered and concentrated in vacuo. The residue is chromatographed over silica gel (100 g) eluting with 30% hexane in ethyl acetate to give the title product (148 mg) as a white foam.

Physical characteristics are as follows:

IR (mull): 2923, 2952, 2855, 1162, 2868, 1667, 1560, 1338, 1461, 1456, 1183, 1407, 1447, 1201, 1091, 634.6, 836.1, 1377 cm$^{-1}$;

UV (EtOH) λ, max CE): 220 (29,300), 239 (23,800), 279 sh (7,790), 287 (8,910), 293 sh (8,590);

$^1$H NMR, 300 MHz, CDCl$_3$, δ: 7.94 (dd, J =1.8, 6.7 Hz, 2 H), 7.78 (dd, J =1.9, 6.7 Hz, 2 H), 6.85 (dd, J =1.4, 3.5 Hz, 1 H), 6.71 (d, J =3.6 Hz, 1 H), 6.43 (br s, 1 H), 5.42 (t, J =6.1 Hz, 1 H), 4.34 (d, J =6.0 Hz, 2 H), 3.84 (d, J =8.4 Hz, 1 H), 2.63 (m, 2 H), 2.50 (m, 2 H), 1.76 (m, 2 H), 1.61 (m, 2 H), 1.47–1.23 (m, 5 H), 0.70 (m, 1 H), 0.54 (m, 2 H), 0.32 (m, 1 H);

MS (EI) m/e (relative intensity) 343 (27), 342 (100), 330 (26), 329 (28), 207 (79), 190 (25), 137 (28), 135 (24), 102 (23), 55 (20);

Analysis Found: C, 61.17, H, 5.82, N, 5.23, S, 11.57.

PREPARATION 84

N-(5-((α-Hydroxy)cyclopropylmethyl)thien-2-ylmethyl)4-fluorobenzenesulfonamide (Formula TT-2) Refer to Chart TT Cyclopropyl (5-aminomethylthien-2-yl) carbinol of formula TT-1 (183 mg) is dissolved in methylene chloride (25 mL) and triethylamine (170 uL) is added. The reaction is cooled to 0° C. and a soln. of the chlorosulfonate (194 mg) in methylene chloride (2.0 mL) is added slowly. The reaction is stirred at 0° C. for 1 h then at 23° C. for 1.5 h. The reaction is poured into EtOAc (200 mL) and washed with water (2×40 mL) and brine. The organic phase is dried over MgSO$_4$, filtered and concentrated in vacuo to a yellow oil. The product is isolated by chromatography over silica gel (150 g), eluting with 5% MeOH in CH$_2$Cl$_2$. The product is crystallized from EtOAc/hexane as white crystals (219 mg).

Physical characteristics are as follows:

IR (mull): 1165, 2924, 1156, 1330, 3260, 2954, 3310, 2854, 2870, 1596, 1294, 841.0, 1091, 1496, 1433 cm$^{-1}$;

UV (EtOH) λ, max (E): 225 (12,300), 236 sh (11,300);

$^1$H NMR 300 MHz, CDCl$_3$, δ: 7.87 (dd, J =5.0, 8.7 Hz, 2 H), 7.20 (t, J =8.6 Hz, 2 H), 6.80 (d, J =3.5 Hz, 1 H), 6.72 (d, J =3.5 Hz, 1 H), 4.77 (br t, J =5.5 Hz, 1 H), 4.31 (d, J =5.9 Hz, 2 H), 4.13 (d, J =8.5 Hz, 1 H), 2.02 (br s, 1 H), 1.21 (m, 1 H), 0.64 (m, 2 H), 0.48 (m, 1 H),0.38 (m, 1 H);

MS (EI) m/e (relative intensity): 182 (82), 181 (32), 153 (100), 152 (36), 140 (28), 138 (29), 137 (48), 112 (70), 95 (27), 69 (59);

Analysis Found: C, 52.59, H, 4.76, N, 4.03.

EXAMPLE 393

N-[3-[Cyclopropyl(5,6,7,8,9,10-hexhydro4-hydroxy-2-oxo-2H-cycloocta[b]pyran-3-yl)methyl]thien-2-ylmethyl]4-cyanobenzenesulfonamide (Formula TT-4) Refer to Chart TT 2H-Cycloocta[b]pyran-2-one of formula TT-3 (64 mg) and N-(5-((α-hydroxy)cyclopropylmethyl)thien-2-ylmethyl)4-fluorobenzenesulfonamide of Preparation 84 (100 mg) are dissolved in methylene chloride (25 mL) and trifluoroacetic acid (3 drops) is added. The reaction is stirred at 23° C. for 45 min. then poured into EtOAc (200 ml) and washed with water (2×40 mL) and brine. The organic layer is dried over MgSO$_4$, filtered and concentrated in vacuo. The product is isolated by column chromatography over silica gel (150 g), eluting with 30% EtOAc in hexane giving the title product (143 mg) as a white foam.

Physical characteristics are as follows:

IR (mull): 2924, 2953, 2855, 1154, 1663, 1166, 1559, 1236, 1091, 838.1, 1462, 1456, 1407, 1202, 1494 cm$^{-1}$;

UV (EtOH), λ, max, (relative intensity): 211 sh (25,600), 216 (26,800), 242 sh (10,200), 295 (8,950);

$^1$H NMR 300 MHz, CDCl$_3$, δ: 7.87 (m, 2 H), 7.17 (m, 2 H), 6.87 (dd, J =1.4, 3.6 Hz, 1 H), 6.72 (d, J =3.6 Hz, 1 H), 5.03 (br t, J =6.1 Hz, 1 H), 4.29 (d, J =6.1 Hz, 2 H), 3.87 (d, J =9.1 Hz, 1 H), 2.63 (m, 2 H), 2.49 (m, 2 H), 1.76 (m, 2 H), 1.65–1.23 (m, 7 H), 0.71 (m, 1 H), 0.54 (m, 2 H), 0.33 (m, 1 H);

MS (EI) m/e (relative intensity): 343 (25), 342 (100), 330 (19), 329 (22), 207 (43), 190 (26), 137 (23), 136 (17), 95 (23), 55 (21);

Analysis Found: C, 57.37, H, 5.32, N, 2.62, S, 11.62.

PREPARATION 85

Cyclopropyl (5-methyl-4-hydroxymethylthien-2-yl) carbinol (Formula UU-2) Refer to Chart UU Thiophene-3-methanol of formula UU-1 (4.56 g) is added to THF (100 mL) and cooled to −78° C. n-Butyl lithium (55 cc) is then added and the reaction stirred for 2 hours at −78°

C. and then the cooling bath is removed for 30 minutes. The reaction temperature is again reduced to −78° C. and methyl iodide (5.68 g), in THF (5 mL), is added. The reaction is stirred for 1.3–1.0 hours at room temperature and then cooled back to −78° C. n-Butyl lithium is then added and the reaction is left stirring for 1 hour at −78° C. and then the cooling bath removed for 30 minutes and cooled back to −78° C. Cyclopropyl carboxaldehyde (2.8 g) is then added in a single portion and stirring continued for 30 minutes. The reaction is quenched with saturated NH4Cl and extracted with ether. The ether extracts are dried and solvent evaporated in vacuo to yield a pale brown oil. Silica gel chromatography (400 g silica gel; eluting with 1/1 EtOAc/hexane) affords 1.21 g of the title product.

Physical characteristics are as follows:

H-NMR (CDCl$_3$)6.82 (s, 1H), 4.43 (s, 2H), 3.99 (d, 1H), 3.34 (broad, OH), 3.03 (broad, OH), 2.36 (s, 3H), 1.24 (m, 1H), 0.49 (m. 2H), 0.34 (m, 1H), 0.28 (m. 1H).

EXAMPLE 394

3-(α-Cyclopropyl (5-methyl-4-hydroxymethylthien-2-ylmethyl)-4-hydroxy- 5,6,7,8,9,10-hexahydrocycloocta[b]pyran-2-one (Formula UU-4) Refer to Chart UU The diol (400 mg) of Preparation 85 and cyclooctyl pyrone of formula UU-3 (450 mg) are dissolved in methylene chloride (25 mL) at 23° C. Trifluoroacetic acid (22 ga needle, 3 drops) is added and the reaction is stirred for 45 minutes. The reaction is poured into EtOAc (400 mL) and washed with water (2×50 mL) and brine. The organic layer is dried over MgSO$_4$, filtered and concentrated in vacuo. The residue is chromatographed over silica gel (300 g), eluting with 30% EtOAc in CH$_2$Cl$_2$ to give the title product (309 mg) as a white foam.

Physical characteristics are as follows:

IR (mull): 2926, 2952, 2854, 1667, 2868, 1555, 1202, 1463, 1456, 1407, 1230, 1633, 1247, 2994, 1377 cm$^{-1}$;

$^1$H NMR 300 MHz, CDCl$_3$, δ: 7.10 (d, J =1.4 Hz, 1 H), 6.53 (s,1 H), 4.55 (s, 2 H), 3.93 (d, J =9.1 Hz, 1 H), 2.62 (m, 2 H), 2.47 (m, 2 H), 2.40 (s, 3 H), 1 60 (m. 2 H), 1.47–1.28 (m, 8 H), 0.72 (m, 1 H), 0.58 (m, 2 H), 0.34 (m, 1 H).

PREPARATION 86

2-Carboxycycloocatanone (Formula VV-1) Refer to Chart VV

To 2-carboethoxycycloocatanone, prepared as described in Organic Synthesis Vol 47, p 20 (16.3 g), is added 0.5N NaOH (160 mL) at 0° C. After stirring for 3 hours below room temperature the reaction is warmed to ambient temperature for 15.5 hours. The reaction is washed with ether (50 mL) and hexane (50 mL) and the aqueous layer is then acidified with 12N HCl at 0° C. The precipitated acid is collected on a filter by suction and washed with water (3×20 mL) and CCl$_4$ (2×20 mL) to give 16.8 g of pure title product.

Physical characteristics are as follows:
H-NMR

PREPARATION 87

2,2-Dimethyl-5,6,7,8,9,10-hexahydro-[4H]-cycloocta-1,3-dioxin-4-one (Formula VV-2) Refer to Chart VV To 2-carboxycyclooctanone of Preparation 86 (16.8 g) is added acetone (15 mL), acetic anhydride (20 mL) and sulfuric acid (0.8 mL, added dropwise) at 0° C. As soon as the sulfuric acid is added the solid dissolved and stirring continued for 1 hour at 0° C. and then the reaction is placed in the refrigerator (4° C.) overnight. The reaction is poured into NaHCO$_3$ (500 mL) containing ice and then stirred for 1 hour at room temperature. The solid is collected on a filter and washed with water and air dried to yield 10.50 g of the product. Recrystallization from ether affords 8.9 g of the title product.

Physical characteristics are as follows:
MP 73.5°–4.5° C.

EXAMPLE 395

3-(α[S]-Ethylbenzyl)-4-hydroxy-5,6,7,8,9,10-hexahydrocycloocta[b]pyran-2-one (Formula VV-5) Refer to Chart VV 3[R]-Phenylvaleric acid of formula VV-3 (400 mg) is added to methylene chloride (5 mL) followed by oxalyl chloride (0.21 mL). That mixture is heated at reflux for 3 hours. The methylene chloride is removed and 1,3,5-trimethylbenzene (10 mL) is added. The solution of the acid chloride is then heated to reflux temperatures and the title product of Preparation 87 [VV-2](210 mg) and triethylamine (210 mg) (both in 1.5 mL of 1,3,5-trimethylbenzene) are added dropwise. After complete addition the reaction is heated for an addition 3 hours. The reaction is cooled to room temperature and the solid removed by filtration. The filtrate is evaporated and the resulting residue is diluted with methanol (35 mL) and 0.5N NaOH (4 mL) and that mixture stirred at room temperature overnight. The methanol is removed and water (35 mL) added. The aqueous is extracted with ether/hexane (2×35 mL) and the aqueous is acidified with 1.6N HCl at 0° C. to pH 3. That aqueous is extracted with ethyl acetate, dried and solvent removed in vacuo to yield 318.5 mg of the title product VV-5. Chromatography over silica gel (EtOAc/methylene chloride 1:8) affords 249.2 mg of the title product.

Physical Characteristics are as follows:
MP 201.0°–2.0° C.

H-NMR 7.36 (m, 5H), 5.8 (s, OH), 4.36 (t, 1H), 2.60 (t, 2H), 2.40 (t, 2H), 2.16 (m, 1H), 2.04 (m, 1H), 1.62 (m, 2H), 1.41 (m, 6H), 1.01 (t, 3H).

[α]D=−156°

EXAMPLE 396

3-(α[R]-Ethylbenzyl)-4-hydroxy-5,6,7,8,9,10-hexahydrocycloocta[b]pyran-2-one (Formula WW-5) Refer to Chart WW 3[S]-Phenylvaleric acid of formula WW-3 (400 mg) is added to methylene chloride (5 mL) followed by oxalyl chloride (0.21 mL). That mixture is heated at reflux for 3 hours. The methylene chloride is removed and 1,3,5-trimethylbenzene (10 mL) is added. The solution of the acid chloride is then heated to reflux temperatures and WW-2 (same as VV-2) (210 mg) and triethylamine (210 mg) (both in 1.5 mL of 1,3,5-trimethylbenzene) are added dropwise. After complete addition the reaction is heated for an additional 7 hours. The reaction is cooled to room temperature and the solid removed by filtration. The filtrate is evaporated and the resulting residue is diluted with methanol (35 mL) and 0.5N NaOH (4 mL) and that mixtured stirred at room temperature overnight. The methanol is removed and water (35 mL) added. The aqueous is extracted with ether/hexane (2×35 mL) and the aqueous is acidified with 1.6N HCl at 0° C. to pH 3. That aqueous is extracted with ethyl acetate, dried and solvent removed in vacuo to yield 287.0 mg of the title product. Chromatography over silica gel (EtOAc/ methylene chloride 1:8) affords 199.4 mg of the title product WW-5.

Physical Characteristics are as follows:

MP 200.5°–1.5° C.

H-NMR 7.36 (m. 5H), 5.8 (s. OH), 4.36 (t, 1H), 2.60 (t. 2H), 2.40 (t. 2H). 2.16 (m, 1H), 2.04 (m, 1H), 1.62 (m, 2H), 1.41 (m, 6H), 1.01 (t, 3H).

$[\alpha]D=+149°$

EXAMPLE 397

N-[3-[Cyclopropyl(5,6,7,8,9, 10-hexahydro-4-hydroxy-2-oxo-2H-cycloocta[b]pyran-3-yl)methyl] phenyl]-N-phenyl-sulfamide (Formula DDD-3 wherein $R_1$ is H and $R_2$ is phenyl) Refer to Chart DDD To a solution of 52.2 mg of 3-[(3-aminophenyl) cyclopropylmethyl]-5,6,7,8,9,10-hexahydro-4-hydroxy-2H-cycloocta[b]pyran-2-one in 2.0 mL of pyridine is added 36.7 mg of N-phenylsulfamoyl chloride (prepared as described in J. A. Kloek; K. L. Leschinsky, J. Org. Chem. (1976) 41:4028). The solution is stirred four days and then concentrated in vacuo. The residue is dissolved in ethyl acetate and water and then washed with two portions of cold 5% aqueous hydrochloric acid. The organic layer is dried sodium sulfate ($Na_2SO_4$) and concentrated to afford 125 mg of an orange solid which is chromatographed over 9 g of 70–230 mesh silica gel (eluted with 5% methanol/ dichloromethane) to afford 55.9 mg of the title compound as a white solid.

Physical characteristics are as follows:

MP 90°–95° C.

Mass spectrum m/z: 495($M^+$+H), 340, 207, 186, 144, 93.

High Resolution Mass Spectrum: Found (m/z) 495.1951 ($M^+$+1).

EXAMPLE 398

N'-[3-[cyclopropyl(5,6,7,8,9,10-hexahydro4-hydroxy-2-oxo-2H-cycloocta[b]pyran-3-yl)methyl] phenyl]-N,N-dimethyl-sulfamide (Formula DDD-3 wherein $R_1$ and $R_2$ are methyl) Refer to Chart DDD Following the general procedure of Example 397 above but utilizing N,N-dimethylsulfamoyl chloride as the sulfonylating reagent, the title compound is prepared.

Physical characteristics are as follows:

MP 190°–193° C.

Mass spectrum m/z: 446(M+), 418, 405, 360, 339, 322, 311, 294, 233, 207, 195, 186, 144, 130, 117.

Anal. Found C, 61.46; H, 6.75; N, 6.10.

EXAMPLE 399

N-[3-[Cyclopropyl(5,6,7,8,9,10-hexahydro-4-hydroxy-2-oxo-2H-cycloocta[b]pyran-3-yl)methyl] phenyl]4-methyl-1-piperazinesulfonamide (Formula DDD-3 wherein $R_1$ and $R_2$ combined form a 4-methylpiperazine ring) Refer to Chart DDD Following the general procedure of Example 397 above but utilizing 4-methylpiperazinyl-sulfamoyl chloride (prepared as described in W. L. Mailer; W. T. Comer; D. Deitchman, J. Med. Chem. (1972) 15:538) as the sulfonylating reagent, the title compound is prepared.

Physical characteristics are as follows:

Mass spectrum m/z: 502($M^+$+1), 391, 338, 324, 241, 177, 163, 149. 99, 71, 58.

High Resolution Mass Spectrum: Found (m/z) 502.2398 ($M^+$+1).

PREPARATION 88

N-Phenyl-3-(cyclopropylhydroxymethyl)-benzenesulfonamide (Formula BBB-3 wherein aryl is phenyl) Refer to Chart BBB To a solution of 970 mg of N-phenyl-3-bromo-benzenesulfonamide, readily prepared from commercially available 3-bromo-benzene sulfonyl chloride, in 55 mL of anhydrous tetrahydrofuran under nitrogen at −78° C. is added 1.9 mL of a 1.6M solution of n-butyllithium in hexane. The solution is stirred for 10 min and then an additional 1.9 mL of n-butyllithium (1.6M in hexane) is added. The solution is stirred for 10 min and then 0.35 mL of cyclopropane carboxaldehyde is added. The solution is stirred for 1 h 30 min and then treated with water and ethyl acetate. The solution is treated with 5% aqueous hydrochloric acid and brine. The layers are separated and the aqueous is extracted with two portions of ethyl acetate. The combined organic layers are dried sodium sulfate ($Na_2SO_4$) and concentrated to afford an oil which is chromatographed over silica (eluted with 5% methanol/dichloromethane) to afford 517 mg (55%) of the title product as a clear oil.

Physical characteristics are as follows:

Mass spectrum m/z: 303($M^+$), 275, 259, 233, 211, 193, 183, 168, 147, 128, 119, 105, 93, 77, 65.

High Resolution Mass Spectrum: Found (m/z) 303.0917 ($M^+$).

EXAMPLE 400

N-Phenyl-3-[cyclopropyl(5,6,7,8,9, 10-hexahydro-4-hydroxy-2-oxo-2H-cycloocta[b]pyran-3-yl)methyl]-benzenesulfonamide (Formula BBB-5) Refer to Chart BBB To a solution of 437 mg of N-phenyl-3-(cyclopropylhydroxymethyl)-benzenesulfonamide of Preparation 88 in 100 mL of dichloromethane in the presence of molecular sieves 3A is added 282.5 mg of 4-hydroxy-5,6, 7,8,9,10-hexahydro-cycloocta[b]pyran-2-one of formula BBB-followed by 52.0 mg of p-toluenesulfonic acid monohydrate. The reaction is heated at reflux for 1 h and 30 min and then concentrated in vacuo. The resulting oil is dissolved in ethyl acetate and treated with water and 1N aqueous sodium hydroxide. The layers are separated and the organic layer is washed with a second portion of 1N aqueous sodium hydroxide. The combined aqueous layers are treated with 5% aqueous hydrochloric acid and extracted with three portions of ethyl acetate. The combined organics are dried (sodium sulfate) ($Na_2SO_4$) and concentrated to afford a yellow oil which is chromatographed over 80 g of silica (eluted with 15% hexane/ethyl acetate) to afford 74 mg of material. This material is rechromatographed as above (elution with 50% hexane/ethyl acetate) to afford 67.3 mg of the title product as a white solid.

Physical characteristics are as follows:

MP 200°–203° C.

Mass spectrum m/z: 480 (M⁺+H), 286, 247, 93.

High Resolution Mass Spectrum: Found (m/z) 480.1850 ($M_+ +1$).

EXAMPLES 401–407

Utilizing procedures analogous to those described above, the following additional compounds of the present invention are prepared:

EXAMPLE 401

N-[3-[Cyclopropyl(5,6,7,8,9,10-hexahydro-4-hydroxy-2-oxo-2H-cycloocta[b]pyran-3-yl)methyl]phenyl]-(R)-benzenesulfonamide

EXAMPLE 402

Sodium Salt of 4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide

EXAMPLE 403

4-(Bromomethyl)-N-[3-[cyclopropyl(5,6,7,8,9,10-hexahydro-4-hydroxy-2-oxo-2H-cycloocta[b]pyran-3-yl)methyl]phenyl]-benzenesulfonamide

EXAMPLE 404

N-[3-cyclopropyl(5,6,7,8,9,10-hexahydro-4-hydroxy-2-oxo-2H-cycloocta[b]pyran-3-yl)methyl]phenyl]-5-(phenylsulfonyl)-, (S)-2-thiophenesulfonamide

EXAMPLE 405

N-[3-[Cyclopropyl(5,6,7,8,9,10-hexahydro-4-hydroxy-2-oxo-2H-cycloocta[b]pyran-3-yl)methyl]phenyl]-3-hydroxy-benzenesulfonamide

EXAMPLE 406

4-Butoxy-N-[3-[cyclopropyl(5,6,7,8,9,10-hexahydro-4-hydroxy-2-oxo-2H-cycloocta[b]pyran-3-yl)methyl]phenyl]-benzenesulfonamide

EXAMPLE 407

N-[3-[Cyclopropyl(5,6,7,8,9,10-hexahydro-4-hydroxy-2-oxo-2H-cycloocta[b]pyran-3-yl)methyl]phenyl]-4-hydroxy-benzenesulfonamide

EXAMPLE 408

3-(Benzyloxyacetylamino)-N-[3-[cyclopropyl(5,6,7,8,9,10-hexahydro-4-hydroxy-2-oxo-2H-cycloocta[b]pyran-3-yl)methyl]phenyl]-benzenesulfonamide. Refer to Chart Z.

A solution of the first title compound of Example 353 (50 mg), benzyloxyacetyl chloride (18 µL), and pyridine (25 µL) in dichloromethane (4 mL) is stirred at room temperature for 18 h. The crude reaction mixture is chromatographed on silica gel to give 50 mg of the title compound.

Physical characteristics are as follows:
white amorphous solid
MS(EI): 642, 551, 338, 233, 207, 144, 91.

TLC(silica gel GF): $R_f$=0.15, 10% ethyl acetate in dichloromethane.

EXAMPLE 409

3-(Hydroxyacetylamino)-N-[3-[cyclopropyl(5,6,7,8,9,10-hexahydro4-hydroxy-2-oxo-2H-cycloocta[b]pyran-3-yl)methyl]phenyl]-benzenesulfonamide. Refer to Chart Z.

A mixture of the title product of Example 408 and 10% palladium on carbon in ethyl acetate (5 mL) is hydrogenated at 40 psi with shaking for 24 h, filtered through celite washing the filter cake with methanol. The combined filtrates are concentrated in vacuo and the resulting material chromatographed on silica gel to give 20 mg of the title compound.

Physical characteristics are as follows:
white amorphous solid
MS(EI): 552, 521, 494, 338, 233, 207, 186, 144, 132.

TLC(silica gel GF): $R_f$=0.15, 5% methanol in dichloromethane.

EXAMPLE 410

2,3,4-Trichloro-N-[3-[cyclopropyl(5,6,7,8,9,10-hexahydro-4-hydroxy-2-oxo-2H-cycloocta[b]pyran-3-yl)methyl]phenyl]-benzenesulfonamide Utilizing procedures analogous to those described in Example 264 above, the following additional compound of the present invention is prepared.

Physical characteristics are as follows:
white amorphous solid
MS(EI): 582, 555, 338, 233, 220; 207, 144.
HRMS: 581.0595.

TLC(silica gel GF): $R_f$=0.29 40% ethyl acetate in hexane.

PREPARATION 89

3-Chlorosulfonyl-morpholinebenzenesulfonamide

To 1.37 g of 1,3-bis(chlorosulfonyl)benzene (Maybridge Chemical Co.) is added 20 ml of methylene chloride and 217 mg of morpholine. The reaction mixture is allowed to stir at room temperature for 18 hours. The mixture is filtered from residual solids, the solids are washed well with methylene chloride and the organic solution is evaporated to dryness. The resulting solids are chromatographed over silica gel using methylene chloride ($R_f$=0.8; methylene chloride) as eluent to give 97 mg of crude 3-chlorosulfonyl-morpholinebenzenesulfonamide of suitable purity for use in the preparation of the bis-sulfonamide compounds.

PREPARATION 90

3-Chlorosulfonyl-N-benzyl-benzenesulfonamide

Substituting benzylamine for morpholine in the reaction described above gives 3-chlorosulfonyl-N-benzyl-benzenesulfonamide.

PREPARATION 91

3-Chlorosulfonyl-N,N-dibenzyl-benzenesulfonamide

Substituting dibenzylamine for morpholine in the reaction described above gives 3-chlorosulfonyl-N,N-dibenzyl-benzenesulfonamide.

PREPARATION 92

3-Chlorosulfonyl-N-n-propylbenzenesulfonamide

Substituting n-propylamine for morpholine in the reaction described above gives 3-chlorosulfonyl-N-n-propylbenzenesulfonamide.

EXAMPLES 411–414

Utilizing the procedure of Example 164 and using the above sulfonyl chlorides the following additional compounds of the present invention are prepared from the title compound of Example 164.

EXAMPLE 411

N-[3-[Cyclopropyl(5,6,7,8,9,10-hexahydro-4-hydroxy-2-oxo-2H-cycloocta[b]pyran-3-yl)-methyl]phenyl]-(3-N-morpholinebenzenesulfonyl)benzenesulfonamide Physical characteristics are as follows:
white amorphous solid.
MS(EI): 628, 599, 479, 461,451,338, 233, 220, 207, 144.
TLC (silica gel GF): $R_f$=0.60 66% ethyl acetate in hexane +0.5% acetic acid.

EXAMPLE 412

N-[3-[Cyclopropyl(5,6,7,8,9,10-hexahydro-4-hydroxy-2-oxo-2H-cycloocta[b]pyran-3-yl)-methyl]phenyl]-(3-N-benzylbenzenesulfonyl)benzenesulfonamide.

Physical characteristics are as follows:
white amorphous solid.
MS(EI): 648, 557, 338, 233, 220, 207, 144, 106, 91.
TLC (silica gel GF): $R_f$=0.75 33% acetone in cyclohexane.

EXAMPLE 413

N-[3-[Cyclopropyl(5,6,7,8,9,10-hexahydro-4-hydroxy-2-oxo-2H-cycloocta[b]pyran-3-yl)-methyl]phenyl]-(3-N,N-dibenzylbenzenesulfonyl)benzenesulfonamide Physical characteristics are as follows:
white amorphous solid.
MS(E1): 738, 647, 338, 196, 144, 91.
TLC (silica gel GF): $R_f$=0.50 50% ethyl acetate in hexane.

EXAMPLE 414

N-[3-[Cyclopropyl(5,6,7,8,9,10-hexahydro-4-hydroxy-2-oxo-2H-cycloocta[b]pyran-3-yl)-methyl]phenyl]-(3-N-ethylbenzenesulfonyl)benzenesulfonamide Physical characteristics are as follows:
white amorphous solid.
MS(EI): 600, 572, 542, 477, 449, 338, 233,220, 207, 144.
TLC (silica gel GF): $R_f$=0.40 50% ethyl acetate in hexane.

EXAMPLE 415

Benzenesulfonamide, N-[3-[cyclopropyl(5,6,7,8,9,10-hexahydro-4-hydroxy-2-oxo-2H-cycloocta[b]pyran-3-yl)methyl]phenyl]-4-[2-[2-(2-methoxyethoxy)ethoxy]ethoxy]-, (Formula Z-2 wherein $R_{60}$ is 4-[2-[2-(2-methoxyethoxy)ethoxy]ethoxy]benzene) Refer to Chart Z Following the general procedure of Example 22 I, and making non-critical variations, but substituting the title compound of Example 164 (M-7) for the title compound of Example 218 and 4-[2-[2-(2-methoxyethoxy)ethoxy]ethoxy]benzenesulfonyl chloride for 4-chlorobenzenesulfonyl chloride, 0.11 g of the title compound is obtained as a white foam.

Physical characteristics are as follows:
MP 53°–61° C. (decomposition).
$^1$H NMR (CDCl$_3$) δ7.64, 7.19, 6.97–6.87, 6.53, 6.29, 4.13, 3.85. 3.75–3.62, 3.54, 3.37, 2.62, 2.47, 1.74, 1.62–1.39, 1.32, 0.70, 0.59, 0.48, 0.18 ppm.
IR (Nujol) 3185, 2951, 2920, 2868, 2856, 1666, 1633, 1605, 1594, 1580, 1559, 1497, 1464, 1457, 1406, 1377, 1335, 1305, 1260, 1236. 1201, 1183, 1155, 1128, 1095, 1075, 836 cm$^{-1}$.
MS (EI) m/z 641,495, 338, 233, 220, 207, 144, 59.

EXAMPLE 416

8-Quinolinesulfonamide, N-[3-[1-(5,6,7,8,9,10-hexahydro4-hydroxy-2-oxo-2H-cycloocta[b]pyran-3-yl)-2-methylpropyl]phenyl]-, (Formula X-5 wherein $R_1$ is 8-quinoline) Refer to Chart X Following the general procedure of Example 221, and making non-critical variations, but substituting the title compound of Example 371 for the title compound of Example 218 and 8-quinolinesulfonyl chloride for 4-chlorobenzenesulfonyl chloride, 0.054 g of the title compound is obtained as off-white crystals.

Physical characteristics are as follows:
MP 141°–150 ° C. (decomposition).
$^1$H NMR (CDCl$_3$) δ9.20, 8.36, 8.26, 7.99, 7.63, 7.52, 7.10–7.00, 6.88, 5.77, 3.64, 2.60–2.35, 1.72, 1.59–1.32, 0.82, 0.60 ppm.
IR (Nujol) 3251, 2956, 2923, 2855, 1662, 1628, 1563, 1554, 1494, 1465, 1410, 1381, 1376, 1222, 1209, 1195, 1185, 1172, 1165, 1160, 1143, 1117, 788, 733 cm$^{-1}$.
Elemental analysis, found: C, 67.32; H, 6.02; N, 5.25; S, 5.92.
MS (EI) m/z 532, 517, 489, 341,298, 147, 128.

EXAMPLE 417

3-Pyridinesulfonamide, N-[3-[1-(5,6,7,8,9,10-hexahydro4-hydroxy-2-oxo-2H-cycloocta[b]pyran-3-yl)-2-methylpropyl]phenyl]-, (Formula X-5 wherein $R_1$ is 3-pyridine) Refer to Chart X Following the general procedure of Example 221, and making non-critical variations, but substituting the title compound of Example 371 for the title compound of Example 218 and 3-pyridinesulfonyl chloride for 4-chlorobenzenesulfonyl chloride, 0.084 g of the title compound is obtained as off-white crystals.

Physical characteristics are as follows:
MP 147°–152° C. (decomposition).
$^1$H NMR (CDCl$_3$) δ8.94, 8.73, 7.98, 7.81. 7.40–7.08. 6.69, 3.70, 2.83, 2.57, 2.49, 1.72, 1.60, 1.43, 0.88, 0.72 ppm.
IR (Nujol) 3065, 3041, 2957, 2924, 2865, 2855, 1675, 1634, 1586, 1546. 1502, 1467, 1459, 1426, 1418, 1409, 1357, 1252, 1225, 1192, 1174, 1119, 1115. 798, 755 cm$^{-1}$.
Elemental analysis, found: C, 64.59; H, 6.33; N, 5.81; S, 6.56.
MS (EI) m/z 482, 467, 439, 340, 78.

EXAMPLE 418

Benzenesulfonamide, N-[3-[1-(5,6,7,8,9,10-hexahydro-4-hydroxy-2-oxo-2H-cycloocta[b]pyran-3-yl)-2-methylpropyl]phenyl]4-fluoro-, (Formula X-5 wherein $R_1$ is 4-fluorobenzene) Refer to Chart X Following the general procedure of Example 221, and making non-critical variations, but substituting the title compound of Example 371 for the title compound of Example 218 and 4-fluorobenzenesulfonyl chloride for 4-chlorobenzenesulfonyl chloride, 0.097 g of the title compound is obtained as off-white solid.

Physical characteristics are as follows:

MP 99°–104° C. (decomposition).

$^1$H NMR (CDCl$_3$) δ7.72, 7.07–6.98, 6.78, 6.05, 3.71, 2.84–2.70, 2.58, 2.46, 1.77–1.33, 0.90, 0.77 ppm.

PREPARATION 93

[3-(1-Hydroxypentyl)phenyl]-carbamic acid, phenylmethyl ester (Formula Y-3 wherein R$_1$ is butyl) Refer to Chart Y Following the general procedure of Preparation 62, and making non-critical variations, but substituting butyl magnesium chloride for propyl magnesium chloride, 3.76 g of the title compound is obtained as off-white crystals.

Physical characteristics are as follows:

MP 83°–86° C.

$^1$H NMR (CDCl$_3$) δ7.40–7.27, 7.06, 6.71, 5.20, 4.63, 1.90, 1.72, 1.32, 0.88 ppm.

IR (Nujol) 3392, 3250, 3101, 3086, 2956, 2926, 2872, 2858, 1695, 1619. 1603, 1568, 1469, 1451, 1375, 1289, 1270, 1246, 1244, 1066, 1042, 794, 772, 734, 696 cm$^{-1}$.

Elemental analysis, found: C, 72.68; H, 7.44; N, 4.52.

MS (EI) m/z 313, 269, 2 13, 206, 91.

EXAMPLE 419

[3-[1-(5,6,7,8,9,10-Hexahydro-4-hydroxy-2-oxo-2H-cycloocta[b]pyran-3-yl)pentyl]phenyl-carbamic acid, phenylmethyl ester (Formula Y-5 wherein R$_1$ is butyl) Refer to Chart Y Following the general procedure of Example 107, and making non-critical variations, but substituting the title compound of Preparation 93 for α-cyclopropylbenzyl alcohol, 0.97 g of the title compound is obtained as a yellow solid.

Physical characteristics are as follows:

MP 66°–71° C. (decomposition).

$^1$H NMR (CDCl$_3$) δ7.45–7.26, 7.13, 6.72, 5.98, 5.19, 4.37, 2.59. 2.41. 2.16–1.93. 1.73, 1.59–1.23, 0.88 ppm.

EXAMPLE 420

3-[1 -(3-Aminophenyl)pentyl]-5,6,7,8,9,10-hexahydro-4-hydroxy-2H-cycloocta[b]pyran-2-one (Formula Y-6 wherein R$_1$ is butyl) Refer to Chart Y Following the general procedure of Example 164 (M-7), and making non-critical variations, but substituting the title product of Example 419 for the title product of Example 119, 0.32 g of the title compound is obtained as a beige foam.

Physical characteristics are as follows:

MP 60°–66° C. (decomposition).

$^1$H NMR (CDCl$_3$) δ7.17, 6.83, 6.71, 6.61, 4.35, 3.74, 2.60, 2.39, 2.06, 1.92, 1.74, 1.57–1.30, 0.89 ppm.

EXAMPLE 421

Benzenesulfonamide, 4-cyano-N-[3-[1-(5,6,7,8,9,10-hexahydro-4-hydroxy-2-oxo-2H-cycloocta[b]pyran-3-yl)pentyl]phenyl]-, (Formula Y-7 wherein R$_1$ is butyl and R$_2$ is 4-cyanobenzene) Refer to Chart Y Following the general procedure of Example 221, and making non-critical variations, but substituting the title compound of Example 420 for the title compound of Example 218 and 4-cyanobenzenesulfonyl chloride for 4-chlorobenzenesulfonyl chloride, 0.098 g of the title compound is obtained as off-white crystals.

Physical characteristics are as follows:

MP 107°–112° C. (decomposition).

$^1$H NMR (CDCl$_3$) δ7.84, 7.70, 7.22, 7.13, 7.04, 5.82, 4.24, 2.62, 2.46, 2.00, 1.73, 1.61–1.20, 0.87 ppm.

IR (Nujol) 3258, 2953, 2924, 2867, 2856, 2234, 1666, 1634, 1607, 1558, 1465, 1404, 1377, 1341, 1226, 1197, 1182, 1167, 1091, 635 cm$^{-1}$.

Elemental analysis, found: C, 66.84; H, 6.36; N, 5.20; S, 5.94.

MS (EI) m/z 520, 477, 463, 354, 326, 195, 102.

EXAMPLE 422

Benzenesulfonamide, N-J3-[1 -(5,6,7,8,9,10-hexahydro-4-hydroxy-2-oxo-2H-cycloocta[b]pyran-3-yl)pentyl]phenyl]-4-fluoro-, (Formula Y-7 wherein R$_1$ is butyl and R$_2$ is 4-fluorobenzene) Refer to Chart Y Following the general procedure of Example 221, and making non-critical variations, but substituting the title compound of Example 420 for the title compound of Example 218 and 4-fluorobenzenesulfonyl chloride for 4-chlorobenzenesulfonyl chloride, 0.11 g of the title compound is obtained as off-white crystals.

Physical characteristics are as follows:

MP 93°–100° C. (decomposition).

$^1$H NMR (CDCl$_3$) δ7.74, 7.22. 7.10–7.00, 6.79. 5.80, 4.27, 2.61, 2.43, 2.00. 1.75. 1.61– 1.17, 0.87 ppm.

IR (Nujol) 3255, 2951, 2921, 2868, 2856, 1666, 1634, 1607, 1592, 1558, 1495, 1466, 1407, 1377, 1338, 1293, 1237, 1199, 1170, 1154, 1110, 1091, 838 cm$^{-1}$.

Elemental analysis. found: C, 65.54; H, 6.16; N, 2.49; S, 5.90.

MS (EI) m/z 513,470, 456, 354, 319, 195, 159, 95.

PREPARATION 94

[3-(1-Hydroxy-3-methylbutyl)phenyl]-carbamic acid, phenylmethyl ester (Formula Y-3 wherein R$_1$ is isobutyl) Refer to Chart Y Following the general procedure of Preparation 62, and making non-critical variations, but substituting isobutyl magnesium chloride for propyl magnesium chloride, 4.13 g of the title compound is obtained as white crystals.

Physical characteristics are as follows:

MP 73°–77° C.

$^1$H NMR (CDCl$_3$) δ7.41–7.33, 7.25, 7.05, 6.74, 5.19, 4.73–4.65, 1.91, 1.73–1.65, 1.47, 0.93 ppm.

IR (Nujol) 3400, 3249, 3085, 2953, 2925, 2869, 2855, 1697, 1615, 1602, 1563, 1450, 1283, 1245, 1177, 1067, 1017, 798, 773, 740, 696 cm$^{-1}$.

Elemental analysis, found: C, 72.58; H, 7.25; N, 4.55.

MS (EI) m/z 313, 257, 213, 91.

EXAMPLE 423

[3-[1-(5,6,7,8,9,10-Hexahydro-4-hydroxy-2-oxo-2H-cycloocta[b]pyran-3-yl)-3-methylbutyl]phenyl-carbamic acid, phenylmethyl ester (Formula Y-5 wherein R$_1$ is isobutyl) Refer to Chart Y Following the general procedure of Example 107, and making non-critical variations, but substituting the title product of Preparation 94 for α-cyclopropylbenzyl alcohol, 1.00 g of the title compound is obtained as an off-white foam.

Physical characteristics are as follows:

MP 73°–78° C. (decomposition).

$^1$H NMR (CDCl$_3$) δ7.38–7.25, 7.13, 6.72, 6.01, 5.19, 4.48, 2.58, 2.41, 1.93, 1.74, 1.62–1.33, 0.96 ppm.

EXAMPLE 424

3-[1-(3-Aminophenyl)-3-methylbutyl]-5,6,7,8,9,10-hexahydro-4-hydroxy-2H-cycloocta[b]pyran-2-one (Formula Y-6 wherein R$_1$ is isobutyl) Refer to Chart Y Following the general procedure of Example 164, and making non-critical variations, but substituting the title product of Example 422 for the title product of Example 119, 0.35 g of the title compound is obtained as a grey foam.

Physical characteristics are as follows:

MP 70°–76° C. (decomposition).

$^1$H NMR (CDCl$_3$) δ7.16, 6.82, 6.72, 6.59, 4.45, 3.88–3.59, 2.59, 2.39, 1.93, 1.84–1.69, 1.67–1.33, 0.97 ppm.

EXAMPLE 425

Benzenesulfonamide, N-[3-[1-(5,6,7,8,9,10-hexahydro-4-hydroxy-2-oxo-2H-cycloocta[b]pyran-3-yl)-3-methylbutyl]phenyl]-4-fluoro-, Formula V-7 wherein R$_1$ is isobutyl and R$_2$ is 4-fluorobenzene) Refer to Chart Y Following the general procedure of Example 221, and making non-critical variations, but substituting the title compound of Example 424 for the title compound of Example 218 and 4-fluorobenzenesulfonyl chloride for 4-chlorobenzenesulfonyl chloride, 0.102 g of the title compound is obtained as a white solid.

Physical characteristics are as follows:

MP 99°–104° C. (decomposition).

$^1$H NMR (CDCl$_3$) δ7.73, 7.20, 7.09–7.00, 6.76, 5.83, 4.38, 2.60, 2.45, 1.87–1.75, 1.60–1.37, 0.92 ppm.

IR (Nujol) 3255, 2953, 2925, 2856, 1665, 1634, 1606, 1592, 1558, 1495, 1466, 1458, 1407, 1384, 1377, 1367, 1337, 1293, 1237, 1198, 1170, 1154, 1091, 838 cm$^{-1}$.

Elemental analysis, found: C, 65.62; H, 6.33; N, 2.50; S, 6.03.

EXAMPLE 426

Benzenesulfonamide, 4-cyano-N-[3-[1-(5,6,7,8,9,10-hexahydro-4-hydroxy-2-oxo-2H-cycloocta[b]pyran-3-yl)-3-methylbutyl]phenyl]-, (Formula Y-7 wherein R$_1$ is isobutyl and R$_2$ is 4-cyanobenzene) Refer to Chart Y Following the general procedure of Example 221, and making non-critical variations, but substituting the title compound of Example 424 for the title compound of Example 218 and 4-cyanobenzenesulfonyl chloride for 4-chlorobenzenesulfonyl chloride, 0.101 g of the title compound is obtained as a white solid.

Physical characteristics are as follows:

MP 109°–114° C. (decomposition).

$^1$H NMR (CDCl$_3$) δ7.84, 7.69, 7.21, 7.13, 7.02, 5.83, 4.34, 2.61, 2.48, 1.99–1.80, 1.77, 1.59, 1.53–1.37, 0.92 ppm.

IR (Nujol) 3253, 2953, 2922, 2866, 2855, 2234, 1665, 1634, 1607, 1558, 1466, 1458, 1404, 1384, 1377, 1367, 1340, 1223, 1197, 1182, 1167, 1091, 635 cm$^{-1}$.

Elemental analysis, found: C, 66.87; H, 6.35; N, 5.07; S, 5.93.

EXAMPLE 427

1H-Imidazole-4-sulfonamide, N-[3-[1-(5,6,7,8,9,10-hexahydro-4-hydroxy-2-oxo-2H-cycloocta[b]pyran-3-yl)-3-methylbutyl]phenyl]- 1 -methyl-, (Formula Y-7 wherein R$_1$ is isobutyl and R$_2$ is 4-(1-methyl) imidazole) Refer to Chart Y Following the general procedure of Example 221, and making non-critical variations but substituting the title compound of Example 424 for the title compound of Example 218 and 1-methylimidazole- 4-sulfonyl chloride for 4-chlorobenzenesulfonyl chloride, 0.100 g of the title compound is obtained as a white solid.

Physical characteristics are as follows:

MP 217° C.

$^1$H NMR (CDCl$_3$, CD$_3$OD) δ5 7.45, 7.38, 7.14, 6.96, 4.24, 3.68, 2.59, 2.53, 2.17, 1.81–1.36, 0.91, 0.89 ppm.

EXAMPLE 428

8-Quinolinesulfonamide, N-[3-[1-(5,6,7,8,9,10-hexahydro4-hydroxy-2-oxo-2H-cycloocta[b]pyran-3-yl)-3-methylbutyl]phenyl]-, (Formula Y-7 wherein R$_1$ is isobutyl and R$_2$ is 8-quinoline) Refer to Chart Y Following the general procedure of Example 221, and making non-critical variations, but substituting the title compound of Example 424 for the title compound of Example 218 and 8-quinolinesulfonyl chloride for 4-chlorobenzenesulfonyl chloride, 0.125 g of the title compound is obtained as a white solid.

Physical characteristics are as follows:

MP 202°–203° C.

$^1$H NMR (CDCl$_3$, CD$_3$OD) δ9.15, 8.28, 8.02, 7.63, 7.55, 7.09, 6.98, 6.72, 4.17, 2.58, 2.47, 1.91, 1.73–1.56, 1.41, 1.29, 0.83, 0.81 ppm.

EXAMPLE 429

3-Pyridinesulfonamide, N-[3-[1-(5,6,7,8,9,10-hexahydro4-hydroxy-2-oxo-2H-cycloocta[b]pyran-3-yl)-3-methylbutyl]phenyl]-, (Formula Y-7 wherein R$_1$ is isobutyl and R$_2$ is 3-pyridine) Refer to Chart Y Following the general procedure of Example 221, and making non-critical variations, but substituting the title compound of Example 424 for the title compound of Example 218 and 3-pyridinesulfonyl chloride for 4-chlorobenzenesulfonyl chloride, 0.112 g of the title compound is obtained as a white solid.

Physical characteristics are as follows:

MP 112°–113° C.

$^1$H NMR (CDCl$_3$, CD$_3$OD) δ8.87, 8.66, 8.04, 7.38, 7.18, 7.06, 6.97, 4.25, 2.59, 2.50, 2.10, 1.82–1.72, 1.60, 1.55–1.42, 0.89, 0.87 ppm.

EXAMPLE 430

Benzenesulfonamide, N-[3-[1-(5,6,7,8,9,10-hexahydro-4-hydroxy-2-oxo-2H-cycloocta[b]pyran-3-yl)butyl]phenyl]-4-fluoro-, (Formula Y-7 wherein R$_1$ is propyl and R$_2$ is 4-fluorobenzene) Refer to Chart Y Following the general procedure of Example 221, and making non-critical variations, but substituting the title compound of Example 376 for the title compound of Example 218 and 4-fluorobenzenesulfonyl chloride for 4-chlorobenzenesulfonyl chloride, 0.089 g of the title compound is obtained as a white solid.

Physical characteristics are as follows:

MP 98°–106° C. (decomposition).

$^1$H NMR (CDCl$_3$) δ7.74, 7.21, 7.10–7.00, 6.80, 5.82, 4.29, 2.61, 2.43, 1.98, 1.74, 1.61–1.25, 0.93 ppm.

IR (Nujol) 3259, 2954, 2925, 2868, 2856, 1.666, 1635, 1606, 1592, 1558, 1495, 1465, 1458, 1407, 1378, 1338, 1293, 1237, 1199, 1170, 1154, 1091, 838 cm$^{-1}$.

Elemental analysis, found: C, 64.78; H, 6.09; N, 2.53; S, 6.09.

MS (EI) m/z 499, 470, 456, 340, 305, 195, 159, 95.

EXAMPLE 431

1H-imidazole-4-sulfonamide, N-[3-[1-(5,6,7,8,9,10-hexahydro-4-hydroxy-2-oxo-2H-cycloocta[b]pyran-3-yl)butyl]phenyl]- 1-methyl-, (Formula Y-7 wherein R$_1$ is propyl and R$_2$ is 4-(1-methyl) imidazole) Refer to Chart Y.

Following the general procedure of Example 221, and making non-critical variations, but substituting the title compound of Example 376 for the title compound of Example 218 and 1-methylimidazole-4-sulfonyl chloride for 4-chlorobenzenesulfonyl chloride, 0.101 g of the title compound is obtained as a white solid.

Physical characteristics are as follows:

MP 208°–211° C.

$^1$H NMR (CDCl$_3$, CD$_3$OD) δ7.43, 7.36, 7.25–7.13, 6.99, 4.20, 2.61–2.56, 2.50–2.46, 2.14–1.97, 1.83, 1.79–1.71, 1.65–1.59, 1.52–1.41, 1.32–1.26, 0.94 ppm.

EXAMPLE 432

8-Quinolinesulfonamide, N-[3-[1-(5,6,7,8,9,10-hexahydro4-hydroxy-2-oxo-2H-cycloocta[b]pyran-3-yl)butyl]phenyl]-, (Formula Y-7 wherein R$_1$ is propyl and R$_2$ is 8-quinoline) Refer to Chart Y Following the general procedure of Example 221, and making non-critical variations, but substituting the title compound of Example 376 for the title compound of Example 218 and 8-quinolinesulfonyl chloride for 4-chlorobenzenesulfonyl chloride, 0.094 g of the title compound is obtained as a white solid.

Physical characteristics are as follows:

MP 240°–242° C.

$^1$H NMR (CDCl$_3$, CD$_3$OD) δ9.19, 8.30, 7.64, 7.57, 7.08, 6.97, 6.79, 4.05, 2.61–2.55, 2.53–2.49, 2.02–1.91, 1.77–1.69, 1.50–1.38, 1.12–1.01, 0.82 ppm.

EXAMPLE 433

3-Pyridinesulfonamide, N-[3-[1-(5,6,7,8,9,10-hexahydro-4-hydroxy-2-oxo-2H-cycloocta[b]pyran-3-yl)butyl]phenyl]-, (Formula Y-7 wherein R$_1$ is propyl and R$_2$ is 3-pyridine) Refer to Chart Y Following the general procedure of Example 221, and making non-critical variations, but substituting the title compound of Example 376 for the title compound of Example 218 and 3-pyridinesulfonyl chloride for 4-chlorobenzenesulfonyl chloride, 0.079 g of the title compound is obtained as white crystals.

Physical characteristics are as follows: Mp 130°–133° C. $^1$H NMR (CDCl$_3$) δ 8.92, 8.78, 8.01, 7.41, 7.28–7.21, 7.13, 7.09–7.05, 6.18, 4.38, 2.62, 2.48, 2.02, 1.78–1.72, 1.63–1.59, 1.50–1.40, 1.32–1.23, 0.93 ppm.

EXAMPLE 434

(R or S)-[3-[1-(5,6,7,8,9,10-Hexahydro-4-hydroxy-2-oxo-2H-cycloocta[b]pyran-3-yl)butyl]phenyl]-carbamic acid, phenylmethyl ester The title compound of Example 375 is separated by HPLC, as described in Example 247, using a 2.0×25 cm Whelk-O I column as the stationary phase and 25% isopropyl alcohol and 0.05% acetic acid in hexane as the mobile phase (15 mL/min).

Physical characteristics are as follows:

The retention time of the title compound was 18.8 min.

EXAMPLE 435

(R or S)-[3-[1-(5,6,7,8,9,10-Hexahydro-4-hydroxy-2-oxo-2H-cycloocta[b]pyran-3-yl)butyl]phenyl]-carbamic acid, phenylmethyl ester The title compound of Example 375 is separated as described in Example 434 above.

Physical characteristics are as follows:

The retention time of the title compound was 23.5 min.

EXAMPLE 436

(R or S)-3-[1-(3-Aminophenyl)butyl]-5,6,7,8,9,10-hexahydro-4-hydroxy-2H-cycloocta[b]pyran-2-one Following the general procedure of Example 164, and making non-critical variations, but substituting the title compound of Example 434 for the title compound of Example 119, 0.25 g of the title compound is obtained as a beige foam.

Physical characteristics are as follows:

$^1$H NMR (CDCl$_3$) δ 7.17, 6.83, 6.72, 6.60, 4.40, 3.83–3.63, 2.60. 2.38, 2.11–1.82, 1.74, 1.62–1.29, 0.97 ppm.

EXAMPLE 437

(R or S)-Benzenesulfonamide, 4-cyano-N-[3-[1-(5,6,7,8,9,10-hexahydro-4-hydroxy-2-oxo-2H-cycloocta[b]pyran-3-yl)butyl]phenyl]-, Following the general procedure of Example 221, and making non-critical variations, but substituting the title compound of Example 436 for the title compound of Example 218 and 4-cyanobenzenesulfonyl chloride for 4-chlorobenzenesulfonyl chloride, 0.056 g of the title compound is obtained as a white solid.

Physical characteristics are as follows:

MP 105°–110° C. (decomposition).

$^1$H NMR (CDCl$_3$) δ 7.84, 7.70, 7.22, 7.12, 7.05–6.98, 5.78, 4.28, 2.63, 2.46, 2.00, 1.74, 1.60–1.22, 0.93 ppm.

EXAMPLE 438

(R or S)-3-[1-(3-Aminophenyl)butyl]-5,6,7,8,9,10-hexahydro-4-hydroxy-2H-cycloocta[b]pyran-2-one Following the general procedure of Example 164, and making non-critical variations, but substituting the title compound of Example 435 for the title compound of Example 119, 0.16 g of the title compound is obtained as a beige foam.

Physical characteristics are as follows:

$^1$H NMR (CDCl$_3$) δ 7.17, 6.83, 6.72, 6.60, 4.40, 3.83–3.63, 2.60, 2.38, 2.11–1.82, 1.74, 1.62–1.29, 0.97 ppm.

EXAMPLE 439

(R or S)-Benzenesulfonamide, 4-cyano-N-[3-[1-(5,6,7,8,9,10-hexahydro-4-hydroxy-2-oxo-2H-cycloocta[b]pyran-3-yl)butyl]phenyl]-, Following the general procedure of Example 221, and making non-critical variations, but substituting the title compound of Example 438 for the title compound of Example 218 and 4-cyanobenzenesulfonyl chloride for 4-chlorobenzenesulfonyl chloride, 0.058 g of the title compound is obtained as a white solid.

Physical characteristics are as follows:

MP 106°–111° C. (decomposition). $^1$H NMR (CDCl$_3$) δ 7.84, 7.70, 7.21, 7.10, 7.03, 5.84, 4.26, 2.63, 2.46, 2.00, 1.74, 1.60–1.22, 0.93 ppm.

EXAMPLES 440–469

The following additional compounds of the present invention are prepared by utilizing procedures analogous to those described above:

440) N-[3-[1-(5,6,7,8,9,10-Hexahydro-4-hydroxy-2-oxo-2H-cycloocta-[b]pyran-3-yl)-2-methylpropyl]phenyl-benzenesulfonamide 441) N-[3-[1-(5,6,7,8,9,10-Hexahydro-4-hydroxy-2-oxo-2H-cycloocta-[b]pyran-3-yl)-2-methylpropyl]phenyl-1-propanesulfonamide 442) N-[3-[1-(5,6,7,8,9,10-Hexahydro-4-hydroxy-2-oxo-2H-cycloocta-[b]pyran-3-yl)-2-methylpropyl]phenyl-2,1,3-benthiadiazole-4-sulfonamide 443) N-[3-[1-(5,6,7,8,9,10-Hexahydro-4-hydroxy-2-oxo-2H-cycloocta-[b]pyran-3-yl)-2-methylpropyl]phenyl-2-thiophenesulfonamide 444) N-[3-[1-(5,6,7,8,9,10-Hexahydro-4-hydroxy-2-oxo-2H-cycloocta-[b]pyran-3-yl)-2-methylpropyl]phenyl-4-(hydroxyamine)-benzenesulfonamide 445) 4-[[[3-[1-(5,6,7,8,9,10-Hexahydro-4-hydroxy-2-oxo-2H-cycloocta-[b]pyran-3-yl)-2-methylpropyl]phenyl]amino]sulfonyl]-benzamide 446) 3-[[[3-[1-(5,6,7,8,9,10-Hexahydro-4-hydroxy-2-oxo-2H-cycloocta-[b]pyran-3-yl)-2-methylpropyl]phenyl]amino]sulfonyl]-benzoic acid, methyl ester 447) N-[3-[1-(5,6,7,8,9,10-Hexahydro-4-hydroxy-2-oxo-2H-cycloocta-[b]pyran-3-yl)-2-methylpropyl]phenyl-3-(hydroxymethyl)-benzenesulfonamide 448) N-[3-[1-(5,6,7,8,9,10-Hexahydro-4-hydroxy-2-oxo-2H-cycloocta-[b]pyran-3-yl)-2-methylpropyl]phenyl-3-[(bis-(2-ethanol))amino]-benzenesulfonamide 449) N-[3-[1-(5,6,7,8,9,10-Hexahydro-4-hydroxy-2-oxo-2H-cycloocta-[b]pyran-3-yl)-2-methylpropyl]phenyl-thiazole-4-sulfonamide 450) N-[3-[1-(5,6,7,8,9,10-Hexahydro-4-hydroxy-2-oxo-2H-cycloocta-[b]pyran-3-yl)butyl]phenyl-benzenesulfonamide 451) N-[3-[1-(5,6,7,8,9,10-Hexahydro-4-hydroxy-2-oxo-2H-cycloocta-[b]pyran-3-yl)butyl]phenyl-1-propanesulfonamide 452) N-[3-[1-(5,6,7,8,9,10-Hexahydro-4-hydroxy-2-oxo-2H-cycloocta-[b]pyran-3-yl)butyl]phenyl-2,1,3-benthiadiazole-4-sulfonamide 453) N-[3-[1-(5,6,7,8,9,10-Hexahydro-4-hydroxy-2-oxo-2H-cycloocta-[b]pyran-3-yl)butyl]phenyl-2-thiophenesulfonamide 454) N-[3-[1-(5,6,7,8,9,10-Hexahydro-4-hydroxy-2-oxo-2H-cycloocta-[b]pyran-3-yl)butyl]phenyl4-(hydroxyamine)-benzenesulfonamide 455) 4-[[[3-[1-(5,6,7,8,9,10-Hexahydro-4-hydroxy-2-oxo-2H-cycloocta-[b]pyran-3-yl)butyl]phenyl]amino]sulfonyl]-benzamide 456) 3-[[[3-[1-(5,6,7,8,9,10-Hexahydro-4-hydroxy-2-oxo-2H-cycloocta-[b]pyran-3-yl)butyl]phenyl]amino]sulfonyl]-benzoic acid, methyl ester 457) N-[3-[1-(5,6,7,8,9,10-Hexahydro-4-hydroxy-2-oxo-2H-cycloocta-[b]pyran-3-yl)butyl]phenyl-3-(hydroxymethyl)-benzenesulfonamide 458) N-[3-[1-(5,6,7,8,9,10-Hexahydro-4-hydroxy-2-oxo-2H-cycloocta-[b]pyran-3-yl)butyl]phenyl-3-[(bis-(2-ethanol))amino]-benzenesulfonamide 459) N-[3-[1-(5,6,7,8,9,10-Hexahydro-4-hydroxy-2-oxo-2H-cycloocta-[b]pyran-3-yl)butyl]phenyl-thiazole-4-sulfonamide 460) N-[3-[1-(5,6,7,8,9,10-Hexahydro-4-hydroxy-2-oxo-2H-cycloocta-[b]pyran-3-yl)-3-methylbutyl]phenyl-benzenesulfonamide 461) N-[3-[1-(5,6,7,8,9,10-Hexahydro-4-hydroxy-2-oxo-2H-cycloocta-[b]pyran-3-yl)-3-methylbutyl]phenyl-1-propanesulfonamide 462) N-[3-[1-(5,6,7,8,9,10-Hexahydro-4-hydroxy-2-oxo-2H-cycloocta-[b]pyran-3-yl)-3-methylbutyl]phenyl-2,1,3-benthiadiazole-4-sulfonamide 463) N-[3-[1-(5,6,7,8,9,10-Hexahydro-4-hydroxy-2-oxo-2H-cycloocta-[b]pyran-3-yl)-3-methylbutyl]phenyl-2-thiophenesulfonamide 464) N-[3-[1-(5,6,7,8,9,10-Hexahydro-4-hydroxy-2-oxo-2H-cycloocta-[b]pyran-3-yl)-3-methylbutyl]phenyl-4-(hydroxyamine)-benzenesulfonamide 465) 4-[[[3-[1-(5,6,7,8,9,10-Hexahydro-4-hydroxy-2-oxo-2H-cycloocta-[b]pyran-3-yl)-3-methylbutyl]phenyl]amino]sulfonyl]-benzamide 466) 3-[[[3-[1-(5,6,7,8,9,10-Hexahydro-4-hydroxy-2-oxo-2H-cycloocta-[b]pyran-3-yl)-3-methylbutyl]phenyl]amino]sulfonyl]-benzoic acid, methyl ester 467) N-[3-[1-(5,6,7,8,9,10-Hexahydro-4-hydroxy-2-oxo-2H-cycloocta-[b]pyran-3-yl)-3-methylbutyl]phenyl-3-(hydroxymethyl)-benzenesulfonamide 468) N-[3-[1-(5,6,7,8,9,10-Hexahydro-4-hydroxy-2-oxo-2H-cycloocta-[b]pyran-3-yl)-3-methylbutyl]phenyl-3-[(bis-(2-ethanol))amino]-benzenesulfonamide 469) N-[3-[1-(5,6,7,8,9,10-Hexahydro-4-hydroxy-2-oxo-2H-cycloocta-[b]pyran-3-yl)-3-methylbutyl]phenyl-thiazole-4-sulfonamide

PREPARATION 95

Cyclopropyl-(4-aminocarbobenzoxyphenyl) methanone (Formula EEE-2) Refer to Chart EEE The amine of the formula EEE-1 (0.92 g) and diisopropylethylamine (0.89 g) are dissolved in dry methylene chloride (20 mL) and cooled in ice. Benzylchloroformate (1.07 g) is added dropwise and the mixture allowed to warm to room temperature over 2 hr. The reaction mixture is washed with 1N·HCl, dried over sodium sulfate and evaporated. The resulting solid is stirred with hexane and filtered (1.15 g) and recrystallized from chloroform-hexane.

Physical characteristics are as follows:

MS m/z 295, 251, 210, 187, 146, 108, 92, 91, 79, 65

PREPARATION 96

Cyclopropyl-(4-aminocarbobenzoxyphenyl) methanol (Formula EEE-3) Refer to Chart EEE The title ketone of Preparation 95 (1.10 g) is suspended in a 1:1 mixture (15 mL) of tetrahydrofuran-ethanol and solid sodium borohydride (0.57 g) added. The reaction mixture is stirred overnight, then evaporated. The residue is partitioned between 1N•HCl and chloroform. The organic layer is dried over sodium sulfate and evaporated to afford the title compound as a colorless oil (1.12 g).

Physical characteristics are as follows:

MS m/z 297, 269, 253, 225, 212, 92, 91, 69, 65, 40

EXAMPLE 470

Carbamic acid, [4-[cyclopropyl (5,6,7,8,9,10-hexahydro-4-hydroxy-2-oxo-2H-cycloocta[b]pyran-3-yl)methyl]phenyl]-phenylmethyl ester (Formula EEE-4) Refer to Chart EEE Cyclooctene-1-acrylic acid, β,2-dihydroxy-δ-lactone of formula J-1 (1.25 g) and cyclopropyl-(4-aminocarbobenzoxyphenyl)methanol of Preparation 96 (1.10 g) are stirred in dry methylene chloride (25 mL). p-Toluene sulfonic acid (0.175 g) is added and the mixture refluxed via a Dean-Stark trap containing 3 Å molecular sieves for 1 hr. After cooling, the solution is washed with sodium bicarbonate solution and dried over sodium sulfate. After evaporation the residue is chromatographed via a flash column of silica gel eluting with 30% ethyl acetate-hexane. The title compound is obtained (1.20 g) as a white foam.

Physical characteristics are as follows:

MS m/z 473, 383, 382, 347, 280, 207, 144, 92, 91, 55.

EXAMPLE 471

3-[(4-Aminophenyl)cyclopropylmethyl]-5,6,7,8,9,10-hexahydro-4-hydroxy-2H-cycloocta[b]pyran-2-one (Formula EEE-5) Refer to Chart EEE The CBZ derivative of Example 470 (1.00 g) is suspended in cyclohexene (50 mL) and 10% palladium on carbon (0.50 g) added. The reaction mixture is heated under nitrogen at reflux for 5 hr. Upon cooling, the mixture is filtered through Celite and washed well with ethyl acetate and chloroform. The title compound is obtained (0.7 g) upon evaporation as a white solid.

Physical characteristics are as follows:

MS m/z 339, 213, 149, 146, 132, 106, 57, 55, 43, 40.

EXAMPLE 472

Benzenesulfonamide, 4-cyano-N-[4-[cyclopropyl (5,6,7,8,9,10-hexahydro-4-hydroxy-2-oxo-2H-cycloocta [b]pyran-3-yl)methyl]phenyl]- (Formula EEE-6, R is 4-cyanophenyl) Refer to Chart EEE The amino compound of Example 471 (0.100 g) is dissolved in methylene chloride (5 mL) and pyridine (70 μl) added. 4-Cyanobenzenesulfonyl chloride (0.059 g) is added and the reaction stirred at room temperature overnight. The organic solution is washed with 1N•HCl, dried over sodium sulfate and evaporated to leave a pink solid. Flash chromatography over silica gel (elution with 33% ethyl acetate-hexane) gives 0.11 g of the title compound.

Physical characteristics are as follows:

MS m/z 504, 338, 207, 194, 186, 166, 144, 117, 55, 40

EXAMPLE 473

Benzenesulfonamide, 4-chloro-N-[4-[cyclopropyl(5,6,7,8,9,10-hexahydro-4-hydroxy-2-oxo-2H-cycloocta[b]pyran-3-yl)methyl]phenyl]- (Formula EEE-6, R is 4-chlorophenyl) Refer to Chart EEE Using procedures described in Example 472, the title compound (0.11 g) is isolated as a white solid.

Physical characteristics are as follows:

MS m/z 513, 338, 207, 144, 130, 117, 111, 69, 67, 55, 40

EXAMPLE 474

Benzenesulfonamide, 4-fluoro-N-[4-[cycloptopyl(5,6,7,8,9,10-hexahydro-4-hydroxy-2-oxo-2H-cycloocta[b]pyran-3-yl)methyl]phenyl]- (Formula EEE-6, R is 4-fluorophenyl) Refer to Chart EEE Using procedures described in Example 472, the title compound (0.08 g) is prepared as a white solid.

Physical characteristics are as follows:

IR (Nujol)2995, 2926, 1665, 1634, 1592, 1559, 1510, 1495, 1463, 1406, 1377, 1337, 1237, 1167, 1155, 1092, 838 cm$^{-1}$.

EXAMPLE 475

Benzenesulfonamide, 3-nitro-N-[4-[cyclopropyl (5,6,7,8,9,10-hexahydro-4-hydroxy-2-oxo-2H-cycloocta[b]pyran-3-yl)methyl]phenyl]- (Formula EEE-6, R is 3-nitrophenyl) Refer to Chart EEE Using procedures described in Example 472 but starting with 0.21 g of the amino compound, the title compound (0.14 g) is obtained as a white solid.

Physical characteristics are as follows:

IR (Nujol) 3268, 2995, 2855, 1670, 1561, 1534, 1509, 1465, 1405, 1377, 1350, 1169, 1126, 1070, 673, 662 cm$^{-1}$.

EXAMPLE 476

N-[4-[Cyclopropyl (5,6,7,8,9,10-hexahydro-4-hydroxy-2-oxo-2H-cycloocta[b]pyran-3-yl)methyl] phenyl]-1-methyl-1H-imidazole-4-sulfonamide (Formula EEE-6, R is N-methylimidazol-4-yl) Refer to Chart EEE Using procedures described in Example 472, the title compound (0.04 g) is prepared as a white solid.

Physical characteristics are as follows:

M.P. 238°–242° C. MS m/z 483, 289, 194, 144, 132, 117, 82, 55, 42, 41, 39.

PREPARATION 97

N-[(S)-4-phenyl-2-oxazolidinone] 3-nitrocinnamate amide (Formula ZZ-2a) Refer to Chart ZZ (S)-(+)-4-Phenyl-2-oxazolidinone (4.44 g) is dissolved in dry degassed THF (45 mL) and cooled to −78° C. n-Butyllithium (Aldrich, 1.6M in hexane, 18.1 mL) is added and the reaction is stirred at −78° C. for 20 minutes. A solution of the acid chloride (29 mmol) of 3-nitrocinnamic acid of formula ZZ-1 (prepared from the corresponding commercially available acid and oxalyl chloride in methylene chloride) in THF (15 mL) is added slowly. The red reaction mixture is allowed to warm to 23° C., then quenched with NH$_4$Cl and extracted with EtOAc (600 mL), then washed with water (3×120 mL) and brine. The organic phase is dried over MgSO$_4$, treated with decolorizing carbon and filtered through celite and silica gel (2 cm). Concentration in vacuo gives a light yellow solid which is recrystallized from EtOAc/Hexane and the crystals washed with ether giving white crystals (6.66 g).

Physical characteristics for the title product are as follows:

MP 146°–8° C.; $^1$H-NMR (CDCl$_3$, δ) 8.38 (t, J=1.9 Hz, 1 H), 8.23 (ddd J=1.0, 2.2 Hz, 1H), 8.03 (d, J=15.7 Hz, 1 H), 7.90 (d, J=7.8 Hz, 1 H), 7.78 (d, J=15.8 Hz, 1 H), 7.58 (t, J=8.0 Hz, 1 H), 7.36 (m, 5 H), 5.57 (dd, J=3.9, 8.7 Hz, 1 H), 4.78 (t, J=8.8 Hz, 1 H), 4.36 (dd, J=3.9, 8.9 Hz, 1 H).

PREPARATION 98

N-[(R)-4-phenyl-2-oxazolidinone] 3-nitrocinnamate amide (Formula ZZ-2b) Refer to Chart ZZ (R)-(−)-4-Phenyl-2-oxazolidinone (25.0 g) is dissolved in dry degassed THF (400 mL) and cooled to −78° C. n-Butyllithium (Aldrich, 1.5M in hexane, 108 mL) is added and the reaction is stirred at −78° C. for 45 minutes. A solution of the acid chloride (160 mmol) of 3-nitrocinnamic acid of formula ZZ-1 (prepared from 31.0 g the corresponding commerically available acid and oxalyl chloride (14.8 mL) in toluene (50 mL)) in THF (100 mL) is added slowly. The red reaction mixture is allowed to warm to 23° C., then quenched with NH$_4$Cl and extracted with EtOAc (600 mL), then washed with water (3×120 mL) and brine. The organic phase is dried over MgSO$_4$, treated with decolorizing carbon and filtered through celite and silica gel (2 cm). Concentration in vacuo gives a dark oil which is chromatographed over silica gel eluting with 40% EtOAc/hexane to yield 15.43 g of the title product after recrystallization from EtOAc/hexane.

Physical characteristics for the title product are as follows:

MP 146°–8° C.; $^1$H-NMR (CDCl$_3$, δ) 8.38 (t, J=1.9 Hz, 1 H), 8.23 (ddd J=1.0, 2.2 Hz, 1 H), 8.03 (d, J=15.7 Hz, 1 H), 7.90 (d, J=7.8 Hz, 1 H), 7.78 (d, J=15.8 Hz, 1 H), 7.58 (t, J=8.0 Hz, 1 H), 7.36 (m, 5 H), 5.57 (dd, J=3.9, 8.7 Hz, 1 H), 4.78 (t, J=8.8 Hz, 1 H), 4.36 (dd, J=3.9, 8.9 Hz, 1 H).

PREPARATION 99

N-[(S)-4-phenyl-2-oxazolidinone] 3(R)-(3-nitrophenyl) penten-4-oate amide (Formula ZZ-3) Refer to Chart ZZ Copper bromide (217 mg) is dissolved in dimethyl sulfide (4.0 mL) and cooled to −78° C. and vinyl magnesium bromide (Aldrich; 1.0M in THF, 2.0 mL) is added. That solution is added via syringe to a −78° C. solution of the amide of Preparation 97 (338 mg) in THF (5.0 mL). The reaction is allowed to warm to 23° C., then quenched with NH$_4$Cl, and extracted with EtOAc (200 mL). The organic phase is washed with water (2×) and brine. Filration through MgSO$_4$ and silica gel (3 cm), then concentration in vacuo gives the title product as a yellow oil (325 mg).

Physical characteristics for the title product are as follows:

$^1$H NMR (CDCl$_3$, δ) 8.07 (m, 2 H) 7.54 (m, 1 H), 7.43 (m, 1 H), 7.35 (m, 3 H), 7.25 (m, 2 H), 5.96 (m, 1 H), 5.33 (dd, 1 H), 5.08 (d, 1 H), 5.01 (d, 1 H), 4.66 (t, 1 H), 4.28 (dd, 1 H), 4.00 (m, 1 H), 3.46 (d, 2 H).

PREPARATION 100

N-[(S)-4-phenyl-2-oxazolidinone] 3(R)-(3-nitrophenyl) pentanoate amide (Formula ZZ-10) Refer to Chart ZZ To CuBr (430 mg) is added dimethyl sulfide (3 mL) and THF (10 mL). The solution is cooled to −40° C., EtMgBr (4.5 mL) is then added. After 15 minutes the resulting solution is added to a solution of the title product of Preparation 97 (676 mg) in THF (10 mL) at −40° C. The mixture is warmed to −15° C. in a period of 40 minutes, quenched with 0.5N HCl solution (6 mL) and warmed to room temperature. The mixture is diluted with water (20 mL) and extracted with ether (60 mL). The organic phase is dried over MgSO$_4$ and concentrated in vacuo to give 1.20 g of the title product. Flash chromatography on silica gel (4:1 hexane-EtOAc) gives 277.0 mg of the title product, followed by an additional 51.0 mg of the title product (70% purity).

Physical characteristics for the title product are as follows:

$^1$H-NMR (CDCl$_3$) 8.03–8.00 (m, 2H), 7.50 (d, 1H), 7.43–7.26 (m, 4H), 7.25–7.23 (m, 2H), 5.31–5.27 (dd, 1H), 4.64–4.49 (t, 1H), 4.26–4.22 (dd, 1H), 3.42–3.26 (m, 2H), 3.22–3.11 (m, 1H), 1.77–1.58 (m, 2H), 0.78–0.74 (t, 3H).

PREPARATION 101

3(R)-(3-Nitrophenyl) pentanoic acid (Formula ZZ-11) Refer to Chart ZZ

To a mixture of N-[(S)-4-phenyl-2-oxazolidinone] 3(R)-(3-nitrophenyl) pentanoate amide of Preparation 100 (277 mg), THF (4 mL), H$_2$O (1 mL) and H$_2$O$_2$ (0.4 mL, 30% solution in water) is added a solution of LiOH (2 mL, 0.8M) at 0 ° C. The mixture is stirred for 80 minutes at 0° C. and quenched with a solution of Na$_2$SO$_3$ (3 mL, 1.3M). The mixture is diluted with water (15 mL) and washed with ether (2×15 mL). The aqueous is acidified with 1.6N HCl solution at 0° C. to pH 3. That aqueous is extracted with CH$_2$Cl$_2$ (2×20 mL). The combined organic layers are dried over MgSO$_4$ and concentrated in vacuo to give 159.7 mg (96%) of the title product which is used without further purification.

Physical characteristics for the title product are as follows:

$^1$H-NHR (CDCl$_3$) 8.11–8.06 (m, 2H), 7.56–7.47 (m, 2H), 3.17–3.08 (m, 1H), 2.79–2.72 (dd, 1H), 2.68–2.57 (dd, 1H), 1.88–1.58 (m, 2H), 0.83–0.78 (t, 3H).

PREPARATION 102

3-(α[S]-Ethyl-(3-nitrophenyl)-4-hydroxy-5,6,7,8,9, 10-hexahydrocycloocta[b]pyran-2-one (Formula ZZ-12) Refer to Chart ZZ To the title product of Preparation 101 (159.7 mg) in CH$_2$Cl$_2$ (5 mL) is added oxalyl chloride (0.1 mL). The mixture is heated at reflux for 2 hours. The methylene chloride and the excess oxalyl chloride are removed, and mesitylene (3 mL) is added. The acid chloride solution is heated at reflux and a solution of the title product of Preparation 87 (VV-2 which is the same as ZZ-6) (84 mg), Et$_3$N (90 mg) in mesitylene (2.5 mL) is added dropwise. After complete addition the reaction is heated at reflux for 40 minutes. The reaction is cooled to room temperature and the solid is removed by filtration. The filtrate is evaperated and the residue is diluted with methanol (20 mL) and 1N NaOH (2 mL). The resulting mixture is stirred at rt for 40 minutes. The methanol is removed and water (10 mL) is added. The aqueous is extracted with ether (2×25 mL) and the the aqueous is acidified with 1.6N HCl solution at 0° C. to pH 3. That aqueous is extracted with CH$_2$Cl$_2$ (2×25 mL). The combined organic layers are dried over MgSO$_4$ and concentrated in vacuo to give 101.0 mg crude title product. Flash chromatography (8:1 CH$_2$Cl$_2$-EtOAc) on silica gel affords 60.0 mg of pure title product.

Physical characteristics for the title product are as follows:

$^1$H-NMR (CDCl$_3$) 8.23 (s, 1H), 8.04–8.01 (d, 1H), 7.80–7.77 (d, 1H), 7.43–7.38 (t, 1H), 7.15 (br s, 1H), 4.33–4.28 (t, 1H), 2.60–2.51 (m, 4H), 2.27–2.17 (m, 2H), 1.62 (m, 2H), 1.45 (m, 4H), 0.96–0.91 (t, 3H).

PREPARATION 103

3-(α[S]-Ethyl-(3-aminophenyl)-4-hydroxy-5,6,7,8,9, 10-hexahydrocycloocta[b]pyran-2-one (ZZ-13) Refer to Chart ZZ A mixture of the title product of Preparation 102 (30 mg), 5% Platinum on activated carbon (13 mg), CH$_2$Cl$_2$ (10 mL) and EtOAc (5 mL) is stirred at room temperature under H$_2$ (1 atm) for 4 h. The catalyst is removed by filtration. The filtrate is dried over MgSO$_4$ and concentrated in vacuo to give 28.0 mg of the title product which is used without purification.

Physical characteristics for the title product are as follows:

$^1$H-NMR (CDCl$_3$) 7.19–7.14 (t, 1H), 6.83–6.81 (d, 1H), 6.72 (s, 1H), 6.61–6.58 (d, 1H), 4.30–4.25 (t, 1H), 2.62–2.58 (m, 2H), 2.46–2.34 (m, 2H), 2.15–1.92 (m, 2H), 1.55–1.39 (m, 6H), 1.02–0.98 (t, 3H).

EXAMPLE 477

N-[3-[(R)Ethyl-(5,6,7,8,9,10-hexahydro-4-hydroxy-2-oxo-2H-cycloocta[b]pyran-3-yl)methyl]phenyl]-4-fluorobenzenesulfonamide (Formula ZZ-14) Refer to Chart ZZ To the title compound of Preparation 103 (18.5 mg) in CH$_2$Cl$_2$ (2 mL) at 0° C. is added triethylamine (6 mg), followed by 4-fluorobenzenesulfonyl chloride (11 mg) in CH$_2$Cl$_2$ (0.5 mL). After 30 minutes at 0° C. the reaction is evaporated in vacuo and purified by flash chromatography on silica gel (20% EtOAc/CH$_2$Cl$_2$) to afford 19.2 mg of the title product.

Physical characteristics for the title product are as follows:

$^1$H-NMR (CDCl$_3$, δ) 7.97 (m, 2H), 7.27 (m, 2H), 7.06 (t, 1H), 6.76 (m, 2H), 6.54 (d, 1H), 4.02 (t, 1H), 3.65 (broad singlet, 1H), 2.52 (t, 2H), 2.44 (t, 2H), 2.12 (m, 2H), 1.62–1.36 (m, 9H), 0.87 (t, 3H).

PREPARATION 104

N-[(R)-4-phenyl-2-oxazolidinone] 3(S)-(3-nitrophenyl-3-cyclopropyl) propionic amide (Formula ZZ-15) Refer to Chart ZZ To a flame dried round bottom flask (100 mL) containing ether (50 mL) is added magnesium turnings (5.0 g). Cyclopropylbromide (4.8 mL) is introduced slowly so as to maintain a gentle reflux. After the addition is complete the reaction is stirred for an additional hour. Copper bromide (1.7 g) and dimethyl sulfide (10 mL) are added to a 250 mL round bottom flask containing THF (20 mL). That mixture is stirred for 15 min at −10° C. The Grignard solution is then added via cannula to the CuBr/(CH$_3$)$_2$S mixture and the reaction stirred for an additional 15 minutes. A solution of the amide of Preparation 98, 4.0 g, in THF (20 mL) is added and the reaction stirred for 20 minutes and then quenched with NH$_4$Cl. The reaction is extracted with EtOAc (1.5 L), washed with water (3×300 mL) and brine, dried over MgSO$_4$, and filtered. The filtrate is concentrated in vacuo and the dark residue is chromatographed over silica gel (1 kg), eluting with 30% EtOAc/hexane to give the title product as a pale yellow oil (1.52 g).

Physical characteristics for the title product are as follows:

$^1$H-NMR (CDCl$_3$, δ) 8.05 (m, 2 H), 7.53 (d, I H), 7.39 (t, 1 H), 7.34 (m, 3 H), 7.23 (m, 2 H), 5.30 (dd, 1 H), 4.63 (t, 1 H), 4.28 (dd, 1 H), 3.50 (d, 2 H), 2.48 (m, 1 H), 1.07 (m, 1 H), 0.52 (m, 1 H), 0.42 (m, 1 H), 0.21 (m, 1 H), 0.12 (m, 1 H).

PREPARATION 105

3(R)-(3-Nitrophenyl-3-cyclopropyl) propionic amide (Formula ZZ-16) Refer to Chart ZZ To a mixture of N-[(R)-4-phenyl-2-oxazolidinone] 3(S)-(3-nitrophenyl-3-cyclopropyl) propionic amide of Preparation 104 (1.09 g), THF (12 mL), H$_2$O (3.5 mL) and H$_2$O$_2$ (1.3 mL, 30% solution in water) is added a solution of LiOH (6 mL, 0.8M) at 0° C. The mixture is stirred for 2 hours at 0° C. and quenched with a solution of Na$_2$SO$_3$ (8 mL, 1.3M). The mixture is diluted with water (20 mL) and washed with ether (2×25 mL). The aqueous is acidified with 1.6N HCl solution at 0° C. to pH 3. That aqueous is extracted with CH$_2$Cl$_2$ (3×25 mL). The combined organic layers are dried over MgSO$_4$ and concentrated in vacuo to give 0.63 g of the title product which is used without further purification.

Physical characteristics for the title product are as follows:

$^1$H-NMR (CDCl$_3$) 8.11–8.09 (m, 2H), 7.58–7.45 (m, 2H), 2.93–2.85 (dd, 1H), 2.83–2.75 (dd, 1H), 2.50–2.44 (m, 1H), 1.08 (m, 1H), 0.66 (m, 1H), 0.48 (m, 1H), 0.34 (m, 1H), 0.17 (m, 1H).

PREPARATION 106

3-(α[S]-Cyclopropyl-(3-nitrophenyl)-4-hydroxy-5,6, 7,8,9,10-hexahydrocycloocta[b]pyran-2-one (Formula ZZ-17) Refer to Chart ZZ To the title product of Preparation 105. (610 mg) in CH$_2$Cl$_2$ (8 mL) is added oxalyl chloride (0.3 mL). The mixture is heated at reflux for 2 hours. The methylene chloride and the excess oxalyl chloride are removed, and mesitylene (10 mL) is added. The acid chloride solution is heated at reflux and a solution of ZZ-6 (Preparation 87 formula VV-2) (273 mg), Et$_3$N (260 mg) in mesitylene (2 mL) is added dropwise. After complete addition the reaction is heated at reflux for 40 minutes. The reaction is cooled to room temperature and the solid is removed by filtration. The filtrate is evaporated and the residue is diluted with methanol (25 mL) and 1N NaOH (4 mL). The resulting mixture is stirred at rt for 40 minutes. The methanol is removed and water (20 mL) is added. The aqueous is extracted with ether (2×25 mL) and the the aqueous is acidified with 1.6N HCl solution at 0° C. to pH 3. That aqueous is extracted with $CH_2Cl_2$ (3×25 mL). The combined organic layers are dried over $MgSO_4$ and concentrated in vacuo to give 423.1 mg crude title product. Flash chromatography (8:1 $CH_2Cl_2$-EtOAc) on silica gel affords 241.0 mg of pure title product.

Physical characteristics for the title product are as follows:

MP 195.0°–7.0° C. $^1$H-NMR ($CDCl_3$) 8.24 (s, 1H), 8.08–8.05 (d, 1H), 7.78–7.75 (d, 1H), 7.48–7.42 (t, 1H), 7.03 (s, 1H), 3.81–3.78 (d, 1H), 2.63–2.51 (m, 4H), 1.74–1.61 (m, 5H), 1.48 (m, 4H), 0.79 (m, 1H), 0.63 (m, 1H), 0.41 (m, 1H), 0.28 (m, 1H).

PREPARATION 107

3-($\alpha$[S]-Cyclopropyl-(3-aminophenyl)-4-hydroxy-5, 6,7,8,9,10-hexahydrocycloocta[b]pyran-2-one (Formula ZZ-18) Refer to Chart ZZ A mixture of the title product of Preparation 106 (180 mg), 5% Platinum on activated carbon (45 mg) and EtOAc (25 mL) is stirred at room temperature under $H_2$ (1 atm) for 4 hours. The catalyst is removed by filtration. The filtrate is dried over $MgSO_4$ and concentrated in vacuo to give 160 mg of crude title product. Flash chromatography (10–50% EtOAc/$CH_2Cl_2$) over silica gel affords 85.0 mg of the title product.

Physical characteristics for the title product are as follows:

$^1$H-NMR ($CDCl_3$) 7.16–7.11 (t, 1H), 6.93–6.90 (d, 1H), 6.79 (s, 1H), 6.60–6.57 (d, 1H), 3.84–3.81 (d, 1H), 2.62–2.58 (m, 2H), 2.45–2.40 (m, 2H), 1.74 (m, 2H), 1.56–1.32 (m, 7H), 0.70–0.66 (m, 1H), 0.59–0.50 (m, 2H), 0.27–0.23 (m, 1H).

EXAMPLE 478

N-[3(S)-[Cyclopropyl-(5,6,7,8,9,10-hexahydro-4-hydroxy-2-oxo-2H-cycloocta[b]pyran-3-yl)methyl] phenyl]-4-fluorobenzenesulfonamide (Formula ZZ-19) Refer to Chart ZZ To the title compound of Preparation 107 (84 mg) in $CH_2Cl_2$ (5 mL) is added triethylamine (25 mg), followed by 4-fluorobenzenesulfonyl chloride (48 mg) in $CH_2Cl_2$ (2 mL) at 0° C. After 2 hours at 0° C., the solvent is removed and the residue is purified by flash chromatography (10–25% EtOAc/$CH_2Cl_2$; silica gel) to yield 24.3 mg of the title product.

Physical characteristics for the title product are as follows:

$^1$H-NMR ($CDCl_3$) 7.91 (m, 2H), 7.26 (t, 2H), 7.05 (t, 1H), 6.78 (m, 2H), 6.53 (d, 1H), 3.65 (s, 1H), 3.29 (d, 1H), 2.50 (m, 4H), 1.70–1.35 (m, 9H), 0.67 (m, 1H), 0.50 (m, 1H), 0.25 (m, 2H).

EXAMPLE 479

N-[3(R)-[Cyclopropyl-(5,6,7,8,9,10-hexahydro-4-hydroxy-2-oxo-2H-cycloocta[b]pyran-3-yl)methyl] phenyl]-4-fluorobenzenesulfonamide•(Formula ZZ-19) Refer to Chart ZZ Utilizing procedures analogous to those described above, the title compound is prepared.

EXAMPLE 480

3-($\alpha$-Cyclopropyl(5-(N-carbo-t-butoxy) aminomethyl)furfur-2-yl)-4-hydroxy-5,6,7,8,9,10-hexahydrocycloocata[b]pyran-2-one Utilizing procedures analogous to those described above, the title compound is prepared.

Physical characteristics are as follows:

$^1$NMR ($CDCl_3$, δ) 7.39 (s, 1H), 6.3 (m, 1H), 6.0 (m, 1H), 4.3 (m, 2H), 3.9 (m, 1H), 2.6 (m, 2H), 2.4 (m, 2H), 1.75 1.28 (m, 18H), 0.70–0.25 (m, 4H).

EXAMPLE 481

3-(Diphenylmethyl)-5,6,7,8,9,10-hexahydro-4-hydroxy-2H-cycloocta[b]pyran-2-one (Formula U-3 wherein $R_1$ is phenyl) Refer to Chart U A solution of diphenylmethanol (300 mg), p-touluenesulfonic acid (50 mg), and the compound of Formula U-1 (200 mg) in toluene (5 mL) is refluxed for 2 h. Additional diphenylmethanol (150 mg) is added and reflux continued for 4 h. The reaction mixture is cooled, poured into 1N sodium hydroxide solution and extracted with ether (50 mL). The aqueous layer is acidified and extracted with dichloromethane, dried, concentrated in vacuo, and triturated with ether to give after filtration and drying 300 mg of the title compound as a white powder.

Physical characteristics are as follows:

MS(EI): 360, 255, 207, 167, 152. HRMS: 360.1723. TLC (silica gel GF): $R_f$=0.40 20% ethyl acetate in hexane with 1% acetic acid.

EXAMPLE 482

3-(1,3-Diphenyl-2-propyl)-5,6,7,8,9-pentahydro-4-hydroxy-2H-cyclohepta[b]pyran-2-one (Formula J-3 wherein n is 3, $R_1$ and $R_2$ are each —$CH_2$-phenyl) Refer to Chart J A solution of the title compound of Preparation 48 (1,3-diphenyl-2-propanol (300 mg)), p-touluenesulfonic acid (50 mg), and the compound of Formula J-1 wherein n is 3 (200 mg) in toluene (5 mL) is refluxed for 2 h. Additional 1,3-diphenyl-2-propanol (150 mg) is added and reflux continued for 4 h. The reaction mixture is cooled, poured into 1N sodium hydroxide solution and extracted with ether (50 mL). The aqueous layer is acidified and extracted with dichloromethane, dried, concentrated in vacuo, and triturated with ether to give after filtration and drying 10 mg of the title compound as a white powder.

Physical characteristics are as follows:

MS(FAB): 375, 361, 307, 291, 270, 193, 181,118, 91. TLC (silica gel GF): $R_f$=0.45 40% ethyl acetate in hexane.

EXAMPLE 483

3-(Phenylcyclobutyl)-5,6,7,8,9,10-hexahydro-4-hydroxy-2H-cycloocta[b]pyran-2-one (Formula U-3 wherein $R_1$ is cyclobutyl) Refer to Chart U A solution of the compound of Formula U-1 (200 mg) and phenylcyclobutanol (500 mg) in dioxane (3 mL) is treated with boron trifluoretherate (500 μL) and stirred at room temperature for 4 h. Additional phenylcyclobutanol (250 mg) is added and stirring continued for 24 h. The mixture is diluted with ethyl acetate, washed with water and brine, dried, filtered, and concentrated in vacuo. The resulting material is chromatographed on silica gel to give the title compound as a white solid (25 mg).

Physical characteristics are as follows:

MP 240°–241° C. MS(EI):324, 296, 195, 172, 144, 131, 115, 103, 91. HRMS: 324.1714.

EXAMPLES 484–486

Utilizing procedures analogous to those described above, the following compounds of the present invention are prepared:

EXAMPLE 484

3-[Cyclopropyl-(3,5-diamino-phenyl)-methyl]-4-hydroxy-5,6,7,8,9,10-hexahydro-cycloocta[b]pyran-2-one Physical characteristics are as follows:

MP 87° C. decomposition Tan/beige amorphus solid. TLC: (Silica Gel GF): $R_f$=0.22 (5% MeOH in $CHCl_3$). HRMS: 354.1948.

EXAMPLE 485

N-[3-[Cyclopropyl-(4-hydroxy-2-oxo-5,6,7,8,9,10-hexahydro-2H-cycloocta[b]pyran-3-yl)-methyl]-5-8-quinolinesulfonylamino-phenyl]-8-quinolinesulfonamide Physical characteristics are as follows:

MP 139°–145° C. Tan/beige amorphus solid. TLC: (Silica Gel GF): $R_f$=0.55 (5% MeOH in $CHCl_3$). HRMS: [M+H]$^+$: 737.2110.

EXAMPLE 486

N-[3-Amino-5-[cyclopropyl]-(4-hydroxy-2-oxo-5,6,7,8,9,10-hexahydro-2H-cycloocta[b]pyran -3-yl) -methyl]-phenyl]-benzenesulfonamide Physical characteristics are as follows:

MP 115° C. decomposition Tan/beige amorphous solid. TLC: (Silica Gel GF): $R_f$=0.18 (5% MeOH in $CHCl_3$). HRMS: 494.1873.

FORMULA CHART

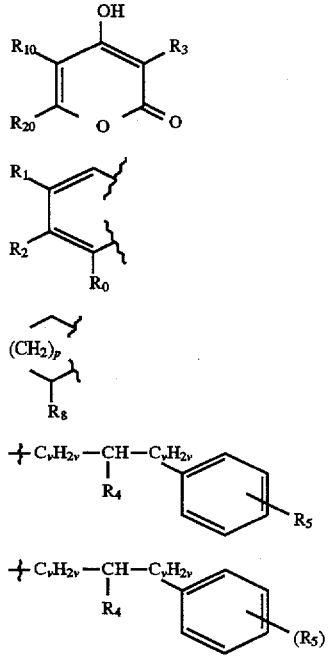
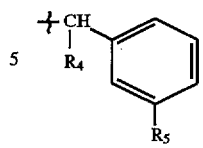
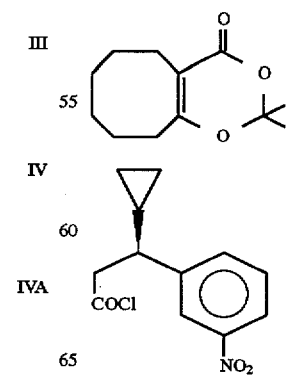

-continued
FORMULA CHART
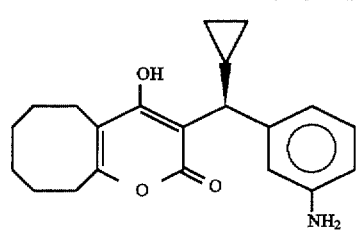
XV
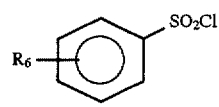
XVI
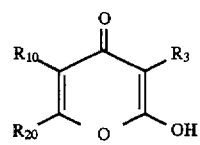
XVII
CHART A
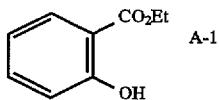
A-1
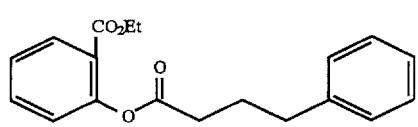
A-2
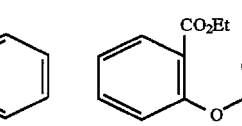
A-4
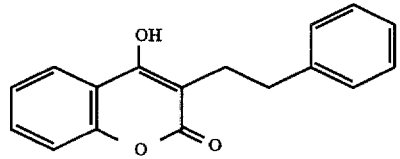
A-3
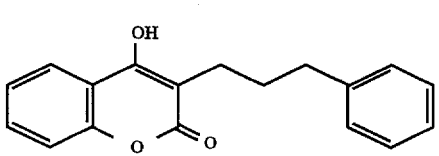
A-5
CHART B
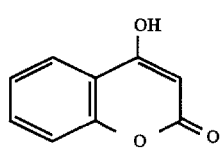
B-1
RCHO (B-2) →
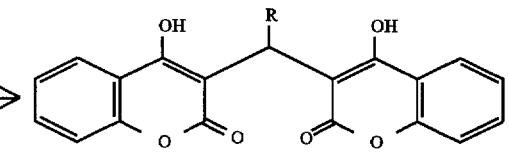
B-3

-continued
CHART B
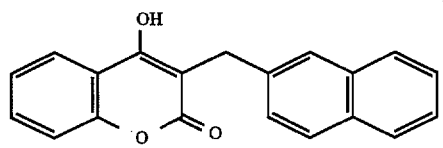
B-4a
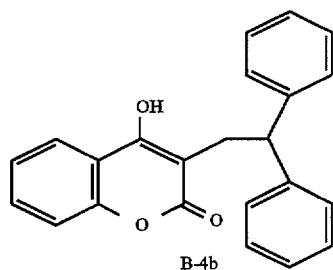
B-4b
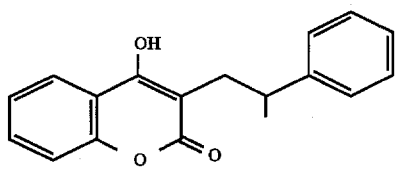
B-4c
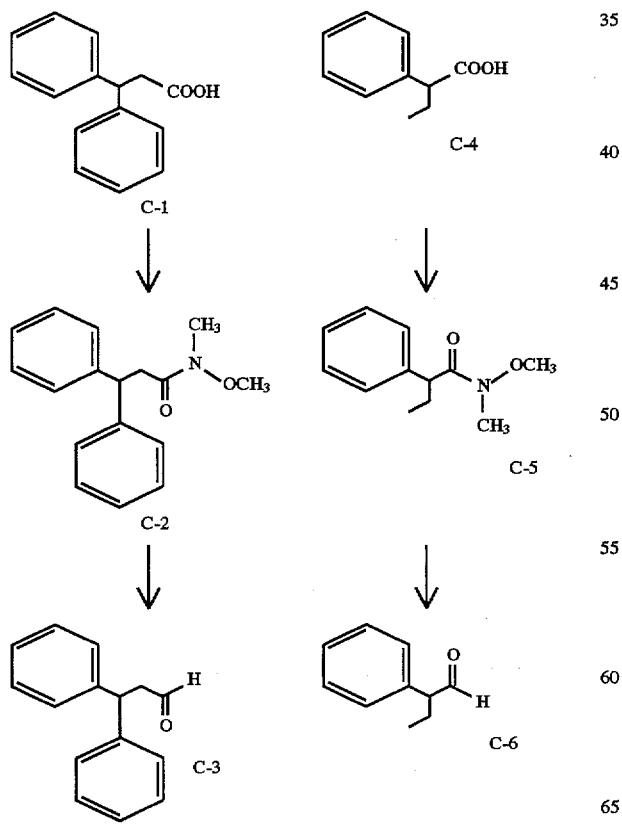
CHART C
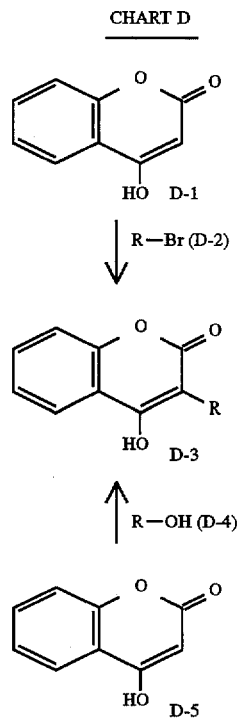
CHART D CHART E
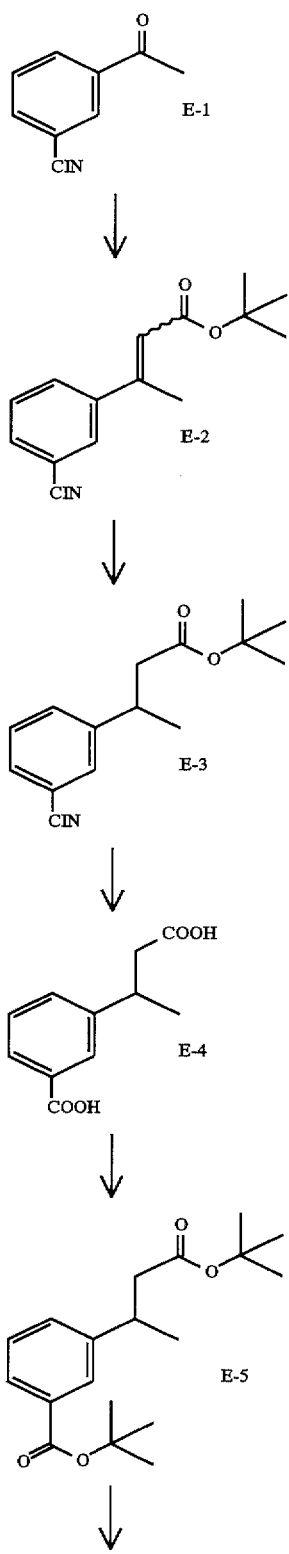
-continued
CHART E
CHART F
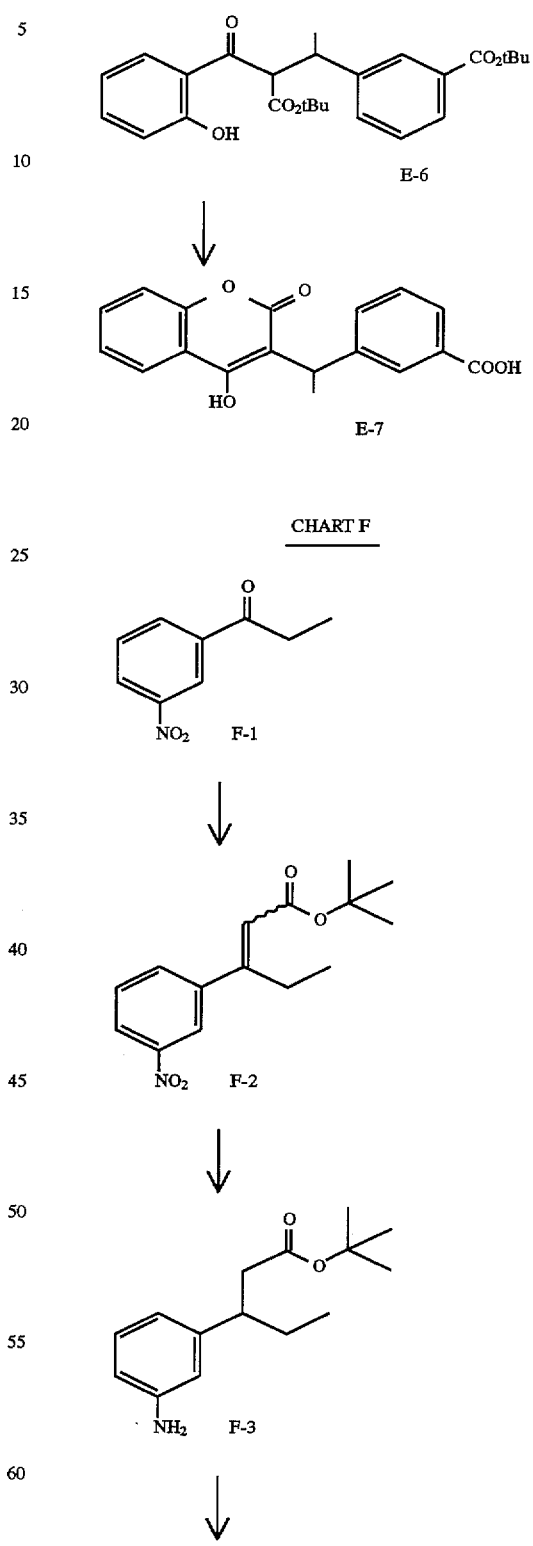

CHART F
-continued
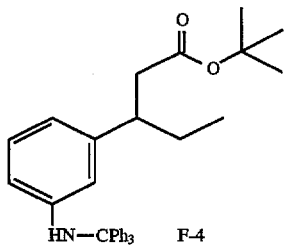
F-4
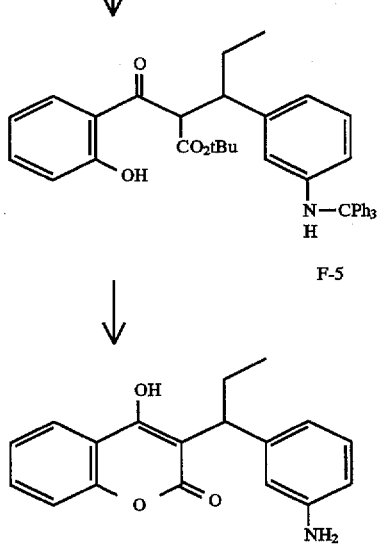
F-5
F-6
CHART G
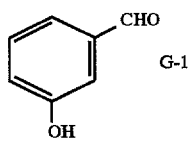
G-1
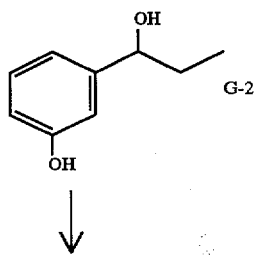
G-2
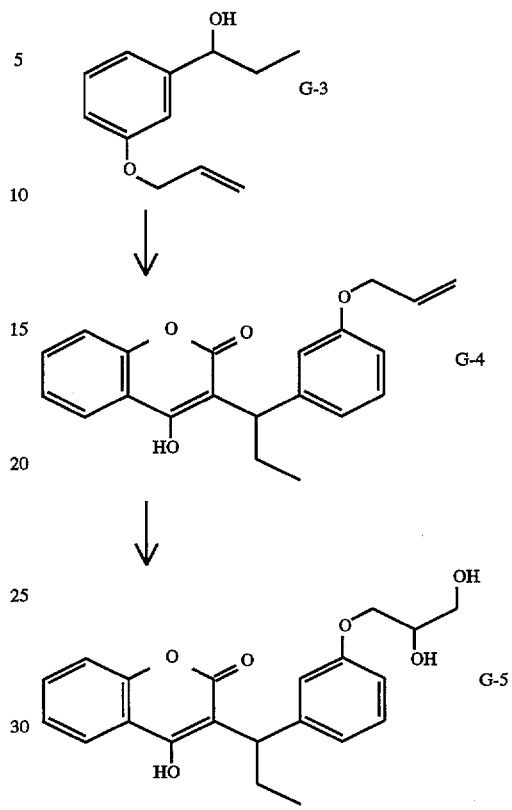
G-3
G-4
G-5
CHART H
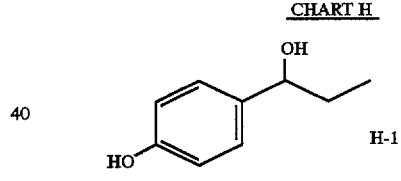
H-1
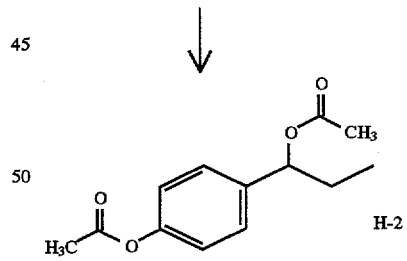
H-2
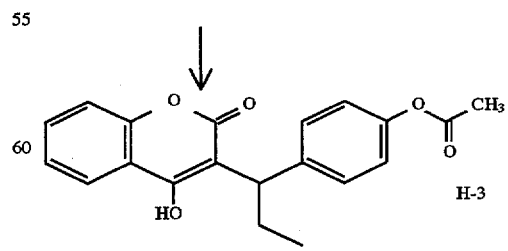
H-3

CHART I
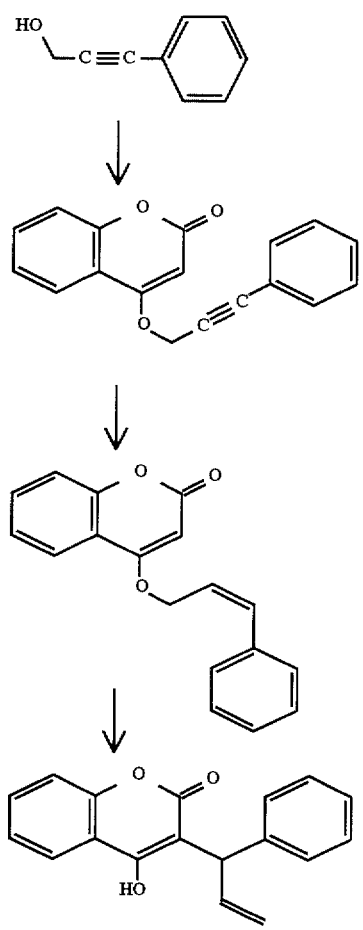
CHART J
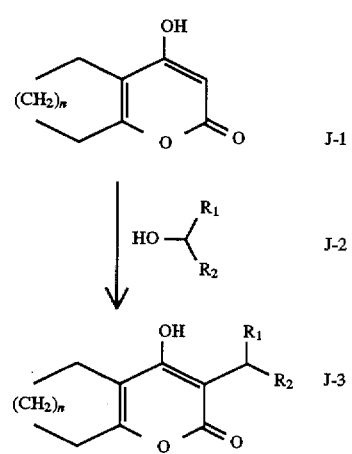
CHART K
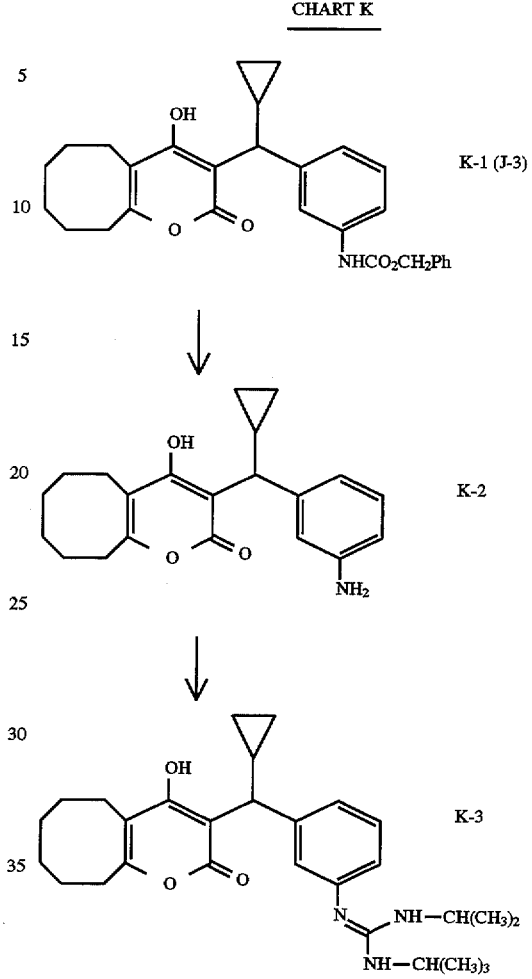
CHART L
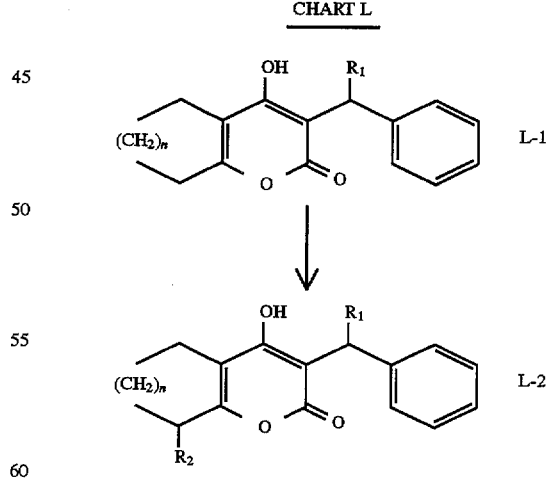

CHART M
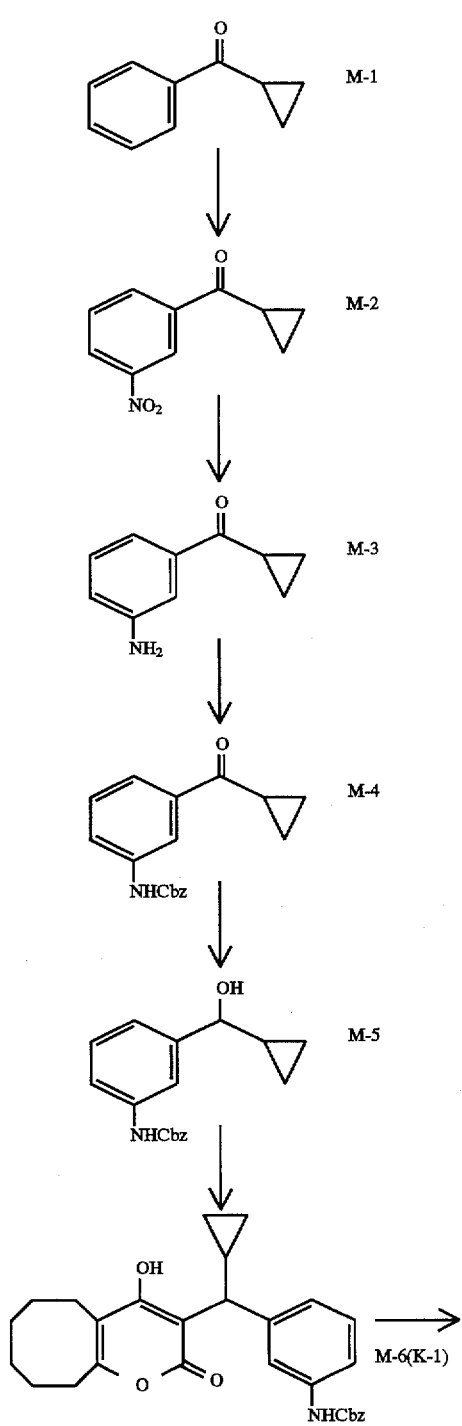
-continued
CHART M
CHART N
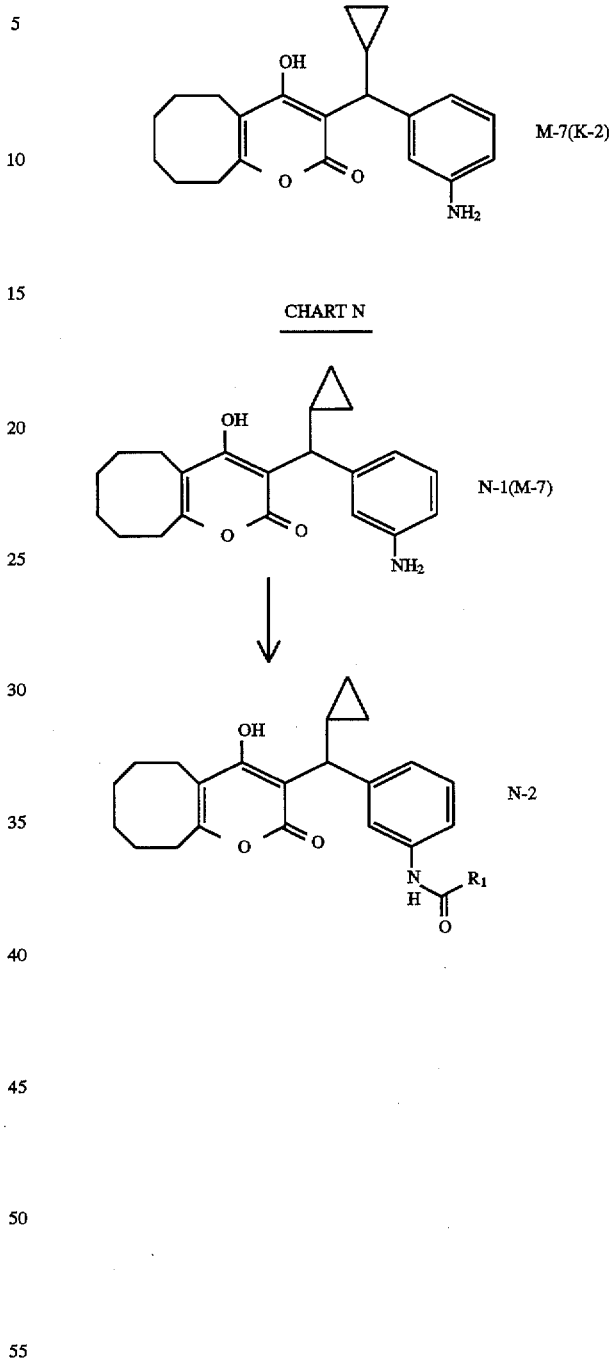

CHART O
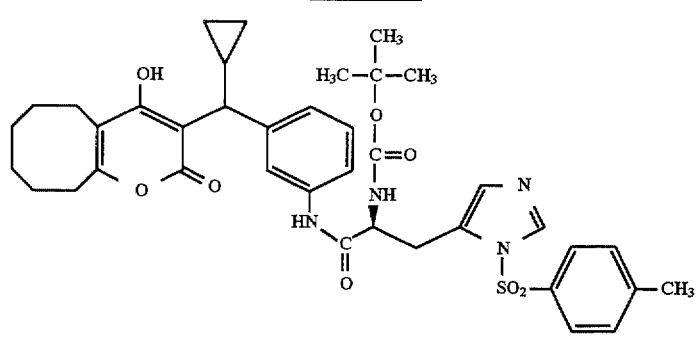
O-1
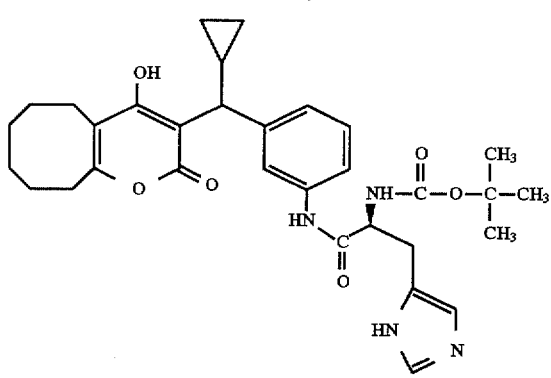
O-2
CHART P
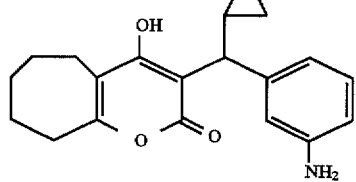
P-1
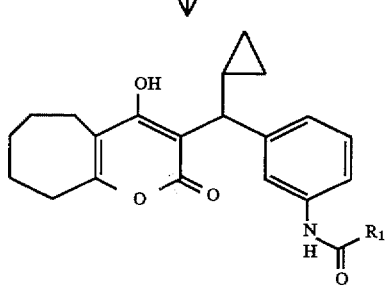
P-2
CHART Q
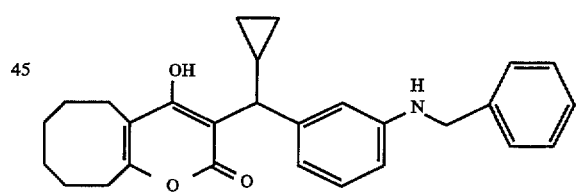
Q-1
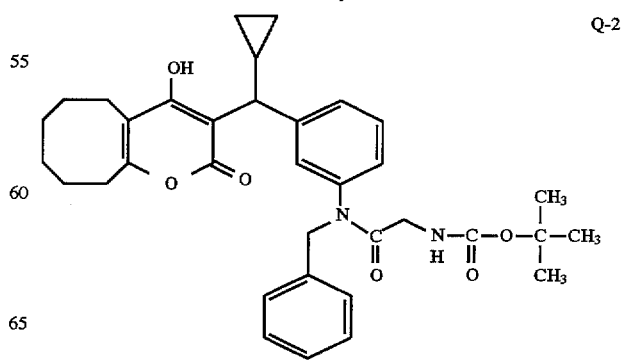
Q-2

CHART R
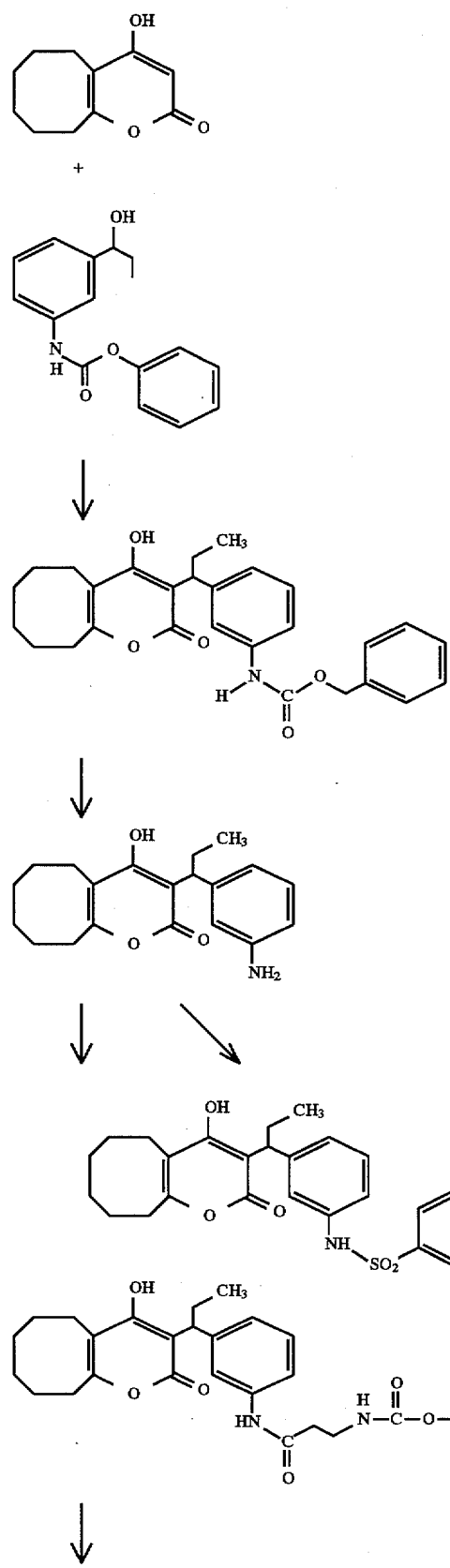
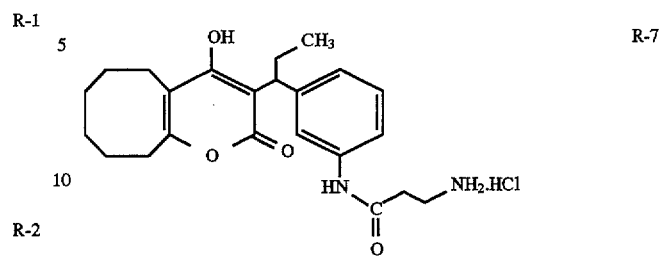
CHART S
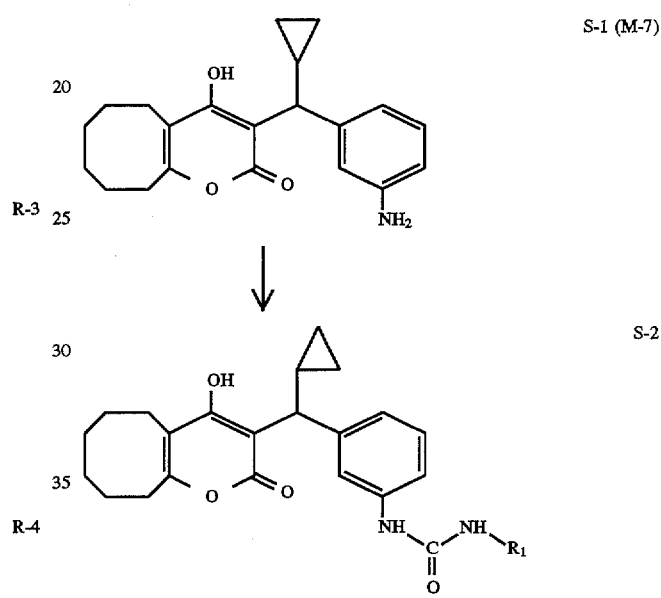
CHART T
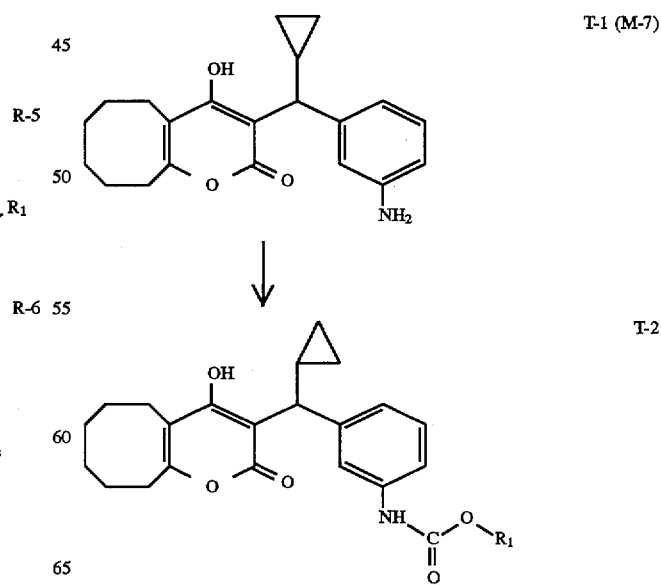

CHART U
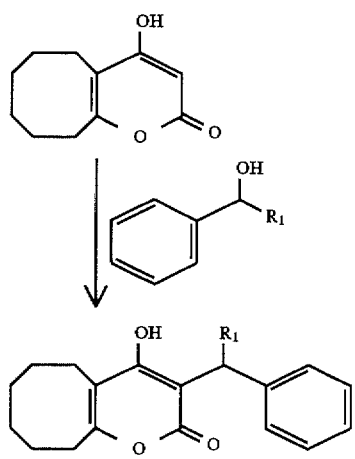
CHART V
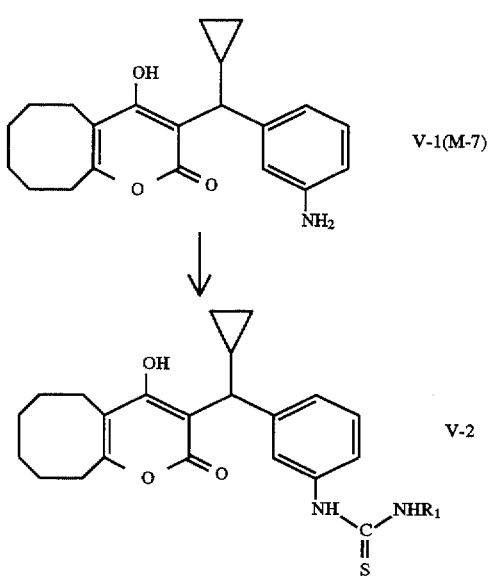
CHART W
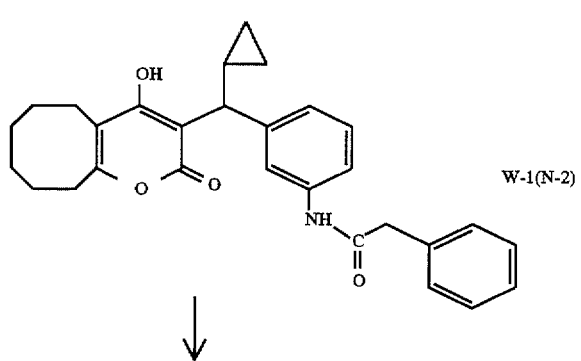
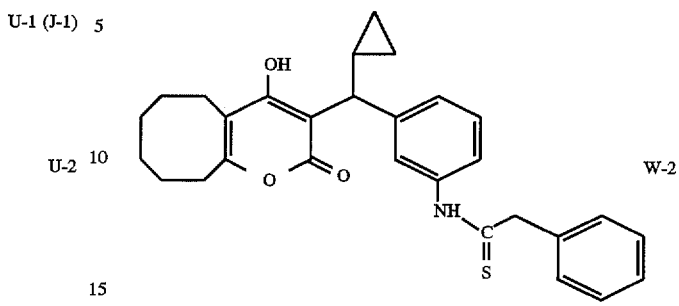
CHART X
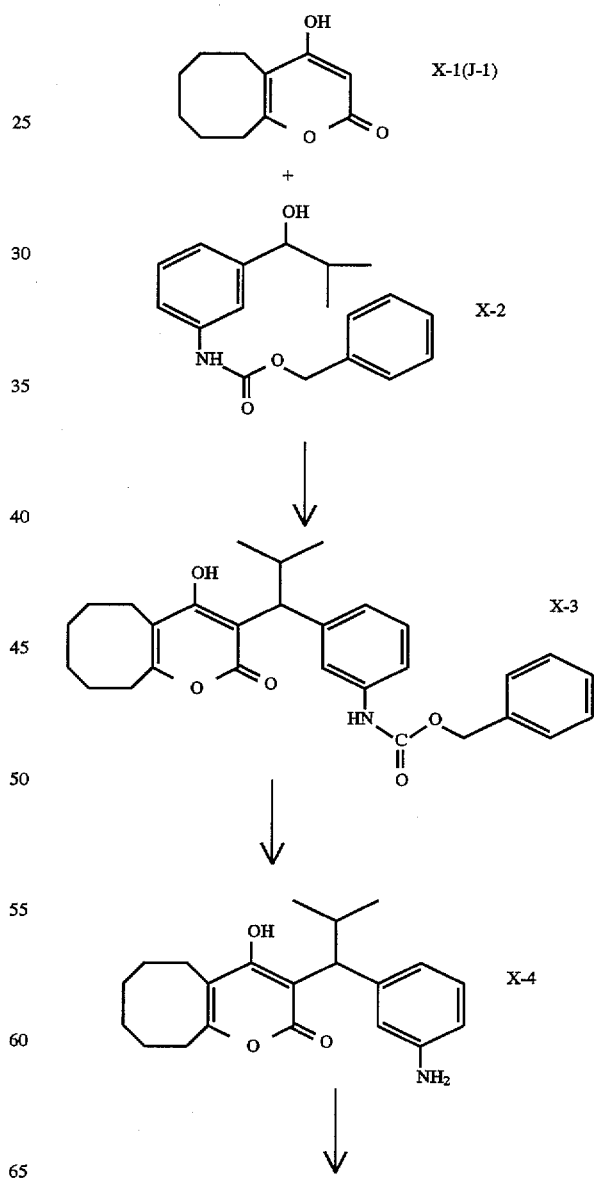

205
-continued
CHART X
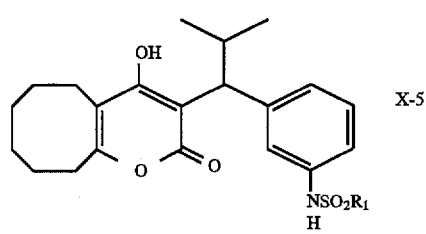 X-5
CHART Y
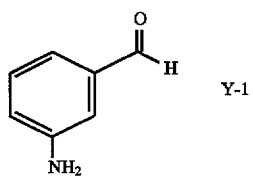 Y-1
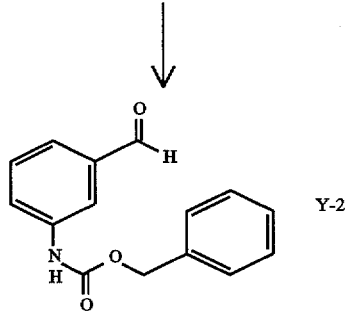 Y-2
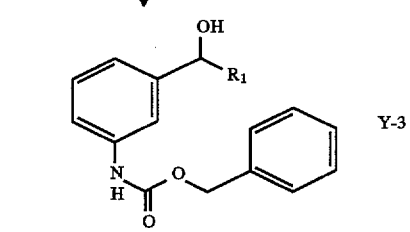 Y-3
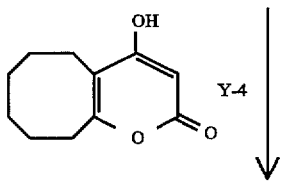 Y-4
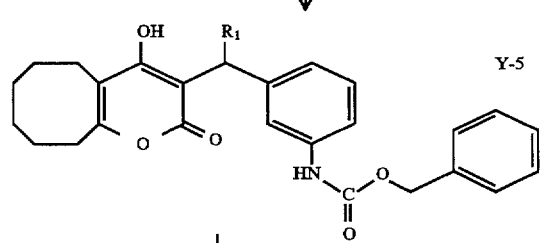 Y-5
206
-continued
CHART Y
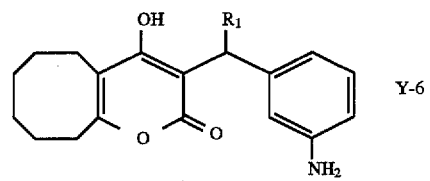 Y-6
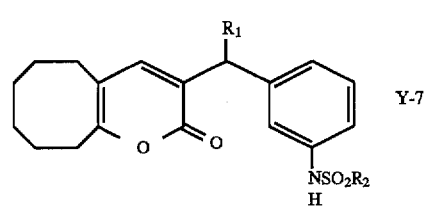 Y-7
CHART Z
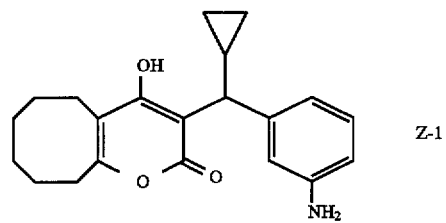 Z-1
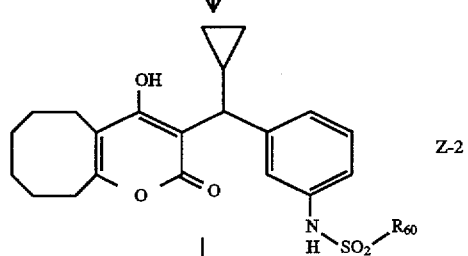 Z-2
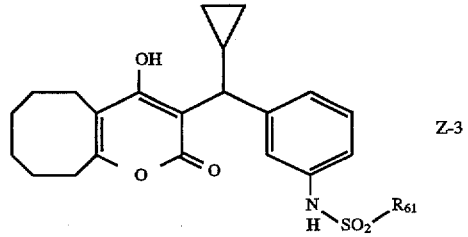 Z-3

CHART AA
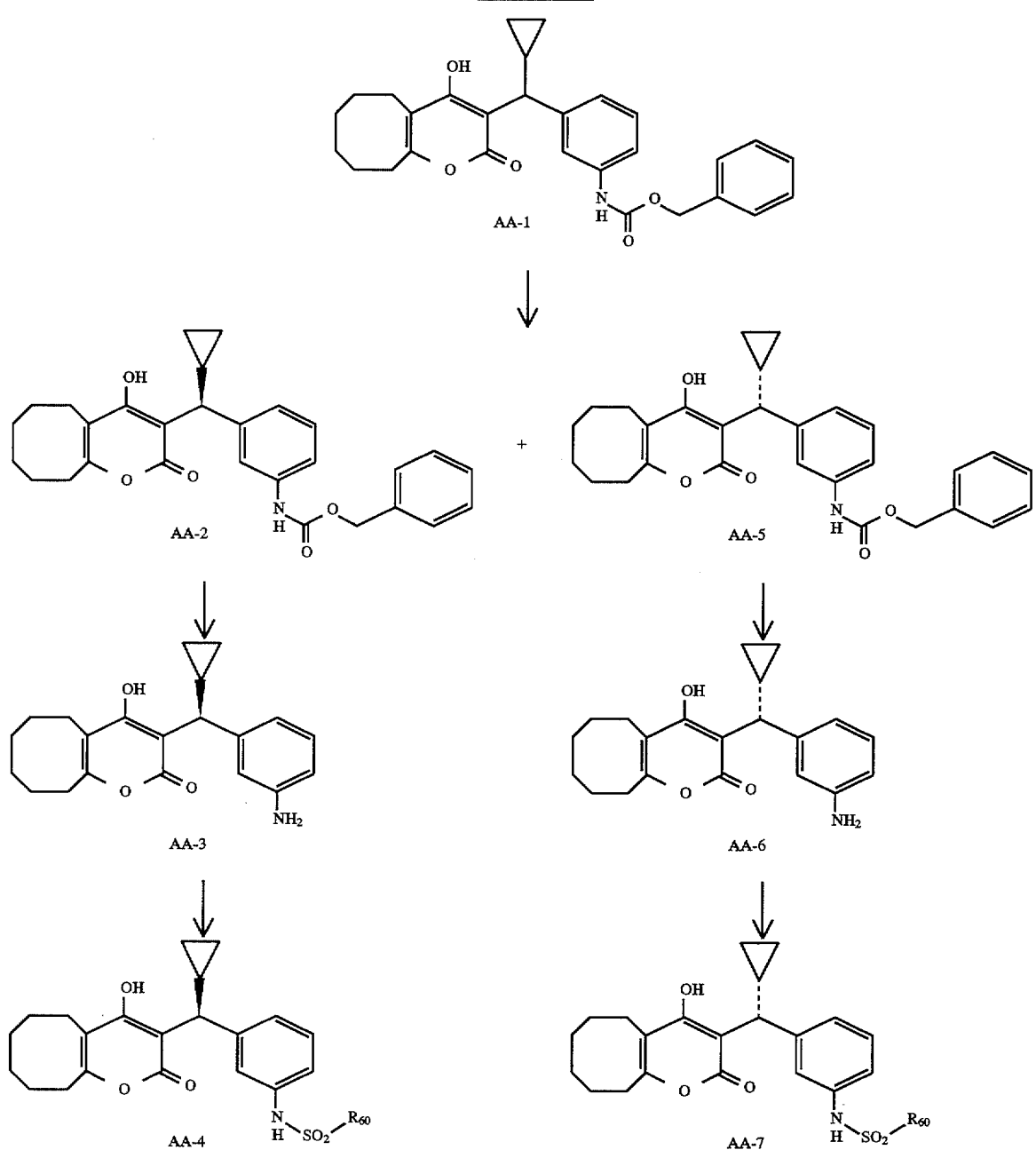

CHART BB
BB-1
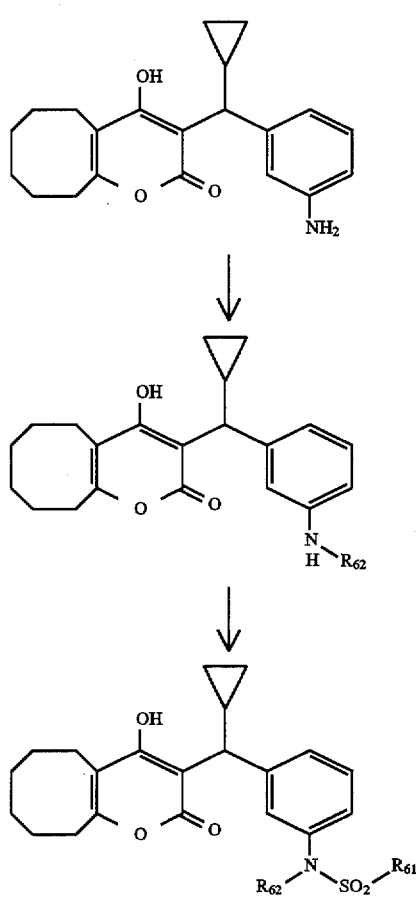
BB-2
BB-3
CHART CC
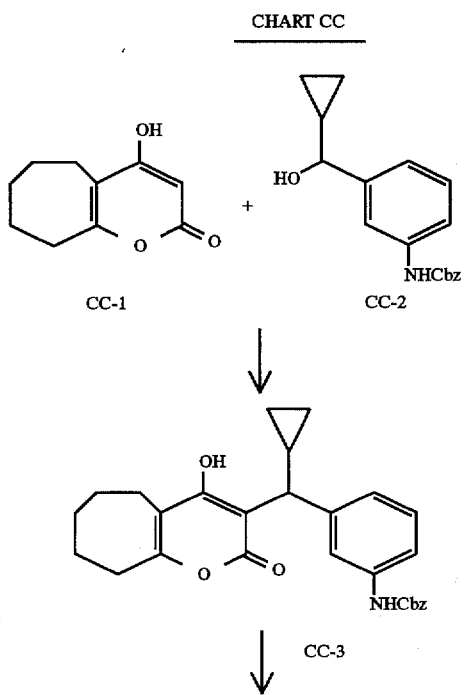
CC-1 + CC-2
CC-3
CHART CC -continued
CC-4
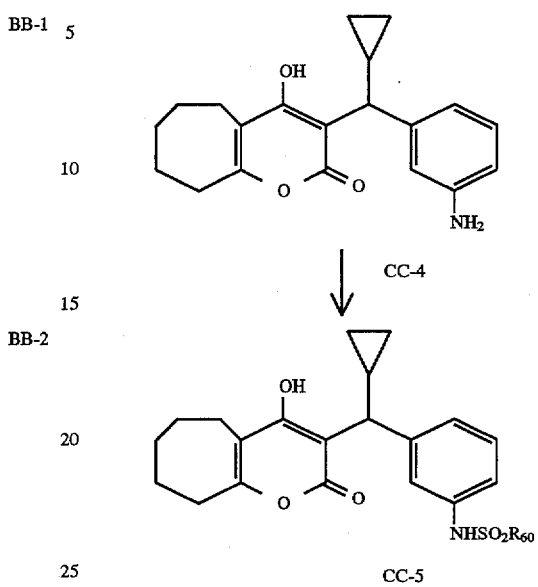
CC-5
CHART DD
DD-1
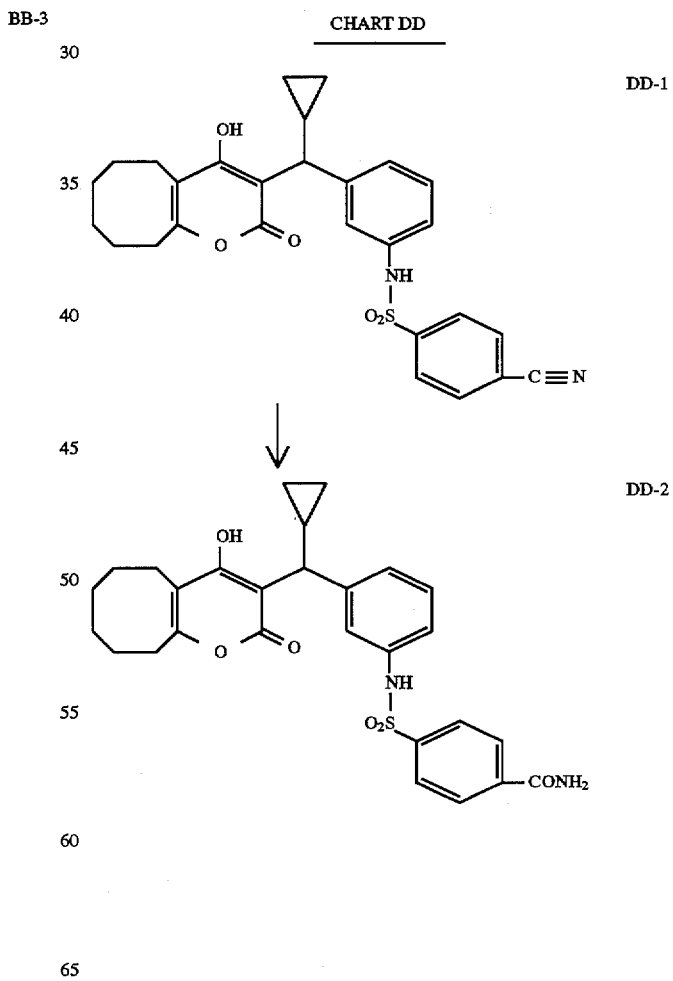
DD-2

CHART EE
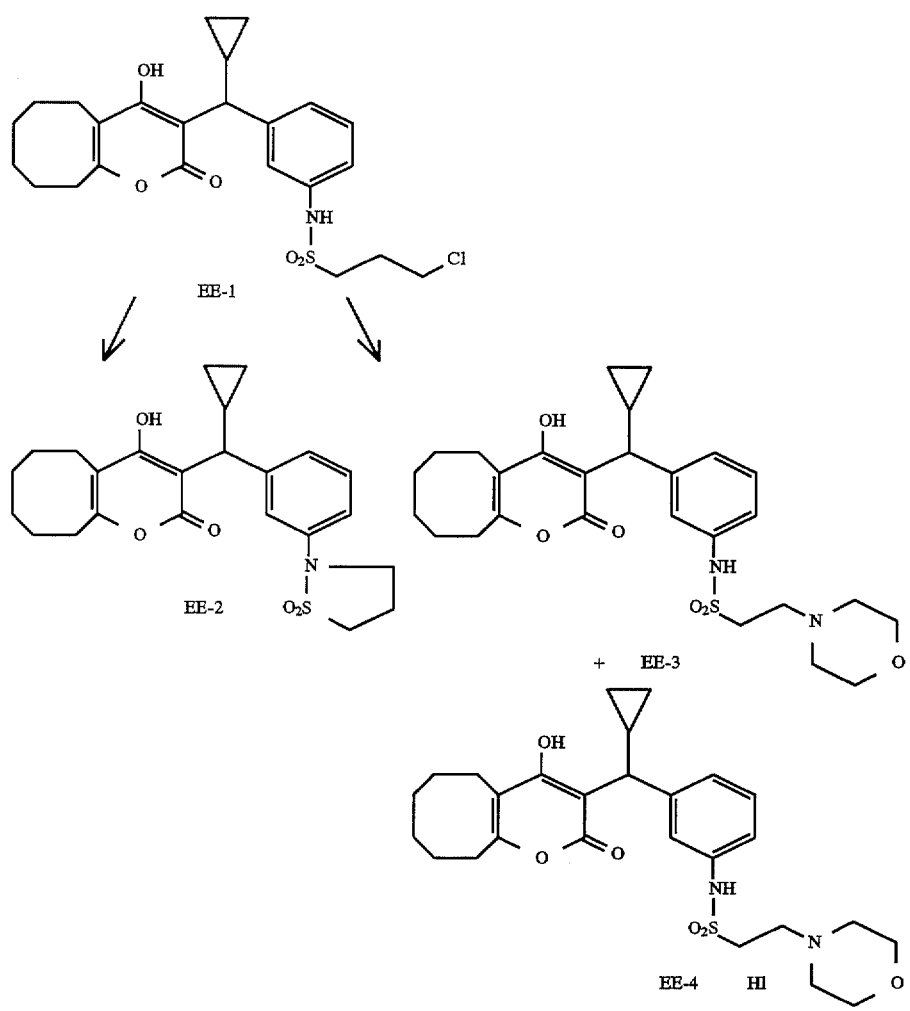
CHART FF
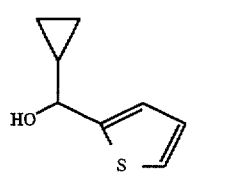  FF-1
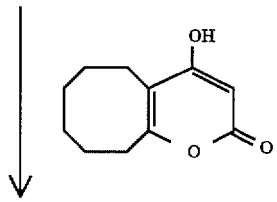  FF-2
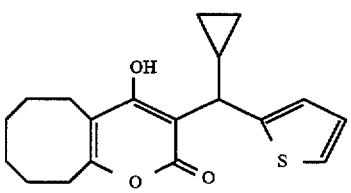  FF-3
CHART GG
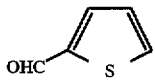  GG-1

CHART GG
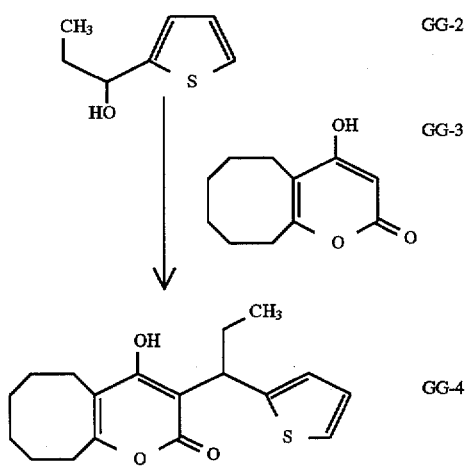
CHART HH
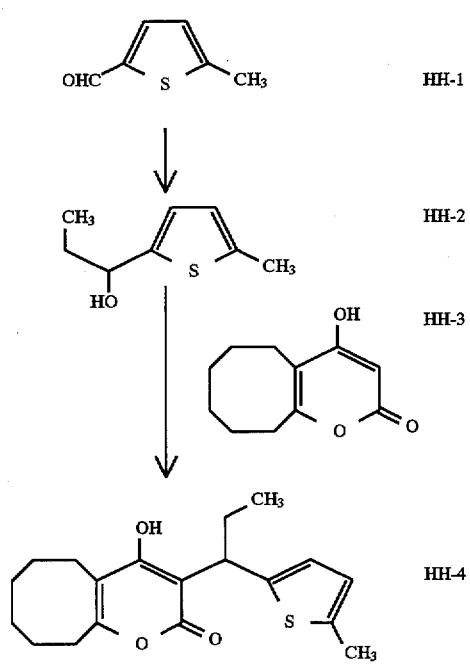
CHART II
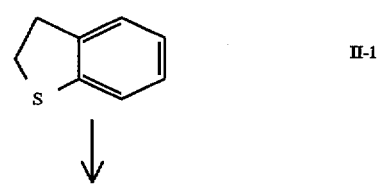
CHART II -continued
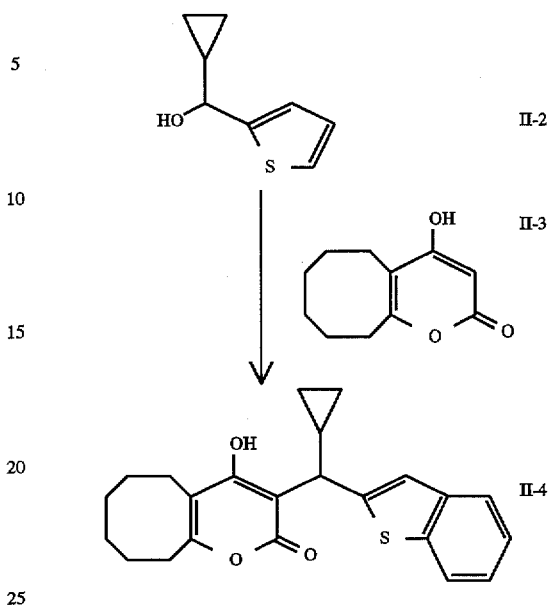
CHART JJ
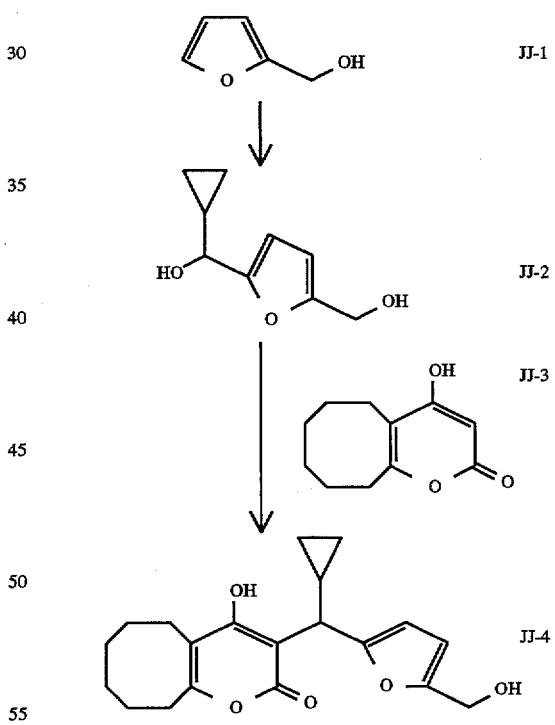
CHART KK
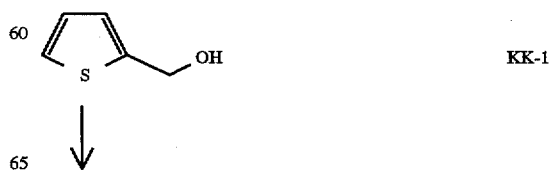

-continued
CHART KK
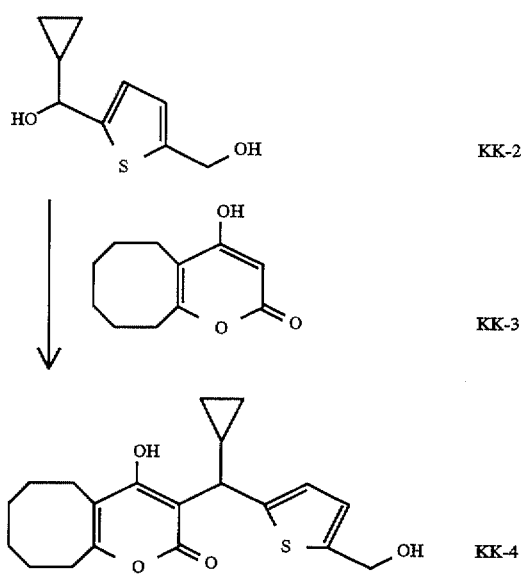
KK-2
KK-3
KK-4
CHART LL
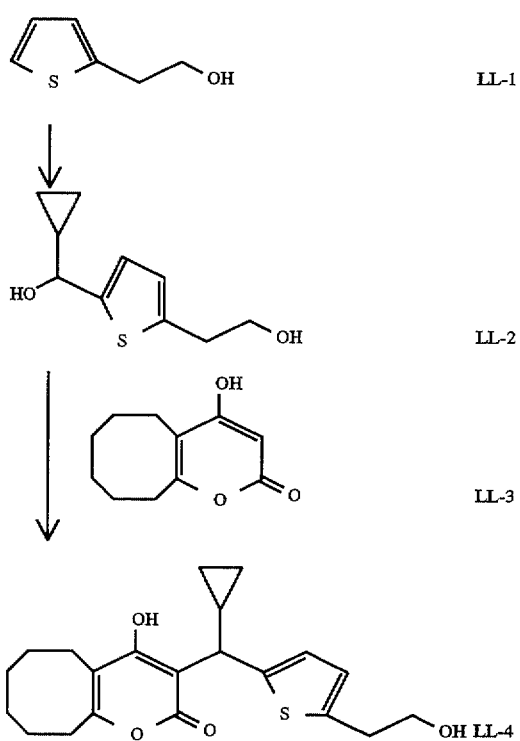
LL-1
LL-2
LL-3
LL-4
CHART MM
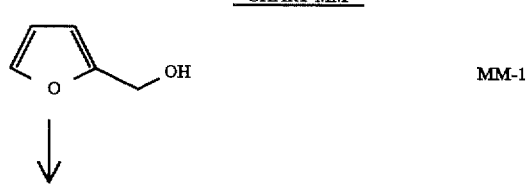
MM-1
-continued
CHART MM
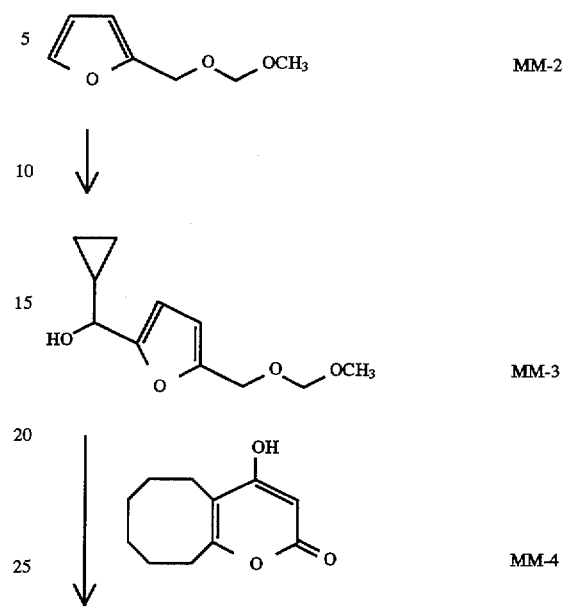
MM-2
MM-3
MM-4
MM-5
CHART NN
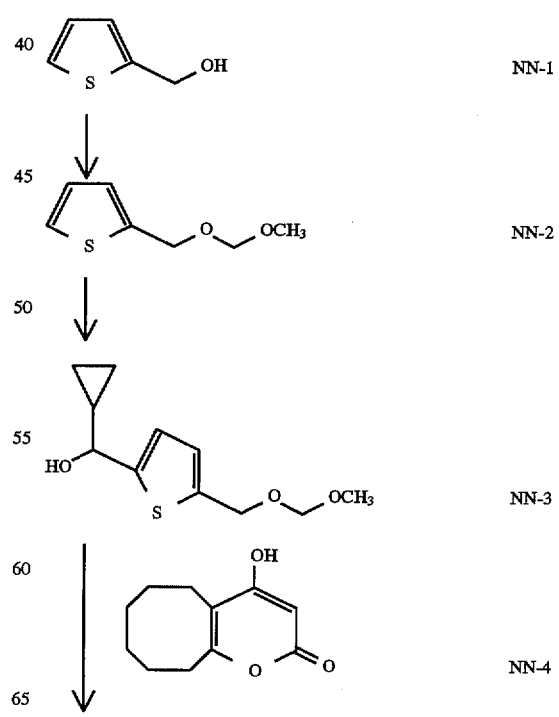
NN-1
NN-2
NN-3
NN-4

CHART NN -continued
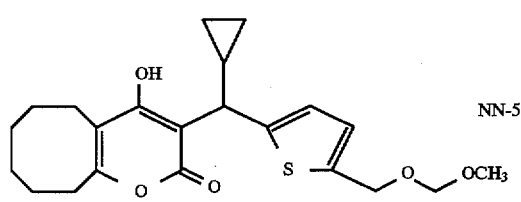
NN-5
CHART OO
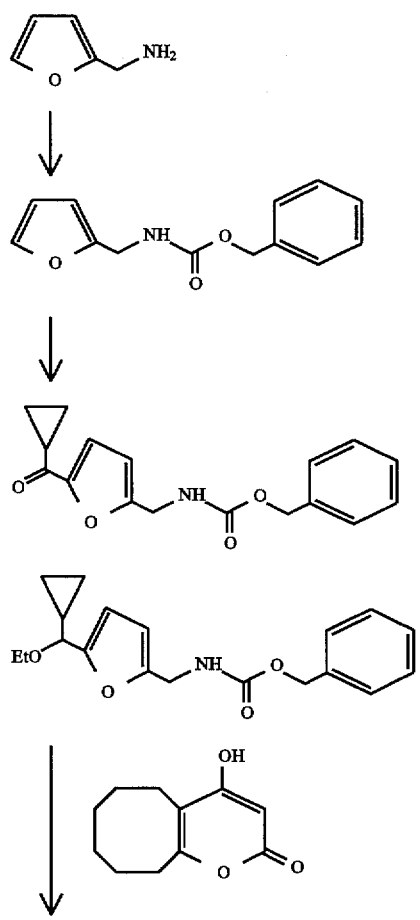
OO-1
OO-2
OO-3
OO-4
OO-5
OO-6
CHART PP
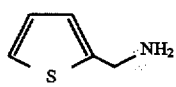
PP-1
CHART PP -continued
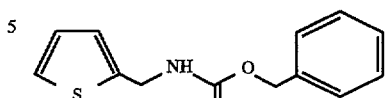
PP-2
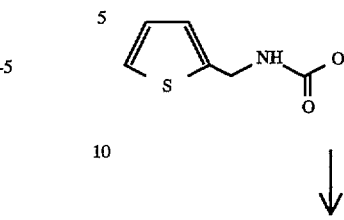
PP-3
PP-4
PP-5
PP-6
CHART QQ
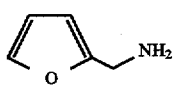
QQ-1
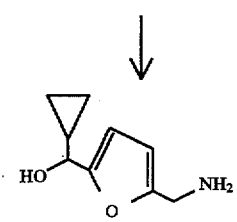
QQ-2

-continued
CHART QQ
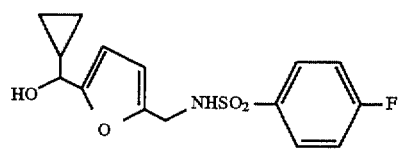 QQ-3
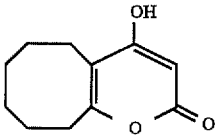 QQ-4
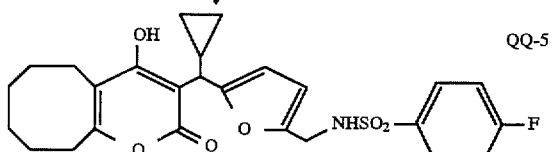 QQ-5
CHART RR
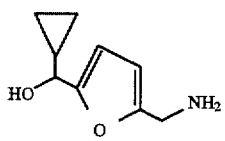 RR-1
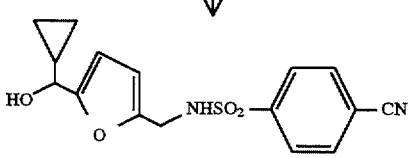 RR-2
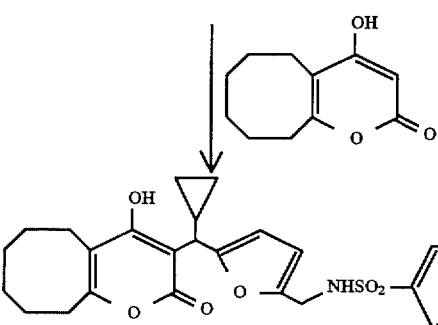 RR-4
CHART SS
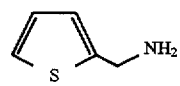 SS-1
-continued
CHART SS
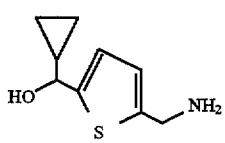 SS-2
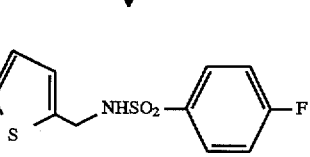 SS-3
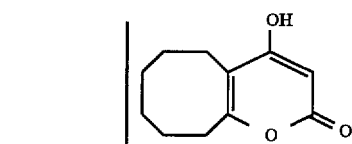 SS-4
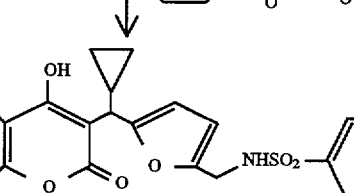 SS-5
CHART TT
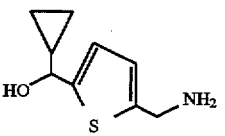 TT-1
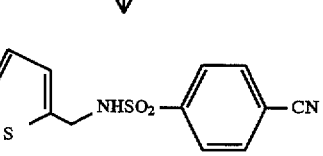 TT-2
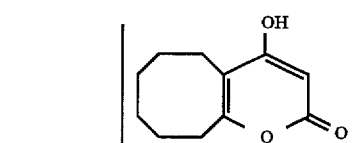 TT-3
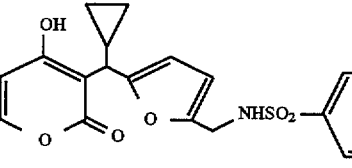 TT-4

CHART UU
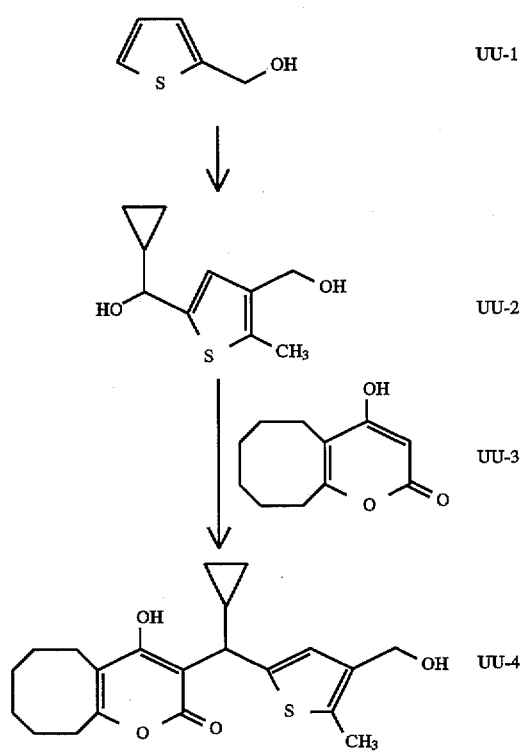
CHART VV
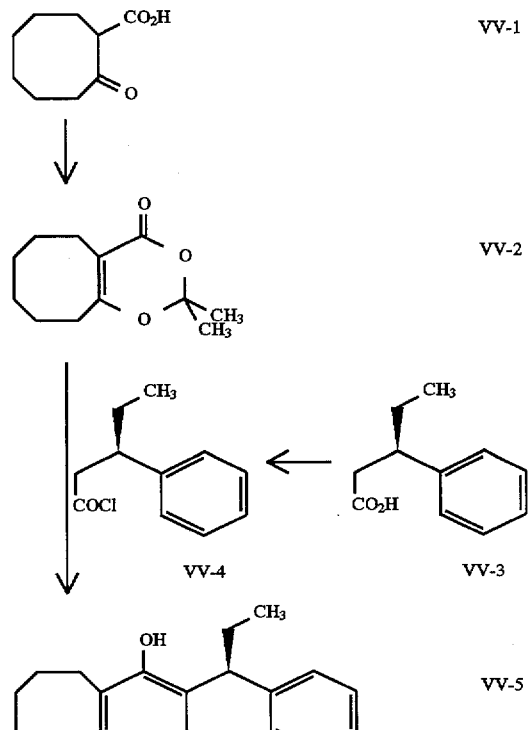
CHART WW
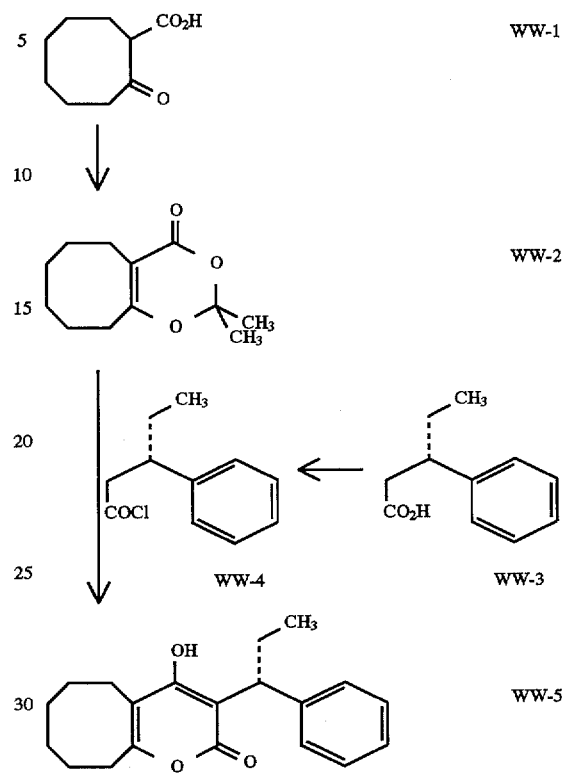
CHART XX
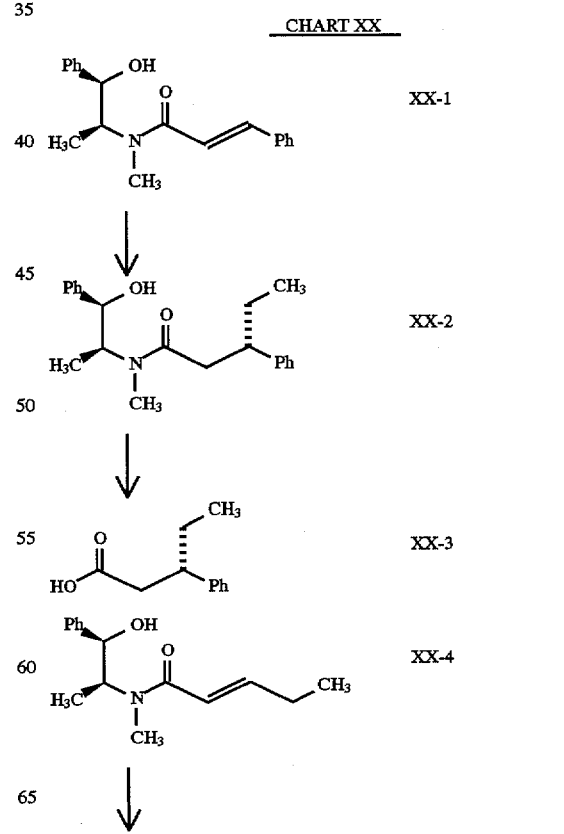

CHART XX -continued
XX-5
XX-6
CHART YY
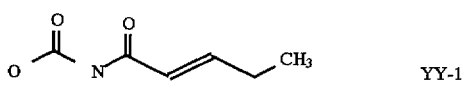
YY-1
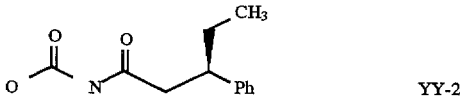
YY-2
YY-3 (XX-6)
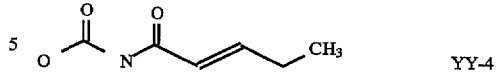
YY-4
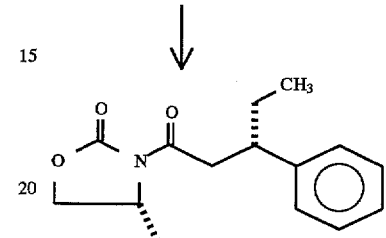
YY-5
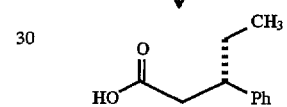
YY-6 (XX-3)
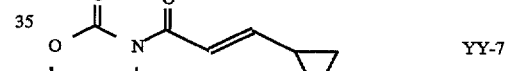
YY-7
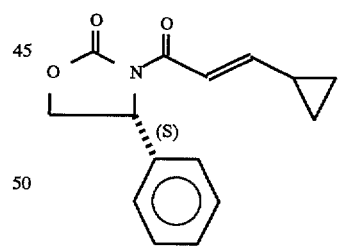
YY-8

CHART ZZ
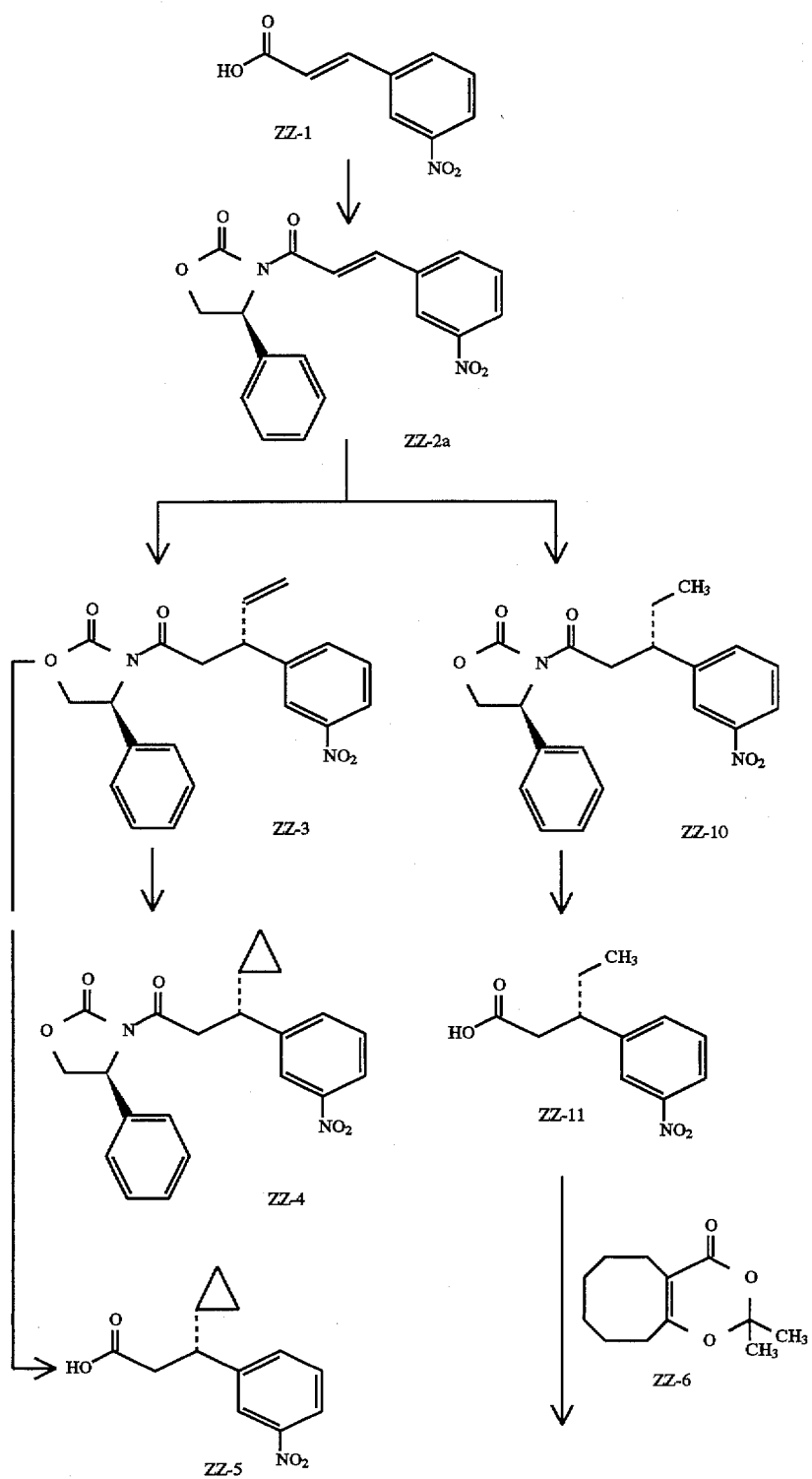

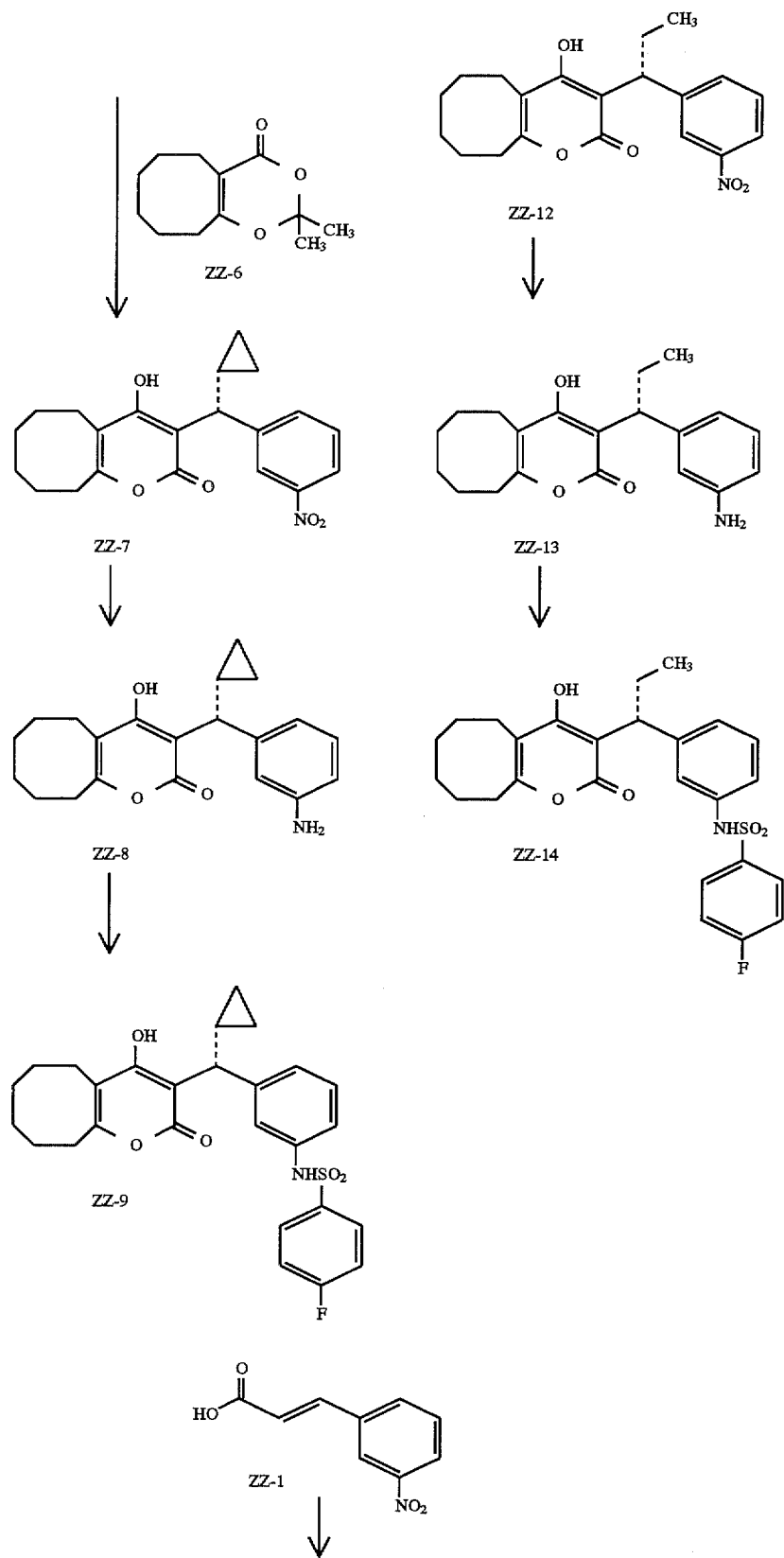

-continued
CHART ZZ
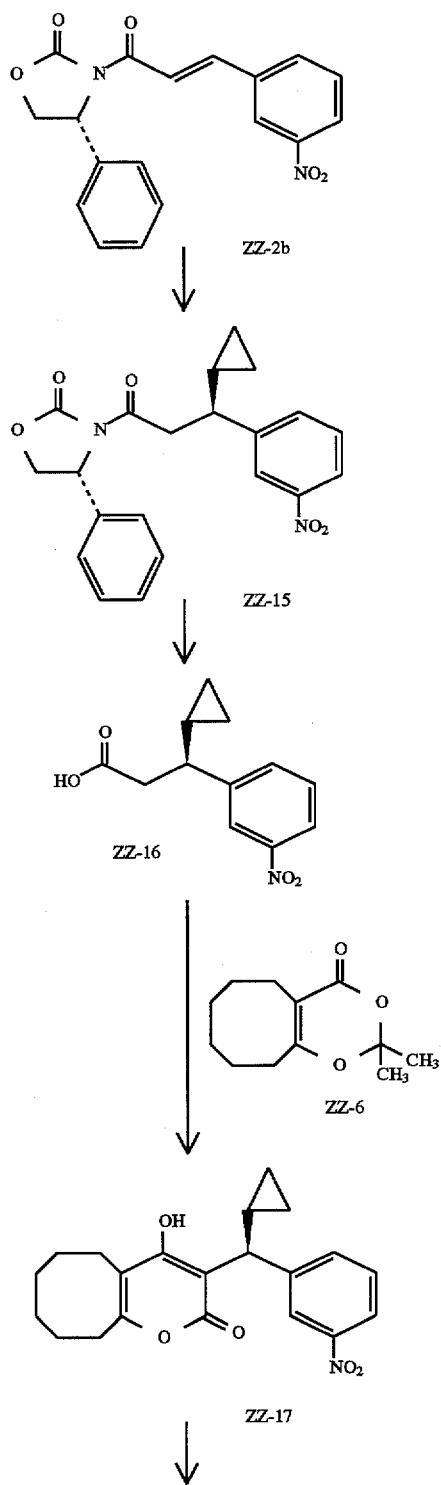

-continued
CHART ZZ
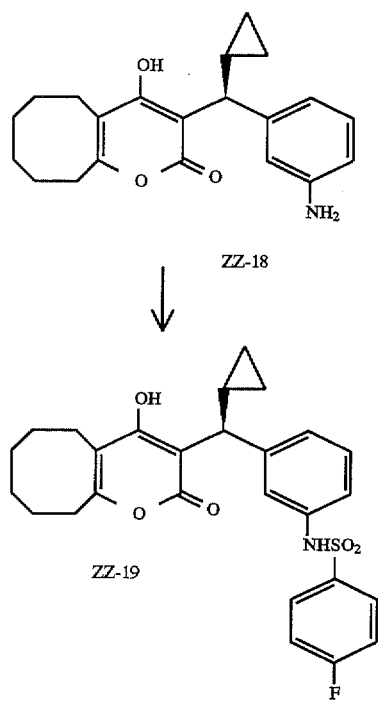
ZZ-18
ZZ-19
CHART AAA
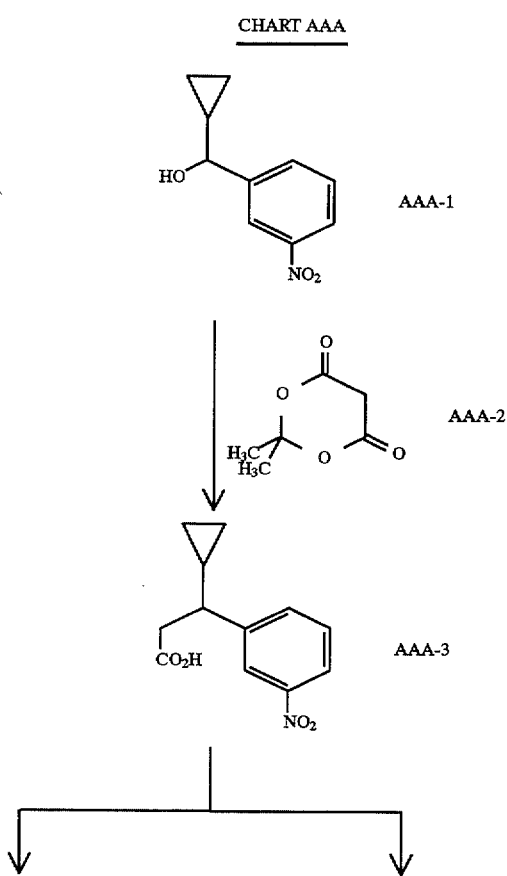
AAA-1
AAA-2
AAA-3

-continued
CHART AAA
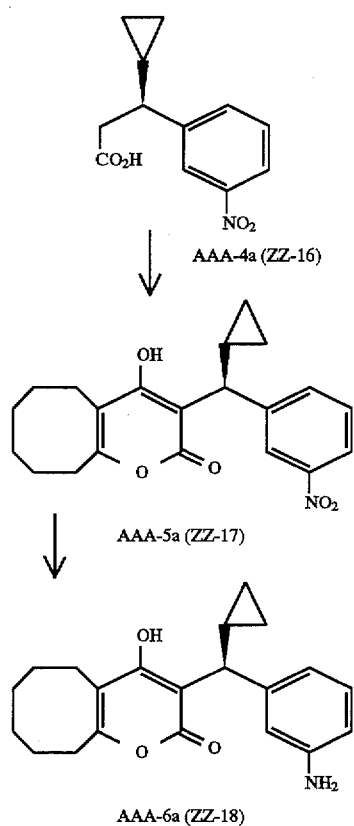
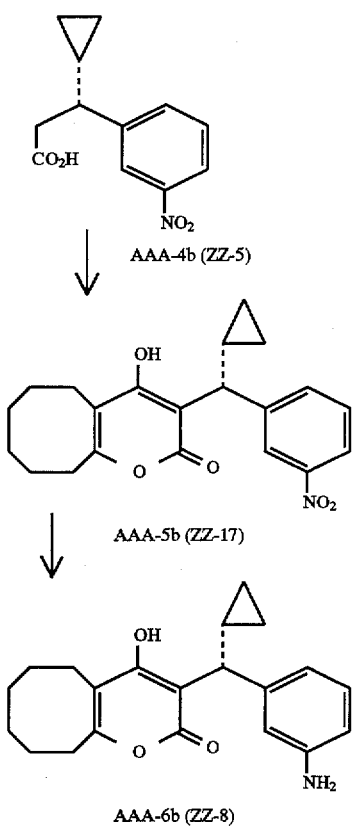
CHART BBB
-continued
CHART BBB
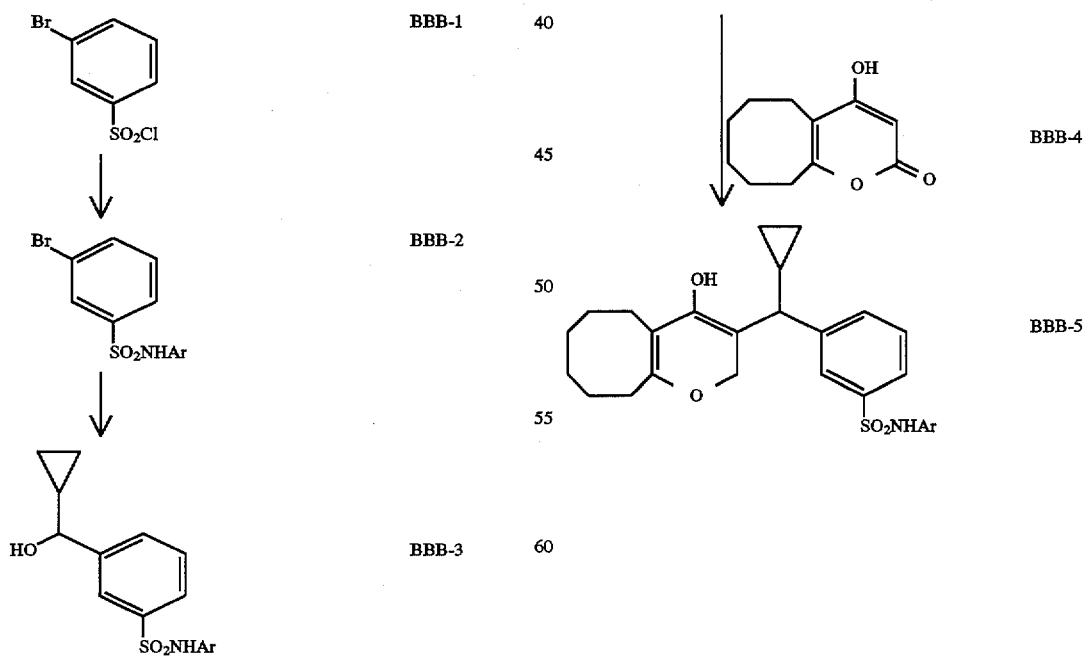

CHART CCC
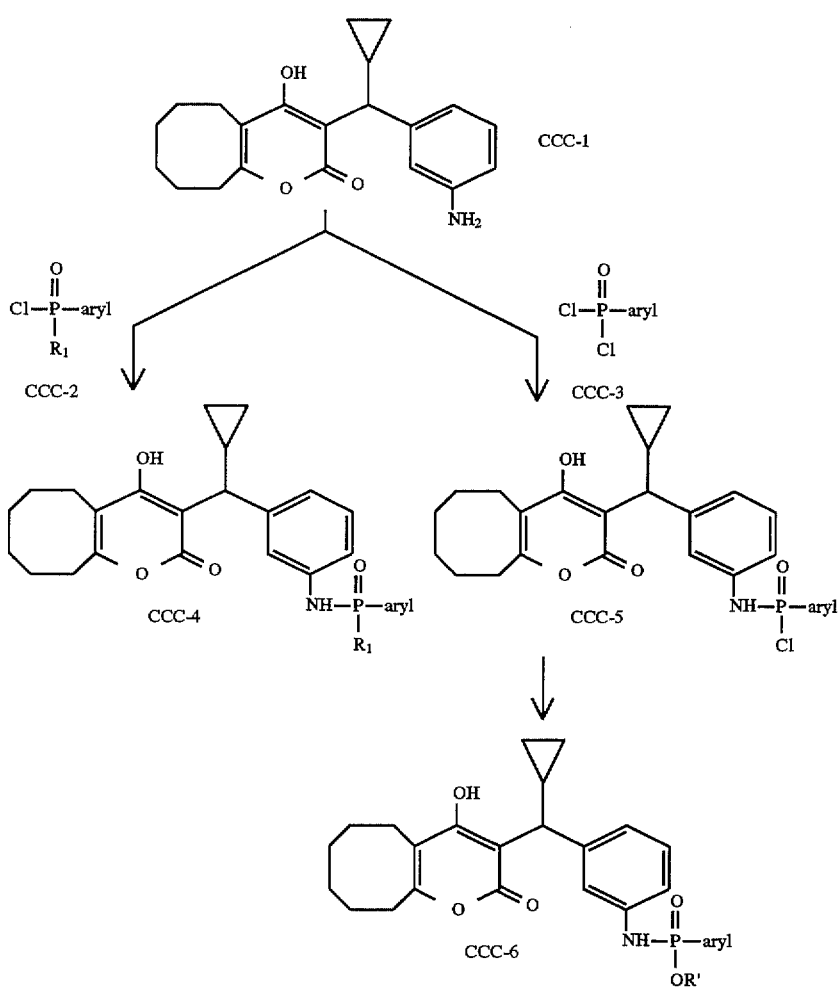
CHART DDD
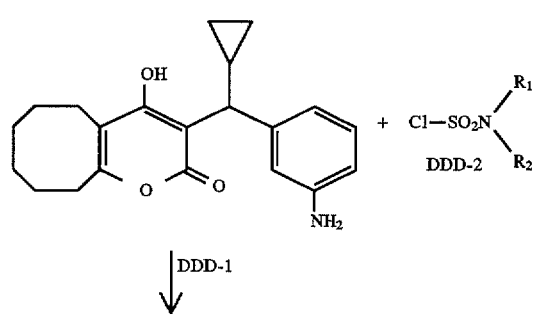
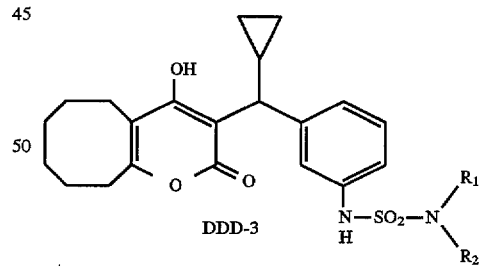
CHART EEE
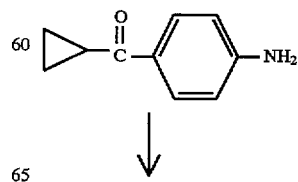

237
-continued
CHART EEE
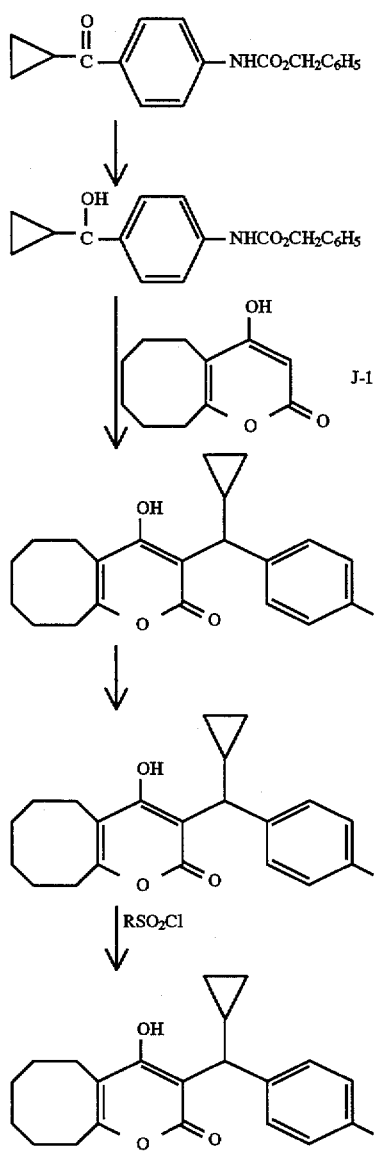
TABLE I
| Compound of Example No. | Mol. Form | Found |
|---|---|---|
| 26 | | 439.1538 |
| 27 | | 400.1413 |
| 28 | | 399.1495 |
| 29 | | 442.1633 |
| 30 | | 513.2247 |
| 31 | | 365.1621 |
| 32 | | 436.1634 |
| 33 | | 497.1834 |
| 34 | | 292.1094 |
| 35 | | 278.0949 |
| 36 | | 298.0995 |
| 37 | | 324.1357 |
| 38 | | 322.1196 |
| 39 | | 280.1085 |
| 40 | HCl salt | 295.1213 |
| 41 | | * |
| 42 | | 494.2427 |
238
TABLE I-continued
| Compound of Example No. | Mol. Form | Found |
|---|---|---|
| 43 | | 452.1946 |
| 44 | | 379.1773 |
| 45 | | 400.1426 |
| 46 | TFA salt | 353.1499 |
| 47 | | 494.2407 |
| 48 | TFA salt | 394.1885 |
| 49 | | 455.2089 |
| 50 | | *** |
| 51 | | *** |
| 52 | TFA salt | 425.1692 |
| 53 | | 441.1939 |
| 54 | | 455.2087 |
| 55 | | 413.1619 |
| 56 | | 433.2248 |
| 57 | | 457.1901 |
| 58 | | *** |
| 59 | | 493.2313 |
| 60 | | 466.2099 |
| 61 | TFA salt | 366.1566 |
| 62 | | 443.1737 |
| 63 | | 466.1872 |
| 64 | | 477.1935 |
| 65 | | 516.1180 |
| 66 | | 366 |
| 78 | | 366.1377 |
| 79 | | 466.1890 |
| 80 | | 286.1201 |
| 81 | | 338.1523 |
| 82 | | 324.1362 |
| 83 | | 276.0997 |
| 84 | | 294.1267 |
| 86 | | 348.0977 |
| 87 | | 298.1017 |
| 88 | | 310 |
| 89 | | 310 |
| 90 | | 294.1268 |
| 92 | | 314.0703 |
| 93 | | 296.1046 |
| 95 | | 296.1043 |
| 96 | | 296.1285 |
| 97 | | 308.1402 |
| 98 | | 305.1067 |
| 99 | | 330.1249 |
| 100 | | 370.1418 |
| 101 | | 291.0908 |
| 103 | | 296.1048 |
| 104 | | 256.1105 |
*MS not obtained
**Low resolution only (no peak match)
***No parent ion found in FAB
TABLE II
| | HIV Protease FITC Assay | | |
|---|---|---|---|
| Compound of Example No. | HIV-1 Dose (uM) | HIV-1 Protease % Inhib | HIV-1 Protease $IC_{50}$ (uM) |
| 1 | 10.000 | 15.3 | |
| | 20.000 | 51.62 | |
| | 100.000 | 66.94 | |
| | 200.000 | 92.79 | |
| 2 | 10.000 | 15.56 | |
| | 20.000 | 48.12 | |
| | 100.000 | 63.56 | |
| | 200.000 | 97.46 | |
| 3 | 1.000 | <10 | |
| | 10.000 | <10 | |
| | 100.000 | 48.8 | |
| 4 | 1.000 | <10 | |
| | 10.000 | 12.41 | |
| | 100.000 | 45.31 | |

TABLE II-continued

| | HIV Protease FITC Assay | | |
|---|---|---|---|
| Compound of Example No. | HIV-1 Dose (uM) | HIV-1 Protease % Inhib | HIV-1 Protease IC$_{50}$ (uM) |
| 5 | 1.000 | 15.36 | |
| | 10.000 | 55.37 | |
| | 100.000 | 95.01 | |
| 6 | 10.000 | 29.25 | |
| | 20.000 | 65.61 | |
| | 100.000 | 88.46 | |
| | 200.000 | 75.21 | |
| 7 | 1.000 | <10 | |
| | 10.000 | 42.48 | |
| | 100.000 | 96.33 | 21.19 |
| 8 | 1.000 | <10 | |
| | 10.000 | 23.72 | |
| | 100.000 | 93.35 | 41.71 |
| 9 | 1.000 | 12.11 | |
| | 10.000 | 64.99 | |
| | 100.000 | 98.34 | 10.57 |
| 10 | 0.098 | <10 | |
| | 0.196 | <10 | |
| | 0.780 | 33.22 | |
| | 1.560 | 53.58 | |
| | 12.500 | 91.55 | |
| | 25.000 | 88.03 | |
| | 50.000 | 101.82 | |
| | 100.000 | 108.98 | 1.71 |
| 11 | 0.098 | <10 | |
| | 0.195 | <10 | |
| | 0.390 | 19.25 | |
| | 0.780 | 27.05 | |
| | 1.560 | 58.1 | |
| | 3.130 | 63.09 | |
| | 6.250 | 70.36 | |
| | 12.500 | 82.04 | |
| | 25.000 | 95.77 | |
| | 50.000 | 90.73 | |
| | 100.000 | 105.4 | 1.89 |
| | 200.000 | 107.45 | |
| 12 | 0.098 | <10 | |
| | 0.196 | <10 | |
| | 0.390 | <10 | |
| | 0.780 | 13.97 | |
| | 1.560 | 17.14 | |
| | 3.130 | 25.41 | |
| | 6.250 | 31.87 | |
| | 12.500 | 53.81 | |
| | 25.000 | 66.55 | |
| | 50.000 | 74.65 | |
| | 100.000 | 87.44 | 12.10 |
| | 200.000 | 87.03 | |
| 13 | 1.000 | <10 | |
| | 10.000 | 34.68 | |
| | 100.000 | 74.56 | |
| 14 | 1.000 | 32.21 | |
| | 10.000 | 64.57 | |
| | 100.000 | 87.06 | |
| 15 | 1.000 | 43.83 | |
| | 10.000 | 89.58 | 1.25 |
| 16 | 1.000 | <10 | |
| | 10.000 | 48.32 | |
| 17 | 1.000 | <10 | |
| | 10.000 | 27.56 | |
| 18 | 1.000 | 13.37 | |
| | 10.000 | 52.54 | |
| 19 | 1.000 | <10 | |
| | 10.000 | 36.79 | |
| 20 | 1.000 | <10 | |
| | 10.000 | 20.33 | |
| | 100.000 | 79.77 | |
| 21 | 1.000 | <10 | |
| | 10.000 | 12.06 | |
| | 100.000 | 74.32 | |
| 74 | 1.000 | <10 | |
| | 10.000 | <10 | |
| | 100.000 | 82.28 | |
| 66 | 1.000 | <10 | |
| | 10.000 | <10 | |
| | 100.000 | 52.59 | |
| 67 | 1.000 | <10 | |
| | 10.000 | 11.74 | |
| | 100.000 | 60.91 | |
| 71 | 1.000 | <10 | |
| | 10.000 | 15 | |
| | 100.000 | 80 | |
| 68 | 1.000 | <10 | |
| | 10.000 | <10 | |
| | 100.000 | 56 | |
| 36 | 1.000 | <10 | |
| | 10.000 | 16.89 | |
| | 100.000 | 81.61 | |
| 72 | 1.000 | <10 | |
| | 10.000 | 18.91 | |
| | 100.000 | 92.35 | |
| 37 | 1.000 | <10 | |
| | 10.000 | 59.55 | |
| | 100.000 | 102.96 | 7.00 |
| 38 | 1.000 | 18.65 | |
| | 10.000 | 83.17 | |
| | 100.000 | 93.37 | 2.80 |
| 70 | 1.000 | <10 | |
| | 10.000 | 10.18 | |
| | 100.000 | 72.18 | |
| 73 | 1.000 | <10 | |
| | 10.000 | 29.85 | |
| | 100.000 | 96.66 | |
| 69 | 1.000 | <10 | |
| | 10.000 | 20.55 | |
| | 100.000 | 92.22 | |
| 34 | 1.000 | <10 | |
| | 10.000 | 50.31 | |
| | 100.000 | 91.1 | 3.60 |
| 35 | 1.000 | <10 | |
| | 10.000 | 19.61 | |
| | 100.000 | 92.6 | 6.80 |
| 75 | 1.000 | 14.5 | |
| | 10.000 | 72.66 | |
| | 100.000 | 96.59 | 2.40 |
| 26 | 1.000 | <10 | |
| | 10.000 | 53.57 | |
| | 100.000 | 95 | |
| | 100.000 | 80 | 20.30 |
| 27 | 1.000 | <10 | |
| | 10.000 | <10 | |
| | 100.000 | 71.98 | |
| 28 | 1.000 | <10 | |
| | 10.000 | 17.89 | |
| | 100.000 | 81.04 | |
| 29 | 1.000 | <10 | |
| | 10.000 | 54.17 | |
| | 100.000 | 98.44 | |
| 30 | 1.000 | <10 | |
| | 10.000 | 65.31 | |
| | 100.000 | 109.39 | |
| 22 | 1.000 | <10 | |
| | 10.000 | <10 | |
| | 100.000 | 58.74 | |
| 31 | 1.000 | <10 | |
| | 10.000 | <10 | |
| | 100.000 | 53.74 | |
| 32 | 1.000 | <10 | |
| | 10.000 | <10 | |
| | 100.000 | 46.45 | |
| 33 | 1.000 | <10 | |
| | 10.000 | 11.18 | |
| | 100.000 | 77.43 | |
| 40 | 1.000 | <10 | |
| | 10.000 | <10 | |
| | 100.000 | 51.33 | |

TABLE II-continued

| Compound of Example No. | HIV Protease FITC Assay | | |
|---|---|---|---|
| | HIV-1 Dose (uM) | HIV-1 Protease % Inhib | HIV-1 Protease IC$_{50}$ (uM) |
| 41 | 1.000 | <10 | |
| | 10.000 | 32.57 | |
| | 100.000 | 80.63 | |
| 42 | 1.000 | 11.46 | |
| | 10.000 | 75.2 | |
| | 100.000 | 112.15 | |
| | 100.000 | 102.8 | 9.90 |
| 43 | 1.000 | 28.39 | |
| | 10.000 | 102.51 | |
| | 100.000 | 122.41 | 2.10 |
| 25 | 1.000 | 11.44 | |
| | 10.000 | 78.63 | |
| | 100.000 | 115.12 | 5.20 |
| 44 | 1.000 | <10 | |
| | 10.000 | <10 | |
| | 100.000 | 55.62 | |
| 45 | 1.000 | <10 | |
| | 10.000 | 28.46 | |
| | 100.000 | 90.9 | |
| 46 | 1.000 | 22.12 | |
| | 10.000 | 96.29 | |
| | 100.000 | 116.41 | |
| | 100.000 | 107 | 4.20 |
| 47 | 1.000 | <10 | |
| | 10.000 | <10 | |
| | 100.000 | 52.95 | |
| 23 | 1.000 | 46.62 | |
| | 10.000 | 96.62 | 0.66 |
| | 100.000 | 104.16 | 0.66 |
| | 100.000 | 104.2 | 0.70 |
| 48 | 1.000 | <10 | |
| | 10.000 | <10 | |
| | 100.000 | 43.3 | |
| 24 | 1.000 | <10 | |
| | 10.000 | 24.21 | |
| | 100.000 | 83.72 | |
| 49 | 1.000 | <10 | |
| | 10.000 | 21.93 | |
| | 100.000 | 60.32 | |
| 50 | 1.000 | 33.5 | |
| | 10.000 | 80.29 | |
| | 100.000 | 95.54 | 2.30 |
| 51 | 1.000 | <10 | |
| | 10.000 | <10 | |
| | 100.000 | 39.64 | |
| 52 | 1.000 | 26.75 | |
| | 10.000 | 81.5 | |
| | 100.000 | 119.84 | 3.10 |
| 53 | 1.000 | <10 | |
| | 10.000 | <10 | |
| | 100.000 | 71.84 | |
| 54 | 1.000 | <10 | |
| | 10.000 | 13.75 | |
| | 10.00 | 60.04 | |
| 55 | 1.000 | <10 | |
| | 10.000 | <10 | |
| | 100.000 | 71.98 | |
| 56 | 1.000 | <10 | |
| | 10.000 | <10 | |
| | 100.000 | 49.52 | |
| 57 | 1.000 | 17.63 | |
| | 10.000 | 94.39 | |
| | 100.000 | 99.32 | 2.80 |
| 58 | 1.000 | 36.28 | |
| | 10.000 | 90.15 | |
| | 100.000 | 108.2 | 1.20 |
| 59 | 1.000 | <10 | |
| | 10.000 | 21.46 | |
| | 100.000 | 82.77 | |
| 60 | 1.000 | 31.5 | |
| | 10.000 | 90.82 | |
| | 100.000 | 116.8 | 1.10 |
| 61 | 1.000 | 77.83 | 1.00 |
| | 10.000 | 115.38 | 1.00 |
| | 100.000 | 119.04 | 1.00 |
| 62 | 1.000 | <10 | |
| | 10.000 | 10.56 | |
| | 100.000 | 78.3 | |
| 63 | 1.000 | 77.58 | 2.00 |
| | 10.000 | 90.32 | 2.00 |
| | 100.000 | 111.31 | 2.00 |
| 64 | 1.000 | 29.09 | 5.80 |
| | 10.000 | 78.09 | 5.80 |
| | 100.000 | 104 | 5.80 |
| 39 | 1.000 | 13.79 | |
| | 10.000 | 69.57 | |
| | 100.000 | 82.05 | 5.00 |
| 76 | 1.000 | <10 | |
| | 10.000 | 47.8 | |
| | 100.000 | 96.48 | |
| 77 | 1.000 | <10 | |
| | 10.000 | 57.8 | |
| | 100.000 | 92.46 | |
| 65 | 1.000 | <10 | |
| | 10.000 | 48.43 | |
| | 100.000 | 86.13 | |
| 104 | 1.000 | 12.15 | 6.74 |
| | 10.000 | 68.74 | 6.74 |
| | 100.000 | 105.84 | 6.74 |
| 78 | 1.000 | <10 | 8.40 |
| | 10.000 | 65.68 | 8.40 |
| | 100.000 | 83.55 | 8.40 |
| 79 | 1.000 | <10 | 13.10 |
| | 10.000 | 61.04 | 13.10 |
| | 100.000 | 80.86 | 13.10 |
| 80 | 1.000 | <10 | 8.50 |
| | 10.000 | 62.58 | 8.50 |
| | 100.000 | 101.62 | 8.50 |
| 81 | 1.000 | 62 | 3.70 |
| | 10.000 | 75.6 | 3.70 |
| | 100.000 | 85.3 | 3.70 |
| 82 | 1.000 | 30.95 | |
| | 10.000 | 69.65 | 0.90 |
| | 100.000 | 88.96 | 0.90 |
| 83 | 1.000 | <10 | |
| | 10.000 | <10 | |
| | 100.000 | 50.08 | |
| 84 | 1.000 | <10 | |
| | 10.000 | 30.2 | |
| 85 | 1.000 | <10 | |
| | 10.000 | 31.6 | |
| | 100.000 | 100.5 | |
| 86 | 1.000 | 10.46 | |
| | 10.000 | 56.94 | |
| | 100.000 | 95.84 | |
| 87 | 1.000 | <10 | |
| | 10.000 | 20.6 | |
| | 100.000 | 78.97 | |
| 88 | 1.000 | 80.04 | |
| | 10.000 | 107.82 | |
| | 100.000 | 117.82 | 1.52 |
| | 1.560 | 49.9 | |
| | 1.570 | 41.7 | |
| | 12.500 | 89.2 | |
| | 12.500 | 80.8 | |
| | 100.000 | 92 | 1.60 |
| | 100.000 | 93.5 | 2.00 |
| 89 | 1.000 | <10 | |
| | 10.000 | 10.3 | |
| | 100.000 | 52.04 | |
| 90 | 1.000 | <10 | |
| | 10.000 | 29.67 | |
| | 100.000 | 89.16 | |

TABLE II-continued

HIV Protease FITC Assay

| Compound of Example No. | HIV-1 Dose (uM) | HIV-1 Protease % Inhib | HIV-1 Protease IC$_{50}$ (uM) |
|---|---|---|---|
| 91 | 1.000 | <10 | |
|  | 10.000 | 38.43 | |
|  | 100.000 | 94.41 | |
|  | 100.000 | 71.61 | |
| 92 | 1.000 | <10 | |
|  | 10.000 | 67.8 | |
|  | 100.000 | 113.14 | |
| 93 | 1.000 | 23.22 | |
|  | 10.000 | 79.42 | |
|  | 100.000 | 109.4 | |
|  | 100.000 | 91.7 | 20.60 |
| 94 | 1.000 | <10 | |
|  | 10.000 | 44.67 | |
|  | 100.000 | 96.37 | |
|  | 100.000 | 82.45 | |
| 95 | 1.000 | <10 | |
|  | 10.000 | 34.71 | |
|  | 100.000 | 79.6 | |
| 96 | 1.000 | <10 | |
|  | 10.000 | <10 | |
|  | 100.000 | 48.7 | |
| 97 | 1.000 | <10 | |
|  | 10.000 | 29.87 | |
|  | 100.000 | 78.24 | |
| 98 | 1.000 | <10 | |
|  | 10.000 | <10 | |
|  | 100.000 | 74.47 | |
| 99 | 1.000 | <10 | |
|  | 10.000 | <10 | |
|  | 100.000 | 43.29 | |
| 100 | 1.000 | <10 | |
|  | 10.000 | 12.32 | |
|  | 100.000 | 53 | |
|  | 1.000 | <10 | |
|  | 10.000 | <10 | |
|  | 100.000 | 40.3 | |
| 101 | 1.000 | <10 | |
|  | 10.000 | <10 | |
|  | 100.000 | 39.21 | |
| 102 | 1.000 | <10 | |
|  | 10.000 | 24.02 | |
|  | 100.000 | 78.8 | |
|  | 100.000 | 75.63 | |
| 103 | 1.000 | <10 | |
|  | 10.000 | 25.67 | |
|  | 100.000 | 80.89 | |
|  | 1.000 | <10 | |
|  | 10.000 | 21.23 | |
|  | 100.000 | 87.29 | |
|  | 100.000 | 73.35 | |
| 105 |  |  | 4.88 |
|  |  |  | 3.88 |
| 106 | 1.000 | <10 | |
|  | 10.000 | 11.7 | |
|  | 100.000 | 71 | |

TABLE III

| Compound of Example No. | CV-1 Cell Assay | |
|---|---|---|
|  | Dose (uM) | % Inhib |
| 10 | 100.0 | 0.00 |
|  | 300.0 | 57.00 |
| 11 | 100.0 | 64.00 |
|  | 300.0 | 78.00 |

TABLE IV

HIV Protease FITC Assay

| Compound of Example No. | HIV-1 Dose (uM) | HIV-1 Protease % Inhib | HIV-1 FITC KI (nM) |
|---|---|---|---|
| 108 | 1.000 | 72.61 | |
|  | 10.000 | 95.45 | |
|  | 100.000 | 94.17 | 59.00 |
|  |  |  | 90.00 |
| 109 | 1.000 | <10 | |
|  | 10.000 | 71.89 | |
|  | 100.000 | 91.96 | 1090.00 |
| 110 | 1.000 | 16.91 | |
|  | 10.000 | 73.82 | |
|  | 100.000 | 99.89 | 410.00 |
| 111 | 1.000 | 36.48 | |
|  | 10.000 | 94.33 | |
|  | 100.000 | 100.65 | 700.00 |
| 107 | 1.000 | 90.73 | |
|  | 10.000 | 100.82 | |
|  | 100.000 | 101.48 | 20.00 |
|  |  |  | 12.00 |
|  |  |  | 7.00 |
| 112 | 1.000 | 70.14 | |
|  | 10.000 | 102.07 | |
|  | 100.000 | 104.69 | 96.00 |
| 113 | 1.000 | 39.58 | |
|  | 10.000 | 99.82 | |
|  | 100.000 | 109.29 | |
| 114 | 1.000 | <10 | |
|  | 10.000 | <10 | |
|  | 100.000 | 14.13 | |
| 115 | 1.000 | 62.1 | |
|  | 10.000 | 102.46 | |
|  | 100.000 | 129.37 | 177.00 |
| 116 | 1.000 | 22.97 | |
|  | 10.000 | 65.66 | |
|  | 100.000 | 102.31 | 558.00 |
| 118 | 0.410 | 68.66 | |
|  | 1.230 | 87.89 | |
|  | 3.700 | 98.96 | |
|  | 11.000 | 109.98 | |
|  | 33.000 | 103.17 | |
|  | 100.000 | 105.25 | 57.00 |
| 117 | 0.410 | 80.14 | |
|  | 1.230 | 93.99 | |
|  | 3.700 | 101.36 | |
|  | 11.000 | 113.61 | |
|  | 33.000 | 107.44 | |
|  | 100.000 | 99.97 | 37.00 |
| 119 | 0.410 | 27.46 | |
|  | 1.230 | 55.43 | |
|  | 3.700 | 82.46 | |
|  | 11.000 | 97.65 | |
|  | 33.000 | 96.76 | |
|  | 100.000 | 101.38 | 257.00 |
| 122 | 0.410 | 35.13 | |
|  | 1.230 | 63.53 | |
|  | 3.700 | 91.69 | |
|  | 11.000 | 98.01 | |
|  | 33.000 | 93.25 | |
|  | 100.000 | 94.27 | 175.00 |
| 123 | 0.410 | 23.71 | |
|  | 1.230 | 59.06 | |
|  | 3.700 | 82.49 | |
|  | 11.000 | 88.31 | |
|  | 33.000 | 83.92 | |
|  | 100.000 | 78.91 | 260.00 |
| 124 | 0.410 | <10 | |
|  | 1.230 | 32.42 | |
|  | 3.700 | 65.59 | |
|  | 11.000 | 81.63 | |
|  | 33.000 | 88.16 | |
|  | 100.000 | 89.39 | 1035.00 |
| 125 | 0.410 | 100.52 | |
|  | 1.230 | 107.7 | |
|  | 3.700 | 107.85 | |
|  | 11.000 | 108.48 | |
|  | 33.000 | 102.27 | |

TABLE IV-continued

| | HIV Protease FITC Assay | | |
|---|---|---|---|
| Compound of Example No. | HIV-1 Dose (uM) | HIV-1 Protease % Inhib | HIV-1 FITC KI (nM) |
| | 100.000 | 105.34 | 24.00 |
| 120 | 0.410 | <10 | |
| | 1.230 | 22.2 | |
| | 3.700 | 54.63 | |
| | 11.000 | 80.69 | |
| | 33.000 | 101.11 | |
| | 100.000 | 105.81 | 982.00 |
| 126 | 0.410 | 25.86 | |
| | 1.230 | 59.05 | |
| | 3.700 | 89.8 | |
| | 11.000 | 96.66 | |
| | 33.000 | 100.02 | |
| | 100.000 | 95.04 | 331.00 |
| 135 | 0.410 | 87.06 | |
| | 1.230 | 92.51 | |
| | 3.700 | 96.65 | |
| | 11.000 | 82.44 | |
| | 33.000 | 71.16 | |
| | 100.000 | 63.63 | 30.00 |
| 121 | 0.123 | 37.11 | |
| | 0.370 | 74.9 | |
| | 1.100 | 99.53 | |
| | 3.300 | 106.16 | |
| | 10.000 | 107.79 | |
| | 30.000 | 108.63 | 24.00 |
| 127 | 0.123 | 52.32 | |
| | 0.370 | 92.55 | |
| | 1.100 | 111.91 | |
| | 3.300 | 115.12 | |
| | 10.000 | 117.38 | |
| | 30.000 | 111.35 | 33.00 |
| 128 | 0.123 | 32.5 | |
| | 0.370 | 85.6 | |
| | 1.100 | 101.62 | |
| | 3.300 | 112.49 | |
| | 10.000 | 107.42 | |
| | 30.000 | 102.3 | 26.00 |
| 129 | 0.123 | 23.19 | |
| | 0.370 | 67.79 | |
| | 1.100 | 96.53 | |
| | 3.300 | 106.34 | |
| | 10.000 | 116.53 | |
| | 30.000 | 120.4 | 31.00 |
| 130 | 0.123 | <10 | |
| | 0.370 | 14.73 | |
| | 1.100 | 54 | |
| | 3.300 | 88.61 | |
| | 10.000 | 103.93 | |
| | 30.000 | 112 | 119.00 |
| 134 | 0.123 | 54.05 | |
| | 0.370 | 97.73 | |
| | 1.100 | 103.67 | |
| | 3.300 | 110.54 | |
| | 10.000 | 110.97 | |
| | 30.000 | 109.35 | 15.00 |
| 131 | 0.123 | 30.73 | |
| | 0.370 | 74.24 | |
| | 1.100 | 98.71 | |
| | 3.300 | 111.87 | |
| | 10.000 | 116.04 | |
| | 30.000 | 105.99 | 30.00 |
| 132 | 0.123 | <10 | |
| | 0.370 | 39.51 | |
| | 1.100 | 76.22 | |
| | 3.300 | 98.14 | |
| | 10.000 | 104.27 | |
| | 30.000 | 102.65 | 50.00 |
| 133 | 0.123 | 19.06 | |
| | 0.370 | 71.18 | |
| | 1.100 | 97.94 | |
| | 3.300 | 100.79 | |
| | 10.000 | 101.2 | |
| | 30.000 | 99.48 | 12.00 |
| 141 | 1.000 | 14.21 | |
| | 10.000 | 77.37 | |
| | 100.000 | 102.75 | |
| 142 | 1.000 | <10 | |
| | 10.000 | 15.65 | |
| | 100.000 | 71.77 | |
| 143 | 1.000 | 10.79 | |
| | 10.000 | 77.11 | |
| | 100.000 | 92.12 | |
| 144 | 1.000 | 25.95 | |
| | 10.000 | 77.03 | |
| | 100.000 | 85.99 | |
| 145 | 1.000 | 37.01 | |
| | 10.000 | 81.05 | |
| | 100.000 | 97.05 | |
| 146 | 1.000 | 54.41 | |
| | 10.000 | 92.66 | |
| | 100.000 | 98.64 | 130.00 |
| 147 | 1.000 | 34.67 | |
| | 10.000 | 86.35 | |
| | 100.000 | 96.53 | |
| 148 | 1.000 | <10 | |
| | 10.000 | 57.85 | |
| | 100.000 | 93.69 | |
| 149 | 1.000 | 28.83 | |
| | 10.000 | 99.21 | |
| | 100.000 | 97.27 | 405.00 |
| 150 | 1.000 | <10 | |
| | 10.000 | 62.44 | |
| | 100.000 | 93.01 | |
| 151 | 1.000 | 29.13 | |
| | 10.000 | 82.85 | |
| | 100.000 | 92.38 | |
| 152 | 0.410 | <10 | |
| | 1.230 | 14.2 | |
| | 3.700 | 35.52 | |
| | 11.000 | 73.68 | |
| | 33.000 | 102.03 | |
| | 100.000 | 109.77 | 1012.00 |
| 138 | 1.000 | 11.89 | |
| | 10.000 | 64.54 | |
| | 100.000 | 99.32 | 2350.00 |
| 137 | 1.000 | 11.27 | |
| | 10.000 | 62.92 | |
| | 100.000 | 89.08 | 1750.00 |
| | | | 2200.00 |
| 154 | 1.000 | 13.63 | |
| | 10.000 | 77.13 | |
| | 100.000 | 96.05 | 520.00 |
| 155 | 1.000 | 15.41 | |
| | 10.000 | 74.9 | |
| | 100.000 | 91.93 | |
| 156 | 1.000 | 17.13 | |
| | 10.000 | 33.56 | |
| | 100.000 | 63.72 | |
| 139 | 1.000 | 36.56 | |
| | 10.000 | 80.73 | |
| | 100.000 | 99.15 | 500.00 |
| 157 | 1.000 | <10 | |
| | 10.000 | <10 | |
| | 100.000 | 63.99 | |
| 158 | 1.000 | <10 | |
| | 10.000 | 26.73 | |
| | 100.000 | 93.38 | |
| 140 | 0.410 | <10 | |
| | 1.230 | 16.49 | |
| | 3.700 | 48.12 | |
| | 11.000 | 71.76 | |
| | 33.000 | 91.07 | |
| | 100.000 | 108.87 | 762.00 |
| 159 | 0.410 | <10 | |
| | 1.230 | 14.39 | |
| | 3.700 | 39.76 | |
| | 11.000 | 74.27 | |
| | 33.000 | 84.24 | |

TABLE IV-continued

HIV Protease FITC Assay

| Compound of Example No. | HIV-1 Dose (uM) | HIV-1 Protease % Inhib | HIV-1 FITC KI (nM) |
|---|---|---|---|
| | 100.000 | 91.14 | 2397.00 |
| 160 | 0.410 | <10 | |
| | 1.230 | <10 | |
| | 3.700 | <10 | |
| | 11.000 | 14.21 | |
| | 33.000 | 40.35 | |
| | 100.000 | 82.56 | |
| 316 | 0.123 | 10 | |
| | 0.370 | 31.24 | |
| | 1.100 | 77.76 | |
| | 3.300 | 98.14 | |
| | 10.000 | 102.56 | |
| | 30.000 | 110.55 | 18.00 |
| 317 | 0.123 | 27.78 | |
| | 0.370 | 46.7 | |
| | 1.100 | 81.71 | |
| | 3.300 | 101.3 | |
| | 10.000 | 102.05 | |
| | 30.000 | 112.86 | 11.00 |
| 318 | 0.123 | 28.3 | |
| | 0.370 | 45.08 | |
| | 1.100 | 84.18 | |
| | 3.300 | 99.67 | |
| | 10.000 | 97.52 | |
| | 30.000 | 105.81 | 9.90 |
| 363 | 0.123 | 10 | |
| | 0.370 | 10 | |
| | 1.100 | 21.51 | |
| | 3.300 | 58.75 | |
| | 10.000 | 84.82 | |
| | 30.000 | 107.37 | |
| 364 | 0.123 | 10 | |
| | 0.370 | 17.22 | |
| | 1.100 | 53.5 | |
| | 3.300 | 78.67 | |
| | 10.000 | 100.25 | |
| | 30.000 | 90.21 | 118.00 |
| 365 | 0.123 | 11.74 | |
| | 0.370 | 31.05 | |
| | 1.100 | 65.28 | |
| | 3.300 | 84.07 | |
| | 10.000 | 94.54 | |
| | 30.000 | 95.78 | 63.00 |
| 319 | 0.123 | 67.05 | |
| | 0.370 | 84.24 | |
| | 1.100 | 93.13 | |
| | 3.300 | 94.29 | |
| | 10.000 | 101.95 | |
| | 30.000 | 101.42 | 4.30 |
| | | | 3.30 |
| | | | 2.10 |
| 320 | 0.123 | 66.37 | |
| | 0.370 | 78.55 | |
| | 1.100 | 98.19 | |
| | 3.300 | 102.32 | |
| | 10.000 | 99.29 | |
| | 30.000 | 99.03 | 3.80 |
| | | | 2.10 |
| 321 | 0.123 | 22.22 | |
| | 0.370 | 62.06 | |
| | 1.100 | 100.03 | |
| | 3.300 | 113.11 | |
| | 10.000 | 118.85 | |
| | 30.000 | 117.97 | 13.20 |
| 322 | 0.123 | 10 | |
| | 0.370 | 10 | |
| | 1.100 | 22.31 | |
| | 3.300 | 61.14 | |
| | 10.000 | 91.75 | |
| | 30.000 | 105.97 | |
| 323 | 0.123 | 62.79 | |
| | 0.370 | 91.81 | |
| | 1.100 | 100.2 | |
| | 3.30 | 104.32 | |
| | 10.000 | 118.05 | |
| | 30.000 | 112.33 | 6.30 |
| 324 | 0.123 | 44.33 | |
| | 0.370 | 87.46 | |
| | 1.100 | 103.02 | |
| | 3.300 | 108.23 | |
| | 10.000 | 115.62 | |
| | 30.000 | 117.15 | 4.00 |
| 325 | 0.123 | 59.78 | |
| | 0.370 | 86.58 | |
| | 1.100 | 95.56 | |
| | 3.300 | 105.1 | |
| | 10.000 | 115.38 | |
| | 30.000 | 114.97 | 3.30 |
| 326 | 0.123 | 51.64 | |
| | 0.370 | 92.56 | |
| | 1.100 | 102.5 | |
| | 3.300 | 105.93 | |
| | 10.000 | 114.14 | |
| | 30.000 | 121.02 | 4.60 |
| 327 | 0.123 | 34.22 | |
| | 0.370 | 68.19 | |
| | 1.100 | 94.75 | |
| | 3.300 | 105.37 | |
| | 10.000 | 105.72 | |
| | 30.000 | 112.78 | 13.50 |
| 264 | 0.123 | 78.52 | |
| | 0.370 | 89.02 | |
| | 1.100 | 99.82 | |
| | 3.300 | 104.42 | |
| | 10.000 | 108.11 | |
| | 30.000 | 108.96 | 2.50 |
| 265 | 0.123 | 25.34 | |
| | 0.370 | 54.77 | |
| | 1.100 | 76.87 | |
| | 3.300 | 86.12 | |
| | 10.000 | 100.44 | |
| | 30.000 | 98.35 | 31.50 |
| 244 | 0.123 | 10 | |
| | 0.370 | 10 | |
| | 1.100 | 10 | |
| | 3.300 | 10 | |
| | 10.000 | 18.84 | |
| | 30.000 | 31.78 | |
| 266 | 0.123 | 79.8 | |
| | 0.370 | 88.42 | |
| | 1.100 | 104.29 | |
| | 3.300 | 100.36 | |
| | 10.000 | 104.64 | |
| | 30.000 | 102.86 | 4.10 |
| 267 | 0.123 | 71.48 | |
| | 0.370 | 83.88 | |
| | 1.100 | 92.02 | |
| | 3.300 | 107.29 | |
| | 10.000 | 106.97 | |
| | 30.000 | 109.94 | 6.20 |
| 269 | | | 5.30 |
| | 0.123 | 77.14 | |
| | 0.370 | 95.65 | |
| | 1.100 | 111.83 | |
| | 3.300 | 114.29 | |
| | 10.000 | 124.96 | |
| | 30.000 | 114.06 | 2.90 |
| 270 | 0.123 | 61.67 | |
| | 0.370 | 93.12 | |
| | 1.100 | 107.2 | |
| | 3.300 | 110.59 | |
| | 10.000 | 115.96 | |
| | 30.000 | 114.73 | 5.50 |
| 258 | | | 7.60 |
| 401 | | | 2.30 |
| 257 | | | 3.00 |
| 261 | | | 3.10 |
| 268 | 0.123 | 71.24 | |

TABLE IV-continued

| Compound of Example No. | HIV Protease FITC Assay | | |
|---|---|---|---|
| | HIV-1 Dose (uM) | HIV-1 Protease % Inhib | HIV-1 FITC KI (nM) |
| | 0.370 | 88 | |
| | 1.100 | 96.15 | |
| | 3.300 | 97.62 | |
| | 10.000 | 101.31 | |
| | 30.000 | 101.17 | 3.10 |
| 271 | 0.123 | 10 | |
| | 0.370 | 16.69 | |
| | 1.100 | 47.45 | |
| | 3.300 | 75.32 | |
| | 10.000 | 88.81 | |
| | 30.000 | 94.23 | 74.30 |
| 272 | 0.123 | 67.1 | |
| | 0.370 | 85.25 | |
| | 1.100 | 95.35 | |
| | 3.300 | 96.23 | |
| | 10.000 | 100.68 | |
| | 30.000 | 104.08 | 2.10 |
| 273 | 0.123 | 68.41 | |
| | 0.370 | 92.26 | |
| | 1.100 | 95.9 | |
| | 3.300 | 98.15 | |
| | 10.000 | 101.66 | |
| | 30.000 | 108.32 | 2.70 |
| 274 | 0.123 | 70 | |
| | 0.370 | 88.17 | |
| | 1.100 | 95.85 | |
| | 3.300 | 98.83 | |
| | 10.000 | 102.79 | |
| | 30.000 | 105.14 | 4.70 |
| 275 | 0.123 | 79.26 | |
| | 0.370 | 120.02 | |
| | 1.100 | 127.95 | |
| | 3.300 | 130.68 | |
| | 10.000 | 132.51 | |
| | 30.000 | 130.57 | 3.90 |
| 276 | 0.123 | 53.36 | |
| | 0.370 | 92.75 | |
| | 1.100 | 99.28 | |
| | 3.300 | 94.72 | |
| | 10.000 | 112.32 | |
| | 30.000 | 123.9 | 11.00 |
| 277 | 0.123 | 10 | |
| | 0.370 | 10 | |
| | 1.100 | 10 | |
| | 3.300 | 37.89 | |
| | 10.000 | 79.93 | |
| | 30.000 | 94.12 | |
| 278 | 0.123 | 36.28 | |
| | 0.370 | 78.17 | |
| | 1.100 | 94.73 | |
| | 3.300 | 100.56 | |
| | 10.000 | 101.68 | |
| | 30.000 | 110.3 | 13.60 |
| 280 | 0.123 | 69.76 | |
| | 0.370 | 95.1 | |
| | 1.100 | 100.54 | |
| | 3.300 | 109.55 | |
| | 10.000 | 109.82 | |
| | 30.000 | 113.5 | 3.00 |
| 279 | 0.123 | 78.2 | |
| | 0.370 | 97.29 | |
| | 1.100 | 105.27 | |
| | 3.300 | 102.79 | |
| | 10.000 | 108.88 | |
| | 30.000 | 94.85 | 4.10 |
| 281 | 0.123 | 55.51 | |
| | 0.370 | 93.52 | |
| | 1.100 | 99.3 | |
| | 3.300 | 109.39 | |
| | 10.000 | 105.4 | |
| | 30.000 | 101.02 | 10.60 |
| 328 | 0.123 | 11.95 | |
| | 0.370 | 45.95 | |
| | 1.100 | 86.57 | |
| | 3.300 | 105.92 | |
| | 10.000 | 113.94 | |
| | 30.000 | 111.06 | 33.00 |
| 329 | 0.123 | 10 | |
| | 0.370 | 10.17 | |
| | 1.100 | 42.19 | |
| | 3.300 | 75.33 | |
| | 10.000 | 91.77 | |
| | 30.000 | 101.52 | |
| 330 | 0.123 | 47.22 | |
| | 0.370 | 83.75 | |
| | 1.100 | 105.73 | |
| | 3.300 | 108.94 | |
| | 10.000 | 114.61 | |
| | 30.000 | 106.38 | 9.30 |
| 331 | 0.123 | 66.39 | |
| | 0.370 | 86.89 | |
| | 1.100 | 99.22 | |
| | 3.300 | 118.95 | |
| | 10.000 | 121.29 | |
| | 30.000 | 105.29 | 4.80 |
| 262 | 0.123 | 83.32 | |
| | 0.370 | 102.6 | |
| | 1.100 | 112.99 | |
| | 3.300 | 121.87 | |
| | 10.000 | 119.5 | |
| | 30.000 | 114.54 | 1.40 |
| | | | 0.44 |
| | | | 1.01 |
| | | | 0.60 |
| | | | 0.60 |
| 332 | 0.123 | 23.14 | |
| | 0.370 | 39.26 | |
| | 1.100 | 71.55 | |
| | 3.300 | 93.95 | |
| | 10.000 | 108.56 | |
| | 30.000 | 114.97 | 47.00 |
| 333 | 0.123 | 10 | |
| | 0.370 | 28.33 | |
| | 1.100 | 62.17 | |
| | 3.300 | 82.05 | |
| | 10.000 | 101.66 | |
| | 30.000 | 110.31 | 104.00 |
| 246 | 0.123 | 10 | |
| | 0.370 | 10 | |
| | 1.100 | 10 | |
| | 3.300 | 10 | |
| | 10.000 | 26.64 | |
| | 30.000 | 49.66 | |
| 245 | 0.123 | 10 | |
| | 0.370 | 10 | |
| | 1.100 | 10.64 | |
| | 3.300 | 50.92 | |
| | 10.000 | 59.51 | |
| | 30.000 | 78.63 | |
| 406 | 0.123 | 37.1 | |
| | 0.370 | 69.39 | |
| | 1.100 | 87.61 | |
| | 3.300 | 85.17 | |
| | 10.000 | 97.39 | |
| | 30.000 | 97.21 | 18.10 |
| 283 | 0.123 | 10 | |
| | 0.370 | 10.6 | |
| | 1.100 | 42.27 | |
| | 3.300 | 64.22 | |
| | 10.000 | 85.12 | |
| | 30.000 | 80.21 | |
| 284 | 0.123 | 37.48 | |
| | 0.370 | 77.05 | |
| | 1.100 | 99.82 | |
| | 3.300 | 106.85 | |
| | 10.000 | 106.87 | |
| | 30.000 | 104.28 | 12.20 |
| 285 | 0.123 | 37.64 | |

TABLE IV-continued

HIV Protease FITC Assay

| Compound of Example No. | HIV-1 Dose (uM) | HIV-1 Protease % Inhib | HIV-1 FITC KI (nM) |
|---|---|---|---|
| | 0.370 | 73.79 | |
| | 1.100 | 84.61 | |
| | 3.300 | 95.04 | |
| | 10.000 | 97.66 | |
| | 30.000 | 91.84 | 7.60 |
| 286 | 0.123 | 30.01 | |
| | 0.370 | 62.4 | |
| | 1.100 | 83.35 | |
| | 3.300 | 92.28 | |
| | 10.000 | 97.44 | |
| | 30.000 | 93.69 | 21.40 |
| 287 | 0.123 | 10 | |
| | 0.370 | 14.06 | |
| | 1.100 | 44.1 | |
| | 3.300 | 68.19 | |
| | 10.000 | 85.78 | |
| | 30.000 | 86.72 | |
| 263 | 0.123 | 82.88 | |
| | 0.370 | 89.92 | |
| | 1.100 | 95.73 | |
| | 3.300 | 98.67 | |
| | 10.000 | 107.98 | |
| | 30.000 | 98.33 | 1.90 |
| 334 | 0.123 | 10 | |
| | 0.370 | 13.61 | |
| | 1.100 | 42.28 | |
| | 3.300 | 69.04 | |
| | 10.000 | 87.61 | |
| | 30.000 | 89.51 | |
| 335 | 0.123 | 48.73 | |
| | 0.370 | 82.88 | |
| | 1.100 | 90.28 | |
| | 3.300 | 96.77 | |
| | 10.000 | 96.48 | |
| | 30.000 | 105.84 | 6.80 |
| 336 | 0.123 | 73.53 | |
| | 0.370 | 87.27 | |
| | 1.100 | 92.95 | |
| | 3.300 | 94.63 | |
| | 10.000 | 103.23 | |
| | 30.000 | 108.08 | 5.30 |
| 337 | 0.123 | 10.11 | |
| | 0.370 | 47.88 | |
| | 1.100 | 93.62 | |
| | 3.300 | 116.43 | |
| | 10.000 | 110.8 | |
| | 30.000 | 111.88 | 37.90 |
| 338 | 0.123 | 39.07 | |
| | 0.370 | 80.12 | |
| | 1.100 | 86.33 | |
| | 3.300 | 96.8 | |
| | 10.000 | 101.65 | |
| | 30.000 | 99.96 | 9.80 |
| 339 | 0.123 | 53.55 | |
| | 0.370 | 81.33 | |
| | 1.100 | 94.89 | |
| | 3.300 | 99.22 | |
| | 10.000 | 104.64 | |
| | 30.000 | 99.83 | 7.40 |
| 340 | 0.123 | 77.79 | |
| | 0.370 | 93.2 | |
| | 1.100 | 90.86 | |
| | 3.300 | 96.54 | |
| | 10.000 | 100.53 | |
| | 30.000 | 96.54 | 1.90 |
| 288 | 0.123 | 46.91 | |
| | 0.370 | 79.06 | |
| | 1.100 | 90.47 | |
| | 3.300 | 92.86 | |
| | 10.000 | 105.45 | |
| | 30.000 | 101.46 | 6.90 |
| 289 | 0.123 | 63.71 | |
| | 0.370 | 80.05 | |
| | 1.100 | 91.12 | |

TABLE IV-continued

HIV Protease FITC Assay

| Compound of Example No. | HIV-1 Dose (uM) | HIV-1 Protease % Inhib | HIV-1 FITC KI (nM) |
|---|---|---|---|
| | 3.300 | 97.3 | |
| | 10.000 | 95.28 | |
| | 30.000 | 100.75 | 2.70 |
| 290 | 0.123 | 90.26 | |
| | 0.370 | 115.12 | |
| | 1.100 | 123.27 | |
| | 3.300 | 119.17 | |
| | 10.000 | 125.99 | |
| | 30.000 | 114.37 | 2.70 |
| 291 | 0.123 | 80.41 | |
| | 0.370 | 108.02 | |
| | 1.100 | 109.27 | |
| | 3.300 | 121.93 | |
| | 10.000 | 117.89 | |
| | 30.000 | 116.55 | 2.60 |
| 292 | 0.123 | 74.42 | |
| | 0.370 | 103.91 | |
| | 1.100 | 111.33 | |
| | 3.300 | 124.78 | |
| | 10.000 | 115.11 | |
| | 30.000 | 111.07 | 4.50 |
| 293 | 0.123 | 54.91 | |
| | 0.370 | 82.42 | |
| | 1.100 | 96.83 | |
| | 3.300 | 107.39 | |
| | 10.000 | 105.38 | |
| | 30.000 | 108.57 | 9.30 |
| 295 | 0.123 | 10 | |
| | 0.370 | 10 | |
| | 1.100 | 25.9 | |
| | 3.300 | 57.05 | |
| | 10.000 | 87.53 | |
| | 30.000 | 100.17 | |
| 294 | 0.123 | 10 | |
| | 0.370 | 20.9 | |
| | 1.100 | 52.87 | |
| | 3.300 | 81.06 | |
| | 10.000 | 94.65 | |
| | 30.000 | 110.5 | 139.00 |
| 251 | | | 1.25 |
| 250 | | | 1.23 |
| 259 | | | 0.71 |
| 255 | | | 0.62 |
| 296 | 0.123 | 14.62 | |
| | 0.370 | 74.77 | |
| | 1.100 | 95.51 | |
| | 3.300 | 103.54 | |
| | 10.000 | 107.8 | |
| | 30.000 | 114.11 | 24.00 |
| 297 | 0.123 | 71.96 | |
| | 0.370 | 86.01 | |
| | 1.100 | 100.52 | |
| | 3.300 | 99.81 | |
| | 10.000 | 101.63 | |
| | 30.000 | 99.54 | 1.60 |
| 298 | 0.123 | 67.39 | |
| | 0.370 | 84.64 | |
| | 1.100 | 94.6 | |
| | 3.300 | 97.5 | |
| | 10.000 | 100.9 | |
| | 30.000 | 100 | 2.50 |
| 299 | 0.123 | 78.54 | |
| | 0.370 | 97.78 | |
| | 1.100 | 97.46 | |
| | 3.300 | 91.67 | |
| | 10.000 | 104.35 | |
| | 30.000 | 98.38 | 2.30 |
| 300 | 0.123 | 68.8 | |
| | 0.370 | 92.23 | |
| | 1.100 | 100.71 | |
| | 3.300 | 101.51 | |
| | 10.000 | 108.25 | |
| | 30.000 | 108.43 | 3.10 |
| 301 | 0.123 | 74.65 | |

TABLE IV-continued

HIV Protease FITC Assay

| Compound of Example No. | HIV-1 Dose (uM) | HIV-1 Protease % Inhib | HIV-1 FITC KI (nM) |
|---|---|---|---|
|  | 0.370 | 91.19 |  |
|  | 1.100 | 101.52 |  |
|  | 3.300 | 100.41 |  |
|  | 10.000 | 104.19 |  |
|  | 30.000 | 114.47 | 4.80 |
| 302 | 0.123 | 78.61 |  |
|  | 0.370 | 97.82 |  |
|  | 1.100 | 104.55 |  |
|  | 3.300 | 112.55 |  |
|  | 10.000 | 115.31 |  |
|  | 30.000 | 112.47 | 2.70 |
| 303 | 0.123 | 67.38 |  |
|  | 0.370 | 96.54 |  |
|  | 1.100 | 97.65 |  |
|  | 3.300 | 109.02 |  |
|  | 10.000 | 109.9 |  |
|  | 30.000 | 97.99 | 5.00 |
| 304 | 0.123 | 25.71 |  |
|  | 0.370 | 60.19 |  |
|  | 1.100 | 85.93 |  |
|  | 3.300 | 97.82 |  |
|  | 10.000 | 103.5 |  |
|  | 30.000 | 95.57 | 27.90 |
| 341 | 0.123 | 59.43 |  |
|  | 0.370 | 92.77 |  |
|  | 1.100 | 109.68 |  |
|  | 3.300 | 107.4 |  |
|  | 10.000 | 120.47 |  |
|  | 30.000 | 122.42 | 5.00 |
| 342 | 0.123 | 42.05 |  |
|  | 0.370 | 72.88 |  |
|  | 1.100 | 88.22 |  |
|  | 3.300 | 87.85 |  |
|  | 10.000 | 107.66 |  |
|  | 30.000 | 104.99 | 10.90 |
| 343 | 0.123 | 39.4 |  |
|  | 0.370 | 74.98 |  |
|  | 1.100 | 91.21 |  |
|  | 3.300 | 104.19 |  |
|  | 10.000 | 111.99 |  |
|  | 30.000 | 105.32 | 6.00 |
| 344 | 0.123 | 10 |  |
|  | 0.370 | 10 |  |
|  | 1.100 | 11.78 |  |
|  | 3.300 | 32.69 |  |
|  | 10.000 | 63.21 |  |
|  | 30.000 | 81.83 |  |
| 305 | 0.123 | 60.37 |  |
|  | 0.370 | 86.24 |  |
|  | 1.100 | 92.37 |  |
|  | 3.300 | 95.2 |  |
|  | 10.000 | 99.81 |  |
|  | 30.000 | 106.54 | 6.20 |
| 306 | 0.123 | 10 |  |
|  | 0.370 | 10 |  |
|  | 1.100 | 24.42 |  |
|  | 3.300 | 53.25 |  |
|  | 10.000 | 74.49 |  |
|  | 30.000 | 86.22 |  |
| 308 | 0.123 | 46.49 |  |
|  | 0.370 | 70.42 |  |
|  | 1.100 | 82.28 |  |
|  | 3.300 | 91.26 |  |
|  | 10.000 | 96.86 |  |
|  | 30.000 | 86.75 | 3.10 |
| 309 | 0.123 | 46.56 |  |
|  | 0.370 | 67.45 |  |
|  | 1.100 | 82.49 |  |
|  | 3.300 | 76.55 |  |
|  | 10.000 | 43.74 |  |
|  | 30.000 | 19.22 | 5.80 |
| 410 | 0.123 | 49.54 |  |
|  | 0.370 | 79.73 |  |
|  | 1.100 | 91.4 |  |
|  | 3.300 | 90.9 |  |
|  | 10.000 | 96.84 |  |
|  | 30.000 | 98.32 | 8.80 |
| 253 | 0.123 | 69.79 |  |
|  | 0.370 | 86.65 |  |
|  | 1.100 | 84.79 |  |
|  | 3.300 | 91.63 |  |
|  | 10.000 | 97.46 |  |
|  | 30.000 | 101.45 | 1.70 |
|  |  |  | 2.40 |
| 252 | 0.123 | 100.07 |  |
|  | 0.370 | 107.91 |  |
|  | 1.100 | 110.57 |  |
|  | 3.300 | 111.98 |  |
|  | 10.000 | 115.86 |  |
|  | 30.000 | 108.96 | 1.60 |
|  |  |  | 1.10 |
| 345 | 0.123 | 50.05 |  |
|  | 0.370 | 77 |  |
|  | 1.100 | 90.39 |  |
|  | 3.300 | 100.56 |  |
|  | 10.000 | 104.61 |  |
|  | 30.000 | 91.85 | 13.10 |
| 346 | 0.123 | 75.09 |  |
|  | 0.370 | 92.5 |  |
|  | 1.100 | 97.31 |  |
|  | 3.300 | 102.38 |  |
|  | 10.000 | 102.7 |  |
|  | 30.000 | 97 | 3.85 |
| 347 | 0.123 | 79.84 |  |
|  | 0.370 | 92.19 |  |
|  | 1.100 | 103.43 |  |
|  | 3.300 | 100.21 |  |
|  | 10.000 | 102.08 |  |
|  | 30.000 | 102.85 | 2.50 |
| 314 | 0.123 | 79.52 |  |
|  | 0.370 | 97.7 |  |
|  | 1.100 | 107.73 |  |
|  | 3.300 | 109.14 |  |
|  | 10.000 | 102.22 |  |
|  | 30.000 | 97.14 | 2.31 |
|  |  |  | 2.01 |
| 260 | 0.123 | 73.79 |  |
|  | 0.370 | 91.66 |  |
|  | 1.100 | 98.97 |  |
|  | 3.300 | 106.23 |  |
|  | 10.000 | 102.36 |  |
|  | 30.000 | 96.86 | 0.93 |
| 256 | 0.123 | 82.51 |  |
|  | 0.370 | 91.28 |  |
|  | 1.100 | 99.01 |  |
|  | 3.300 | 95.02 |  |
|  | 10.000 | 101.04 |  |
|  | 30.000 | 96.12 | 0.42 |
| 307 | 0.123 | 19.52 |  |
|  | 0.370 | 66.55 |  |
|  | 1.100 | 85.23 |  |
|  | 3.300 | 97.75 |  |
|  | 10.000 | 104.73 |  |
|  | 30.000 | 90.27 | 7.60 |
| 349 | 0.123 | 10 |  |
|  | 0.370 | 38.43 |  |
|  | 1.100 | 69.01 |  |
|  | 3.300 | 86.41 |  |
|  | 10.000 | 96.72 |  |
|  | 30.000 | 88.45 | 33.80 |
| 310 | 0.123 | 46.21 |  |
|  | 0.370 | 86.18 |  |
|  | 1.100 | 94.87 |  |
|  | 3.300 | 99.05 |  |
|  | 10.000 | 102.79 |  |
|  | 30.000 | 102.21 | 2.37 |
| 311 | 0.123 | 20.75 |  |
|  | 0.370 | 71.24 |  |

TABLE IV-continued

| Compound of Example No. | HIV Protease FITC Assay | | |
|---|---|---|---|
| | HIV-1 Dose (uM) | HIV-1 Protease % Inhib | HIV-1 FITC KI (nM) |
| | 1.100 | 86.43 | |
| | 3.300 | 91.96 | |
| | 10.000 | 99.54 | |
| | 30.000 | 99.48 | 6.33 |
| 348 (First Title Compound) | 0.123 | 28.13 | |
| | 0.370 | 80.67 | |
| | 1.100 | 102.66 | |
| | 3.300 | 108.46 | |
| | 10.000 | 113.04 | |
| | 30.000 | 108.91 | 6.90 |
| 348 (Second Title Compound) | 0.123 | 38.62 | |
| | 0.370 | 81.05 | |
| | 1.100 | 102.34 | |
| | 3.300 | 108.55 | |
| | 10.000 | 112.78 | |
| | 30.000 | 98.7 | 1.70 |
| 352 | 0.123 | 49.67 | |
| | 0.370 | 78.53 | |
| | 1.100 | 97.9 | |
| | 3.300 | 104.5 | |
| | 10.000 | 101.85 | |
| | 30.000 | 94.59 | 2.84 |
| 353 (First Title Compound) | 0.123 | 48.58 | |
| | 0.370 | 83.12 | |
| | 1.100 | 92.65 | |
| | 3.300 | 97.32 | |
| | 10.000 | 102.6 | |
| | 30.000 | 92.88 | 2.25 |
| 312 | 0.123 | 48.17 | |
| | 0.370 | 83.6 | |
| | 1.100 | 89.74 | |
| | 3.300 | 106.17 | |
| | 10.000 | 114 | |
| | 30.000 | 109.93 | 4.00 |
| 403 | 0.123 | 41.64 | |
| | 0.370 | 77.47 | |
| | 1.100 | 92.92 | |
| | 3.300 | 94.76 | |
| | 10.000 | 95.57 | |
| | 30.000 | 97.01 | 5.00 |
| 365A | 0.123 | 83.76 | |
| | 0.370 | 105.53 | |
| | 1.100 | 114.88 | |
| | 3.300 | 115.96 | |
| | 10.000 | 116.92 | |
| | 30.000 | 116.11 | 1.86 |
| 254 | 0.123 | 82.28 | |
| | 0.370 | 97.98 | |
| | 1.100 | 107.75 | |
| | 3.300 | 111.05 | |
| | 10.000 | 112.1 | |
| | 30.000 | 103.1 | 0.65 |
| 404 | 0.123 | 58.26 | |
| | 0.370 | 85.28 | |
| | 1.100 | 102.83 | |
| | 3.300 | 108.5 | |
| | 10.000 | 105.5 | |
| | 30.000 | 102.67 | 2.87 |
| 161 | 0.123 | 20.02 | |
| | 0.370 | 67.29 | |
| | 1.100 | 98.69 | |
| | 3.300 | 103.91 | |
| | 10.000 | 106.32 | |
| | 30.000 | 111.13 | 32.00 |
| 162 | 0.123 | 14.81 | |
| | 0.370 | 55.98 | |
| | 1.100 | 92.25 | |
| | 3.300 | 99.34 | |
| | 10.000 | 101.57 | |
| | 30.000 | 108.88 | 40.00 |
| 163 | 0.123 | 17.66 | |
| | 0.370 | 55.95 | |
| | 1.100 | 84.23 | |
| | 3.300 | 98.56 | |
| | 10.000 | 107.38 | |
| | 30.000 | 104.74 | 34.00 |
| 170 | 0.123 | 23.25 | |
| | 0.370 | 62.26 | |
| | 1.100 | 92.5 | |
| | 3.300 | 99.3 | |
| | 10.000 | 107.29 | |
| | 30.000 | 110.83 | 31.00 |
| 171 | 0.123 | 33.13 | |
| | 0.370 | 73.44 | |
| | 1.100 | 96.52 | |
| | 3.300 | 103.16 | |
| | 10.000 | 109.98 | |
| | 30.000 | 108.64 | 23.00 |
| 172 | 0.123 | <10 | |
| | 0.370 | <10 | |
| | 1.100 | 31.92 | |
| | 3.300 | 73.45 | |
| | 10.000 | 97.83 | |
| | 30.000 | 109.61 | |
| 173 | 0.123 | <10 | |
| | 0.370 | <10 | |
| | 1.100 | 15.01 | |
| | 3.300 | 36.54 | |
| | 10.000 | 76.69 | |
| | 30.000 | 97.16 | |
| 174 | 0.123 | 11.38 | |
| | 0.370 | 35.75 | |
| | 1.100 | 75.02 | |
| | 3.300 | 95.89 | |
| | 10.000 | 104.18 | |
| | 30.000 | 97.78 | 35.00 |
| 175 | 0.123 | <10 | |
| | 0.370 | <10 | |
| | 1.100 | 19.41 | |
| | 3.300 | 55.47 | |
| | 10.000 | 88.54 | |
| | 30.000 | 104.57 | |
| 176 | 0.123 | <10 | |
| | 0.370 | 27.32 | |
| | 1.100 | 82.58 | |
| | 3.300 | 104.01 | |
| | 10.000 | 109.26 | |
| | 30.000 | 117.62 | 37.00 |
| 177 | 0.123 | <10 | |
| | 0.370 | 16.86 | |
| | 1.100 | 53.85 | |
| | 3.300 | 88.93 | |
| | 10.000 | 103.65 | |
| | 30.000 | 104.3 | 55.00 |
| 178 | 0.123 | 16.24 | |
| | 0.370 | 45.55 | |
| | 1.100 | 86.44 | |
| | 3.300 | 98.82 | |
| | 10.000 | 104.94 | |
| | 30.000 | 102.6 | 27.00 |
| 179 | 0.123 | <10 | |
| | 0.370 | 38.65 | |
| | 1.100 | 71.63 | |
| | 3.300 | 87.25 | |
| | 10.000 | 93.69 | |
| | 30.000 | 91.08 | 19.00 |
| 180 | 0.123 | <10 | |
| | 0.370 | <10 | |
| | 1.100 | 31.3 | |
| | 3.300 | 67.67 | |
| | 10.000 | 94.14 | |
| | 30.000 | 109.37 | |
| 181 | 0.123 | <10 | |
| | 0.370 | <10 | |
| | 1.100 | 10.44 | |

TABLE IV-continued

HIV Protease FITC Assay

| Compound of Example No. | HIV-1 Dose (uM) | HIV-1 Protease % Inhib | HIV-1 FITC KI (nM) |
|---|---|---|---|
| | 3.300 | 35.1 | |
| | 10.000 | 66.6 | |
| | 30.000 | 79.26 | |
| 182 | 0.123 | <10 | |
| | 0.370 | 22.26 | |
| | 1.100 | 51.02 | |
| | 3.300 | 83.72 | |
| | 10.000 | 99.18 | |
| | 30.000 | 98.67 | 117.00 |
| 183 | 0.123 | 20.92 | |
| | 0.370 | 56.5 | |
| | 1.100 | 85.54 | |
| | 3.300 | 97.33 | |
| | 10.000 | 95.76 | |
| | 30.000 | 89.71 | 13.00 |
| 184 | 0.123 | <10 | |
| | 0.370 | 18.04 | |
| | 1.100 | 60.74 | |
| | 3.300 | 85.97 | |
| | 10.000 | 96.51 | |
| | 30.000 | 93.08 | 46.00 |
| 185 | 0.123 | 18.73 | |
| | 0.370 | 40.26 | |
| | 1.100 | 71.53 | |
| | 3.300 | 92.59 | |
| | 10.000 | 97.64 | |
| | 30.000 | 91.75 | 22.00 |
| 186 | 0.123 | <10 | |
| | 0.370 | <10 | |
| | 1.100 | 29.2 | |
| | 3.300 | 64.59 | |
| | 10.000 | 88.74 | |
| | 30.000 | 100.99 | |
| 187 | 0.123 | <10 | |
| | 0.370 | 10.6 | |
| | 1.100 | 32.87 | |
| | 3.300 | 67.96 | |
| | 10.000 | 89.99 | |
| | 30.000 | 90.15 | |
| 188 | 0.123 | 27.26 | |
| | 1.100 | 82.16 | |
| | 0.370 | 57.02 | |
| | 3.300 | 88.4 | |
| | 10.000 | 88.31 | |
| | 30.000 | 84.46 | 26.00 |
| 189 | 0.123 | 15.66 | |
| | 0.370 | 37.62 | |
| | 1.100 | 69.77 | |
| | 3.300 | 89.35 | |
| | 10.000 | 98.11 | |
| | 30.000 | 99.35 | 36.00 |
| 190 | 0.123 | <10 | |
| | 0.370 | <10 | |
| | 1.100 | 35.86 | |
| | 3.300 | 79.27 | |
| | 10.000 | 96 | |
| | 30.000 | 102.5 | |
| 191 | 0.123 | <10 | |
| | 0.370 | 16.94 | |
| | 1.100 | 54.96 | |
| | 3.300 | 93.35 | |
| | 10.000 | 100.92 | |
| | 30.000 | 100.04 | |
| 192 | 0.123 | <10 | |
| | 0.370 | <10 | |
| | 1.100 | 24.9 | |
| | 3.300 | 68.77 | |
| | 10.000 | 102.31 | |
| | 30.000 | 102.35 | |
| 193 | 0.123 | <10 | |
| | 0.370 | <10 | |
| | 1.100 | 35.01 | |
| | 3.300 | 70.38 | |
| | 10.000 | 97.73 | |
| | 30.000 | 105.39 | |
| 194 | 0.123 | <10 | |
| | 0.370 | 39.7 | |
| | 1.100 | 81.89 | |
| | 3.300 | 102.84 | |
| | 10.000 | 108.17 | |
| | 30.000 | 107.45 | 28.00 |
| 195 | 0.123 | <10 | |
| | 0.370 | 23.47 | |
| | 1.100 | 71.37 | |
| | 3.300 | 90.85 | |
| | 10.000 | 108.07 | |
| | 30.000 | 117.26 | 22.00 |
| 196 | 0.123 | 67.96 | |
| | 0.370 | 81.2 | |
| | 1.100 | 91.83 | |
| | 3.300 | 97.93 | |
| | 10.000 | 104.68 | |
| | 30.000 | 95.75 | 3.00 |
| 197 | 0.123 | 33.98 | |
| | 0.370 | 65.6 | |
| | 1.100 | 76.61 | |
| | 3.300 | 88.68 | |
| | 10.000 | 91.75 | |
| | 30.000 | 89.62 | 14.10 |
| 198 | 0.123 | 67.11 | |
| | 0.370 | 91.89 | |
| | 1.100 | 107.19 | |
| | 3.300 | 111.11 | |
| | 10.000 | 114.95 | |
| | 30.000 | 115.88 | 6.90 |
| 199 | 0.123 | 55.99 | |
| | 0.370 | 86.55 | |
| | 1.100 | 97.62 | |
| | 3.300 | 106.12 | |
| | 10.000 | 114.48 | |
| | 30.000 | 106.98 | 10.40 |
| 200 | 0.123 | 64.6 | |
| | 0.370 | 88.48 | |
| | 1.100 | 90.89 | |
| | 3.300 | 103.22 | |
| | 10.000 | 105.15 | |
| | 30.000 | 99.1 | 2.90 |
| 201 | 0.123 | 31.16 | |
| | 0.370 | 60.1 | |
| | 1.100 | 80 | |
| | 3.300 | 95.36 | |
| | 10.000 | 100.21 | |
| | 30.000 | 107.07 | 13.90 |
| 202 | 0.123 | 20.11 | |
| | 0.370 | 48.13 | |
| | 1.100 | 73.14 | |
| | 3.300 | 88.12 | |
| | 10.000 | 93.82 | |
| | 30.000 | 94.36 | 43.00 |
| 203 | 0.123 | 15.63 | |
| | 0.370 | 55.8 | |
| | 1.100 | 81.33 | |
| | 3.300 | 94.35 | |
| | 10.000 | 104.01 | |
| | 30.000 | 94.35 | 31.80 |
| 204 | 0.123 | 49 | |
| | 0.370 | 86.53 | |
| | 1.100 | 106.92 | |
| | 3.300 | 114.18 | |
| | 10.000 | 116.83 | |
| | 30.000 | 116.04 | 11.00 |
| 205 | 0.123 | 12.58 | |
| | 0.370 | 56.41 | |
| | 1.100 | 76.57 | |
| | 3.300 | 94.18 | |
| | 10.000 | 109.32 | |
| | 30.000 | 103.94 | 26.10 |
| 206 | 0.123 | <10 | |

TABLE IV-continued

HIV Protease FITC Assay

| Compound of Example No. | HIV-1 Dose (uM) | HIV-1 Protease % Inhib | HIV-1 FITC KI (nM) |
|---|---|---|---|
|  | 0.370 | 17.93 |  |
|  | 1.100 | 48.05 |  |
|  | 3.300 | 76.43 |  |
|  | 10.000 | 95.84 |  |
|  | 30.000 | 93.11 |  |
| 207 | 0.123 | 13.96 |  |
|  | 0.370 | 44.08 |  |
|  | 1.100 | 74.03 |  |
|  | 3.300 | 93.81 |  |
|  | 10.000 | 83.02 |  |
|  | 30.000 | 78.74 | 33.40 |
| 208 | 0.123 | <10 |  |
|  | 0.370 | <10 |  |
|  | 1.100 | 22.94 |  |
|  | 3.300 | 57.62 |  |
|  | 10.000 | 76.76 |  |
|  | 30.000 | 84.4 |  |
| 209 | 0.123 | <10 |  |
|  | 0.370 | 43.24 |  |
|  | 1.100 | 79.98 |  |
|  | 3.300 | 96.02 |  |
|  | 10.000 | 104.21 |  |
|  | 30.000 | 100.09 | 24.10 |
| 210 | 0.123 | 19.67 |  |
|  | 0.370 | 31.46 |  |
|  | 1.100 | 58.11 |  |
|  | 3.300 | 77.58 |  |
|  | 10.000 | 88.76 |  |
|  | 30.000 | 97.28 | 55.00 |
| 211 | 0.123 | <10 |  |
|  | 0.370 | 37.24 |  |
|  | 1.100 | 64.49 |  |
|  | 3.300 | 89.56 |  |
|  | 10.000 | 101.21 |  |
|  | 30.000 | 100.77 | 42.00 |
| 213 | 0.123 | 74.4 |  |
|  | 0.370 | 82.24 |  |
|  | 1.100 | 94.45 |  |
|  | 3.300 | 102.35 |  |
|  | 10.000 | 109.03 |  |
|  | 30.000 | 99.28 | 3.50 |
| 214 | 0.123 | 18.66 |  |
|  | 0.370 | 54 |  |
|  | 1.100 | 74.08 |  |
|  | 3.300 | 88.57 |  |
|  | 10.000 | 95.18 |  |
|  | 30.000 | 96.19 | 19.30 |
| 215 | 0.123 | 13.49 |  |
|  | 0.370 | 43.33 |  |
|  | 1.100 | 76.11 |  |
|  | 3.300 | 97.93 |  |
|  | 10.000 | 107.1 |  |
|  | 30.000 | 98.49 | 27.80 |
| 216 | 0.123 | <10 |  |
|  | 0.370 | <10 |  |
|  | 1.100 | <10 |  |
|  | 3.300 | <10 |  |
|  | 10.000 | 10.88 |  |
|  | 30.000 | 31.42 |  |
| 217 | 0.123 | <10 |  |
|  | 0.370 | <10 |  |
|  | 1.100 | <10 |  |
|  | 3.300 | 31.61 |  |
|  | 10.000 | 64.15 |  |
|  | 30.00 | 72.93 |  |
| 218 | 0.123 | <10 |  |
|  | 0.370 | <10 |  |
|  | 1.100 | 26.24 |  |
|  | 3.300 | 65.18 |  |
|  | 10.000 | 88.04 |  |
|  | 30.000 | 91.38 |  |
| 219 | 0.123 | 52.1 |  |
|  | 0.370 | 80.99 |  |
|  | 1.100 | 92.55 |  |
|  | 3.300 | 100.02 |  |
|  | 10.000 | 108.63 |  |
|  | 30.000 | 97.33 | 10.40 |
| 220 | 0.123 | <10 |  |
|  | 0.370 | <10 |  |
|  | 1.100 | 25.21 |  |
|  | 3.300 | 63.61 |  |
|  | 10.000 | 93.97 |  |
|  | 30.000 | 100.6 |  |
| 221 | 0.123 | 79.73 |  |
|  | 0.370 | 101.4 |  |
|  | 1.100 | 116.32 |  |
|  | 3.300 | 116.79 |  |
|  | 10.000 | 119.02 |  |
|  | 30.000 | 123.55 | 3.50 |
| 222 | 0.123 | 80.39 |  |
|  | 0.370 | 94.06 |  |
|  | 1.100 | 103.28 |  |
|  | 3.300 | 110.48 |  |
|  | 10.000 | 110.71 |  |
|  | 30.000 | 110.26 | 3.10 |
| 223 | 0.123 | 11.13 |  |
|  | 0.370 | 31.33 |  |
|  | 1.100 | 62.31 |  |
|  | 3.300 | 85.69 |  |
|  | 10.000 | 102.35 |  |
|  | 30.000 | 101.49 | 71.60 |
| 224 | 0.123 | <10 |  |
|  | 0.370 | 10.86 |  |
|  | 1.100 | 42.42 |  |
|  | 3.300 | 72.31 |  |
|  | 10.000 | 83.71 |  |
|  | 30.000 | 95.31 |  |
| 225 | 0.123 | <10 |  |
|  | 0.370 | <10 |  |
|  | 1.100 | 14.88 |  |
|  | 3.300 | 47.01 |  |
|  | 10.000 | 77.22 |  |
|  | 30.000 | 91.73 |  |
| 226 | 0.123 | 14.15 |  |
|  | 0.370 | 43.71 |  |
|  | 1.100 | 74.1 |  |
|  | 3.300 | 87.57 |  |
|  | 10.000 | 100.72 |  |
|  | 30.000 | 103.62 | 18.90 |
| 227 | 0.123 | <10 |  |
|  | 0.370 | 41.74 |  |
|  | 1.100 | 81.14 |  |
|  | 3.300 | 91.12 |  |
|  | 10.000 | 90.07 |  |
|  | 30.000 | 80.94 | 21.90 |
| 165 | 0.410 | 61.74 |  |
|  | 1.230 | 86.71 |  |
|  | 3.700 | 98.41 |  |
|  | 11.000 | 106.2 |  |
|  | 33.000 | 111.31 |  |
|  | 100.000 | 114.27 | 86.00 |
| 166 | 0.410 | <10 |  |
|  | 1.230 | 13.21 |  |
|  | 3.700 | 33.39 |  |
|  | 11.000 | 58.91 |  |
|  | 33.000 | 89.12 |  |
|  | 100.000 | 100.02 |  |
| 167 | 0.410 | 83.16 |  |
|  | 1.230 | 99.48 |  |
|  | 3.700 | 113.13 |  |
|  | 11.000 | 114.1 |  |
|  | 33.000 | 113.9 |  |
|  | 100.000 | 116.19 | 28.00 |
| 168 | 0.123 | <10 |  |
|  | 0.370 | 12.38 |  |
|  | 1.100 | 46.35 |  |
|  | 3.300 | 74.89 |  |
|  | 10.000 | 94.67 |  |

TABLE IV-continued

| | HIV Protease FITC Assay | | |
|---|---|---|---|
| Compound of Example No. | HIV-1 Dose (uM) | HIV-1 Protease % Inhib | HIV-1 FITC KI (nM) |
| | 30.000 | 107.35 | 135.00 |
| 169 | 0.123 | <10 | |
| | 0.370 | <10 | |
| | 1.100 | 13.07 | |
| | 3.300 | 44.38 | |
| | 10.000 | 76.82 | |
| | 30.000 | 99.88 | |
| 164 | 0.123 | <10 | |
| | 0.370 | 14.64 | |
| | 1.100 | 46.22 | |
| | 3.300 | 87.3 | |
| | 10.000 | 99.68 | |
| | 30.000 | 102.14 | 78.00 |
| 212 | 0.123 | <10 | |
| | 0.370 | <10 | |
| | 1.100 | <10 | |
| | 3.300 | 32.53 | |
| | 10.000 | 59.51 | |
| | 30.000 | 69.5 | |
| 367 | 0.123 | <10 | |
| | 0.370 | <10 | |
| | 1.100 | 23.67 | |
| | 3.300 | 58.55 | |
| | 10.000 | 86.14 | |
| | 30.000 | 101.6 | |
| 366 | 0.123 | <10 | |
| | 0.370 | <10 | |
| | 1.100 | 40.33 | |
| | 3.300 | 72.93 | |
| | 10.000 | 92.17 | |
| | 30.000 | 106.62 | |
| 368 | 0.123 | <10 | |
| | 0.370 | <10 | |
| | 1.100 | 17.39 | |
| | 3.300 | 54.46 | |
| | 10.000 | 77.77 | |
| | 30.000 | 86.75 | |
| 370 | 0.123 | <10 | |
| | 0.370 | <10 | |
| | 1.100 | <10 | |
| | 3.300 | <10 | |
| | 10.000 | 19.4 | |
| | 30.000 | 33.08 | |
| 369 | 0.123 | 54.86 | |
| | 0.370 | 83.46 | |
| | 1.100 | 96.02 | |
| | 3.300 | 97.1 | |
| | 10.000 | 110.73 | |
| | 30.000 | 93.94 | 28.50 |
| 372 | 0.123 | 65.28 | |
| | 0.370 | 91.27 | |
| | 1.100 | 104.8 | |
| | 3.300 | 108.35 | |
| | 10.000 | 108.6 | |
| | 30.000 | 106.29 | 5.87 |
| 373 | 0.123 | 31.82 | |
| | 0.370 | 68.9 | |
| | 1.100 | 86.98 | |
| | 3.300 | 97.07 | |
| | 10.000 | 102.4 | |
| | 30.000 | 104.95 | 18.30 |
| 371 | 0.123 | 86.78 | |
| | 0.370 | 108.97 | |
| | 1.100 | 109.96 | |
| | 3.300 | 112.93 | |
| | 10.000 | 108.07 | |
| | 30.000 | 109.68 | 7.35 |
| 375 | 0.123 | <10 | |
| | 0.370 | 10.25 | |
| | 1.100 | 28.46 | |
| | 3.300 | 57.38 | |
| | 10.000 | 78.95 | |
| | 30.000 | 86 | |
| 376 | 0.123 | 10.64 | |

TABLE IV-continued

| | HIV Protease FITC Assay | | |
|---|---|---|---|
| Compound of Example No. | HIV-1 Dose (uM) | HIV-1 Protease % Inhib | HIV-1 FITC KI (nM) |
| | 0.370 | 33.67 | |
| | 1.100 | 75.35 | |
| | 3.300 | 96.53 | |
| | 10.000 | 101.90 | |
| | 30.000 | 102.89 | 195.00 |
| 377 | 0.123 | <10 | |
| | 0.370 | 11.83 | |
| | 1.100 | 39.6 | |
| | 3.300 | 66.07 | |
| | 10.000 | 83.74 | |
| | 30.000 | 94.66 | 4.00 |
| | 0.123 | 92.9 | |
| | 0.370 | 107.27 | |
| | 1.100 | 114.54 | |
| | 3.300 | 114.03 | |
| | 10.000 | 107.37 | |
| | 30.000 | 101.29 | |
| 313 | 0.123 | 104.34 | |
| | 0.370 | 96.49 | |
| | 1.100 | 100.61 | |
| | 3.300 | 100.19 | |
| | 10.000 | 105.53 | |
| | 30.000 | 101.95 | 1.17 |
| 356 | 0.123 | 97.71 | |
| | 0.370 | 97.24 | |
| | 1.100 | 97.9 | |
| | 3.300 | 101.17 | |
| | 10.000 | 102.05 | |
| | 30.000 | 100.33 | 1.32 |
| 136 | 0.410 | 56.64 | |
| | 1.230 | 80.14 | |
| | 3.700 | 90.06 | |
| | 11.000 | 92.44 | |
| | 33.000 | 91.63 | |
| | 100.000 | 102.73 | 108.00 |
| 228 | | | 34.80 |
| 229 | 0.123 | 16.89 | |
| | 0.370 | 54.29 | |
| | 1.100 | 88.78 | |
| | 3.300 | 102.85 | |
| | 10.000 | 107.75 | |
| | 30.000 | 104.86 | 10.60 |
| | | | 11.90 |
| | | | 16.20 |
| 232 | 0.123 | 19.32 | |
| | 0.370 | 51.17 | |
| | 1.100 | 80.39 | |
| | 3.300 | 95.34 | |
| | 10.000 | 103.64 | |
| | 30.000 | 94.99 | 30.00 |
| 235 | 0.123 | 24.77 | |
| | 0.370 | 71.82 | |
| | 1.100 | 92.71 | |
| | 3.300 | 104.58 | |
| | 10.000 | 103.08 | |
| | 30.000 | 99.54 | 11.00 |
| 236 | | | 10.00 |
| | | | 8.00 |
| 237 | | | 60.00 |
| | | | 117.00 |
| 233 | | | 147.00 |
| | | | 180.00 |
| | | | 302.00 |
| 234 | | | 12.80 |
| | | | 13.00 |
| | | | 18.80 |
| 230 | | | 264.00 |
| | | | 280.00 |
| 231 | | | 109.00 |
| | | | 126.00 |
| 242 | 0.123 | <10 | |
| | 0.370 | <10 | |
| | 1.100 | 13.81 | |
| | 3.300 | 35.96 | |

TABLE IV-continued

| Compound of Example No. | HIV Protease FITC Assay | | |
|---|---|---|---|
| | HIV-1 Dose (uM) | HIV-1 Protease % Inhib | HIV-1 FITC KI (nM) |
| | 10.000 | 65.35 | |
| | 30.000 | 78.92 | |
| 386 | 0.123 | <10 | |
| | 0.370 | <10 | |
| | 1.100 | 14.33 | |
| | 3.300 | 35.35 | |
| | 10.000 | 64.45 | |
| | 30.000 | 96.28 | |
| 243 | 0.123 | <10 | |
| | 0.370 | <10 | |
| | 1.100 | <10 | |
| | 3.300 | 24.42 | |
| | 10.000 | 44.72 | |
| | 30.000 | 54.28 | |
| 238 | 0.123 | 30.5 | |
| | 0.370 | 76.39 | |
| | 1.100 | 96.26 | |
| | 3.300 | 99.93 | |
| | 10.000 | 115.66 | |
| | 30.000 | 115.42 | 13.40 |
| 239 | 0.123 | 69.55 | |
| | 0.370 | 88.01 | |
| | 1.100 | 98.34 | |
| | 3.300 | 102.72 | |
| | 10.000 | 107.4 | |
| | 30.000 | 100.72 | 2.20 |
| 287 | 0.123 | <10 | |
| | 0.370 | <10 | |
| | 1.100 | 36.69 | |
| | 3.300 | 64.32 | |
| | 10.000 | 92.75 | |
| | 30.000 | 106.21 | |
| 379 | 0.123 | <10 | |
| | 0.370 | 48.64 | |
| | 1.100 | 84.49 | |
| | 3.300 | 96.22 | |
| | 10.000 | 106.83 | |
| | 30.000 | 113.1 | 18.30 |
| 240 | 0.123 | 54.87 | |
| | 0.370 | 89.42 | |
| | 1.100 | 111.38 | |
| | 3.300 | 113.39 | |
| | 10.000 | 114.19 | 4.20 |
| | 30.000 | 109.5 | 5.00 |
| 241 | 0.123 | 81.78 | |
| | 0.370 | 91.77 | |
| | 1.100 | 98.65 | |
| | 3.300 | 101.51 | |
| | 10.000 | 110.04 | 1.32 |
| | 30.000 | 104.34 | 1.90 |
| 480 | 0.123 | <10 | |
| | 0.370 | <10 | |
| | 1.100 | <10 | |
| | 3.300 | 19.2 | |
| | 10.000 | 45.45 | |
| | 30.000 | 78.15 | |
| 388 | 0.123 | <10 | |
| | 0.370 | 42.8 | |
| | 1.100 | 76.04 | |
| | 3.300 | 96.45 | |
| | 10.000 | 98.23 | |
| | 30.000 | 93.72 | 21.70 |
| 389 | 0.123 | <10 | |
| | 0.370 | 21.15 | |
| | 1.100 | 58.02 | |
| | 3.300 | 78.74 | |
| | 10.000 | 96.38 | |
| | 30.000 | 98.74 | 46.20 |
| 380 | 0.123 | <10 | |
| | 0.370 | 21.48 | |
| | 1.100 | 57.18 | |
| | 3.300 | 82.52 | |
| | 10.000 | 103.26 | |
| | 30.000 | 107.7 | 87.90 |
| 384 | 0.123 | 12.21 | |
| | 0.370 | 47.4 | |
| | 1.100 | 79.24 | |
| | 3.300 | 92.88 | |
| | 10.000 | 102.72 | |
| | 30.000 | 101.92 | 24.10 |
| 381 | 0.123 | <10 | |
| | 0.370 | 24.08 | |
| | 1.100 | 62.33 | |
| | 3.300 | 80.42 | |
| | 10.000 | 99.85 | |
| | 30.000 | 96.7 | 39.10 |
| 385 | 0.123 | <10 | |
| | 0.370 | 48.52 | |
| | 1.100 | 89.46 | |
| | 3.300 | 103.6 | |
| | 10.000 | 107.38 | |
| | 30.000 | 106.71 | 12.40 |
| 398 | 0.123 | 10.47 | |
| | 0.370 | 40.87 | |
| | 1.100 | 74.23 | |
| | 3.300 | 91.47 | |
| | 10.000 | 105.24 | |
| | 30.000 | 105.17 | 41.50 |
| 397 | 0.123 | 35.71 | |
| | 0.370 | 92.92 | |
| | 1.100 | 105.15 | |
| | 3.300 | 108.84 | |
| | 10.000 | 116.15 | |
| | 30.000 | 112.72 | 7.30 |
| 393 | 0.123 | <10 | |
| | 0.370 | <10 | |
| | 1.100 | <10 | |
| | 3.300 | 37.51 | |
| | 10.000 | 66.29 | |
| | 30.000 | 89.76 | |
| 392 | 0.123 | <10 | |
| | 0.370 | <10 | |
| | 1.100 | 11.47 | |
| | 3.300 | 47.01 | |
| | 10.000 | 77.59 | |
| | 30.000 | 99.66 | |
| 282 | 0.123 | <10 | |
| | 0.370 | <10 | |
| | 1.100 | 10.56 | |
| | 3.300 | 43.22 | |
| | 10.000 | 65.32 | |
| | 30.000 | 96.32 | |
| 315 | 0.123 | 80.69 | |
| | 0.370 | 94.73 | |
| | 1.100 | 91.93 | |
| | 3.300 | 95.17 | |
| | 10.000 | 86.65 | |
| | 30.000 | 81.39 | 2.58 |
| 365B (First Title Compound) | 10.000 | 83.85 | |
| | 30.000 | 78.81 | |
| 365B (Second Title Compound) | 0.123 | 33.25 | |
| | 0.370 | 68.18 | |
| | 1.100 | 94.03 | |
| | 3.300 | 87.33 | |
| | 10.000 | 92.56 | |
| | 30.000 | 89.11 | |
| 365B (Third Title Compound) | 0.123 | 29.06 | |
| | 0.370 | 56.47 | |
| | 1.100 | 93.46 | |
| | 3.300 | 90.63 | |
| | 10.000 | 90.94 | |
| | 30.000 | 85.31 | 14.30 |
| 365C | 0.123 | 63.03 | |
| | 0.370 | 93.59 | |
| | 1.100 | 102.09 | |

TABLE IV-continued

| Compound of Example No. | HIV Protease FITC Assay | | |
|---|---|---|---|
| | HIV-1 Dose (uM) | HIV-1 Protease % Inhib | HIV-1 FITC KI (nM) |
| | 3.300 | 71.47 | |
| | 10.000 | 87.50 | |
| | 30.000 | 83.47 | 16.60 |
| 353 (Second Title Compound) | 0.123 | 61.39 | |
| | 0.370 | 92.71 | |
| | 1.100 | 102.79 | |
| | 3.300 | 110.06 | |
| | 10.000 | 113.06 | |
| | 30.000 | 107.2 | 2.40 |
| 350 | 0.123 | 22.25 | |
| | 0.370 | 64.26 | |
| | 1.100 | 82.19 | |
| | 3.300 | 98.33 | |
| | 10.000 | 102.02 | |
| | 30.000 | 101.46 | 6.60 |
| 351 | 0.123 | 11.21 | |
| | 0.370 | 49.28 | |
| | 1.100 | 76.6 | |
| | 3.300 | 93.86 | |
| | 10.000 | 97.8 | |
| | 30.000 | 95.76 | 16.40 |
| 354 | 0.123 | 71.38 | |
| | 0.370 | 86.43 | |
| | 1.100 | 96.07 | |
| | 3.300 | 100.46 | |
| | 10.000 | 103.33 | |
| | 30.000 | 108.2 | 1.45 |
| 383 | 0.123 | <10 | |
| | 0.370 | <10 | |
| | 1.100 | 28.86 | |
| | 3.300 | 72.98 | |
| | 10.000 | 90.2 | |
| | 30.000 | 94.63 | |
| 390 | 0.123 | <10 | |
| | 0.370 | <10 | |
| | 1.100 | 13.14 | |
| | 3.300 | 43.57 | |
| | 10.000 | 66.38 | |
| | 30.000 | 85.2 | |
| 391 | 0.123 | <10 | |
| | 0.370 | <10 | |
| | 1.100 | <10 | |
| | 3.300 | 28.32 | |
| | 10.000 | 59.13 | |
| | 30.000 | 84.2 | |
| 400 | 0.123 | 17.41 | |
| | 0.370 | 54.76 | |
| | 1.100 | 78.68 | |
| | 3.300 | 94.69 | |
| | 10.000 | 114.27 | |
| | 30.000 | 109.34 | 35.80 |
| 394 | 0.123 | 72.74 | |
| | 0.370 | 102 | |
| | 1.100 | 109.48 | |
| | 3.300 | 115.21 | |
| | 10.000 | 119.6 | |
| | 30.000 | 122.96 | 6.04 |
| 399 | 0.123 | <10 | |
| | 0.370 | 21.59 | |
| | 1.100 | 54.12 | 186.00 |
| 378 | 0.123 | 102.78 | |
| | 0.370 | 110.63 | |
| | 1.100 | 111.64 | |
| | 3.300 | 117.82 | |
| | 10.000 | 112.42 | |
| | 30.000 | 112.1 | 1.06 |
| 357 | 0.123 | 103.88 | |
| | 0.370 | 97.18 | |
| | 1.100 | 101.03 | |
| | 3.300 | 98.28 | |
| | 10.000 | 96.83 | |
| | 30.000 | 89.6 | 0.62 |
| 355 (First Title Compound) | 0.123 | 117.42 | |
| | 0.370 | 117.25 | |
| | 1.100 | 115.36 | |
| | 3.300 | 103.4 | |
| | 10.000 | 72.63 | |
| | 30.000 | 61.88 | 2.14 |
| 355 (Second Title Compound) | 0.123 | 112.03 | |
| | 0.370 | 110.58 | |
| | 1.100 | 107.13 | |
| | 3.300 | 109.56 | |
| | 10.000 | 110.07 | |
| | 30.000 | 108.3 | 1.06 |
| 374 | 0.123 | 121.27 | |
| | 0.370 | 121.33 | |
| | 1.100 | 131.15 | |
| | 3.300 | 124.56 | |
| | 10.000 | 129.21 | |
| | 30.000 | 127.57 | 1.30 |
| | | | .72 |
| 402 | 0.123 | 103.69 | |
| | 0.370 | 106.4 | |
| | 1.100 | 110.07 | |
| | 3.300 | 100.22 | |
| | 10.000 | 98.03 | |
| | 30.000 | 98.47 | 0.62 |
| 405 | 0.123 | 46.49 | |
| | 0.370 | 88.58 | |
| | 1.100 | 101.46 | |
| | 3.300 | 105.91 | |
| | 10.000 | 101.32 | |
| | 30.000 | 77.2 | 3.13 |
| 407 | 0.123 | 26.77 | |
| | 0.370 | 74.71 | |
| | 1.100 | 91.17 | |
| | 3.300 | 98.12 | |
| | 10.000 | 106.67 | |
| | 30.000 | 112.74 | 6.60 |
| 416 | 0.123 | 50.89 | |
| | 0.370 | 87.96 | |
| | 1.100 | 101.5 | |
| | 3.300 | 99.67 | |
| | 10.000 | 98.61 | |
| | 30.000 | 97.84 | 4.24 |
| 415 | 0.123 | 125.51 | |
| | 0.370 | 120.88 | |
| | 1.100 | 127.73 | |
| | 3.300 | 123.88 | |
| | 10.000 | 124.78 | |
| | 30.000 | 119.96 | 2.30 |
| 417 | 0.123 | 36.4 | |
| | 0.370 | 65.92 | |
| | 1.100 | 89.22 | |
| | 3.300 | 95.13 | |
| | 10.000 | 102.04 | |
| | 30.000 | 97.28 | 20.00 |
| 421 | 0.123 | 93.86 | |
| | 0.370 | 103.79 | |
| | 1.100 | 99.07 | |
| | 3.300 | 97.92 | |
| | 10.000 | 108.01 | |
| | 30.000 | 89.95 | 2.10 |
| 422 | 0.123 | 100.11 | |
| | 0.370 | 95.39 | |
| | 1.100 | 96.51 | |
| | 3.300 | 103 | |
| | 10.000 | 97.57 | |
| | 30.000 | 95.2 | 6.10 |
| 430 | 0.123 | 72.34 | |
| | 0.370 | 98.15 | |
| | 1.100 | 96.61 | |
| | 3.300 | 103.84 | |
| | 10.000 | 104.81 | |
| | 30.000 | 97.34 | 2.10 |

TABLE IV-continued

| Compound of Example No. | HIV Protease FITC Assay | | |
|---|---|---|---|
| | HIV-1 Dose (uM) | HIV-1 Protease % Inhib | HIV-1 FITC KI (nM) |
| 425 | 0.123 | 97.4 | |
| | 0.370 | 109.08 | |
| | 1.100 | 101.23 | |
| | 3.300 | 107.87 | |
| | 10.000 | 98.49 | |
| | 30.000 | 98.51 | 2.80 |
| 426 | 0.123 | 101.79 | |
| | 0.370 | 117.23 | |
| | 1.100 | 109.31 | |
| | 3.300 | 101.96 | |
| | 10.000 | 102.21 | |
| | 30.000 | 106.39 | 1.48 |
| 437 | 0.123 | 68.11 | |
| | 0.370 | 87.12 | |
| | 1.100 | 103.48 | |
| | 3.300 | 107.83 | |
| | 10.000 | 112.21 | |
| | 30.000 | 105.41 | 2.30 |
| 439 | 0.123 | 60.96 | |
| | 0.370 | 68.15 | |
| | 1.100 | 92.17 | |
| | 3.300 | 92.32 | |
| | 10.000 | 96.45 | |
| | 30.000 | 94.26 | 3.00 |
| 431 | 0.123 | 108.57 | |
| | 0.370 | 108.96 | |
| | 1.100 | 109.06 | |
| | 3.300 | 112.08 | |
| | 10.000 | 105.13 | |
| | 30.000 | 106.25 | 0.89 |
| 432 | 0.123 | 100.88 | |
| | 0.370 | 104.12 | |
| | 1.100 | 110.61 | |
| | 3.300 | 109.18 | |
| | 10.000 | 107.36 | |
| | 30.000 | 98.03 | 2.10, 1.65 |
| 433 | 0.123 | 102.86 | |
| | 0.370 | 109.29 | |
| | 1.100 | 103.83 | |
| | 3.300 | 104.14 | |
| | 10.000 | 109.18 | |
| | 30.000 | 108.26 | 2.24 |
| 427 | 0.123 | 94.23 | |
| | 0.370 | 92.79 | |
| | 1.100 | 91.17 | |
| | 3.300 | 89.97 | |
| | 10.000 | 89.6 | |
| | 30.000 | 81.91 | 0.65 |
| 428 | 0.123 | 86.35 | |
| | 0.370 | 84.04 | |
| | 1.100 | 86.49 | |
| | 3.300 | 87.09 | |
| | 10.000 | 87.93 | |
| | 30.000 | 84.18 | 3.33 |
| 153 | 1.000 | <10 | |
| | 10.000 | 34.04 | |
| | 100.000 | 79.57 | |
| | 100.000 | 115.36 | |
| 470 | 0.123 | <10 | |
| | 0.370 | <10 | |
| | 1.100 | 16.1 | |
| | 3.300 | 59.17 | |
| | 10.000 | 102.12 | |
| | 30.000 | 117.86 | |
| 471 | 0.123 | <10 | |
| | 0.370 | <10 | |
| | 1.100 | 37.55 | |
| | 3.300 | 75.61 | |
| | 10.000 | 101.69 | |
| | 30.000 | 110.33 | |
| 472 | 0.123 | <10 | |
| | 0.370 | <10 | |
| | 1.100 | <10 | |
| | 3.300 | 15.54 | |
| | 10.000 | 82.17 | |
| | 30.000 | 109.55 | |
| 473 | 0.123 | <10 | |
| | 0.370 | <10 | |
| | 1.100 | <10 | |
| | 3.300 | 14.38 | |
| | 10.000 | 73.58 | |
| | 30.000 | 86.82 | |
| 474 | 0.123 | <10 | |
| | 0.370 | <10 | |
| | 1.100 | <10 | |
| | 3.300 | 11.44 | |
| | 10.000 | 40.4 | |
| | 30.000 | 57.21 | |
| 475 | 0.123 | <10 | |
| | 0.370 | 11.78 | |
| | 1.100 | 27.92 | |
| | 3.300 | 84.09 | |
| | 10.000 | 103.25 | |
| | 30.000 | 110.38 | |
| 476 | 0.123 | <10 | |
| | 0.370 | <10 | |
| | 1.100 | 19.52 | |
| | 3.300 | 53.12 | |
| | 10.000 | 83.04 | |
| | 30.000 | 83.12 | |
| 408 | 0.123 | 38.41 | |
| | 0.370 | 70.06 | |
| | 1.100 | 88.91 | |
| | 3.300 | 98.46 | |
| | 10.000 | 91.65 | |
| | 30.000 | 106.63 | 14.00 |
| 409 | 0.123 | 65.09 | |
| | 0.370 | 90.48 | |
| | 1.100 | 102.43 | |
| | 3.300 | 103.09 | |
| | 10.000 | 100.83 | |
| | 30.000 | 107.68 | 3.30 |
| 411 | 0.123 | 71.13 | |
| | 0.370 | 79.36 | |
| | 1.100 | 98.46 | |
| | 3.300 | 103.8 | |
| | 10.000 | 106.99 | |
| | 30.000 | 106.23 | 2.50 |
| 412 | 0.123 | 37.75 | |
| | 0.123 | 37.75 | |
| | 0.370 | 69.16 | |
| | 1.100 | 92.01 | |
| | 3.300 | 102.09 | |
| | 10.000 | 99.04 | |
| | 30.000 | 102.09 | 9.20 |
| 413 | 0.123 | <10 | |
| | 0.370 | 17.43 | |
| | 1.100 | 43.1 | |
| | 3.300 | 77.74 | |
| | 10.000 | 95.18 | |
| | 30.000 | 92.68 | 104.00 |
| 414 | 0.123 | 62.73 | |
| | 0.370 | 85.78 | |
| | 1.100 | 103.16 | |
| | 3.300 | 105.93 | |
| | 10.000 | 104.38 | |
| | 30.000 | 109.61 | 3.50 |
| 429 | 0.123 | 88.58 | |
| | 0.370 | 98.23 | |
| | 1.100 | 99.86 | |
| | 3.300 | 102.76 | |
| | 10.000 | 107.47 | |
| | 30.000 | 107.95 | 9.25 |
| 418 | 0.123 | 81.8 | |
| | 0.370 | 87.53 | |
| | 1.100 | 98.6 | |
| | 3.300 | 110.12 | |
| | 10.000 | 119.01 | |

TABLE IV-continued

| Compound of Example No. | HIV Protease FITC Assay | | |
|---|---|---|---|
| | HIV-1 Dose (uM) | HIV-1 Protease % Inhib | HIV-1 FITC KI (nM) |
| | 30.000 | 122.57 | 10.90 |
| 481 | 0.123 | <10 | |
| | 0.370 | 118.23 | |
| | 1.100 | 51.2 | |
| | 3.300 | 85.33 | |
| | 10.000 | 98.05 | |
| | 30.000 | 106.59 | 182.00 |
| 482 | 0.123 | <10 | |
| | 0.370 | <10 | |
| | 1.100 | <10 | |
| | 3.300 | 19.96 | |
| | 10.000 | 63.22 | |
| | 30.000 | 92.61 | |
| 483 | 0.123 | <10 | |
| | 0.370 | 44.75 | |
| | 1.100 | 73.2 | |
| | 3.300 | 85.22 | |
| | 10.000 | 69.53 | |
| | 30.000 | 76.68 | 33.00 |
| 484 | 0.123 | <10 | |
| | 0.370 | <10 | |
| | 1.100 | <10 | |
| | 3.300 | 17.74 | |
| | 10.000 | 37.21 | |
| | 30.000 | 51.57 | |
| 485 | 0.123 | <10 | |
| | 0.370 | <10 | |
| | 1.100 | <10 | |
| | 3.300 | <10 | |
| | 10.000 | 13.06 | |
| | 30.000 | 54.18 | |
| 486 | 0.123 | <10 | |
| | 0.370 | 40 | |
| | 1.100 | 73.96 | |
| | 3.300 | 97.5 | |
| | 10.000 | 125.88 | |
| | 30.000 | 109.36 | 55.00 |

We claim:

1. A method of inhibiting a retrovirus in a mammalian cell infected with said retrovirus which comprises treating said cell with an effective amount of a compound of the formula I

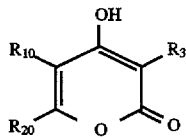     I wherein $R_{10}$ and $R_{20}$ taken together are a) 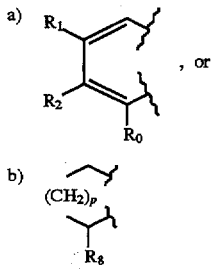   II b) 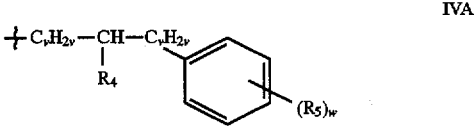   III wherein $R_0$ is —H;
wherein $R_1$ is
a) —H,
b) —OCH$_n$H$_{2n+1}$,
c) —F,
d) —NH$_2$—, or
e) —O—C$_n$H$_{2n}$Het;
wherein $R_2$ is
a) —H,
b) —OC$_n$H$_{2n+1}$,
c) —CF$_3$,
d) —O—C$_n$H$_{2n}$—CH=CH$_2$, or
e) —O—C$_n$H$_{2n}$—Het;
or wherein $R_1$ and $R_2$ taken together are phenyl;
or wherein $R_0$ and $R_2$ taken together are phenyl;
wherein $R_3$ is a) 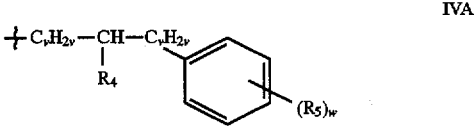   IVA b) diphenylethyl-,
c) diphenylethenyl-,
d) —CH—(C$_3$–C$_6$ cycloalkyl)$_2$,
e) -5,6,7,8,9-tetrahydro-5H-benzocycloheptenyl,
f) -1,2,3,4-tetrahydro-naphthalenyl substituted by one (1) or two (2) —OC$_n$H$_{2n+1}$ or —CH$_3$,
g) —CH(C$_n$H$_{2n+1}$)—C(O)—O—C$_n$H$_{2n+1}$,
h) —CH(CH$_2$-phenyl)$_2$,
i) —C$_v$H$_{2v}$—CH(R$_4$)—C$_v$H$_{2v}$—Het—R$_5$,
j) —C$_v$H$_{2v}$—CH(R$_4$)—C$_v$H$_{2v}$—Het,
k) diphenylmethyl-,
l) diphenylpropyl-, or
m) phenylcyclobutyl-;
wherein $R_4$ is
a) —C$_m$H$_{2m+1}$,
b) —CH$_2$—C(O)—O—C$_n$H$_{2n+1}$,
c) —C$_3$–C$_6$ cycloalkyl,
d) —C$_n$H$_{2n}$—C$_3$–C$_6$ cycloalkyl, or
e) C$_2$–C$_6$ alkenyl;
wherein each $R_5$ is independently
a) —H,
b) —NH$_2$,
c) —C(O)—C$_n$H$_{2n+1}$,
d) (o-) or (m-) —O—C$_n$H$_{2n}$—CH=CH$_2$,
e) —C$_1$-C$_5$ alkoxy substituted on each carbon atom by zero (0) or one (1) hydroxy,
f) —O—C(O)—C$_n$H$_{2n+1}$,
g) —Br,
h) —CN,
i) —C$_m$H$_{2m}$—X$_1$—C$_t$H$_{2t+1}$,
j) —X$_1$—C$_n$H$_{2n}$-halo,
k) —X$_1$—C$_n$H$_{2n}$—NH$_2$,
l) —X$_1$—C$_n$H$_{2n}$—NH—C(O)—O—C$_n$H$_{2n+1}$
m) —X$_1$—C$_n$H$_{2n}$—CH(NH—C(O)—O—C$_n$H$_{2n+1}$)C(O)—O—C$_n$H$_{2n+1}$,
n) —X$_1$—C$_m$H$_{2m}$—CH(NH—C(O)—O—C$_n$H$_{2n+1}$)C$_n$H$_{2n}$—Het,
o) —X$_1$—C$_n$H$_{2n}$—CH(NH$_2$)COOH,
p) —X$_1$—C$_n$H$_{2n}$—C(O)—O—C$_n$H$_{2n+1}$,
q) —X$_1$—C$_n$H$_{2n}$—C$_3$–C$_6$ cycloalkyl,
r) —C$_m$H$_{2m}$—X$_1$—C$_m$H$_{2m}$-aryl,
s) —X$_1$—C$_m$H$_{2m}$—O-aryl, t) $-C_mH_{2m}-X_1-C_mH_{2m}-O-C_nH_{2n+1}$,
u) $-C_mH_{2m}-X_1-C_mH_{2m}-Het$,
v) $-X_1-C_nH_{2n}-C(O)-Het$,
w) $-X_1-C_nH_{2n}-C(O)-NH-C_nH_{2n}-Het$,
x) $-X_1-C_nH_{2n}-S-Het$,
y) $-C_mH_{2m}-X_1-O-C_nH_{2n}-aryl$,
z) $-C_mH_{2m}-X_1-O-C_nH_{2n}-Het$,
a1) $-X_1-H$,
b1) $-X_1-CH=CH_2$,
c1) $-X_1-CH=CH-aryl$,
d1) $-X_1-N(R_{40})_2$,
e1) $-X_1-C_nH_{2n}-phthalimido$,
f1) $-X_1-(penta-fluoro)-phenyl$,
g1) $-X_1-C_nH_{2n}-bicyclo[2.2.1]heptane$,
h1) $-C_u-H_{2u}-R_{30}$,
i1) $-N=C-(NH-CH(C_nH_{2n+1})_2)_2$,
j1) $-NH-P(O)(R_9)-aryl$,
k1) $-NH-P(O)(O-R_{11})-aryl$,
l1) $-NH-C(S)-NH-R_{42}$, or
m1) $-NH-C(S)-CH_2-R_{42}$;
wherein $X_1$ is
 a) $-NH-C(O)-$,
 b) $-C(O)-NH-$,
 c) $-NH-SO_2-$,
 d) $-SO_2-NH-$,
 e) $-NH-SO_2-NH-$,
 f) $-C(O)-O-$,
 g) $-O-C(O)-$,
 h) $-N(C_nH_{2n}-aryl)-C(O)-$,
 i) $-NH-C(O)-NH-$,
 j) $-N(C_nH_{2n}-aryl)-SO_2-$, or
 k) $-N(C_mH_{2m}-C_nH_{2n+1})-SO_2-$;
wherein m is zero (0) to five (5) inclusive;
wherein n is one (1) to five (5) inclusive;
wherein p is one (1) to eight (8) inclusive;
wherein q is zero (0) to five (5) inclusive;
wherein r is one (1) to eight (8) inclusive;
wherein s is one (1) to six (6) inclusive;
wherein t is one (1) to twelve (12) inclusive;
wherein u is two (2) to six (6) inclusive;
wherein v is zero (0) to two (2) inclusive;
wherein w is one (1) or two (2);
wherein aryl is
 a) phenyl substituted by zero (0) to three (3) $R_6$,
 b) naphthyl substituted by zero (0) to three (3) $R_6$, or
 c) biphenyl substituted by zero (0) to three (3) $R_6$;
wherein Het is a 5-, 6- or 7-membered saturated or unsaturated ring containing from one (1) to three (3) heteroatoms selected from the group consisting of nitrogen, oxygen and sulfur; and including any bicyclic group in which any of the above heterocyclic rings is fused to a benzene ring or another heterocycle; and the ring may be connected through a carbon or secondary nitrogen in the ring or an exocyclic nitrogen; and if chemically feasible, the nitrogen and sulfur atoms may be in the oxidized forms; and if chemically feasible, the nitrogen atom may be in the protected form; and substituted by zero (0) to three (3) $R_7$;
wherein $R_6$ and $R_7$ are independently
 a) $-C_1-C_5$ alkyl, substituted by zero (0) to three (3) halo or substituted on each carbon atom by zero (0) or one (1) hydroxy,
 b) $-OH$,
 c) $-C_1-C_5$ alkyl-OH,
 d) $-O-C_1-C_5$ alkyl substituted by zero (0) to three (3) halo or substituted on each carbon atom by zero (0) or one (1) hydroxy,
 e) $-O-C_2-C_7$ alkenyl substituted by zero (0) or one (1) hydroxy,
 f) halo,
 g) $-NH_2$,
 h) $-NH_2-C_1-C_5$ alkyl,
 i) mono- or di-$C_1-C_5$ alkylamino,
 j) $-NH-OH$,
 k) $-N(C_nH_{2n}-OH)_2$,
 l) $-C(O)-NH_2$,
 m) $-C(O)-C_1-C_5$ alkyl,
 n) $-CHO$,
 o) $-COOH$,
 p) $-COX_2$,
 q) nitro,
 r) $-CN$,
 s) $-SO_3H$,
 t) $-SO_2NH_2$,
 u) $-SO_2-R_{42}$,
 v) $-NR_{40}-SO_2-R_{42}$,
 w) $-SO_2-NR_{40}R_{41}$,
 x) $-O[C_nH_{2n}O]_qC_nH_{2n+1}$,
 y) $-C(O)-O-C_nH_{2n+1}$,
 z) $-NR_{40}-C(O)-C_nH_{2n+1}$,
 a1) $-C_nH_{2n}-NR_{40}-C(O)-R_{41}$,
 b1) $-N=N-phenyl$ substituted by zero (0) or one (1) $-N(C_nH_{2n+1})_2$,
 c1) isoxazolyl,
 d1) pyridinyl,
 e1) $-X_3-C_uH_{2u}-R_{30}$,
 f1) morpholino,
 g1) piperidino,
 h1) piperazino,
 i1) $-NR_{40}R_{41}$,
 j1) $-OR_{40}$, k1) 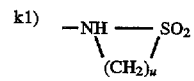

l1) $-C_nH_{2n}-O-C_nH_{2n}-OC_nH_{2n+1}$,
 m1) $-N-methyl-piperazino$,
 n) $-SO_2-morpholino$,
 o1) $-SO_2-piperazino$,
 p1) $-SO_2-N-methyl-piperazino$,
 q1) $-SO_2-piperidino$, or
 r1) $-NR_{40}-C(O)-C_nH_{2n}-O-R_{41}$;
wherein $X_2$ is $-NR_{40}R_{41}$;
wherein $X_3$ is
 a) $-O-$,
 b) $-CH_2-O-$,
 c) $-SO_2NR_{40}-$,
 d) $-NR_{40}SO_2-$,
 e) $-C(O)-$,
 f) $-C(O)NR_{40}-$, g) —NR$_{40}$C(O), or h) —NR$_{40}$—;

wherein R$_8$ is a) —H, b) —C$_n$H$_{2n}$-phenyl substituted by zero (0) to three (3) R$_6$, c) —C$_n$H$_{2n}$-Het, d) —C$_n$H$_{2n}$—C$_3$–C$_6$ cycloalkyl, e) —C$_r$—H$_{2r+1}$, f) —C$_n$—H$_{2n}$—CH=CH$_2$, g) —C$_S$H$_{2S+1}$ substituted by one (1) or two (2) hydroxy, h) —CH$_2$-epoxide, i) —C$_n$H$_{2n}$-oxiranyl, j) —(C$_n$H$_{2n}$—O)$_n$—C$_n$H$_{2n+1}$, k) —C(O)—C$_S$H$_{2S+1}$, or l) —CH(OH)—C$_3$–C$_6$ cycloalkyl;

wherein R$_9$ is a) C$_1$–C$_4$ alkyl, or b) aryl;

wherein R$_{11}$ is a) —H, b) —C$_1$–C$_4$ alkyl, c) aryl, or d) pharmaceutically acceptable salts;

wherein R$_{12}$ is a) C$_1$–C$_4$ alkyl, b) C$_1$–C$_3$ alkoxy, c) dimethylamino, d) diethylamino, e) CF$_3$, f) CN, g) halo, h) —NH$_2$, i) —OH, j) —SO$_2$—NH$_2$, or k) —C(O)—NH$_2$;

wherein R$_{30}$ is a) morpholino, b) piperidino, c) piperazino, d) —NR$_{40}$R$_{41}$, e) —OR$_{40}$,

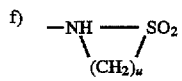

g) —N-methyl-piperazino, or h) halo;

wherein R$_{40}$ and R$_{41}$ are independently a) —H, b) —C$_1$–C$_4$ alkyl, c) phenyl substituted by zero (0) to three (3) R$_{12}$, or d) —C$_n$H$_{2n}$-phenyl substituted by zero (0) to three (3) R$_{12}$;

wherein R$_{42}$ is a) C$_1$–C$_4$ alkyl, b) phenyl substituted by zero (0) to three (3) R$_{12}$, or c) —C$_n$H$_{2n}$-phenyl substituted by zero (0) to three (3) R$_{12}$;

provided that:

1) when R$_{10}$ and R$_{20}$ taken together are the moiety of formula II, and R$_1$ and R$_2$ are independently —H, —F, or —OC$_n$H$_{2n+1}$, and R$_3$ is the moiety of formula IVA, and R$_4$ is —C$_m$H$_{2m+1}$ or cyclohexyl, then R$_5$ is other than —H, —Br or —OC$_n$H$_{2n+1}$;

2) when R$_5$ is —C$_m$H$_{2m}$—X$_1$—O—C$_n$H$_{2n}$-aryl, —C$_m$H$_{2m}$—X$_1$—O—C$_n$H$_{2n}$—Het, or X$_1$—N(R$_{40}$)$_2$, X$_1$ is not —C(O)—NH—, —NHSO$_2$—, —SO$_2$—NH—, —NH—SO$_2$—NH—, —C(O)—O—, —NH—C(O)—NH—, —N(C$_n$H$_{2n}$-aryl)—SO$_2$—;

3) when R$_5$ is —X$_1$—C$_m$H$_{2m}$—O-aryl or —C$_m$H$_{2m}$—X$_1$—C$_m$—H$_{2m}$—O—C$_n$H$_{2n+1}$, and m is zero (0), then X$_1$ is not —C(O)—NH—, —NH—SO$_2$—, —SO$_2$—NH—, —NH—SO$_2$—NH—, —C(O)—O—, —NH—C(O)—NH—, —N—(CH$_n$H$_{2n}$-aryl)—SO$_2$—, or —N(C$_m$H$_{2m}$—C$_n$H$_{2n+1}$)—SO$_2$—;

4) R$_4$ in the moiety of formula IVA is C$_2$–C$_6$ alkenyl only when R$_{10}$ and R$_{20}$ taken together are the moiety of formula III;

5) R$_3$ is diphenylethyl, diphenylmethyl, diphenylpropyl, diphenylethenyl or phenylcyclobutyl, only when R$_{10}$ and R$_{20}$ taken together are the moiety of formula III; and 6) when R$_{10}$ and R$_{20}$ taken together are the moiety of formula II, and R$_1$ and R$_2$ are independently —H, —F, —OC$_n$H$_{2n+1}$ or —NH$_2$, R$_3$ is other than —CH(C$_n$H$_{2n+1}$)—C(O)—O—C$_n$H$_{2n+1}$;

or a pharmaceutically acceptable salts thereof.

2. A compound of formula 1 as defined in claim 1, with the additional proviso that:

7) when R$_{10}$ and R$_{20}$ taken together are a moiety of formula II and R$_0$, R$_1$ and R$_2$ are each H, then R$_3$ is neither 5-(C$_{1-3}$ alkoxy)-1,2,3,4-tetrahydro-1-naphthenyl nor a moiety of formula IVA when v is zero, w is one, R$_5$ is H or methoxy, and R$_4$ is —CH$_2$—COO(C$_{1-3}$ alkyl) and 8) when R$_{10}$ and R$_{20}$ taken together are a moiety of formula II and R$_0$, R$_1$ and R$_2$ are each H, then R$_3$ is other than 3-methylene-4-hydroxybenzopyran-2-one.

3. The compound of claim 2 wherein R$_{10}$ and R$_{20}$ taken together are the moiety of formula III and R$_3$ is the moiety of formula IV.

4. The compound of claim 2 wherein R$_{10}$ and R$_{20}$ taken together are the moiety of formula II wherein R$_0$ is H, R$_1$ is H or —OC$_n$H$_{2n+1}$ and R$_2$ is H or —OC$_n$H$_{2n+1}$;

wherein R$_3$ is

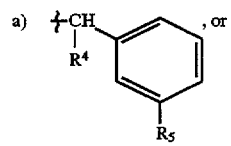

b) -5,6,7,8,9-tetrahydro-5H-benzocycloheptenyl;

wherein R$_4$ is a) -cyclopropyl, or b) C$_m$H$_{2m+1}$;

wherein R$_5$ is a) —H, b) —X$_1$C$_n$H$_{2n}$—NH$_2$, c) —X$_1$—C$_n$H$_{2n}$—NH—C(O)—O—C$_n$H$_{2n+1}$, d) —X$_1$—C$_n$H$_{2n}$—CH(NH$_2$)COOH, e) —X$_1$—C$_n$H$_{2n}$-aryl, or f) —X$_1$—C$_m$H$_{2m}$—Het;

wherein X₁ is —NH—C(O)—;
wherein m is two (2) to four (4), inclusive;
wherein n is one (1) to four (4), inclusive.

5. The compound of claim 2 selected from:

3-(Cyclopropylphenylmethyl)-4-hydroxycoumarin,
3-(2-Cyclohexyl-1-phenylethyl)-4-hydroxycoumarin,
Coumarin, 4-hydroxy-3-[1-(4-propionylphenyl)propyl]-,
Coumarin, 7-trifluoromethyl-4-hydroxy-3-(1-phenylpropyl)-,
Coumarin, 6-amino-4-hydroxy-3-(1-phenylpropyl)-,
Coumarin, 4-hydroxy-3-[1-[4-(2,3-dihydroxy)propoxyphenyl]propyl]-,
Coumarin, 3-[1-(3-cyanophenyl)propyl]-4-hydroxy-,
2H-Naphtho[1,2-b]pyran-2-one, 4-hydroxy-3-(1-phenylpropyl)-,
Coumarin, 3-[1-(3-cyanophenyl)ethyl]-4-hydroxy-,
Coumarin, 3-[1-(3-aminophenyl)propyl]-4-hydroxy-, monohydrochloride,
4-Hydroxy-3-[α-tert-butyloxycarbonylmethyl]benzylcoumarin,
3-(1'-(3-Allyloxyphenyl)propyl)-4-hydroxycoumarin,
3-(1'-(3-((2,3-dihydroxy)propyloxy)phenyl)propyl)-4-hydroxycoumarin,
3-(1'-(4-Acetoxyphenyl)propyl)4-hydroxycoumarin,
3-Cyclopropylphenylmethyl-4-hydroxy-7-methoxy coumarin,
3-(1'-(2-Acetoxyphenyl)propyl)-4-hydroxycoumarin,
3-(1'-(2-Allyloxyphenyl)propyl)-4-hydroxycoumarin,
4-Hydroxy-3-(5-6,7,8,9-tetrahydro-5H-benzocycloheptenyl)-coumarin,
Coumarin, 3-[1-[3-[[[(2-benzimidazolyl)methyl]amino]carbonyl]phenyl]ethyl]-4-hydroxy-,
Coumarin, 4-hydroxy-3-[1-[3-[[[(2-pyridinyl)methyl]amino]carbonyl]phenyl]ethyl]-,
Coumarin, 4-hydroxy-3-[1-[3-[[(phenylmethyl)amino]carbonyl]phenyl]ethyl]-,
Benzamide, 3-[1-(4-hydroxy-2-oxo-2H-1-benzopyran-3-yl)ethyl]-N-[2-methyl-1-[[(2-pyridinylmethyl)amino]carbonyl]butyl]-,
4-Hydroxy-3-[1-[3-[[[(1,1-dimethylethoxycarbonyl)methyl]amino]carbonyl]phenyl]ethyl]-coumarin,
Coumarin, 3-[1-[3-[(butylamino)carbonyl]phenyl]ethyl]-4-hydroxy-,
Coumarin, 4-hydroxy-3-[1-[3-[[[(4-morpholino)carbonyl]methyl]amino]carbonyl]phenyl]ethyl]-,
Coumarin, 3-[1-[3-[[[[[(2-benzimidazolyl)methyl]amino]carbonyl]methyl]amino]carbonyl]phenyl]ethyl]-4-hydroxy-,
Coumarin, 4-hydroxy-3-[1-[3-[[(1-naphthoxymethyl)carbonyl]amino]phenyl]propyl]-,
Carbamic acid, [1-[[[3-[1-(4-hydroxy-2-oxo-2H-1-benzopyran-3-yl)propyl]phenyl]amino]carbonyl]-2-methylpropyl]-, 1,1-dimethylethyl ester,
Coumarin, 4-hydroxy-3-[1-[3-[[[[(1,1-dimethylethoxycarbonyl)amino]methyl]carbonyl]amino]phenyl]propyl]-,
4-Hydroxy-3-[1-[3-[(1-oxo-3-phenylpropyl)amino]phenyl]propyl]-coumarin,
Coumarin, 4-hydroxy-3-[1-[3-[(1-oxopentyl)amino]phenyl]propyl]-,
Coumarin, 4-hydroxy-3-[1-[3-[[(2-pyridinyl)carbonyl]amino]phenyl]propyl]-,
Coumarin, 3-[1-[3-[[(aminomethyl)carbonyl]amino]phenyl]propyl]-4-hydroxy-, trifluoroacetate (salt),
Coumarin, 4-hydroxy-3-[1-[3-[[1-oxo-3-methyl-3-[(1,1-dimethylethoxycarbonyl)amino]butyl]amino]phenyl]propyl]-,
4-Hydroxy-3-[1-[3-[[3-[(1,1-dimethylethoxycarbonyl)amino]-1-oxopropyl]amino]phenyl]propyl]-coumarin,
Coumarin, 3-[1-[3-[(3-amino-3-methyl-1-oxobutyl)amino]phenyl]propyl]-4-hydroxy-, trifluoroacetate (salt),
3-[1-[3-[(3-Amino-1-oxopropyl)amino]phenyl]propyl]-4-hydroxy-coumarin, trifluoroacetate (salt),
Coumarin, 4-hydroxy-3-[1-[3-[(1-oxo-3-phenylpentyl)amino]phenyl]propyl]-,
Coumarin, 4-hydroxy-3-[1-[3-[[4-[(1,1-dimethylethoxycarbonyl)amino]-1-oxobutyl]amino]phenyl]propyl]-,
L-Glutamine, N2-[(1,1-dimethylethoxy)carbonyl]-N-[3-[1-(4-hydroxy-2-oxo-2H-1-benzopyran-3-yl)propyl]phenyl]-, 1,1-dimethylethyl ester,
L-Glutamine, N-[3-[1-(4-hydroxy-2-oxo-2H-1-benzopyran-3-yl)propyl]phenyl]-, mono (trifluoroacetate) (salt),
Coumarin, 4-hydroxy-3-[1-[3-[(1-oxo-4-phenylbutyl)amino]phenyl]propyl]-,
Coumarin, 4-hydroxy-3-[1-[3-[(1-oxo-5-phenylpentyl)amino]phenyl]propyl]-,
Coumarin, 4-hydroxy-3-[1-[3-[[(phenylmethyl)carbonyl]amino]phenyl]propyl]-,
Coumarin, 3-[1-[3-[(3-cyclohexyl-1-oxopropyl)amino]phenyl]propyl]4-hydroxy-,
Coumarin, 4-hydroxy-7-methoxy-3-[1-[3-[(1-oxo-3-phenylpropyl)amino]phenyl]propyl],
Coumarin, 4-hydroxy-3-[1-[3-[[3-[(1,1-dimethylethoxycarbonyl)amino]-1-oxopropyl]amino]phenyl]propyl]-7-methoxy-,
1-Pyrrolidinecarboxylic acid, 2-[[[3-[1-(4-hydroxy-2-oxo-2H-1-benzopyran-3-yl) propyl]phenyl]amino]carbonyl]-, 1,1-dimethylethyl ester,
Carbamic acid, [2-[[3-[1-(4-hydroxy-2-oxo-2H-1-benzopyran-3-yl)propyl]phenyl]amino]-1-methyl-2-oxoethyl]-, 1,1-dimethylethyl ester,
Propanamide, 2-amino-N-[3-[1-(4-hydroxy-2-oxo-2H-1-benzopyran-3-yl)propyl]phenyl]-, mono (trifluoroacetate) (salt),
Coumarin, 4-hydroxy-3-[1-[3-[[3-(4-hydroxyphenyl)-1-oxopropyl]amino]phenyl]propyl]-,
Coumarin, 4-hydroxy-3-[1-[3-[[3-(1H-indol-1-yl)-1-oxopropyl]amino]phenyl]propyl],
Coumarin, 4-hydroxy-3-[1-[3-[[3-(1-naphthyl)-1-oxopropyl]amino]phenyl]propyl]-,
4-Hydroxy-3-(1-(6-methoxy)-1,2,3,4-tetrahydronaphthyl)-coumarin,
4-Hydroxy-3-(1-(7-methoxy)-1,2,3,4-tetrahydronaphthyl)-coumarin,
Coumarin, 3-[1-[3-[[3-[(2-benzothiazolyl)thio]-1-oxopropyl]amino]phenyl]propyl]4-hydroxy-,
3-(Dicyclopropyl)methyl-4-hydroxycoumarin,
Coumarin, 7-(allyloxy)-3-(.alpha.-ethylbenzyl)4-hydroxy-,
Coumarin, 3-[.alpha.-ethyl-[[[2-(indol-3-yl)ethyl]carbonyl]amino]benzyl]-4-hydroxy-, Coumarin, 3-[bis(cyclopropyl)methyl]-4-hydroxy-7-methoxy-, Ethenesulfonic acid (3-(1-(4-hydroxy-2-oxo-2H-chromen-3-yl)-propyl)-phenyl)-amide; or [2-[[[3-[1-(4-hydroxy-2-oxo-2H-1-benzopyran-3-yl)propyl]phenyl]amino]sulfonyl]ethenyl]-, Ethanesulfonic acid (3-(1-(4-hydroxy-2-oxo-2H-chromen-3-yl)-propyl)-phenyl)-amide; or [2-[[[3-[1-(4-hydroxy-2-oxo-2H-1-benzopyran-3-yl)propyl]phenyl]amino]sulfonyl]ethyl]-, 2-(1,3-Dioxo-1,3-dihydro-isoindol-2-yl)-ethanesulfonic acid(3-(1-(4-hydroxy-2-oxo-2H-chromen-3-yl)-propyl)-phenyl)amide; or [2-[[[3-[1-(4-hydroxy-2-oxo-2H-1-benzopyran-3-yl)propyl]phenyl]amino]sulfonyl] ethyl]-phthalimido]-, and 2-(N-t-butyloxycarbonyl-amino)-ethanesulfonic acid (3-(1-(4-hydroxy-2-oxo-2H-chromen-3-yl)-propyl)-phenyl)-amide; or Carbamic acid, [2-[[[3-[1-(4-hydroxy-2-oxo-2H-1-benzopyran-3-yl)propyl]phenyl] amino]sulfonyl]ethyl]-, 1,1-dimethylethyl ester.

6. The compound of claim 4 selected from 3-(Cyclopropylphenylmethyl)-4-hydroxycoumarin, Coumarin, 4-hydroxy-3-[1-[3-[[[[(1,1-dimethylethoxycarbonyl)amino]methyl]carbonyl] amino]phenyl]propyl]-, Coumarin, 3-[1-[3-[[(aminomethyl)carbonyl]amino] phenyl]propyl]4-hydroxy-, trifluoroacetate (salt), 4-Hydroxy-3-(5-6,7,8,9-tetrahydro-5H-benzocycloheptenyl)-coumarin, Coumarin, 4-hydroxy-3-[1-[3-[[4-[(1,1-dimethylethoxycarbonyl)amino]-1-oxobutyl]amino] phenyl]propyl]-, L-Glutamine, N-[3-[1-(4-hydroxy-2-oxo-2H-1-benzopyran-3-yl)propyl]phenyl]-, mono (trifluoroacetate) (salt), 3-Cyclopropylphenylmethyl-4-hydroxy-7-methoxy coumarin, Coumarin, 4-hydroxy-7-methoxy-3-[1-[3-[(1-oxo-3-phenylpropyl)amino]phenyl]propyl]-, Coumarin, 4-hydroxy-3-[1-[3-[[3-(1H-indol-1-yl)-1-oxopropyl]amino]phenyl]propyl]-, Coumarin, 3-(.alpha.-ethylbenzyl)-4-hydroxy-7-(1-methylethoxy)-, 4-Hydroxy-3-[1-[3-[[3-[(1,1-dimethylethoxycarbonyl) amino]-1-oxopropyl]amino]phenyl]propyl]-coumarin, Coumarin, 4-hydroxy-3-[1-[3-[[3-[(1,1-dimethylethoxycarbonyl)amino]-1-oxopropyl]amino] phenyl]propyl]-7-methoxy-, Carbamic acid, [2-[[3-[1-(4-hydroxy-2-oxo-2H-1-benzopyran-3-yl)propyl]phenyl]amino]-1-methyl-2-oxoethyl]-, 1,1-dimethylethyl ester, Propanamide, 2-amino-N-[3-[1-(4-hydroxy-2-oxo-2H-1-benzopyran-3-yl)propyl]phenyl]-, mono (trifluoroacetate) (salt), and Coumarin, 7-ethoxy-3-(.alpha.-ethylbenzyl)4-hydroxy-.

7. A compound selected from

4-Hydroxy-3-(2-naphthylmethyl)coumarin, 3-(1-(4-Ethylphenyl)-butyl)-4-hydroxycoumarin, Coumarin, 4-hydroxy-3-[1-(3-methylphenyl)butyl]-, Coumarin, 4-hydroxy-3-[1-(3-methoxyphenyl)propyl]-, Coumarin, 7-methoxy-3-(.alpha.-propylbenzyl)4-hydroxy-, 3-(1'-(2-Methoxyphenyl)propyl)4-hydroxycoumarin, 3-(α,α-Dimethylbenzyl)4-hydroxy coumarin, 4-Hydroxy-7-(2-morpholin4-yl-ethoxy)-3-(1-phenyl-propyl)-chromen-2-one, 4-Hydroxy-3-(1-phenyl-cyclopropyl)-chromen-2-one, N-(2-Hydroxy-indan-1-yl)-3-(1-(4-hydroxy-2-oxo-2H-chromen-3-yl)-propyl)-benzamide, 3-(1-Benzyl-propyl)-4-hydroxy-chromen-2-one, 3-(1-Benzyl-3-phenyl-propyl)4-hydroxy-chromen-2-one, 3-(1-Benzyl-2-phenyl-ethyl)4-hydroxy-chromen-2-one, 3-(1-Benzyl-butyl)-4-hydroxy-chromen-2-one, N-(1H-B enzoimidazol-2-ylmethyl)-3-(1-(4-hydroxy-2-oxo-2H-chromen-3-yl)-propyl)-benzamide, 3-(1-(4-Hydroxy-2-oxo-2H-chromen-3-yl)-propyl)-N-(2-methyl-1-(pyridin-2-ylmethylcarbomoyl)-butyl)-benzamide, Acetic acid 4-(1-(4-Hydroxy-2-oxo-2H-chromen-3-yl)-1-methyl-ethyl)-phenylester, 4-Hydroxy-7-(2-(2-methoxy-ethoxy)-ethoxy)-3-(1-phenyl-propyl)-chromen-2-one, 3-(2,2-Dimethyl-1-phenyl-propyl)4hydroxy-chromen-2-one, 4-Hydroxy-6',8'-Dimethyl-3',4'-dihydro-2'H-[3',4'] bicromenyl -2-one, 4-Hydroxy-7-(2-(2-methoxy-ethoxy)-ethoxy)-ethoxy)-3-(1-phenyl-propyl)-chromen-2-one, 3-(1-Ethyl-3-phenyl-propyl)-4-hydroxy-chromen-2-one, 3-(1-Ethyl-4-phenyl-butyl)4-hydroxy-chromen-2-one, 2-((4-Hydroxy-2-oxo-2H-chromen-3-yl)-phenyl-methyl) -malonic acid dimethyl ester, 4-Hydroxy-3',4'-dihydro-2'H-[3,4']bichromenyl-2-one, 3-(1-Benzyl-1,2,3,4-tetrahydro-quinolin4-yl)4-hydroxy-chromin-2-one, 4-Hydroxy-3-(3-hydroxy-1-phenyl-propyl)-chromen-2-one, 3-(1-(4-Bromophenyl)-2-methylpropyl)-4-hydroxycoumarin, Butanoic acid, 2-(4-hydroxy-2-oxo-2H-1-benzopyran-3-yl)-, ethyl ester, 3-(1,2-Diphenylethyl)-4-hydroxycoumarin, 4-Hydroxy-3-(2,2-diphenyl ethyl)-coumarin, 3-(1,2-Diphenylethenyl)-4-hydroxycoumarin, Coumarin, 6-fluoro4-hydroxy-3-(1-phenylpropyl)-, Coumarin, 3-[1-(4-bromophenyl)propyl]-4-hydroxy-, 3-(1'-(3-Bromophenyl)propyl)4-hydroxycoumarin, Coumarin, 3-(.alpha.-ethylbenzyl)-4-hydroxy-7-(1-methylethoxy)-, and Coumarin, 7-ethoxy-3-(.alpha.-ethylbenzyl)-4-hydroxy- Benzamide, N-(2,3-dihydro-2-hydroxy-1H-inden-1-yl)-3-[1-(4-hydroxy-2-oxo-2H-1-benzopyran-3-yl)ethyl]-;

Coumarin, 4-hydroxy-3-(1-phenylpropyl)-7-propoxy;

3-[Cyclopropyl-[3-[(phenylmethyl)amino]phenyl] methyl]-5,6,7,8,9,10-hexahydro-4-hydroxy-2H-cycloocta[b]pyran-2-one;

3-[Cyclopropyl-[3-[(2-phenylethyl)amino]phenyl] methyl]-5,6,7,8,9,10-hexahydro-4-hydroxy-2H-cycloocta[b]pyran-2-one; and N'-[3-[cyclopropyl(5,6,7,8,9,10-hexahydro-4-hydroxy-2-oxo-2H-cycloocta[b]pyran-3-yl)methyl]phenyl]-N,N-dimethyl-sulfamide.

8. The compound of claim 2 wherein $R_{10}$ and $R_{20}$ taken together are the moiety of formula III;

wherein $R_3$ is as defined in claim 4;

wherein $R_4$ is
  a) —$C_nH_{2n+1}$, or
  b) —cyclopropyl;

wherein $R_5$ is —H;

wherein $R_8$ is
  a) —H,
  b) —$C_nH_{2n}$—CH=CH$_2$,
  c) —$C_nH_{2n+1}$,
  d) —$C_n$—H$_{2n}$—cyclopropyl,
  e) —CH(OH)—$C_nH_{2n+1}$, or
  f) —$C_nH_{2n}$—tetrahydrofuranyl;

wherein n is one (1) to five (5) inclusive; and wherein p is three (3) to five (5) inclusive.

9. The compound of claim 2 selected from:

6,7-Dihydro-4-hydroxy-3-(1-phenylpropyl)-cyclopenta[b]pyran-2(5H)-one, 3-(Cyclopropylphenylmethyl)-6,7-dihydro-4-hydroxy-cyclopenta[b]pyran-2(5H)-one, 5,6,7,8-Tetrahydro-4-hydroxy-3-(1-phenylpropyl)-2H-1-benzopyran-2-one, 3-(Cyclopropylphenylmethyl)-5,6,7,8-tetrahydro-4-hydroxy-2H-1-benzopyran-2-one, 6,7,8,9-Tetrahydro-4-hydroxy-3-(1-phenylpropyl)-cyclohepta[b]pyran-2(5H)-one, 3-(Cyclopropylphenylmethyl)-6,7,8,9-tetrahydro-4-hydroxy-cyclohepta[b]pyran-2(5H)-one, 5,6,7,8,9,10-Hexahydro4-hydroxy-3-(1-phenylpropyl)-2H-cycloocta[b]pyran-2-one, 3-(Cyclopropylphenylmethyl)-5,6,7,8,9,10-hexahydro-4-hydroxy-2h-cycloocta[b]pyran-2-one, 3-(Dicyclopropylmethyl)-5,6,7,8,9,10-hexahydro4-hydroxy-2H-cycloocta[b]pyran-2-one, 3-(3-(1-Benzyloxy-vinylamino)-phenyl)-cyclopropyl-methyl)-4-hydroxy-5,6,7,8,9,10-hexahydro-cycloocta[b]pyran-2-one, 3-(Cyclopropyl-phenyl-methyl)-4-hydroxy-6,7,8,9,10,11-hexahydro-5H-cycloocta[b]pyran-2-one, 3-(Cyclopropylphenylmethyl)-5,6,7,8,9,10,11,12-octahydro-4-hydroxy-2H-cyclodeca[b]pyran-2-one, 3-(Cyclopropylphenylmethyl)-5,6,7,8,9,10,11,12,13,14-decahydro-4-hydroxy-2H-cyclododeca[b]pyran-2-one, 10-Benzyl-4-hydroxy-3-(1-phenyl-propyl-5,6,7,8,9,10-hexahydro-cycloocta[b]pyran-2-one, 10-Benzyl-3-dicyclopropylmethyl 4-hydroxy -5,6,7,8,9,10-hexahydro-cycloocta[b ]pyran-2-one, 8-Cyclopropylmethyl-4-hydroxy-3-(1-phenyl-propyl)-5,6,7,8-tetrahydro-chromen-2-one, 9-Cyclopropylmethyl-3-(cyclopropyl-phenyl-methyl)-4-hydroxy-6,7,8,9-tetrahydro-5-H-cyclohepta[b]pyran-2-one, N-(3-(cyclopropyl-(4-hydroxy-2-oxo-5,6,7,8,9,10-hexahydro-2H-cycloocta[b]pyran-3-yl)-methyl)-phenyl)-N',N"-diisopropyl-guanidine, 3-(1-Benzyl-2-phenyl-ethyl)-4-hydroxy-5,6,7,8,9,10-hexahydro-cycloocta[b]pyran-2-one, 4-Hydroxy-10-methyl-3-(1 -phenyl-propyl)-5,6,7,8,9,10-hexahydro-cycloocta[b]pyran-2-one, 9-But-3-enyl-3-(cyclopropyl-phenyl-methyl) 4-hydroxy-6,7, 8,9-tetrahydro-5H-cyclohepta[b]pyran-2-one, 10-Cyclopropylmethyl-3-(cyclopropyl-phenyl-methyl)-4-hydroxy-5,6,7,8,9, 10-hexahydro-cycloocta[b]pyran-2-one, 3-(Cyclopropyl-phenyl-methyl)-10-ethyl-4-hydroxy-5,6,7,8,9,10-hexahydro-cycloocta[b]pyran-2-one, 3-(Cyclopropyl-phenyl-methyl)-4-hydroxy-10-propyl-5,6,7,8,9,10-hexahydro-cycloocta[b]pyran-2-one, 10-Butyl-3-(cyclopropyl-phenyl-methyl)-4-hydroxy-5,6,7,8,9,10-hexahydro-cycloocta[b]pyran-2-one, 3-(Cyclopropyl-phenyl-methyl)4-hydroxy-10-(tetrahydro-pyran-2-ylmethyl)-5,6,7,8,9,10-hexahydro-cycloocta[b]pyran-2-one, 3-(Cyclopropyl-phenyl-methyl)-4-hydroxy-10-(1-hydroxy-propyl)-5,6,7,8,9,10-hexahydro-cycloocta[b]pyran-2-one, 3-(Cyclopropyl-phenyl-methyl)-4-hydroxy-10-isobutyl-5,6,7,8,9,10-hexahydro-cycloocta[b]pyran-2-one, 3-(Cyclopropyl-phenylmethyl)-4-hydroxy-10-(3-methyl-butyl)-5,6,7,8,9,10-hexahydro-cycloocta[b]pyran-2-one, 3-(Cyclopropyl-phenyl-methyl)-4-hydroxy-10-(tetrahydro-furan-3-ylmethyl)-5,6,7,8,9,10-hexahydro-cycloocta[b]pyran-2-one, 3-(Cyclopropylphenylmethyl)-5,6,7,8,9-pentahydro-10-(1-methyl-2-hydroxyethyl)(2-methyl-2-hydroxy ethyl)-4-hydroxy-2h-cycloocta[b]pyran-2-one, 3-(Cyclopropylphenylmethyl)-5,6,7,8,9-pentahydro-10-(2-methyl-2-hydroxy ethyl)(2-methyl-2-hydroxy ethyl)-4-hydroxy-2h-cycloocta[b]pyran-2-one, and 3-(Cyclopropylphenylmethyl)-5,6,7,8,9-pentahydro-10-(2,3 - epoxypropyl) 4-hydroxy-2h -cycloocta[b]pyran-2-one.

10. The compound of claim 8 selected from the group consisting of:

5,6,7,8,9,10-Hexahydro-4-hydroxy-3-(1-phenylpropyl)-2H-cycloocta[b]pyran-2-one, 3-(Cyclopropylphenylmethyl)-5,6,7,8,9,10-hexahydro-4-hydroxy-2h-cycloocta[b]pyran-2-one, 3-(Cyclopropylphenylmethyl)-6,7,8,9-tetrahydro4-hydroxy-cyclohepta[b]pyran-2(5H)-one, 3-(Dicyclopropylmethyl)-5,6,7,8,9,10-hexahydro-4-hydroxy-2H-cycloocta[b]pyran-2-one, 3-(Cyclopropyl-phenyl-methyl)-4-hydroxy-6,7,8,9,10,11-hexahydro-5 H-cycloocta[b]pyran-2-one, 9-Cyclopropylmethyl-3 -(cyclopropyl-phenyl-methyl)-4-hydroxy-6,7,8,9-tetrahydro-5-H-cyclohepta[b]pyran-2-one, 9-But-3-enyl-3-(cyclopropyl-phenyl-methyl)-4-hydroxy-6,7,8,9-tetrahydro-5H-cyclohepta[b]pyran-2-one, 10-Cyclopropylmethyl-3-(cyclopropyl-phenyl-methyl)-4-hydroxy-5,6,7,8,9,10-hexahydro-cycloocta[b]pyran-2-one, 3 -(Cyclopropyl-phenyl-methyl)-10-ethyl4-hydroxy-5,6,7,8,9,10-hexahydro-cycloocta[b]pyran-2-one, 3-(Cyclopropyl-phenyl-methyl)-4-hydroxy-10-propyl-5,6,7,8,9,10-hexahydro-cycloocta[b]pyran-2-one, 10-Butyl-3-(cyclopropyl-phenyl-methyl)-4-hydroxy-5,6,7,8,9,10-hexahydro-cycloocta[b]pyran-2-one, 3-(Cyclopropyl-phenyl-methyl)-4-hydroxy-10-(1-hydroxy-propyl)-5,6,7,8,9,10-hexahydro-cycloocta[b]pyran-2-one, 3-(Cyclopropyl-phenyl-methyl)-4-hydroxy-10-isobutyl-5,6,7,8,9,10-hexahydro-cycloocta[b]pyran-2-one, 3-(Cyclopropyl-phenylmethyl)4-hydroxy-10-(3-methyl-butyl)-5,6,7,8,9,10-hexahydro-cycloocta[b]pyran-2-one, and 3-(Cyclopropyl-phenyl-methyl)4-hydroxy-10-(tetrahydro-furan-3-ylmethyl)-5,6,7,8,9,10-hexahydro-cycloocta[b]pyran-2-one.

11. The compound of claim 2 of the formula VII

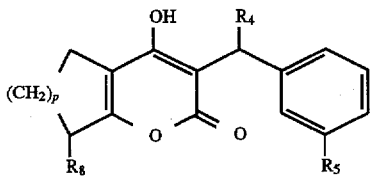

wherein $R_4$ is
 a) $C_mH_{2m+1}$, or
 b) cyclopropyl;
wherein $R_5$ is
 a) —$X_1$—$C_mH_{2m}$-aryl,
 b) —$X_1$—$C_mH_{2m}$-Het,
 c) —$X_1$—CH=CH-aryl,
 d) —$X_1$—$C_nH_{2n}$—NH—C(O)-O-$C_nH_{2n+1}$,
 e) —$X_1$—$C_tH_{2t+1}$,
 f) —$X_1$—$C_mH_{2m}$—Ch(NH—C(O)-O-$C_nH_{2n+1}$)$C_nH_{2n}$-Het, or
 g) —$X_1$—$C_nH_{2n}$-halo;
wherein $X_1$ is
 a) —NHSO$_2$—, or
 b) —NHC(O)—;
wherein m is zero (0) to four (4) inclusive;
wherein n is one (1) to four (4) inclusive;
wherein p is three (3) or four (4);
wherein t is three (3) or four (4);
wherein aryl is
 a) phenyl substituted by zero (0) to two (2) $R_6$, or
 b) naphthyl;
wherein Het is a 5- or 6-membered saturated or unsaturated ring containing from one (1) to three (3) heteroatoms selected from the group consisting of nitrogen, oxygen and sulfur, and including any bicyclic group in which any of the above heterocyclic rings is fused to a benzene ring or another heterocycle; and substituted by zero (0) to two (2) $R_7$;
and pharmaceutically acceptable salts thereof.

12. The compound of claim 11
wherein aryl is phenyl;
wherein Het is
 a) imidazolyl,
 b) quinolinyl,
 c) benzothiadiazolyl,
 d) benzofurazanyl,
 e) thiophenyl,
 f) pyridinyl, or
 g) thiazolyl;
wherein $R_6$ is
 a) methyl,
 b) ethyl,
 c) —Cl,
 d) —F,
 e) —Br,
 f) —I,
 g) —NO$_2$,
 h) —OCH$_3$,
 i) —CF$_3$,
 j) —CN,
 k) —COOH,
 l) —N=N-phenyl,
 m) —NH—OH,
 n) —N(CH$_3$)$_2$,
 o) —NH$_2$,
 p) —OCF$_3$,
 q) —CH$_2$—Br,
 r) —C(O)NH$_2$,
 s) —C(O)OCH$_3$,
 t) —OH,

 X v) —CH$_2$OH,
 w) —NH—(CH$_2$)$_2$—OH,
 x) —N((CH$_2$)$_2$—OH)$_2$,
 y) —NHSO$_2$—(CH$_2$)$_3$—Cl,
 z) —O[C$_2$H$_4$—O]$_3$—CH$_3$,
 a1) —NH—C(O)—CH$_2$—OH,
 b1) —SO$_2$-morpholino,
 c1) —SO$_2$—NH—CH$_2$-phenyl, or
 d1) —SO$_2$—NH—C$_3$H$_7$;
wherein $R_7$ is
 a) methyl,
 b) —SO$_2$-phenyl,
 c) —Cl,
 d) —Br,
 e) isoxazolyl, or
 f) pyridinyl;
wherein $R_8$ is —H;
wherein u is three (3).

13. The compound of claim 11 of the formula VIII

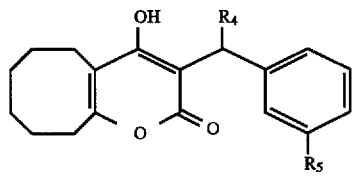 VIII wherein $R_4$ is
 a) $C_mH_{2m+1}$, or
 b) cyclopropyl;
wherein $R_5$ is
 a) —$X_1$-aryl,
 b) —$X_1$-Het, or
 c) —$X_1$—CH(NH—C(O)—O—$C_nH_{2n+1}$)—CH$_2$-Het;
wherein $X_1$ is
 a) —NHSO$_2$—, or
 b) —NHC(O)—;
wherein m is two (2) to four (4) inclusive;
wherein n is four (4);
wherein aryl is phenyl substituted by one (1) or two (2) $R_6$;
wherein Het is a 5- or 6-membered saturated or unsaturated ring containing from one (1) to three (3) heteroatoms selected from the group consisting of nitrogen, oxygen and sulfur, and including any bicyclic group in which any of the above heterocyclic rings is fused to a benzene ring or another heterocycle; and substituted by zero (0) or one (1) $R_7$;
and pharmaceutically acceptable salts thereof.

14. The compound of claim 13 of the formula IX

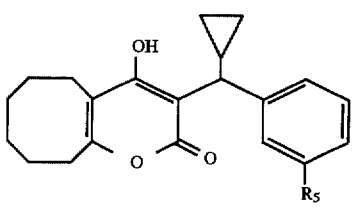

wherein R₅ is
a) —NHSO₂-aryl, or
b) —NHSO₂-Het;
wherein aryl is phenyl substituted by one (1) R₆;
wherein Het is a 5- or 6-membered saturated or unsaturated ring containing from one (1) to three (3) heteroatoms selected from the group consisting of nitrogen, oxygen and sulfur; and including any bicyclic group in which any of the above heterocyclic rings is fused to a benzene ring; and substituted by zero (0) or one (1) R₇;
and pharmaceutically acceptable salts thereof.

15. The compound of claim 14
wherein Het is
a) quinolinyl,
b) benzothiadiazolyl,
c) imidazolyl, or
d) thiazolyl;
wherein R₆ is
a) —CN,
b) —Cl,
c) —F,
d) —NHOH,
e) —C(O)NH₂,
f) —C(O)OCH₃,

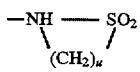

h) —NHSO₂—(CH₂)₃—Cl,
i) —CH₂—OH, or
j) —N((CH₂)₂—OH)₂;
wherein R₇ is methyl;
wherein u is three (3);
and pharmaceutically acceptable salts thereof.

16. A compound of claim 11 selected from the group consisting of:

N-[3-[Cyclopropyl(5,6,7,8,9,10-hexahydro-4-hydroxy-2-oxo-2H-cycloocta[b]pyran-3-yl)methyl]phenyl]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-2-phenyl-ethenesulfonamide;

Carbamic acid, [3-[[3-[cyclopropyl(5,6,7,8,9,10-hexahydro-4-hydroxy-2-oxo-2H-cycloocta[b]pyran-3-yl)methyl]phenyl]amino]-3-oxopropyl]-, 1,1-dimethylethyl ester;

N-[3-[Cyclopropyl(5,6,7,8,9,10-hexahydro-4-hydroxy-2-oxo-2H-cycloocta[b]pyran-3-yl)methyl]phenyl]-1-propanesulfonamide;

N-[3-[Cyclopropyl(5,6,7,8,9,10-hexahydro-4-hydroxy-2-oxo-2H-cycloocta[b]pyran-3-yl)methyl]phenyl]-4-methyl-benzenesulfonamide;

N-[3-[Cyclopropyl(5,6,7,8,9,10-hexahydro-4-hydroxy-2-oxo-2H-cycloocta[b]pyran-3-yl)methyl]phenyl]-1-butanesulfonamide;

4-Chloro-N-[3-[cyclopropyl(5,6,7,8,9,10-hexahydro-4-hydroxy-oxo-2H-cycloocta[b]pyran-3-yl)methyl]phenyl]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-2-naphthalenesulfonamide;

3,4-Dichloro-N-[3-[cyclopropyl(5,6,7,8,9,10-hexahydro-4-hydroxy-2-oxo-2H-cycloocta[b]pyran-3-yl)methyl]phenyl]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-(R)-benzenesulfonamide;

(−)-N-[3-[Cyclopropyl(5,6,7,8,9,10-hexahydro-4-hydroxy-2-oxo-2H-cycloocta[b]pyran-3-yl)methyl]phenyl]-2-phenyl-[(E)]-ethenesulfonamide;

(+)-N-[3-[Cyclopropyl(5,6,7,8,9,10-hexahydro-4-hydroxy-2-oxo-2H-cycloocta[b]pyran-3-yl)methyl]phenyl]-2-phenyl-[(E)]-ethenesulfonamide;

Carbamic acid, [2-[[3-[cyclopropyl(5,6,7,8,9,10-hexahydro-4-hydroxy-2-oxo-2H-cycloocta[b]pyran-3-yl)methyl]phenyl]amino]-2-oxyethyl]-, 1,1-dimethylethyl ester;

Carbamic acid, [2-[[3-[cyclopropyl(5,6,7,8,9,10-hexahydro-4-hydroxy-2-oxo-2H-cycloocta[b]pyran-3-yl)methyl]phenyl]amino]-1-(S)-(1H-imidazol-4-ylmethyl)-2-oxoethyl], 1,1-dimethylethyl ester;

N-[3-[Cyclopropyl(5,6,7,8,9,10-hexahydro-4-hydroxy-2-oxo-2H-cycloocta[b]pyran-3-yl)methyl]phenyl]-4-fluoro-benzenesulfonamide;

4-Bromo-N-[3-[cyclopropyl(5,6,7,8,9,10-hexahydro-4-hydroxy-2-oxo-2H-cycloocta[b]pyran-3-yl)methyl]phenyl]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-4-nitro-benzenesulfonamide;

N-[3-[Cyclopropyl(5,6,7,8,9,10-hexahydro-4-hydroxy-2-oxo-2H-cycloocta[b]pyran-3-yl)methyl]phenyl]-3-nitro-benzenesulfonamide;

N-[3-[Cyclopropyl(5,6,7,8,9,10-hexahydro-4-hydroxy-2-oxo-2H-cycloocta[b]pyran-3-yl)methyl]phenyl]-4-methoxy-benzenesulfonamide;

N-[3-[Cyclopropyl(5,6,7,8,9,10-hexahydro-4-hydroxy-2-oxo-2H-cycloocta[b]pyran-3-yl)methyl]phenyl]-3-(trifluoromethyl)-benzenesulfonamide;

N-[3-[Cyclopropyl(5,6,7,8,9,10-hexahydro-4-hydroxy-2-oxo-2H-cycloocta[b]pyran-3-yl)methyl]phenyl]-2,4-difluoro-benzenesulfonamide;

3-Chloro-N-[3-[cyclopropyl(5,6,7,8,9,10-hexahydro-4-hydroxy-2-oxo-2H-cycloocta[b]pyran-3-yl)methyl]phenyl]-1-propanesulfonamide;

4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide;

Sodium Salt of 4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-8-quinolinesulfonamide;

Carbamic acid, [2-[[3-(R or S)-[cyclopropyl(5,6,7,8,9,10)-hexahydro-4-hydroxy-2-oxo-2H-cycloocta[b]pyran-3-yl)methyl]phenyl]amino]-2-oxoethyl]-, 1,1-dimethyl ethyl ester;

N-[3-[Cyclopropyl(5,6,7,8,9,10-hexahydro-4-hydroxy-2-oxo-2H-cycloocta[b]pyran-3-yl)methyl]phenyl]-2,1,3-benzothiadiazole-4-sulfonamide;

3-Chloro-N-[3-[cyclopropyl(5,6,7,8,9,10-hexahydro-4-hydroxy-2-oxo-2H-cycloocta[b]pyran-3-yl)methyl]phenyl]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-4-benzofurazansulfonamide;

3-Bromo-N-[3-[cyclopropyl(5,6,7,8,9,10-hexahydro-4-hydroxy-2-oxo-2H-cycloocta[b]pyran-3-yl)methyl]phenyl]-benzenesulfonamide;

3-[[[3-[Cyclopropyl(5,6,7,8,9,10-hexahydro-4-hydroxy-2-oxo-2H-cycloocta[b]pyran-3-yl)methyl]phenyl]amino]sulfonyl]-benzoic acid;

(+)-4-Chloro-N-[3-[cyclopropyl(5,6,7,8,9,10-hexahydro-4-hydroxy-2-oxo-2H-cycloocta[b]pyran-3-yl)methyl]phenyl]-benzenesulfonamide;

(−)-4-Chloro-N-[3-[cyclopropyl(5,6,7,8,9,10-hexahydro-4-hydroxy-2-oxo-2H-cycloocta[b]pyran-3-yl)methyl]phenyl]-benzenesulfonamide;

(+)-4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide;

(−)-4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide;

N-[3-[Cyclopropyl(5,6,7,8,9,10-hexahydro-4-hydroxy-2-oxo-2H-cycloocta-3-yl)methyl]phenyl]-1-methyl-(S)-1H-imidazole-4-sulfonamide;

N-[3-[Cyclopropyl(5,6,7,8,9,10-hexahydro-4-hydroxy-2-oxo-2H-cycloocta[b]pyran-3-yl)methyl]phenyl]-4-(phenylsulfonyl)-2-thiophenesulfonamide;

N-[3-[Cyclopropyl(5,6,7,8,9,10-hexahydro-4-hydroxy-2-oxo-2H-cycloocta[b]pyran-3-yl)methyl]phenyl]-5-(phenylsulfonyl)-2-thiophenesulfonamide;

N-[3-[Cyclopropyl(5,6,7,8,9,10-hexahydro-4-hydroxy-2-oxo-2H-cycloocta[b]pyran-3-yl)methyl]phenyl]-4-iodo-benzenesulfonamide;

5-Chloro-N-[3-[cyclopropyl(5,6,7,8,9,10-hexahydro-4-hydroxy-2-oxo-2H-cycloocta[b]pyran-3-yl)methyl]phenyl]-2-thiophenesulfonamide;

4,5-Dichloro-N-[3-[cyclopropyl(5,6,7,8,9,10-hexahydro-4-hydroxy-2-oxo-2H-cycloocta[b]pyran-3-yl)methyl]phenyl]-2-thiophenesulfonamide;

4,5-Dibromo-N-[3-[cyclopropyl(5,6,7,8,9,10-hexahydro-4-hydroxy-2-oxo-2H-cycloocta[b]pyran-3-yl)methyl]phenyl]-2-thiophenesulfonamide;

Benzenesulfonamide, 4-chloro-N-[3-[1-(5,6,7,8,9,10-hexahydro-4-hydroxy-2-oxo-2H-cycloocta[b]pyran-3-yl)propyl]phenyl]-;

Benzenesulfonamide, 4-cyano-N-[3-[1-(5,6,7,8,9,10-hexahydro-4-hydroxy-2-oxo-2H-cycloocta[b]pyran-3-yl)propyl]phenyl]-;

N-[3-[Cyclopropyl(5,6,7,8,9,10-hexahydro-4-hydroxy-2-oxo-2H-cycloocta[b]pyran-3-yl)methyl]phenyl]-4-ethyl-benzenesulfonamide;

N-[3-[Cyclopropyl(5,6,7,8,9,10-hexahydro-4-hydroxy-2-oxo-2H-cycloocta[b]pyran-3-yl)methyl]phenyl]-4-(phenylazo)-benzenesulfonamide;

(+)-N-[3-[Cyclopropyl(5,6,7,8,9,10-hexahydro-4-hydroxy-2-oxo-2H-cycloocta[b]pyran-3-yl)methyl]phenyl]-4-fluoro-benzenesulfonamide;

(−)-N-[3-[Cyclopropyl(5,6,7,8,9,10-hexahydro-4-hydroxy-2-oxo-2H-cycloocta[b]pyran-3-yl)methyl]phenyl]-4-fluoro-benzenesulfonamide;

Carbamic acid, [2-[[3-(R or S)-[cyclopropyl(5,6,7,8,9,10-hexahydro-4-hydroxy-2-oxo-2H-cycloocta[b]pyran-3-yl)methyl]phenyl]amino]-1-(S)-(1H-imidazol-4-ylmethyl)-2-oxoethyl]-, 1,1 dimethyl ethyl ester;

Carbamic acid, [2-[[3-(R or S)-[Cyclopropyl(5,6,7,8,9,10-hexahydro-4-hydroxy-2-oxo-2H-cycloocta[b]pyran-3-yl)methyl]phenyl]amino]-1-(S)-(1H-imidazol-4-ylmethyl)-2-oxoethyl]-, 1,1 dimethyl ethyl ester;

N-[3-[Cyclopropyl(5,6,7,8,9,10-hexahydro-4-hydroxy-2-oxo-2H-cycloocta[b]pyran-3-yl)methyl]phenyl]-benzeneethanesulfonamide;

N-[3-[Cyclopropyl(5,6,7,8,9,10-hexahydro-4-hydroxy-2-oxo-2H-cycloocta[b]pyran-3-yl)methyl]phenyl]-5-(3-isoxazolyl)-2-thiophenesulfonamide;

N-[3-[Cyclopropyl(5,6,7,8,9,10-hexahydro-4-hydroxy-2-oxo-2H-cycloocta[b]pyran-3-yl)methyl]phenyl]-3-pyridinesulfonamide;

(+) -N-[3-[Cyclopropyl(5,6,7,8,9,10-hexahydro-4-hydroxy-2-oxo-2H-cycloocta[b]pyran-3-yl)methyl]phenyl]-8-quinolinesulfonamide;

(−)-N-[3-[Cyclopropyl(5,6,7,8,9,10-hexahydro-4-hydroxy-2-oxo-2H-cycloocta[b]pyran-3-yl)methyl]phenyl]-8-quinolinesulfonamide;

N-[3-[Cyclopropyl(5,6,7,8,9,10-hexahydro-4-hydroxy-2-oxo-2H-cycloocta[b]pyran-3-yl)methyl]phenyl]-5-(2-pyridinyl)-2-thiophenesulfonamide;

N-[3-[cyclopropyl(5,6,7,8,9,10-hexahydro-4-hydroxy-2-oxo-2H-cycloocta[b]pyran-3-yl)methyl]phenyl]-4-(hydroxyamino)-benzenesulfonamide;

N-[3-[Cyclopropyl(5,6,7,8,9,10-hexahydro-4-hydroxy-2-oxo-2H-cycloocta[b]pyran-3-yl)methyl]phenyl]-4-(dimethylamino)-benzenesulfonamide;

3-Amino-N-[3-[cyclopropyl(5,6,7,8,9,10-hexahydro-4-hydroxy-2-oxo-2H-cycloocta[b]pyran-3-yl)methyl]phenyl]-benzenesulfonamide and;

N-[3-[Cyclopropyl(5,6,7,8,9,10-hexahydro-4-hydroxy-2-oxo-2-cycloocta[b]pyran-3-yl)methyl]phenyl]-4-(trifluoromethoxy)-benzenesulfonamide;

4-(Bromomethyl)-N-[3-[cyclopropyl(5,6,7,8,9,10-hexahydro-4-hydroxy-2-oxo-2H-cycloocta[b]pyran-3-yl)methyl]phenyl]-benzenesulfonamide;

4-[[[3-[Cyclopropyl(5,6,7,8,9,10-hexahydro-4-hydroxy-2-oxo-2H-cycloocta[b]pyran-3-yl)methyl]phenyl]amino]sulfonyl]-benzamide;

(−)-N-[3-[Cyclopropyl(5,6,7,8,9,10-hexahydro-4-hydroxy-2-oxo-2H-cycloocta-3-yl)methyl]phenyl]-1-methyl-1H-imidazole-4-sulfonamide;

N-[3-cyclopropyl(5,6,7,8,9,10-hexahydro-4-hydroxy-2-oxo-2H -cycloocta[b]pyran-3-yl)methyl]phenyl]-5-(phenylsulfonyl)-, (S)-2-thiophenesulfonamide;

N-[3-[Cyclopropyl(5,6,7,8,9,10-hexahydro-4-hydroxy-2-oxo-2H-cycloocta[b]pyran-3-yl)methyl]phenyl]-5-methyl-3-pyridinesulfonamide;

N-[3-[Cyclopropyl(5,6,7,8,9,10-hexahydro-4-hydroxy-2-oxo-2H-cycloocta[b]pyran-3-yl)methyl]phenyl]-3-(hydroxyamino)-benzenesulfonamide;

3-[[[3-[Cyclopropyl(5,6,7,8,9,10-hexahydro-4-hydroxy-2-oxo-2H-cycloocta[b]pyran-3-yl)methyl]phenyl]amino]sulfonyl]-benzoic acid, methyl ester;

N-[3-[Cyclopropyl(5,6,7,8,9,10-hexahydro-4-hydroxy-2-oxo-2H-cycloocta[b]pyran-3-yl)methyl]phenyl]-3-hydroxy-benzenesulfonamide;

Benzenesulfonamide, 4-cyano-N-[3-[1-(5,6,7,8,9,10-hexahydro-4-hydroxy-2-oxo-2H-cycloocta[b]pyran-3-yl)butyl]phenyl]-;

N-[3-[Cyclopropyl[3-(2-isothiazolidinyl)phenyl]methyl-(5,6,7,8,9,10-hexahydro-4-hydroxy-S,S'-dioxide)methyl]phenyl]-3-[(phenylsulfonyl)amino]-4-2H-cycloocta[b]pyran-2-one;

3-Chloro-N-[3-[cyclopropyl(5,6,7,8,9,10-hexahydro-4-hydroxy-2-oxo-2H-cycloocta[b]pyran-3-yl)methyl]phenyl]-3-[(phenylsulfonyl)amino]-propanesulfonamide;

N-[3-[Cyclopropyl(5,6,7,8,9,10-hexahydro-4-hydroxy-2-oxo-2H-cycloocta[b]pyran-3-yl)methyl]phenyl]-3-[methanol]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-3-[(2-ethanol)amino]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-3-[(bis-(2-ethanol))amino]-benzenesulfonamide;

N-[3-[1-(5,6,7,8,9,10-Hexahydro-4-hydroxy-2-oxo-2H-cycloocta[b]pyran-3-yl)-2-methylpropyl]phenyl]-1-methyl-1H-imidazole-4-sulfonamide;

3-(Hydroxyacetylamino)-N-[3-[cyclopropyl(5,6,7,8,9,10-hexahydro-4-hydroxy-2-oxo-2H-cycloocta[b]pyran-3-yl)methyl]phenyl]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-(3-N-morpholinebenzenesulfonyl)benzenesulfonamide;

N-[3-[Cyclopropyl(5,6,7,8,9,10-hexahydro-4-hydroxy-2-oxo-2H-cycloocta[b]pyran-3-yl)methyl]phenyl]-(3-N-ethylbenzenesulfonyl)benzenesulfonamide;

8-Quinolinesulfonamide, N-[3-[1-(5,6,7,8,9,10-hexahydro-4-hydroxy-2-oxo-2H-cycloocta[b]pyran-3-yl)-2-methylpropyl]phenyl]-;

Benzenesulfonamide, N-[3-[cyclopropyl(5,6,7,8,9,10-hexahydro-4-hydroxy-2-oxo-2H-cycloocta[b]pyran-3-yl)methyl]phenyl]-4-[2-[2-(2-methoxyethoxy)ethoxy]ethoxy]-;

Benzenesulfonamide, 4-cyano-N-[3-[1-(5,6,7,8,9,10-hexahydro-4-hydroxy-2-oxo-2H-cycloocta[b]pyran-3-yl)pentyl]phenyl]-;

Benzenesulfonamide, N-[3-[1-(5,6,7,8,9,10-hexahydro-4-hydroxy-2-oxo-2H-cycloocta[b]pyran-3-yl)butyl]phenyl]-4-fluoro-;

Benzenesulfonamide, N-[3-[1-(5,6,7,8,9,10-hexahydro-4-hydroxy-2-oxo-2H-cycloocta[b]pyran-3-yl)-3-methylbutyl]phenyl]-4-fluoro-;

Benzenesulfonamide, 4-cyano-N-[3-[1-(5,6,7,8,9,10-hexahydro-4-hydroxy-2-oxo-2H-cycloocta[b]pyran-3-yl)-3-methylbutyl]phenyl]-;

(R or S)-Benzenesulfonamide, 4-cyano-N-[3-[1-(5,6,7,8,9,10-hexahydro-4-hydroxy-2-oxo-2H-cycloocta[b]pyran-3-yl)butyl]phenyl]-;

(R or S)-Benzenesulfonamide, 4-cyano-N-[3-[1-(5,6,7,8,9,10-hexahydro-4-hydroxy-2-oxo-2H-cycloocta[b]pyran-3-yl)butyl]phenyl]-;

1H-Imidazole-4-sulfonamide, N-[3-[1-(5,6,7,8,9,10-hexahydro-4-hydroxy-2-oxo-2H-cycloocta[b]pyran-3-yl)butyl]phenyl]-1-methyl-;

8-Quinolinesulfonamide, N-[3-[1-(5,6,7,8,9,10-hexahydro-4-hydroxy-2-oxo-2H-cycloocta[b]pyran-3-yl)butyl]phenyl]-;

3-Pyridinesulfonamide, N-[3-[1-(5,6,7,8,9,10-hexahydro-4-hydroxy-2-oxo-2H-cycloocta[b]pyran-3-yl)butyl]phenyl]-;

1H-Imidazole4-sulfonamide, N-[3-[1-(5,6,7,8,9,10-hexahydro-4-hydroxy-2-oxo-2H-cycloocta[b]pyran-3-yl)-3-methylbutyl]phenyl]-1-methyl-;

8-Quinolinesulfonamide, N-[3-[1-(5,6,7,8,9,10-hexahydro-4-hydroxy-2-oxo-2H-cycloocta[b]pyran-3-yl)-3-methylbutyl]phenyl]-;

N-[3-[Cyclopropyl(5,6,7,8,9,10-hexahydro-4-hydroxy-2-oxo-2H-cycloocta[b]pyran-3-yl)methyl]phenyl]-(3-N-benzylbenzenesulfonyl)benzenesulfonamide;

3-Pyridinesulfonamide, N-[3-[1-(5,6,7,8,9,10-hexahydro-4-hydroxy-2-oxo-2H-cycloocta[b]pyran-3-yl)-2-methylpropyl]phenyl]-;

Benzenesulfonamide, N-[3-[1-(5,6,7,8,9,10-hexahydro-4-hydroxy-2-oxo-2H-cycloocta[b]pyran-3-yl)-2-methylpropyl]phenyl]-4-fluoro-;

Benzenesulfonamide, N-[3-[1-(5,6,7,8,9,10-hexahydro-4-hydroxy-2-oxo-2H-cycloocta[b]pyran-3-yl)pentyl]phenyl]-4-fluoro-;

3-Pyridinesulfonamide, N-[3-[1-(5,6,7,8,9,10-hexahydro-4-hydroxy-2-oxo-2H-cycloocta[b]pyran-3-yl)-3-methylbutyl]phenyl]-;

3-Iodo-N-[3-[cyclopropyl(5,6,7,8,9,10-hexahydro-4-hydroxy-2-oxo-2H-cycloocta[b]pyran-3-yl)methyl]phenyl]-1-propanesulfonamide;

N-[3-[(R)Ethyl-(5,6,7,8,9,10-hexahydro-4-hydroxy-2-oxo-2H-cycloocta[b]pyran-3-yl)methyl]phenyl]-4-fluorobenzenesulfonamide;

N-[3(S)-[Cyclopropyl-(5,6,7,8,9,10-hexahydro-4-hydroxy-2-oxo-2H-cycloocta[b]pyran-3-yl)methyl]phenyl]-4-fluorobenzenesulfonamide;

N-[3(R)-[Cyclopropyl-(5,6,7,8,9,10-hexahydro-4-hydroxy-2-oxo-2H-cycloocta[b]pyran-3-yl)methyl]phenyl]-4-fluorobenzenesulfonamide; and N-[3-[Cyclopropyl(5,6,7,8,9,10-hexahydro-4-hydroxy-2-oxo-2H-cycloocta-3-yl)methyl]phenyl]-thiazole4-sulfonamide.

17. A compound of claim 13 selected from the group consisting of:

4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide;

Sodium Salt of 4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-8-quinolinesulfonamide;

N-[3-[Cyclopropyl(5,6,7,8,9,10-hexahydro-4-hydroxy-2-oxo-2H-cycloocta[b]pyran-3-yl)methyl]phenyl]-2,1,3-benzothiadiazole-4-sulfonamide;

(+)-4-Chloro-N-[3-[cyclopropyl (5,6,7,8,9,10-hexahydro-4-hydroxy-2-oxo-2H-cycloocta[b]pyran-3-yl)methyl]phenyl]-benzenesulfonamide;

(−)-4-Chloro-N-[3-[cyclopropyl(5,6,7,8,9,10-hexahydro-4-hydroxy-2-oxo-2H-cycloocta[b]pyran-3-yl)methyl]phenyl]-benzenesulfonamide;

(+)-4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide;

(−)-4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide;

N-[3-[Cyclopropyl(5,6,7,8,9,10-hexahydro-4-hydroxy-2-oxo-2H-cycloocta-3-yl)methyl]phenyl]-1-methyl-(S)-1H-imidazole4-sulfonamide;

N-[3-[Cyclopropyl(5,6,7,8,9,10-hexahydro-4-hydroxy-2-oxo-2H-cycloocta[b]pyran-3-yl)methyl]phenyl]-4- fluoro-benzenesulfonamide; (+)-N-[3-[Cyclopropyl(5,6,7,8,9,10-hexahydro-4-hydroxy-2-oxo-2H-cycloocta[b]pyran-3-yl)methyl]phenyl]-4-fluoro-benzenesulfonamide;

(−)-N-[3-[Cyclopropyl(5,6,7,8,9,10-hexahydro-4-hydroxy-2-oxo-2H-cycloocta[b]pyran-3-yl)methyl]phenyl]-4-fluoro-benzenesulfonamide;

Carbamic acid, [2-[[3-(R or S)-[Cyclopropyl(5,6,7,8,9,10-hexahydro-4-hydroxy-2-oxo-2H-cycloocta[b]pyran-3-yl)methyl]phenyl]amino]-1-(S)-(1H-imidazol-4-ylmethyl)-2-oxoethyl]-, 1,1 dimethyl ethyl ester;

(+)-N-[3-[Cyclopropyl(5,6,7,8,9,10-hexahydro-4-hydroxy-2-oxo-2H-cycloocta[b]pyran-3-yl)methyl]phenyl]-8-quinolinesulfonamide;

(−)-N-[3-[Cyclopropyl(5,6,7,8,9,10-hexahydro-4-hydroxy-2-oxo-2H-cycloocta[b]pyran-3-yl)methyl]phenyl]-8-quinolinesulfonamide;

N-[3-[cyclopropyl(5,6,7,8,9,10-hexahydro-4-hydroxy-2-oxo-2H-cycloocta[b]pyran-3-yl)methyl]phenyl]-4-(hydroxyamino)-benzenesulfonamide;

4-[[[3-[Cyclopropyl(5,6,7,8,9,10-hexahydro-4-hydroxy-2-oxo-2H-cycloocta[b]pyran-3-yl)methyl]phenyl]amino]sulfonyl]-benzamide;

(−)-N-[3-[Cyclopropyl(5,6,7,8,9,10-hexahydro-4-hydroxy-2-oxo-2H-cycloocta-3-yl)methyl]phenyl]-1-methyl-1H-imidazole-4-sulfonamide;

3-[[[3-[Cyclopropyl(5,6,7,8,9,10-hexahydro-4-hydroxy-2-oxo-2H-cycloocta[b]pyran-3-yl)methyl]phenyl]amino]sulfonyl]-benzoic acid, methyl ester;

Benzenesulfonamide, 4-cyano-N-[3-[1-(5,6,7,8,9,10-hexahydro-4-hydroxy-2-oxo-2H-cycloocta[b]pyran-3-yl)butyl]phenyl]-;

N-[3-[Cyclopropyl[3-(2-isothiazolidinyl)phenyl]methyl-(5,6,7,8,9,10-hexahydro-4-hydroxy-S,S'-dioxide)methyl]phenyl]-3-[(phenylsulfonyl)amino]-4-2H-cycloocta[b]pyran-2-one;

3-Chloro-N-[3-[cyclopropyl(5,6,7,8,9,10-hexahydro-4-hydroxy-2-oxo-2H-cycloocta[b]pyran-3-yl)methyl]phenyl]-3-[(phenylsulfonyl)amino]-1-propanesulfonamide;

N-[3-[Cyclopropyl(5,6,7,8,9,10-hexahydro-4-hydroxy-2-oxo-2H-cycloocta[b]pyran-3-yl)methyl]phenyl]-3-[methanol]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-3-[(bis-(2-ethanol))amino]-benzenesulfonamide;

N-[3-[1-(5,6,7,8,9,10-Hexahydro-4-hydroxy-2-oxo-2H-cycloocta[b]pyran-3-yl)-2-methylpropyl]phenyl]-1-methyl-1H-imidazole-4-sulfonamide;

Benzenesulfonamide, 4-cyano-N-[3-[1-(5,6,7,8,9,10-hexahydro-4-hydroxy-2-oxo-2H-cycloocta[b]pyran-3-yl)-3-methylbutyl]phenyl]-;

1H-Imidizole-4-sulfonamide, N-[3-[1-(5,6,7,8,9,10-hexahydro-4-hydroxy-2-oxo-2H-cycloocta[b]pyran-3-yl)butyl]phenyl]-1-methyl-;

1H-Imidazole-4-sulfonamide, N-[3-[1-(5,6,7,8,9,10-hexahydro-4-hydroxy-2-oxo-2H-cycloocta[b]pyran-3-yl)-3-methylbutyl]phenyl]-1-methyl-;

8-Quinolinesulfonamide, N-[3-[1-(5,6,7,8,9,10-hexahydro-4-hydroxy-2-oxo-2H-cycloocta[b]pyran-3-yl)-2-methylpropyl]phenyl]-;

3-Pyridinesulfonamide, N-[3-[1-(5,6,7,8,9,10-hexahydro-4-hydroxy-2-oxo-2H-cycloocta[b]pyran-3-yl)-2-methylpropyl]phenyl]-;

Benzenesulfonamide, N-[3-[1-(5,6,7,8,9,10-hexahydro-4-hydroxy-2-oxo-2H-cycloocta[b]pyran-3-yl)-2-methylpropyl]phenyl]-4-fluoro-;

Benzenesulfonamide, 4-cyano-N-[3-[1-(5,6,7,8,9,10-hexahydro-4-hydroxy-2-oxo-2H-cycloocta[b]pyran-3-yl)pentyl]phenyl]-;

Benzenesulfonamide, N-[3-[1-(5,6,7,8,9,10-hexahydro-4-hydroxy-2-oxo-2H-cycloocta[b]pyran-3-yl)pentyl]phenyl]-4-fluoro-;

Benzenesulfonamide, N-[3-[1-(5,6,7,8,9,10-hexahydro-4-hydroxy-2-oxo-2H-cycloocta[b]pyran-3-yl)-3-methylbutyl]phenyl]-4-fluoro-;

8-Quinolinesulfonamide, N-[3-[1-(5,6,7,8,9,10-hexahydro-4-hydroxy-2-oxo-2H-cycloocta[b]pyran-3-yl)-3-methylbutyl]phenyl]-;

3-Pyridinesulfonamide, N-[3-[1-(5,6,7,8,9,10-hexahydro-4-hydroxy-2-oxo-2H-cycloocta[b]pyran-3-yl)-3-methylbutyl]phenyl]-;

Benzenesulfonamide, N-[3-[1-(5,6,7,8,9,10-hexahydro-4-hydroxy-2-oxo-2H-cycloocta[b]pyran-3-yl)butyl]phenyl]-4-fluoro-;

8-Quinolinesulfonamide, N-[3-[1-(5,6,7,8,9,10-hexahydro-4-hydroxy-2-oxo-2H-cycloocta[b]pyran-3-yl)butyl]phenyl]-;

3-Pyridinesulfonamide, N-[3-[1-(5,6,7,8,9,10-hexahydro-4-hydroxy-2-oxo-2H-cycloocta[b]pyran-3-yl)butyl]phenyl]-;

(R or S)-Benzenesulfonamide, 4-cyano-N-[3-[1-(5,6,7,8,9,10-hexahydro-4-hydroxy-2-oxo-2H-cycloocta[b]pyran-3-yl)butyl]phenyl]-;

(R or S)-Benzenesulfonamide, 4-cyano-N-[3-[1-(5,6,7,8,9,10-hexahydro-4-hydroxy-2-oxo-2H-cycloocta[b]pyran-3-yl)butyl]phenyl]-;

N-[3-[(R)Ethyl-(5,6,7,8,9,10-hexahydro-4-hydroxy-2-oxo-2H-cycloocta[b]pyran-3-yl)methyl]phenyl]-4-fluorobenzenesulfonamide;

N-[3(S)-[Cyclopropyl-(5,6,7,8,9,10-hexahydro-4-hydroxy-2-oxo-2H-cycloocta[b]pyran-3-yl)methyl]phenyl]-4-fluorobenzenesulfonamide;

N-[3(R)-[Cyclopropyl-(5,6,7,8,9,10-hexahydro-4-hydroxy-2-oxo-2H-cycloocta[b]pyran-3-yl)methyl]phenyl]-4-fluorobenzenesulfonamide; and N-[3-[Cyclopropyl(5,6,7,8,9,10-hexahydro-4-hydroxy-2-oxo-2H-cycloocta-3-yl)methyl]phenyl]-thiazole-4-sulfonamide.

18. A compound of claim 14 selected from the group consisting of:

4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide;

Sodium Salt of 4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-8-quinolinesulfonamide;

N-[3-[Cyclopropyl(5,6,7,8,9,10-hexahydro-4-hydroxy-2-oxo-2H-cycloocta[b]pyran-3-yl)methyl]phenyl]-2,1,3-benzothiadiazole-4-sulfonamide;

(+)4-Chloro-N-[3-[cyclopropyl(5,6,7,8,9,10-hexahydro-4-hydroxy-2-oxo-2H-cycloocta[b]pyran-3-yl)methyl]phenyl]-benzenesulfonamide;

(−)-4-Chloro-N-[3-[cyclopropyl(5,6,7,8,9,10-hexahydro-4-hydroxy-2-oxo-2H-cycloocta[b]pyran-3-yl)methyl]phenyl]-benzenesulfonamide;

(+)4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide;

(−)4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide;

N-[3-[Cyclopropyl(5,6,7,8,9,10-hexahydro-4-hydroxy-2-oxo-2H-cycloocta-3-yl)methyl]phenyl]-1-methyl-(S)-1H-imidazole-4-sulfonamide;

N-[3-[Cyclopropyl(5,6,7,8,9,10-hexahydro-4-hydroxy-2-oxo-2H-cycloocta[b]pyran-3-yl)methyl]phenyl]-4-fluoro-benzenesulfonamide;

(+)-N-[3-[Cyclopropyl(5,6,7,8,9,10-hexahydro-4-hydroxy-2-oxo-2H-cycloocta[b]pyran-3-yl)methyl]phenyl]-4-fluoro-benzenesulfonamide;

(−)-N-[3-[Cyclopropyl(5,6,7,8,9,10-hexahydro-4-hydroxy-2-oxo-2H-cycloocta[b]pyran-3-yl)methyl]phenyl]-4-fluoro-benzenesulfonamide;

(+)-N-[3-[Cyclopropyl(5,6,7,8,9,10-hexahydro-4-hydroxy-2-oxo-2H-cycloocta[b]pyran-3-yl)methyl]phenyl]-8-quinolinesulfonamide;

(−)-N-[3-[Cyclopropyl(5,6,7,8,9,10-hexahydro-4-hydroxy-2-oxo-2H-cycloocta[b]pyran-3-yl)methyl]phenyl]-8-quinolinesulfonamide;

N-[3-[cyclopropyl(5,6,7,8,9,10-hexahydro-4-hydroxy-2-oxo-2H-cycloocta[b]pyran-3-yl)methyl]phenyl]-4-(hydroxyamino)-benzenesulfonamide;

4-[[[3-[Cyclopropyl(5,6,7,8,9,10-hexahydro-4-hydroxy-2-oxo-2H-cycloocta[b]pyran-3-yl)methyl]phenyl]amino]sulfonyl]-benzamide;

(−)-N-[3-[Cyclopropyl(5,6,7,8,9,10-hexahydro-4-hydroxy-2-oxo-2H-cycloocta-3-yl)methyl]phenyl]-1-methyl-1H-imidazole-4-sulfonamide;

3-[[[3-[Cyclopropyl(5,6,7,8,9,10-hexahydro-4-hydroxy-2-oxo-2H-cycloocta[b]pyran-3-yl)methyl]phenyl]amino]sulfonyl]-benzoic acid, methyl ester;

N-[3-[Cyclopropyl[3-(2-isothiazolidinyl)phenyl]methyl-(5,6,7,8,9,10-hexahydro-4-hydroxy-S,S'-dioxide)methyl]phenyl]-3-[(phenylsulfonyl)amino]4-2H-cycloocta[b]pyran-2-one;

3-Chloro-N-[3-[cyclopropyl(5,6,7,8,9,10-hexahydro-4-hydroxy-2-oxo-2H-cycloocta[b]pyran-3-yl)methyl]phenyl]-3-[(phenylsulfonyl)amino]-1-propanesulfonamide;

N-[3-[Cyclopropyl(5,6,7,8,9,10-hexahydro-4-hydroxy-2-oxo-2H-cycloocta[b]pyran-3-yl)methyl]phenyl]-3-[methanol]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-3-[(bis-(2-ethanol))amino]-benzenesulfonamide;

N-[3(S)-[Cyclopropyl-(5,6,7,8,9,10-hexahydro-4-hydroxy-2-oxo-2H-cycloocta[b]pyran-3-yl)methyl]phenyl]-4-fluorobenzenesulfonamide;

N-[3(R)-[Cyclopropyl-(5,6,7,8,9,10-hexahydro4-hydroxy-2-oxo-2H-cycloocta[b]pyran-3-yl) methyl]phenyl]-4-fluorobenzenesulfonamide, and;

N-[3-[Cyclopropyl(5,6,7,8,9,10-hexahydro-4-hydroxy-2-oxo-2H-cycloocta-3-yl)methyl]phenyl]-thiazole-4-sulfonamide.

19. A compound of claim 2 selected from:

3-(Cyclopropylphenylmethyl)-5,6,7,8,9,10-hexahydro-4-hydroxy-10-(2-hydroxy-1-methylethyl)-2H-cyclooct[b]pyran-2-one;

3-(Cyclopropylphenylmethyl)-5,6,7,8,9,10-hexahydro-4-hydroxy-10-(2-hydroxypropyl)-2H-cycloocta[b]pyran-2-one;

3-(Cyclopropylphenylmethyl)-5,6,7,8,9,10-hexahydro-4-hydroxy-10-(oxiranylmethyl)-2H-cycloocta[b]pyran-2-one;

3-[(3-Aminophenyl)cyclopropylmethyl]-5,6,7,8,9,10-hexahydro-4-hydroxy-2H-cycloocta[b]pyran-2-one;

Carbamic acid, [3-[[3-[cyclopropyl(4-hydroxy-2-oxo-2H-1-benzopyran-3-yl)methyl]phenyl]amino]-3-oxopropyl]-,1,1-dimethylethyl ester;

Carbamic acid, [3-[cyclopropyl(4-hydroxy-7-methoxy-2-oxo-2H-1-benzopyran-3-yl)methyl]phenyl]-, phenylmethyl ester;

Carbamic acid, [3-[[3-[cyclopropyl(4-hydroxy-7-methoxy-2-oxo-2H-1-benzopyran-3-yl)methyl]phenyl]amino]-3-oxopropyl]-,1,1-dimethylethyl ester;

Coumarin, 4-hydroxy-3-(α-(3-((3-(1H-indol-1-yl)-1-oxopropyl)amino)phenyl)cyclopropylmethyl);

3-(Cyclopropylphenylmethyl)-5,6,7,8,9,10-hexahydro-4-hydroxy-10-[(tetrahydro-2-furanyl)methyl]-2H-cycloocta[b]pyran-2-one;

3-(Cyclopropylphenylmethyl)-5,6,7,8,9,10-hexahydro-4-hydroxy-10-[(tetrahydro-2furanyl)methyl]-2H-cycloocta[b]pyran-2-one;

3-(Cyclopropylphenylmethyl)-5,6,7,8,9,10-hexahydro-4-hydroxy-10-[2-(2-methoxyethoxy)ethyl]-2H-cycloocta[b]pyran-2-one;

3-(Cyclopropylphenylmethyl)-5,6,7,8,9,10-hexahydro-4-hydroxy-10-(hydroxymethyl)-2H-cycloocta[b]pyran-2-one;

3-(Cyclopropylphenylmethyl)-5,6,7,8,9,10-hexahydro-4-hydroxy-10-(1-oxopropyl)-2H-cycloocta[b]pyran-2-one;

3-(Cyclopropylphenylmethyl)-5,6,7,8,9,10-hexahydro-4-hydroxy-10-(1-hydroxy-1-methylethyl)-2H-cycloocta[b]pyran-2-one;

10-(Cyclopropylhydroxymethyl)-3-(cyclopropylphenylmethyl)-5,6,7,8,9,10-hexahydro-4-hydroxy-2H-cycloocta[b]pyran-2-one;

3-(Cyclopropylphenylmethyl)-5,6,7,8,9,10-hexahydro-4-hydroxy-10-(methoxymethyl)-2H-cycloocta[b]pyran-2-one;

3-(Cyclopropylphenylmethyl)-5,6,7,8,9,10-hexahydro-4-hydroxy-10-(2-methoxyethyl)-2H-cycloocta[b]pyran-2-one;

3-(Cyclopropylphenylmethyl)-5,6,7,8,9,10-hexahydro-4-hydroxy-10-[(tetrahydro-2H-pyran-3-yl)methyl]-2H-cycloocta[b]pyran-2-one;

3-(Cyclopropylphenylmethyl)-6,7,8,9-tetrahydro-4-hydroxy-9-[2-(2-methoxyethoxy)ethyl]-cyclohepta[b]pyran-2(5H)-one;

3-(Cyclopropylphenylmethyl)-6,7,8,9-tetrahydro-4-hydroxy-9-[2-[2-(2-methoxyethoxy)ethoxy]ethyl]-cyclohepta[b]pyran-2(5H)-one;

3-(Cyclopropylphenylmethyl)-6,7,8,9-tetrahydro-4-hydroxy-9-(phenylmethyl)-cyclohepta[b]pyran-2(5H)-one;

3-(Cyclopropylphenylmethyl)-6,7,8,9-tetrahydro-4-hydroxy-9-(2-methylpropyl)cyclohepta[b]pyran-2(5H)-one;

3-(Cyclopropylphenylmethyl)-6,7,8,9-tetrahydro-4-hydroxy-9-(3-methylbutyl)cyclohepta[b]pyran-2(5H)-one;

3-(Cyclopropylphenylmethyl)-9-ethyl-6,7,8,9-tetrahydro-4-hydroxy-cyclohepta[b]pyran-(2(5H)-one;

3-(Cyclopropylphenylmethyl)-9-[2-(1,3-dioxolan-2-yl)
  ethyl]-6,7,8,9-tetrahydro-4-hydroxycyclohepta[b]
  pyran-2(5H)-one;
3-(Cyclopropylphenylmethyl)-6,7,8,9-tetrahydro-4-
  hydroxy-9-[(tetrahydro-2H-pyran-3-yl)methyl]-
  cyclohepta[b]pyran-2(5H)-one;
3-(Cyclopropylphenylmethyl)-6,7,8,9-tetrahydro-4-
  hydroxy-9-propyl-cyclohepta[b]pyran-(5H)-one;
3-(Cyclopropylphenylmethyl)-6,7,8,9-tetrahydro-4-
  hydroxy-9-[(tetrahydro-2-furanyl)methyl]cyclohepta
  [b]pyran-2(5H)-one;
3-(Cyclopropylphenylmethyl)-6,7,8,9-tetrahydro-4-
  hydroxy-9-[(tetrahydro-2H-pyran-2-yl)methyl]-
  cyclohepta[b]pyran-2(5H)-one;
3-(Cyclopropylphenylmethyl)-6,7,8,9-tetrahydro-4-
  hydroxy-9-[(tetrahydro-3-furanyl)methyl]-cyclohepta
  [b]pyran-2(5H)-one;
3-(Cyclopropylphenylmethyl)-6,7,8,9-tetrahydro-4-
  hydroxy-9-(2-hydroxypropyl)-cyclohepta[b]pyran-2
  (5H)-one;
3-(Cyclopropylphenylmethyl)-6,7,8,9-tetrahydro-4-
  hydroxy-9-(methoxyethyl)-cyclohepta[b]pyran-2(5H)-
  one;
3-(Cyclopropylphenylmethyl)-6,7,8,9-tetrahydro-4-
  hydroxy-9-(2-methoxyethyl)-cyclohepta[b]pyran-2
  (5H)-one;
9-(Cyclopropylhydroxymethyl)-3-
  (cyclopropylphenylmethyl)-6,7,8,9-tetrahydro-4-
  hydroxy-cyclohepta[b]pyran-2(5H)-one;
Carbamic acid, [3-[[3-[cyclopropyl(5,6,7,8,9,10-
  hexahydro-4-hydroxy-2-oxo-2H-cycloocta[b]pyran-3-
  yl)methyl]phenyl]amino]-3-oxopropyl]-, 1,1-
  dimethylethyl ester;
1H-Indole-1-propanamide, N-[3-[cyclopropyl(5,6,7,8,9,
  10-hexahydro-4-hydroxy-2-oxo-2H-cycloocta[b]
  pyran-3-yl)methyl]phenyl]-;
Carbamic acid, [2-[[3-[cyclopropyl(5,6,7,8,9,10-
  hexahydro-4-hydroxy-2-oxo-2H-cycloocta[b]pyran-3-
  yl)methyl]phenyl]amino]-1-(S)-methyl-2-oxy ethyl]-,
  1,1-dimethylethyl ester;
Carbamic acid, [2-[[3-[cyclopropyl(5,6,7,8,9,10-
  hexahydro-4-hydroxy-2-oxo-2H-cycloocta[b]pyran-3-
  yl)methyl]phenyl]amino]-1-[[1-(S)-[(4-methylphenyl)
  sulfonyl]-1H-imidazol-5-yl]methyl]-2-oxoethyl]-, 1,1-
  dimethylethyl ester;
Carbamic acid, [2-[[3-[cyclopropyl(5,6,7,8,9,10-
  hexahydro-4-hydroxy-2-oxo-2H-cycloocta[b]pyran-3-
  yl)methyl]phenyl]amino]-2-oxyethyl]-, 1,1-
  dimethylethyl ester;
Carbamic acid, [4-[[3-[cyclopropyl(5,6,7,8,9,10-
  hexahydro-4-hydroxy-2-oxo-2H-cycloocta[b]pyran-3-
  yl)methyl]phenyl]amino]4-oxybutyl]-, 1,1-
  dimethylethyl ester;
1-(S)-Pyrrolidinecarboxylic acid, 2-[[[3-[cyclopropyl(5,
  6,7,8,9,10-hexahydro-4-hydroxy-2-oxo-2H-cycloocta
  [b]pyran-3-yl)methyl]phenyl]amino]carbonyl]-, 1,1-
  dimethylethyl ester;
Carbamic acid, [2-[[3-[cyclopropyl(5,6,7,8,9,10-
  hexahydro-4-hydroxy-2-oxo-2H-cycloocta[b]pyran-3-
  yl)methyl]phenyl]amino]-1-(R)-methyl-2-oxyethyl]-,
  1,1-dimethylethyl ester;
Carbamic acid, [2-[[3-[cyclopropyl(5,6,7,8,9,10-
  hexahydro-4-hydroxy-2-oxo-2H-cycloocta[b]pyran-3-
  yl)methyl]phenyl]amino]-1-(R)-(1H-imidazol-4-
  ylmethyl)-2-oxoethyl]-, 1,1-dimethylethyl ester;
1-Piperidinepropanamide, N-[3-[cyclopropyl(5,6,7,8,9,
  10-hexahydro-4-hydroxy-2-oxo-2H-cycloocta[b]
  pyran-3-yl)methyl]phenyl]-;
Benzamide, 4-chloro-N-[3-[cyclopropyl(5,6,7,8,9,10-
  hexahydro-4-hydroxy-2-oxo-2H-cycloocta[b]pyran-3-
  yl)methyl]phenyl]-;
N-[3-[Cyclopropyl(5,6,7,8,9,10-hexahydro-4-hydroxy-2-
  oxo-2H-cycloocta[b]pyran-3-yl)methyl]phenyl]-.
  benzacetamide;
N-[3-[Cyclopropyl(5,6,7,8,9,10-hexahydro-4-hydroxy-2-
  oxo-2H-cycloocta[b]pyran-3-yl)methyl]phenyl]-3-
  phenyl-2-propenamide;
N-[3-[Cyclopropyl(5,6,7,8,9,10-hexahydro-4-hydroxy-2-
  oxo-2H-cycloocta[b]pyran-3-yl)methyl]phenyl]-
  butanamide;
Benzamide, N-[3-[cyclopropyl(5,6,7,8,9,10-hexahydro-
  4-hydroxy-2-oxo-2H-cycloocta[b]pyran-3-yl)methyl]
  phenyl]-4-fluoro-;
Benzamide, N-[3-[cyclopropyl(5,6,7,8,9,10-hexahydro-
  4-hydroxy-2-oxo-2H-cycloocta[b]pyran-3-yl)methyl]
  phenyl];
1-Naphthalenecarboxamide, N-[3-[cyclopropyl(5,6,7,8,9,
  10-hexahydro-4-hydroxy-2-oxo-2H-cyclooct[b]pyran-
  3-yl)methyl]phenyl]-;
Carbamic acid, [2-[[3-[cyclopropyl(5,6,7,8,9,10-
  hexahydro-4-hydroxy-2-oxo-2H-cycloocta[b]pyran-3-
  yl)methyl]phenyl]amino]-1-(S)-(1H-imidazol-4-
  ylmethyl)-2-oxoethyl]-, 1,1-dimethylethyl ester;
Carbamic acid, [3-[[3-[cyclopropyl(2,5,6,7,8,9-
  hexahydro-4-hydroxy-2-oxocyclohepta[b]pyran-3-yl)
  methyl]phenyl]amino]-3-oxopropyl]-, 1,1-
  dimethylethyl ester;
1H-Indole-1-propanamide, N-[3-[cyclopropyl(2,5,6,7,8,
  9-hexahydro-4-hydroxy-2-oxocyclohepta[b]pyran-3-
  yl)methyl]phenyl]-;
Carbamic acid, [2-[[3-[cyclopropyl(5,6,7,8,9,10-
  hexahydro-4-hydroxy-2-oxo-2H-cycloocta[b]pyran-3-
  yl)methyl]phenyl](phenylmethyl)amino]-2-oxyethyl]-,
  1,1-dimethylethyl ester;
Carbamic Acid, [3-[1-(5,6,7,8,9,10-hexahydro-4-
  hydroxy-2-oxo-2H-cycloocta[b]pyran-3-yl)propyl]
  phenyl]-, phenyl methyl ester;
2H-Cycloocta[b]pyran-2-one, 3-[1-(3-aminophenyl)
  propyl]-5,6,7,8,9,10-hexahydro-4-hydroxy-;
Carbamic acid, [3-[[3-[1-(5,6,7,8,9,10-hexahydro-4-
  hydroxy-2-oxo-2H-cycloocta[b]pyran-3-yl)propyl]
  phenyl]amino]-3-oxopropyl]-, 1,1-dimethylethyl ester
Propanamide, 3-amino-N-[3-[1-(5,6,7,8,9,10-hexahydro-
  4-hydroxy-2-oxo-2H-cycloocta[b]pyran-3-yl)propyl]
  phenyl]-, monohydrochloride;
Benzenesulfonamide, 4-chloro-N-[3-[1-(5,6,7,8,9,10-
  hexahydro-4-hydroxy-2-oxo-2H-cycloocta[b]pyran-3-
  yl)propyl]phenyl]-;
Benzenesulfonamide, 4-cyano-N-[3-[1-(5,6,7,8,9,10-
  hexahydro-4-hydroxy-2-oxo-2H-cycloocta[b]pyran-3-
  yl)propyl]phenyl]-;
N-[3-[Cyclopropyl(5,6,7,8,9,10-hexahydro-4-hydroxy-2-
  oxo-2H-cycloocta[b]pyran-3-yl)methyl]phenyl]-N'-
  ethyl-urea;
N-[3-[Cyclopropyl(5,6,7,8,9,10-hexahydro-4-hydroxy-2-
  oxo-2H-cycloocta[b]pyran-3-yl)methyl]phenyl]-N'-
  phenyl-urea;
[3-[Cyclopropyl(5,6,7,8,9,10-hexahydro-4-hydroxy-2-
  oxo-2H-cycloocta[b]pyran-3-yl)methyl]phenyl]-, phe-
  nyl ester carbamic acid;

[3-[Cyclopropyl(5,6,7,8,9,10-hexahydro-4-hydroxy-2-oxo-2H-cycloocta[b]pyran-3-yl)methyl]phenyl]-, ethyl ester carbamic acid;

2H-Cycloocta[b]pyran-2-one,5,6,7,8,9,10-hexahydro-4-hydroxy-3-(2-methyl-1-phenylpropyl)-;

(+)-(R)-3-(Cyclopropylphenylmethyl)-5,6,7,8,9,10-hexahydro-4-hydroxy-2H-cyclo[b]pyran-2-one;

(−)-(S)-3-(Cyclopropylphenylmethyl)-5,6,7,8,9,10-hexahydro-4-hydroxy-2H-cyclo[b]pyran-2-one;

(R or S)-3-(Cyclopropylphenylmethyl)-6,7,8,9-tetrahydro-4-hydroxy-cyclohepta[b]pyran-2(5H)-one;

(R or S)-3-(Cyclopropylphenylmethyl)-6,7,8,9-tetrahydro-4-hydroxy-cyclohepta[b]pyran-2(5H)-one;

3-(R)-(Cyclopropylphenylmethyl)-4-hydroxy-10-(R and S)-propyl-5,6,7,8,9,10-hexahydro-cycloocta[b]pyran-2-one;

3-(R)-(Cyclopropylphenylmethyl)-4-hydroxy-10-(R or S)-propyl-5,6,7,8,9,10-hexahydro-cycloocta[b]pyran-2-one;

3-(R)-(Cyclopropylphenylmethyl)-4-hydroxy-10-(R or S)-propyl-5,6,7,8,9,10-hexahydro-cycloocta[b]pyran-2-one;

3-(S)-(Cyclopropylphenylmethyl)-4-hydroxy-10-(R and S)-propyl-5,6,7,8,9,10-hexahydro-cycloocta[b]pyran-2-one;

3-(S)-(Cyclopropylphenylmethyl)-4-hydroxy-10-(R or S)-propyl-5,6,7,8,9,10-hexahydro-cycloocta[b]pyran-2-one;

3-(S)-(Cyclopropylphenylmethyl)-4-hydroxy-10-(R or S)-propyl-5,6,7,8,9,10-hexahydro-cycloocta[b]pyran-2-one;

Carbamic acid, [2-[[3-(R or S)-[cyclopropyl(5,6,7,8,9,10-hexahydro-4-hydroxy-2-oxo-2H-cycloocta[b]pyran-3-yl)methyl]phenyl]amino]-2-oxoethyl]-, 1,1-dimethyl ethyl ester;

Carbamic acid, [2-[[3-(R or S)-[cyclopropyl(5,6,7,8,9,10)-hexahydro-4-hydroxy-2-oxo-2H-cycloocta[b]pyran-3-yl)methyl]phenyl]amino]-2-oxoethyl]-, 1,1-dimethyl ethyl ester;

Carbamic acid, [2-[[3-(R or S)-[cyclopropyl(5,6,7,8,9,10-hexahydro-4-hydroxy-2-oxo-2H-cycloocta[b]pyran-3-yl)methyl]phenyl]amino]-1-(S)-(1H-imidazol-4-ylmethyl)-2-oxoethyl]-, 1,1 dimethyl ethyl ester;

Carbamic acid, [2-[[3-(R or S)-[Cyclopropyl(5,6,7,8,9,10-hexahydro-4-hydroxy-2-oxo-2H-cycloocta[b]pyran-3-yl)methyl]phenyl]amino]-1-(S)-(1H-imidazol-4-ylmethyl)-2-oxoethyl]-, 1,1 dimethyl ethyl ester;

N-[3-[Cyclopropyl(5,6,7,8,9,10-hexahydro-4-hydroxy-2-oxo-2H-cycloocta[b]pyran-3-yl)methyl]phenyl]-N-(phenylmethyl)-benzenesulfonamide;

N-[3-[Cyclopropyl(5,6,7,8,9,10-hexahydro-4-hydroxy-2-oxo-2H-cycloocta[b]pyran-3-yl)methyl]phenyl]-N-(phenylmethyl)-methanesulfonamide;

N-[3-[cyclopropyl(5,6,7,8,9,10-hexahydro-4-hydroxy-2-oxo-2H-cycloocta[b]pyran-3-yl)methyl]phenyl]-N-(2-phenylethyl)-benzenesulfonamide;

(−)-3[(3-aminophenyl)cyclopropylmethyl]-5,6,7,8,9,10-hexahydro-4-hydroxy-2H-cycloocta[b]pyran-2-one; and (+)-3[(3-aminophenyl)cyclopropylmethyl]-5,6,7,8,9,10-hexahydro-4-hydroxy-2H-cycloocta[b]pyran-2-one;

(−)-3 -[Cyclopropyl-[3-amino]phenyl]methyl]-5,6,7,8,9,10-hexahydro-4-hydroxy-2H-cycloocta[b]pyran-2-one;

(+)-3-[Cyclopropyl-[3-amino]-5,6,7,8,9,10-hexahydro-4-hydroxy-2H-cycloocta[b]pyran-2-one;

(−)-4-Chloro-N-[3-[cyclopropyl (5,6,7,8,9,10-hexahydro-4-hydroxy-2-oxo-2H-cycloocta[b]pyran-3-yl)methyl]phenyl]-benzenesulfonamide;

(+)4-Chloro-N-[3-[cyclopropyl(5,6,7,8,9,10-hexahydro-4-hydroxy-2-oxo-2H-cycloocta[b]pyran-3-yl)methyl]phenyl]-benzenesulfonamide;

(−)-N-[3 -[Cyclopropyl(5,6,7,8,9,10-hexahydro-4-hydroxy-2-oxo-2H-cycloocta[b]pyran-3-yl)methyl]phenyl]4-fluoro-benzenesulfonamide;

(+)-N-[3-[Cyclopropyl(5,6,7,8,9,10-hexahydro-4-hydroxy-2-oxo-2H-cycloocta[b]pyran-3-yl)methyl]phenyl]-4-fluoro-benzenesulfonamide;

(−)-4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide;

(−)-N-[3-[Cyclopropyl(5,6,7,8,9,10-hexahydro-4-hydroxy-2-oxo-2H-cycloocta[b]pyran-3-yl)methyl]phenyl]-8-quinolinesulfonamide;

(−)-N-[3-[Cyclopropyl(5,6,7,8,9,10-hexahydro-4-hydroxy-2-oxo-2H-cycloocta[b]pyran-3-yl)methyl]phenyl]-2-phenyl-[(E)]-ethenesulfonamide;

(−)-N-[3-[Cyclopropyl(5,6,7,8,9,10-hexahydro-4-hydroxy-2-oxo-2H-cycloocta[b]pyran-3-yl)methyl]phenyl]-benzenesulfonamide;

(+)-4-Cyano-N-[3-[cyclopropyl(5,6,7,8,9,10-hexahydro4-hydroxy-2-oxo-2H-cycloocta[b]pyran-3-yl)methyl]phenyl]-benzenesulfonamide;

(+)-N-[3-[Cyclopropyl(5,6,7,8,9,10-hexahydro-4-hydroxy-2-oxo-2H-cycloocta[b]pyran-3-yl)methyl]phenyl]-8-quinolinesulfonamide;

(+)-N-[3-[Cyclopropyl(5,6,7,8,9,10-hexahydro-4-hydroxy-2-oxo-2H-cycloocta[b]pyran-3-yl)methyl]phenyl]-2-phenyl-[(E)]-ethenesulfonamide;

4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-8-quinolinesulfonamide;

4-Chloro-N-[3-[cyclopropyl(5,6,7,8,9,10-hexahydro-4-hydroxy-oxo-2H-cycloocta[b]pyran-3-yl)methyl]phenyl]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-4-(1,1-dimethylethyl)-benzenesulfonamide;

N-[3-[Cyclopropyl(5,6,7,8,9,10-hexahydro-4-hydroxy-2-oxo-2H-cycloocta[b]pyran-3-yl)methyl]phenyl]-2-naphthalenesulfonamide;

N-[3-[Cyclopropyl(5,6,7,8,9,10-hexahydro-4-hydroxy-2-oxo-2H-cycloocta[b]pyran-3-yl)methyl]phenyl]-4-(trifluoromethyl)-benzenesulfonamide;

3,4-Dichloro-N-[3-[cyclopropyl(5,6,7,8,9,10-hexahydro-4-hydroxy-2-oxo-2H-cycloocta[b]pyran-3-yl)methyl]phenyl]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-1-naphthalenesulfonamide;

2,5-Dichloro-N-[3-[cyclopropyl(5,6,7,8,9,10-hexahydro-4-hydroxy-2-oxo-2H-cycloocta[b]pyran-3-yl)methyl]phenyl]-benzenesulfonamide;

4-Bromo-N-[3-[cyclopropyl(5,6,7,8,9,10-hexahydro-4-hydroxy-2-oxo-2H-cycloocta[b]pyran-3-yl)methyl]phenyl]-benzenesulfonamide;

N-[3-[Cyclopropyl(5,6,7,8,9,10-hexahydro-4-hydroxy-2-oxo-2H-cycloocta[b]pyran-3-yl)methyl]phenyl]4-nitro-benzenesulfonamide;

N-[3-[Cyclopropyl(5,6,7,8,9,10-hexahydro-4-hydroxy-2-oxo-2H-cycloocta[b]pyran-3-yl)methyl]phenyl]-3-nitro-benzenesulfonamide;

N-[3-[Cyclopropyl(5,6,7,8,9,10-hexahydro-4-hydroxy-2-oxo-2H-cycloocta[b]pyran-3-yl)methyl]phenyl]4-methoxy-benzenesulfonamide;

4-[[[3-[Cyclopropyl(5,6,7,8,9,10-hexahydro-4-hydroxy-2-oxo-2H-cycloocta[b]pyran-3-yl)methyl]phenyl]amino]sulfonyl]-benzoic acid;

N-[3-[Cyclopropyl(5,6,7,8,9,10-hexahydro-4-hydroxy-2-oxo-2H-cycloocta[b]pyran-3-yl)methyl]phenyl]-2,4,6-trimethyl-benzenesulfonamide;

N-[3-[Cyclopropyl(5,6,7,8,9,10-hexahydro-4-hydroxy-2-oxo-2H-cycloocta[b]pyran-3-yl)methyl]phenyl]-2,3,4,5,6-pentafluoro-benzenesulfonamide;

N-[3-[Cyclopropyl(5,6,7,8,9,10-hexahydro-4-hydroxy-2-oxo-2H-cycloocta[b]pyran-3-yl)methyl]phenyl]-2,4-difluoro-benzenesulfonamide;

N-[3-[Cyclopropyl(5,6,7,8,9,10-hexahydro-4-hydroxy-2-oxo-2H-cycloocta[b]pyran-3-yl)methyl]phenyl]-3-(trifluoromethyl)-benzenesulfonamide;

N-[3-[Cyclopropyl(5,6,7,8,9,10-hexahydro-4-hydroxy-2-oxo-2H-cycloocta[b]pyran-3-yl)methyl]phenyl]-2-fluoro-benzenesulfonamide;

4-Butoxy-N-[3-[cyclopropyl(5,6,7,8,9,10-hexahydro-4-hydroxy-2-oxo-2H-cycloocta[b]pyran-3-yl)methyl]phenyl]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-5-(dimethylamino)-1-naphthalenesulfonamide;

3,5-Dichloro-N-[3-[cyclopropyl(5,6,7,8,9,10-hexahydro-4-hydroxy-2-oxo -2H-cycloocta[b]pyran-3-yl)methyl]]phenyl]-2-hydroxylbenzenesulfonamide;

2,3-Dichloro-N-[3-[cyclopropyl(5,6,7,8,9,10-hexahydro-4-hydroxy-2-oxo-2H-cycloocta[b]pyran-3-yl)methyl]phenyl]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-2-(trifluoromethyl)-benzenesulfonamide;

2-Chloro-N-[3-[cyclopropyl(5,6,7,8,9,10-hexahydro-4-hydroxy-2-oxo-2H-cycloocta[b]pyran-3-yl)methyl]phenyl]-6-methyl-benzenesulfonamide;

3,5-Dichloro-N-[3-[cyclopropyl(5,6,7,8,9,10-hexahydro-4-hydroxy-2-oxo-2H-cycloocta[b]pyran-3-yl)methyl]phenyl]-benzenesulfonamide;

3-Chloro-N-[3-[cyclopropyl(5,6,7,8,9,10-hexahydro-4-hydroxy-2-oxo-2H-cycloocta[b]pyran-3-yl)methyl]phenyl]-benzenesulfonamide;

N-[3-[Cyclopropyl(5,6,7,8,9,10-hexahydro-4-hydroxy-2-oxo-2H-cycloocta[b]pyran-3 -yl)methyl]phenyl]4-benzofurazansulfonamide;

3-Bromo-N-[3-[cyclopropyl(5,6,7,8,9,10-hexahydro-4-hydroxy-2-oxo-2H-cycloocta[b]pyran-3-yl)methyl]phenyl]-benzenesulfonamide;

3-[[[3-[Cyclopropyl(5,6,7,8,9,10-hexahydro-4-hydroxy-2-oxo-2H-cycloocta[b]pyran-3-yl)methyl]phenyl]amino]sulfonyl]-benzoic acid;

2-Chloro-N-[3-[cyclopropyl(5,6,7,8,9,10-hexahydro-4-hydroxy-2-oxo-2H-cycloocta[b]pyran-3-yl)methyl]phenyl]-benzenesulfonamide;

5-Chloro-N-[3-[cyclopropyl(5,6,7,8,9,10-hexahydro-4-hydroxy-2-oxo-2H-cycloocta[b]pyran-3-yl)methyl]phenyl]-1,3-dimethyl-1H-pyrazole-4-sulfonamide;

2,6-Dichloro-N-[3-[cyclopropyl (5,6,7,8,9,10-hexahydro-4-hydroxy-2-oxo-2H-cycloocta[b]pyran-3-yl)methyl]phenyl]-benzenesulfonamide;

N-[[5-[[[3-[Cyclopropyl(5,6,7,8,9,10-hexahydro-4-hydroxy-2-oxo-2H-cycloocta[b]pyran-3-yl)methyl]phenyl]amino]sulfonyl]-2-thienyl]methyl]-benzamide;

N-[3-[Cyclopropyl(5,6,7,8,9,10-hexahydro-4-hydroxy-2-oxo-2H-cycloocta-3-yl)methyl]phenyl]-1-methyl-(S)-1H-imidazole-4-sulfonamide;

N-[3-[Cyclopropyl(5,6,7,8,9,10-hexahydro-4-hydroxy-2-oxo-2H-cycloocta[b]pyran-3-yl)methyl]phenyl]-4-(phenylsulfonyl)-2-thiophenesulfonamide;

N-[3-[Cyclopropyl(5,6,7,8,9,10-hexahydro-4-hydroxy-2-oxo-2H-cycloocta[b]pyran-3-yl)methyl]phenyl]-5-(phenylsulfonyl)-2-thiophenesulfonamide;

N-[3-[Cyclopropyl(5,6,7,8,9,10-hexahydro-4-hydroxy-2-oxo-2H-cycloocta[b]pyran-3-yl)methyl]phenyl]4-iodo-benzenesulfonamide;

5-Chloro-N-[3-[cyclopropyl(5,6,7,8,9,10-hexahydro-4-hydroxy-2-oxo-2H-cycloocta[b]pyran-3-yl)methyl]phenyl]-2-thiophenesulfonamide;

4,5-Dichloro-N-[3-[cyclopropyl(5,6,7,8,9,10-hexahydro-4-hydroxy-2-oxo-2H-cycloocta[b]pyran-3-yl)methyl]phenyl]-2-thiophenesulfonamide;

4,5-Dibromo-N-[3-[cyclopropyl(5,6,7,8,9,10-hexahydro-4-hydroxy-2-oxo-2H-cycloocta[b]pyran-3-yl)methyl]phenyl]-2-thiophenesulfonamide;

2,5-Dichloro-N-[3-[cyclopropyl(5,6,7,8,9,10-hexahydro-4-hydroxy-2-oxo-2H-cycloocta[b]pyran-3-yl)methyl]phenyl]-3-thiophenesulfonamide;

2,4-Dichloro-N-[3-[cyclopropyl(5,6,7,8,9,10-hexahydro-4-hydroxy-2-oxo-2H-cycloocta[b]pyran-3-yl)methyl]phenyl]-benzenesulfonamide;

2,4,6-Trichloro-N-[3-[cyclopropyl(5,6,7,8,9,10-hexahydro-4-hydroxy-2-oxo-2H-cycloocta[b]pyran-3-yl)methyl]phenyl]-benzenesulfonamide;

N-[4-[[[3-[Cyclopropyl(5,6,7,8,9,10-hexahydro-4-hydroxy-2-oxo-2H-cycloocta[b]pyran-3-yl)methyl]phenyl]amino]sulfonyl]phenyl]-acetamide N-[3-[Cyclopropyl(5,6,7,8,9,10-hexahydro-4-hydroxy-2-oxo-2H-cycloocta[b]pyran-3-yl)methyl]phenyl]-4-(phenylazo)-benzenesulfonamide;

N-[3-[Cyclopropyl(5,6,7,8,9,10-hexahydro-4-hydroxy-2-oxo-2H-cycloocta[b]pyran-3-yl)methyl]phenyl]-4-[[4-(dimethylamino)phenyl]azo]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-5-(2-pyridinyl)-2-thiophenesulfonamide;

3-Chloro-N-[3-[cyclopropyl(5,6,7,8,9,10-hexahydro-4-hydroxy-2-oxo-2H-cycloocta[b]pyran-3-yl)methyl]phenyl]-2-methyl-benzenesulfonamide;

N-[3-[Cyclopropyl(5,6,7,8,9,10-hexahydro-4-hydroxy-2-oxo-2-cycloocta[b]pyran-3- yl)methyl]phenyl]-4-(trifluoromethoxy)-benzenesulfonamide;

3-Chloro-N-[3-[cyclopropyl(5,6,7,8,9,10-hexahydro-4-hydroxy-2-oxo-2H-cycloocta[b]pyran-3-yl)methyl]phenyl]-3-[(phenylsulfonyl)amino]-1-propanesulfonamide;

N-[3-[Cyclopropyl(5,6,7,8,9,10-hexahydro-2-oxo-2H-cylcloocta[b]pyran-3-yl)methyl]phenyl]-3-pyridinesulfonamide;

N-[3-[Cyclopropyl(5,6,7,8,9,10-hexahydro-4-hydroxy-2-oxo-2H-cycloocta[b]pyran-3-yl)methyl]phenyl]-5-methyl-3-pyridinesulfonamide;

N-[3-[Cyclopropyl(5,6,7,8,9,10-hexahydro-4-hydroxy-2-oxo-2H-cycloocta[b]pyran-3-yl)methyl]phenyl]-ethanesulfonamide;

N-[3-[Cyclopropyl(5,6,7,8,9,10-hexahydro-4-hydroxy-2-oxo-2H-cycloocta[b]pyran-3-yl)methyl]phenyl]-methanesulfonamide;

N-[3-[Cyclopropyl(5,6,7,8,9,10-hexahydro-4-hydroxy-2-oxo-2H-cycloocta[b]pyran-3-yl)methyl]phenyl]-ethanesulfonamide;

N-[3-[Cyclopropyl(5,6,7,8,9,10-hexahydro-4-hydroxy-2-oxo-2H-cycloocta[b]pyran-3-yl)methyl]phenyl]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-2-phenyl-ethenesulfonamide;

N-[3-[Cyclopropyl(5,6,7,8,9,10-hexahydro-4-hydroxy-2-oxo-2H-cycloocta[b]pyran-3-yl)methyl]phenyl]-benzenemethanesulfonamide;

N-[5-[[[3-[Cyclopropyl(5,6,7,8,9,10-hexahydro-4-hydroxy-2-oxo-2H-cycloocta[b]pyran-3-yl)methyl]phenyl]amino]sulfonyl]-4-methyl-2-thiazolyl]-acetamide;

N-[3-[Cyclopropyl(5,6,7,8,9,10-hexahydro-4-hydroxy-2-oxo-2H-cycloocta[b]pyran-3-yl)methyl]phenyl]-2-thiophenesulfonamide;

N-[3-[Cyclopropyl(5,6,7,8,9,10-hexahydro-4-hydroxy-2-oxo-2H-cycloocta[b]pyran-3-yl)methyl]phenyl]-1-propanesulfonamide;

N-[3-[Cyclopropyl(5,6,7,8,9,10-hexahydro-4-hydroxy-2-oxo-2H-cycloocta[b]pyran-3-yl)methyl]phenyl]-4-methyl-benzenesulfonamide;

N-[3-[Cyclopropyl(5,6,7,8,9,10-hexahydro-4-hydroxy-2-oxo-2H-cycloocta[b]pyran-3-yl)methyl]phenyl]-1-butanesulfonamide;

N-[3-[Cyclopropyl(5,6,7,8,9,10-hexahydro-4-hydroxy-2-oxo-2H-cycloocta[b]pyran-3-yl)methyl]phenyl]-1,3-dihydro-1,3-dioxo-2H-isoindole-2-ethanesulfonamide;

N-[3-[Cyclopropyl(5,6,7,8,9,10-hexahydro-4-hydroxy-2-oxo-2H-cycloocta[b]pyran-3-yl)methyl]phenyl]-2-propanesulfonamide;

N-[3-[Cyclopropyl(5,6,7,8,9,10-hexahydro-4-hydroxy-2-oxo-2H-cycloocta[b]pyran-3-yl)methyl]phenyl]-2,6-dimethyl-benzenesulfonamide;

N-[3-[Cyclopropyl(5,6,7,8,9,10-hexahydro-4-hydroxy-2-oxo-2H-cycloocta[b]pyran-3 -yl)methyl]phenyl]-2-methyl-benzenesulfonamide;

3-Chloro-N-[3-[cyclopropyl(5,6,7,8,9,10-hexahydro-4-hydroxy-2-oxo-2H-cycloocta[b]pyran-3-yl)methyl]phenyl]-1-propanesulfonamide;

N-[3-[Cyclopropyl(5,6,7,8,9,10-hexahydro-4-hydroxy-2-oxo-2H-cycloocta[b]pyran-3-yl)methyl]phenyl]-3,5-bis(trifluoromethyl)-benzenesulfonamide;

N-[3-[Cyclopropyl(5,6,7,8,9,10-hexahydro-4-hydroxy-2-oxo-2H-cycloocta[b]pyran-3-yl)methyl]phenyl]-7,7-dimethyl-2-oxo-bicyclo[2.2.1]heptane-1-methanesulfonamide;

N-[3-[Cyclopropyl(5,6,7,8,9,10-hexahydro-4-hydroxy-2-oxo-2H-cycloocta[b]pyran-3-yl)methyl]phenyl]-2,6-dimethoxy-benzenesulfonamide;

N-[3-[Cyclopropyl(5,6,7,8,9,10-hexahydro-4-hydroxy-2-oxo-2H-cycloocta[b]pyran-3-yl)methyl]phenyl]-3,4-dimethoxy-benzenesulfonamide;

N-[3-[Cyclopropyl(5,6,7,8,9,10-hexahydro-4-hydroxy-2-oxo-2H-cycloocta[b]pyran-3-yl)methyl]phenyl]-3-methyl-benzenesulfonamide;

2-Bromo-N-[3-[cyclopropyl(5,6,7,8,9,10-hexahydro-4-hydroxy-2-oxo-2H-cycloocta[b]pyran-3-yl)methyl]phenyl]-6-methoxy-benzenesulfonamide;

N-[3-[Cyclopropyl(5,6,7,8,9,10-hexahydro-4-hydroxy-2-oxo-2H-cycloocta[b]pyran-3-yl)methyl]phenyl]-3,5-dimethyl-4-isoxazolesulfonamide;

2-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-2,1,3-benzothiadiazole-4-sulfonamide;

N-[3-[Cyclopropyl(5,6,7,8,9,10-hexahydro-4-hydroxy-2-oxo-2H-cycloocta[b]pyran-3-yl) methyl]phenyl]-4-ethyl-benzenesulfonamide;

N-[3-[Cyclopropyl(5,6,7,8,9,10-hexahydro-4-hydroxy-2-oxo-2H-cycloocta[b]pyran-3-yl)methyl]phenyl]-4-propyl-benzenesulfonamide;

N-[3-[Cyclopropyl(5,6,7,8,9,10-hexahydro-4-hydroxy-2-oxo-2H-cycloocta[b]pyran-3-yl)methyl]phenyl]-1-octanesulfonamide;

N-[3-[Cyclopropyl(5,6,7,8,9,10-hexahydro-4-hydroxy-2-oxo-2H-cycloocta[b]pyran-3-yl)methyl]phenyl]-1-dodecanesulfonamide;

N-[3-[Cyclopropyl(5,6,7,8,9,10-hexahydro-4-hydroxy-2-oxo-2H-cycloocta[b]pyran-3-yl)methyl]phenyl]-4-(1-methylethyl)-benzenesulfonamide;

N-[3-[Cyclopropyl(5,6,7,8,9,10-hexahydro-4-hydroxy-2-oxo-2H-cycloocta[b]pyran-3-yl)methyl]phenyl]-benzeneethanesulfonamide;

N-[3-[Cyclopropyl(5,6,7,8,9,10-hexahydro-4-hydroxy-2-oxo-2H-cycloocta[b]pyran-3-yl)methyl]phenyl]-5-(3-isoxazolyl)-2-thiophenesulfonamide;

4-Amino-N-[3-[cyclopropyl(5,6,7,8,9,10-hexahydro-4-hydroxy-2-oxo-2H-cycloocta[b]pyran-3-yl)methyl]phenyl]-benzenesulfonamide; and N-[3-[cyclopropyl(5,6,7,8,9,10-hexahydro-4-hydroxy-2-oxo-2H-cycloocta[b]pyran-3-yl)methyl]phenyl]-4-(hydroxyamino)-benzenesulfonamide;

N-[3-[Cyclopropyl(5,6,7,8,9,10-hexahydro-4-hydroxy-2-oxo-2H-cycloocta[b]pyran-3-yl)methyl]phenyl]-4-[(phenylsulfonyl)amino]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-3-[(phenylsulfonyl)amino]-benzenesulfonamide;

N-[3-[[[3-[Cyclopropyl(5,6,7,8,9,10-hexahydro-4-hydroxy-2-oxo-2H-cycloocta[b]pyran-3-yl)methyl]phenyl]amino]sulfonyl]phenyl]-benzamide;

N-[3-[Cyclopropyl(5,6,7,8,9,10-hexahydro-4-hydroxy-2-oxo-2H-cycloocta[b]pyran-3-yl)methyl]phenyl]-4-(dimethylamino)-benzenesulfonamide;

3-Amino-N-[3-[cyclopropyl(5,6,7,8,9,10-hexahydro-4-hydroxy-2-oxo-2H-cycloocta[b]pyran-3-yl)methyl]phenyl]-benzenesulfonamide; and N-[3-[Cyclopropyl(5,6,7,8,9,10-hexahydro-4-hydroxy-2-oxo-2H-cycloocta[b]pyran-3-yl)methyl]phenyl]-3-(hydroxyamino)-benzenesulfonamide;

3-[[[3-[Cyclopropyl(5,6,7,8,9,10-hexahydro-4-hydroxy-2-oxo-2H-cycloocta[b]pyran-3-yl)methyl]phenyl]amino]sulfonyl]-benzoic acid, methyl ester;

N-[3-[Cyclopropyl(5,6,7,8,9,10-hexahydro-4-hydroxy-2-oxo-2H-cycloocta[b]pyran-3-yl)methyl]phenyl]-3-[(2-ethanol)amino]-benzenesulfonamide; and N-[3-[Cyclopropyl(5,6,7,8,9,10-hexahydro-4-hydroxy-2-oxo-2H-cycloocta[b]pyran-3-yl)methyl]phenyl]-3-[(bis-(2-ethanol))amino]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-3-[methanol]-benzenesulfonamide;

N-[3-[Cyclopropyl[3-(2-isothiazolidinyl)phenyl]methyl-(5,6,7,8,9,10-hexahydro-4-hydroxy-S,S'-dioxide)methyl]phenyl]-3-[(phenylsulfonyl)amino]-4-2H-cycloocta[b]pyran-2-one;

N-[3-[Cyclopropyl(5,6,7,8,9,10-hexahydro-4-hydroxy-2-oxo-2H-cycloocta[b]pyran-3-yl)methyl]phenyl]-3-(2-methoxyethyoxymethoxy)-benzenesulfonamide;

N-[3-[Cyclopropyl(5,6,7,8,9,10-hexahydro-4-hydroxy-2-oxo-2H-cycloocta[b]pyran-3-yl)methyl]phenyl]-3-hydroxy-benzenesulfonamide;

N-[3-[Cyclopropyl(5,6,7,8,9,10-hexahydro-4-hydroxy-2-oxo-2H-cycloocta[b]pyran-3-yl)methyl]phenyl]-3-(4-morpholineethoxy)-benzenesulfonamide;

N-[3-[Cyclopropyl(5,6,7,8,9,10-hexahydro-4-hydroxy-2-oxo-2H-cycloocta[b]pyran-3-yl)methyl]phenyl]-3-(N,N-diethylaminoethoxy)-benzenesulfonamide;

N-[3-[Cyclopropyl(5,6,7,8,9,10-hexahydro-4-hydroxy-2-oxo-2H-cycloocta[b]pyran-3-yl)methyl]phenyl]-4-hydroxy-benzenesulfonamide;

N-[3-[Cyclopropyl(2,5,6,7,8,9-hexahydro-4-hydroxy-2-oxocyclohepta[b]pyran-3-yl)methyl]phenyl]-ethenesulfonamide;

N-[3-[Cyclopropyl(2,5,6,7,8,9-hexahydro-4-hydroxy-2-oxocyclohepta[b]pyran-3-yl)methyl]phenyl]-methanesulfonamide;

N-[3-[Cyclopropyl(2,5,6,7,8,9-hexahydro-4-hydroxy-2-oxocyclohepta[b]pyran-3-yl)methyl]phenyl]-ethanesulfonamide;

Thiourea, N-[3-[cyclopropyl(5,6,7,8,9,10-hexahydro-4-hydroxy-2-oxo-2H-cycloocta[b]pyran-3-yl)methyl]phenyl]-N'-phenyl-;

Thiourea, N-[3-[cyclopropyl(5,6,7,8,9,10-hexahydro-4-hydroxy-2-oxo-2H-cycloocta[b]pyran-3-yl)methyl]phenyl]-N'-ethyl-;

Benzeneethanethioamide, N-[3-[cyclopropyl(5,6,7,8,9,10-hexahydro-4-hydroxy-2-oxo-2H-cycloocta[b]pyran-3-yl)methyl]phenyl]-;

5,6,7,8,9,10-Hexahydro-4-hydroxy-3-(1-phenylbutyl)-2H-cycloocta[b]pyran-2-one;

[3-[1-(5,6,7,8,9,10-Hexahydro-4-hydroxy-2-oxo-2H-cycloocta[b]pyran-3-yl)-2-methylpropyl]phenyl]-carbamic acid, phenylmethyl ester;

3-[1-(3-Aminophenyl)-2-methylpropyl]-5,6,7,8,9,10-hexahydro-4-hydroxy-2H-cycloocta[b]pyran-2-one;

4-Cyano-N-[3-[1-(6,7,8,9,10-hexahydro-4-hydroxy-2-oxo-2H-cycloocta[b]pyran-3-yl)-2-methylpropyl]phenyl]-benzenesulfonamide;

4-Chloro-N-[3-[1-(6,7,8,9,10-hexahydro-4-hydroxy-2-oxo-2H-cycloocta[b]pyran-3-yl)-2-methylpropyl]phenyl]-benzenesulfonamide;

N-[3-[1-(5,6,7,8,9,10-Hexahydro-4-hydroxy-2-oxo-2H-cycloocta[b]pyran-3-yl)-2-methylpropyl]phenyl]-1-methyl-1H-imidazole-4-sulfonamide;

[3-[1-(5,6,7,8,9,10-Hexahydro-4-hydroxy-2-oxo-2H-cycloocta[b]pyran-3-yl)butyl]phenyl]-carbamic acid, phenylmethyl ester;

3-[1-(3-Aminophenyl)butyl]-5,6,7,8,9,10-hexahydro-4-hydroxy-2H-cycloocta[b]pyran-2-one;

Benzenesulfonamide, 4-chloro-N-[3-[1-(5,6,7,8,9,10-hexahydro-4-hydroxy-2-oxo-2H-cycloocta[b]pyran-3-yl)butyl]phenyl]-;

Benzenesulfonamide, 4-cyano-N-[3-[1-(5,6,7,8,9,10-hexahydro-4-hydroxy-2-oxo-2H-cycloocta[b]pyran-3-yl)butyl]phenyl]-;

3-(α-Cyclopropyl thien-2-ylmethyl)-4-hydroxy-5,6,7,8,9,10-hexahydrocycloocta[b]pyran-2-one;

3(α-Ethyl thien-2-ylmethyl)-4-hydroxy-5,6,7,8,9,10-hexahydrocycloocta[b]pyran-2-one;

3-(α-Ethyl (5-methylthien-2-ylmethyl)-4-hydroxy-5,6,7,8,9,10-hexahydrocycloocta[b]pyran-2-one;

3-(α-Ethyl benzo[b]thien-2-ylmethyl)-4-hydroxy-5,6,7,8,9,10-hexahydrocycloocta[b]pyran-2-one;

3-(α-Cyclopropyl (5-hydroxymethylfurfur-2-yl)-4-hydroxy-5,6,7,8,9,10-hexahydrocycloocta[b]pyran-2-one;

3-(α-Cyclopropyl (5-hydroxymethylthien-2-ylmethyl)-4-hydroxy-5,6,7,8,9,10-hexahydrocycloocta[b]pyran-2-one;

3-(α-Cyclopropyl (5-(2-hydroxyethyl)thien-2-ylmethyl)-4-hydroxy-5,6,7,8,9,10-hexahydrocycloocta[b]pyran-2-one;

3-(α-Cyclopropyl (5-(2-hydroxymethyl (methoxymethylether)furfur-2-yl)-4-hydroxy-5,6,7,8,9,10-hexahydrocycloocta[b]pyran-2-one;

3-(α-Cyclopropyl (5-(2-hydroxymethyl (methoxymethylether)thien-2-ylmethyl)-4-hydroxy-5,6,7,8,9,10-hexahydrocycloocta[b]pyran-2-one;

3-(α-Cyclopropyl (5-(N-carbobenzoxy)aminomethyl) furfur-2-yl)-4-hydroxy-5,6,7,8,9,10-hexahydrocycloocta[b]pyran-2-one;

3-(α-Cyclopropyl (5-(N-carbobenzoxy)aminomethyl) thien-2-ylmethyl)-4-hydroxy-5,6,7,8,9,10-hexahydrocycloocta[b]pyran-2-one;

N-[3-[Cyclopropyl(5,6,7,8,9,10-hexhydro-4-hydroxy-2-oxo-2H-cycloocta[b]pyran-3-yl)methyl]furfur-2-ylmethyl]4-fluorobenzenesulfonamide;

N-[3-[Cyclopropyl(5,6,7,8,9,10-hexhydro-4-hydroxy-2-oxo-2H-cycloocta[b]pyran-3-yl)methyl]furfur-2-ylmethyl]4-cyanobenzenesulfonamide;

N-[3-[Cyclopropyl(5,6,7,8,9,10-hexhydro-4-hydroxy-2-oxo-2H-cycloocta[b]pyran-3-yl)methyl]thien-2-ylmethyl]4-cyanobenzenesulfonamide;

N-[3-[Cyclopropyl(5,6,7,8,9,10-hexhydro-4-hydroxy-2-oxo-2H-cycloocta[b]pyran-3-yl)methyl]thien-2-ylmethyl]4-cyanobenzenesulfonamide;

3-(α-Cyclopropyl (5-methyl-4-hydroxymethylthien-2-ylmethyl)-4-hydroxy-5,6,7,8,9,10-hexahydrocycloocta[b]pyran-2-one;

3-(α[S]-Ethylbenzyl)-4-hydroxy-5,6,7,8,9,10-hexahydrocycloocta[b]pyran-2-one;

3-(α[R]-Ethylbenzyl)-4-hydroxy-5,6,7,8,9,10-hexahydrocycloocta[b]pyran-2-one;

N-[3-[Cyclopropyl(5,6,7,8,9,10-hexahydro-4-hydroxy-2-oxo-2H-cycloocta[b]pyran-3-yl)methyl]phenyl]-N-phenyl-sulfamide;

N'-[3-[cyclopropyl(5,6,7,8,9,10-hexahydro-4-hydroxy-2-oxo-2H-cycloocta[b]pyran-3-yl)methyl]phenyl]-N,N-dimethyl-sulfamide;

N-[3-[Cyclopropyl(5,6,7,8,9,10-hexahydro-4-hydroxy-2-oxo-2H-cycloocta[b]pyran-3-yl)methyl]phenyl]-4-methyl-1-piperazinesulfonamide;

N-Phenyl-3-[cyclopropyl(5,6,7,8,9,10-hexahydro-4-hydroxy-2-oxo-2H-cycloocta[b]pyran-3-yl)methyl]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-(R)-benzenesulfonamide;

Sodium Salt of 4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide;

N-[3-[Cyclopropyl(5,6,7,8,9,10-hexahydro-4-hydroxy-2-oxo-2H-cycloocta[b]pyran-3-yl)methyl]phenyl]-4-(dimethylamino)-benzenesulfonamide;

4-(Bromomethyl)-N-[3-[cyclopropyl(5,6,7,8,9,10-hexahydro-4-hydroxy-2-oxo-2H-cycloocta[b]pyran-3-yl)methyl]phenyl]-benzenesulfonamide;

4-[[[3-[Cyclopropyl(5,6,7,8,9,10-hexahydro-4-hydroxy-2-oxo-2H-cycloocta[b]pyran-3-yl)methyl]phenyl]amino]sulfonyl]-benzamide;

N-[3-cyclopropyl(5,6,7,8,9,10-hexahydro-4-hydroxy-2-oxo-2H-cycloocta[b]pyran-3-yl)methyl]phenyl]-5-(phenylsulfonyl)-, (S)-2-thiophenesulfonamide;

N-[3-[Cyclopropyl(5,6,7,8,9,10-hexahydro-4-hydroxy-2-oxo-2H-cycloocta[b]pyran-3-yl)methyl]phenyl]-3-hydroxy-benzenesulfonamide;

N-[3-[Cyclopropyl(5,6,7,8,9,10-hexahydro-4-hydroxy-2-oxo-2H-cycloocta[b]pyran-3-yl)methyl]phenyl]-4-fluoro-benzenesulfonamide;

4-Butoxy-N-[3-[cyclopropyl(5,6,7,8,9,10-hexahydro-4-hydroxy-2-oxo-2H-cycloocta[b]pyran-3-yl)methyl]phenyl]-benzenesulfonamide;

5-Chloro-N-[3-[cyclopropyl(5,6,7,8,9,10-hexahydro-4-hydroxy-2-oxo-2H-cycloocta[b]pyran-3-yl)methyl]phenyl]-1,3-dimethyl-1H-pyrazole-4-sulfonamide;

2,4-Dichloro-N-[3-[cyclopropyl(5,6,7,8,9,10-hexahydro-4-hydroxy-2-oxo-2H-cycloocta[b]pyran-3-yl)methyl]phenyl]benzenesulfonamide;

N-[3-[Cyclopropyl(5,6,7,8,9,10-hexahydro-4-hydroxy-2-oxo-2H-cycloocta[b]pyran-3-yl)methyl]phenyl]-4-hydroxy-benzenesulfonamide;

3-(Benzyloxyacetylamino)-N-[3-[cyclopropyl(5,6,7,8,9,10-hexahydro-4-hydroxy-2-oxo-2H-cycloocta[b]pyran-3-yl)methyl]phenyl]-benzenesulfonamide;

3-(Hydroxyacetylamino)-N-[3-[cyclopropyl(5,6,7,8,9,10-hexahydro-4-hydroxy-2-oxo-2H-cycloocta[b]pyran-3-yl)methyl]phenyl]-benzenesulfonamide;

2,3,4-Trichloro-N-[3-[cyclopropyl(5,6,7,8,9,10-hexahydro-4-hydroxy-2-oxo-2H-cycloocta[b]pyran-3-yl)methyl]phenyl]-benzenesulfonamide;

N-[3-[Cyclopropyl(5,6,7,8,9,10-hexahydro-4-hydroxy-2-oxo-2H-cycloocta[b]pyran-3-yl)-methyl]phenyl]-(3-N-morpholinebenzenesulfonyl)benzenesulfonamide;

N-[3-[Cyclopropyl(5,6,7,8,9,10-hexahydro-4-hydroxy-2-oxo-2H-cycloocta[b]pyran-3-yl)-methyl]phenyl]-(3-N-benzylbenzenesulfonyl)benzenesulfonamide;

N-[3-[Cyclopropyl(5,6,7,8,9,10-hexahydro-4-hydroxy-2-oxo-2H-cycloocta[b]pyran-3-yl)-methyl]phenyl]-(3-N,N-dibenzylbenzenesulfonyl)benzenesulfonamide;

N-[3-[Cyclopropyl(5,6,7,8,9,10-hexahydro-4-hydroxy-2-oxo-2H-cycloocta[b]pyran-3-yl)-methyl]phenyl]-(3-N-ethylbenzenesulfonyl)benzenesulfonamide;

Benzenesulfonamide, N-[3-[cyclopropyl(5,6,7,8,9,10-hexahydro-4-hydroxy-2-oxo-2H-cycloocta[b]pyran-3-yl)methyl]phenyl]4-[2-[2-(2-methoxyethoxy)ethoxy]ethoxy]-;

8-Quinolinesulfonamide, N-[3-[1-(5,6,7,8,9,10-hexahydro-4-hydroxy-2-oxo-2H-cycloocta[b]pyran-3-yl)-2-methylpropyl]phenyl]-;

3-Pyridinesulfonamide, N-[3-[1-(5,6,7,8,9,10-hexahydro-4-hydroxy-2-oxo-2H-cycloocta[b]pyran-3-yl)-2-methylpropyl]phenyl]-;

Benzenesulfonamide, N-[3-[1-(5,6,7,8,9,10-hexahydro-4hydroxy-2-oxo-2H-cycloocta[b]pyran-3-yl)-2-methylpropyl]phenyl]-4-fluoro-;

[3-[1-(5,6,7,8,9,10-Hexahydro-4-hydroxy-2-oxo-2H-cycloocta[b]pyran-3-yl)pentyl]phenylcarbamic acid, phenylmethyl ester;

3-[1-(3-Aminophenyl)pentyl]-5,6,7,8,9,10-hexahydro-4-hydroxy-2H-cycloocta[b]pyran-2-one;

Benzenesulfonamide, 4-cyano-N-[3-[1-(5,6,7,8,9,10-hexahydro-4-hydroxy-2-oxo-2H-cycloocta[b]pyran-3-yl)pentyl]phenyl]-;

Benzenesulfonamide, N-[3-[1-(5,6,7,8,9,10-hexahydro-4-hydroxy-2-oxo-2H-cycloocta[b]pyran-3-yl)pentyl]phenyl]-4-fluoro-;

[3-[1-(5,6,7,8,9,10-Hexahydro-4-hydroxy-2-oxo-2H-cycloocta[b]pyran-3-yl)-3-methylbutyl]phenylcarbamic acid, phenylmethyl ester;

3-[1-(3-Aminophenyl)-3-methylbutyl]-5,6,7,8,9,10-hexahydro-4-hydroxy-2H-cycloocta[b]pyran-2-one;

Benzenesulfonamide, N-[3-[1-(5,6,7,8,9,10-hexahydro-4-hydroxy-2-oxo-2H-cycloocta[b]pyran-3-yl)-3-methylbutyl]phenyl]-4-fluoro-;

Benzenesulfonamide, 4-cyano-N-[3-[1-(5,6,7,8,9,10-hexahydro-4-hydroxy-2-oxo-2H-cycloocta[b]pyran-3-yl)-3-methylbutyl]phenyl]-;

1H-Imidazole-4-sulfonamide, N-[3-[1-(5,6,7,8,9,10-hexahydro-4-hydroxy-2-oxo-2H-cycloocta[b]pyran-3-yl)-3-methylbutyl]phenyl]-1-methyl-;

8-Quinolinesulfonamide, N-[3-[1-(5,6,7,8,9,10-hexahydro-4-hydroxy-2-oxo-2H-cycloocta[b]pyran-3-yl)-3-methylbutyl]phenyl]-;

3-Pyridinesulfonamide, N-[3-[1-(5,6,7,8,9,10-hexahydro-4-hydroxy-2-oxo-2H-cycloocta[b]pyran-3-yl)-3-methylbutyl]phenyl]-;

Benzenesulfonamide, N-[3-[1-(5,6,7,8,9,10-hexahydro-4-hydroxy-2-oxo-2H-cycloocta[b]pyran-3-yl)butyl]phenyl]-4-fluoro-;

1H-Imidazole4-sulfonamide, N-[3-[1-(5,6,7,8,9,10-hexahydro-4-hydroxy-2-oxo-2H-cycloocta[b]pyran-3-yl)butyl]phenyl]-1-methyl-;

8-Quinolinesulfonamide, N-[3-[1-(5,6,7,8,9,10-hexahydro-4-hydroxy-2-oxo-2H-cycloocta[b]pyran-3-yl)butyl]phenyl]-;

3-Pyridinesulfonamide, N-[3-[1-(5,6,7,8,9,10-hexahydro-4-hydroxy-2-oxo-2H-cycloocta[b]pyran-3-yl)butyl]phenyl]-;

(R or S)-[3-[1-(5,6,7,8,9,10-Hexahydro-4-hydroxy-2-oxo-2H-cycloocta[b]pyran-3-yl)butyl]phenyl]-carbamic acid, phenylmethyl ester;

(R or S)-[3-[1-(5,6,7,8,9,10-Hexahydro-4-hydroxy-2-oxo-2H-cycloocta[b]pyran-3-yl)butyl]phenyl]-carbamic acid, phenylmethyl ester;

(R or S)-3-[1-(3-Aminophenyl)butyl]-5,6,7,8,9,10-hexahydro-4-hydroxy-2H-cycloocta[b]pyran-2-one;

(R or S)-Benzenesulfonamide, 4-cyano-N-[3-[1-(5,6,7,8,9,10-hexahydro-4-hydroxy-2-oxo-2H-cycloocta[b]pyran-3-yl)butyl]phenyl]-;

(R or S)-3-[1-(3-Aminophenyl)butyl]-5,6,7,8,9,10-hexahydro-4-hydroxy-2H-cycloocta[b]pyran-2-one;

(R or S)-Benzenesulfonamide, 4-cyano-N-[3-[1-(5,6,7,8,9,10-hexahydro-4-hydroxy-2-oxo-2H-cycloocta[b]pyran-3-yl)butyl]phenyl]-;

N-[3-[1-(5,6,7,8,9,10-Hexahydro-4-hydroxy-2-oxo-2H-cycloocta-[b]pyran-3-yl)-2-methylpropyl]phenyl-benzenesulfonamide;

N-[3-[1-(5,6,7,8,9,10-Hexahydro-4-hydroxy-2-oxo-2H-cycloocta-[b]pyran-3-yl)-2-methylpropyl]phenyl-1-propanesulfonamide;

N-[3-[1-(5,6,7,8,9,10-Hexahydro-4-hydroxy-2-oxo-2H-cycloocta-[b]pyran-3-yl)-2-methylpropyl]phenyl-2,1,3-benthiadiazole-4-sulfonamide;

N-[3-[1-(5,6,7,8,9,10-Hexahydro-4-hydroxy-2-oxo-2H-cycloocta-[b]pyran-3-yl)-2-methylpropyl]phenyl-2-thiophenesulfonamide;

N-[3-[1-(5,6,7,8,9,10-Hexahydro-4-hydroxy-2-oxo-2H-cycloocta-[b]pyran-3-yl)-2-methylpropyl]phenyl-4-(hydroxyamine)-benzenesulfonamide;

4-[[[3-[1-(5,6,7,8,9,10-Hexahydro-4-hydroxy-2-oxo-2H-cycloocta-[b]pyran-3-yl)-2-methylpropyl]phenyl]amino]sulfonyl]-benzamide;

3-[[[3-[1-(5,6,7,8,9,10-Hexahydro-4-hydroxy-2-oxo-2H-cycloocta-[b]pyran-3-yl)-2-methylpropyl]phenyl]amino]sulfonyl]-benzoic acid, methyl ester;

N-[3-[1-(5,6,7,8,9,10-Hexahydro-4-hydroxy-2-oxo-2H-cycloocta-[b]pyran-3-yl)-2-methylpropyl]phenyl-3-(hydroxymethyl)-benzenesulfonamide;

N-[3-[1-(5,6,7,8,9,10-Hexahydro-4-hydroxy-2-oxo-2H-cycloocta-[b]pyran-3-yl)-2-methylpropyl]phenyl-3-[(bis-(2-ethanol))amino]-benzenesulfonamide;

N-[3-[1-(5,6,7,8,9,10-Hexahydro-4-hydroxy-2-oxo-2H-cycloocta-[b]pyran-3-yl)-2-methylpropyl]phenyl-thiazole-4-sulfonamide;

N-[3-[1-(5,6,7,8,9,10-Hexahydro-4-hydroxy-2-oxo-2H-cycloocta-[b]pyran-3-yl)butyl]phenyl-benzenesulfonamide;

N-[3-[1-(5,6,7,8,9,10-Hexahydro-4-hydroxy-2-oxo-2H-cycloocta-[b]pyran-3-yl)butyl]phenyl-1-propanesulfonamide;

N-[3-[1-(5,6,7,8,9,10-Hexahydro-4-hydroxy-2-oxo-2H-cycloocta-[b]pyran-3-yl)butyl]phenyl-2,1,3-benthiadiazole-4-sulfonamide;

N-[3-[1-(5,6,7,8,9,10-Hexahydro-4-hydroxy-2-oxo-2H-cycloocta-[b]pyran-3-yl)butyl]phenyl-2-thiophenesulfonamide;

N-[3-[1-(5,6,7,8,9,10-Hexahydro-4-hydroxy-2-oxo-2H-cycloocta-[b]pyran-3-yl)butyl]phenyl-4-(hydroxyamine)-benzenesulfonamide;

4-[[[3-[1-(5,6,7,8,9,10-Hexahydro-4-hydroxy-2-oxo-2H-cycloocta-[b]pyran-3-yl)butyl]phenyl]amino]sulfonyl]-benzamide;

3-[[[3-[1-(5,6,7,8,9,10-Hexahydro-4-hydroxy-2-oxo-2H-cycloocta-[b]pyran-3-yl)butyl]phenyl]amino]sulfonyl]-benzoic acid, methyl ester;

N-[3-[1-(5,6,7,8,9,10-Hexahydro-4-hydroxy-2oxo-2H-cycloocta-[b]pyran-3-yl)butyl]phenyl-3-(hydroxymethyl)-benzenesulfonamide;

N-[3-[1-(5,6,7,8,9,10-Hexahydro-4-hydroxy-2-oxo-2H-cycloocta-[b]pyran-3-yl)butyl]phenyl-3-[(bis-(2-ethanol))amino]-benzenesulfonamide;

N-[3-[1-(5,6,7,8,9,10-Hexahydro-4-hydroxy-2-oxo-2H-cycloocta-[b]pyran-3-yl)butyl]phenyl-thiazole-4-sulfonamide;

N-[3-[1-(5,6,7,8,9,10-Hexahydro-4-hydroxy-2-oxo-2H-cycloocta-[b]pyran-3-yl)-3-methylbutyl]phenyl-benzenesulfonamide;

N-[3-[1-(5,6,7,8,9,10-Hexahydro-4-hydroxy-2-oxo-2H-cycloocta-[b]pyran-3-yl)-3-methylbutyl]phenyl-1-propanesulfonamide;

N-[3-[1-(5,6,7,8,9,10-Hexahydro-4-hydroxy-2-oxo-2H-cycloocta-[b]pyran-3-yl)-3-methylbutyl]phenyl-2,1,3-benthiadiazole-4-sulfonamide;

N-[3-[1-(5,6,7,8,9,10-Hexahydro-4-hydroxy-2-oxo-2H-cycloocta-[b]pyran-3-yl)-3-methylbutyl]phenyl-2-thiophenesulfonamide;

N-[3-[1-(5,6,7,8,9,10-Hexahydro-4-hydroxy-2-oxo-2H-cycloocta-[b]pyran-3-yl)-3-methylbutyl]phenyl-4-(hydroxyamine)-benzenesulfonamide;

4-[[[3-[1-(5,6,7,8,9,10-Hexahydro-4-hydroxy-2-oxo-2H-cycloocta-[b]pyran-3-yl-3-methylbutyl]phenyl]amino]sulfonyl]-benzamide;

3-[[[3-[1-(5,6,7,8,9,10-Hexahydro-4-hydroxy-2-oxo-2H-cycloocta-[b]pyran-3-yl)-3-methylbutyl]phenyl]amino]sulfonyl]-benzoic acid, methyl ester;

N-[3-[1-(5,6,7,8,9,10-Hexahydro-4-hydroxy-2-oxo-2H-cycloocta-[b]pyran-3-yl)-3-methylbutyl]phenyl-3-(hydroxymethyl)-benzenesulfonamide;

N-[3-[1-(5,6,7,8,9,10-Hexahydro-4-hydroxy-2-oxo-2H-cycloocta-[b]pyran-3-yl)-3-methylbutyl]phenyl-3-[(bis-(2-ethanol))amino]-benzenesulfonamide;

N-[3-[1-(5,6,7,8,9,10-Hexahydro-4-hydroxy-2-oxo-2H-cycloocta-[b]pyran-3-yl)-3-methylbutyl]phenyl-thiazole-4-sulfonamide;

Carbamic acid, [4-[cyclopropyl (5,6,7,8,9,10-hexahydro-4-hydroxy-2-oxo-2H-cycloocta[b]pyran-3-yl)methyl]phenyl]-phenylmethyl ester;

3-[(4-Aminophenyl)cyclopropylmethyl]-5,6,7,8,9,10-hexahydro-4-hydroxy-2H-cycloocta[b]pyran-2-one;

Benzenesulfonamide, 4-cyano-N-[4-[cyclopropyl (5,6,7,8,9,10-hexahydro-4-hydroxy-2-oxo-2H-cycloocta[b]pyran-3-yl)methyl]phenyl]-;

Benzenesulfonamide, 4-chloro-N-[4-[cyclopropyl(5,6,7,8,9,10-hexahydro-4-hydroxy-2-oxo-2H-cycloocta[b]pyran-3-yl)methyl]phenyl]-;

Benzenesulfonamide, 4-fluoro-N-[4-[cyclopropyl(5,6,7,8,9,10-hexahydro-4-hydroxy-2-oxo-2H-cycloocta[b]pyran-3-yl)methyl]phenyl]-;

Benzenesulfonamide, 3-nitro-N-[4-[cyclopropyl (5,6,7,8,9,10-hexahydro-4-hydroxy-2-oxo-2H-cycloocta[b]pyran-3-yl)methyl]phenyl]-;

N-[4-[Cyclopropyl (5,6,7,8,9,10-hexahydro-4-hydroxy-2-oxo-2H-cycloocta[b]pyran-3-yl)methyl]phenyl]-1-methyl-1H-imidazole-4-sulfonamide;

N-[3-[(R)Ethyl-(5,6,7,8,9,10-hexahydro-4-hydroxy-2-oxo-2H-cycloocta[b]pyran-3-yl)methyl]phenyl]-4-fluorobenzenesulfonamide;

N-[3(S)-[Cyclopropyl-(5,6,7,8,9,10-hexahydro-4-hydroxy-2-oxo-2H-cycloocta[b]pyran-3-yl)methyl]phenyl]-4-fluorobenzenesulfonamide;

N-[3(R)-[Cyclopropyl-(5,6,7,8,9,10-hexahydro-4-hydroxy-2-oxo-2H-cycloocta[b]pyran-3-yl)methyl]phenyl]-4-fluorobenzenesulfonamide;

3-(α-Cyclopropyl(5-(N-carbo-t-butoxy)aminomethyle)furfur-2-yl)-4-hydroxy-5,6,7,8,9,10-hexahydrocycloocata[b]pyran-2-one;

3-(Diphenylmethyl)-5,6,7,8,9,10-hexahydro-4-hydroxy-2H-cycloocta[b]pyran-2-one;

3-(1,3-Diphenyl-2-propyl)-5,6,7,8,9-pentahydro-4-hydroxy-2H-cyclohepta[b]pyran-2-one;

3-(Phenylcyclobutyl)-5,6,7,8,9,10-hexahydro-4-hydroxy-2H-cycloocta[b]pyran-2-one;

3-[Cyclopropyl-(3,5-diamino-phenyl)-methyl]-4-hydroxy-5,6,7,8,9,10-hexahydro-cycloocta[b]pyran-2-one;

N-{3-[Cyclopropyl-(4-hydroxy-2-oxo-5,6,7,8,9,10-hexahydro-2H-cycloocta[b]pyran-3-yl)-methyl]-5-8-quinolinesulfonylamino-phenyl}-8-quinolinesulfonamide;

N-{3-Amino-5-[cyclopropyl]-(4-hydroxy-2-oxo-5,6,7,8,9,10-hexahydro-2H-cycloocta[b]pyran-3-yl)-methyl]-phenyl}-benzenesulfonamide;

3-Iodo-N-[3-[cyclopropyl(5,6,7,8,9,10-hexahydro-4-hydroxy-2-oxo-2H-cycloocta[b]pyran-3-yl)methyl]phenyl]-1-propanesulfonamide; and N-[3-[Cyclopropyl(5,6,7,8,9,10-hexahydro-4-hydroxy-2-oxo-2H-cycloocta-3-yl) methyl]phenyl]-thiazole-4-sulfonamide.

20. The compound of any of claims 3, 11 and 13, wherein $R_5$ is a moiety containing $X_1$ wherein $X_1$ is —NHSO$_2$—.

21. The compound of claim 13 selected from:

N-[3-[Cyclopropyl(5,6,7,8,9,10-hexahydro-4-hydroxy-2-oxo-2H-cycloocta[b]pyran-3-yl)methyl]phenyl]-4-fluoro-benzenesulfonamide;

Sodium Salt of N-[3-[Cyclopropyl(5,6,7,8,9,10-hexahydro-4-hydroxy-2-oxo-2H-cycloocta[b]pyran-3-yl)methyl]phenyl]-4-fluoro-benzenesulfonamide;

N-[3(S)-[Cyclopropyl(5,6,7,8,9,10-hexahydro-4-hydroxy-2-oxo-2H-cycloocta[b]pyran-3-yl)methyl]phenyl]-4-fluoro-benzenesulfonamide;

N-[3(R)-[Cyclopropyl(5,6,7,8,9,10-hexahydro-4-hydroxy-2-oxo-2H-cycloocta[b]pyran-3-yl)methyl]phenyl]-4-fluoro-benzenesulfonamide;

4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide;

Sodium Salt of 4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide;

(+)-4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide;

(−)-4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide;

(+)-N-[3-[Cyclopropyl(5,6,7,8,9,10-hexahydro-4-hydroxy-2-oxo-2H-cycloocta[b]pyran-3-yl)methyl]phenyl]-8-quinolinesulfonamide;

(−)-N-[3-[Cyclopropyl(5,6,7,8,9,10-hexahydro-4-hydroxy-2-oxo-2H-cycloocta[b]pyran-3-yl)methyl]phenyl]-8-quinolinesulfonamide;

(−)-N-[3-[Cyclopropyl(5,6,7,8,9,10-hexahydro-4-hydroxy-2-oxo-2H-cycloocta-3-yl)methyl]phenyl]-1-methyl-1H-imidazole-4-sulfonamide;

N-[3-[1-(5,6,7,8,9,10-Hexahydro-4-hydroxy-2-oxo-2H-cycloocta[b]pyran-3-yl)-2-methylpropyl]phenyl]-1-methyl-1H-imidazole-4-sulfonamide;

N-[3-[Cyclopropyl[3-(2-isothiazolidinyl)phenyl]methyl-(5,6,7,8,9,10-hexahydro-4-hydroxy-S,S'-dioxide)methyl]phenyl]-3-[(phenylsulfonyl)amino]-4-2H-cycloocta[b]pyran-2-one;

1H-Imidazole4-sulfonamide, N-[3-[1-(5,6,7,8,9,10-hexahydro-4-hydroxy-2-oxo-2H-cycloocta[b]pyran-3-yl)butyl]phenyl]-1-methyl- and;

1H-Imidazole4-sulfonamide, N-[3-[1-(5,6,7,8,9,10-hexahydro-4-hydroxy-2-oxo-2H-cycloocta[b]pyran-3-yl)-3-methylbutyl]phenyl]-1-methyl-.

22. The compound of claim 14 selected from:

N-[3-[Cyclopropyl(5,6,7,8,9,10-hexahydro-4-hydroxy-2-oxo-2H-cycloocta[b]pyran-3-yl)methyl]phenyl]-4-fluoro-benzenesulfonamide;

Sodium Salt of N-[3-[Cyclopropyl(5,6,7,8,9,10-hexahydro-4-hydroxy-2-oxo-2H-cycloocta[b]pyran-3-yl)methyl]phenyl]-4-fluoro-benzenesulfonamide;

N-[3(S)-[Cyclopropyl(5,6,7,8,9,10-hexahydro-4-hydroxy-2-oxo-2H-cycloocta[b]pyran-3-yl)methyl]phenyl]-4-fluoro-benzenesulfonamide;

N-[3(R)-[Cyclopropyl(5,6,7,8,9,10-hexahydro-4-hydroxy-2-oxo-2H-cycloocta[b]pyran-3-yl)methyl]phenyl]-4-fluoro-benzenesulfonamide;

4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide;

Sodium Salt of 4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide;

(+)-4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide and;

(−)-4-Cyano-N-[3-[cyclopropyl(5,6,7,8,9,10-hexahydro-4-hydroxy-2-oxo-2H-cycloocta[b]pyran-3-yl)methyl]phenyl]-benzenesulfonamide.

23. The method of claim 1 wherein the compound is as defined in any of claims 2 to 22.

24. The method of claim 1 wherein the compound is as defined in claim 19.

25. A method of inhibiting a retrovirus in a mammalian cell infected with said retrovirus which comprises treating said cell with an effective amount of a compound selected from the group consisting of:

4-Hydroxy-3-(α-methylbenzyl)-coumarin,

4-Hydroxy-3-phenethylcoumarin,

4-Hydroxy-3-(3-phenylpropyl)coumarin,

4-Hydroxy-3-diphenylmethylcoumarin,

4-Hydroxy-3-(3-hydroxy-1-phenylbutyl)-coumarin,

4-Hydroxy-3-(2-methyl-1-phenylpropyl)-coumarin,

4-Hydroxy-3-(1-phenylbutyl)-coumarin,

4-Hydroxy-3-(1-phenylpentyl)-coumarin,

4-Hydroxy-3-(3-methyl-1-phenylbutyl)-coumarin,

4-Hydroxy-3-(2-phenylpropyl)coumarin,

4-Hydroxy-3-(1,3-diphenylpropyl)-coumarin,

4-Hydroxy-3-(1-(4-methylphenyl)-butyl)-coumarin,

4-Hydroxy-3-(1,3-diphenylpropyl)-coumarin,

4-Hydroxy-3-(1-(4-methylphenyl)-butyl)-coumarin,

Coumarin, 4-hydroxy-3-[1-(4-hydroxyphenyl)propyl]-,

4-Hydroxy-3-(1-(1-naphthyl)-propyl)-coumarin,

Coumarin, 4-hydroxy-7-methoxy-3-(1-phenylpropyl)-,

Coumarin, 4-hydroxy-6-methoxy-3-(1-phenylpropyl)-,

Coumarin, 4,7-dihydroxy-3-(1-phenylpropyl)-,

Coumarin, 4,6-dihydroxy-3-(1-phenylpropyl)-,

Coumarin, 4-hydroxy-7-methyl-3-(1-phenylpropyl)-,

Coumarin, 7-chloro-4-hydroxy-3-(1-phenylpropyl)-,

Coumarin, 4-hydroxy-3-[1-(4-methoxyphenyl)propyl]-,

Coumarin, 4-hydroxy-3-[1-(3-hydroxyphenyl)propyl]-,

4-Hydroxy-3-(1-phenyl-2-propenyl)-coumarin,

Coumarin, 3-(α-ethyl-p-fluorobenzyl)-4-hydroxy-,
4-Hydroxy-3-[1-(1,2,3,4-tetrahydro)naphthyl]-coumarin,
4-Hydroxy-3-[1-indanyl]-coumarin,
4-Hydroxy-3-(1-phenylpropyl)-coumarin,
3-(1-(4-Bromophenyl)-2-methylpropyl)4-hydroxycoumarin,
Butanoic acid, 2-(4-hydroxy-2-oxo-2H-1-benzopyran-3-yl)-, ethyl ester,
3-(1,2-Diphenylethyl)-4-hydroxycoumarin,
4-Hydroxy-3-(2,2-diphenylethyl)-coumarin,
3-(1,2-Diphenylethenyl)-4-hydroxycoumarin,
Coumarin, 6-fluoro-4-hydroxy-3-(1-phenylpropyl)-,
Coumarin, 3-[1-(4-bromophenyl)propyl]-4hydroxy-,
3-(1'-(3-Bromophenyl)propyl)-4-hydroxycoumarin,
Coumarin, 3-(α-ethylbenzyl)-4-hydroxy-7-(1-methylethoxy)-, and
Coumarin, 7-ethoxy-3-(α-ethylbenzyl)-4-hydroxy-.

26. A process for making a compound of the formula XI

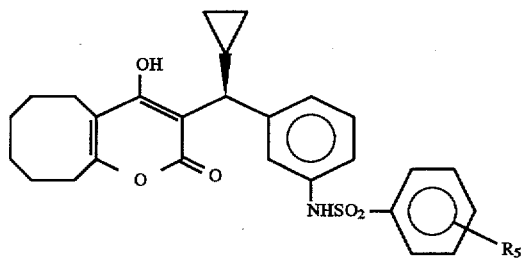

XI wherein $R_6$ is as defined in claim 1 which comprises:

a) reacting a compound of the formula XII

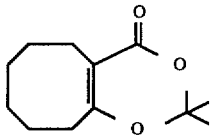

XII with a compound of the formula XIII

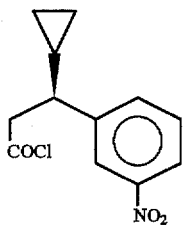

XIII in a hydrocarbon solvent in the presence of a trialkylamine at an elevated temperature to yield a compound of the formula XIV;

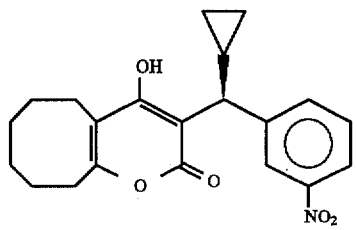

XIV b) hydrogenating the compound of formula XIV with a catalyst in an organic solvent to obtain a compound of the formula XV; and

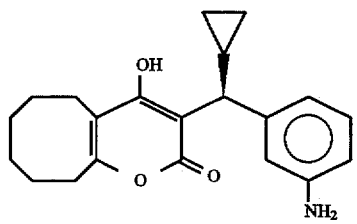

XV c) reacting the compound of formula XV with a benzenesulfonyl chloride of the formula XVI

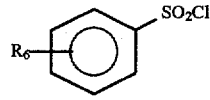

XVI wherein $R_6$ is as defined above.

27. The process of claim 26 wherein $R_6$ is F or CN.

* * * * *